(12) United States Patent
Ruben et al.

(10) Patent No.: US 6,693,077 B1
(45) Date of Patent: *Feb. 17, 2004

(54) KERATINOCYTE GROWTH FACTOR-2

(75) Inventors: Steven M. Ruben, Brookeville, MD (US); Pablo Jimenez, Chatham, NJ (US); D. Roxanne Duan, Gaithersburg, MD (US); Mark A. Rampy, Montgomery Village, MD (US); Donna Mendrick, Mount Airy, MD (US); Jun Zhang, San Diego, CA (US); Jian NI, Germantown, MD (US); Paul A. Moore, North Bethesda, MD (US); Timothy A. Coleman, Gaithersburg, MD (US); Joachim R. Gruber, Dallas, TX (US); Patrick J. Dillon, Carlsbad, CA (US); Reiner L. Gentz, Belo Horizonte-Mg (BR)

(73) Assignee: Human Genome Sciences, Inc., Rockville, MD (US)

(*) Notice: Subject to any disclaimer, the term of this patent is extended or adjusted under 35 U.S.C. 154(b) by 0 days.
This patent is subject to a terminal disclaimer.

(21) Appl. No.: 09/610,651

(22) Filed: Jun. 30, 2000

Related U.S. Application Data

(63) Continuation-in-part of application No. 09/345,373, filed on Jul. 1, 1999, which is a continuation of application No. 09/023,082, filed on Feb. 13, 1998, now Pat. No. 6,077,692, which is a continuation-in-part of application No. 08/910,875, filed on Aug. 13, 1997, and a continuation-in-part of application No. 08/862,432, filed on May 23, 1997, which is a division of application No. 08/461,195, filed on Jun. 5, 1995, which is a continuation-in-part of application No. PCT/US95/01790, filed on Feb. 14, 1995, application No. 09/610,651, which is a continuation-in-part of application No. 08/696,135, filed on Aug. 13, 1996, which is a continuation-in-part of application No. 08/461,195, filed on Jun. 5, 1995, which is a continuation-in-part of application No. PCT/US95/01790, filed on Feb. 14, 1995.

(60) Provisional application No. 60/205,417, filed on May 19, 2000, provisional application No. 60/198,322, filed on Apr. 19, 2000, provisional application No. 60/171,677, filed on Dec. 22, 1999, provisional application No. 60/163,375, filed on Nov. 3, 1999, provisional application No. 60/149,935, filed on Aug. 19, 1999, provisional application No. 60/148,628, filed on Aug. 12, 1999, provisional application No. 60/144,024, filed on Jul. 15, 1999, provisional application No. 60/143,648, filed on Jul. 14, 1999, provisional application No. 60/142,343, filed on Jul. 2, 1999, provisional application No. 60/039,045, filed on Feb. 28, 1997, provisional application No. 60/055,561, filed on Aug. 13, 1997, and provisional application No. 60/023,852, filed on Aug. 13, 1996.

(51) Int. Cl.$^7$ .......................... A61K 38/18; C07K 14/50
(52) U.S. Cl. .............................. 514/12; 514/2; 530/399
(58) Field of Search ........................ 514/2, 12; 530/399

(56) References Cited

U.S. PATENT DOCUMENTS

| | | |
|---|---|---|
| 5,194,596 A | 3/1993 | Tischer et al. |
| 5,350,836 A | 9/1994 | Kopchick et al. |
| 5,580,856 A | 12/1996 | Prestrelski et al. |
| 5,677,278 A | 10/1997 | Gospodarowicz et al. |
| 5,703,047 A | 12/1997 | Wilson |
| 5,731,170 A | 3/1998 | Rubin et al. |
| 5,773,252 A | 6/1998 | Greene et al. |
| 5,773,586 A | 6/1998 | Gospodarowicz et al. |
| 5,814,605 A | 9/1998 | Pierce et al. |
| 5,824,643 A | 10/1998 | Pierce et al. |
| 5,843,883 A | 12/1998 | Gospodarowicz et al. |
| 5,863,767 A | 1/1999 | Gospodarowicz et al. |
| 6,077,692 A | 6/2000 | Ruben et al. |
| 6,238,888 B1 | 5/2001 | Gentz et al. |

FOREIGN PATENT DOCUMENTS

| | | |
|---|---|---|
| EP | 0 619 370 A1 | 10/1994 |
| GB | 2 321 852 A | 8/1998 |
| JP | 7-345689 | 12/1995 |
| JP | 8-103240 | 3/1996 |
| JP | 8-214378 | 7/1996 |
| JP | 10-330283 | 12/1998 |
| JP | 10-330284 | 12/1998 |
| JP | 10-330285 | 12/1998 |
| WO | WO 90/08771 | 8/1990 |
| WO | WO 92/14480 | 9/1992 |
| WO | WO 92/22304 | 12/1992 |
| WO | WO 93/21908 | 11/1993 |
| WO | WO 94/22427 | 10/1994 |
| WO | WO 94/23032 | 10/1994 |
| WO | WO 95/01434 | 1/1995 |
| WO | WO 95/03831 | 2/1995 |
| WO | WO 95/24928 | 9/1995 |
| WO | WO 95/24928 A3 | 10/1995 |
| WO | WO 96/11949 | 4/1996 |
| WO | WO 96/11950 | 4/1996 |
| WO | WO 96/11951 | 4/1996 |
| WO | WO 96/11952 | 4/1996 |
| WO | WO 96/22369 | 7/1996 |

(List continued on next page.)

OTHER PUBLICATIONS

Bowie, J.U. et al., "Deciphering the Message in Protein Sequences: Tolerance to Amino Acid Substitutions," *Science* 247:1306–1310, American Association for the Advancement of Science (1990).

(List continued on next page.)

*Primary Examiner*—Christine J. Saoud
(74) *Attorney, Agent, or Firm*—Human Genome Sciences, Inc.

(57) ABSTRACT

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a Keratinocyte Growth Factor, sometimes hereinafter referred to as "KGF-2" also formerly known as Fibroblast Growth Factor 12 (FGF-12). This invention further relates to the therapeutic use of KGF-2 to promote or accelerate wound healing. This invention also relates to novel mutant forms of KGF-2 that show enhanced activity, increased stability, higher yield or better solubility.

48 Claims, 64 Drawing Sheets

FOREIGN PATENT DOCUMENTS

| WO | WO 96/25422 | 8/1996 |
|---|---|---|
| WO | WO 97/20929 | 12/1997 |
| WO | WO 98/06844 | 2/1998 |
| WO | WO 98/16243 | 4/1998 |
| WO | WO 98/16642 | 4/1998 |
| WO | WO 99/32135 | 7/1999 |
| WO | WO 99/41282 | 8/1999 |
| WO | WO 00/72872 | 12/2000 |
| WO | WO 01/02433 | 1/2001 |

OTHER PUBLICATIONS

Finch, P. W. et al., "Human KGF Is FGF–Related with Properties of a Paracrine Effector of Epithelial Cell Growth," *Science* 245:752–755, American Association for the Advancement of Science (1989).

Hartung, H. et al., "Murine FGF–12 and FGF–13: expression in embryonic nervous system, connective tissue and heart," *Mech. Develop.* 64:31–39, Elsevier Science Ireland Ltd. (Jun. 1997).

Hartung, H. et al., "Assigment of Fgf12 to mouse chromosome bands 16B1→B3 in situ hybridization," *Cytogenet. Cell Genet.* 76:185–186, Karger A.G. (Apr. 1997).

Jimenez, P. et al., "Effect of Topical Keratinocyte Growth Factor–2 on Wound Healing In A Glucocorticoid–Impaired Model," *J. Cutan. Pathol.* 24:105, The American Society of Dermatopathology, Munksgaard (Feb. 1997).

Jimenez, P.A. et al., "Effect of Keratinocyte Growth Factor–2 on Cell Proliferation In Vivo," *FASEB J.* 11:A523, Abstract No. 3025, Federation of American Societies for Experimental Biology (Apr. 1997).

Jimenez, P.A. and Rampy, M.A., "Keratinocyte Growth Factor–2 Accelerates Wound Healing in Incisional Wounds," *J. Surg. Res.* 81:238–242, Academic Press, Inc. (Feb. 1999).

Kelley, M. J. et al., "Emergence of the keratinocyte growth factor multigene family during the great ape radiation," *Proc. Natl. Acad. Sci. USA* 89:9287–9291, National Academy of Sciences of the USA (1992).

Mason, I.J. et al., "FGF–7 (keratinocyte growth factor) expression during mouse development suggests roles in myogenesis, forebrain regionalisation and epithelial–mesenchymal interactions," *Mech. Dev.* 45:15–30, Elsevier Science Ireland Ltd. (Jan. 1994).

Miyamoto, M. et al., "Molecular Cloning of a Novel Cytokine cDNA Encoding the Ninth Member of the Fibroblast Growth Factor Family, Which Has a Unique Secretion Property," *Mol. Cell. Biol.* 13(7):4251–4259, American Society for Microbiology (1993).

Ngo, J.T. et al., "Computional Complexity, Protein Structure Prediction, and the Levinthal Paradox," in: *The Protein Folding Problem and Tertiary Structure Prediction*, Merz, Jr., K. and Le Grand, S., eds., Birkhauser, Boston, Massachusetts, pp. 491–495 (1994).

Robson, B. and Garnier, J., "Modern ideas and notations relating to primary structure," in: *Introduction to Protein Engineering*, Robson, B. and Gernier, J., eds., Elsevier Science, Amsterdam, The Netherlands, p. 41 (1986).

Ron, D. et al., "Expression of Biologically Active Recombinant Keratinocyte Growth Factor," *J. Biol. Chem.* 268(4):2984–2988, American Society for Biochemistry and Molecular Biology, Inc. (1993).

Wells, J.A., "Additivity of Mutational Effects in Proteins," *Biochemistry* 29:8509–8517, American Chemical Society (1990).

Yamasaki, M. et al., "Structure and Expression of the Rat mRNA Encoding a Novel Member of the Fibroblast Growth Factor Family," *J. Biol. Chem.* 271:15918–15921, The American Society for Biochemistry and Molecular Biology, Inc. (Jul. 1996).

Yan, G. et al., "Sequence of Rat Keratinocyte Growth Factor (Heparin–Binding Growth Factor Type 7)," *In Vitro Cell. Dev. Biol.* 27A:437–438, Tissue Culture Association (1991).

NCBI Entrez, GenBank Report with Revision History, Accession No. M79878, McCombie, W.R. et al. (1992).

NCBI Entrez, GenBank Report with Revision History, Accession No. T52063, Hillier, L. et al. (Feb. 1995).

NCBI Entrez, GenBank Report with Revision History, Accession No. D46201, Sasaki, T. et al. (Aug. 1995).

NCBI Entrez, GenBank Report with Revision History, Accesssion No. D46420, Sasaki, T. et al. (Aug. 1995).

NCBI Entrez, GenBank Report with Revision History, Accession No. D54216, Fujiwara, T. et al. (Sep. 1995).

NCBI Entrez, GenBank Report with Revision History, Accession No. D68729, Kohara, Y. et al. (Dec. 1995).

NCBI Entrez, GenBank Report with Revision History, Accession No. D69248, Kohara, Y. et al. (Dec. 1995).

NCBI Entrez, GenBank Report with Revision History, Accession No. D65627, Kohara, Y. et al. (Dec. 1995).

NCBI Entrez, GenBank Report with Revision History, Accession No. D66221, Kohara, Y. et al. (Dec. 1995).

NCBI Entrez, GenBank Report wtih Revision History, Accession No. C02000, Okubo, K. (Jul. 1996).

NCBI Entrez, GenBank Report with Revision History, Accession No. W29377, Marra, M. et al. (Sep. 1996).

NCBI Entrez, GenBank Report with Revision History, Accession No. W32720, Hillier, L. et al. (Oct. 1996).

NCBI Entrez, GenBank Report with Revision History, Accession No. W60824, Hillier, L. et al. (Oct. 1996).

NCBI Entrez, GenBank Report with Revision History, Accession No. T70682, Shen, B. et al. (Oct. 1996).

NCBI Entrez, GenBank Report with Revision History, Accession No. AA094753, Liew, C.C. (Oct. 1996).

NCBI Entrez, GenBank Report with Revision History, Accession No. AA133331, Hillier, L. et al. (Nov. 1996).

NCBI Entrez, GenBank Report with Revision History, Accession No. AA190058, Marra, M. et al. (Jan. 1997).

NCBI Entrez, GenBank Report with Revision History, Accession No. AA018953, Hillier, L. et al. (Jan. 1997).

NCBI Entrez, GenBank Report with Revision History, Accession No. AA240978, Marra, M. et al. (Mar. 1997).

NCBI Entrez, GenBank Report with Revision History, Accession No. AA289560, Marra, M. et al. (Apr. 1997).

NCBI Entrez, GenBank Report with Revision History, Accession No. AA296993, Adams, M.D. et al. (Apr. 1997).

NCBI Entrez, GenBank Report with Revision History, Accession No. AA298937, Adams, M.D. et al. (Apr. 1997).

NCBI Entrez, GenBank Report with Revision History, Accession No. AA312184, Adams, M.D. et al. (Apr. 1997).

NCBI Entrez, GenBank Report with Revision History, Accession No. AA312483, Adams, M.D. et al. (Apr. 1997).

NCBI Entrez, GenBank Report with Revision History, Accession No. AA356781, Adams, M.D. et al. (Apr. 1997).

NCBI Entrez, GenBank Report with Revision History, Accession No. AA412789, Marra, M. et al. (May 1997).

NCBI Entrez, GenBank Report with Revision History, Accession No. AA472256, Marra, M. et al. (Jun. 1997).

NCBI Entrez, GenBank Report with Revision History, Accession No. U67918, Jimenez, P.A. et al., National Center for Biotechnology Information (Jul. 1997).

NCBI Entrez, GenBank Report with Revision History, Accession No. C38464, Kohara, Y. et al. (Sep. 1997).

NCBI Entrez, GenBank Report with Revision History, Accession No. C56505, Kohara, Y. et al. (Sep. 1997).

NCBI Entrez, GenBank Report with Revision History, Accession No. C57074, Kohara, Y. et al. (Sep. 1997).

NCBI Entrez, GenBank Report with Revision History, Accession No. C58558, Kohara, Y. et al. (Sep. 1997).

NCBI Entrez, GenBank Report with Revision History, Accession No. C58846, Kohara, Y. et al. (Sep. 1997).

NCBI Entrez, GenBank Report with Revision History, Accession No. C59317, Kohara, Y. et al. (Sep. 1997).

NCBI Entrez, GenBank Report with Revision History, Accession No. C59311, Kohara, Y. et al. (Sep. 1997).

NCBI Entrez, GenBank Report with Revision History, Accession No. AA605609, Clark, M. et al. (Sep. 1997).

NCBI Entrez, GenBank Report with Revision History, Accession No. AA621871, NCI–CGAP (Oct. 1997).

NCBI Entrez, GenBank Report with Revision History, Accession No. AA621888, NCI–CGAP (Oct. 1997).

NCBI Entrez, GenBank Report with Revision History, Accession No. AA675470, Marra, M. et al. (Nov. 1997).

NCBI Entrez, GenBank Report with Revision History, Accession No. AA675519, Marra, M. et al. (Nov. 1997).

NCBI Entrez, GenBank Report with Revision History, Accession No. AA838994, Marra, M. et al. (Feb. 1998).

NCBI Entrez, GenBank Report with Revision History, Accession No. H35048, Lee, N.H. et al. (Apr. 1998).

NCBI Entrez, GenBank Report with Revision History, Accession No. AA906051, NCI–CGAP (May 1998).

NCBI Entrez, GenBank Report with Revision History, Accession No. C78836, Ko, M.S.H. et al. (Jun. 1998).

English language translation of JP 7–345689.

English language translation of JP 8–103240.

English language translation of JP 8–214378.

English language translation of WO 97/20929.

English language translation of JP 10–330283.

English language translation of JP 10–330284.

English language translation of JP 10–330285.

International Search Report for International Application No. PCT/US95/01790, mailed Jun. 7, 1995.

Copy of Co–pending U.S. application No. 09/248,998, filed Feb. 12, 1999, Jimenez et al.

Copy of Co–pending U.S. application No. 09/345,373, filed Jul. 1, 1999, Ruben et al.

Copy of Co–pending U.S. application No. 09/585,541, filed Jun. 2, 2000, Gentz et al.

Copy of Co–pending U.S. publication No. US 2002/0016295 A1, published Feb. 7, 2002 (U.S. application No. 09/853,666, filed May 14, 2001), Gentz et al.

Copy of Co–pending U.S. application No. 10/035,212, filed Jan. 4, 2002, Ruben et al.

Copy of Co–pending U.S. application No. 10/075,446, filed Feb. 15, 2002, Ruben et al.

Copy of pp. 1–75 (pp. 1 and 2 partially redacted), portion of Table 2 and SEQ ID NO:40589 of non published co–pending U.S. application No. 09/912,292, Rosen et al.

Copy of Co–pending U.S. application No. 10/194,443, filed Jul. 12, 2002, Laird.

```
     ATGTGGAAATGGATACTGACACATTGTGCCTCAGCCTTTCCCCACCTGCCCGGCTGCTGC
 1   ---------+---------+---------+---------+---------+---------+   60
     TACACCTTTACCTATGACTGTGTAACACGGAGTCGGAAAGGGGTGGACGGGCCGACGACG

M  W  K  W  I  L  T  H  C  A  S  A  F  P  H  L  P  G  C  C

TGCTGCTGCTTTTTGTTGCTGTTCTTGGTGTCTTCCGTCCCTGTCACCTGCCAAGCCCTT
 61  ---------+---------+---------+---------+---------+---------+  120
     ACGACGACGAAAAACAACGACAAGAACCACAGAAGGCAGGGACAGTGGACGGTTCGGGAA

C  C  C  F  L  L  L  F  L  V  S  S  V  P  V  T  C  Q  A  L

GGTCAGGACATGGTGTCACCAGAGGCCACCAACTCTTCTTCCTCCTCCTTCTCCTCTCCT
121  ---------+---------+---------+---------+---------+---------+  180
     CCAGTCCTGTACCACAGTGGTCTCCGGTGGTTGAGAAGAAGGAGGAGGAAGAGGAGAGGA

G  Q  D  M  V  S  P  E  A  T  N  S  S  S  S  F  S  S  P

TCCAGCGCGGGAAGGCATGTgCGGAGCTACAATCACCTTCAAGGAGATGTCCGCTGGAGA
181  ---------+---------+---------+---------+---------+---------+  240
     AGGTCGCGCCCTTCCGTACAcGCCTCGATGTTAGTGGAAGTTCCTCTACAGGCGACCTCT

S  S  A  G  R  H  V  R  S  Y  N  H  L  Q  G  D  V  R  W  R

MATCH WITH FIG. 1B
```

FIG.1A

MATCH WITH FIG. 1A

```
    AAGCTATTCTCTTTCACCAAGTACTTTCTCAAGATTGAGAAGAACGGGAAGGTCAGCGGG
241 ----------+---------+---------+---------+---------+---------+ 300
    TTCGATAAGAGAAAGTGGTTCATGAAAGAGTTCTAACTCTTCTTGCCCTTCCAGTCGCCC

K  L  F  S  F  T  K  Y  F  L  K  I  E  K  N  G  K  V  S  G

ACCAAGAAGGAGAACTGCCCGTACAGCATCCTGGAGATAACATCAGTAGAAATCGGAGTT
301 ----------+---------+---------+---------+---------+---------+ 360
    TGGTTCTTCCTCTTGACGGGCATGTCGTAGGACCTCTATTGTAGTCATCTTTAGCCTCAA

T  K  K  E  N  C  P  Y  S  I  L  E  I  T  S  V  E  I  G  V

GTTGCCGTCAAAGCCATTAACAGCAACTATTACTTAGCCATGAACAAGAAGGGGAAACTC
361 ----------+---------+---------+---------+---------+---------+ 420
    CAACGGCAGTTTCGGTAATTGTCGTTGATAATGAATCGGTACTTGTTCTTCCCCTTTGAG

V  A  V  K  A  I  N  S  N  Y  Y  L  A  M  N  K  K  G  K  L

TATGGCTCAAAAGAATTTAACAATGACTGTAAGCTGAAGGAGAGGATAGAGGAAAATGGA
421 ----------+---------+---------+---------+---------+---------+ 480
    ATACCGAGTTTTCTTAAATTGTTACTGACATTCGACTTCCTCTCCTATCTCCTTTTACCT

Y  G  S  K  E  F  N  N  D  C  K  L  K  E  R  I  E  E  N  G
```

MATCH WITH FIG. 1C

FIG. 1B

MATCH WITH FIG. 1B

```
     TACAATACCTATGCATCATTTAACTGGCAGCATAATGGGAGGCAAATGTATGTGGCATTG
481  ---------+---------+---------+---------+---------+---------+  540
     ATGTTATGGATACGTAGTAAATTGACCGTCGTATTACCCTCCGTTTACATACACCGTAAC

Y  N  T  Y  A  S  F  N  W  Q  H  N  G  R  Q  M  Y  V  A  L

AATGGAAAAGGAGCTCCAAGGAGAGGACAGAAAACACGAAGGAAAAACACCTCTGCTCAC
541  ---------+---------+---------+---------+---------+---------+  600
     TTACCTTTTCCTCGAGGTTCCTCTCCTGTCTTTTGTGCTTCCTTTTTGTGGAGACGAGTG

N  G  K  G  A  P  R  R  G  Q  K  T  R  R  K  N  T  S  A  H

TTTCTTCCAATGGTGGTACACTCATAG
601  ---------+---------+-------  627
     AAAGAAGGTTACCACCATGTGAGTATC

```
         1                                                         50
FGF4   MS.GPGTAAV ALLPAVLLAL LA........ .PWAGRGGAA APTAPNGTLE
FGF6   MSRGAGRLQG TLWALVFLGI LV........ .GMVVPSPAG TR.ANNTLLD
FGF5   .......MSL SFLLLLFFSH LILSAWAHGE KRLAPKGQPG PAATDRNPIG
FGF1   .......... .......... .......... .......... ..........
FGF2   .......... .......... .......... .......... ..........
FGF9   .......... .......... .......... ..MAPLGEVG NYFGVQDAVP
FGF7   .......... ......MHKW ILTWILPTLL .....YRSCF HIICLVGTIS
KGF2   .......... ......MWKW ILTHCASAFP HLPGCCCCCF LLLFLVSSVP
FGF3   .......... .......... .......... .......MGL IWLLLLSLLE
FGF8   MGSPRSALSC LLLHLLVLCL QAQVRSAAQK RGPGAGNPAD TLGQGHEDRP 51                                                        100
FGF4   AELERRWESL VALSLARLPV AA..QPKEAA VQSGAGDY.. ...LLGIKRL
FGF6   S...RGWGTL LSRSRAGLAG EI......AG VNWESG.Y.. ...LVGIKRQ
FGF5   SSSRQSSSSA MSSSSASSSP AASLGSQGSG LEQSSFQW.. ...SPSGRRT
FGF1   ......MAEG EITTFTALTE KFN...LPPG .......N.. ...YK...KP
FGF2   ......MAAG SITTLPALPE DGGSGAFPPG .......H.. ...FK...DP
FGF9   FGNVPVLPVD SPVLLSDHLG QSEAGGLPRG PAVTDLDH.. ...LKGILRR
FGF7   LACNDMTPEQ M...ATNVNC ......SSPE RHTRSYDY.. ...MEGGDIR
KGF2   VTCQALGQDM VSPEATNSSS SSFSSPSSAG RHVRSYNH.. ...LQ.GDVR
FGF3   PGWPAAGPGA .......... ...RLRRDAG GRGGVYEH.. ...L.GGAPR
FGF8   FGQRSRAGKN FTNPAPNYPE EGSKEQRDSV LPKVTQRHVR EQSLVTDQLS

MATCH WITH FIG. 2B
```

FIG. 2A

MATCH WITH FIG. 2A

```
         101                                                              150
FGF4     RRL.....YC  NVGIGFHLQA  LPDGRIGGAH  ADT.RDSLLE  LSPVERGV.V
FGF6     RRL.....YC  NVGIGFHLQV  LPDGRISGTH  EEN.PYSLLE  ISTVERGV.V
FGF5     GSL.....YC  RVGIGFHLQI  YPDGKVNGSH  EAN.MLSVLE  IFAVSQGI.V
FGF1     KLL.....YC  SNG.GHFLRI  LPDGTVDGTR  DRSDQHIQLQ  LSAESVGE.V
FGF2     KRL.....YC  KNG.GFFLRI  HPDGRVDGVR  EKSDPHIKLQ  LQAEERGV.V
FGF9     RQL.....YC  R.T.GFHLEI  FPNGTIQGTR  KDHSRFGILE  FISIAVGL.V
FGF7     VRR.....LF  CRT.QWYLRI  DKRGKVKGTQ  EMKNNYNIME  IRTVAVGI.V
KGF2     WRK.....LF  SFT.KYFLKI  EKNGKVSGTK  KENCPYSILE  ITSVEIGV.V
FGF3     RRK.....LY  CAT.KYHLQL  HPSGRVNGSL  .ENSAYSILE  ITAVEVGI.V
FGF8     RRLIRTYQLY  SRTSGKHVQV  LANKRINAMA  EDGDPFAKLI  VETDTFGSRV 151                                                              200
FGF4     SIFGVASRFF  VAMSSKGKLY  G.SPFFTDEC  TFKEILLPNN  YNAYESYKYP
FGF6     SLFGVRSALF  VAMNSKGRLY  A.TPSFQEEC  KFRETLLPNN  YNAYESDLYQ
FGF5     GIRGVFSNKF  LAMSKKGKLH  A.SAKFTDDC  KFRERFQENS  YNTYASAIHR
FGF1     YIKSTETGQY  LAMDTDGLLY  G.SQTPNEEC  LFLERLEENH  YNTYISKKH.
FGF2     SIKGVCANRY  LAMKEDGRLL  A.SKCVTDEC  FFFERLESNN  YNTYRSRKY.
FGF9     SIRGVDSGLY  LGMNEKGELY  G.SEKLTQEC  VFREQFEENW  YNTYSSNLYK
FGF7     AIKGVESEFY  LAMNKEGKLY  A.KKECNEDC  NFKELILENH  YNTYAS....
KGF2     AVKAINSNYY  LAMNKKGKLY  G.SKEFNNDC  KLKERIEENG  YNTYAS....
FGF3     AIRGLFSGRY  LAMNKRGRLY  A.SEHYSAEC  EFVERIHELG  YNTYASRLYR
FGF8     RVRGAETGLY  ICMNKKGKLI  AKSNGKGKDC  VFTEIVLENN  YTALQNAKY.
```

MATCH WITH FIG. 2C

FIG. 2B

MATCH WITH FIG. 2B

```
            201                                                           250
FGF4    ..........  GM......FI  ALSKNGKTKK  G..NRVSPTM  KVTHFLPRL.
FGF6    ..........  GT......YI  ALSKYGRVKR  G..SKVSPIM  TVTHFLPRI.
FGF5    ..........  TEKTGREWYV  ALNKRGKAKR  GCSPRVKPQH  ISTHFLPRFK
FGF1    ..........  ...AEKNWFV  GLKKNGSCKR  G..PRTHYGQ  KAILFLPLPV
FGF2    ..........  ...T..SWYV  ALKRTGQYKL  G..SKTGPGQ  KAILFLPMSA
FGF9    HV........  ..DTGRRYYV  ALNKDGTPRE  G..TRTKRHQ  KFTHFLPRPV
FGF7    .......AKW  THNGGEM.FV  ALNQKGIPVR  G..KKTKKEQ  KTAHFLPMAI
KGF2    .......FNW  QHNGRQM.YV  ALNGKGAPRR  G..QKTRRKN  TSAHFLPMVV
FGF3    TVSSTPGARR  QPSAERLWYV  SVNGKGRPRR  G..FKTRRTQ  KSSLFLPRVL
FGF8    ..........  .....EGWYM  AFTRKGRPRK  G..SKTRQHQ  REVHFMKRLP 251                                                           300
FGF4    ..........  ..........  ..........  ..........  ..........
FGF6    ..........  ..........  ..........  ..........  ..........
FGF5    QSEQPELSFT  VTVPEKKNPP  SPIKSKIPLS  APRKNTNSVK  YRLKFRFG..
FGF1    SSD.......  ..........  ..........  ..........  ..........
FGF2    KS........  ..........  ..........  ..........  ..........
FGF9    DPDKVPELYK  DILSQS....  ..........  ..........  ..........
FGF7    T.........  ..........  ..........  ..........  ..........
KGF2    HS........  ..........  ..........  ..........  ..........
FGF3    DHRDHEMVRQ  LQSGLPRPPG  KGVQPRRRRQ  KQSPDNLEPS  HVQASRLGSQ
FGF8    RGHHTTEQSL  RFEFLNYPPF  TRSLRGSQRT  WAPEPR....  ..........
```

MATCH WITH FIG. 2D

FIG. 2C

MATCH WITH FIG. 2C

301
    FGF4      . . . . . . .
    FGF6      . . . . . . .
    FGF5      . . . . . . .
    FGF1      . . . . . . .
    FGF2      . . . . . . .
    FGF9      . . . . . . .
    FGF7      . . . . . . .
    *KGF2*    . . . . . . .
    FGF3      LEASAH
    FGF8      . . . . . . .

FIG.2D

```
GGAATTCCGG GAAGAGAGGG AAGAAAACAA CGGCGACTGG GCAGCTGCCT CCACTTCTGA      60
CAACTCCAAA GGGATATACT TGTAGAAGTG GCTCGCAGGC TGGGGCTCCG CAGAGAGAGA     120
CCAGAAGGTG CCAACCGCAG AGGGGTGCAG ATATCTCCCC CTATTCCCCA CCCCACCTCC     180
CTTGGGTTTT GTTCACCGTG CTGTCATCTG TTTTTCAGAC CTTTTTGGCA TCTAACATGG     240
TGAAGAAAGG AGTAAAGAAG AGAACAAAGT AACTCCTGGG GGAGCGAAGA GCGCTGGTGA     300
CCAACACCAC CAACGCCACC ACCAGCTCCT GCTGCTGCGG CCACCCACGT CCACCATTTA     360
CCGGGAGGCT CCAGAGGCGT AGGCAGCGGA TCCGAGAAAG GAGCGAGGGG AGTCAGCCGG     420
CTTTTCCGAG GAGTTATGGA TGTTGGTGCA TTCACTTCTG GCCAGATCCG CGCCCAGAGG     480
GAGCTAACCA GCAGCCACCA CCTCGAGCTC TCTCCTTGCC TTGCATCGGG TCTTACCCTT     540
CCAGTATGTT CCTTCTGATG AGACAATTTC CAGTGCCGAG AGTTTCAGTA CA ATG         595
                                                          Met
```

```
TGG AAA TGG ATA CTG ACA CAT TGT GCC TCA GCC TTT CCC CAC CTG CCC       643
Trp Lys Trp Ile Leu Thr His Cys Ala Ser Ala Phe Pro His Leu Pro

GGC TGC TGC TGC TGC TGC TTT TTG TTG CTG TTC TTG GTG TCT TCC GTC       691
Gly Cys Cys Cys Cys Cys Phe Leu Leu Leu Phe Leu Val Ser Ser Val

CCT GTC ACC TGC CAA GCC CTT GGT CAG GAC ATG GTG TCA CCA GAG GCC       739
Pro Val Thr Cys Gln Ala Leu Gly Gln Asp Met Val Ser Pro Glu Ala

ACC AAC TCT TCT TCC TCC TCC TTC TCC TCT CCT TCC AGC GCG GGA AGG       787
Thr Asn Ser Ser Ser Ser Ser Phe Ser Ser Pro Ser Ser Ala Gly Arg

CAT GTG CGG AGC TAC AAT CAC CTT CAA GGA GAT GTC CGC TGG AGA AAG       835
His Val Arg Ser Tyr Asn His Leu Gln Gly Asp Val Arg Trp Arg Lys

CTA TTC TCT TTC ACC AAG TAC TTT CTC AAG ATT GAG AAG AAC GGG AAG       883
Leu Phe Ser Phe Thr Lys Tyr Phe Leu Lys Ile Glu Lys Asn Gly Lys

GTC AGC GGG ACC AAG AAG GAG AAC TGC CCG TAC AGC ATC CTG GAG ATA       931
Val Ser Gly Thr Lys Lys Glu Asn Cys Pro Tyr Ser Ile Leu Glu Ile

ACA TCA GTA GAA ATC GGA GTT GTT GCC GTC AAA GCC ATT AAC AGC AAC       979
Thr Ser Val Glu Ile Gly Val Val Ala Val Lys Ala Ile Asn Ser Asn

TAT TAC TTA GCC ATG AAC AAG AAG GGG AAA CTC TAT GGC TCA AAA GAA      1027
Tyr Tyr Leu Ala Met Asn Lys Lys Gly Lys Leu Tyr Gly Ser Lys Glu

TTT AAC AAT GAC TGT AAG CTG AAG GAG AGG ATA GAG GAA AAT GGA TAC      1075
Phe Asn Asn Asp Cys Lys Leu Lys Glu Arg Ile Glu Glu Asn Gly Tyr
```

FIG.3A

| | |
|---|---|
| AAT ACC TAT GCA TCA TTT AAC TGG CAG CAT AAT GGG AGG CAA ATG TAT<br>Asn Thr Tyr Ala Ser Phe Asn Trp Gln His Asn Gly Arg Gln Met Tyr | 1123 |
| GTG GCA TTG AAT GGA AAA GGA GCT CCA AGG AGA GGA CAG AAA ACA CGA<br>Val Ala Leu Asn Gly Lys Gly Ala Pro Arg Arg Gly Gln Lys Thr Arg | 1171 |
| AGG AAA AAC ACC TCT GCT CAC TTT CTT CCA ATG GTG GTA CAC TCA<br>Arg Lys Asn Thr Ser Ala His Phe Leu Pro Met Val Val His Ser | 1216 |
| TAGAGGAAGG CAACGTTTGT GGATGCAGTA AAACCAATGG CTCTTTTGCC AAGAATAGTG | 1276 |
| GATATTCTTC ATGAAGACAG TAGATTGAAA GGCAAAGACA CGTTGCAGAT GTCTGCTTGC | 1336 |
| TTAAAAGAAA GCCAGCCTTT GAAGGTTTTT GTATTCACTG CTGACATATG ATGTTCTTTT | 1396 |
| AATTAGTTCT GTGTCATGTC TTATAATCAA GATATAGGCA GATCGAATGG GATAGAAGTT | 1456 |
| ATTCCCAAGT GAAAAACATT GTGGCTGGGT TTTTTGTTGT TGTTGTCAAG TTTTTGTTTT | 1516 |
| TAAACCTCTG AGATAGAACT TAAAGGACAT AGAACAATCT GTTGAAAGAA CGATCTTCGG | 1576 |
| GAAAGTTATT TATGGAATAC GAACTCATAT CAAAGACTTC ATTGCTCATT CAAGCCTAAT | 1636 |
| GAATCAATGA ACAGTAATAC GTGCAAGCAT TTACTGGAAA GCACTTGGGT CATATCATAT | 1696 |
| GCACAACCAA AGGAGTTCTG GATGTGGTCT CATGGAATAA TTGAATAGAA TTTAAAAATA | 1756 |
| TAAACATGTT AGTGTGAAAC TGTTCTAACA ATACAAATAG TATGGTATGC TTGTGCATTC | 1816 |
| TGCCTTCATC CCTTTCTATT TCTTTCTAAG TTATTTATTT AATAGGATGT TAAATATCTT | 1876 |
| TTGGGGTTTT AAAGAGTATC TCAGCAGCTG TCTTCTGATT TATCTTTTCT TTTTATTCAG | 1936 |
| CACACCACAT GCATGTTCAC GACAAAGTGT TTTTAAAACT TGGCGAACAC TTCAAAAATA | 1996 |
| GGAGTTGGGA TTAGGGAAGC AGTATGAGTG CCCGTGTGCT ATCAGTTGAC TTAATTTGCA | 2056 |
| CTTCTGCAGT AATAACCATC AACAATAAAT ATGGCAATGC TGTGCCATGG CTTGAGTGAG | 2116 |
| AGATGTCTGC TATCATTTGA AAACATATAT TACTCTCGAG GCTTCCTGTC TCAAGAAATA | 2176 |
| GACCAGAAGG CCAAATTCTT CTCTTTCAAT ACATCAGTTT GCCTCCAAGA ATATACTAAA | 2236 |
| AAAAGGAAAA TTAATTGCTA AATACATTTA AATAGCCTAG CCTCATTATT TACTCATGAT | 2296 |
| TTCTTGCCAA ATGTCATGGC GGTAAAGAGG CTGTCCACAT CTCTAAAAAC CCTCTGTAAA | 2356 |
| TTCCACATAA TGCATCTTTC CCAAAGGAAC TATAAAGAAT TTGGTATGAA GCGCAACTCT | 2416 |

FIG.3B

```
CCCAGGGGCT TAAACTGAGC AAATCAAATA TATACTGGTA TATGTGTAAC CATATACAAA    2476
AACCTGTTCT AGCTGTATGA TCTAGTCTTT ACAAAACCAA ATAAAACTTG TTTTCTGTAA    2536
ATTTAAAGAG CTTTACAAGG TTCCATAATG TAACCATATC AAAATTCATT TTGTTAGAGC    2596
ACGTATAGAA AAGAGTACAT AAGAGTTTAC CAATCATCAT CACATTGTAT TCCACTAAAT    2656
AAATACATAA GCCTTATTTG CAGTGTCTGT AGTGATTTTA AAAATGTAGA AAAATACTAT    2716
TTGTTCTAAA TACTTTTAAG CAATAACTAT AATAGTATAT TGATGCTGCA GTTTTATCTT    2776
CATATTTCTT GTTTTGAAAA AGCATTTTAT TGTTTGGACA CAGTATTTTG GTACAAAAAA    2836
AAAGACTCAC TAAATGTGTC TTACTAAAGT TTAACCTTTG GAAATGCTGG CGTTCTGTGA    2896
TTCTCCAACA AACTTATTTG TGTCAATACT TAACCAGCAC TTCCAGTTAA TCTGTTATTT    2956
TTAAAAATTG CTTTATTAAG AAATTTTTTG TATAATCCCA TAAAAGGTCA TATTTTTCCC    3016
ATTCTTCAAA AAAACTGTAT TTCAGAAGAA ACACATTTGA GGCACTGTCT TTTGGCTTAT    3076
AGTTTAAATT GCATTTCATC ATACTTTGCT TCCAACTTGC TTTTTGGCAA ATGAGATTAT    3136
AAAAATGTTT AATTTTTGTG GTTGGAATCT GGATGTTAAA ATTTAATTGG TAACTCAGTC    3196
TGTGAGCTAT AATGTAATGC ATTCCTATCC AAACTAGGTA TCTTTTTTTC CTTTATGTTG    3256
AAATAATAAT GGCACCTGAC ACATAGACAT AGACCACCCA CAACCTAAAT TAAATGTTTG    3316
GTAAGACAAA TACACATTGG ATGACCACAG TAACAGCAAA CAGGGCACAA ACTGGATTCT    3376
TATTTCACAT AGACATTTAG ATTACTAAAG AGGGCTATGT GTAAACAGTC ATCATTATAG    3436
TACTCAAGAC ACTAAAACAG CTTCTAGCCA AATATATTAA AGCTTGCAGA GGCCAAAAAT    3496
AGAAAACATC TCCCCTGTCT CTCCCACATT TCCCTCACAG AAAGACAAAA AACCTGCCTG    3556
GTGCAGTAGC TCACACCTGT AATCCCAGCA GTTTGGGAGA CTGTGGGAAG ATGGCTTGAG    3616
TCCAGGAGTT CTAGACAGGC CTGAGAAACC TAGTGAGACA TCCTTCTCTT AAACAAAACA    3676
AAACAAAACA AATGTAGCCA TGCGTGGTGG CATATACCTG TGGTCCCAAC TACTCAGGAG    3736
GCTGAAACGG AAGGATCTCT TGGGCCCCAG GAGTTTGAGG CTGCAGTGAG CTATAATCTT    3796
GCCATTGCAC TCCAGCCTGG GTGAAAAAGA GCCAGAAAGA AGGAAAGAG AGAAAAGAGA    3856
AAAGAAAGAG AGAAAAGACA GAAAGACAGG AAGGAAGGAA GGAAGGAAGG AAGGAAGGAA    3916
GGAAGCAAGG AAAGAAGGAA GGAAGGAAAG AAGGGAGGGA AGGAAGGAGA GAGAAAGAAA    3976
GATTGTTTGG TAAGGAGTAA TGACATTCTC TTGCATTTAA AAGTGGCATA TTTGCTTGAA    4036
```

FIG.3C

ATGGAAATAG AATTCTGGTC CCTTTTGCAA CTACTGAAGA AAAAAAAAAG CAGTTTCAGC    4096
CCTGAATGTT GTAGATTTGA AAAAAAAAAA AAAAAAACTC GAGGGGGGGC CCGTACCCAA    4156
TTCGCCCTAT AGTGAGTCGT A                                              4177

FIG.3D 1-3 MINIMAL CELL ACCUMULATION, NO GRANULATION
4-6 IMMATURE GRANULATION, INFLAMMATORY CELLS, CAPILLARIES
10-12 FIBROBLASTS, COLLAGEN, EPITHELIUM 1-3 MINIMAL CELL ACCUMULATION, NO GRANULATION
4-6 IMMATURE GRANULATION, INFLAMMATORY CELLS, CAPILLARIES
7-9 GRANULATION TISSUE, CELLS, FIBROBLASTS, NEW EPITHELIUM
10-12 FIBROBLASTS, COLLAGEN, EPITHELIUM

ATGAGAGGATCGCATCACCATCACCATCACGGATCCTGCCAGGCTCTGGGTC
AGGACATGGTTTCTCCGGAAGCTACCAACTCTTCCTCTTCCTCTTTCTCTTCCC
CGTCTTCCGCTGGTCGTCACGTTCGTTCTTACAACCACCTGCAGGGTGACGTTC
GTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTG
GAGATAACATCAGTAGAAATCGGAGTTGTTGCCGTCAAAGCCATTAACAG
CAACTATTACTTAGCCATGAACAAGAAGGGGAAACTCTATGGCTCAAAAG
AATTTAACAATGACTGTAAGCTGAAGGAGAGGATAGAGGAAAATGGAT
ACAATACCTATGCATCATTTAACTGGCAGCATAATGGGAGGCAAATGTAT
GTGGCATTGAaTGGAAAAGGAGCTCCAaGGAGAGGACAGAAAACACGAAG
GAAAAACACCTCTGCTCACTTTCTTCCAATGGTGGTACACTCATAG

MRGSHHHHHGSCQALGQDMVSPEATNSSSSSFSSPSSAGRHVRSYNHLQGD
VRWRKLFSFTKYFLKIEKNGKVSGTKKENCPYSILEITSVEIGVVAVKAINSN
YYLAMNKKGKLYGSKEFNNDCKLKERIEENGYNTYASFNWQHNGRQMYVA
LNGKGAPRRGQKTRRKNTSAHFLPMVVHS kgf-2 synthetic cys37 Bam HI
AAAGGATCCTGCCAGGCTCTGGGTCAGGACATG

FIG.15

ATGTGGAAATGGATACTGACCCACTGCGCTTCTGCTTTCCCGCACCTGCCGGGTTGCTGC 60
Met Trp Lys Trp Ile Leu Thr His Cys Ala Ser Ala Phe Pro His Leu Pro Gly Cys Cys

TGCTGCTGCTTCCTGCTGCTGTTCCTGGTTTCTTCTGTTCCGGTTACCTGCCAGGCTCTG 120
Cys Cys Cys Phe Leu Leu Leu Phe Leu Val Ser Ser Val Pro Val Thr Cys Gln Ala Leu

GGTCAGGACATGGTTTCTCCGGAAGCTACCAACTCTTCCTCTTCCTCTTTCTCTTCCCCG 180
Gly Gln Asp Met Val Ser Pro Glu Ala Thr Asn Ser Ser Ser Ser Ser Phe Ser Ser Pro

ACTTCCGCTGGTCGTCACGTTCGTTCTTACAACCACCTGCAGGGTGACGTTCGTTGGCGT 240
Thr Ser Ala Gly Arg His Val Arg Ser Tyr Asn His Leu Gln Gly Asp Val Arg Trp Arg

AAACTGTTCTCTTTCACCAAATACTTCCTGAAAATCGAAAAAAACGGTAAAGTTTCTGGG 300
Lys Leu Phe Ser Phe Thr Lys Tyr Phe Leu Lys Ile Glu Lys Asn Gly Lys Val Ser Gly

ACCAAGAAGGAGAACTGCCCCGTACAGCATCCTGGAGATAACATCAGTAGAAATCGGAGTT 360
Thr Lys Lys Glu Asn Cys Pro Tyr Ser Ile Leu Glu Ile Thr Ser Val Glu Ile Gly Val

GTTGCCGTCAAAGCCATTAACAGCAACTATTACTTAGCCATGAACAAGAAGGGGAAACTC 420
Val Ala Val Lys Ala Ile Asn Ser Asn Tyr Tyr Leu Ala Met Asn Lys Lys Gly Lys Leu

TATGGCTCAAAAGAATTTAACAATGACTGTAAGCTGAAGGAGAGGATAGAGGAAAATGGA 480
Tyr Gly Ser Lys Glu Phe Asn Asn Asp Cys Lys Leu Lys Glu Arg Ile Glu Glu Asn Gly

TACAATACCTATGCATCATTTAACTGGCAGCATAATGGGAGGCAAATGTATGTGGCATTG 540
Tyr Asn Thr Tyr Ala Ser Phe Asn Trp Gln His Asn Gly Arg Gln Met Tyr Val Ala Leu

AATGGAAAAGGAGCTCCAAGGAGAGGACAGAAAACACGAAGGAAAAACACCTCTGCTCAC 600
Asn Gly Lys Gly Ala Pro Arg Arg Gly Gln Lys Thr Arg Arg Lys Asn Thr Ser Ala His

TTTCTTCCAATGGTGGTACACTCATAG 627
Phe Leu Pro Met Val Val His Ser *

FIG.23

```
ATGACCTGCCAGGCTCTGGGTCAGGACATGGTTTCTCCGGAAGCTACCAACTCTTCCTCT    60
MetThrCysGlnAlaLeuGlyGlnAspMetValSerProGluAlaThrAsnSerSerSer

TCCTCTTTCTCTTCCCCGTCTTCCGCTGGTCGTCACGTTCGTTCTTACAACCACCTGCAG   120
SerSerPheSerSerProSerSerAlaGlyArgHisValArgSerTyrAsnHisLeuGln

GGTGACGTTCGTTGGCGTAAACTGTTCTCTTTCACCAAATACTTCCTGAAAATCGAAAAA   180
GlyAspValArgTrpArgLysLeuPheSerPheThrLysTyrPheLeuLysIleGluLys

AACGGTAAAGTTTCTGGGACCAAGAAGGAGAACTGCCCGTACAGCATCCTGGAGATAACA   240
AsnGlyLysValSerGlyThrLysLysGluAsnCysProTyrSerIleLeuGluIleThr

TCAGTAGAAATCGGAGTTGTTGCCGTCAAAGCCATTAACAGCAACTATTACTTAGCCATG   300
SerValGluIleGlyValValAlaValLysAlaIleAsnSerAsnTyrTyrLeuAlaMet

AACAAGAAGGGGAAACTCTATGGCTCAAAAGAATTTAACAATGACTGTAAGCTGAAGGAG   360
AsnLysLysGlyLysLeuTyrGlySerLysGluPheAsnAsnAspCysLysLeuLysGlu

AGGATAGAGGAAAATGGATACAATACCTATGCATCATTTAACTGGCAGCATAATGGGAGG   420
ArgIleGluGluAsnGlyTyrAsnThrTyrAlaSerPheAsnTrpGlnHisAsnGlyArg

CAAATGTATGTGGCATTGAATGGAAAAGGAGCTCCAAGGAGAGGACAGAAAACACGAAGG   480
GlnMetTyrValAlaLeuAsnGlyLysGlyAlaProArgArgGlyGlnLysThrArgArg

AAAAACACCTCTGCTCACTTTCTTCCAATGGTGGTACACTCATAG   525
LysAsnThrSerAlaHisPheLeuProMetValValHisSer *
```

FIG.24A

```
ATGACTTGCCAGGCACTGGGTCAAGACATGGTTTCCCCGGAAGCTACCAACAGCTCCAGCTCTAGCTTCA
|----|----|----|----|----|----|----|----|----|----|----|----|----|----|  70
TACTGAACGGTCCGTGACCCAGTTCTGTACCAAAGGGGCCTTCGATGGTTGTCGAGGTCGAGATCGAAGT
  M  T  C  Q  A  L  G  Q  D  M  V  S  P  E  A  T  N  S  S  S  S  F

GCAGCCCATCTAGCGCAGGTCGTCACGTTCGCTCTTACAACCACTTACAGGGTGATGTTCGTTGGCGCAA
|----|----|----|----|----|----|----|----|----|----|----|----|----|----| 140
CGTCGGGTAGATCGCGTCCAGCAGTGCAAGCGAGAATGTTGGTGAATGTCCCACTACAAGCAACCGCGTT
   S  S  P  S  S  A  G  R  H  V  R  S  Y  N  H  L  Q  G  D  V  R  W  R  K

ACTGTTCAGCTTTACCAAGTACTTCCTGAAAATCGAAAAAAACGGTAAAGTTTCTGGGACCAAGAAGGAG
|----|----|----|----|----|----|----|----|----|----|----|----|----|----| 210
TGACAAGTCGAAATGGTTCATGAAGGACTTTTAGCTTTTTTTGCCATTTCAAAGACCCTGGTTCTTCCTC
   L  F  S  F  T  K  Y  F  L  K  I  E  K  N  G  K  V  S  G  T  K  K  E

AACTGCCCGTACAGCATCCTGGAGATAACATCAGTAGAAATCGGAGTTGTTGCCGTCAAAGCCATTAACA
|----|----|----|----|----|----|----|----|----|----|----|----|----|----| 280
TTGACGGGCATGTCGTAGGACCTCTATTGTAGTCATCTTTAGCCTCAACAACGGCAGTTTCGGTAATTGT
   N  C  P  Y  S  I  L  E  I  T  S  V  E  I  G  V  V  A  V  K  A  I  N

GCAACTATTACTTAGCCATGAACAAGAAGGGGAAACTCTATGGCTCAAAAGAATTTAACAATGACTGTAA
|----|----|----|----|----|----|----|----|----|----|----|----|----|----| 350
CGTTGATAATGAATCGGTACTTGTTCTTCCCCTTTGAGATACCGAGTTTTCTTAAATTGTTACTGACATT
   S  N  Y  Y  L  A  M  N  K  K  G  K  L  Y  G  S  K  E  F  N  N  D  C  K

GCTGAAGGAGAGGATAGAGGAAAATGGATACAATACCTATGCATCATTTAACTGGCAGCATAATGGGAGG
|----|----|----|----|----|----|----|----|----|----|----|----|----|----| 420
CGACTTCCTCTCCTATCTCCTTTTACCTATGTTATGGATACGTAGTAAATTGACCGTCGTATTACCCTCC
   L  K  E  R  I  E  E  N  G  Y  N  T  Y  A  S  F  N  W  Q  H  N  G  R

CAAATGTATGTGGCATTGAATGGAAAAGGAGCTCCAAGGAGAGGACAGAAAACACGAAGGAAAAACACCT
|----|----|----|----|----|----|----|----|----|----|----|----|----|----| 490
GTTTACATACACCGTAACTTACCTTTTCCTCGAGGTTCCTCTCCTGTCTTTTGTGCTTCCTTTTTGTGGA
   Q  M  Y  V  A  L  N  G  K  G  A  P  R  R  G  Q  K  T  R  R  K  N  T

CTGCTCACTTTCTTCCAATGGTGGTACACTCATAG
|----|----|----|----|----|----|-->  525
GACGAGTGAAAGAAGGTTACCACCATGTGAGTATC
   S  A  H  F  L  P  M  V  V  H  S
```

FIG.24B

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
KERIEENGYNTYASFNWQHNGRQMYVALNGKGAPRRGQKTRRKNTSAHFLPMVVHS.

FIG. 25

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAGGAGAGGATA
GAGGAAAATGGATACAATACCTATGCATCATTTAACTGGCAGCATAATGGGAGGCAA
ATGTATGTGGCATTGAATGGAAAAGGAGCTCCAAGGAGAGGACAGAAAACACGAAGG
AAAAACACCTCTGCTCACTTTCTTCCAATGGTGGTACACTCATAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLKERIEENGYNTYASFNWQHNGRQMYVA
LNGKGAPRRGQKTRRKNTSAHFLPMVVHS.

FIG. 26

ATGGTTCGTTGGCGTAAACTGTTCTCTTTCACCAAATACTTCCTGAAAATCGAAAAA
AACGGTAAAGTTTCTGGGACCAAGAAGGAGAACTGCCCGTACAGCATCCTGGAGATA
ACATCAGTAGAAATCGGAGTTGTTGCCGTCAAAGCCATTAACAGCAACTATTACTTA
GCCATGAACAAGAAGGGGAAACTCTATGGCTCAAAAGAATTTAACAATGACTGTAAG
CTGAAGGAGAGGATAGAGGAAAATGGATACAATACCTATGCATCATTTAACTGGCAG
CATAATGGGAGGCAAATGTATGTGGCATTGAATGGAAAAGGAGCTCCAAGGAGAGGA
CAGAAAACACGAAGGAAAAACACCTCTGCTCACTTTCTTCCAATGGTGGTACACTCA
TAG

MVRWRKLFSFTKYFLKIEKNGKVSGTKKENCPYSILEITSVEIGVVAVKAINSNYYLAM
NKKGKLYGSKEFNNDCKLKERIEENGYNTYASFNWQHNGRQMYVALNGKGAPRRGQKTR
RKNTSAHFLPMVVHS.

FIG.27

ATGGAAAAAAACGGTAAAGTTTCTGGGACCAAGAAGGAGAACTGCCCGTACAGCAT
CCTGGAGATAACATCAGTAGAAATCGGAGTTGTTGCCGTCAAAGCCATTAACAGCA
ACTATTACTTAGCCATGAACAAGAAGGGGAAACTCTATGGCTCAAAAGAATTTAAC
AATGACTGTAAGCTGAAGGAGAGGATAGAGGAAAATGGATACAATACCTATGCATC
ATTTAACTGGCAGCATAATGGGAGGCAAATGTATGTGGCATTGAATGGAAAAGGAG
CTCCAAGGAGAGGACAGAAAACACGAAGGAAAAACACCTCTGCTCACTTTCTTCCA
ATGGTGGTACACTCATAG

MEKNGKVSGTKKENCPYSILEITSVEIGVVAVKAINSNYYLAMNKKGKLYGSKEFNNDC
KLKERIEENGYNTYASFNWQHNGRQMYVALNGKGAPRRGQKTRRKNTSAHFLPMVVH
S.

FIG.28

ATGGAGAACTGCCCGTACAGCATCCTGGAGATAACATCAGTAGAAATCGGAGTTGT
TGCCGTCAAAGCCATTAACAGCAACTATTACTTAGCCATGAACAAGAAGGGGAAAC
TCTATGGCTCAAAAGAATTTAACAATGACTGTAAGCTGAAGGAGAGGATAGAGGAA
AATGGATACAATACCTATGCATCATTTAACTGGCAGCATAATGGGAGGCAAATGTA
TGTGGCATTGAATGGAAAAGGAGCTCCAAGGAGAGGACAGAAAACACGAAGGAAAA
ACACCTCTGCTCACTTTCTTCCAATGGTGGTACACTCATAG

MENCPYSILEITSVEIGVVAVKAINSNYYLAMNKKGKLYGSKEFNNDCKLKERIEENGY
NTYASFNWQHNGRQMYVALNGKGAPRRGQKTRRKNTSAHFLPMVVHS.

FIG.29

ATGGTCAAAGCCATTAACAGCAACTATTACTTAGCCATGAACAAGAAGGGGAAACT
CTATGGCTCAAAAGAATTTAACAATGACTGTAAGCTGAAGGAGAGGATAGAGGAAA
ATGGATACAATACCTATGCATCATTTAACTGGCAGCATAATGGGAGGCAAATGTAT
GTGGCATTGAATGGAAAAGGAGCTCCAAGGAGAGGACAGAAAACACGAAGGAAAAA
CACCTCTGCTCACTTTCTTCCAATGGTGGTACACTCATAG

MVKAINSNYYLAMNKKGKLYGSKEFNNDCKLKERIEENGYNTYASFNWQHNGRQMY
VALNGKGAPRRGQKTRRKNTSAHFLPMVVHS.

FIG.30

ATGGGGAAACTCTATGGCTCAAAAGAATTTAACAATGACTGTAAGCTGAAGGAGAG
GATAGAGGAAAATGGATACAATACCTATGCATCATTTAACTGGCAGCATAATGGGA
GGCAAATGTATGTGGCATTGAATGGAAAAGGAGCTCCAAGGAGAGGACAGAAAACA
CGAAGGAAAAACACCTCTGCTCACTTTCTTCCAATGGTGGTACACTCATAG

MGKLYGSKEFNNDCKLKERIEENGYNTYASFNWQHNGRQMYVALNGKGAPRRGQKT
RRKNTSAHFLPMVVHS.

FIG.31

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAG

MTCQALGQDMVSPEATNSSSSSFSSPSSAGRHVRSYNHLQGDVRWRKLFSFTKYFLKIE
KNGKVSGTKKENCPYSILEITSVEIGVVAVKAINSNYYLAMNKKGKLYGSKEFNNDCKL
K

FIG.32

ATGGCTGGTCGTCACGTTCGTTCTTACAACCACCTGCAGGGTGACGTTCGTTGGCGT
AAACTGTTCTCTTTCACCAAATACTTCCTGAAAATCGAAAAAAACGGTAAAGTTTCT
GGGACCAAGAAGGAGAACTGCCCGTACAGCATCCTGGAGATAACATCAGTAGAAATC
GGAGTTGTTGCCGTCAAAGCCATTAACAGCAACTATTACTTAGCCATGAACAAGAAG
GGGAAACTCTATGGCTCAAAAGAATTTAACAATGACTGTAAGCTGAAG

MAGRHVRSYNHLQGDVRWRKLFSFTKYFLKIEKNGKVSGTKKENCPYSILEITSVEIGV
VAVKAINSNYYLAMNKKGKLYGSKEFNNDCKLK

FIG.33

C-37 To Ser

ATGACCTCTCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTGCCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG.34

C-106 To Ser

ATGACCTGCCAGGCTCTGGGTCAGGACATGGTTTCTCCGGAAGCTACCAACTCTTCC
TCTTCCTCTTTCTCTTCCCCGTCTTCCGCTGGTCGTCACGTTCGTTCTTACAACCAC
CTGCAGGGTGACGTTCGTTGGCGTAAACTGTTCTCTTTCACCAAATACTTCCTGAAA
ATCGAAAAAAACGGTAAAGTTTCTGGGACCAAGAAGGAGAACTCTCCGTACAGCATC
CTGGAGATAACATCAGTAGAAATCGGAGTTGTTGCCGTCAAAGCCATTAACAGCAAC
TATTACTTAGCCATGAACAAGAAGGGGAAACTCTATGGCTCAAAAGAATTTAACAAT
GACTGTAAGCTGAAGGAGAGGATAGAGGAAAATGGATACAATACCTATGCATCATTT
AACTGGCAGCATAATGGGAGGCAAATGTATGTGGCATTGAATGGAAAAGGAGCTCCA
AGGAGAGGACAGAAAACACGAAGGAAAAACACCTCTGCTCACTTTCTTCCAATGGTG
GTACACTCATAG

FIG.35

EFFECT OF KGF-2 Δ33 ON NORMAL WOUND HEALING RAT MODEL

| TREATMENT GROUPS | WOUND SIZE (mm) | % WOUND CLOSURE | HISTOLOGICAL SCORE | RE-EPITH. (μm) | BrdU SCORE |
|---|---|---|---|---|---|
| NO TREATMENT | 25.9±2.5 | 58.8±3.7 | 6.8±0.2 | 1142±141 | 3.8±0.4 |
| BUFFER | 25.1±1.7 | 60.2±2.6 | 6.4±0.2 | 923±61 | 5.0±0.4 |
| KGF-2/Δ33 (0.1μg) | 22.0±0.9 | 65±1.4 | 6.8±0.2 | 1275±148 | 4.6±0.7 |
| KGF-2/Δ33 (0.4μg) | 21.1±1.4 | 68.4±2.4 | 8.0±0.5* $p=0.0445$ | 1310±182 | 4.2±0.7 |
| KGF-2/Δ33 (1.0μg) | 19.9±1.5 | 66.2±2.1 | 8.4±0.4* $p=0.0159$ $p=0.0053$† | 1389±115 $p=0.0074$† | 3.3±0.25 $p=0.0217$† |
| KGF-2/Δ33 (4.0μg) | 18.1±1.6* $p=0.0398$ $p=0.0200$† | 71.2±2.6* $p=0.0367$ $p=0.0217$† | 8.5±0.3* $p=0.0047$ $p=0.0445$† | 1220±89 $p=0.0254$† | 5.3±0.9 |

FIG.37

```
                                          -35         Operator 1
1   AAGCTTAAAAAACTGCAAAAAATAGT TTGACT TGTGAGCGGATAACAAT -10              Operator 2
50   TAAGAT GTACCCA ATTGTGAGCGGATAACAAT TTCACACATTAA

S/D
94   A GAGGAG AAATTA  CATATG
```

FIG. 51

KERATINOCYTE GROWTH FACTOR-2

CROSS-REFERENCE TO RELATED APPLICATIONS

The present application claims benefit under 35 U.S.C. § 119(e) of U.S. Provisional Application Nos. 60/205,417, filed May 19, 2000; 60/198,322, filed Apr. 19, 2000; 60/171,677, filed Dec. 22, 1999; 60/163,375, filed Nov. 3, 1999; 60/149,935, filed Aug. 19, 1999; 60/148,628, filed Aug. 12, 1999; 60/144,024, filed Jul. 15, 1999; 60/143,648, filed Jul. 14, 1999; and 60/142,343, filed Jul. 2, 1999; said present application is a continuation-in-part of U.S. application Ser. Nos. 09/345,373, filed Jul. 1, 1999 and 08/696,135, filed Aug. 13, 1996; said U.S. application Ser. No. 09/345,373 is a continuation of U.S. application Ser. No. 09/023,082, filed Feb. 13, 1998, now U.S. Pat. No. 6,077,692, issued Jun. 20, 2000, which is a continuation-in-part of U.S. application Ser. Nos. 08/910,875, filed Aug. 13, 1997 and 08/862,432, filed May 23, 1997; said U.S. application Ser. No. 09/023,082 claims benefit under 35 U.S.C. § 119(e) of U.S. Provisional Application Nos. 60/039,045, filed Feb. 28, 1997 and 60/055,561, filed Aug. 13, 1997; said U.S. application Ser. No. 08/910,875 claims benefit under 35 U.S.C. § 119(e) of U.S. Provisional Application Ser. No. 60/023,852, filed Aug. 13, 1996; said U.S. application Ser. No. 08/862,432 is a divisional of U.S. application Ser. No. 08/461,195, filed Jun. 5, 1995, which is a continuation-in-part of International Application No. PCT/US95/01790, filed Feb. 14, 1995; said U.S. application Ser. No. 08/696,135 is a continuation-in-part of U.S. application Ser. No. 08/461,195, filed Jun. 5, 1995, which is a continuation-in-part of International Application No. PCT/US95/01790, filed Feb. 14, 1995; all of which are incorporated by reference herein in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a Keratinocyte Growth Factor, sometimes hereinafter referred to as "KGF-2" also formerly known as Fibroblast Growth Factor 12 (FGF-12). This invention further relates to the therapeutic use of KGF-2 to promote or accelerate wound healing. This invention also relates to novel mutant forms of KGF-2 that show enhanced activity, increased stability, higher yield or better solubility. In addition, this invention relates to a method of purifying the KGF-2 polypeptide.

BACKGROUND OF THE INVENTION

The fibroblast growth factor family has emerged as a large family of growth factors involved in soft-tissue growth and regeneration. It presently includes several members that share a varying degree of homology at the protein level, and that, with one exception, appear to have a similar broad mitogenic spectrum, i.e., they promote the proliferation of a variety of cells of mesodermal and neuroectodermal origin and/or promote angiogenesis.

The pattern of expression of the different members of the family is very different, ranging from extremely restricted expressions of some stages of development, to rather ubiquitous expression in a variety of tissues and organs. All the members appear to bind heparin and heparin sulfate proteoglycans and glycosaminoglycans and strongly concentrate in the extracellular matrix. KGF was originally identified as a member of the FGF family by sequence homology or factor purification and cloning. Keratinocyte growth factor (KGF) was isolated as amitogen for a cultured murine keratinocyte line (Rubin, J. S. et al., *Proc. Natl. Acad Sci. USA* 86:802–806 (1989)). Unlike the other members of the FGF family, it has little activity on mesenchyme-derived cells but stimulates the growth of epithelial cells. The Keratinocyte growth factor gene encodes a 194-amino acid polypeptide (Finch, P. W. et al., *Science* 245:752–755 (1989)). The N-terminal 64 amino acids are unique, but the remainder of the protein has about 30% homology to bFGF. KGF is the most divergent member of the FGF family. The molecule has a hydrophobic signal sequence and is efficiently secreted. Post-translational modifications include cleavage of the signal sequence and N-linked glycosylation at one site, resulting in a protein of 28 kDa. Keratinocyte growth factor is produced by fibroblast derived from skin and fetal lung (Rubin et al. (1989)). The Keratinocyte growth factor mRNA was found to be expressed in adult kidney, colon and ilium, but not in brain or lung (Finch, P. W. et al. *Science* 245:752–755 (1989)). KGF displays the conserved regions within the FGF protein family. KGF binds to the FGF-2 receptor with high affinity.

Impaired wound healing is a significant source of morbidity and may result in such complications as dehiscence, anastomotic breakdown and, non-healing wounds. In the normal individual, wound healing is achieved uncomplicated. In contrast, impaired healing is associated with several conditions such as diabetes, infection, immunosuppression, obesity and malnutrition (Cruse, P. J. and Foord, R., *Arch. Surg.* 107:206 (1973); Schrock, T. R. et al., *Ann. Surg.* 177:513 (1973); Poole, G. U., Jr., *Surgery* 97:631 (1985); Irvin, G. L. et al., *Am. Surg.* 51:418 (1985)).

Wound repair is the result of complex interactions and biologic processes. Three phases have been described in normal wound healing: acute inflammatory phase, extracellular matrix and collagen synthesis, and remodeling (Peacock, E. E., Jr., *Wound Repair*, 2nd edition, WB Saunders, Philadelphia (1984)). The process involves the interaction of keratinocytes, fibroblasts and inflammatory cells at the wound site.

Tissue regeneration appears to be controlled by specific peptide factors which regulate the migration and proliferation of cells involved in the repair process (Barrett, T. B. et al., *Proc. Natl. Acad. Sci. USA* 81:6772–6774 (1985); Collins, T. et al., *Nature* 316:748–750 (1985)). Thus, growth factors may be promising therapeutics in the treatment of wounds, burns and other skin disorders (Rifkin, D. B. and Moscatelli, *J. Cell. Biol.* 109:1–6 (1989); Sporn, M. B. et al, *J. Cell. Biol.* 105:1039–1045 (1987); Pierce, G. F. et al, *J. Cell Biochem.* 45;319–326 (1991)). The sequence of the healing process is initiated during an acute inflammatory phase with the deposition of provisional tissue. This is followed by re-epithelialization, collagen synthesis and deposition, fibroblast proliferation, and neovascularization, all of which ultimately define the remodeling phase (Clark, R. A. F., *J. Am. Acad. Dermatol.* 13:701 (1985)). These events are influenced by growth factors and cytokines secreted by inflammatory cells or by the cells localized at the edges of the wound (Assoian, R. K. et al., *Nature* (Lond.) 309:804 (1984); Nemeth, G. G. et al., "Growth Factors and Their Role in Wound and Fracture Healing," *Growth Factors and Other Aspects of Wound Healing in Biological and Clinical Implications*, New York (1988), pp. 1–17.

Several polypeptide growth factors have been identified as being involved in wound healing, including keratinocyte growth factor (KGF) (Antioniades, H. et al., *Proc. Natl. Acad. Sci. USA* 88:565 (1991)), platelet derived growth factor (PDGF)(Antioniades, H. et al., *Proc. Natl. Acad. Sci. USA* 88:565 (1991); Staiano-Coico, L. et al., *Jour. Exp. Med.* 178:865–878 (1993)), basic fibroblast growth factor (bFGF) (Golden, M. A. et al., *J. Clin. Invest.* 87:406 (1991)), acidic fibroblast growth factor (aFGF) (Mellin, T. N. et al., *J. Invest. Dermatol.* 104:850–855 (1995)), epidermal growth factor (EGF) (Whitby, D. J. and Ferguson, W. J., *Dev. Biol.* 147:207 (1991)), transforming growth factor-α (TGF-α) (Gartner, M. H. et al., *Surg. Forum* 42:643 (1991); Todd, R. et al., *Am. J. Pathol.* 138;1307 (1991)), transforming growth factor-β (TGF-β) (Wong, D. T. W. et al., *Am. J. Pathol.* 143:622 (1987)), neu differentiation factor (rNDF) (Danilenko, D. M. et al., *J. Clin. Invest.* 95;842–851 (1995)), insulin-like growth factor I (IGF-1), and insulin-like growth factor II (IGF-II) (Cromack, D. T. et al., *J. Surg. Res.* 42:622 (1987)).

It has been reported that rKGF-1 in the skin stimulates epidermal keratinocytes, keratinocytes within hair follicles and sebaceous glands (Pierce, G. F. et al., *J. Exp. Med.* 179:831–840 (1994)).

SUMMARY OF THE INVENTION

The present invention provides isolated nucleic acid molecules comprising a polynucleotide encoding the keratinocyte growth factor (KGF-2) having the amino acid sequence as shown in FIG. 1 [SEQ ID NO:2] or the amino acid sequence encoded by the cDNA clones deposited as ATCC Deposit Number 75977 on Dec. 16, 1994. The nucleotide sequence determined by sequencing the deposited KGF-2 clone, which is shown in FIG. 1 [SEQ ID NO:1], contains an open reading frame encoding a polypeptide of 208 amino acid residues, including an initiation codon at positions 1–3, with a predicted leader sequence of about 35 or 36 amino acid residues, and a deduced molecular weight of about 23.4 kDa. The amino acid sequence of the mature KGF-2 is shown in FIG. 1, amino acid residues about 36 or 37 to 208 [SEQ ID NO:2].

The polypeptide of the present invention has been putatively identified as a member of the FGF family, more particularly the polypeptide has been putatively identified as KGF-2 as a result of amino acid sequence homology with other members of the FGF family.

In accordance with one aspect of the present invention, there are provided novel mature polypeptides which are KGF-2 as well as biologically active and diagnostically or therapeutically useful fragments, analogs and derivatives thereof. The polypeptides of the present invention are of human origin.

In accordance with another aspect of the present invention, there are provided isolated nucleic acid molecules encoding human KGF-2, including mRNAs, DNAs, cDNAs, genomic DNA, as well as antisense analogs thereof, and biologically active and diagnostically or therapeutically useful fragments thereof.

In accordance with another aspect of the present invention, there is provided a process for producing such polypeptide by recombinant techniques through the use of recombinant vectors, such as cloning and expression plasmids useful as reagents in the recombinant production of KGF-2 proteins, as well as recombinant prokaryotic and/or eukaryotic host cells comprising a human KGF-2 nucleic acid sequence.

In accordance with yet a further aspect of the present invention, there is provided a process for utilizing such polypeptide, or polynucleotide encoding such polypeptide for therapeutic purposes, for example, to stimulate epithelial cell proliferation and basal keratinocytes for the purpose of wound healing, and to stimulate hair follicle production and healing of dermal wounds. KGF-2 may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. KGF-2 can be used to promote dermal reestablishment subsequent to dermal loss.

KGF-2 can be used to increase the adherence of skin grafts to a wound bed and to stimulate re-epithelialization from the wound bed. The following are types of grafts that KGF-2 could be used to increase adherence to a wound bed: autografts, artificial skin, allografts, autodermic grafts, autoepidermic grafts, avacular grafts, Blair-Brown grafts, bone grafts, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, or thick split graft. KGF-2 can be used to promote skin strength and to improve the appearance of aged skin.

It is believed that KGF-2 will also produce changes in hepatocyte proliferation, and epithelial cell proliferation in the lung, breast, pancreas, stomach, small intestine, and large intestine. KGF-2 can promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. KGF-2 can promote proliferation of endothelial cells, keratinocytes, and basal keratinocytes.

KGF-2 can also be used to reduce the side effects of gut toxicity that result from radiation, chemotherapy treatments or viral infections. KGF-2 may have a cytoprotective effect on the small intestine mucosa. KGF-2 may also stimulate healing of mucositis (mouth ulcers) that result from chemotherapy and viral infections.

KGF-2 can further be used in full regeneration of skin in full and partial thickness skin defects, including burns, (i.e., repopulation of hair follicles, sweat glands, and sebaceous glands), treatment of other skin defects such as psoriasis. KGF-2 can be used to treat epidermolysis bullosa, a defect in adherence of the epidermis to the underlying dermis which results in frequent, open and painful blisters by accelerating reepithelialization of these lesions. KGF-2 can also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, KGF-2 could be used to promote the resurfacing of the mucosal surface to aid more rapid healing and to prevent progression of inflammatory bowel disease. KGF-2 treatment is expected to have a significant effect on the production of mucus throughout the gastrointestinal tract and could be used to protect the intestinal mucosa from injurious substances that are ingested or following surgery. KGF-2 can be used to treat diseases associated with the under expression of KGF-2.

Moreover, KGF-2 can be used to prevent and heal damage to the lungs due to various pathological states. A growth factor such as KGF-2 which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated with KGF-2. Also, KGF-2 could be used to stimulate the proliferation of and differentiation of type II pneumocytes, which may help treat or prevent disease such as hyaline membrane diseases, such as infant respiratory distress syndrome and bronchopulmonary displasia, in premature infants.

KGF-2 could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetrachloride and other hepatotoxins known in the art).

In addition, KGF-2 could be used treat or prevent the onset of diabetes mellitus. In patients with newly diagnosed Types I and II diabetes, where some islet cell function remains, KGF-2 could be used to maintain the islet function so as to alleviate, delay or prevent permanent manifestation of the disease. Also, KGF-2 could be used as an auxiliary in islet cell transplantation to improve or promote islet cell function.

In accordance with yet a further aspect of the present invention, there are provided antibodies against such polypeptides.

In accordance with another aspect of the present invention, there are provided nucleic acid probes comprising nucleic acid molecules of sufficient length to specifically hybridize to human KGF-2 sequences.

In accordance with a further aspect of the present invention, there are provided mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2.

In accordance with yet another aspect of the present invention, there are provided antagonists to such polypeptides, which may be used to inhibit the action of such polypeptides, for example, to reduce scarring during the wound healing process and to prevent and/or treat tumor proliferation, diabetic retinopathy, rheumatoid arthritis, oesteoarthritis and tumor growth. KGF-2 antagonists can also be used to treat diseases associated with the over expression of KGF-2.

In accordance with yet another aspect of the present invention, there are provided diagnostic assays for detecting diseases or susceptibility to diseases related to mutations in KGF-2 nucleic acid sequences or over-expression of the polypeptides encoded by such sequences.

In accordance with another aspect of the present invention, there is provided a process for utilizing such polypeptides, or polynucleotides encoding such polypeptides, for in vitro purposes related to scientific research, synthesis of DNA and manufacture of DNA vectors.

Thus, one aspect of the invention provides an isolated nucleic acid molecule comprising a polynucleotide having a nucleotide sequence selected from the group consisting of: (a) a nucleotide sequence encoding the KGF-2 polypeptide having the complete amino acid sequence in FIG. 1 [SEQ ID NO:2]; (b) a nucleotide sequence encoding the mature KGF-2 polypeptide having the amino acid sequence at positions 36 or 37 to 208 in FIG. 1 [SEQ ID NO:2]; (c) a nucleotide sequence encoding the KGF-2 polypeptide having the complete amino acid sequence encoded by the cDNA clone contained in ATCC Deposit No. 75977; (d) a nucleotide sequence encoding the mature KGF-2 polypeptide having the amino acid sequence encoded by the cDNA clone contained in ATCC Deposit No.75977; and (e) a nucleotide sequence complementary to any of the nucleotide sequences in (a), (b), (c) or (d) above. p Further embodiments of the invention include isolated nucleic acid molecules that comprise a polynucleotide having a nucleotide sequence at least 80% identical, and more preferably at least 85%, 90%, 91%, 92%, 93%, 94%, 95%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a KGF-2 having an amino acid sequence in (a), (b), (c) or (d), above.

The invention further provides an isolated KGF-2 polypeptide having amino acid sequence selected from the group consisting of: (a) the amino acid sequence of the KGF-2 polypeptide having the complete 208 amino acid sequence, including the leader sequence shown in FIG. 1 [SEQ ID NO:2]; (b) the amino acid sequence of the mature KGF-2 polypeptide (without the leader) having the amino acid sequence at positions 36 or 37 to 208 in FIG. 1 [SEQ ID NO:2]; (c) the amino acid sequence of the KGF-2 polypeptide having the complete amino acid sequence, including the leader, encoded by the cDNA clone contained in ATCC Deposit No.75977; and (d) the amino acid sequence of the mature KGF-2 polypeptide having the amino acid sequence encoded by the cDNA clone contained in ATCC Deposit No. 75977. The polypeptides of the present invention also include polypeptides having an amino acid sequence with at least 80% similarity, and more preferably at least 90%, 95%, 96%, 97%, 98% or 99% similarity to those described in (a), (b), (c) or (d) above, as well as polypeptides having an amino acid sequence at least 80% identical, more preferably at least 85% identical, and still more preferably 90%, 91%, 92%, 93%, 94%, 95%, 97%, 98% or 99% identical to those above.

An additional aspect of the invention relates to a peptide or polypeptide which has the amino acid sequence of an epitope-bearing portion of a KGF-2 polypeptide having an amino acid sequence described in (a), (b), (c) or (d), above. Peptides or polypeptides having the amino acid sequence of an epitope-bearing portion of a KGF-2 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a KGF-2 polypeptide having an amino acid sequence described in (a), (b), (c) or (d) above.

In accordance with another aspect of the present invention, novel variants of KGF-2 are described. These can be produced by deleting or substituting one or more amino acids of KGF-2. Natural mutations are called allelic variations. Allelic variations can be silent (no change in the encoded polypeptide) or may have altered amino acid sequence. In order to attempt to improve or alter the characteristics of native KGF-2, protein engineering may be employed. Recombinant DNA technology known in the art can be used to create novel polypeptides. Muteins and deletion mutations can show, e.g., enhanced activity or increased stability. In addition, they could be purified in higher yield and show better solubility at least under certain purification and storage conditions.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 2A–2D are an illustration of a comparison of the amino acid sequence of the polypeptide of the present invention and other fibroblast growth factors. [SEQ ID NOS: 13–22].

FIGS. 3A–3D show the full length mRNA and amino acid sequence for the KGF-2 gene. [SEQ ID NOS:23 and 24].

FIG. 15 shows the DNA sequence and the protein expressed from the pQE60-Cys37 construct [SEQ ID NOS :29 and 30]. The expressed KGF-2 protein contains the sequence from Cysteine at position 37 to Serine at position 208 with a 6×(His) tag attached to the N-terminus of the protein.

FIG. 23 shows the DNA and protein sequence [SEQ ID NOS:38 and 39] for the E. coli optimized full length KGF-2.

FIGS. 24A and B show the DNA and protein sequences [SEQ ID NOS:42, 43, 54, and 55] for the E. coli optimized mature KGF-2.

FIG. 25 shows the DNA and the encoded protein sequence [SEQ ID NOS:65 and 66] for the KGF-2 deletion construct comprising amino acids 36 to 208 of KGF-2.

FIG. 26 shows the DNA and the encoded protein sequence [SEQ ID NOS:67 and 68] for the KGF-2 deletion construct comprising amino acids 63 to 208 of KGF-2.

FIG. 27 shows the DNA and the encoded protein sequence [SEQ ID NOS:69 and 70] for the KGF-2 deletion construct comprising amino acids 77 to 208 of KGF-2.

FIG. 28 shows the DNA and the encoded protein sequence [SEQ ID NOS:71 and 72] for the KGF-2 deletion construct comprising amino acids 93 to 208 of KGF-2.

FIG. 29 shows the DNA and the encoded protein sequence [SEQ ID NOS:73 and 74] for the KGF-2 deletion construct comprising amino acids 104 to 208 of KGF-2.

FIG. 30 shows the DNA and the encoded protein sequence [SEQ ID NOS:75 and 76] for the KGF-2 deletion construct comprising amino acids 123 to 208 of KGF-2.

FIG. 31 shows the DNA and the encoded protein sequence [SEQ ID NOS:77 and 78] for the KGF-2 deletion construct comprising amino acids 138 to 208 of KGF-2.

FIG. 32 shows the DNA and the encoded protein sequence [SEQ ID NOS:79 and 80] for the KGF-2 deletion construct comprising amino acids 36 to 153 of KGF-2.

FIG. 33 shows the DNA and the encoded protein sequence [SEQ ID NOS:81 and 82] for the KGF-2 deletion construct comprising amino acids 63 to 153 of KGF-2.

FIG. 34 shows the DNA sequence for the KGF-2 Cysteine-37 to Serine mutant construct [SEQ ID NO:83].

FIG. 35 shows the DNA sequence for the KGF-2 Cysteine-37/Cysteine-106 to Serine mutant construct [SEQ ID NO:84].

FIG. 37 shows the effect of KGF-2 Δ33 on wound healing in normal rats. Male, SD, 250–300 g, rats (n=5) were given 6 mm full-thickness dorsal wounds. Wounds were measured with a caliper and treated with various concentrations of KGF-2Δ33 and buffer for four days commencing on the day of surgery. On the final day, wounds were harvested. Statistical analysis was performed using an unpaired t-test. *Value is compared to No Treatment Control. †Value is compared to Buffer Control.

FIG. 51 shows the nucleotide sequence of the regulatory elements of the pHE promoter (SEQ ID NO:148). The two lac operator sequences, the Shine-Delgarno sequence (S/D), and the terminal HindIII and NdeI restriction sites (italicized) are indicated.

DETAILED DESCRIPTION

Figure 22A:
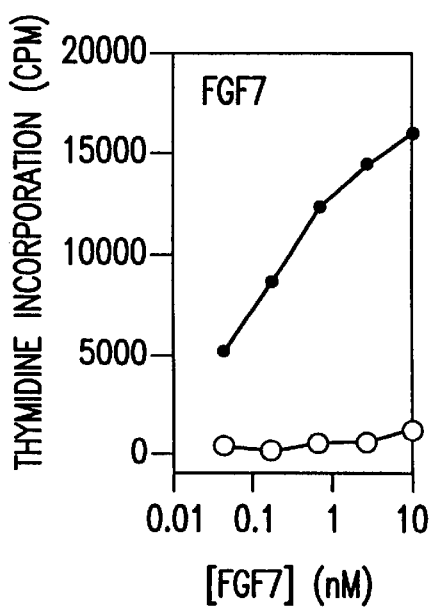
FIG. 22 (A) shows the stimulation of thymidine incorporation by KGF-2 and FGF7 in Baf3 cells transfected with FGFR1b and FGFR2. The effects of KGF-2 (right panel) and FGF7 (left panel) on the proliferation of Baf3 cells transfected with FGFR1iiib (open circle) or FGFR2iiib/KGFR (solid circle) were examined. Y-axis represents the amount of [3H]thymidine incorporation (cpm) into DNA of Baf3 cells. X-axis represents the final concentration of KGF-2 or FGF7 added to the tissue culture media. (B) shows the stimulation of thymidine incorporation by KGF-2Δ33 in Baf3 cells transfected with FGFR2iiib (C) shows the stimulation of thymidine incorporation by KGF-2 (white bar), KGF-2Δ33 (black bar) and KGF-2Δ28 (grey bar) in Baf3 cells transfected with FGFR2iiib.
Figures 1, 22A:
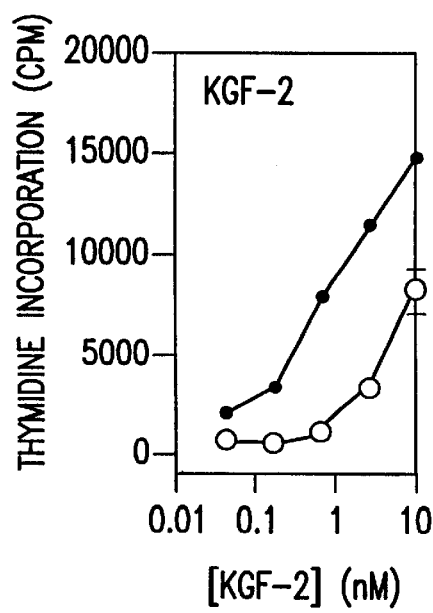
FIGS. 1A–1C illustrate the cDNA and corresponding deduced amino acid sequence of the polypeptide of the present invention. The initial 35 or 36 amino acid residues represent the putative leader sequence (underlined). The standard one letter abbreviations for amino acids are used. Sequencing inaccuracies are a common problem when attempting to determine polynucleotide sequences. Sequencing was performed using a 373 Automated DNA sequencer (Applied Biosystems, Inc.). Sequencing accuracy is predicted to be greater than 97% accurate. [SEQ ID NO:1].

In accordance with an aspect of the present invention, there is provided an isolated nucleic acid (polynucleotide) which encodes for the polypeptide having the deduced amino acid sequence of FIG. 1 (SEQ ID NO:2) or for the polypeptide encoded by the cDNA of the clone deposited as ATCC Deposit No. 75977 on Dec. 16, 1994 at the American Type Culture Collection Patent Depository, 10801 University Boulevard, Manassas, Va. 20110-2209 or the polypeptide encoded by the cDNA of the clone deposited as ATCC Deposit No. 75901 on Sep. 29, 1994 at the American Type Culture Collection Patent Depository, 10801 University Boulevard, Manassas, Va. 20110-2209.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 (SEQ ID NO:1); DNA molecules comprising the coding sequence for the mature KGF-2 protein shown in FIG. 1 (last 172 or 173 amino acids) (SEQ ID NO:2); and DNA molecules which comprise a sequence substantially different from those described above but which, due to the degeneracy of the genetic code, still encode the KGF-2 protein. Of course, the genetic code is well known in the art. Thus, it would be routine for one skilled in the art to generate the degenerate variants described above.

A polynucleotide encoding a polypeptide of the present invention may be obtained from a human prostate and fetal lung. A fragment of the cDNA encoding the polypeptide was initially isolated from a library derived from a human normal prostate. The open reading frame encoding the full length protein was subsequently isolated from a randomly primed human fetal lung cDNA library. It is structurally related to the FGF family. It contains an open reading frame encoding a protein of 208 amino acid residues of which approximately the first 35 or 36 amino acid residues are the putative leader sequence such that the mature protein comprises 173 or 172 amino acids. The protein exhibits the highest degree of homology to human keratinocyte growth factor with 45% identity and 82% similarity over a 206 amino acid stretch. It is also important that sequences that are conserved through the FGF family are found to be conserved in the protein of the present invention.

In addition, results from nested PCR of KGF-2 cDNA from libraries showed that there were potential alternative spliced forms of KGF-2. Specifically, using primers flanking the N-terminus of the open reading frame of KGF-2, PCR products of 0.2 kb and 0.4 kb were obtained from various cDNA libraries. A 0.2 kb size was the expected product for KGF-2 while the 0.4 kb size may result from an alternatively spliced form of KGF-2. The 0.4 kb product was observed in libraries from stomach cancer, adult testis, duodenum and pancreas.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the predicted mature polypeptide of FIG. 1 (SEQ ID NO:2) or for the predicted mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as intron or non-coding sequence 5' and/or 3' of the coding sequence for the predicted mature polypeptide. In addition, a full length mRNA has been obtained which contains 5' and 3' untranslated regions of the gene (FIG. 3 (SEQ ID NO:23)).

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO. 2) or the polypeptide encoded by the cDNA of the deposited clone. The variant of the polynucleotide may be a naturally occurring allelic variant of the polynucleotide or a nonnaturally occurring variant of the polynucleotide.

Thus, the present invention includes polynucleotides encoding the same predicted mature polypeptide as shown in FIG. 1 (SEQ ID NO:2) or the same predicted mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

The present invention includes polynucleotides encoding mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example the method disclosed by Wrighton et al., *Science* 273:458–463 (1996) to generate mimetic KGF-2 peptides.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encode polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I. et al. *Cell* 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

Further embodiments of the invention include isolated nucleic acid molecules comprising a polynucleotide having a nucleotide sequence at least 80% identical, and more preferably at least 85%, 90%, 91%, 92%, 93%, 94%, 95%, 97%, 98% or 99% identical to (a) a nucleotide sequence encoding the full-length KGF-2 polypeptide having the complete amino acid sequence in FIG. 1 (SEQ ID NO:2), including the predicted leader sequence; (b) a nucleotide sequence encoding the mature KGF-2 polypeptide (full-length polypeptide with the leader removed) having the amino acid sequence at positions about 36 or 37 to 208 in FIG. 1 (SEQ ID NO:2); (c) a nucleotide sequence encoding the full-length KGF-2 polypeptide having the complete amino acid sequence including the leader encoded by the cDNA clone contained in ATCC Deposit No. 75977; (d) a nucleotide sequence encoding the mature KGF-2 polypeptide having the amino acid sequence encoded by the cDNA clone contained in ATCC Deposit No. 75977; (e) a nucleotide sequence encoding any of the KGF-2 analogs or deletion mutants described below; or (f) a nucleotide sequence complementary to any of the nucleotide sequences in (a), (b), (c),(d), or (e).

By a polynucleotide having a nucleotide sequence at least, for example, 95% "identical" to a reference nucleotide sequence encoding a KGF-2 polypeptide is intended that the nucleotide sequence of the polynucleotide is identical to the reference sequence except that the polynucleotide sequence may include up to five point mutations per each 100 nucleotides of the reference nucleotide sequence encoding the KGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80%, 85%, 90%, 91%, 92%, 93%, 94%, 95%, 97%, 98% or 99% identical to, for instance, the nucleotide sequence shown in FIG. 1 (SEQ ID NO:1) or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 80%, 85%, 90%, 91%, 92%, 93%, 94%, 95%, 97%, 98% or 99% identical to the nucleic acid sequence shown in FIG. 1 [SEQ ID NO:1] or to the nucleic acid sequence of the deposited cDNA, irrespective of whether they encode a polypeptide having KGF-2 activity. This is because even where a particular nucleic acid molecule does not encode a polypeptide having KGF-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having KGF-2 activity include, inter alia, (1) isolating the KGF-2 gene or allelic variants thereof in a cDNA library; (2) in situ hybridization (e.g., "FISH") to metaphase chromosomal spreads to provide precise chromosomal location of the KGF-2 gene, as described in Verma et al., *Human Chromosomes. A Manual of Basic Techniques*, Pergamon Press, New York (1988); and Northern Blot analysis for detecting KGF-2 mRNA expression in specific tissues.

Preferred, however, are nucleic acid molecules having sequences at least 80%, 85%, 90%, 91%, 92%, 93%, 94%, 95%, 97%, 98% or 99% identical to the nucleic acid sequence shown in FIG. 1 [SEQ ID NO:1] or to the nucleic acid sequence of the deposited cDNA which do, in fact, encode a polypeptide having KGF-2 protein activity. By "a polypeptide having KGF-2 activity" is intended polypeptides exhibiting activity similar, but not necessarily identical, to an activity of the wild-type KGF-2 protein of the invention or an activity that is enhanced over that of the wild-type KGF-2 protein (either the full-length protein or, preferably, the mature protein), as measured in a particular biological assay.

Assays of KGF-2 activity are disclosed, for example, in Examples 10 and 11 below. These assays can be used to measure KGF-2 activity of partially purified or purified native or recombinant protein.

KGF-2 stimulates the proliferation of epidermal keratinocyes but not mesenchymal cells such as fibroblasts. Thus, "a polypeptide having KGF-2 protein activity" includes polypeptides that exhibit the KGF-2 activity, in the keratinocyte proliferation assay set forth in Example 10 and will bind to the FGF receptor isoforms 1-iiib and 2-iiib (Example 11). Although the degree of activity need not be identical to that of the KGF-2 protein, preferably, "a polypeptide having KGF-2 protein activity" will exhibit substantially similar activity as compared to the KGF-2 protein (i.e., the candidate polypeptide will exhibit greater activity or not more than about tenfold less and, preferably, not more than about twofold less activity relative to the reference KGF-2 protein).

Of course, due to the degeneracy of the genetic code, one of ordinary skill in the art will immediately recognize that a large number of the nucleic acid molecules having a sequence at least 80%, 85%, 90%, 91%, 92%, 93%, 94%, 95%, 97%, 98% or 99% identical to the nucleic acid sequence of the deposited cDNA or the nucleic acid sequence shown in FIG. 1 [SEQ ID NO:1] will encode a polypeptide "having KGF-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having KGF-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention further relates to polynucleotides which hybridize to the hereinabove-described sequences if there is at least 70%, preferably at least 80%, and more preferably at least 85% and still more preferably 90%, 91%, 92%, 93%, 94%, 95%, 97%, 98% or 99% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

An example of "stringent hybridization conditions" includes overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Also contemplated are nucleic acid molecules that hybridize to the KGF-2 polynucleotides at moderately high stringency hybridization conditions. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 3° C. in a solution comprising 6×SSPE (20× SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, polynucleotides hybridizing to a larger portion of the reference polynucleotide (e.g., the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 [SEQ ID NO:1]. By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 [SEQ ID NO:1]). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, edited by Sambrook, J., Fritsch, E. F. and Maniatis, T., (1989), Cold Spring Harbor Laboratory Press, the entire disclosure of which is hereby incorporated herein by reference.

Since a KGF-2 cDNA clone has been deposited and its determined nucleotide sequence is provided in FIG. 1 [SEQ ID NO:1], generating polynucleotides which hybridize to a portion of the KGF-2 cDNA molecule would be routine to the skilled artisan. For example, restriction endonuclease cleavage or shearing by sonication of the KGF-2 cDNA clone could easily be used to generate DNA portions of various sizes which are polynucleotides that hybridize to a portion of the KGF-2 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the KGF-2 cDNA shown in FIG. 1 [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

The invention further provides isolated nucleic acid molecules comprising a polynucleotide encoding an epitope-bearing portion of the KGF-2 protein. In particular, isolated nucleic acid molecules are provided encoding polypeptides comprising the following amino acid residues in FIG. 1 (SEQ ID NO:2), which the present inventors have determined are antigenic regions of the KGF-2 protein:
1. Gly41-Asn71: GQDMVSPEATNSSSSSFSSPSSAGRH-VRSYN [SEQ ID NO:25];
2. Lys91-Ser109: KIEKNGKVSGTKKENCPYS [SEQ ID NO:26];
3. Asn135-Tyr164: NKKGKLYGSKEFNNDCKLK-ERIEENGYNTY [SEQ ID NO 27]; and
4. Asn181-Ala199: NGKGAPRRGQKTRRKNTSA [SEQ ID NO:28].

Also, there are two additional shorter predicted antigenic areas, Gln74-Arg78 of FIG. 1 (SEQ ID NO:2) and Gln170-Gln175 of FIG. 1 (SEQ ID NO:2). Methods for generating such epitope-bearing portions of KGF-2 are described in detail below.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

KGF-2 Polypeptides and Fragments

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

As one of ordinary skill would appreciate, due to the possibilities of sequencing errors discussed above, as well as the variability of cleavage sites for leaders in different known proteins, the actual KGF-2 polypeptide encoded by the deposited cDNA comprises about 208 amino acids, but may be anywhere in the range of 200–220 amino acids; and the actual leader sequence of this protein is about 35 or 36 amino acids, but may be anywhere in the range of about 30 to about 40 amino acids.

The terms "fragment," "derivative" and "analog" when referring to the polypeptide, of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the KGF-2 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the KGF-2 polypeptide which show substantial KGF-2 polypeptide activity or which include regions of KGF-2 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

The present invention includes mimetic peptides of KGF-2 which can be used as therapeutic peptides. Mimetic KGF-2 peptides are short peptides which mimic the biological activity of the KGF-2 protein by binding to and activating the cognate receptors of KGF-2. Mimetic KGF-2 peptides can also bind to and inhibit the cognate receptors of KGF-2. KGF-2 receptors include, but are not limited to, FGFR2iiib and FGFR1iiib. Such mimetic peptides are obtained from methods such as, but not limited to, phage display or combinatorial chemistry. For example, the method disclosed by Wrighton et al. *Science* 273:458–463 (1996) can be used to generate mimetic KGF-2 peptides.

The polypeptides and polynucleotides of the present invention are preferably provided in an isolated form, and preferably are purified to homogeneity.

The polypeptides of the present invention are preferably in an isolated form. By "isolated polypeptide" is intended a polypeptide removed from its native environment. Thus, a polypeptide produced and/or contained within a recombinant host cell is considered isolated for purposes of the present invention. Also intended are polypeptides that have been purified, partially or substantially, from a recombinant host cell or a native source.

The polypeptides of the present invention include the polypeptide of SEQ ID NO:2 (in particular the mature polypeptide) as well as polypeptides which have at least 80%, 85%, 90%, 91%, 92%, 93%, 94%, 95%, 97%, 98% or 99% similarity (more preferably at least 80%, 85%, 90%, 91%, 92%, 93%, 94%, 95%, 97%, 98% or 99% identity) to the polypeptide of SEQ ID NO:2 and also include portions of such polypeptides with such portion of the polypeptide (such as the deletion mutants described below) generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482–489, 1981) to find the best segment of similarity between two sequences.

By a polypeptide having an amino acid sequence at least, for example, 95% "identical" to a reference amino acid sequence of a KGF-2 polypeptide is intended that the amino acid sequence of the polypeptide is identical to the reference sequence except that the polypeptide sequence may include up to five amino acid alterations per each 100 amino acids of the reference amino acid of the KGF-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 91%, 92%, 93%, 94%, 95%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990)6:237–245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, CutoffScore=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

As described in detail below, the polypeptides of the present invention can be used to raise polyclonal and monoclonal antibodies, which are useful in diagnostic assays for detecting KGF-2 protein expression as described below or as agonists and antagonists capable of enhancing or inhibiting KGF-2 protein function. Further, such polypeptides can be used in the yeast two-hybrid system to "capture" KGF-2 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30, 40, 50, 60, 70, 80, 90, 100, or 150 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate KGF-2-specific antibodies include the following:

1. Gly41-Asn71: GQDMVSPEATNSSSSSFSSPSSAGRH-VRSYN [SEQ ID NO:25];
2. Lys91-Ser109: KIEKNGKVSGTKKENCPYS [SEQ ID NO:26];
3. Asn135-Tyr164: NKKGKLYGSKEFNNDCKLK-ERIEENGYNTY [SEQ ID NO:27]; and
4. Asn181-Ala199: NGKGAPRRGQKTRRKNTSA [SEQ ID NO:28].

Also, there are two additional shorter predicted antigenic areas, Gln74-Arg78 of FIG. 1 (SEQ ID NO:2) and Gln170-Gln175 of FIG. 1 (SEQ ID NO:2).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC Deposit No. 75977 or encoded by a polynucleotide that hybridizes to the complement of the sequence of SEQ ID NO:1 or contained in ATCC Deposit No. 75977 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1) polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al, *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, *Proc. Natl. Acad. Sci. USA* 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additionally preferred antigenic epitopes comprise, or alternatively consist of, the amino acid sequence of residues: M-1 to H-15; W-2 to L-16; K-3 to P-17; W-4 to G-18; I-5 to C-19; L-6 to C-20; T-7 to C-2 1; H-8 to C-22; C-9 to C-23; A-1 to F-24; S-11 to L-25; A-12 to L-26; F-13 to L-27; P-14 to F-28; H-15 to L-29; L-16 to V-30; P-17 to S-31; G-18 to S-32; C-19 to V-33; C-20 to P-34; C-21 to V-35; C-22 to T-36; C-23 to C-37; F-24 to Q-38; L-25 to A-39; L-26 to L-40; L-27 to G-41; F-28 to Q-42; L-29 to D-43; V-30 to M-44; S-31 to V-45; S-32 to S-46; V-33 to P-47; P-34 to E-48; V-35 to A-49; T-36 to T-50; C-37 to N-51; Q-38to S-52; A-39 to S-53; L-40 to S-54; G-41 to S-55; Q-42 to S-56; D-43 to F-57; M-44 to S-58; V-45 to S-59; S-46 to P-60; P-47 to S-61; E-48 to S-62; A-49 to A-63; T-50 to G-64; N-51 to R-65; S-52 to H-66; S-53 to V-67; S-54 to R-68; S-55 to S-69; S-56 to Y-70; F-57 to N-71; S-58 to H-72; S-59 to L-73; P-60 to Q-74; S-61 to G-75; S-62 to D-76; A-63 to V-77; G-64 to R-78; R-65 to W-79; H-66 to R-80; V-67 to K-81; R-68 to L-82; S-69 to F-83; Y-70 to S-84; N-71 to F-85; H-72 to T-86; L-73 to K-87; Q-74 to Y-88; G-75 to F-89; D-76 to L-90; V-77 to K-9 1; R-78 to I-92; W-79 to E-93; R-80 to K-94; K-81 to N-95; L-82 to G-96; F-83 to K-97; S-84 to V-98; F-85 to S-99; T-86 to G-100; K-87 to T-101; Y-88 to K-102; F-89 to K-103; L-90 to E-104; K-91 to N-105; I-92 to C-106; E-93 to P-107; K-94 to Y-108; N-95 to S-109; G-96to I-110; K-97 to L-111; V-98 to E-112; S-99 to I-113; G-100 to T-114; T-101 to S-115; K-102 to V-116; K-103 to E-117; E-104 to I-118; N-105 to G-119; C-106 to V-120; P-107 to V-121; Y-108 to A-122; S-109 to V-123; I-110 to K-124; L-111 to A-125; E-112 to I-126; I-113 to N-127; T-114 to S-128; S-115 to N-129; V-116 to Y-130; E-117 to Y-131; I-118 to L-132; G-119 to A-133; V-120 to M-134; V-121 to N-135; A-122 to K-136; V-123 to K-137; K-124 to G-138; A-125 to K-139; I-126 to L-140; N-127 to Y-141; S-128 to G-142; N-129 to S-143; Y-130 to K-144; Y-131 to E-145; L-132 to F-146; A-133 to N-147; M-134 to N-148; N-135 to D-149; K-136 to C-150; K-137 to K-151; G-138 to L-152; K-139 to K-153; L-140 to E-154; Y-141 to R-155; G-142 to I-156; S-143 to E-157; K-144 to E-158; E-145 to N-159; F-146 to G-160; N-147 to Y-161; N-148 to N-162; D-149 to T-163; C-150 to Y-164; K-151 to A-165 L-152 to S-166; K-153 to F-167; E-154 to N-168; R-155 to W-169; I-156 to Q-170; E-157 to H-171; E-158 to N-172; N-159 to G-173; G-160 to R-174; Y-161 to Q-175; N-162 to M-176; T-163 to Y-177; Y-164 to V-178; A-165 to A-179; S-166 to L-180; F-167 to N-181; N-168 to G-182; W-169 to K-183; Q-170 to G-184; H-171 to A-185; N-172 to P-186; G-173 to R-187; R-174 to R-188; Q-175 to G-189; M-176 to Q-190; Y-177 to K-191; V-178 to T-192; A-179 to R-193; L-180 to R-194; N-181 to K-195; G-182 to N-196; K-183 to T-197; G-184 to S-198; A-185 to A-199; P-186 to H-200; R-187 to F-201; R-188 to L-202; G-189 to P-203; Q-190 to M-204; K-191 to V-205; T-192 to V-206; R-193 to H-207; and/or R-194 to S-208 of SEQ ID NO:2. Polynucleotides encoding these polypeptide fragments are also encompassed by the invention.

Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., *Cell* 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910–914; and Bittle et al., *J. Gen. Virol.* 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, KGF-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric KGF-2 protein or protein fragment alone (Fountoulakis et al., *J Biochem* 270:3958–3964 (1995)).

In accordance with the present invention, novel variants of KGF-2 are also described. These can be produced by deleting or substituting one or more amino acids of KGF-2. Natural mutations are called allelic variations. Allelic variations can be silent (no change in the encoded polypeptide) or may have altered amino acid sequence.

In order to attempt to improve or alter the characteristics of native KGF-2, protein engineering may be employed. Recombinant DNA technology known to those skilled in the art can be used to create novel polypeptides. Muteins and deletions can show, e.g., enhanced activity or increased stability. In addition, they could be purified in higher yield and show better solubility at least under certain purification and storage conditions. Set forth below are examples of mutations that can be constructed.

The KGF-2 polypeptides of the invention may be in monomers or multimers (i.e., dimers, trimers, tetramers and higher multimers). Accordingly, the present invention relates to monomers and multimers of the KGF-2 polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in the deposited clone (including fragments, variants, splice variants, and fusion proteins, corresponding to these as described herein). These homomers may contain KGF-2 polypeptides having identical or different amino acid sequences. In a specific embodiment, a homomer of the invention is a multimer containing only KGF-2 polypeptides having an identical amino acid sequence. In another specific embodiment, a homomer of the invention is a multimer containing KGF-2 polypeptides having different amino acid sequences. In specific embodiments, the multimer of the invention is a homodimer (e.g., containing KGF-2 polypeptides having identical or different amino acid sequences) or a homotrimer (e.g., containing KGF-2 polypeptides having identical and/ or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the KGF-2 polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the KGF-2 polypeptides of the invention. Such covalent associations may involve one or more amino acid residues contained in the polypeptide sequence (e.g., that recited in SEQ ID NO:2, or contained in the polypeptides encoded by the clone HPRCC57 or the clone contained in ATCC Deposit No. 75977 or 75901). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a KGF-2 fusion protein. In one example, covalent associations are between the heterologous sequence contained in a fusion protein of the invention (see, e.g., U.S. Pat. No. 5,478,925). In a specific example, the covalent associations are between the heterologous sequence contained in a KGF-2-Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478, 925, which is herein incorporated by reference in its entirety).

Polynucleotide and Polypeptide Fragments

The present invention is further directed to fragments of the isolated nucleic acid molecules described herein. By a fragment of an isolated nucleic acid molecule having, for example, the nucleotide sequence of the deposited cDNA (clone HPRCC57), a nucleotide sequence encoding the polypeptide sequence encoded by the deposited cDNA, a nucleotide sequence encoding the polypeptide sequence depicted in FIG. 1 (SEQ ID NO:2), the nucleotide sequence shown in FIG. 1 (SEQ ID NO:1), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length. These fragments have numerous uses that include, but are not limited to, diagnostic probes and primers as discussed herein. Of course, larger fragments, such as those of 501-1500 nt in length are also useful according to the present invention as are fragments corresponding to most, if not all, of the nucleotide sequences of the deposited cDNA (clone HPRCC57) or as shown in FIG. 1 (SEQ ID NO:1). By a fragment at least 20 nt in length, for example, is intended fragments which include 20 or more contiguous bases from, for example, the nucleotide sequence of the deposited cDNA, or the nucleotide sequence as shown in FIG. 1 (SEQ ID NO:1).

Moreover, representative examples of KGF-2 polynucleotide fragments include, for example, fragments having a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, and/or 2001 to the end of SEQ ID NO:1 or the complementary strand thereto, or the cDNA contained in the deposited clone. In this context "about" includes the particularly recited ranges, larger or smaller by several (5, 4, 3, 2, or 1) nucleotides, at either terminus or at both termini.

Preferably, the polynucleotide fragments of the invention encode a polypeptide which demonstrates a KGF-2 functional activity. By a polypeptide demonstrating a KGF-2 "functional activity" is meant, a polypeptide capable of displaying one or more known functional activities associated with a full-length (complete) KGF-2 protein. Such functional activities include, but are not limited to, biological activity, antigenicity [ability to bind (or compete with a KGF-2 polypeptide for binding) to an anti-KGF-2 antibody], immunogenicity (ability to generate antibody which binds to a KGF-2 polypeptide), ability to form multimers with KGF-2 polypeptides of the invention, and ability to bind to a receptor or ligand for a KGF-2 polypeptide.

The functional activity of KGF-2 polypeptides, and fragments, variants derivatives, and analogs thereof, can be assayed by various methods.

For example, in one embodiment where one is assaying for the ability to bind or compete with full-length KGF-2 polypeptide for binding to anti-KGF-2 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a KGF-2 ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E. et al., *Microbiol. Rev.* 59:94–123 (1995). In another embodiment, physiological correlates of KGF-2 binding to its substrates (signal transduction) can be assayed.

In addition, assays described herein (see Examples) and otherwise known in the art may routinely be applied to measure the ability of KGF-2 polypeptides and fragments, variants derivatives and analogs thereof to elicit KGF-2 related biological activity (either in vitro or in vivo). Other methods will be known to the skilled artisan and are within the scope of the invention.

The present invention is further directed to fragments of the KGF-2 polypeptide described herein. By a fragment of an isolated the KGF-2 polypeptide, for example, encoded by the deposited cDNA (clone HPRCC57), the polypeptide sequence encoded by the deposited cDNA, the polypeptide sequence depicted in FIG. 1 (SEQ ID NO:2), is intended to encompass polypeptide fragments contained in SEQ ID NO:2 or encoded by the cDNA contained in the deposited clone. Protein fragments may be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, 161-180, 181-200, 201-220, 221-240, 241-260, 261-280, or 281 to the end of the coding region. Moreover, polypeptide fragments can be at least 20, 30, 40, 50, 60, 70, 80, 90, 100, 110, 120, 130, 140, or 150 amino acids in length. In this context "about" includes the particularly recited ranges, larger or smaller by several (5, 4, 3, 2, or 1) amino acids, at either extreme or at both extremes.

Even if deletion of one or more amino acids from the N-terminus of a protein results in modification of loss of one or more biological functions of the protein, other functional activities (e.g., biological activities, ability to multimerize, ability to bind KGF-2 ligand) may still be retained. For example, the ability of shortened KGF-2 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an KGF-2 mutein with a large number of deleted N-terminal amino acid residues may retain some biological or immunogenic activities. In fact, peptides composed of as few as six KGF-2 amino acid residues may often evoke an immune response.

Accordingly, polypeptide fragments include the secreted KGF-2 protein as well as the mature form. Further preferred polypeptide fragments include the secreted KGF-2 protein or the mature form having a continuous series of deleted residues from the amino or the carboxy terminus, or both. For example, any number of amino acids, ranging from 1–60, can be deleted from the amino terminus of either the secreted KGF-2 polypeptide or the mature form. Similarly, any number of amino acids, ranging from 1–30, can be deleted from the carboxy terminus of the secreted KGF-2 protein or mature form. Furthermore, any combination of the above amino and carboxy terminus deletions are preferred. Similarly, polynucleotide fragments encoding these KGF-2 polypeptide fragments are also preferred.

Particularly, N-terminal deletions of the KGF-2 polypeptide can be described by the general formula m-208, where m is an integer from 2 to 207, where m corresponds to the position of the amino acid residue identified in SEQ ID NO:2. More in particular, the invention provides polynucleotides encoding polypeptides comprising, or alternatively consisting of, the amino acid sequence of residues of W-2 to S-208; K-3 to S-208; W-4 to S-208; I-5 to S-208; L-6 to S-208; T-7 to S-208; H-8 to S-208; C-9 to S-208; A-10 to S-208; S-11 to S-208; A-12 to S-208; F-13 to S-208; P-14 to S-208; H15 to S-208; L-16 to S-208; P-17 to S-208; G-18 to S-208; C-19 to S-208; C-20 to S-208; C-21 to S-208; C-22 to S-208; C-23 to S-208; F-24 to S-208; L-25 to S-208; L-26 to S-208; L-27 to S-208; F-28 to S-208; L-29 to S-208; V-30 to S-208; S-31 to S-208; S-32 to S-208; V-33 to S-208; P-34 to S-208; V-35 to S-208; T-36 to S-208; C-37 to S-208; Q-38 to S-208; A-39 to S-208; L-40 to S-208; G-41 to S-208; Q-42 to S-208; D-43 to S-208; M-44 to S-208; V-45 to S-208; S-46 to S-208; P-47 to S-208; E-48 to S-208; A-49 to S-208; T-50 to S-208; N-51 to S-208; S-52 to S-208; S-53 to S-208; S-54 to S-208; S-55 to S-208; S-56 to S-208; F-57 to S-208; S-58 to S-208; S-59 to S-208; P-60 to S-208; S-61 to S-208; S-62 to S-208; A-63 to S-208; G-64 to S-208; R-65 to S-208; H-66 to S-208; V-67 to S-208; R-68 to S-208; S-69 to S-208; Y-70 to S-208; N-71 to S-208; H-72 to S-208; L-73 to S-208; Q-74 to S-208; G-75 to S-208; D-76 to S-208; V-77 to S-208; R-78 to S-208; W-79 to S-208; R-80 to S-208; K-81 to S-208; L-82 to S-208; F-83 to S-208; S-84 to S-208; F-85 to S-208; T-86 to S-208; K-87 to S-208; Y-88 to S-208; F-89 to S-208; L-90 to S-208; K-91 to S-208; I-92 to S-208; E-93 to S-208; K-94 to S-208; N-95 to S-208; G-96 to S-208; K-97 to S-208; V-98 to S-208; S-99 to S-208; G-100 to S-208; T-101 to S-208; K-102 to S-208; K-103 to S-208; E-104 to S-208; N-105 to S-208; C-106 to S-208; P-107 to S-208; Y-108 to S-208; S-109 to S-208; I-110 to S-208; L-116 to S-208; E-112 to S-208; I-113 to S-208; T-114 to S-208; S-115 to S-208; V-116 to S-208; E-117 to S-208; I-118 to S-208; G-119 to S-208; V-120 to S-208; V-121 to S-208; A-122 to S-208; V-123 to S-208; K-124 to S-208; A-125 to S-208; I-126 to S-208; N-127 to S-208; S-128 to S-208; N-129 to S-208; Y-130 to S-208; Y-131 to S-208; L-132 to S-208; A-133 to S-208; M-134 to S-208; N-135 to S-208; K-136 to S-208; K-137 to S-208; G-138 to S-208; K-139 to S-208; L-140 to S-208; Y-141 to S-208; G-142 to S-208; S-143 to S-208; K-144 to S-208; E-145 to S-208; F-146 to S-208; N-147 to S-208; N-148 to S-208; D-149 to S-208; C-150 to S-208; K-151 to S-208; L-152 to S-208; K-153 to S-208; E-154 to S-208; R-155 to S-208; I-156 to S-208; E-157 to S-208; E-158 to S-208; N-159 to S-208; G-160 to S-208; Y-161 to S-208; N-162 to S-208; T-163 to S-208; Y-164 to S-208; A-165 to S-208; S-166 to S-208; F-167 to S-208; N-168 to S-208; W-169 to S-208; Q-170 to S-208; H-171 to S-208; N-172 to S-208; G-173 to S-208; R-174 to S-208; Q-175 to S-208; M-176 to S-208; Y-177 to S-208; V-178 to S-208; A-179 to S-208; L-180 to S-208; N-181 to S-208; G-182 to S-208; K-183 to S-208; G-184 to S-208; A-185 to S-208; P-186 to S-208; R-187 to S-208; R-188 to S-208; G-189 to S-208; Q-190 to S-208; K-191 to S-208; T-192 to S-208; R-193 to S-208; R-194 to S-208; K-195 to S-208; N-196 to S-208; T-197 to S-208; S-198 to S-208; A-199 to S-208; H-200 to S-208; F-201 to S-208; L-202 to S-208; P-203 to S-208; of SEQ ID NO:2. Polynucleotides encoding these polypeptides are also encompassed by the invention.

Particularly preferred are fragments comprising or consisting of: S69-S208; A63-S208; Y70-S208; V77-S208; E93-S208; E104-S208; V123-S208; G138-S208; R80-S208; A39-S208; S69-V178; S69-G173; S69-R188; S69-S198; S84-S208; V98-S208; A63-N162; S69-N162; and M35-N162.

Also as mentioned above, even if deletion of one or more amino acids from the C-terminus of a protein results in modification of loss of one or more biological functions of the protein, other functional activities (e.g., biological activities, ability to multimerize, ability to bind KGF-2 ligand) may still be retained. For example the ability of the shortened KGF-2 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an KGF-2 mutein with a large number of deleted C-terminal amino acid residues may retain some biological or immunogenic activities. In fact, peptides composed of as few as six KGF-2 amino acid residues may often evoke an immune response.

Accordingly, the present invention further provides polypeptides having one or more residues deleted from the carboxy terminus of the amino acid sequence of the KGF-2 polypeptide shown in FIG. 1 (SEQ ID NO:2), as described by the general formula 1–n, where n is an integer from 2 to 207, where n corresponds to the position of amino acid residue identified in SEQ ID NO:2. More in particular, the invention provides polynucleotides encoding polypeptides comprising, or alternatively consisting of, the amino acid sequence of residues M-1 to H-207; M-1 to V-206; M-1 to V-205; M-1 to M-204; M-1 to P-203; M-1 to L-202; M-1 to F-201; M-1 to H-200; M-1 to A-199; M-1 to S-198; M-1 to T-197; M-1 to N-196; M-1 to K-195; M-1 to R-194; M-1 to R-193; M-1 to T-192; M-1 to K-191; M-1 to Q-190; M-1 to G-189; M-1 to R-188; M-1 to R-187; M-1 to P-186; M-1 to A-185; M-1 to G-184; M-1 to K-183; M-1 to G-182; M-1 to N-181; M-1 to L-180; M-1 to A-179; M-1 to V-178; M-1 to Y-177; M-1 to M-176; M-1 to Q-175; M-1 to R-174; M-1 to G-173; M-1 to N-172; M-1 to H-171; M-1 to Q-170; M-1 to W-169; M-1 to N-168; M-1 to F-167; M-1 to S-166; M-1 to A-165; M-1 to Y-164; M-1 to T-163; M-1 to N-162; M-1 to Y-161; M-1 to G-160; M-1 to N-159; M-1 to E-158; M-1 to E-157; M-1 to 1–156; M-1 to R-155; M-1 to E-154; M-1 to K-153; M-1 to L-152; M-1 to K-151; M-1 to C-150; M-1 to D-149; M-1 to N-148; M-1 to N-147; M-1 to F-146; M-1 to E-145; M-1 to K-144; M-1 to S-143; M-1 to G-142; M-1 to Y-141; M-1 to L-140; M-1 to K-139; M-1 to G-138; M-1 to K-137; M-1 to K-136; M-1 to N-135; M-1 to M-134; M-1 to A-133; M-1 to L-132; M-1 to Y-131; M-1 to Y-130; M-1 to N-129; M-1 to S-128; M-1 to N-127; M-1 to I-126; M-1 to A-125; M-1 to K-124; M-1 to V-123; M-1 to A-122; M-1 to V-121; M-1 to V-120; M-1 to G-119; M-1 to I-118; M-1 to E-117; M-1 to V-116; M-1 to S-115; M-1 to T-114; M-1 to I-113; M-1 to E-112; M-1 to L-111; M-1 to I-110; M-1 to S-109; M-1 to Y-108; M-1 to P-107; M-1 to C-106; M-1 to N-105; M-1 to E-104; M-1 to K-103; M-1 to K-102; M-1 to T-101; M-1 to G-100; M-1 to S-99; M-1 to V-98; M-1 to K-97; M-1 to G-96; M-1 to N-95; M-1 to K-94; M-1 to E-93; M-1 to I-92; M-1 to K-91; M-1 to L-90; M-1 to F-89; M-1 to Y-88; M-1 to K-87; M-1 to T-86; M-1 to F-85; M-1 to S-84; M-1 to F-83; M-1 to L-82; M-1 to K-81; M-1 to R-80; M-1 to W-79; M-1 to R-78; M-1 to V-77; M-1 to D-76; M-1 to G-75; M-1 to Q-74; M-1 to L-73; M-1 to H-72; M-1 to N-71; M-1 to Y-70; M-1 to S-69; M-1 to R-68; M-1 to V-67; M-1 to H-66; M-1 to R-65; M-1 to G-64; M-1 to A-63; M-1 to S-62; M-1 to S-61; M-1 to P-60; M-1 to S-59; M-1 to S-58; M-1 to F-57; M-1 to S-56; M-1 to S-55; M-1 to S-54; M-1 to S-53; M-1 to S-52; M-1 to N-51; M-1 to T-50; M-1 to A-49; M-1 to E-48; M-1 to P-47; M-1 to S-46; M-1 to V-45; M-1 to M-44; M-1 to D-43; M-1 to Q-42; M-1 to G-41; M-1 to L-40; M-1 to A-39; M-1 to Q-38; M-1 to C-37; M-1 to T-36; M-1 to V-35; M-1 to P-34; M-1 to V-33; M-1 to S-32; M-1 to S-31; M-1 to V-30; M-1 to L-29; M-1 to F-28; M-1 to L-27; M-1 to L-26; M-1 to L-25; M-1 to F-24; M-1 to C-23; M-1 to C-22; M-1 to C-21; M-1 to C-20; M-1 to C-19; M-1 to G-18; M-1 to P-17; M-1 to L-16; M-1 to H-15; M-1 to P-14; M-1 to F-13; M-1 to A-12; M-1 to S-11; M-1 to A-10; M-1 to C-9; M-1 to H-8; M-1 to T-7; of SEQ ID NO:2. Polynucleotides encoding these polypeptides are also encompassed by the invention.

Likewise, C-terminal deletions of the KGF-2 polypeptide of the invention shown as SEQ ID NO:2 include polypeptides comprising the amino acid sequence of residues: S-69 to H-207; S-69 to V-206; S-69 to V-205; S-69 to M-204; S-69 to P-203; S-69 to L-202; S-69 to F-201; S-69 to H-200; S-69 to A-199; S-69 to S-198; S-69 to T-197; S-69 to N-196; S-69 to K-195; S-69 to R-194; S-69 to R-193; S-69 to T-192; S-69 to K-191; S-69 to Q-190; S-69 to G-189; S-69 to R-188; S-69 to R-187; S-69 to P-186; S-69 to A-185; S-69 to G-184; S-69 to K-183; S-69 to G-182; S-69 to N-181; S-69 to L-180; S-69 to A-179; S-69 to V-178; S-69 to Y-177; S-69 to M-176; S-69 to Q-175; S-69 to R-174; S-69 to G-173; S-69 to N-172; S-69 to H-171; S-69 to Q-170; S-69 to W-169; S-69 to N-168; S-69 to F-167; S-69 to S-166; S-69 to A-165; S-69 to Y-164; S-69 to T-163; S-69 to N-162; S-69 to Y-161; S-69 to G-160; S-69 to N-159; S-69 to E-158; S-69 to E-157; S-69 to I-156; S-69 to R-155; S-69 to E-154; S-69 to K-153; S-69 to L-152; S-69 to K-151; S-69 to C-150; S-69 to D-149; S-69 to N-148; S-69 to N-147; S-69 to F-146; S-69 to E-145; S-69 to K-144; S-69 to S-143; S-69 to G-142; S-69 to Y-141; S-69 to L-140; S-69 to K-139; S-69 to G-138; S-69 to K-137; S-69 to K-136; S-69 to N-135; S-69 to M-134; S-69 to A-133; S-69 to L-132; S-69 to Y-131; S-69 to Y-130; S-69 to N-129; S-69 to S-128; S-69 to N-127; S-69 to I-126; S-69 to A-125; S-69 to K-124; S-69 to V-123; S-69 to A-122; S-69 to V-121; S-69 to V-120; S-69 to G-119; S-69 to I-118; S-69 to E-117; S-69 to V-116; S-69 to S-115; S-69 to T-114; S-69 to I-113; S-69 to E-112; S-69 to L-111; S-69 to I-110; S-69 to S-109; S-69 to Y-108; S-69 to P-107; S-69 to C-106; S-69 to N-105; S-69 to E-104; S-69 to K-103; S-69 to K-102; S-69 to T-101; S-69 to G-100; S-69 to S-99; S-69 to V-98; S-69 to K-97; S-69 to G-96; S-69 to N-95; S-69 to K-94; S-69 to E-93; S-69 to I-92; S-69 to K-91; S-69 to L-90; S-69 to F-89; S-69 to Y-88; S-69 to K-87; S-69 to T-86; S-69 to F-85; S-69 to S-84; S-69 to F-83; S-69 to L-82; S-69 to K-8 1; S-69 to R-80; S-69 to W-79; S-69 to R-78; S-69 to V-77; S-69 to D-76; S-69 to G-75; of SEQ ID NO:2.

In addition, any of the above listed N- or C-terminal deletions can be combined to produce a N- and C-terminal deleted KGF-2 polypeptide. The invention also provides polypeptides having one or more amino acids deleted from both the amino and the carboxyl termini, which may be described generally as having residues m-n of SEQ ID NO:2, where n and m are integers as described above. In addition, N- or C-terminal deletion mutants may also contain site specific amino acid substitutions. Polynucleotides encoding these polypeptides are also encompassed by the invention.

Also included are a nucleotide sequence encoding a polypeptide consisting of a portion of the complete KGF-2 amino acid sequence encoded by the cDNA clone contained in ATCC Deposit No. 75977, where this portion excludes any integer of amino acid residues from 1 to about 198 amino acids from the amino terminus of the complete amino acid sequence encoded by the cDNA clone contained in ATCC Deposit No. 75977, or any integer of amino acid residues from 1 to about 198 amino acids from the carboxy terminus, or any combination of the above amino terminal and carboxy terminal deletions, of the complete amino acid sequence encoded by the cDNA clone contained in ATCC Deposit No. 75977. Polynucleotides encoding all of the above deletion mutant polypeptide forms also are provided.

The present application is also directed to proteins containing polypeptides at least 80%, 85%, 90%, 91%, 92%, 93%, 94%, 95%, 97%, 98% or 99% identical to the KGF-2 polypeptide sequence set forth herein m-n. In preferred embodiments, the application is directed to proteins containing polypeptides at least 80%, 85%, 90%, 91%, 92%, 93%, 94%, 95%, 97%, 98% or 99% identical to polypeptides having the amino acid sequence of the specific KGF-2- and C-terminal deletions recited herein. Polynucleotides encoding these polypeptides are also encompassed by the invention.

Among the especially preferred fragments of the invention are fragments characterized by structural or functional attributes of KGF-2. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) KGF-2 (SEQ ID NO:2). Certain preferred regions are those set out in FIG. 4 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of KGF-2. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of KGF-2.

The data representing the structural or functional attributes of KGF-2 set forth in FIG. 1 and/or Table I, as described above, was generated using the various modules and algorithms of the DNA*STAR set on default parameters. In a preferred embodiment, the data presented in columns VIII, IX, XIII, and XIV of Table I can be used to determine regions of KGF-2 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 4, but may, as shown in Table I, be represented or identified by using tabular representations of the data presented in FIG. 4. The DNA*STAR computer algorithm used to generate FIG. 4 (set on the original default parameters) was used to present the data in FIG. 4 in a tabular format (See Table I). The tabular format of the data in FIG. 4 may be used to easily determine specific boundaries of a preferred region.

The above-mentioned preferred regions set out in FIG. 4 and in Table I include, but are not limited to, regions of the aforementioned types identified by analysis of the amino acid sequence set out in FIG. 1. As set out in FIG. 4 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index. The columns are labeled with the headings "Res", "Position", and Roman Numerals I–XIV. The column headings refer to the following features of the amino acid sequence presented in FIG. 3, and Table I: "Res": amino acid residue of SEQ ID NO:2 and FIGS. 1A and 1B; "Position": position of the corresponding residue within SEQ ID NO:2 and FIGS. 1A and 1B; I: Alpha, Regions-Garnier-Robson; II: Alpha, Regions-Chou-Fasman; III: Beta, Regions-Garnier-Robson; IV: Beta, Regions-Chou-Fasman; V: Turn, Regions-Garnier-Robson; VI: Turn, Regions-Chou-Fasman; VII: Coil, Regions-Garnier-Robson; VIII: Hydrophilicity Plot-Kyte-Doolittle; IX: Hydrophobicity Plot-Hopp-Woods; X: Alpha, Amphipathic Regions-Eisenberg; XI: Beta, Amphipathic Regions-Eisenberg; XII: Flexible Regions-Karplus-Schulz; XIII: Antigenic Index-Jameson-Wolf; and XIV: Surface Probability Plot-Emini.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | — | — | — | — | — | −0.08 | 0.73 | * | — | — | −0.60 | 0.82 |
| Trp | 2 | A | A | — | — | — | — | — | −0.50 | 0.99 | * | — | — | −0.60 | 0.45 |
| Lys | 3 | A | A | — | — | — | — | — | −0.42 | 1.24 | * | — | — | −0.60 | 0.29 |
| Trp | 4 | A | A | — | — | — | — | — | −0.07 | 1.30 | * | — | — | −0.60 | 0.42 |
| Ile | 5 | A | A | — | — | — | — | — | −0.34 | 1.19 | * | — | — | −0.60 | 0.55 |
| Leu | 6 | A | A | — | — | — | — | — | −0.33 | 0.84 | * | — | — | −0.60 | 0.15 |
| Thr | 7 | — | A | B | — | — | — | — | −0.34 | 1.34 | * | — | — | −0.60 | 0.14 |
| His | 8 | — | A | — | — | T | — | — | −0.98 | 0.81 | * | — | — | −0.20 | 0.27 |
| Cys | 9 | — | A | — | — | T | — | — | −1.39 | 0.63 | — | — | — | −0.20 | 0.33 |
| Ala | 10 | — | A | — | — | T | — | — | −0.71 | 0.73 | * | — | — | −0.20 | 0.20 |
| Ser | 11 | — | A | — | — | T | — | — | 0.07 | 0.67 | * | — | — | −0.20 | 0.23 |
| Ala | 12 | — | A | — | — | T | — | — | −0.43 | 0.67 | * | — | — | −0.20 | 0.57 |
| Phe | 13 | — | A | B | — | — | — | — | −0.61 | 0.79 | — | — | — | −0.60 | 0.47 |
| Pro | 14 | — | — | — | — | T | — | — | −0.29 | 0.71 | — | — | — | 0.00 | 0.54 |
| His | 15 | — | — | — | — | T | — | — | −0.37 | 0.76 | — | — | — | 0.00 | 0.53 |
| Leu | 16 | — | — | — | — | T | T | — | −0.73 | 0.83 | — | — | — | 0.20 | 0.33 |
| Pro | 17 | — | — | — | — | T | T | — | −0.81 | 0.61 | — | — | — | 0.20 | 0.11 |
| Gly | 18 | — | — | — | — | T | T | — | −0.78 | 0.76 | — | — | — | 0.20 | 0.04 |
| Cys | 19 | — | — | — | — | T | T | — | −1.23 | 0.83 | — | — | — | 0.20 | 0.03 |
| Cys | 20 | — | — | — | — | T | T | — | −1.90 | 0.71 | — | — | — | 0.20 | 0.01 |
| Cys | 21 | — | — | B | — | — | T | — | −1.90 | 1.07 | — | — | — | −0.20 | 0.01 |
| Cys | 22 | — | — | B | — | — | T | — | −2.50 | 1.33 | — | — | — | −0.20 | 0.01 |
| Cys | 23 | — | — | B | — | — | T | — | −2.97 | 1.44 | — | — | — | −0.20 | 0.02 |
| Phe | 24 | — | — | B | B | — | — | — | −3.00 | 1.56 | — | — | — | −0.60 | 0.03 |
| Leu | 25 | — | — | B | B | — | — | — | −3.14 | 1.77 | — | — | — | −0.60 | 0.05 |
| Leu | 26 | — | — | B | B | — | — | — | −3.33 | 1.89 | — | — | — | −0.60 | 0.08 |
| Leu | 27 | — | — | B | B | — | — | — | −2.97 | 1.96 | — | — | — | −0.60 | 0.07 |
| Phe | 28 | — | — | B | B | — | — | — | −2.60 | 1.56 | — | — | — | −0.60 | 0.11 |
| Leu | 29 | — | — | B | B | — | — | — | −2.76 | 1.26 | — | — | — | −0.60 | 0.18 |
| Val | 30 | — | — | B | B | — | — | — | −2.16 | 1.21 | — | — | — | −0.60 | 0.16 |
| Ser | 31 | — | — | — | B | T | — | — | −2.20 | 0.96 | — | — | — | −0.20 | 0.29 |
| Ser | 32 | — | — | — | B | — | — | C | −1.70 | 0.81 | — | — | — | −0.40 | 0.26 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 33 | — | — | B | B | — | — | — | −1.67 | 0.61 | — | — | — | −0.60 | 0.51 |
| Pro | 34 | — | — | B | B | — | — | — | −0.86 | 0.54 | — | * | — | −0.60 | 0.20 |
| Val | 35 | — | — | B | B | — | — | — | −0.59 | 0.56 | — | — | — | −0.60 | 0.26 |
| Thr | 36 | — | — | B | B | — | — | — | −1.10 | 0.67 | — | * | — | −0.60 | 0.36 |
| Cys | 37 | — | — | B | B | — | — | — | −1.14 | 0.71 | — | * | — | −0.60 | 0.19 |
| Gln | 38 | — | — | B | B | — | — | — | −0.29 | 0.71 | — | * | — | −0.60 | 0.25 |
| Ala | 39 | — | — | B | B | — | — | — | −0.08 | 0.47 | — | — | — | −0.60 | 0.30 |
| Leu | 40 | — | — | B | B | — | — | — | 0.18 | −0.01 | — | — | — | 0.30 | 0.95 |
| Gly | 41 | — | — | B | — | — | T | — | −0.37 | 0.03 | — | — | F | 0.25 | 0.54 |
| Gln | 42 | — | — | B | — | — | T | — | 0.00 | 0.27 | * | — | F | 0.25 | 0.40 |
| Asp | 43 | — | — | B | — | — | T | — | −0.21 | 0.16 | — | — | F | 0.25 | 0.65 |
| Met | 44 | — | — | B | — | — | T | — | 0.38 | −0.10 | — | — | F | 1.00 | 1.01 |
| Val | 45 | — | — | B | — | — | — | — | 0.60 | −0.53 | — | — | — | 0.95 | 1.01 |
| Ser | 46 | — | — | B | — | — | T | — | 0.63 | −0.43 | — | — | F | 0.85 | 0.61 |
| Pro | 47 | — | — | B | — | — | T | — | 0.63 | 0.06 | — | — | F | 0.49 | 0.89 |
| Glu | 48 | A | — | B | — | — | T | — | 0.33 | −0.16 | — | — | F | 1.48 | 1.93 |
| Ala | 49 | A | — | — | — | — | T | — | 0.63 | −0.41 | — | — | F | 1.72 | 1.93 |
| Thr | 50 | A | — | — | — | — | — | — | 1.19 | −0.41 | — | — | F | 1.76 | 1.67 |
| Asn | 51 | — | — | — | — | — | T | C | 1.19 | −0.46 | — | — | F | 2.40 | 1.29 |
| Ser | 52 | — | — | — | — | — | T | C | 1.10 | −0.07 | — | — | F | 2.16 | 1.72 |
| Ser | 53 | — | — | — | — | — | T | C | 0.40 | −0.19 | — | — | F | 1.92 | 1.59 |
| Ser | 54 | — | — | — | — | T | T | — | 0.69 | 0.11 | — | — | F | 1.13 | 0.86 |
| Ser | 55 | — | — | — | — | — | T | C | 0.70 | 0.10 | — | — | F | 0.69 | 0.86 |
| Ser | 56 | — | — | — | — | T | T | — | 0.49 | 0.10 | — | — | F | 0.65 | 0.86 |
| Phe | 57 | — | — | — | — | T | T | — | 0.49 | 0.14 | — | — | F | 0.65 | 0.99 |
| Ser | 58 | — | — | — | — | — | T | C | 0.49 | 0.14 | — | — | F | 0.69 | 0.99 |
| Ser | 59 | — | — | — | — | — | T | C | 0.20 | 0.14 | — | — | F | 0.93 | 0.99 |
| Pro | 60 | — | — | — | — | — | T | C | 0.16 | 0.26 | * | — | F | 1.32 | 1.15 |
| Ser | 61 | — | — | — | — | — | T | C | 0.57 | −0.10 | * | — | F | 2.01 | 0.85 |
| Ser | 62 | — | — | — | — | — | T | C | 1.23 | −0.49 | * | — | F | 2.40 | 1.25 |
| Ala | 63 | — | — | — | — | — | — | C | 0.68 | −0.37 | * | — | F | 1.96 | 1.10 |
| Gly | 64 | — | — | B | — | — | — | — | 1.09 | −0.16 | * | — | F | 1.37 | 0.61 |
| Arg | 65 | — | — | B | — | — | — | — | 1.00 | −0.54 | * | — | F | 1.43 | 0.89 |
| His | 66 | — | — | B | — | — | — | — | 1.06 | −0.54 | * | — | — | 1.19 | 1.18 |
| Val | 67 | — | — | B | — | — | — | — | 1.36 | −0.29 | * | — | — | 0.65 | 1.36 |
| Arg | 68 | — | — | B | — | — | T | — | 1.91 | −0.31 | * | — | — | 0.85 | 1.53 |
| Ser | 69 | — | — | B | — | — | T | — | 1.44 | 0.19 | * | * | — | 0.25 | 1.53 |
| Tyr | 70 | — | — | B | — | — | T | — | 1.33 | 0.37 | * | * | — | 0.25 | 1.70 |
| Asn | 71 | — | — | — | — | T | T | — | 1.02 | 0.13 | * | * | — | 0.65 | 1.50 |
| His | 72 | — | — | — | — | — | — | C | 1.88 | 0.56 | * | * | — | −0.05 | 1.11 |
| Leu | 73 | — | — | — | — | — | T | C | 0.91 | 0.17 | * | * | — | 0.45 | 1.18 |
| Gln | 74 | — | — | B | — | — | T | — | 1.32 | 0.06 | * | * | F | 0.25 | 0.55 |
| Gly | 75 | — | — | B | — | — | T | — | 1.28 | −0.34 | — | * | F | 0.85 | 0.79 |
| Asp | 76 | — | — | B | — | — | T | — | 1.39 | 0.07 | — | * | F | 0.40 | 1.00 |
| Val | 77 | — | — | B | B | — | — | — | 1.47 | −0.61 | — | * | F | 0.90 | 1.13 |
| Arg | 78 | — | — | B | B | — | — | — | 1.47 | −1.01 | * | * | — | 0.75 | 2.29 |
| Trp | 79 | — | — | B | B | — | — | — | 0.77 | −0.76 | * | * | — | 0.75 | 1.13 |
| Arg | 80 | — | — | B | B | — | — | — | 0.81 | 0.03 | * | * | — | −0.15 | 1.32 |
| Lys | 81 | — | — | B | B | — | — | — | 0.11 | −0.23 | — | * | — | 0.30 | 0.90 |
| Leu | 82 | — | — | B | B | — | — | — | 0.66 | 0.56 | * | * | — | −0.60 | 0.74 |
| Phe | 83 | — | — | B | B | — | — | — | 0.59 | 0.13 | * | — | — | −0.30 | 0.55 |
| Ser | 84 | — | — | B | B | — | — | — | 0.63 | 0.13 | * | — | — | −0.30 | 0.55 |
| Phe | 85 | A | — | — | B | — | — | — | −0.18 | 0.89 | * | — | — | −0.45 | 1.04 |
| Thr | 86 | A | — | — | B | — | — | — | −1.03 | 0.99 | * | — | — | −0.45 | 1.04 |
| Lys | 87 | A | A | — | B | — | — | — | −0.18 | 0.89 | * | * | — | −0.60 | 0.64 |
| Tyr | 88 | A | A | — | B | — | — | — | −0.37 | 0.50 | * | * | — | −0.45 | 1.48 |
| Phe | 89 | A | A | — | B | — | — | — | −0.07 | 0.40 | * | — | — | −0.30 | 0.72 |
| Leu | 90 | A | A | — | B | — | — | — | 0.68 | −0.09 | * | * | — | 0.30 | 0.62 |
| Lys | 91 | A | A | — | B | — | — | — | 0.99 | −0.09 | * | * | F | 0.45 | 0.79 |
| Ile | 92 | A | A | — | — | — | — | — | 0.60 | −0.44 | * | * | F | 0.60 | 1.48 |
| Glu | 93 | A | — | — | — | — | T | — | 0.89 | −0.80 | * | * | F | 1.30 | 1.77 |
| Lys | 94 | A | — | — | — | — | T | — | 0.73 | −1.49 | * | * | F | 1.30 | 1.77 |
| Asn | 95 | A | — | — | — | — | T | — | 1.24 | −0.84 | — | * | F | 1.30 | 1.88 |
| Gly | 96 | A | — | — | — | — | T | — | 0.86 | −1.14 | * | * | F | 1.64 | 1.45 |
| Lys | 97 | A | — | — | — | — | T | — | 1.43 | −0.71 | * | * | F | 1.63 | 0.72 |
| Val | 98 | A | — | — | — | — | — | — | 1.48 | −0.23 | — | * | F | 1.67 | 0.64 |
| Ser | 99 | — | — | — | — | — | — | C | 1.48 | −0.63 | — | — | F | 2.66 | 1.30 |
| Gly | 100 | — | — | — | — | T | T | — | 1.48 | −1.06 | — | * | F | 3.40 | 1.30 |
| Thr | 101 | — | — | B | — | — | T | — | 1.82 | −1.06 | — | * | F | 2.66 | 3.04 |
| Lys | 102 | — | — | B | — | — | T | — | 1.11 | −1.30 | — | * | F | 2.49 | 3.65 |
| Lys | 103 | — | — | — | — | T | T | — | 1.76 | −1.11 | — | — | F | 2.72 | 1.98 |
| Glu | 104 | — | — | — | — | T | — | — | 1.81 | −1.11 | — | — | F | 2.35 | 2.12 |
| Asn | 105 | — | — | — | — | T | — | — | 1.86 | −0.84 | — | — | F | 2.18 | 1.66 |
| Cys | 106 | — | — | B | — | — | T | — | 1.28 | −0.46 | — | — | — | 1.70 | 1.11 |
| Pro | 107 | — | — | — | — | T | T | — | 0.42 | 0.23 | — | — | — | 1.18 | 0.45 |
| Tyr | 108 | — | — | — | — | T | T | — | 0.38 | 0.91 | — | — | — | 0.71 | 0.23 |
| Ser | 109 | — | — | B | — | — | T | — | −0.51 | 0.51 | * | — | — | 0.14 | 0.75 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ile | 110 | — | — | B | B | — | — | — | −0.82 | 0.63 | * | — | — | −0.43 | 0.34 |
| Leu | 111 | — | — | B | B | — | — | — | −0.46 | 0.69 | — | — | — | −0.60 | 0.31 |
| Glu | 112 | — | — | B | B | — | — | — | −1.10 | 0.31 | — | — | — | −0.30 | 0.31 |
| Ile | 113 | — | — | B | B | — | — | — | −0.86 | 0.57 | — | — | — | −0.60 | 0.33 |
| Thr | 114 | — | — | B | B | — | — | — | −1.44 | −0.11 | — | — | F | 0.45 | 0.69 |
| Ser | 115 | — | — | B | B | — | — | — | −0.90 | −0.11 | — | — | F | 0.45 | 0.28 |
| Val | 116 | A | — | — | B | — | — | — | −0.94 | 0.31 | — | — | — | −0.30 | 0.40 |
| Glu | 117 | A | — | — | B | — | — | — | −1.80 | 0.27 | — | — | — | −0.30 | 0.20 |
| Ile | 118 | A | — | — | B | — | — | — | −1.50 | 0.43 | — | — | — | −0.60 | 0.11 |
| Gly | 119 | A | — | — | B | — | — | — | −2.04 | 0.54 | — | * | — | −0.60 | 0.15 |
| Val | 120 | A | — | — | B | — | — | — | −1.70 | 0.54 | — | * | — | −0.60 | 0.07 |
| Val | 121 | A | — | — | B | — | — | — | −1.43 | 0.54 | * | — | — | −0.60 | 0.19 |
| Ala | 122 | A | — | — | B | — | — | — | −2.32 | 0.36 | * | — | — | −0.30 | 0.19 |
| Val | 123 | — | — | B | B | — | — | — | −1.43 | 0.61 | * | — | — | −0.60 | 0.18 |
| Lys | 124 | — | — | B | B | — | — | — | −1.39 | 0.37 | — | — | — | −0.30 | 0.39 |
| Ala | 125 | — | — | B | — | — | — | — | −0.53 | 0.11 | — | — | — | −0.10 | 0.52 |
| Ile | 126 | — | — | B | — | — | — | — | 0.08 | 0.01 | * | — | — | 0.05 | 1.13 |
| Asn | 127 | — | — | B | — | — | — | T | 0.42 | 0.13 | * | — | F | 0.25 | 0.88 |
| Ser | 128 | — | — | B | — | — | — | T | 0.47 | 0.89 | * | — | F | 0.10 | 1.37 |
| Asn | 129 | — | — | B | — | — | — | T | −0.17 | 1.07 | * | — | — | −0.05 | 1.61 |
| Tyr | 130 | — | — | B | — | — | — | T | −0.18 | 0.89 | — | * | — | −0.05 | 1.01 |
| Tyr | 131 | A | A | — | — | — | — | — | 0.71 | 1.10 | — | * | — | −0.60 | 0.75 |
| Leu | 132 | A | A | — | — | — | — | — | 0.76 | 1.11 | — | — | — | −0.60 | 0.75 |
| Ala | 133 | A | A | — | — | — | — | — | 1.10 | 0.71 | — | — | — | −0.60 | 0.95 |
| Met | 134 | A | A | — | — | — | — | — | 0.76 | −0.04 | — | * | — | 0.45 | 1.22 |
| Asn | 135 | A | — | — | — | — | — | T | 1.04 | −0.37 | — | * | — | 0.85 | 1.46 |
| Lys | 136 | A | — | — | — | — | — | T | 0.48 | −1.06 | — | * | F | 1.30 | 2.89 |
| Lys | 137 | A | — | — | — | — | — | T | 1.04 | −0.87 | — | * | F | 1.30 | 2.41 |
| Gly | 138 | A | — | — | — | — | — | T | 1.29 | −0.73 | — | * | F | 1.30 | 2.34 |
| Lys | 139 | A | — | — | — | — | — | — | 1.59 | −0.70 | * | * | F | 1.10 | 1.16 |
| Leu | 140 | — | — | B | — | — | — | — | 1.63 | −0.31 | — | * | F | 0.65 | 0.78 |
| Tyr | 141 | — | — | B | — | — | — | T | 1.59 | −0.31 | — | * | F | 1.00 | 1.57 |
| Gly | 142 | — | — | B | — | — | — | T | 0.84 | −0.74 | — | * | F | 1.30 | 1.36 |
| Ser | 143 | — | — | B | — | — | — | T | 1.19 | 0.04 | — | * | F | 0.40 | 1.43 |
| Lys | 144 | — | — | B | — | — | — | — | 1.14 | −0.24 | — | * | F | 1.00 | 1.47 |
| Glu | 145 | A | — | — | — | — | — | — | 1.96 | −0.60 | * | — | F | 1.10 | 2.38 |
| Phe | 146 | A | — | — | — | — | — | — | 1.53 | −1.03 | * | * | F | 1.10 | 2.97 |
| Asn | 147 | A | — | — | — | — | — | T | 1.92 | −0.84 | * | * | F | 1.15 | 0.80 |
| Asn | 148 | A | — | — | — | — | — | T | 1.41 | −0.84 | — | * | F | 1.15 | 0.92 |
| Asp | 149 | A | — | — | — | — | — | T | 1.41 | −0.16 | — | * | F | 0.85 | 0.88 |
| Cys | 150 | A | — | — | — | — | — | T | 1.41 | −0.94 | * | * | F | 1.30 | 1.09 |
| Lys | 151 | A | A | — | — | — | — | — | 2.22 | −1.34 | * | * | F | 0.90 | 1.17 |
| Leu | 152 | A | A | — | — | — | — | — | 1.33 | −1.74 | * | * | F | 0.90 | 1.37 |
| Lys | 153 | A | A | — | — | — | — | — | 1.33 | −1.06 | * | * | F | 0.90 | 1.80 |
| Glu | 154 | A | A | — | — | — | — | — | 1.33 | −1.63 | * | * | F | 0.90 | 1.56 |
| Arg | 155 | A | A | — | — | — | — | — | 2.00 | −1.63 | * | * | F | 0.90 | 3.27 |
| Ile | 156 | A | A | — | — | — | — | — | 1.61 | −1.91 | * | * | F | 1.24 | 2.63 |
| Glu | 157 | A | A | — | — | — | — | — | 2.18 | −1.49 | * | * | F | 1.58 | 1.50 |
| Glu | 158 | A | A | — | — | — | — | — | 2.13 | −0.73 | * | * | F | 1.92 | 1.20 |
| Asn | 159 | — | — | — | — | T | T | — | 1.82 | −0.33 | * | * | F | 2.76 | 2.76 |
| Gly | 160 | — | — | — | — | T | T | — | 1.47 | −0.53 | * | * | F | 3.40 | 2.30 |
| Tyr | 161 | — | — | — | — | T | T | — | 1.77 | 0.23 | — | — | F | 2.16 | 2.08 |
| Asn | 162 | — | — | — | — | — | T | C | 1.47 | 0.73 | — | — | F | 1.32 | 1.31 |
| Thr | 163 | — | — | — | — | — | — | C | 0.77 | 0.71 | — | — | — | 0.63 | 1.77 |
| Tyr | 164 | — | — | B | — | — | — | — | 0.77 | 1.07 | — | * | — | −0.06 | 0.98 |
| Ala | 165 | — | — | B | — | — | — | — | 0.82 | 0.71 | — | * | — | −0.40 | 0.98 |
| Ser | 166 | — | — | B | — | — | — | T | 1.07 | 1.23 | — | * | — | −0.20 | 0.71 |
| Phe | 167 | — | — | B | — | — | — | T | 1.03 | 1.14 | — | * | — | −0.20 | 0.79 |
| Asn | 168 | — | — | — | — | — | T | T | 1.34 | 0.89 | — | * | — | 0.35 | 1.06 |
| Trp | 169 | — | — | — | — | — | T | T | 1.24 | 0.79 | — | * | — | 0.35 | 1.27 |
| Gln | 170 | — | — | — | — | — | — | C | 1.94 | 0.83 | * | * | — | 0.11 | 1.45 |
| His | 171 | — | — | — | — | — | T | C | 2.24 | 0.04 | * | * | — | 0.77 | 1.77 |
| Asn | 172 | — | — | — | — | — | T | C | 2.34 | 0.04 | * | * | F | 1.08 | 2.92 |
| Gly | 173 | — | — | — | — | T | T | — | 2.10 | −0.26 | * | * | F | 2.04 | 1.67 |
| Arg | 174 | — | — | — | — | T | T | — | 1.53 | 0.10 | * | * | F | 1.60 | 1.92 |
| Gln | 175 | — | — | B | B | — | — | — | 0.94 | 0.24 | * | — | — | 0.34 | 0.89 |
| Met | 176 | — | — | B | B | — | — | — | 0.17 | 0.34 | * | — | — | 0.18 | 0.90 |
| Tyr | 177 | — | — | B | B | — | — | — | 0.17 | 0.60 | * | * | — | −0.28 | 0.38 |
| Val | 178 | — | — | B | B | — | — | — | 0.17 | 1.00 | — | * | — | −0.44 | 0.35 |
| Ala | 179 | — | — | B | B | — | — | — | 0.10 | 1.03 | — | * | — | −0.60 | 0.35 |
| Leu | 180 | — | — | B | B | — | — | — | −0.24 | 0.41 | — | * | — | −0.30 | 0.45 |
| Asn | 181 | — | — | — | — | T | T | — | −0.23 | 0.09 | * | — | F | 1.25 | 0.60 |
| Gly | 182 | — | — | — | — | T | T | — | −0.20 | −0.06 | * | * | F | 2.15 | 0.60 |
| Lys | 183 | — | — | — | — | T | T | — | 0.77 | −0.13 | * | * | F | 2.60 | 1.13 |
| Gly | 184 | — | — | — | — | T | C | — | 1.47 | −0.81 | * | * | F | 3.00 | 1.37 |
| Ala | 185 | — | — | — | — | — | C | — | 1.93 | −1.21 | * | * | F | 2.50 | 2.72 |
| Pro | 186 | — | — | B | — | — | T | — | 1.93 | −1.21 | * | — | F | 2.20 | 1.35 |

TABLE I-continued

| Res | Position | I | II | III | IV | V | VI | VII | VIII | IX | X | XI | XII | XIII | XIV |
|-----|----------|---|----|----|----|----|----|-----|------|------|---|----|-----|------|-----|
| Arg | 187 | — | — | B | — | — | T | — | 2.32 | -0.81 | * | — | F | 1.90 | 2.35 |
| Arg | 188 | — | — | B | — | — | T | — | 1.97 | -1.24 | * | — | F | 1.60 | 4.66 |
| Gly | 189 | — | — | B | — | — | T | — | 2.42 | -1.26 | * | — | F | 1.30 | 4.35 |
| Gln | 190 | — | — | B | — | — | — | — | 3.12 | -1.69 | * | — | F | 1.10 | 4.35 |
| Lys | 191 | — | — | B | — | — | — | — | 3.38 | -1.69 | * | — | F | 1.10 | 4.35 |
| Thr | 192 | — | — | B | — | — | — | — | 3.27 | -1.69 | * | — | F | 1.44 | 8.79 |
| Arg | 193 | — | — | B | — | — | — | — | 2.84 | -1.71 | — | — | F | 1.78 | 8.16 |
| Arg | 194 | — | — | — | — | T | — | — | 2.89 | -1.63 | * | — | F | 2.52 | 5.89 |
| Lys | 195 | — | — | — | — | T | — | — | 2.30 | -1.24 | * | — | F | 2.86 | 5.47 |
| Asn | 196 | — | — | — | — | T | T | — | 2.22 | -1.23 | — | * | F | 3.40 | 2.82 |
| Thr | 197 | — | — | — | — | — | T | C | 1.83 | -0.73 | — | — | F | 2.86 | 1.96 |
| Ser | 198 | — | — | — | — | — | T | C | 0.91 | 0.06 | — | — | F | 1.47 | 0.85 |
| Ala | 199 | — | — | B | — | — | T | — | 0.59 | 0.74 | — | — | — | 0.48 | 0.44 |
| His | 200 | — | — | B | — | — | — | — | -0.06 | 0.77 | — | — | — | -0.06 | 0.47 |
| Phe | 201 | — | — | B | B | — | — | — | -0.91 | 0.90 | * | — | — | -0.60 | 0.34 |
| Leu | 202 | — | — | B | B | — | — | — | -1.46 | 1.16 | — | — | — | -0.60 | 0.25 |
| Pro | 203 | — | — | B | B | — | — | — | -1.19 | 1.30 | — | — | — | -0.60 | 0.14 |
| Met | 204 | — | — | B | B | — | — | — | -0.90 | 1.30 | * | — | — | -0.60 | 0.22 |
| Val | 205 | A | — | — | B | — | — | — | -1.26 | 0.90 | * | — | — | -0.60 | 0.35 |
| Val | 206 | A | — | — | B | — | — | — | -0.94 | 0.64 | — | — | — | -0.60 | 0.29 |
| His | 207 | A | — | — | B | — | — | — | -0.52 | 0.64 | — | — | — | -0.60 | 0.38 |
| Ser | 208 | A | — | — | B | — | — | — | -0.70 | 0.46 | — | — | — | -0.60 | 0.65 |

Among highly preferred fragments in this regard are those that comprise regions of KGF-2 that combine several structural features, such as several of the features set out above.

Moreover, the techniques of gene-shuffling, motif-shuffling, exon-shuffling, and/or codon-shuffling (collectively referred to as "DNA shuffling") may be employed to modulate the activities of KGF-2 thereby effectively generating agonists and antagonists of KGF-2. See generally, U.S. Pat. Nos. 5,605,793; 5,811,238; 5,830,721; 5,834,252; and 5,837,458; and Patten, P. A. et al., *Curr. Opinion Biotechnol.* 8:724–33 (1997); Harayama, S., *Trends Biotechnol.* 16(2):76–82 (1998); Hansson, L. O. et al., *J. Mol. Biol.* 287:265–76 (1999); and Lorenzo, M. M. and Blasco, R., *Biotechniques* 24(2):308–13 (1998) (each of these patents and publications are hereby incorporated by reference).

In one embodiment, alteration of KGF-2 polynucleotides and corresponding polypeptides may be achieved by DNA shuffling. DNA shuffling involves the assembly of two or more DNA segments into a desired KGF-2 molecule by homologous, or site-specific, recombination. In another embodiment, KGF-2 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of KGF-2 may be recombined with one or more components, motifs, sections, parts, domains, fragments, etc. of one or more heterologous molecules. In preferred embodiments, the heterologous molecules are KGF-2 family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF). Other preferred fragments are biologically active KGF-2 fragments. Biologically active fragments are those exhibiting activity similar, but not necessarily identical, to an activity of the KGF-2 polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the KGF-2 receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis. All of these above assays can be used as diagnostic or prognostic markers. The molecules discovered using these assays can be used to treat disease or to bring about a particular result in a patient (e.g., blood vessel growth) by activating or inhibiting the KGF-2 molecule. Moreover, the assays can discover agents which may inhibit or enhance the production of KGF-2 from suitably manipulated cells or tissues.

Therefore, the invention includes a method of identifying compounds which bind to KGF-2 comprising the steps of:

(a) incubating a candidate binding compound with KGF-2; and (b) determining if binding has occurred. Moreover, the invention includes a method of identifying agonists/antagonists comprising the steps of: (a) incubating a candidate compound with KGF-2, (b) assaying a biological activity, and (c) determining if a biological activity of KGF-2 has been altered.

Also, one could identify molecules bind KGF-2 experimentally by using the beta-pleated sheet regions disclosed in FIG. 4 and Table 1. Accordingly, specific embodiments of the invention are directed to polynucleotides encoding polypeptides which comprise, or alternatively consist of, the amino acid sequence of each beta pleated sheet regions disclosed in FIG. 3/Table 1.

Additional embodiments of the invention are directed to polynucleotides encoding KGF-2 polypeptides which comprise, or alternatively consist of, any combination or all of the beta pleated sheet regions disclosed in FIG. 4/Table 1. Additional preferred embodiments of the invention are directed to polypeptides which comprise, or alternatively consist of, the KGF-2 amino acid sequence of each of the beta pleated sheet regions disclosed in FIG. 4/Table 1. Additional embodiments of the invention are directed to KGF-2 polypeptides which comprise, or alternatively consist of, any combination or all of the beta pleated sheet regions disclosed in FIG. 4/Table 1.

Other preferred embodiments of the invention are fragments of KGF-2 which bind to the KGF-2 receptor. Fragments which bind to the KGF-2 receptor may be useful as agonists or antagonists of KGF-2. For example, fragments of KGF-2 which bind the receptor may prevent binding to KGF-2 and active portions thereof. Other fragments may bind to the receptor and specifically deactivate the receptor and receptor activation or may specifically antibodies that recognize the receptor-ligand complex, and, preferably, do not specifically recognize the unbound receptor or the unbound ligand. Likewise, included in the invention are fragments which activate the receptor. These fragments may act as receptor agonists, i.e., potentiate or activate either all or a subset of the biological activities of the ligand-mediated receptor activation, for example, by inducing dimerization of the receptor. The fragments may be specified as agonists, antagonists or inverse agonists for biological activities comprising the specific biological activities of the peptides of the invention disclosed herein.

Non-limiting examples of fragments of KGF-2 which bind the KGF-2 receptor include amino acids 147-155, 95-105, 78-94, 119-146, 70-94, 78-105, 114-146, 70-105, 86-124, 100-139, 106-146, 160-209, and/or 156-209 of SEQ ID NO:2. Also preferred are polynucleotides encoding such polypeptides.

Other preferred fragments are biologically active KGF-2 fragments. Biologically active fragments are those exhibiting activity similar, but not necessarily identical, to an activity of the KGF-2 polypeptide. The biological activity of the fragments may include an improved desired activity, or a decreased undesirable activity.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 and 613 of SEQ ID NO:1, b is an integer of 15 to 627, where both a and b correspond to the positions of nucleotide residues shown in SEQ ID NO:1, and where b is greater than or equal to a +14.

Amino Terminal and Carboxy Terminal Deletions

Various members of the FGF family have been modified using recombinant DNA technology. Positively charged molecules have been substituted or deleted in both aFGF and bFGF that are important for heparin binding. The modified molecules resulted in reduced heparin binding activity. Accordingly, it is known that the amount of modified molecule sequestered by heparin in a patient would be reduced, increasing the potency as more FGF would reach the appropriate receptor. (EP 0 298 723).

Native KGF-2 is relatively unstable in the aqueous state and it undergoes chemical and physical degradation resulting in loss of biological activity during processing and storage. Native KGF-2 is also prone to aggregation in aqueous solution, at elevated temperatures and it becomes inactivated under acidic conditions.

In order to improve or alter one or more characteristics of native KGF-2, protein engineering may be employed. Ron et al., *J. Biol. Chem.*, 268(4): 2984–2988 (1993) reported modified KGF proteins that had heparin binding activity even if the 3, 8, or 27 amino terminal amino acid residues were missing. The deletion of 3 and 8 amino acids had full activity. More deletions of KGF have been described in PCT/IB95/0097 1. The deletion of carboxyterminal amino acids can enhance the activity of proteins. One example is interferon gamma that shows up to ten times higher activity by deleting ten amino acid residues from the carboxy terminus of the protein (Döbeli et al., *J. of Biotechnology* 7:199–216 (1988)). Thus, one aspect of the invention is to provide polypeptide analogs of KGF-2 and nucleotide sequences encoding such analogs that exhibit enhanced stability (e.g., when exposed to typical pH, thermal conditions or other storage conditions) relative to the native KGF-2 polypeptide.

Particularly preferred KGF-2 polypeptides are shown below (numbering starts with the first amino acid in the protein (Met) (FIG. 1 (SEQ ID NO:2)):

Thr (residue 36) -- Ser (residue 208)
Cys (37) -- Ser (208)
Gln (38) -- Ser (208)
Ala (39) -- Ser (208)
Leu (40) -- Ser (208)
Gly (41) -- Ser (208)
Gln (42) -- Ser (208)
Asp (43) -- Ser (208)
Met (44) -- Ser (208)
Val (45) -- Ser (208)
Ser (46) -- Ser (208)
Pro (47) -- Ser (208)
Glu (48) -- Ser (208)
Ala (49) -- (Ser (208)
Thr (50) -- Ser (208)
Asn (51) -- Ser (208)
Ser (52) -- Ser (208)
Ser (53) -- Ser (208)
Ser (54) -- Ser (208)
Ser (55) -- Ser (208)
Ser (56) -- Ser (208)
Phe (57) -- Ser (208)
Ser (59) -- Ser (208)

-continued

Ser (62) -- Ser (208)
Ala (63) -- Ser (208)
Gly (64) -- Ser (208)
Arg (65) -- Ser (208)
Val (67) -- Ser (208)
Ser (69) -- Ser (208)
Val (77) -- Ser (208)
Arg (80) -- Ser (208)
Met (1), Thr (36), or Cys (37) -- His (207)
Met (1), Thr (36), or Cys (37) -- Val (206)
Met (1), Thr (36), or Cys (37) -- Val (205)
Met (1), Thr (36), or Cys (37) -- Met (204)
Met (1), Thr (36), or Cys (37) -- Pro (203)
Met (1), Thr (36), or Cys(37) -- Leu (202)
Met (1), Thr (36), or Cys (37) -- Phe (201)
Met (1), Thr (36), or Cys (37) -- His (200)
Met (1), Thr (36), or Cys (37) -- Ala (199)
Met (1), Thr (36), or Cys (37) -- Ser (198)
Met (1), Thr (36), or Cys (37) -- Thr (197)
Met (1), Thr (36), or Cys (37) -- Asn (196)
Met (1), Thr (36), or Cys (37) -- Lys (195)
Met (1), Thr (36), or Cys (37) -- Arg (194)
Met (1), Thr (36), or Cys (37) -- Arg (193)
Met (1), Thr (36), or Cys (37) -- Thr (192)
Met (1), Thr (36), or Cys (37) -- Lys (191)
Met (1), Thr (36), or Cys (37) -- Arg (188)
Met (1), Thr (36), or Cys (37) -- Arg (187)
Met (1), Thr (36), or Cys (37) -- Lys (183)

Preferred embodiments include the N-terminal deletions Ala (63)-Ser (208) (KGF-2Δ28) (SEQ ID NO:68) and Ser (69)-Ser (208) (KGF-2Δ33) (SEQ ID NO:96). Other preferred N-terminal and C-terminal deletion mutants are described in Examples 13 and 16 (c) of the specification and include: Ala (39)-Ser (208) (SEQ ID NO:116); Pro (47)-Ser (208) of FIG. 1 (SEQ ID NO:2); Val (77)-Ser (208) (SEQ ID NO:70); Glu (93)-Ser (208) (SEQ ID NO:72); Glu (104)-Ser (208) (SEQ ID NO:74); Val (123)-Ser (208) (SEQ ID NO:76); and Gly (138)-Ser (208) (SEQ ID NO:78). Other preferred C-terminal deletion mutants include: Met (1), Thr (36), or Cys (37)-Lys (153) of FIG. 1 (SEQ ID NO:2).

Also included by the present invention are deletion mutants having amino acids deleted from both the-terminus and the C-terminus. Such mutants include all combinations of the N-terminal deletion mutants and C-terminal deletion mutants described above, e.g., Ala (39)-His (200) of FIG. 1 (SEQ ID NO:2), Met (44)-Arg (193) of FIG. 1 (SEQ ID NO:2), Ala (63)-Lys (153) of FIG. 1 (SEQ ID NO:2), Ser (69)-Lys (153) of FIG. 1 (SEQ ID NO:2), etc. etc. etc . . . . Those combinations can be made using recombinant techniques known to those skilled in the art.

Thus, in one aspect, N-terminal deletion mutants are provided by the present invention. Such mutants include those comprising the amino acid sequence shown in FIG. 1 (SEQ ID NO:2) except for a deletion of at least the first 38 N-terminal amino acid residues (i.e., a deletion of at least Met (1)-Gin (38)) but not more than the first 147 N-terminal amino acid residues of FIG. 1 (SEQ ID NO:2). Alternatively, the deletion will include at least the first 38 N-terminal amino acid residues (i.e., a deletion of at least Met (1)-Gin (38)) but not more than the first 137 N-terminal amino acid residues of FIG. 1 (SEQ ID NO:2). Alternatively, the deletion will include at least the first 46 N-terminal amino acid residues but not more than the first 137 N-terminal amino acid residues of FIG. 1 (SEQ ID NO:2). Alternatively, the deletion will include at least the first 62 N-terminal amino acid residues but not more than the first 137 N-terminal amino acid residues of FIG. 1 (SEQ ID NO:2). Alternatively, the deletion will include at least the first 68 N-terminal amino acid residues but not more than the first 137 N-terminal amino acid residues of FIG. 1 (SEQ ID NO:2). Alternatively, the deletion will include at least the first 76 N-terminal amino acid residues but not more than the first 137 N-terminal amino acid residues of FIG. 1 (SEQ ID NO:2). Alternatively, the deletion will include at least the first 92 N-terminal amino acid residues but not more than the first 137 N-terminal amino acid residues of FIG. 1 (SEQ ID NO:2). Alternatively, the deletion will include at least the first 103 N-terminal amino acid residues but not more than the first 137 N-terminal amino acid residues of FIG. 1 (SEQ ID NO:2). Alternatively, the deletion will include at least the first 122 N-terminal amino acid residues but not more than the first 137 N-terminal amino acid residues of FIG. 1 (SEQ ID NO:2).

In addition to the ranges of N-terminal deletion mutants described above, the present invention is also directed to all combinations of the above described ranges, e.g., deletions of at least the first 62 N-terminal amino acid residues but not more than the first 68 N-terminal amino acid residues of FIG. 1 (SEQ ID NO:2); deletions of at least the first 62 N-terminal amino acid residues but not more than the first 76 N-terminal amino acid residues of FIG. 1 (SEQ ID NO:2); deletions of at least the first 62 N-terminal amino acid residues but not more than the first 92 N-terminal amino acid residues of FIG. 1 (SEQ ID NO:2); deletions of at least the first 62 N-terminal amino acid residues but not more than the first 103 N-terminal amino acid residues of FIG. 1 (SEQ ID NO:2); deletions of at least the first 68 N-terminal amino acid residues but not more than the first 76 N-terminal amino acid residues of FIG. 1 (SEQ ID NO:2); deletions of at least the first 68 N-terminal amino acid residues but not more than the first 92 N-terminal amino acid residues of FIG. 1 (SEQ ID NO:2); deletions of at least the first 68 N-terminal amino acid residues but not more than the first 103 N-terminal amino acid residues of FIG. 1 (SEQ ID NO:2); deletions of at least the first 46 N-terminal amino acid residues but not more than the first 62 N-terminal amino acid residues of FIG. 1 (SEQ ID NO:2); deletions of at least the first 46 N-terminal amino acid residues but not more than the first 68 N-terminal amino acid residues of FIG. 1 (SEQ ID NO:2); deletions of at least the first 46 N-terminal amino acid residues but not more than the first 76 N-terminal amino acid residues of FIG. 1 (SEQ ID NO:2); etc. etc. etc. . . .

In another aspect, C-terminal deletion mutants are provided by the present invention. Preferably, the N-terminal amino acid residue of said C-terminal deletion mutants is amino acid residue 1 (Met), 36 (Thr), or 37 (Cys) of FIG. 1 (SEQ ID NO:2). Such mutants include those comprising the amino acid sequence shown in FIG. 1 (SEQ ID NO:2) except for a deletion of at least the last C-terminal amino acid residue (Ser (208)) but not more than the last 55 C-terminal amino acid residues (i.e., a deletion of amino acid residues Glu (154)—Ser (208)) of FIG. 1 (SEQ ID NO:2). Alternatively, the deletion will include at least the last C-terminal amino acid residue but not more than the last 65 C-terminal amino acid residues of FIG. 1 (SEQ ID NO:2). Alternatively, the deletion will include at least the last 10 C-terminal amino acid residues but not more than the last 55 C-terminal amino acid residues of FIG. 1 (SEQ ID NO:2).

Alternatively, the deletion will include at least the last 20 C-terminal amino acid residues but not more than the last 55 C-terminal amino acid residues of FIG. 1 (SEQ ID NO:2). Alternatively, the deletion will include at least the last 30 C-terminal amino acid residues but not more than the last 55 C-terminal amino acid residues of FIG. 1 (SEQ ID NO:2).

Alternatively, the deletion will include at least the last 40 C-terminal amino acid residues but not more than the last 55 C-terminal amino acid residues of FIG. 1 (SEQ ID NO:2). Alternatively, the deletion will include at least the last 50 C-terminal amino acid residues but not more than the last 55 C-terminal amino acid residues of FIG. 1 (SEQ ID NO:2).

In addition to the ranges of C-terminal deletion mutants described above, the present invention is also directed to all combinations of the above described ranges, e.g., deletions of at least the last C-terminal amino acid residue but not more than the last 10 C-terminal amino acid residues of FIG. 1 (SEQ ID NO:2); deletions of at least the last C-terminal amino acid residue but not more than the last 20 C-terminal amino acid residues of FIG. 1 (SEQ ID NO:2); deletions of at least the last C-terminal amino acid residue but not more than the last 30 C-terminal amino acid residues of FIG. 1 (SEQ ID NO:2); deletions of at least the last C-terminal amino acid residue but not more than the last 40 C-terminal amino acid residues of FIG. 1 (SEQ ID NO:2); deletions of at least the last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 40 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc. etc. etc. . . .

In yet another aspect, also included by the present invention are deletion mutants having amino acids deleted from both the—terminal and C-terminal residues. Such mutants include all combinations of the N-terminal deletion mutants and C-terminal deletion mutants described above. Such mutants include those comprising the amino acid sequence shown in FIG. 1 (SEQ ID NO:2) except for a deletion of at least the first 46 N-terminal amino acid residues but not more than the first 137 N-terminal amino acid residues of FIG. 1 (SEQ ID NO:2) and a deletion of at least the last C-terminal amino acid residue but not more than the last 55 C-terminal amino acid residues of FIG. 1 (SEQ ID NO:2). Alternatively, a deletion can include at least the first 62, 68, 76, 92, 103, or 122 N-terminal amino acids but not more than the first 137 N-terminal amino acid residues of FIG. 1 (SEQ ID NO:2) and a deletion of at least the last 10, 20, 30, 40, or 50 C-terminal amino acid residues but not more than the last 55 C-terminal amino acid residues of FIG. 1 (SEQ ID NO:2). Further included are all combinations of the above described ranges.

Substitution of Amino Acids

A further aspect of the present invention also includes the substitution of amino acids. Native mature KGF-2 contains 44 charged residues, 32 of which carry a positive charge. Depending on the location of such residues in the protein's three dimensional structure, substitution of one or more of these clustered residues with amino acids carrying a negative charge or a neutral charge may alter the electrostatic interactions of adjacent residues and may be useful to achieve increased stability and reduced aggregation of the protein. Aggregation of proteins cannot only result in a loss of activity but be problematic when preparing pharmaceutical formulations, because they can be immunogenic (Pinckard et al., *Clin. Exp. Immunol.* 2:331–340(1967), Robbins et al., *Diabetes* 36: 838–845 (1987), Cleland et al., *Crit. Rev. Therapeutic Drug Carrier Systems* 10: 307–377 (1993)). Any modification should give consideration to minimizing charge repulsion in the tertiary structure of the protein molecule. Thus, of special interest are substitutions of charged amino acid with another charge and with neutral or negatively charged amino acids. The latter results in proteins with a reduced positive charge to improve the characteristics of KGF-2. Such improvements include increased stability and reduced aggregation of the analog as compared to the native KGF-2 protein.

The replacement of amino acids can also change the selectivity of binding to cell surface receptors. Ostade et al., *Nature* 361: 266–268 (1993), described certain TNF alpha mutations resulting in selective binding of TNF alpha to only one of the two known TNF receptors.

A further embodiment of the invention relates to a polypeptide which comprises the amino acid sequence of a KGF-2 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a KGF-2 polypeptide, which contains at least one, but not more than 20, 19, 18, 17, 16, 15, 14, 13, 12, 11, 10, 9, 8, 7, 6, 5, 4, 3, 2 or 1 amino acid substitutions. In specific embodiments, the number of additions, substitutions, and/or deletions in the amino acid sequence of FIG. 1 or fragments thereof (e.g., the mature form and/or other fragments described herein), is 1–5, 5–10, 5–25, 5–50, 10–50 or 50–150, conservative amino acid substitutions are preferable.

KGF-2 molecules may include one or more amino acid substitutions, deletions or additions, either from natural mutation or human manipulation. The mutations can be made in full-length KGF-2, mature KGF-2, any other appropriate fragments of KGF-2, for example, A63-S208, S69-S208, V77-S208, R80-S208 or E93-S208. Examples of some preferred mutations are: Ala (49) Gln, Asn (51) Ala, Ser (54) Val, Ala (63) Pro, Gly (64) Glu, Val (67) Thr, Trp (79) Val, Arg (80) Lys, Lys (87) Arg, Tyr (88) Trp, Phe (89) Tyr, Lys (91) Arg, Ser (99) Lys, Lys (102) Gln, Lys 103 (Glu), Glu (104) Met, Asn (105) Lys, Pro (107) Asn, Ser (109) Asn, Leu (111) Met, Thr (114) Arg, Glu (117) Ala, Val (120) Ile, Val (123) Ile, Ala (125) Gly, Ile (126) Val, Asn (127) Glu, Asn (127) Gin, Tyr (130) Phe, Met (134) Thr, Lys (136) Glu, Lys (137) Glu, Gly (142) Ala, Ser (143) Lys, Phe (146) Ser, Asn (148) Glu, Lys (151) Asn, Leu (152) Phe, Glu (154) Gly, Glu (154) Asp, Arg (155) Leu, Glu (157) Leu, Gly (160) His, Phe (167) Ala, Asn (168) Lys, Gin (170) Thr, Arg (174) Gly, Tyr (177) Phe, Gly (182) Gln, Ala (185) Val, Ala (185) Leu, Ala (185) Ile, Arg (187) Gin (190) Lys, Lys (195) Glu, Thr (197) Lys, Ser (198) Thr, Arg (194) Glu, Arg (194) Gin, Lys (191) Glu, Lys (191) Gin, Arg (188) Glu, Arg (188) Gin, Lys (183) Glu, Arg (187) Ala, Arg (188) Ala, Arg 174 (Ala), Lys (183) Ala, Lys (144) Ala, Lys (151) Ala, Lys (153) Ala, Lys (136) Ala, Lys (137) Ala, and Lys (139) Ala.

By the designation, for example, Ala (49) Gin is intended that the Ala at position 49 of FIG. 1 (SEQ ID NO:2) is replaced by Gln.

Additionally, the following mutants are particularly preferred: S69-S208 with a point mutation at R188E; S69-S208 with a point mutation at K191 E; S69-S208, with a point mutation at K149E; S69-S208 with a point mutation at K183Q; S69-S208 with a point mutation at K183E; A63-S208 with a point mutation at R68G; A63-S208 with a point mutation at R68S; A63-S208 with a point mutation at R68A; A63-S208 with point mutations at R78A, R80A and K81A; A63-S208 with point mutations at K81A, K87A and K91A; A63-S208 with point mutations at R78A, R80A, K81A, K87A and K91A; A63-S208 with point mutations at K136A, K137A, K139A and K144A; A63-S208 with point mutations at K151A, K153A and K155A; A63-S208 with point mutations at R68G, R78A, R80A, and K81A; A63-S208 with point mutations at R68G, K81A, K87A and K91A; A63-S208 with point mutations at R68G, R78A, R80A, K81A, K87A and K91A; A63-S208 with point mutations at R68G, K136A, K137A, K139A, and K144A; A63-208 with point mutations at R68G, K136A, K153A, and R155A; A63-S208 with point mutations at R68S, R78A, R80A, and K81A; A63-S208 with point mutations at R68S, K81A, R87A and K91A; A63-S208 with point mutations at R68S, R78A, R80A, K81A, K87A and K91 A; A63-S208 with point mutations at R68S, K136A, K137A, K139A, and K144A; A63-208 with point mutations at R68S, K151A, K153A, and R155A; A63-S208 with point mutations at R68A, R78A, R80A and K81A; A63-S208 with point mutations at R68A, K81A, K87A, and K91A; A63-S208 with point mutations at R68A, R78A, R80A, K81A, K87A, and K91A; A63-S208 with point mutations at R68A, K136A, K137A, K139A and K144A; and A63-S208 with point mutations at R68A, K151A, K153A and R155A. Also preferred are: A63-S208 with the positively charged residues between and including R68 to K91 are replaced with alanine [A63-S208 (R68-K91A)]; full length KGF-2 with the positively charged residues between and including R68 to K91 replaced with alanine [KGF-2(R68-K91A)]; A63-S208 with the positively charged residues between and including R68 to K91 replaced with neutral residues, such as G, S and/or A; full length KGF-2 with the positively charged residues between and including R68 to K91 replaced with neutral residues, such as G, S and/or A; A63-S208 with the positively charged residues between and including R68 to K91 replaced with negatively charged acidic residues, such as D and/or E; full length KGF-2 with the positively charged residues between and including R68 to K91 replaced with negatively charged acidic residues, such as D and/or E; full length KGF-2 with point mutations at R78A, R80A, and K81A; full length KGF-2 with point mutations at K81A, K87A and K91A; full length KGF-2 with a point mutation at R68G; full length KGF-2 with a point mutation at R68S; full length KGF-2 with a point mutation at R68A; A63-S208 with point mutations at R174A and K183A; and A63-S208 with point mutations at R187A and R188A.

Also preferred is A63-S208 with a point mutation at R188E, K191E, K149E, K183Q, or K183E; S69-S208 with point mutations at R78A, R80A and K81A; S69-S208 with point mutations at K81A, K87A and K91A; S69-S208 with point mutations at R174A and K183A; S69-S208 with point mutations at R187A and R188A; V77-S208 with a point mutation at R188E, K191E, K149E, K183Q, or K183E; V77-S208 with point mutations at R78A, R80A and K81A; V77-S208 with point mutations at K81A, K87A and K91A; V77-S208 with point mutations at R174A and K183A; V77-S208 with point mutations at R187A and R188A; R80-S208 with a point mutation at R188E, K191E, K149E, K183Q, or K183E; R80-S208 with point mutations at R174A and K183A; R80-S208 with point mutations at R187A and R188A; E93-S208 with a point mutation at R188E, K191E, K149E, K183Q, or K183E; E93-S208 with point mutations at R174A and K183A; or E93-S208 with point mutations at R187A and R188A.

All of the above point mutations may also be made in the full length KGF-2, the mature KGF-2, or any other fragment of KGF-2 described herein. By the designation, for sample, R188E is intended that the Arginine at position 188 is replaced with a Glutamic Acid.

In addition site directed mutations may be made at each amino acids of KGF-2, preferably between amino acids A63 to E93. Each amino acid can be replaced by any of the other 19 remaining amino acids. For example preferred mutations include: A63 replaced with C, D, E, F, G, H, I, K, L, M, N, P, Q, R, S, T, V, W, or Y; G64 replaced with A, C, D, E, F, H, I, K, L, M, N, P, Q, R, S, T, V, W, or Y; R65 replaced with A, C, D, E, F, G, H, I, K, L, M, N, P, Q, S, T, V, W, or Y; H66 replaced with A, C, D, E, F, G, I, K, L, M, N, P, Q, R, S, T, V, W, or Y; V67 replaced with A, C, D, E, F, G, H, I, K, L, M, N, P, Q, R, S, T, W, or Y; R68 replaced with A, C, D, E, F, G, H, I, K, L, M, N, P, Q, S, T, V, W, or Y; S69 replaced with A, C, D, E, F, G, H, I, K, L, M, N, P, Q, R, T, V, W, or Y; Y70 replaced with A, C, D, E, F, G, H, I, K, L, M, N, P, Q, R, S, T, V, or W; N71 replaced with A, C, D, E, F, G, H, I, K, L, M, P, Q, R, S, T, V, W, or Y; H72 replaced with A, C, D, E, F, G, I, K, L, M, N, P, Q, R, S, T, V, W, or Y; L73 replaced with A, C, D, E, F, G, H, I, K, M, N, P, Q, R, S, T, V, W, or Y; Q74 replaced with A, C, D, E, F, G, H, I, K, L, M, N, P, R, S, T, V, W, or Y; G75 replaced with A, C, D, E, F, H, I, K, L, M, N, P, Q, R, S, T, V, W, or Y; D76 replaced with A, C, E, F, G, H, I, K, L, M, N, P, Q, R, S, T, V, W, or Y; V77 replaced with A, C, D, B, F, G, H, I, K, L, M, N, P, Q, R, S, T, W, or Y; R78 replaced with A, C, D, E, F, G, H, I, K, L, M, N, P, Q, S, T, V, W, or Y; W79 replaced with A, C, D, E, F, G, H, I, K, L, M, N, P, Q, R, S, T, V, or Y; R80 replaced with A, C, D, E, F, G, H, I, K, L, M, N, P, Q, S, T, V, W, or Y; K81 replaced with A, C, D, E, F, G, H, K, L, M, N, P, Q, R, S, T, V, W, or Y; L82 replaced with A, C, D, E, F, G, H, I, K, M, N, P, Q, R, S, T, V, W, or Y; F83 replaced with A, C, D, E, G, H, I, K, L, M, N, P, Q, R, S, T, V, W, or Y; S84 replaced with A, C, D, E, F, G, H, I, K, L, M, N, P, Q, R, T, V, W, or Y; F85 replaced with A, C, D, E, G, H, I, K, L, M, N, P, Q, R, S, T, V, W, or Y; T86 replaced with A, C, D, E, F, G, H, I, K, L, M, N, P, Q, R, S, V, W, or Y; K87 replaced with A, C, D, E, F, G, H, I, L, M, N, P, Q, R, S, T, V, W, or Y; Y88 replaced with A, C, D, E, F, G, H, I, K, L, M, N, P, Q, R, S, T, V, or W; F89 replaced with A, C, D, E, G, H, I, K, L, M, N, P, Q, R, S, T, V, W, or Y; L90 replaced with A, C, D, E, F, G, H, I, K, M, N, P, Q, R, S, T, V, W, or Y; K91 replaced with A, C, D, E, F, G, H, I, L, M, N, P, Q, R, S, T, V, W, or Y; I92 replaced with A, C, D, E, F, G, H, K, L, M, N, P, Q, R, S, T, V, W, or Y; and/or E93 replaced with A, C, D, F, G, H, I, K, L, M, N, P, Q, R, S, T, V, W, or Y.

These mutations can be made in the N-terminal deletion constructs previously described, particularly constructs beginning with amino acids M1, T36, C37, or A63. Additionally, more than one amino acid (e.g. 2, 3, 4, 5, 6, 7, 8, 9 and 10) can be replaced in this region (A63 to E93) with other amino acids. The resulting constructs can be screened for loss of heparin binding, loss of KGF-2 activity, and/or loss of enzymatic cleavage between amino acids R68 and S69.

Preferred mutations are located at amino acid positions R68 and S69 in N-terminal deletion constructs M1, T36, C37 and A63, as well as mutations in the heparin binding domain, of all of the above listed N-terminal mutants, especially T36, C37, A63, S69, V77, R80 or E93. The heparin binding domain is between Arg 174 and Lys 183. Preferred Arg68 mutants replace the arginine with Gly, Ser or Ala; preferred Arg 187 mutants replace the arginine with alanine.

Two ways in which mutations can be made is either by site directed mutagenesis or accelerated mutagenesis (Kuchner and Arnold, *Tibtech* 5:523–530 (1997); Crameri et al., *Nature* (1998); and Christians et al., *Nature Biotechnology* 17:259264 (1999)). These methods are well known in the art.

Changes are preferably of minor nature, such as conservative amino acid substitutions that do not significantly affect the folding or activity of the protein. Examples of conservative amino acid substitutions known to those skilled in the art are set forth below:

| | |
|---|---|
| Aromatic: | phenylalanine |
| | tryptophan |
| | tyrosine |
| Hydrophobic: | leucine |
| | isoleucine |
| | valine |
| Polar: | glutamine |
| | asparagine |
| Basic: | arginine |
| | lysine |
| | histidine |
| Acidic: | aspartic acid |
| | glutamic acid |
| Small: | alanine |
| | serine |
| | threonine |
| | methionine |
| | glycine |

Of course, the number of amino acid substitutions a skilled artisan would make depends on many factors, including those described above. Generally speaking, the number of substitutions for any given KGF-2 polypeptide will not be more than 50, 40, 30, 20, 10, 5, or 3, depending on the objective. For example, a number of substitutions that can be made in the C-terminus of KGF-2 to improve stability are described above and in Example 22.

Particularly preferred are KGF-2 molecules with conservative amino acid substitutions, including: MI replaced with A, G, I, L, S, T, or V; W2 replaced with F, or Y; K3 replaced with H, or R; W4 replaced with F, or Y; 15 replaced with A, G, L, S, T, M, or V; L6 replaced with A, G, I, S, T, M, or V; T7 replaced with A, G, I, L, S, M, or V; H8 replaced with K, or R; A10 replaced with G, I, L, S, T, M, or V; S11 replaced with A, G, I, L, T, M, or V; A12 replaced with G, I, L, S, T, M, or V; F13 replaced with W, or Y; H15 replaced with K, or R; L16 replaced with A, G, I, S, T, M, or V; G18 replaced with A, I, L, S, T, M, or V; F24 replaced with W, or Y; L25 replaced with A, G, I, S, T, M, or V; L26 replaced with A, G, I, S, T, M, or V; L27 replaced with A, G, I, S, T, M, or V; F28 replaced with W, or Y; L29 replaced with A, G, I, S, T, M, or V; V30 replaced with A, G, I, L, S, T, or M; S31 replaced with A, G, I, L, T, M, or V; S32 replaced with A, G, I, L, T, M, or V; V33 replaced with A, G, I, L, S, T, or M; V35 replaced with A, G, I, L, S, T, or M; T36 replaced with A, G, I, L, S, M, or V; Q38 replaced with N; A39 replaced with G, I, L, S, T, M, or V; L40 replaced with A, G, I, S, T, M, or V; G41 replaced with A, I, L, S, T, M, or V; Q42 replaced with N; D43 replaced with E; M44 replaced with A, G, I, L, S, T, or V; V45 replaced with A, G, I, L, S, T, or M; S46 replaced with A, G, I, L, T, M, or V; E48 replaced with D; A49 replaced with G, I, L, S, T, M, or V; T50 replaced with A, G, I, L, S, M, or V; N51 replaced with Q; S52 replaced with A, G, I, L, T, M, or V; S53 replaced with A, G, I, L, T, M, or V; S54 replaced with A, G, I, L, T, M, or V; S55 replaced with A, G, I, L, T, M, or V; S56 replaced with A, G, I, L, T, M, or V; F57 replaced with W, or Y; S58 replaced with A, G, I, L, T, M, or V; S59 replaced with A, C, I, L, T, M, or V; S61 replaced with A, C, I, L, T, M, or V; S62 replaced with A, G, I, L, T, M, or V; A63 replaced with G, G, L, S, T, M, or V; G64 replaced with A, I, L, S, T, M, or V; R65 replaced with H, or K; H66 replaced with K, or R; V67 replaced with A, G, I, L, S, T, or M; R68 replaced with H, or K; S69 replaced with A, G, I, L, T, M, or V; Y70 replaced with F, or W; N71 replaced with Q; H72 replaced with K, or R; L73 replaced with A, G, I, S, T, M, or V; Q74 replaced with N; G75 replaced with A, I, L, S, T, M, or V; D76 replaced with E; V77 replaced with A, G, I, L, S, T, or M; R78 replaced with H, or K; W79 replaced with F, or Y; R80 replaced with H, or K; K81 replaced with H, or R; L82 replaced with A, G, I, S, T, M, or V; F83 replaced with W, or Y; S84 replaced with A, G, I, L, T, M, or V; F85 replaced with W, or Y; T86 replaced with A, G, I, L, S, M, or V; K87 replaced with H, or R; Y88 replaced with F, or W; F89 replaced with W, or Y; L90 replaced with A, G, I, S, T, M, or V; K91 replaced with H, or R; 192 replaced with A, G, L, S, T, M, or V; E93 replaced with D; K94 replaced with H, or R; N95 replaced with Q; G96 replaced with A, I, L, S, T, M, or V; K97 replaced with H, or R; V98 replaced with A, G, I, L, S, T, or M; S99 replaced with A, G, I, L, T, M, or V; G100 replaced with A, I, L, S, T, M, or V; T101 replaced with A, G, I, L, S, M, or V; K102 replaced with H, or R; K103 replaced with H, or R; E104 replaced with D; N105 replaced with Q; Y108 replaced with F, or W; S109 replaced with A, G, I, L, T, M, or V; I110 replaced with A, G, L, S, T, M, or V; L111 replaced with A, G, I, S, T, M, or V; E112 replaced with D; I113 replaced with A, G, L, S, T, M, or V; T114 replaced with A, G, I, L, S, M, or V; S115 replaced with A, G, I, L, T, M, or V; V116 replaced with A, G, I, L, S, T, or M; E117 replaced with D; I118 replaced with A, G, L, S, T, M, or V; G119 replaced with A, I, L, S, T, M, or V; V120 replaced with A, G, I, L, S, T, or M; V121 replaced with A, G, I, L, S, T, or M; A122 replaced with G, I, L, S, T, M, or V; V123 replaced with A, G, I, L, S, T, or M; K124 replaced with H, or R; A125 replaced with G, I, L, S, T, M, or V; I126 replaced with A, G, L, S, T, M, or V; N127 replaced with Q; S128 replaced with A, G, I, L, T, M, or V; N129 replaced with Q; Y130 replaced with F, or W; Y131 replaced with F, or W; L132 replaced with A, G, I, S, T, M, or V; A133 replaced with G, I, L, S, T, M, or V; M134 replaced with A, G, I, L, S, T, or V; N135 replaced with Q; K136 replaced with H, or R; K137 replaced with H, or R; G138 replaced with A, I, L, S, T, M, or V; K139 replaced with H, or R; L140 replaced with A, G, I, S, T, M, or V; Y141 replaced with F, or W; G142 replaced with A, I, L, S, T, M, or V; S143 replaced with A, G, I, L, T, M, or V; K144 replaced with H, or R; E145 replaced with D; F146 replaced with W, or Y; N 147 replaced with Q; N 148 replaced with Q; D149 replaced with E; K151 replaced with H, or R; L152 replaced with A, G, I, S, T, M, or V; K153 replaced with H, or R; E154 replaced with D; R155 replaced with H, or K; I156 replaced with A, G, L, S, T, M, or V; E157 replaced with D; E158 replaced with D; N159 replaced with Q; G160 replaced with A, I, L, S, T, M, or V; Y161 replaced with F, or W; N162 replaced with Q; T163 replaced with A, G, I, L, S, M, or V; Y164 replaced with F, or W; A 165 replaced with G, I, L, S, T, M, or V; S 166 replaced with A, G, I, L, T, M, or V; F 167 replaced with W, or Y; N 168 replaced with Q; W169 replaced with F, or Y; Q170 replaced with N; H171 replaced with K, or R; N172 replaced with Q; G173 replaced with A, I, L, S, T, M, or V; R174 replaced with H, or K; Q175 replaced with N; M176 replaced with A, G, I, L, S, T, or V; Y177 replaced with F, or W; V178 replaced with A, G, I, L, S, T, or M; A179 replaced with G, I, L, S, T, M, or V; L180 replaced with A, G, I, S, T, M, or V; N181 replaced with Q; G182 replaced with A, I, L, S, T, M, or V; K183 replaced with H, or R; G1184 replaced with A, I, L, S, T, M, or V; A185 replaced with G, I, L, S, T, M, or V; R187 replaced with H, or K; R188 replaced with H, or K; G189 replaced with A, I, L, S, T, M, or V; Q190 replaced with N; K191 replaced with H, or R; T192 replaced with A, G, I, L, S, M, or V; R193 replaced with H, or K; R194 replaced with H, or K; K195 replaced with H, or R; N196 replaced with Q; T197 replaced with A, G, I, L, S, M, or V; S198 replaced with A, G, I, L, T, M, or V; A199 replaced with G, I, L, S, T, M, or V; H200 replaced with K, or R; F201 replaced with W, or Y; L202 replaced with A, G, I, S, T, M, or V; M204 replaced with A, G, I, L, S, T, or V; V205 replaced with A, G, I, L, S, T, or M; V206 replaced with A, G, I, L, S, T, or M; H207 replaced with K, or R; or S208 replaced with A, G, I, L, T, M, or V.

However, also preferred are KGF-2 molecules with non-conservative amino acid substitutions, including: M1 replaced with D, E, H, K, R, N, Q, F, W, Y, P, or C; W2 replaced with D, E, H, K, R, N, Q, A, G, I, L, S, T, M, V, P, or C; K3 replaced with D, E, A, G, I, L, S, T, M, V, N, Q, F, W, Y, P, or C; W4 replaced with D, E, H, K, R, N, Q, A, G, I, L, S, T, M, V, P, or C; 15 replaced with D, E, H, K, R, N, Q, F, W, Y, P, or C; L6 replaced with D, E, H, K, R, N, Q, F, W, Y, P, or C; T7 replaced with D, E, H, K, R, N, Q, F, W, Y, P, or C; H8 replaced with D, E, A, G, I, L, S, T, M, V, N, Q, F, W, Y, P, or C; C9 replaced with D, E, H, K, R, A, G, I, L, S, T, M, V, N, Q, F, W, Y, or P; A10 replaced with D, E, H, K, R, N, Q, F, W, Y, P, or C; S11 replaced with D, E, H, K, R,N, Q, F, W, Y, P, or C; A12 replaced with D, E, H, K, R, N, Q, F, W, Y, P, or C; F13 replaced with D, E, H, K, R, N, Q, A, G, I, L, S, T, M, V, P, or C; P14 replaced with D, E, H, K, R, A, G, I, L, S, T, M, V, N, Q, F, W, Y, or C; H15 replaced with D, E, A, G, I, L, S, T, M, V, N, Q, F, W, Y, P, or C; L16 replaced with D, E, H, K, R, N, Q, F, W, Y, P, or C; P17 replaced with D, E, H, K, R, A, G, I, L, S, T, M, V, N, Q, F, W, Y, or C; G118 replaced with D, E, H, K, R, N, Q, F, W, Y, P, or C; C19 replaced with D, E, H, K, R, A, G,I, L, S, T, M, V, N, Q, F, W, Y,or P; C20 replaced with D, E, H, K, R, A, G, I, L, S, T, M, V, N, Q, F, W, Y, or P; C21 replaced with D, E, H, K, R, A, G, I, L, S, T, M, V, N, Q, F, W, Y, or P; C22 replaced with D, E, H, K, R, A, G, I, L, S, T, M, V, N, Q, F, W, Y, or P; C23 replaced with D, E, H, K, R, A, G, I, L, S, T, M, V, N, Q, F, W, Y, or P; F24 replaced with D, E, H, K, R, N, Q, A, G, I, L, S, T, M, V, P, or C; L25 replaced with D, E, H, K, R, N, Q, F, W, Y, P, or C; L26 replaced with D, E, H, K, R, N, Q, F, W, Y, P, or C; L27 replaced with D, E, H, K, R, N, Q, F, W, Y, P, or C; F28 replaced with D, E, H, K, R, N, Q, A, G, I, L, S, T, M, V, P, or C; L29 replaced with D, E, H, K, R, N, Q, F, W, Y, P, or C; V30 replaced with D, E, H, K, R, N, Q, F, W, Y, P, or C; S31 replaced with D, E, H, K, R, N, Q, F, W, Y, P, or C; S32 replaced with D, E, H, K, R, N, Q, F, W, Y, P, or C; V33 replaced with D, E, H, K, R, N, Q, F, W, Y, P, or C; P34 replaced with D, E, H, K, R, A, G, I, L, S, T, M, V, N, Q, F, W, Y, or C; V35 replaced with D, E, H, K, R, N, Q, F, W, Y, P, or C; T36 replaced with D, E, H, K, R, N, Q, F, W, Y, P, or C; C37 replaced with D, E, H, K, R, A, G, I, L, S, T, M, V, N, Q, F, W, Y, or P; Q38 replaced with D, E, H, K, R, A, G, I, L, S, T, M, V, F, W, Y, P, or C; A39 replaced with D, E, H, K, R, N, Q, F, W, Y, P, or C; L40 replaced with D, E, H, K, R, N, Q, F, W, Y, P, or C; G41 replaced with D, E, H, K, R, N, Q, F, W, Y, P, or C; Q42 replaced with D, E, H, K, R, A, G, I, L, S, T, M, V, F, W, Y, P, or C; D43 replaced with H, K, R, A, G, I, L, S, T, M, V, N, Q, F, W, Y, P, or C; M44 replaced with D, E, H, K, R, N, Q, F, W, Y, P, or C; V45 replaced with D, E, H, K, R, N, Q, F, W, Y, P, or C; S46 replaced with D, E, H, K, R, N, Q, F, W, Y, P, or C; P47 replaced with D, E, H, K, R, A, G, I, L, S, T, M, V, N, Q, F, W, Y, or C; E48 replaced with H, K, R, A, G, I, L, S, T, M, V, N, Q, F, W, Y, P, or C; A49 replaced with D, E, H, K, R, N, Q, F, W, Y, P, or C; T50 replaced with D, E, H, K, R, N, Q, F, W, Y, P, or C; N51 replaced with D, E, H, K, R, A, G, I, L, S, T, M, V, F, W, Y, P, or C; S52 replaced with D, E, H, K, R, N, Q, F, W, Y, P, or C; S53 replaced with D, E, H, K, R, N, Q, F, W, Y, P, or C; S54 replaced with D, E, H, K, R, N, Q, F, W, Y, P, or C; S55 replaced with D, E, H, K, R, N, Q, F, W, Y, P, or C; S56 replaced with D, E, H, K, R, N, Q, F, W, Y, P, or C; F57 replaced with D, E, H, K, R, N, Q, A, G, I, L, S, T, M, V, P, or C; S58 replaced with D, E, H, K, R, N, Q, F, W, Y, P, or C; S59 replaced with D, E, H, K, R, N, Q, F, W, Y, P, or C; P60 replaced with D, E, H, K, R, A, G, I, L, S, T, M, V, N, Q, F, W, Y, or C; S61 replaced with D, E, H, K, R, N, Q, F, W, Y, P, or C; S62 replaced with D, E, H, K, R, N, Q, F, W, Y, P, or C; A63 replaced with D, E, H, K, R, N, Q, F, W, Y, P, or C; G64 replaced with D, E, H, K, R, N, Q, F, W, Y, P, or C; R65 replaced with D, E, A, G, I, L, S, T, M, V, N, Q, F, W, Y, P, or C; H66 replaced with D, E, A, G, I, L, S, T, M, V, N, Q, F, W, Y, P, or C; V67 replaced with D, E, H, K, R, N, Q, F, W, Y, P, or C; R68 replaced with D, E, A, G, I, L, S, T, M, V, N, Q, F, W, Y, P, or C; S69 replaced with D, E, H, K, R, N, Q, F, W, Y, P, or C; Y70 replaced with D, E, H, K, R, N, Q, A, G, I, L, S, T, M, V, P, or C; N71 replaced with D, E, H, K, R, A, G, I, L, S, T, M, V, F, W, Y, P, or C; H72 replaced with D, E, A, G, I, L, S, T, M, V, N, Q, F, W, Y, P, or C; L73 replaced with D, E, H, K, R, N, Q, F, W, Y, P, or C; Q74 replaced with D, E, H, K, R, A, G, I, L, S, T, M, V, F, W, Y, P, or C; G75 replaced with D, E, H, K, R, N, Q, F, W, Y, P, or C; D76 replaced with H, K, R, A, G, I, L, S, T, M, V, N, Q, F, W, Y, P, or C; V77 replaced with D, E, H, K, R, N, Q, F, W, Y, P, or C; R78 replaced with D, E, A, G, I, L, S, T, M, V, N, Q, F, W, Y, P, or C; W79 replaced with D, E, H, K, R, N, Q, A, G, I, L, S, T, M, V, P, or C; R80 replaced with D, E, A, G, I, L, S, T, M, V, N, Q, F, W, Y, P, or C; K81 replaced with D, E, A, G, I, L, S, T, M, V, N, Q, F, W, Y, P, or C; L82 replaced with D, E, H, K, R, N, Q, F, W, Y, P, or C; F83 replaced with D, E, H, K, R, N, Q, A, G, I, L, S, T, M, V, P, or C; S84 replaced with D, E, H, K, R, N, Q, F, W, Y, P, or C; F85 replaced with D, E, H, K, R, N, Q, A, G, I, L, S, T, M, V, P, or C; T86 replaced with D, E, H, K, R, N, Q, F, W, Y, P, or C; K87 replaced with D, E, A, G, I, L, S, T, M, V, N, Q, F, W, Y, P, or C; Y88 replaced with D, E, H, K, R, N, Q, A, G, I, L, S, T, M, V, P, or C; F89 replaced with D, E, H, K, R, N, Q, A, G, I, L, S, T, M, V, P, or C; L90 replaced with D, E, H, K, R, N, Q, F, W, Y, P, or C; K91 replaced with D, E, A, G, I, L, S, T, M, V, N, Q, F, W, Y, P, or C; 192 replaced with D, E, H, K, R, N, Q, F, W, Y, P, or C; E93 replaced with H, K, R, A, G, I, L, S, T, M, V, N, Q, F, W, Y, P, or C; K94 replaced with D, E, A, G, I, L, S, T, M, V, N, Q, F, W, Y, P, or C; N95 replaced with D, E, H, K, R, A, G, I, L, S, T, M, V, F, W, Y, P, or C; G96 replaced with D, E, H, K, R, N, Q, F, W, Y, P, or C; K97 replaced with D, E, A, G, I, L, S, T, M, V, N, Q, F, W, Y, P, or C; V98 replaced with D, E, H, K, R, N, Q, F, W, Y, P, or C; S99 replaced with D, E, H, K, R, N, Q, F, W, Y, P, or C; G100 replaced with D, E, H, K, R, N, Q, F, W, Y, P, or C; T101 replaced with D, E, H, K, R, N, Q, F, W, Y, P, or C; K102 replaced with D, E, A, G, I, L, S, T, M, V, N, Q, F, W, Y, P, or C; K103 replaced with D, E, A, G, I, L, S, T, M, V, N, Q, F, W, Y, P, or C; E104 replaced with H, K, R, A, G, I, L, S, T, M, V, N, Q, F, W, Y, P, or C; N105 replaced with D, E, H, K, R, A, G, I, L, S, T, M, V, F, W, Y, P, or C; C106 replaced with D, E, H, K, R, A, G, I, L, S, T, M, V, N, Q, F, W, Y, or P; P107 replaced with D, E, H, K, R, A, G, I, L, S, T, M, V, N, Q, F, W, Y, or C; Y108 replaced with D, E, H, K, R, N, Q, A, G, I, L, S, T, M, V, P, or C; S109 replaced with D, E, H, K, R, N, Q, F, W, Y, P, or C; I110 replaced with D, E, H, K, R, N, Q, F, W, Y, P, or C; L111 replaced with D, E, H, K, R, N, Q, F, W, Y, P, or C; E112 replaced with H, K, R, A,G, I, L, S, T, M, V, N, Q, F, W, Y, P, or C; I113 replaced with D, E, H, K, R, N, Q, F, W, Y, P, or C; T114 replaced with D, E, H, K, R, N, Q, F, W, Y, P, or C; S115 replaced with D, E, H, K, R, N, Q, F, W, Y, P, or C; V116 replaced with D, E, H, K, R, N, Q, F, W, Y, P, or C; E117 replaced with H, K, R, A, G, I, L, S, T, M, V, N, Q, F, W, Y, P, or C; I118 replaced with D, E, H, K, R, N, Q, F, W, Y, P, or C; G119 replaced with D, E, H, K, R, N, Q, F, W, Y, P, or C; V120 replaced with D, E, H, K, R, N, Q, F, W, Y, P, or C; V121 replaced with D, E, H, K, R, N, Q, F, W, Y, P, or C; A122 replaced with D, E, H, K, R, N, Q, F, W, Y, P, or C; V123 replaced with D, E, H, K, R, N, Q, F, W, Y, P, or C; K124 replaced with D, E, A, G, I, L, S, T, M, V, N, Q, F, W, Y, P, or C; A125 replaced with D, E, H, K, R, N, Q, F, W, Y, P, or C; I126 replaced with D, E, H, K, R, N, Q, F, W, Y, P, or C; N127 replaced with D, E, H, K, R, A,G, I, L, S, T, M, V, F, W, Y, P, or C; S128 replaced with D, E, H, K, R, N, Q, F, W, Y, P, or C; N129 replaced with D, E, H, K, R, A, G, I, L, S, T, M, V, F, W, Y, P, or C; Y130 replaced with D, E, H, K, R, N, Q, A, G, I, L, S, T, M, V, P, or C; Y131 replaced with D, E, H, K, R, N, Q, A, G, I, L, S, T, M, V, P, or C; L132 replaced with D, E, H, K, R, N, Q, F, W, Y, P, or C; A133 replaced with D, E, H, K, R, N, Q, F, W, Y, P, or C; M134 replaced with D, E, H, K, R, N, Q, F, W, Y, P, or C; N135 replaced with D, E, H, K, R, A, G, I, L, S, T, M, V, F, W, Y, P, or C; K136 replaced with D, E, A, G, I, L, S, T, M, V, N, Q, F, W, Y, P, or C; K137 replaced with D, E, A, G, I, L, S, T, M, V, N, Q, F, W, Y, P, or C; G138 replaced with D, E, H, K, R, N, Q, F, W, Y, P, or C; K139 replaced with D, E, A, G, I, L, S, T, M, V, N, Q, F, W, Y, P, or C; L140 replaced with D, E, H, K, R, N, Q, F, W, Y, P, or C; Y141 replaced with D, E, H, K, R, N, Q, A, G, I, L, S, T, M, V, P, or C; G142 replaced with D, E, H, K, R, N, Q, F, W, Y, P, or C; S143 replaced with D, E, H, K, R, N, Q, F, W, Y, P, or C; K144 replaced with D, E, A, G, I, L, S, T, M, V, N, Q, F, W, Y, P, or C; E145 replaced with H, K, R, A, G, I, L, S, T, M, V, N, Q, F, W, Y, P, or C; F146 replaced with D, E, H, K, R, N, Q, A, G, I, L, S, T, M, V, P, or C; N147 replaced with D, E, H, K, R, A, G, I, L, S, T, M, V, F, W, Y, P, or C; N148 replaced with D, E, H, K, R, A, G, I, L, S, T, M, V, F, W, Y, P, or C; D149 replaced with H, K, R, A, G, I, L, S, T, M, V, N, Q, F, W, Y, P, or C; C150 replaced with D, E, H, K, R, A, G, I, L, S, T, M, V, N, Q, F, W, Y, or P; K151 replaced with D, E, A, G, I, L, S, T, M, V, N, Q, F, W, Y, P, or C; L152 replaced with D, E, H, K, R, N, Q, F, W, Y, P, or C; K153 replaced with D, E, A, G, I, L, S, T, M, V, N, Q, F, W, Y, P, or C; E154 replaced with H, K, R, A, G, I, L, S, T, M, V, N, Q, F, W, Y, P, or C; R155 replaced with D, E, A, G, I, L, S, T, M, V, N, Q, F, W, Y, P, or C; I156 replaced with D, E, H, K, R, N, Q, F, W, Y, P, or C; E157 replaced with H, K, R, A, G, I, L, S, T, M, V, N, Q, F, W, Y, P, or C; E158 replaced with H, K, R, A, G, I, L, S, T, M, V, N, Q, F, W, Y, P, or C; N159 replaced with D, E, H, K, R, A, G, I, L, S, T, M, V, F, W, Y, P, or C; G160 replaced with D, E, H, K, R, N, Q, F, W, Y, P, or C; Y161 replaced with D, E, H, K, R, N, Q, A, G, I, L, S, T, M, V, P, or C; N162 replaced with D, E, H, K, R, A, G, I, L, S, T, M, V, F, W, Y, P, or C; T163 replaced with D, E, H, K, R, N, Q, F, W, Y, P, or C; Y164 replaced with D, E, H, K, R, N, Q, A, G, I, L, S, T, M, V, P, or C; A165 replaced with D, E, H, K, R, N, Q, F, W, Y, P, or C; S166 replaced with D, E, H, K, R, N, Q, F, W, Y, P, or C; F167 replaced with D, E, H, K, R, N, Q, A, G, I, L, S, T, M, V, P, or C; N168 replaced with D, E, H, K, R, A, G, I, L, S, T, M, V, F, W, Y, P, or C; W169 replaced with D, E, H, K, R, N, Q, A, G, I, L, S, T, M, V, P, or C; Q170 replaced with D, E, H, K, R, A, G, I, L, S, T, M, V, F, W, Y, P, or C; H171 replaced with D, E, A, G, I, L, S, T, M, V, N, Q, F, W, Y, P, or C; N172 replaced with D, E, H, K, R, A, G, I, L, S, T, M, V, F, W, Y, P, or C; G173 replaced with D, E, H, K, R, N, Q, F, W, Y, P, or C; R174 replaced with D, E, A, G, I, L, S, T, M, V, N, Q, F, W, Y, P, or C; Q175 replaced with D, E, H, K, R, A, G, I, L, S, T, M, V, F, W, Y, P, or C; M176 replaced with D, E, H, K, R, N, Q, F, W, Y, P, or C; Y177 replaced with D, E, H, K, R, N, Q, A, G, I, L, S, T, M, V, P, or C; V178 replaced with D, E, H, K, R, N, Q, F, W, Y, P, or C; A179 replaced with D, E, H, K, R, N, Q, F, W, Y, P, or C; L180 replaced with D, E, H, K, R, N, Q, F, W, Y, P, or C; N181 replaced with D, E, H, K, R, A, G, I, L, S, T, M, V, F, W, Y, P, or C; G182 replaced with D, E, H, K, R, N, Q, F, W, Y, P, or C; K183 replaced with D, E, A, G, I, L, S, T, M, V, N, Q, F, W, Y, P, or C; G184 replaced with D, E, H, K, R, N, Q, F, W, Y, P, or C; A185 replaced with D, E, H, K, R, N, Q, F, W, Y, P, or C; P186 replaced with D, E, H, K, R, A, G, I, L, S, T, M, V, N, Q, F, W, Y, or C; R187 replaced with D, E, A, G, I, L, S, T, M, V, N, Q, F, W, Y, P, or C; R188 replaced with D, E, A, G, I, L, S, T, M, V, N, Q, F, W, Y, P, or C; G189 replaced with D, E, H, K, R, N, Q, F, W, Y, P, or C; Q190 replaced with D, E, H, K, R, A, G, I, L, S, T, M, V, F, W, Y, P, or C; K191 replaced with D, E, A, G, I, L, S, T, M, V, N, Q, F, W, Y, P, or C; T192 replaced with D, E, H, K, R, N, Q, F, W, Y, P, or C; R193 replaced with D, E, A, G, I, L, S, T, M, V, N, Q, F, W, Y, P, or C; R194 replaced with D, E, A, G, I, L, S, T, M, V, N, Q, F, W, Y, P, or C; K195 replaced with D, E, A, G, I, L, S, T, M, V, N, Q, F, W, Y, P, or C; N196 replaced with D, E, H, K, R, A, G, I, L, S, T, M, V, F, W, Y, P, or C; T197 replaced with D, E, H, K, R, N, Q, F, W, Y, P, or C; S198 replaced with D, E, H, K, R, N, Q, F, W, Y, P, or C; A199 replaced with D, E, H, K, R, N, Q, F, W, Y, P, or C; H200 replaced with D, E, A, G, I, L, S, T, M, V, N, Q, F, W, Y, P, or C; F201 replaced with D, E, H, K, R, N, Q, A, G, I, L, S, T, M, V, P, or C; L202 replaced with D, E, H, K, R, N, Q, F, W, Y, P, or C; P203 replaced with D, E, H, K, R, A, G, I, L, S, T, M, V, N, Q, F, W, Y, or C; M204 replaced with D, E, H, K, R, N, Q, F, W, Y, P, or C; V205 replaced with D, E, H, K, R, N, Q, F, W, Y, P, or C; V206 replaced with D, E, H, K, R, N, Q, F, W, Y, P, or C; H207 replaced with D, E, A, G, I, L, S, T, M, V, N, Q, F, W, Y, P, or C; or S208 replaced with D, E, H, K, R, N, Q, F, W, Y, P, or C.

The substitution mutants can be tested in any of the assays described herein for activity. Particularly preferred are KGF-2 molecules with conservative substitutions that maintain the activities and properties of the wild type protein; have an enhanced activity or property compared to the wild type protein, while all other activities or properties are maintained; or have more than one enhanced activity or property compared to the wild type protein. In contrast, KGF-2 molecules with nonconservative substitutions preferably lack an activity or property of the wild type protein, while maintaining all other activities and properties; or lack more than one activity or property of the wild type protein.

For example, activities or properties of KGF-2 that may be altered in KGF-2 molecules with conservative or nonconservative substitutions include, but are not limited to: stimulation of growth of keratinocytes, epithelial cells, hair follicles, hepatocytes, renal cells, breast tissue, bladder cells, prostate cells, pancreatic cells; stimulation of differentiation of muscle cells, nervous tissue, prostate cells, lung cells, hepatocytes, renal cells, breast tissue; promotion of wound healing; angiogenesis stimulation; reduction of inflammation; cytoprotection; heparin binding; ligand binding; stability; solubility; and/or properties which affect purification.

Amino acids in KGF-2 that are essential for function can be identified by methods well known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro and in vivo proliferative activity. (See, e.g., Examples 10 and 11). Sites that are critical for ligand-receptor binding can also be determined by structural analysis such as crystallization, nuclear magnetic resonance or photoaffinity labelling. (See for example: Smith et al., *J. Mol. Biol.*, 224: 899–904 (1992); and de Vos et al. *Science*, 255: 306–312 (1992).)

Another aspect of the present invention substitutions of serine for cysteine at amino acid positions 37 and 106 and 150. An uneven number of cysteines means that at least one cysteine residue is available for intermolecular crosslinks or bonds that can cause the protein to adopt an undesirable tertiary structure. Novel KGF-2 proteins that have one or more cysteine replaced by serine or e.g. alanine are generally purified at a higher yield of soluble, correctly folded protein. Although not proven, it is believed that the cysteine residue at position 106 is important for function. This cysteine residue is highly conserved among all other FGF family members.

A further aspect of the present invention are fusions of KGF-2 with other proteins or fragments thereof such as fusions or hybrids with other FGF proteins, e.g. KGF (FGF-7), bFGF, aFGF, FGF-5, FGF-6, etc. Such a hybrid has been reported for KGF (FGF-7). In the published PCT application no. 90/08771 a chimeric protein has been produced consisting of the first 40 amino acid residues of KGF and the C-terminal portion of aFGF. The chimera has been reported to target keratinocytes like KGF, but lacked susceptibility to heparin, a characteristic of aFGF but not KGF. Fusions with parts of the constant domain of immunoglobulins (IgG) show often an increased half-life time in vivo. This has been shown, e.g., for chimeric proteins consisting of the first two domains of the human CD4-polypeptide with various domains of the constant regions of the heavy or light chains of mammalian immunoglobulins (European Patent application, Publication No. 394 827, Traunecker et al., *Nature* 331:84–86 (1988). Fusion proteins that have a disulfide-linked dimeric structure can also be more efficient in binding monomeric molecules alone (Fountoulakis et al., *J. of Biochemistry*, 270: 3958–3964, (1995)).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., *Curr. Opinion Biotechnol.* 8:724–33 (1997); Harayama, *Trends Biotechnol.* 16(2):76–82 (1998); Hansson, et al., *J. Mol. Biol.* 287:265–76 (1999); and Lorenzo and Blasco, *Biotechniques* 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antigenic/hydrophilic Parts of KGF-2

As demonstrated in FIG. 4A–4E, there are 4 major highly hydrophilic regions in the KGF-2 protein. Amino acid residues Gly41-Asn71, Lys91-Ser109, Asn135-Tyr164 and Asn181-Ala199 [SEQ ID NOS:25–28]. There are two additional shorter predicted antigenic areas, Gln74-Arg78 of FIG. 1 (SEQ ID NO:2) and Gln170-Gln175 of FIG. 1 (SEQ ID NO:2). Hydrophilic parts are known to be mainly at the outside (surface) of proteins and, therefore, available for antibodies recognizing these regions. Those regions are also likely to be involved in the binding of KGF-2 to its receptor (s). Synthetic peptides derived from these areas can interfere with the binding of KGF-2 to its receptor(s) and, therefore, block the function of the protein. Synthetic peptides from hydrophilic parts of the protein may also be agonistic, i.e. mimic the function of KGF-2.

Thus, the present invention is further directed to isolated polypeptides comprising a hydrophilic region of KGF-2 wherein said polypeptide is not more than 150 amino acids in length, preferably not more than 100, 75, or 50 amino acids in length, which comprise one or more of the above described KGF-2 hydrophilic regions.

Epitope-bearing Portions of KGF-2

In another aspect, the invention provides peptides and polypeptides comprising epitope-bearing portions of the polypeptides of the present invention. These epitopes are immunogenic or antigenic epitopes of the polypeptides of the present invention. An "immunogenic epitope" is defined as a part of a protein that elicits an antibody response in vivo when the whole polypeptide of the present invention, or fragment thereof, is the immunogen. On the other hand, a region of a polypeptide to which an antibody can bind is defined as an "antigenic determinant" or "antigenic epitope." The number of in vivo immunogenic epitopes of a protein generally is less than the number of antigenic epitopes. See, e.g., Geysen, et al., *Proc. Natl. Acad. Sci. USA* 81:3998–4002 (1983). However, antibodies can be made to any antigenic epitope, regardless of whether it is an immunogenic epitope, by using methods such as phage display. See e.g., Petersen G. et al., *Mol. Gen. Genet.* 249:425–431 (1995). Therefore, included in the present invention are both immunogenic epitopes and antigenic epitopes.

A list of exemplified amino acid sequences comprising immunogenic epitopes are shown in Table 1 below. It is pointed out that Table 1 only lists amino acid residues comprising epitopes predicted to have the highest degree of antigenicity using the algorithm of Jameson and Wolf, (1988) *Comp. Appl. Biosci.* 4:181–186 (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Table 1 and portions of polypeptides not listed in Table 1 are not considered non-immunogenic. The immunogenic epitopes of Table 1 is an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194,392; 4,433,092; and 5,480,971 (said references incorporated by reference in their entireties).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to KGF-2-specific antibodies include: a polypeptide comprising amino acid residues in SEQ ID NO:2 from about Gly41-Asn71; Lys91-Ser109; Asn135-Tyr164; Asn181-Ala199; Gln74-Arg78; and Gln170-Gln175. These polypeptide fragments have been determined to bear antigenic epitopes of the KGF-2 protein by the analysis of the Jameson-Wolf antigenic index, as shown in FIG. 4, above.

It is particularly pointed out that the amino acid sequences of Table 1 comprise immunogenic epitopes. Table 1 lists only the critical residues of immunogenic epitopes determined by the Jameson-Wolf analysis. Thus, additional flanking residues on either the N-terminal, C-terminal, or both— and C-terminal ends may be added to the sequences of Table 1 to generate an epitope-bearing polypeptide of the present invention. Therefore, the immunogenic epitopes of Table 1 may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences. Polypeptides of the present invention comprising immunogenic or antigenic epitopes are at least 7 amino acids residues in length. "At least" means that a polypeptide of the present invention comprising an immunogenic or antigenic epitope may be 7 amino acid residues in length or any integer between 7 amino acids and the number of amino acid residues of the full length polypeptides of the invention. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. However, it is pointed out that each and every integer between 7 and the number of amino acid residues of the full length polypeptide are included in the present invention.

The immuno and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., *Antibodies: A Laboratory Manual*, Cold Spring Harbor Laboratory Press; 2nd Ed, Cold Spring Harbor, N.Y. (1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten, R. A., *Proc. Natl. Acad. Sci. USA* 82:5131–5135 (1985)). This "Simultaneous Multiple Peptide Synthesis (SMPS)" process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al. (1985) *Proc. Natl. Acad. Sci.* 82:5131–5135 at 5134).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as m-maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Chemical Modifications

The KGF wild type and analogs may be further modified to contain additional chemical moieties not normally part of the protein. Those derivatized moieties may improve the solubility, the biological half life or absorption of the protein. The moieties may also reduce or eliminate any desirable side effects of the proteins and the like. An overview for those moieties can be found in REMINGTON'S PHARMACEUTICAL SCIENCES, 18th ed., Mack Publishing Co., Easton, Pa. (1990). Polyethylene glycol (PEG) is one such chemical moiety which has been used for the preparation of therapeutic proteins. The attachment of PEG to proteins has been shown to protect against proteolysis, Sada et al., J. Fermentation Bioengineering 71: 137–139 (1991). Various methods are available for the attachment of certain PEG moieties. For review, see: Abuchowski et al., in Enzymes as Drugs. (Holcerberg and Roberts, eds.) pp. 367–383 (1981). Many published patents describe derivatives of PEG and processes how to prepare them, e.g., Ono et al., U.S. Pat. No. 5,342,940; Nitecki et al., U.S. Pat. No. 5,089,261; Delgado et al., U.S. Pat. No. 5,349,052. Generally, PEG molecules are connected to the protein via a reactive group found on the protein. Amino groups, e.g. on lysines or the amino terminus of the protein are convenient for this attachment among others.

The entire disclosure of each document cited in this section on "Polypeptides and Peptides" is hereby incorporated herein by reference.

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a KGF-2 polypeptide can be synthesized by use of a peptide synthesizer. Furthermore, if desired, nonclassical amino acids or chemical amino acid analogs can be introduced as a substitution or addition into the KGF-2 polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses KGF-2 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., *J. Immunol.* 147:60–69 (1991); U.S. Pat. Nos. 4,474,893; 4,714,681; 4,925,648; 5,573,920; 5,601,819; Kostelny et al., *J. Immunol.* 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: amino acids 41–71, 91–109, 135–164, 181–199, 74–78, and 170–175 of SEQ ID NO:2, as well as polynucleotides that encode these epitopes. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., ANTIBODIES: A LABORATORY MANUAL, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., ANTIBODIES: A LABORATORY MANUAL, (Cold Spring Harbor Laboratory Press, 2nd ed. 1988); Hammerling, et al., in: MONOCLONAL ANTIBODIES AND T-CELL HYBRIDOMAS 563–681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) *J. Immunol. Methods* 182:41–50; Ames, R. S. et al. (1995) *J. Immunol. Methods* 184:177–186; Kettleborough, C. A. et al. (1994) *Eur. J. Immunol.* 24:952–958; Persic, L. el al. (1997) *Gene* 187:9–18; Burton, D. R. et al. (1994) *Advances in Immunology* 57:191–280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al. (1992) *BioTechniques* 12(6): 864–869; and Sawai, H. et al. (1995) *AJRI* 34:26–34; and Better, M. et al. (1988) *Science* 240:1041–1043 (said references incorporated by reference in their entireties).

Examples of techniques which can be used to produce single-chain Fvs and antibodies include those described in U.S. Pat. Nos. 4,946,778 and 5,258,498; Huston et al. (1991) *Methods in Enzymology* 203:46–88; Shu, L. et al. (1993) *PNAS* 90:7995–7999; and Skerra, A. et al. (1988) *Science* 240:1038–1040. For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., BioTechniques 4:214 (1986); Gillies, S. D. et al. (1989) *J. Immunol. Methods* 125:191–202; and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., (1991) Molecular Immunology 28(4/5):489–498; Studnicka G. M. et al. (1994) *Protein Engineering* 7(6):805–814; Roguska M. A. et al. (1994) *PNAS* 91:969–973), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6):1981–1988 (1998); Chen et al., *Cancer Res.* 58(16):3668–3678 (1998); Harrop et al., *J. Immunol.* 161 (4):1786–1794 (1998); Zhu et al., *Cancer Res.* 58(15):3209–3214 (1998); Yoon et al., *J. Immunol.* 160(7):3170–3179 (1998); Prat et al., *J. Cell. Sci.* 111(Pt2):237–247 (1998); Pitard et al., *J. Immunol. Methods* 205(2):177–190 (1997); Liautard et al., *Cytokine* 9(4):233–241 (1997); Carlson et al., *J. Biol. Chem.* 272(17):11295–11301 (1997); Taryman et al., *Neuron* 14(4):755–762 (1995); Muller et al., *Structure* 6(9):1153–1167 (1998); Bartunek et al., *Cytokine* 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety). In a preferred embodiment, levels of KGF-2 are detected in a purified sample using goat and chicken antibodies (see example 50, below).

As discussed in more detail below, the antibodies of the present invention may be used either alone or in combination with other compositions. The antibodies may further be recombinantly fused to a heterologous-polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., (1989) *J. Immunol. Methods* 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489–498 (1991); Studnicka et al., *Protein Engineering* 7(6):805–814 (1994); Roguska. et al.,*PNAS* 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers el al., *Bio/technology* 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The invention further relates to antibodies that act as agonists or antagonists of the polypeptides of the present invention. Antibodies which act as agonists or antagonists of the polypeptides of the present invention include, for example, antibodies which disrupt receptor/ligand interactions with the polypeptides of the invention either partially or fully. For example, the present invention includes antibodies that disrupt the ability of the proteins of the invention to multimerize. In another example, the present invention includes antibodies which allow the proteins of the invention to multimerize, but disrupts the ability of the proteins of the invention to bind one or more KGF-2 receptor(s)/ligand(s). In yet another example, the present invention includes antibodies which allow the proteins of the invention to multimerize, and bind KGF-2 receptor(s)/ligand(s), but blocks biological activity associated with the KGF-2/receptor/ligand complex.

Antibodies which act as agonists or antagonists of the polypeptides of the present invention also include, both receptor-specific antibodies and ligand-specific antibodies. Included are receptor-specific antibodies that do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., *Blood* 92(6):1981–1988 (1998); Chen, Z. et al., *Cancer Res.* 58(16):3668–3678 (1998); Harrop, J. A. et al., *J. Immunol.* 161(4):1786–1794 (1998); Zhu, Z. et al., *Cancer Res.* 58(15):3209–3214 (1998); Yoon, D. Y. et al., *J. Immunol.* 160(7):3170–3179 (1998); Prat, M. et al., *J. Cell. Sci.* 111(Pt2):237–247 (1998); Pitard, V. et al., *J. Immunol. Methods* 205(2):177–190 (1997); Liautard, J. et al., *Cytokinde* 9(4):233–241 (1997); Carlson, N. G. et al., *J. Biol. Chem.* 272(17):11295–11301 (1997); Taryman, R. E. et al., *Neuron* 14(4):755–762(1995); Muller, Y. A. et al., *Structure* 6(9):1153–1167 (1998); Bartunek, P. et al., *Cytokine* 8(1):14–20 (1996) (said references incorporated by reference in their entireties).

As discussed above, antibodies to the KGF-2 proteins of the invention can, in turn, be utilized to generate anti-idiotype antibodies that "mimic" KGF-2 using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to KGF-2 and competitively inhibit KGF-2 multimerization and/or binding to ligand can be used to generate anti-idiotypes that "mimic" the KGF-2 multimerization and/or binding domain and, as a consequence, bind to and neutralize KGF-2 and/or its ligand. Such neutralizing anti-idiotypes or Fab fragments of such anti-idiotypes can be used in therapeutic regimens to neutralize KGF-2 ligand. For example, such anti-idiotypic antibodies can be used to bind KGF-2, or to bind KGF-2 ligands/receptors, and thereby block KGF-2 biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2nd Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851–855 (1984); Neuberger et al., *Nature* 312:604–608 (1984); Takeda et al., *Nature* 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, *Science* 242:423–42 (1988); Huston et al., *Proc. Natl. Acad. Sci. USA* 85:5879–5883 (1988); and Ward et al., *Nature* 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science* 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101–3109(1985); Van Heeke & Schuster, *J. Biol. Chem.* 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERA, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596 (1993); Mulligan, *Science* 260:926–932(1993); and Morgan and Anderson, *Ann. Rev. Biochem.* 62:191–217 (1993); May, 1993, *TIB TECH* 11(5):155–215); and hygro, which confers resistance to hygromycin (Santerre et al., *Gene* 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:52 (1986); Kohler, *Proc. Natl. Acad Sci. USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91–99 (1994); U.S. Pat. No. 5,474,981; Gillies et al., *PNAS* 89:1428–1432 (1992); Fell et al., *J. Immunol.* 146:2446–2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., *Proc. Natl. Acad. Sci. USA* 88:10535–10539 (1991); Zheng et al., *J. Immunol.* 154:5590–5600 (1995); and Vil et al., *Proc. Nall. Acad. Sci. USA* 89:11337–11341 (1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, Bennett et al., *J. Molecular Recognition* 8:52–58 (1995); Johanson et al., *J. Biol. Chem.* 270:9459–9471 (1995).)

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Nall. Acad. Sci. USA* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", *Immunol. Rev.* 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison el al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1. The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Vectors and Host Cells

The present invention also relates to vectors which include the isolated DNA molecules of the present invention, host cells which are genetically engineered with the recombinant vectors, and the production of KGF-2 polypeptides or fragments thereof by recombinant techniques.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the KGF-2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequences) (promoter) to direct cDNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, and Bowes melanoma cells; adenoviruses and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 50:
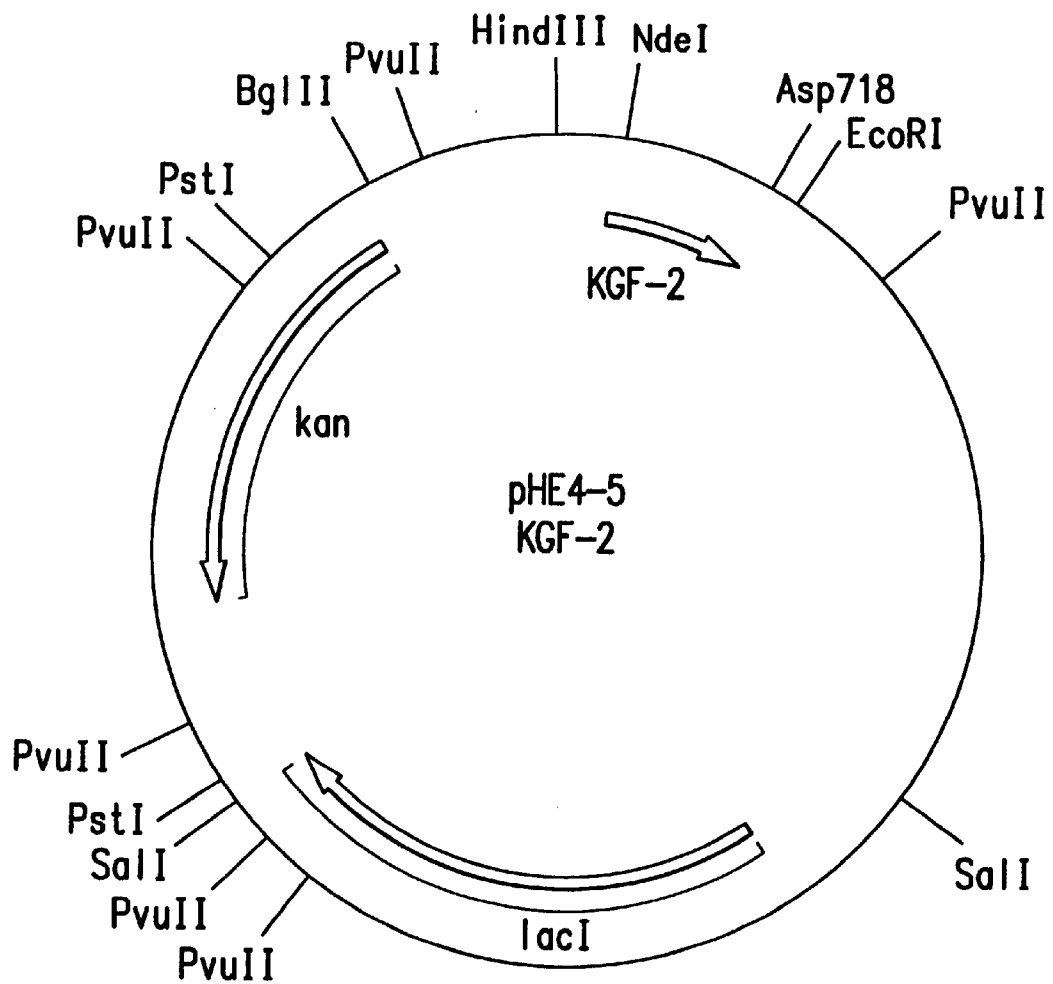
FIG. 50 shows a schematic representation of the pHE4–5 expression vector (SEQ ID NO:147) and the subcloned KGF-2 cDNA coding sequence. The locations of the kanamycin resistance marker gene, the KGF-2 coding sequence, the oriC sequence, and the lacIq coding sequence are indicated.

As summarized in FIGS. 50 and 51, components of the pHE4-5 vector (SEQ ID NO:147) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding KGF-2 (SEQ ID NO:1), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lad gene which confers tight regulation of the lac operator. Amann, E. et al., *Gene* 69:301–315 (1988); Stark, M., *Gene* 51:255–267 (1987).

The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g., isopropyl B-D-thiogalactopyranoside (IPTG). KGF-2 thus is not produced in appreciable quantities in uninduced host cells containing the pHE4-5 vector. Induction of these host cells by the addition of an agent such as IPTG, however, results in the expression of the KGF-2 coding sequence.

The promoter/operator sequences of the pHE4-5 vector (SEQ ID NO:148) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located down-stream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4-5 vector except for the KGF-2 coding sequence. Features of the pHE4 vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:147). The pHE4-5 vector containing a cDNA insert encoding KGF-2Δ33 was deposited at the ATCC on Jan. 9, 1998 as ATCC No. 209575.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that KGF-2 polypeptides may in fact be expressed by a host cell lacking a recombinant vector.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L. et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5-receptor has been fused with Fc portions for the purpose of high-throughput screening assays to identify antagonists of hIL-5. See, D. Bennett et al., *J. Mol. Recognition*, Vol. 8 52–58 (1995) and K. Johanson et al., *J. Biol. Chem.*, 270(16):9459–9471 (1995).

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEMI (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

KGF-2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture).

Depending upon the host employed in a recombinant production procedure, the polypeptides of the present invention may be glycosylated or may be non-glycosylated. Polypeptides of the invention may also include an initial methionine amino acid residue.

KGF-2 polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the KGF-2 polypeptides may be glycosylated or may be non-glycosylated. In addition, KGF-2 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express KGF-2 protein in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia patoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia patoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a KGF-2 polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a KGF-2 polypeptide of the invention, as set forth herein, in a Pichia yeast system essentially as described in "Pichia Protocols: Methods in Molecular Biology," D. R. Higgins and J. Cregg, eds. The Humana Press, Totowa, N.J., 1998. This expression vector allows expression and secretion of a KGF-2 protein of the invention by virtue of the strong AOX1 promoter linked to the Pichia patoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PA0815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a KGF-2 polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., KGF-2 coding sequence), and/or to include genetic material (e.g., heterologous polynucleotide sequences) that is operably associated with KGF-2 polynucleotides of the invention, and which activates, alters, and/or amplifies endogenous KGF-2 polynucleotides. For example, techniques known in the art may be used to operably associate heterologous control regions (e.g., promoter and/or enhancer) and endogenous KGF-2 polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Diagnostic and Therapeutic Applications of KGF-2

As used in the section below, "KGF-2" is intended to refer to the full-length and mature forms of KGF-2 described herein and to the KGF-2 analogs, derivatives and mutants described herein. This invention is also related to the use of the KGF-2 gene as part of a diagnostic assay for detecting diseases or susceptibility to diseases related to the presence of mutations in the KGF-2 nucleic acid sequences.

Individuals carrying mutations in the KGF-2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature 324:163–166 (1986)) prior to analysis. RNA or cDNA may also be used for the same purpose. As an example, PCR primers complementary to the nucleic acid encoding KGF-2 can be used to identify and analyze KGF-2 mutations. For example, deletions and insertions can be detected by a change in size of the amplified product in comparison to the normal genotype. Point mutations can be identified by hybridizing amplified DNA to radiolabeled KGF-2 RNA or alternatively, radiolabeled KGF-2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230:1242 (1985)).

Sequence changes at specific locations may also be revealed by nuclease protection assays such as RNase and Si protection or the chemical cleavage method (e.g., Cotton et al., *PNAS, USA*, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of KGF-2 protein in various tissues since an over-expression of the proteins compared to normal control tissue samples may detect the presence of a disease or susceptibility to a disease, for example, a tumor. Assays used to detect levels of KGF-2 protein in a sample derived from a host are well-known to those of skill in the art and include radioimmunoassays, competitive-binding assays, Western Blot analysis, ELISA assays and "sandwich" assays. An ELISA assay (Coligan, et al., *Current Protocols in Immunology*, 1(2), Chapter 6, (1991)) initially comprises preparing an antibody specific to the KGF-2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like bovine serum albumen. Next, the monoclonal antibodies attach to any KGF-2 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to KGF-2. Unattached reporter antibody is then washed out. Peroxidase substrates are then added to the dish and the amount of color developed in a given time period is a measurement of the amount of KGF-2 protein present in a given volume of patient sample when compared against a standard curve.

A competition assay may be employed wherein antibodies specific to KGF-2 are attached to a solid support and labeled KGF-2 and a sample derived from the host are passed over the solid support and the amount of label detected, for example by liquid scintillation chromatography, can be correlated to a quantity of KGF-2 in the sample.

A "sandwich" assay is similar to an ELISA assay. In a "sandwich" assay KGF-2 is passed over a solid support and binds to antibody attached to a solid support. A second antibody is then bound to the KGF-2. A third antibody which is labeled and specific to the second antibody is then passed over the solid support and binds to the second antibody and an amount can then be quantified.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler & Milstein, *Nature*, 256:495–497 (1975)), the trioma technique, the human B-cell hybridoma technique (Kozbor, et al., *Immunology Today* 4:72 (1983)), and the EBV-hybridoma technique to produce human monoclonal antibodies (Cole, et al., *Monoclonal Antibodies and Cancer Therapy*, Alan R. Liss, Inc., pp. 77–96 (1985)).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The polypeptides of the present invention have been shown to stimulate growth of epithelium. Thus, the polypeptides of the present invention may be employed to stimulate growth of epithelium. "Epithelium" refers to the covering of internal and external surfaces of the body, including the lining of vessels and other small cavities. It consists of cells joined by small amounts of cementing substances. Epithelium is classified into types on the basis of the number of layers deep and the shape of the superficial cells. Epithelial cells include anterius corneae, Barrett's epithelium, capsular epithelium, ciliated epithelium, columnar epithelium, corneal epithelium, cubical epithelium, epithelium ductus semicircularis, enamel epithelium, false epithelium, germinal epithelium, gingival epithelium, glandular epithelium, glomerular epithelium, laminated epithelium, epithelium of the lend, mesenchymal epithelium, olfactory epithelium, pavement epithelium, pigmentary epithelium, protective epithelium, pseudostratified epithelium, pyramidal epithelium, respiratory epithelium, rod epithelium, seminiferous epithelium, sensory epithelium, simple epithelium, squamous epithelium, stratified epithelium, subcapsular epithelium, sulcular epithelium, tessellated epithelium, transitional epithelium, and epithelial cells of the eye, tongue, glands, oral mucosa, duodenum, ileum, jejunum, cecum, nasal passages, esophagus, colon, mammary glands, and the female and male reproductive systems.

"Glands" refer to an aggregation of cells, specialized to secrete or excrete materials not related to their ordinary metabolic needs. Examples of glands which may include epithelial cells include: absorbent clangs, accessory glands, acinar glands, acid glands, admaxillary glands, adrenal glands, aggregate glands, Albarran's gland, anal glands, alveolar glands, anteprostatic glands, aortic glands, apical glands of the tongue, apocrine glands, areolar glands, arterial glands, arteriococcygeal glands, arytenoid glands, Aselli's glands, Avicenna's glands, atribiliary gland, axillary glands, Bartholin's glands, Bauhin's glands, Baumgarten's glands, glands of the biliary mucosa, Blandin's glands, blood vessel glands, Boerhaave's glands, Bonnot's glands, Bowman's glands, brachial glands, bronchial glands, Bruch's glands, Brunner's glands, buccal glands, bulbocavernous glands, cardiac glands, carotid glands, celiac glands, ceruminous glands, cervical glands of the uterus, choroid glands, Ciaccio's glands, ciliary glands of the conjunctiva, circumanal glands, Cloquet's glands, Cobelli's glands, coccygeal glands, coil glands, compound glands, conglobate gland, conjunctival glands, Cowper's gland, cutaneous glands, cytogenic glands, ductless glands, duodenal glands, Duverney's gland, Ebner's gland, eccrine glands, Eglis' glands, endocrine glands, endoepithelial glands, esophageal glands, excretory glands, exocrine glands, follicular glands of the duct, fundus glands, gastric glands, gastroepiploic glands, glands of Gay, genital glands, gingival glands, Gley's glands, globate glands, glomerate glands, glossopalatine glands, Guerin's glands, guttural glands, glands of Haller, Harder's glands, haversian glands, hedonic glands, hemal glands, hemal lymph glands, hematopoietic glands, hemolymph glands, Henle's glands, hepatic glands, heterocrine glands, hibernating glands, holocrine glands and incretory glands.

Further examples of glands include intercarotid glands, intermediate glands, interscapular glands, interstitial glands, intestinal glands, intraepithelial glands, intramuscular glands of the tongue,jugular gland, Krause's glands, labial glands of the mouth, lacrimal glands, accessory lacrimal glands, lactiferous gland, glands of the large intestine, large sweat glands, laryngeal glands, lenticular glands of the stomach and tongue, glands of Lieberkuhn, lingual glands, anterior lingual glands, Littre's glands, Luschka's gland, lymph glands, extraparotid lymph glands, malar glands, mammary glands, accessory mammary glands, mandibular glands, Manz' glands, Mehlis' glands, meibomian glands, merocrine glands, mesenteric glands, mesocolic glands, mixed glands, molar glands, Moll's glands, monoptyphic glands, Montgomery's glands, Morgagni's glands, glands of the mouth, mucilaginous glands, muciparous glands, mucous glands, lingual mucous glands, mucous glands of the auditory tube, mucous glands of the duodenum, mucous glands of the eustachian tube, multicellular glands, myometrial glands, Naboth's glands, nabothian glands, nasal glands, glands of the neck, odoriferous glands of the prepuce, oil glands, olfactory glands, oxyntic glands, pacchionian glands, palatine glands, pancreaticosplenic glands, parafrenal glands, parathyroid glands, parurethral glands, parotid glands, accessory parotid glands, pectoral glands, peptic glands, perspiratory glands, Peyre's glands, pharyngeal glands, Philip's glands, pineal glands, and pituitary.

Other examples of glands include Poirier's glands, polyptychich glands, preen gland, pregnancy glands, prehyoid glands, preputial glands, prostate gland, puberty glands, pyloric glands, racemose glands, retrolingual glands, retromolar glands, Rivinus gland, Rosenmuller gland, saccular gland, salivary glands, abdominal salivary glands, external salivary glands, internal salivary glands, Sandstrom's glands, Schuller's glands, sebaceous glands, sebaceous glands of the conjunctiva, sentinal glands, seromucous glands, serous glands, Serres' glands, Sigmunds glands, Skene's glands, simple gland, glands of the small intestine, solitary glands of the large intestine, splenoid gland, Stahr's gland, stapyline glands, subauricular glands, sublingual glands, submandibular glands, suboriferous glands, suprarenal glands, accessory suprarenal glands, Suzanne's gland, sweat glands, synovial glands, tarsal glands, Theile's glands, thymus gland, thyroid gland, accessory thyroid glands, glands of the tongue, tracheal glands, tachoma glands, tubular glands, tubuloacinar glands, tympanic glands, glands of Tyson, unicellular glands, urethral glands, urethral glands of the female urethra, uropygial gland, uterine glands, utricular glands, vaginal glands, vascular glands, vestibular glands (greater and lesser), Virchow's gland, vitelline gland, bulbovaginal gland, Waldeyer's glands, Weber's glands, glands of Wolfring, glands of Zeis and Zuckerkandl's glands.

Thus, KGF-2 may be employed to stimulate the growth of any of these cells or cells within these glands.

The polypeptides of the present invention may be employed to stimulate new blood vessel growth or angiogenesis. Particularly, the polypeptides of the present invention may stimulate keratinocyte cell growth and proliferation. Accordingly the present invention provides a process for utilizing such polypeptides, or polynucleotides encoding such polypeptides for therapeutic purposes, for example, to stimulate epithelial cell proliferation and basal keratinocytes for the purpose of wound healing, and to stimulate hair follicle production and healing of dermal wounds.

As noted above, the polypeptides of the present invention may be employed to heal dermal wounds by stimulating epithelial cell proliferation. These wounds may be of superficial nature or may be deep and involve damage of the dermis and the epidermis of skin. Thus, the present invention provides a method for the promotion of wound healing that involves the administration of an effective amount of KGF-2 to an individual.

The individual to which KGF-2 is administered may heal wounds at a normal rate or may be healing impaired. When administered to an individual who is not healing impaired, KGF-2 is administered to accelerate the normal healing process. When administered to an individual who is healing impaired, KGF-2 is administered to facilitate the healing of wounds which would otherwise heal slowly or not at all. As noted below, a number of afflictions and conditions can result in healing impairment. These afflictions and conditions include diabetes (e.g., Type II diabetes mellitus), treatment with both steroids and other pharmacological agents, and ischemic blockage or injury. Steroids which have been shown to impair wound healing include cortisone, hydrocortisone, dexamethasone, and methylprednisolone.

Non-steroid compounds, e.g., octreotide acetate, have also been shown to impair wound healing. Waddell, B. el al., *Am. Surg.* 63:446–449 (1997). The present invention is believed to promote wound healing in individuals undergoing treatment with such non-steroid agents.

A number of growth factors have been shown to promote wound healing in healing impaired individuals. See, e.g., Steed, D. et al., *J. Am. Coll. Surg.* 183:61–64 (1996); Richard, J. et al., *Diabetes Care* 18: 64–69 (1995); Steed, D., *J. Vasc. Surg.* 21:71–78 (1995); Kelley, S. et al., *Proc. Soc. Exp. Biol.* 194:320–326 (1990). These growth factors include growth hormone-releasing factor, platelet-derived growth factor, and basic fibroblast growth factor. Thus, the present invention also encompasses the administration of KGF-2 in conjunction with one or more additional growth factors or other agent which promotes wound healing.

The present invention also provides a method for promoting the healing of anastomotic and other wounds caused by surgical procedures in individuals which both heal wounds at a normal rate and are healing impaired. This method involves the administration of an effective amount of KGF-2 to an individual before, after, and/or during anastomotic or other surgery. Anastomosis is the connecting of two tubular structures, as which happens, for example, when a midsection of intestine is removed and the remaining portions are linked together to reconstitute the intestinal tract. Unlike with cutaneous healing, the healing process of anastomotic wounds is generally obscured from view. Further, wound healing, at least in the gastrointestinal tract, occurs rapidly in the absence of complications; however, complications often require correction by additional surgery. Thornton, F. and Barbul, A., *Surg. Clin. North Am.* 77:549–573 (1997). As shown in Examples 21 and 28, treatment with KGF-2 causes a significant decrease in peritoneal leakage and anastomotic constriction following colonic anastomosis. KGF-2 is believed to cause these results by accelerating the healing process thus decreasing the probability of complications arising following such procedures.

Thus, the present invention also provides a method for accelerating healing after anastomoses or other surgical procedures in an individual, which heals wounds at a normal rate or is healing impaired, compromising the administration of an effective amount of KGF-2.

The polypeptides of the present invention may also be employed to stimulate differentiation of cells, for example muscle cells, cells which make up nervous tissue, prostate cells, and lung cells.

KGF-2 may be clinically useful in stimulating healing of wounds including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, and burns resulting from heat exposure or chemicals, in normal individuals and those subject to conditions which induce abnormal wound healing such as uremia, malnutrition, vitamin deficiencies, obesity, infection, immunosuppression and complications associated with systemic treatment with steroids, radiation therapy, and antineoplastic drugs and antimetabolites. KGF-2 is also useful for promoting the healing of wounds associated with ischemia and ischemic injury, e.g., chronic venous leg ulcers caused by an impairment of venous circulatory system return and/or insufficiency.

KGF-2 can also be used to promote dermal reestablishment subsequent to dermal loss. In addition, KGF-2 can be used to increase the tensile strength of epidermis and epidermal thickness.

KGF-2 can be used to increase the adherence of skin grafts to a wound bed and to stimulate re-epithelialization from the wound bed. The following are types of grafts that KGF-2 could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. KGF-2 can be used to promote skin strength and to improve the appearance of aged skin.

It is believed that KGF-2 will also produce changes in hepatocyte proliferation, and epithelial cell proliferation in the lung, breast, pancreas, stomach, small intestine, and large intestine. KGF-2 can promote proliferation of epithelial cells such as sebocytes, hair follicles, hepatocytes, type II pneumocytes, mucin-producing goblet cells, and other epithelial cells and their progenitors contained within the skin, lung, liver, kidney and gastrointestinal tract. As shown in Example 31, KGF-2 stimulates the proliferation of hepatocytes. Thus, KGF-2 can also be used prophylactically or therapeutically to prevent or attenuate acute or chronic viral hepatitis as well as fulminant or subfulminant liver failure caused by diseases such as acute viral hepatitis, cirrhosis, drug- and toxin-induced hepatitis (e.g., acetaminophen, carbon tetrachloride, methotrexate, organic arsenicals, and other hepatotoxins known in the art), autoimmune chronic active hepatitis, liver transplantation, and partial hepatectomy (Cotran et al. *Pathologic basis of disease.* ($5^{th}$ ed). Philadelphia, W.B. Saunders Company, 1994). KGF-2 can also be used to stimulate or promote liver regeneration and in patients with alcoholic liver disease. KGF-2 can be used to treat fibrosis of the liver.

Approximately 80% of acute pancreatitis cases are associated with biliary tract disease and alcoholism (Rattner D. W., *Scand J Gastroenterol* 31:6–9 (1996); Cotran et al. *Pathologic basis of disease.* ($5^{th}$ ed). Philadelphia, W.B. Saunders Company, 1994). Acute pancreatitis is an important clinical problem with significant morbidity and mortality (Banerjee et al., *British Journal of Surgery* 81:1096–1103 (1994)). The pathogenesis of this disease is still somewhat unresolved but it is widely recognized that pancreatic enzymes are released within the pancreas leading to proteolysis, interstitial inflammation, fat necrosis, and hemorrhage. Acute pancreatitis can lead to disseminated intravascular coagulation, adult respiratory distress syndrome, shock, and acute renal tubular necrosis (Cotran et al. *Pathologic basis of disease.* ($5^{th}$ ed). Philadelphia, W.B. Saunders Company, 1994). Despite palliative measures, about 5% of these patients die of shock during the first week of the clinical course. In surviving patients, sequelae may include pancreatic abscess, pseudocyst, and duodenal obstruction (Cotran et al. *Pathologic basis of disease.* ($5^{th}$ ed). Philadelphia, W.B. Saunders Company, 1994). Chronic pancreatitis is often a progressive destruction of the pancreas caused by repeated flare-ups of acute pancreatitis. Chronic pancreatitis appears to incur a modestly increased risk of pancreatic carcinoma (Cotran et al. *Pathologic basis of disease.* ($5^{th}$ ed). Philadelphia, W.B. Saunders Company, 1994).

As indicated above and in Example 31, KGF-2 also promotes proliferation of pancreatic cells. Thus, in a further aspect, KGF-2 can be used prophylactically or therapeutically to prevent or attenuate acute or chronic pancreatitis.

KGF-2 can also be used to reduce the side effects of gut toxicity that result from the treatment of viral infections, radiation therapy, chemotherapy or other treatments. KGF-2 may have a cytoprotective effect on the small intestine mucosa. KGF-2 may also be used prophylactically or therapeutically to prevent or attenuate mucositis and to stimulate healing of mucositis (e.g., oral, esophageal, intestinal, colonic, rectal, and anal ulcers) that result from chemotherapy, other agents and viral infections. Thus the present invention also provides a method for preventing or treating diseases or pathological events of the mucosa, including ulcerative colitis, Crohn's disease, and other diseases where the mucosa is damaged, comprising the administration of an effective amount of KGF-2. The present invention similarly provides a method for preventing or treating oral (including odynophagia associated with mucosal injury in the pharynx and hypopharynx), esophageal, gastric, intestinal, colonic and rectal mucositis irrespective of the agent or modality causing this damage.

In addition, KGF-2 could be used to treat and/or prevent: blisters and burns due to chemicals; ovary injury, for example, due to treatment with chemotherapeutics or treatment with cyclophosphamide; radiation- or chemotherapy-induced cystitis; or high-dose chemotherapy-induced intestinal injury. KGF-2 could be used to promote internal healing, donor site healing, internal surgical wound healing, or healing of incisional wounds made during cosmetic surgery.

KGF-2 can promote proliferation of endothelial cells, keratinocytes, and basal keratinocytes. Thus, the present invention also provides a method for stimulating the proliferation of such cell types which involves contacting cells with an effective amount of KGF-2. KGF-2 may be administered to an individual in an effective amount to stimulate cell proliferation in vivo or KGF-2 may be contacted with such cells in vitro.

The present invention further provides a method for promoting urothelial healing comprising administering an effective amount of KGF-2 to an individual. Thus, the present invention provides a method for accelerating the healing or treatment of a variety of pathologies involving urothelial cells (i.e., cells which line the urinary tract). Tissue layers comprising such cells may be damaged by numerous mechanisms including catheterization, surgery, or bacterial infection (e.g., infection by an agent which causes a sexually transmitted disease, such as gonorrhea).

The present invention also encompasses methods for the promotion of tissue healing in the female genital tract comprising the administration of an effective amount of KGF-2. Tissue damage in the female genital tract may be caused by a wide variety of conditions including Candida infections trichomoniasis, Gardnerella, gonorrhea, chlamydia, mycoplasma infections and other sexually transmitted diseases.

As shown in Examples 10, 18, and 19, KGF-2 stimulates the proliferation of epidermal keratinocytes and increases epidermal thickening. Thus, KGF-2 can be used in full regeneration of skin; in full and partial thickness skin defects, including burns (i.e., repopulation of hair follicles, sweat glands, and sebaceous glands); and the treatment of other skin defects such as psoriasis.

KGF-2 can be used to treat epidermolysis bullosa, a defect in adherence of the epidermis to the underlying dermis which results in frequent, open and painful blisters by accelerating reepithelialization of these lesions. KGF-2 can also be used to treat gastric and duodenal ulcers and help heal the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, KGF-2 could be used to promote the resurfacing of the mucosal surface to aid more rapid healing and to prevent or attenuate progression of inflammatory bowel disease. KGF-2 treatment is expected to have a significant effect on the production of mucus throughout the gastrointestinal tract and could be used to protect the intestinal mucosa from injurious substances that are ingested or following surgery. As noted above, KGF-2 can also be used to promote healing of intestinal or colonic anastomosis. KGF-2 can further be used to treat diseases associate with the under expression of KGF-2.

As shown in Example 32 below, KGF-2 stimulates proliferation of lung epithelial cells. Thus, KGF-2 can be administered prophylactically to reduce or prevent damage to the lungs caused by various pathological states. KGF-2 can also be administered during or after a damaging event occurs to promote healing. For example, KGF-2 can stimulate proliferation and differentiation and promote the repair of alveoli and bronchiolar epithelium to prevent, attenuate, or treat acute or chronic lung damage. Emphysema, which results in the progressive loss of alveoli, and inhalation injuries, i.e., resulting from smoke inhalation and burns, that cause necrosis of the bronchiolar epithelium and alveoli could be effectively treated using KGF-2 as could damage attributable to chemotherapy, radiation treatment, lung cancer, asthma, black lung and other lung damaging conditions. Also, KGF-2 could be used to stimulate the proliferation of and differentiation of type II pneumocytes, which may help treat or prevent disease such as hyaline membrane diseases, such as infant respiratory distress syndrome and bronchopulmonary dysplasia, in premature infants.

The three causes of acute renal failure are prerenal (e.g., heart failure), intrinsic (e.g., nephrotoxicity induced by chemotherapeutic agents) and postrenal (e.g., urinary tract obstruction) which lead to renal tubular cell death, obstruction of the tubular lumens, and back flow of filtrate into the glomeruli (reviewed by Thadhani et al. *N. Engl. J. Med.* 334:1448–1460(1996)). Growth factors such as insulin-like growth factor I, osteogenic protein-1, hepatocyte growth factor, and epidermal growth factor have shown potential for ameliorating renal disease in animal models. Taub et al. *Cylokine* 5:175–179 (1993); Vukicevic et al. *J. Am. Soc. Nephrol.* 7:1867 (1996). As shown in Example 31 below, KGF-2 stimulates proliferation of renal epithelial cells and, thus, is useful for alleviating or treating renal diseases and pathologies such as acute and chronic renal failure and end stage renal disease.

KGF-2 could stimulate the proliferation and differentiation of breast tissue and therefor could be used to promote healing of breast tissue injury due to surgery, trauma, or cancer.

In addition, KGF-2 could be used treat or prevent the onset of diabetes mellitus. In patients with newly diagnosed Types I and II diabetes, where some islet cell function remains, KGF-2 could be used to maintain the islet function so as to alleviate, delay or prevent permanent manifestation of the disease. Also, KGF-2 could be used as an auxiliary in islet cell transplantation to improve or promote islet cell function.

Further, the anti-inflammatory property of KGF-2, could be beneficial for treating acute and chronic conditions in which inflammation is a key pathogenesis of the diseases including, but not limiting to, psoriasis, eczema, dermatitis and/or arthritis. Thus, the present invention provides a method for preventing or attenuating inflammation, and diseases involving inflammation, in an individual comprising the administration of an effective amount of KGF-2.

KGF-2 can be used to promote healing and alleviate damage of brain tissue due to injury from trauma, surgery or chemicals.

In addition, since KGF-2 increases the thickness of the epidermis, the protein could be used for improving aged skin, reducing wrinkles in skin, and reducing scarring after surgery. Scarring of wound tissues often involves hyperproliferation of dermal fibroblasts. As noted in Example 10, fibroblast proliferation is not stimulated by KGF-2. Therefore, KGF-2 appears to be mitogen specific for epidermal keratinocytes and induces wound healing with minimal scarring. Thus, the present invention provides a method for promoting the healing of wounds with minimal scarring involving the administration of an effective amount of KGF-2 to an individual. KGF-2 may be administered prior to, during, and/or after the process which produces the wound (e.g., cosmetic surgery, accidental or deliberate tissue trauma caused by a sharp object).

As noted above, KGF-2 also stimulates the proliferation of keratinocytes and hair follicles and therefore can be used to promote hair growth from balding scalp, and in hair transplant patients. Thus, the present invention further provides a method for promoting hair growth comprising the administration of an amount KGF-2 sufficient to stimulate the production of hair follicles.

The present invention also provides a method for protecting an individual from the effects of ionizing radiation, chemotherapy, or treatment with anti-viral agents comprising the administration of an effective amount of KGF-2. The present invention further provides a method for treating tissue damage which results from exposure to ionizing radiation, chemotherapeutic agents, or anti-viral agents comprising the administration of an effective amount of KGF-2. An individual may be exposed to ionizing radiation for a number of reasons, including for therapeutic purposes (e.g., for the treatment of hyperproliferative disorders), as the result of an accidental release of a radioactive isotope into the environment, or during non-invasive medical diagnostic procedures (erg., X-rays). Further, a substantial number of individuals are exposed to radioactive radon in their work places and homes. Long-term continuous environmental exposure has been used to calculate estimates of lost life expectancy. Johnson, W. and Kearfott, K., *Health Phys.* 73:312–319 (1997). As shown in Example 23, the proteins of the present invention enhance the survival of animals exposed to radiation. Thus, KGF-2 can be used to increase survival rate of individuals suffering radiation-induced injuries, to protect individuals from sub-lethal doses of radiation, and to increase the therapeutic ratio of irradiation in the treatment of afflictions such as hyperproliferative disorders.

KGF-2 may also be used to protect individuals against dosages of radiation, chemotherapeutic drugs or antiviral agents which normally would not be tolerated. When used in this manner, or as otherwise described herein, KGF-2 may be administered prior to, after, and/or during radiation therapy/exposure, chemotherapy or treatment with anti-viral agents. High dosages of radiation and chemotherapeutic agents may be especially useful when treating an individual having an advanced stage of an affliction such as a hyperproliferative disorder.

In another aspect, the present invention provides a method for preventing or treating conditions such as radiation-induced oral and gastro-intestinal injury, mucositis, intestinal fibrosis, proctitis, radiation-induced pulmonary fibrosis, radiation-induced pneumonitis, radiation-induced pleural retraction, radiation-induced hemopoietic syndrome, radiation-induced myelotoxicity, comprising administering an effective amount of KGF-2 to an individual.

KGF-2 may be used alone or in conjunction with one or more additional agents which confer protection against radiation or other agents. A number of cytokines (e.g., IL-1, TNF, IL-6, IL-12) have been shown to confer such protection. See, e.g., Neta, R. et al., *J. Exp. Med.* 173:1177 (1991). Additionally, IL-11 has been shown to protect small intestinal mucosal cells after combined irradiation and chemotherapy, Du, X. X. et al., *Blood* 83:33 (1994), and radiation-induced thoracic injury. Redlich, C. A. et al., *J. Immun.* 157:1705–1710 (1996). Several growth factors have also been shown to confer protection to radiation exposure, e.g., fibroblast growth factor and transforming growth factor beta-3. Ding, I. et al., *Acta Oncol.* 36:337–340 (1997); Potten, C. et al., *Br. J. Cancer* 75:1454–1459 (1997).

Hemorrhagic cystitis is a syndrome associated with certain disease states as well as exposure to drugs, viruses, and toxins. It manifests as diffuse bleeding of the endothelial lining of the bladder. Known treatments include intravesical, systemic, and nonpharmacologic therapies (West, N. J., *Pharmacotherapy* 17:696–706 (1997). Some cytotoxic agents used clinically have side effects resulting in the inhibition of the proliferation of the normal epithelial in the bladder, leading to potentially life-threatening ulceration and breakdown in the epithelial lining. For example, cyclophosphamide is a cytotoxic agent which is biotransformed principally in the liver to active alkylating metabolites by a mixed function microsomal oxidase system. These metabolites interfere with the growth of susceptible rapidly proliferating malignant cells. The mechanism of action is believed to involve cross-linking of tumor cell DNA (Physicians' Desk reference, 1997).

Cyclophosphamide is one example of a cytotoxic agent which causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment and occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Figure 52:
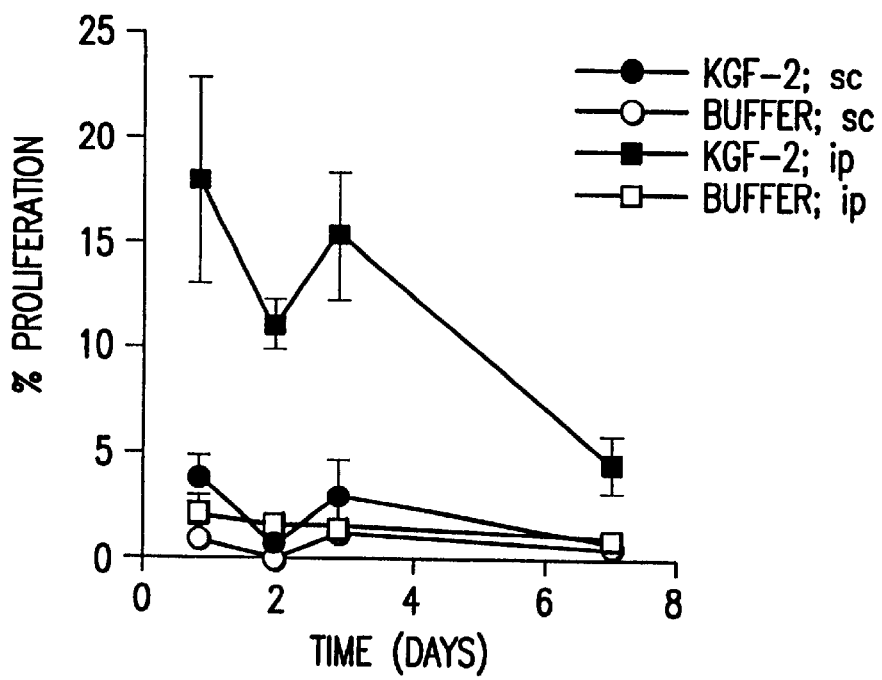
FIG. 52 shows the proliferation of bladder epithelium following ip or sc administration of KGF-2 Δ33.
Figure 53:
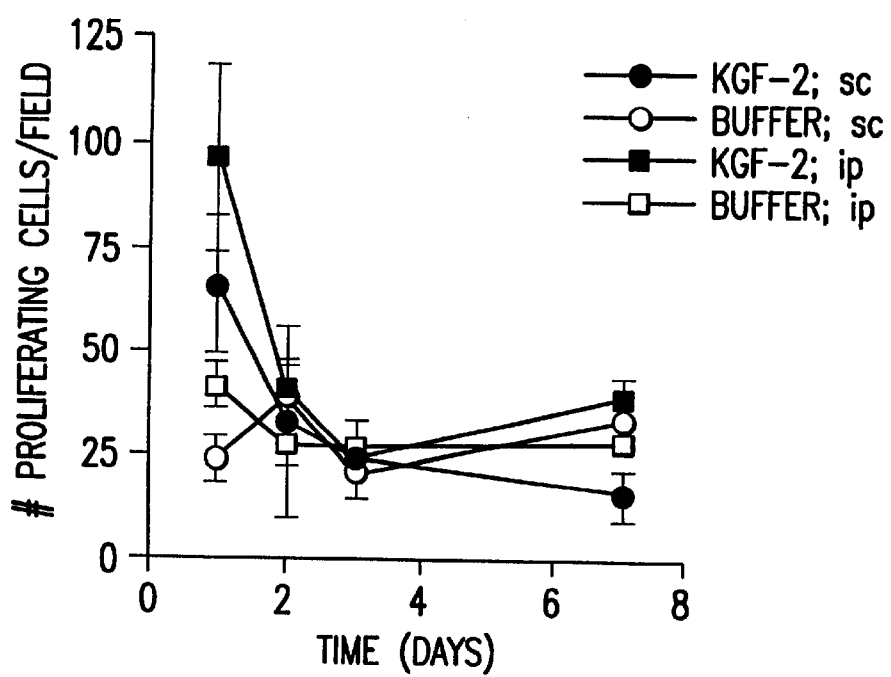
FIG. 53 shows the proliferation of prostatic epithelial cells after systemic administration of KGF-2 Δ33.

As shown in FIGS. 52 and 53, systemic administration of KGF-2 to an individual stimulates proliferation of bladder and prostatic epithelial cells. Thus, in one aspect, the present invention provides a method of stimulating proliferation of bladder epithelium and prostatic epithelial cells by administering to an individual an effective amount of a KGF-2 polypeptide. More importantly, as FIGS. 54 and 55 demonstrate, KGF-2 can be used to reduce damage caused by cytotoxic agents having side effects resulting in the inhibition of bladder and prostate epithelial cell proliferation. To reduce such damage, KGF-2 can be administered either before, after, or during treatment with or exposure to the cytotoxic agent. Accordingly, in a further aspect, there is provided a method of reducing damage caused by an inhibition of the normal proliferation of epithelial cells of the bladder or prostate by administering to an individual an effective amount of KGF-2. As indicated, inhibitors of normal proliferation of bladder or prostate epithelium include radiation therapy (causing acute or chronic radiation damage) and cytotoxic agents such as chemotherapeutic or antineoplastic drugs including, but not limited to, cyclophosphamide, busulfan, and ifosfamide. In a further aspect, KGF-2 is administered to reduce or prevent fibrosis and ulceration of the urinary bladder. Preferably, KGF-2 is administered to reduce or prevent hemorrhagic cystitis. Suitable doses, formulations, and administration routes are described below.

As used herein, by "individual" is intended an animal, preferably a mammal (such as apes, cows, horses, pigs, boars, sheep, rodents, goats, dogs, cats, chickens, monkeys, rabbits, ferrets, whales, and dolphins), and more preferably a human.

The signal sequence of KGF-2 encoding amino acids 1 through 35 or 36 may be employed to identify secreted proteins in general by hybridization and/or computational search algorithms.

The nucleotide sequence of KGF-2 could be employed to isolate 5' sequences by hybridization. Plasmids comprising the KGF-2 gene under the control of its native promoter/enhancer sequences could then be used in in vitro studies aimed at the identification of endogenous cellular and viral transactivators of KGF-2 gene expression.

The KGF-2 protein may also be employed as a positive control in experiments designed to identify peptidomimetics acting upon the KGF-2 receptor.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

Fragments of the full length KGF-2 gene may be used as a hybridization probe for a cDNA library to isolate the full length KGF-2 genes and to isolate other genes which have a high sequence similarity to these genes or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete KGF-2 gene including regulatory and promotor regions, exons, and introns. An example of a screen comprises isolating the coding region of the KGF-2 gene by using the known DNA sequence to synthesize an oligonucleotide probe. Labeled oligonucleotides having a sequence complementary to that of the gene of the present invention are used to screen a library of human cDNA, genomic DNA or cDNA to determine which members of the library the probe hybridizes to.

This invention provides a method for identification of the receptors for the KGF-2 polypeptide. The gene encoding the receptor can be identified by numerous methods known to those of skill in the art, for example, ligand panning and FACS sorting (Coligan et al., Current Protocols in Immun., 1(2), Chapter 5 (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and rescreening process, eventually yielding a single clone that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to x-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify those which agonize the action of KGF-2 or block the function of KGF-2. An example of such an assay comprises combining a mammalian Keratinocyte cell, the compound to be screened and $^3$[H] thymidine under cell culture conditions where the keratinocyte cell would normally proliferate. A control assay may be performed in the absence of the compound to be screened and compared to the amount of keratinocyte proliferation in the presence of the compound to determine if the compound stimulates proliferation of Keratinocytes.

To screen for antagonists, the same assay may be prepared in the presence of KGF-2 and the ability of the compound to prevent Keratinocyte proliferation is measured and a determination of antagonist ability is made. The amount of Keratinocyte cell proliferation is measured by liquid scintillation chromatography which measures the incorporation of $^3$[H] thymidine.

In another method, a mammalian cell or membrane preparation expressing the KGF-2 receptor would be incubated with labeled KGF-2 in the presence of the compound. The ability of the compound to enhance or block this interaction could then be measured. Alternatively, the response of a known second messenger system following interaction of KGF-2 and receptor would be measured and compared in the presence or absence of the compound. Such second messenger systems include but are not limited to, cAMP guanylate cyclase, ion channels or phosphoinositide hydrolysis.

Examples of potential KGF-2 antagonists include an antibody, or in some cases, an oligonucleotide, which binds to the polypeptide. Alternatively, a potential KGF-2 antagonist may be a mutant form of KGF-2 which binds to KGF-2 receptors, however, no second messenger response is elicited and therefore the action of KGF-2 is effectively blocked.

Another potential KGF-2 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res. 6:3073 (1979); Cooney el al., Science 241:456 (1988); and Dervan et al., Science 251:1360 (1991)), thereby preventing transcription and the production of KGF-2. The antisense RNA oligonucleotide hybridizes to the cDNA in vivo and blocks translation of the cDNA molecule into KGF-2 polypeptide (Antisense—Okano, J., Neurochem. 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of KGF-2.

Potential KGF-2 antagonists include small molecules which bind to and occupy the binding site of the KGF-2 receptor thereby making the receptor inaccessible to KGF-2 such that normal biological activity is prevented. Examples of small molecules include but are not limited to small peptides or peptide-like molecules.

The KGF-2 antagonists may be employed to prevent the induction of new blood vessel growth or angiogenesis in tumors. Angiogenesis stimulated by KGF-2 also contributes to several pathologies which may also be treated by the antagonists of the present invention, including diabetic retinopathy, and inhibition of the growth of pathological tissues, such as in rheumatoid arthritis.

KGF-2 antagonists may also be employed to treat glomerulonephritis, which is characterized by the marked proliferation of glomerular epithelial cells which form a cellular mass filling Bowman's space.

The antagonists may also be employed to inhibit the over-production of scar tissue seen in keloid formation after surgery, fibrosis after myocardial infarction or fibrotic lesions associated with pulmonary fibrosis and restenosis. KGF-2 antagonists may also be employed to treat other proliferative diseases which are stimulated by KGF-2, including cancer and Kaposi's sarcoma.

KGF-2 antagonists may also be employed to treat keratitis which is a chronic infiltration of the deep layers of the cornea with uveal inflammation characterized by epithelial cell proliferation.

The antagonists may be employed in a composition with a pharmaceutically acceptable carrier, e.g., as hereinafter described.

The polypeptides, agonists and antagonists of the present invention may be employed in combination with a suitable pharmaceutical carrier to comprise a pharmaceutical composition. Such compositions comprise a therapeutically effective amount of the polypeptide, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The polypeptide having KGF-2 activity may be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in *Remington's Pharmaceutical Sciences* (latest edition), Mack Publishing Company, Easton, Pa.

The KGF-2 composition to be used in the therapy will be formulated and dosed in a fashion consistent with good medical practice, taking into account the clinical condition of the individual patient (especially the side effects of treatment with KGF-2 alone), the site of delivery of the KGF-2 composition, the method of administration, the scheduling of administration, and other factors known to practitioners. The "effective amount" of KGF-2 for purposes herein is thus determined by such considerations.

The pharmaceutical compositions may be administered in a convenient manner such as by the oral, topical, intravenous, intraperitoneal, intramuscular, intraarticular, subcutaneous, intranasal, intratracheal or intradermal routes. The pharmaceutical compositions are administered in an amount which is effective for treating and/or prophylaxis of the specific indication. In most cases, the dosage is from about 1 $\mu$g/kg to about 30 mg/kg body weight daily, taking into account the routes of administration, symptoms, etc. However, the dosage can be as low as 0.001 $\mu$g/kg. For example, in the specific case of topical administration dosages are preferably administered from about 0.01 $\mu$g to 9 mg per cm$^2$.

As a general proposition, the total pharmaceutically effective amount of the KGF-2 administered parenterally per more preferably dose will be in the range of about 1 $\mu$g/kg/day to 100 mg/kg/day of patient body weight, although, as noted above, this will be subject to therapeutic discretion. If given continuously, the KGF-2 is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution or bottle solution may also be employed.

A course of KGF-2 treatment to affect the fibrinolytic system appears to be optimal if continued longer than a certain minimum number of days, 7 days in the case of the mice. The length of treatment needed to observe changes and the interval following treatment for responses to occur appears to vary depending on the desired effect. Such treatment lengths are indicated in the Examples below.

The KGF-2 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., *Biopolymers* 22:547–556 (1983)), poly (2-hydroxyethyl methacrylate) (R. Langer et al., *J. Biomed Mater. Res.* 15:167–277 (1981), and R. Langer, *Chem. Tech.* 12:98–105 (1982)), ethylene vinyl acetate (R. Langer et al., *Id.*) or poly-D-(−)-3-hydroxybutyric acid (EP 133,988). Sustained-release KGF-2 compositions also include liposomally entrapped KGF-2. Liposomes containing KGF-2 are prepared by methods known per se: DE 3,218,121; Epstein, et al., *Proc. Natl. Acad Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal KGF-2 therapy.

For parenteral administration, in one embodiment, the KGF-2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the KGF-2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in *Remington's Pharmaceutical Sciences* (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

KGF-2 is typically formulated in such vehicles at a concentration of about 0.01 μg/ml to 100 mg/ml, preferably 0.01 μg/ml to 10 mg/ml, at a pH of about 3 to 8. It will be understood that the use of certain of the foregoing excipients, carriers, or stabilizers will result in the formation of KGF-2 salts.

KGF-2 to be used for therapeutic administration must be sterile. Sterility is readily accomplished by filtration through sterile filtration membranes (e.g., 0.2 micron membranes). Therapeutic KGF-2 compositions generally are placed into a container having a sterile access port, for example, an intravenous solution bag or vial having a stopper pierceable by a hypodermic injection needle.

KGF-2 ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous KGF-2 solution, and the resulting mixture is lyophilized. The infusion solution is prepared by reconstituting the lyophilized KGF-2 using bacteriostatic Water-for-Injection.

Dosaging may also be arranged in a patient specific manner to provide a predetermined concentration of an KGF-2 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracisternally, intradermally, intravaginally, intraperitoneally, topically (as by powders, ointments, gels, creams, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Preferred KGF-2 formulations are described in U.S. Provisional Appln. No. 60/068493, filed Dec. 22, 1997, which is herein incorporated by reference.

The KGF-2 polypeptides, agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention. Further, before the cells are reintroduced into the patient, they may be seeded onto cell carriers, including biodegradable matrices (e.g. polyglycolic acid), tissue substitutes or equivalents (ex. artificial skin), artificial organs, and collagen derived matrices, etc.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle. Examples of other delivery vehicles include an HSV-based vector system, adeno-associated virus vectors, and inert vehicles, for example, dextran coated ferrite particles.

Retroviruses from which the retroviral plasmid vectors hereinabove mentioned may be derived include, but are not limited to, Moloney Murine Leukemia virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques Vol.* 7, No. 9:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cell lines which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527–1533 (1990); Treat el al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC *Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., *Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Antibody-based Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma el al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D., et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., *Id.*, p. 146). Unless otherwise provided, ligation may be accomplished using known buffers and conditions with 10 units of T4 DNA ligase ("ligase") per 0.5 µg of approximately equimolar amounts of the DNA fragments to be ligated.

A cell has been "transformed" by exogenous DNA when such exogenous DNA has been introduced inside the cell membrane. Exogenous DNA may or may not be integrated (covalently linked) inter-chromosomal DNA making the genome of the cell. Prokaryote and yeast, for example, the exogenous DNA may be maintained on an episomal element, such a plasmid. With respect to eukaryotic cells, a stably transformed or transfected cell is one in which the exogenous DNA has become integrated into the chromosome so that it is inherited by daughter cells through chromosome replication. This ability is demonstrated by the ability of the eukaryotic cell to establish cell lines or clones comprised of a population of daughter cell containing the exogenous DNA. An example of transformation is exhibited in Graham, F. & Van der Eb, A., *Virology*, 52:456–457 (1973).

"Transduction" or "transduced" refers to a process by which cells take up foreign DNA and integrate that foreign DNA into their chromosome. Transduction can be accomplished, for example, by transfection, which refers to various techniques by which cells take up DNA, or infection, by which viruses are used to transfer DNA into cells.

Gene Thierapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the KGF-2 polypeptide of the present invention. This method requires a polynucleotide which codes for a KGF-2 polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a KGF-2 polynucleotide ex vivo, with the engineered cells then being provided to a patient to be treated with the polypeptide. Such methods are well-known in the art. For example, see Belldegrun, A., et al., *J. Natl. Cancer Inst.* 85: 207–216 (1993); Ferrantini, M. et al., *Cancer Research* 53:1107–1112 (1993); Ferrantini, M. et al., *J. Immunology* 153:4604–4615 (1994); Kaido, T. et al., *Int. J. Cancer* 60:221–229 (1995); Ogura, H. et al., *Cancer Research* 50:5102–5106 (1990); Santodonato, L. et al., *Human Gene Therapy* 7:1–10 (1996); Santodonato, L. et al., *Gene Therapy* 4:1246–1255 (1997); and Zhang, J.-F. et al., *Cancer Gene Therapy* 3:31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the KGF-2 polynucleotide constructs can be delivered by any method that delivers injectable materials to the cells of an animal, such as, injection into the interstitial space of tissues (heart, muscle, skin, lung, liver, and the like). The KGF-2 polynucleotide constructs may be delivered in a pharmaceutically acceptable liquid or aqueous carrier.

In one embodiment, the KGF-2 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the KGF-2 polynucleotides can also be delivered in liposome formulations and lipofectin formulations and the like can be prepared by methods well known to those skilled in the art. Such methods are described, for example, in U.S. Pat. Nos. 5,593,972, 5,589, 466, and 5,580,859, which are herein incorporated by reference.

The KGF-2 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/NV5, pcDNA3.1, and pRc/CMV2 available from Invitrogen. Other suitable vectors will be readily apparent to the skilled artisan.

Any strong promoter known to those skilled in the art can be used for driving the expression of KGF-2 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for KGF-2.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The KGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. in vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked KGF-2 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced in the Examples, naked KGF-2 nucleic acid sequences can be administered in vivo results in the successful expression of KGF-2 polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the KGF-2 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* (1987) 84:7413–7416, which is herein incorporated by reference); mRNA (Malone et al., *Proc. Natl. Acad. Sci. USA* (1989) 86:6077–6081, which is herein incorporated by reference); and purified transcription factors (Debs et al., *J. Biol. Chem.* (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl Acad. Sci. USA* (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner el al., *Proc. Natl. Acad. Sci. USA* 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15 EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger el al., Methods of Immunology (1983),101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ratio will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding KGF-2. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA 12, T 19-14X, VT-19-17-H2, RCRE, RCRIP, GP+E-86, GP+envAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding KGF-2. Such retroviral vector particles then may be employed, to transduce eukaryotic cells, either in vitro or in vivo. The transduced eukaryotic cells will express KGF-2.

In certain other embodiments, cells are engineered, ex vivo or in vivo, with KGF-2 polynucleotide contained in an adenovirus vector. Adenovirus can be manipulated such that it encodes and expresses KGF-2, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis.109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The KGF-2 polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the KGF-2 polynucleotide construct.

These viral particles are then used to transduce eukaryotic cells, either ex vivo or in vivo. The transduced cells will contain the KGF-2 polynucleotide construct integrated into its genome, and will express KGF-2.

Another method of gene therapy involves operably associating heterologous control regions and endogenous polynucleotide sequences (e.g. encoding KGF-2) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4,1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the KGF-2 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous KGF-2 sequence is placed under the control of the promoter. The promoter then drives the expression of the endogenous KGF-2 sequence.

The polynucleotides encoding KGF-2 may be administered along with other polynucleotides encoding other angiogenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding KGF-2 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281,1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits, sheep, cattle, horses and pigs, with humans being particularly preferred.

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); May, *TIBTECH* 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, *Proc. Natl. Acad. Sci. USA* 86:8932–8935 (1989); Zijlstra et al., *Nature* 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO 93/14188, WO 93/20221). Alternatively, the nucleic acid can be introduced intracellularly and incorporated within host cell DNA for expression, by homologous recombination (Koller and Smithies, *Proc. Natl. Acad Sci. USA* 86:8932–8935 (1989); Zijlstra et al., *Nature* 342:435–438 (1989)).

In a specific embodiment, viral vectors that contains nucleic acid sequences encoding an antibody of the invention are used. For example, a retroviral vector can be used (see Miller et al., *Meth. Enzymol.* 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., *Biotherapy* 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434(1991); Rosenfeld et al., *Cell* 68:143–155 (1992); Mastrangeli et al., *J. Clin. Invest.* 91:225–234 (1993); PCT Publication WO94/12649; and Wang, et al., *Gene Therapy* 2:775–783 (1995). In a preferred embodiment, adenovirus vectors are used.

Adeno-associated virus (AAV) has also been proposed for use in gene therapy (Walsh et al., *Proc. Soc. Exp. Biol. Med.* 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599–618(1993);Cohenetal., *Meth. Enzymol.* 217:618–644(1993); Cline, *Pharmac. Ther.* 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, *Cell* 71:973–985 (1992); Rheinwald, *Meth. Cell Bio.* 21A:229 (1980); and Pittelkow and Scott, *Mayo Clinic Proc.* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Immune Activity

KGF-2 polynucleotides or polypeptides, or agonists or antagonists of KGF-2, may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, KGF-2 polynucleotides or polypeptides, or agonists or antagonists of KGF-2, can be used as a marker or detector of a particular immune system disease or disorder.

KGF-2 polynucleotides or polypeptides, or agonists or antagonists of KGF-2, may be useful in treating or detecting deficiencies or disorders of hematopoietic cells. KGF-2 polynucleotides or polypeptides, or agonists or antagonists of KGF-2, could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, KGF-2 polynucleotides or polypeptides, or agonists or antagonists of KGF-2, can also be used to modulate hemostatic (the stopping of bleeding) or thrombolytic activity (clot formation). For example, by increasing hemostatic or thrombolytic activity, KGF-2 polynucleotides or polypeptides, or agonists or antagonists of KGF-2, could be used to treat blood coagulation disorders (e.g., afibrinogenemia, factor deficiencies), blood platelet disorders (e.g. thrombocytopenia), or wounds resulting from trauma, surgery, or other causes. Alternatively, KGF-2 polynucleotides or polypeptides, or agonists or antagonists of KGF-2, that can decrease hemostatic or thrombolytic activity could be used to inhibit or dissolve clotting, important in the treatment of heart attacks (infarction), strokes, or scarring.

KGF-2 polynucleotides or polypeptides, or agonists or antagonists of KGF-2, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of KGF-2 polynucleotides or polypeptides, or agonists or antagonists of KGF-2, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyclitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by KGF-2 polynucleotides or polypeptides, or agonists or antagonists of KGF-2. Moreover, these molecules can be used to treat anaphylaxis, hypersensitivity to an antigenic molecule, or blood group incompatibility.

KGF-2 polynucleotides or polypeptides, or agonists or antagonists of KGF-2, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of KGF-2 polynucleotides or polypeptides, or agonists or antagonists of KGF-2, that inhibits an immune response, particularly the proliferation, differentiation, or chemotaxis of T-cells, may be an effective therapy in preventing organ rejection or GVHD.

Similarly, KGF-2 polynucleotides or polypeptides, or agonists or antagonists of KGF-2, may also be used to modulate inflammation. For example, KGF-2 polynucleotides or polypeptides, or agonists or antagonists of KGF-2, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperprolferative Disorders

KGF-2 polynucleotides or polypeptides, or agonists or antagonists of KGF-2, can be used to treat or detect hyperproliferative disorders, including neoplasms. KGF-2 polynucleotides or polypeptides, or agonists or antagonists of KGF-2, may inhibit the proliferation of the disorder through direct or indirect interactions. Alternatively, KGF-2 polynucleotides or polypeptides, or agonists or antagonists of KGF-2, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by KGF-2 polynucleotides or polypeptides, or agonists or antagonists of KGF-2, include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by KGF-2 polynucleotides or polypeptides, or agonists or antagonists of KGF-2. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

KGF-2 polynucleotides or polypeptides, or agonists or antagonists of KGF-2, encoding KGF-2 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, and ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic venoocclusive disease, hypertension, hypotension, ischemia, peripheral vascular diseases, phlebitis, pulmonary venoocclusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

KGF-2 polynucleotides or polypeptides, or agonists or antagonists of KGF-2, are especially effective for the treatment of critical limb ischemia and coronary disease. As shown in the Examples, administration of KGF-2 polynucleotides and polypeptides to an experimentally induced ischemia rabbit hindlimb may restore blood pressure ratio, blood flow, angiographic score, and capillary density.

KGF-2 polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. KGF-2 polypeptides may be administered as part of a pharmaceutical composition, described in more detail below. Methods of delivering KGF-2 polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203(1985); Patz, *Am. J. Opthalmol.* 94:715–743(1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the KGF-2 polynucleotides and/or polypeptides of the invention, as well as agonists or antagonists of KGF-2.

Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).

Ocular disorders associated with neovascularization which can be treated with the KGF-2 polynucleotides and polypeptides of the present invention (including KGF-2 agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated with the KGF-2 polynucleotides and polypeptides of the present invention (including KGF-2 agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with the KGF-2 polynucleotides and polypeptides of the present invention (including KGF-2 agonist and/or antagonists) include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

Digestive Diseases

KGF-2 has been shown to stimulate the proliferation of cells of the gastrointestinal tract. Thus, KGF-2 polynucleotides, polypeptides, agonists, and/or antagonists can be used to treat and/or detect digestive diseases.

Examples of digestive diseases which can be treated or detected include: biliary tract diseases (such as bile duct diseases which include bile duct neoplasms, bile duct obstruction, Caroli's disease, cholangitis; common bile duct diseases such as choledochal cyst, common bile duct calculi, and common bile duct neoplasms; bile reflux, biliary atresia, biliary dyskinesia, biliary fistula, biliary tract neoplasms, gallbladder neoplasms, cholelithiasis such as common bile duct calculi; cholestasis, bile duct obstruction, alagille syndrome and liver cirrhosis; gallbladder diseases such as cholecystitis, cholelithiasis and gallbladder neoplasms; hemobilia and postcholecystectomy syndrome), digestive system abnormalities (such as imperforate anus, Barrett esophagus, biliary atresia, diaphragmatic eventration, esophageal atresia, Hirschsprung Disease, intestinal atresia, Meckel's Diverticulum), digestive system fistula (which includes biliary fistula and esophageal fistula such as tracheoesophageal fistula, gastric fistula, intestinal fistula such as rectal fistula), digestive system fistula (such as intestinal fistula such as rectal fistula which includes rectovaginal fistula and pancreatic fistula), digestive system neoplasms (such as biliary tract neoplasms which includes common bile duct neoplasms, gallbladder neoplasms), esophageal neoplasms, gastrointestinal neoplasms, such as intestinal neoplasms such as cecal neoplasms which include appendiceal neoplasms such as colonic polyps such as adenomatous polyposis coli, colorectal neoplasms such as hereditary colorectal neoplasms and nonpolyposis, sigmoid neoplasms, duodenal neoplasms, duodenal neoplasms, ileal neoplasms, intestinal polyps such as colonic polyps such as adenomatous polyposis coli, Gardner Syndrome and Peutz-Jeghers Syndrome, jejunal neoplasms, rectal neoplasms such as anus neoplasms), digestive system neoplasms (such as gastrointestinal neoplasms such as intestinal neoplasms such as rectal neoplasms which include anus neoplasms and anal gland neoplasms, stomach neoplasms, pancreatic neoplasms and peritoneal neoplasms), esophageal diseases (such as Barrett Esophagus, esophageal and gastric varices, esophageal atresia, esophageal cyst, esophageal diverticulum such as Zenker's Diverticulum, esophageal motility disorders such as CREST Syndrome, deglutition disorders such as Plummer-Vinson Syndrome, esophageal achalasia, diffuse esophageal spasm and gastroesophageal reflux, esophageal neoplasms, esophageal perforation such as Mallory-Weiss Syndrome, esophageal stenosis, esophagitis such as peptic esophagitis, diaphragmatic hernia such as traumatic diaphragmatic hernia, hiatal hernia.)

Examples of gastrointestinal diseases which can be treated or detected include gastroenteritis such as cholera morbus, gastrointestinal hemorrhage (such as hematemesis, melena and peptic ulcer), hernia (such as diaphragmatic hernia which include traumatic diaphragmatic hernia and hiatal hernia, femoral hernia, inguinal hernia, obturator hernia, umbilical hernia and ventral hernia), intestinal diseases (such as cecal diseases which include appendicitis, cecal neoplasms such as appendiceal neoplasms, colonic diseases such as colitis which include ischemic colitis, ulcerative colitis such as toxic megacolon, enterocolitis such as pseudomembranous entercolitis, proctocolitis, functional colonic diseases such as colonic pseudo-obstruction, colonic neoplasms such as colonic polyps such as adenomatous polyposis coli, colorectal neoplasms such as hereditary colorectal neoplasms and nonpolyposis, sigmoid neoplasms, colonic diverticulities, colonic diverticulosis, megacolon such as Hirschsprung Disease and toxic megacolon, sigmoid diseases such as proctocolitis and sigmoid neoplasms, constipation, Crohn's disease, diarrhea such as infantile diarrhea, dysentery such as amebic dysentery and bacillary dysentery, duodenal diseases such as duodenal neoplasms, duodenal obstruction such as superior mesenteric artery syndrome, duodenal ulcer such as Curling's Ulcer and duodenitis, enteritis such as enterocolitis which includes pseudomembranous entercolitis, ileal diseases such as ileal neoplasms and ileitis, immunoproliferative small intestinal disease, inflammatory bowel diseases such as ulcerative colitis and Crohn's Disease, intestinal atresia, parasitic intestinal diseases such as anisakiasis, balantidiasis, blastocystis infections, cryptosporidiosis, dientamoebiasis, dientamoebiasis, amebic dysentery and giardiasis, intestinal fistula such as rectal fistula which include rectovaginal fistula, intestinal neoplasms such as cecal neoplasms which include appendiceal neoplasms, colonic neoplasms such as colonic polyps which include adenomatous polyposis coli, colorectal neoplasms such as hereditary colorectal neoplasms and nonpolyposis, sigmoid neoplasms, duodenal neoplasms, ileal neoplasms, intestinal polyps such as colonic polyps such as adenomatous polyposis coli, Gardner Syndrome, Peutz-Jeghers Syndrome, intestinal obstruction such as afferent loop syndrome, duodenal obstruction, impacted feces, intestinal pseudo-obstruction such as colonic pseudo-obstruction, intussusception, intestinal perforation, intestinal polyps such as colonic polyps which include adenomatous polyposis coli, jejunal diseases such as jejunal neoplasms, malabsorption syndromes such as blind loop syndrome, celiac disease, lactose intolerance, intestinal lipodystrophy, short bowel syndrome, tropical sprue, occlusion mesenteric vascular, pneumatosis cystoides intestinalis, protein-losing enteropathies such as intestinal lymphangiectasis, rectal diseases such as anus diseases which include anus neoplasms such anal gland neoplasms, fissure in ano, pruritus ani, fecal incontinence, hemorrhoids, proctitis such as proctocolitis, rectal fistula such as rectovaginal fistula, rectal neoplasms such as anus neoplasms such as anal gland neoplasms, rectal diseases such as rectal prolapse, peptic ulcer, Peptic esophagitis, marginal ulcer, peptic ulcer hemorrhage, peptic ulcer perforation, stomach ulcer, Zollinger-Ellison Syndrome, postgastrectomy syndromes such as dumping syndrome, stomach diseases such as achlorhydria, duodenogastric reflux such as bile reflux, gastric fistula, gastric mucosa prolapse, gastric outlet obstruction such as pyloric stenosis, gastritis such as atrophic gastritis and hypertrophic gastritis, gastroparesis, stomach dilatation, stomach diverticulum, stomach neoplasms, stomach rupture, stomach ulcer and stomach volvulus, gastrointestinal tuberculosis, visceroptosis, vomiting such as hematemesis and hyperemesis gravidarum), pancreatic diseases such as cystic fibrosis, pancreatic cyst such as pancreatic pseudocyst, pancreatic fistula, pancreatic insufficiency, pancreatic neoplasms and pancreatitis), peritoneal diseases such as chyloperitoneum, hemoperitoneum, mesenteric cyst, mesenteric lymphadenitis, mesenteric vascular occlusion, peritoneal paniculitis, peritoneal neoplasms, peritonitis, pneumoperitoneum, subphrenic abscess and peritoneal tuberculosis.

Digestive diseases which may be treated or detected also include liver diseases. Liver diseases include acute yellow atrophy, intrahepatic cholestasis such as alagille syndrome and biliary liver cirrhosis, fatty liver such as alcoholic fatty liver and Reye's Syndrome, hepatic vein thrombosis, hepatic veno-occlusive disease, hepatitis such as alcoholic hepatitis, animal hepatitis such as animal viral hepatitis such as infectious canine hepatitis and Rift Valley Fever, toxic hepatitis, human viral hepatitis such as delta infection, hepatitis A, hepatitis B, hepatitis C, chronic active hepatitis and hepatitis E, hepatolenticular degeneration, hepatomegaly, hepatorenal syndrome, portal hypertension such as Cruveilhier-Baumgarten Syndrome and Esophageal and gastric varices, liver abscess such as amebic liver abscess, liver cirrhosis such as alcoholic liver cirrhosis, biliary liver cirrhosis and experimental liver cirrhosis, alcoholic liver diseases such as alcoholic fatty liver, alcoholic hepatitis and alcoholic liver cirrhosis, parasitic liver diseases such as hepatic echinococcosis, fascioliasis, and amebic liver abscess, liver failure such as hepatic encephalopathy and acute liver failure, liver neoplasms, peliosis hepatis, erythrohepatic porphyria, and hepatic porphyria such as acute intermittent porphyria and porphyria cutanea tarda, hepatic tuberculosis and Zellweger Syndrome).

Examples of stomatognathic diseases which can be treated or detected include jaw diseases (such as cherubism, giant cell granuloma, jaw abnormalities such as cleft palate, micrognathism, Pierre Robin Syndrome, prognathism and retrognathism, jaw cysts such as nonodontogenic cysts, odontogenic cysts such as basal cell nevus syndrome, dentigerous cyst, calcifying odontogenic cyst, periodontal cyst such as radicular cyst, edentulous jaw such as partially edentulous jaw, jaw neoplasms such as mandibular neoplasms, maxillary neoplasms and palatal neoplasms, mandibular diseases such as craniomandibular disorders which include temporomandibular joint diseases such as temporomandibular joint syndrome, mandibular neoplasms, prognathism and retrognathism, maxillary diseases such as maxillary neoplasms), mouth diseases (such as Behcet's Syndrome, Burning Mouth Syndrome, oral candidiasis, dry socket, focal epithelial hyperplasia, oral leukoedema, oral lichen planus, lip diseases such as cheilitis, cleft lip, herpes labialis and lip neoplasms, Ludwig's Angina, Melkersson-Rosenthal Syndrome, mouth abnormalities such as cleft lip, cleft palate, fibromatosis gingivae, macroglossia, macrostomia, microstomia and velopharyngeal insufficiency, edentulous mouth such as edentulous jaw such as partially edentulous jaw, mouth neoplasms such as gingival neoplasms such as gingival neoplasms, oral leukoplakia such as hairy leukoplakia, lip neoplasms, palatal neoplasms, salivary gland neoplasms such as parotid neoplasms, sublingual gland neoplasms and submandibular gland neoplasms and tongue neoplasms, noma, oral fistula such as dental fistula, oroantral fistula and salivary gland fistula, oral hemorrhage such as gingival hemorrhage, oral manifestations, oral submucous fibrosis, periapical periodontitis such as periapical abscess and periapical granuloma and radicular cyst), periodontal diseases (such as alveloar bone loss, furcation defects such as gingival hemorrhage, gingival hyperplasia, gingival hypertrophy, gingival neoplasms, gingival recession, gingivitis such as gingival crevicular fluid, gingival pocket, necrotizing ulcerative gingivitis, giant cell granuloma and pericoronitis, periodontal attachment loss, periodontal cyst, periodontitis such as periodontal abscess, periodontal pocket and periodontosis, tooth exfoliation, tooth loss, tooth migration such as mesial movement of teeth and tooth mobility), ranula, salivary gland diseases (such as Mikulicz' Disease, parotid diseases such as parotid neoplasms and parotitis such as mumps, salivary gland calculi such as salivary duct calculi, salivary gland fistula, salivary gland neoplasms such as parotid neoplasms, sublingual gland neoplasms and submandibular gland neoplasms), sialadenitis, necrotizing sialometaplasia, sialorrhea, submandibular gland diseases such as submandibular gland neoplasms, xerostomia such as Sjogren's syndrome, stomatitis (such as Stevens-Johnson Syndrome, aphthous stomatitis, aphthous stomatitis, denture stomatitis and herpetic stomatitis), tongue diseases (such as glossalgia, glossitis such as benign migratory glossitis), macroglossia, tongue diseases (such as fissured tongue, hairy tongue and tongue neoplasms and oral tuberculosis), pharyngeal diseases (such as pharyngeal diseases such as nasopharyngeal diseases such as nasopharyngeal neoplasms and nasopharyngitis), peritonsillar abscess, pharyngeal neoplasms such as hypopharyngeal neoplasms, nasopharyngeal neoplasms and oropharyngeal neoplasms which include tonsillar neoplasms, pharyngitis, retropharyngeal abscess, tonsillitis and velopharyngeal insufficiency), stomatognathic system abnormalties, temporomandibular joint diseases such as temporomandibular joint syndrome, tooth diseases (such as bruxism, dental depositis which includes dental calculus and dental plague, dental leakage, dental pulp diseases which includes dental pulp autolysis, dental pulp calcification, dental pulp exposure, dental pulp gangrene, secondary dentin and pulpitis, dentin sensitivity, dental focal infection, hypercementosis, malocclusion such as traumatic dental occlusion, diastema, angle class I malocclusion, angle class II malocclusion, angle class III malocclusion, mottled enamel, tooth abnormalities such as amelogenesis imperfecta such as dental enamel hypoplasia, anodonitia, dens in dente, dentin dysplasia, dentinogenesis imperfecta, fused teeth, odontodysplasia and supernumerary tooth, tooth abrasion, tooth deminerlization such as dental caries which includes dental fissures and root caries, tooth discoloration, tooth erosion, ectopic tooth eruption, impacted tooth, tooth injuries such as tooth Fractures such as cracked tooth syndrome and tooth luxation, tooth loss, tooth resorption such as root resorption and unerupted tooth and toothache).

Ocular Diseases

KGF-2 has been shown to stimulate proliferation of cells of the eye. Thus, KGF-2 polynucleotides, polypeptides, agonists, and/or antagonists can be used to treat and/or detect ocular diseases.

Examples of ocular diseases which can be treated or detected include asthenopia, conjunctival diseases, conjunctival neoplasms, conjunctivitis (allergic, bacterial, inclusion, ophthalmia neonatorum, trachoma, viral, acute hemorrhagic), keratoconjunctivitis, keratoconjunctivitis (infectious or sicca), Reiter's Disease, Pterygium, xerophthalmia, corneal diseases, corneal dystrophies (hereditary), Fuchs' Endothelial Dystrophy, corneal edema, corneal neovascularization, corneal opacity, arcus senilis, keratitis, acanthamoeba keratitis, corneal ulcer, herpetic keratitis, dendritic keratitis, keratoconjunctivitis, keratoconus, trachoma, eye abnormalities (aniridia, WAGR Syndrome, Anophthamos, blepharophimosis, coloboma, ectopia lentis, hydrophthalmos, microphthalmos, retinal dysplasia), hereditary eye diseases (albinism, ocular albinism, oculocutaneous albinism, choroideremia, hereditary corneal dystrophies, gyrate atrophy, hereditary optic atrophy, retinal dysplasa, retinitis pigmentosa), eye hemorrhage (choroid hemorrhage, hyphema, retinal hemorrhage, vitreous hemmorrhage), eye infections (corneal ulcer, bacterial eye infections, bacterial conjunctivitis, inclusion conjunctivitis, ophthalmia neonatorum, trachoma, hordeolum, infectious keratoconjunctivitis, ocular tuberculosis), fungal eye infections, parasitic eye infections (acanthamoeba keratitis, ocular onchocerciasis, ocular toxoplasmosis), viral eye infections (viral conjunctivitis, acute hemorrhagic conjunctivitis, cytomegalovirus retinitis, Herpes Zoster Ophthalmicus, herpetic keratitis, dendritic keratitis), suppurative uveitis (endophthalmitis, panophthalmitis), eye injuries (eye burns, eye foreign bodies, penetrating eye injuries), eye manifestations, eye neoplasms (conjunctival neoplasms, eyelid neoplasms, orbital neoplasms, uveal neoplasms (choroid neoplasms, iris neoplasms), eyelid diseases (blepharitis, blepharophimosis, blepharoptosis, belpharospasm, chalazion, ectropion, entropion, eyelid neoplasms, hordeolum), lacrimal aparatus diseases (dacroyocystitis, dry eye sundromes, keratoconjunctivitis sicca, Sjogren's Syndrome, xerophthalmia, lacrimal duct obstruction), lens diseases (aphakia, poscataract aphakia, cataract, lens subluxation, ectopia lentis, ocular hypertension, glaucoma (angle-closure, neovascular, open-angle, hydrophthalmos), ocular hypotension, ocular motility disorders (amblyopia, nystagmus, oculomotor nerve paralysis, ophthalmoplegia (Duane's Syndrome, Horner's Syndrome, Chronic progressive external ophthalmoplegia, Kearns Syndrome), strabismus (esotropia), optic nerve diseases (optic atrophy, hereditary optic atrophy, optic disk drusen, optic neuritis, neuromyelitis optica, papilledema), orbital diseases (enophthalmos, exophthalmos, Graves' Disease, orbital plasma cell granuloma, orbital neoplasms), abnomal pupillary functions (anisocoria, tonic pupil, Adie's Syndrome, miosis, mydriasis, Horner's Syndrome), refractive errors (aniseikonia, anisometropia, astigmatism, hyperopia, myopia, presbyopia), retinal diseases (angioid streaks, diabetic retinopathy, retinal artery occusion, retinal degeneration, macular degeneration, cystoid macular edema, retinal drusen, retinitis pigmentosa, Kearns Syndrome, retinal detachment, retinal dysplasia, retinal hemorrhage, retinal neovascularization, retinal perforations, retinal vein occlusion, retinitis (chorioretinitis, cytomegalovirus retinitis, acute retinal necrosis syndrome), retinopathy of prematurity, proliferative vitreoretinopathy), scleral diseases (scleritis), uveal diseases (choroid diseases, choroid hemorrahage, choroid neoplasms, choroideremia, choroiditis, chorioretinitis, pars lanitis, gyrate atrophy), iris diseases (exfoliation syndrome, iridocyclitis, iris neoplasms), uveitis (panuveitis, sympathetic ophthalmia, anterior behcet's syndrome, iriocyclitis, iritis, posterior uveitis, choroiditis, chorioretinitis, pars planitis, intermediate uveitis, pars planitis, suppurative uveitis (endophthalmitis, panophthalmitis), uveomeningoencephalitic syndrome), vision disorders (amblyoia, blindness, hemianopsia, color vision defects, diplopia, night blindness, scotoma, subnormal vision), and proliferative vitreoretinopathy.

Skin and Connective Tissue Diseases

KGF-2 stimulates the proliferation of the cells of the skin and connective tissue. Therefore, KGF-2 polynucleotides, polypeptides, agonists, and/or antagonists can be used to treat and/or detect diseases of the skin and/or connective tissue.

Examples of connective tissue diseases include: cartilage diseases, such as relapsing polychondritis and Tietze's Syndrome; cellulitis; collagen diseases, such as Ehler's Danlos syndrome, keloids (including acne keloids), mucopolysaddaridosis I, necrobiotic disorders (including granuloma annulare, necrobiosis lipoidica), and osteogenesis imperfecta; cutis laxa; dermatomyositis; Dupytren's contracture; homocystinuria; lupus erythematosis (including cutaneous, discoid, panniculitis, systemic and nephritis; marfan syndrome; mixed connective tissue disease; mucinosis, including follicular, mucopolysaccaridoses (I, II, UU, IV, IV, and VII), myxedema, scleredemo adultorum and synovial cysts; connective tissue neoplasms; noonan syndromel osteopoikilosis; panniculitis, including erythema induratum, nodular nonsuppurative and peritoneal; penile induration; pseudoxanthoma elasticum; rheumatic diseases, including arthritis (rheumatoid, juvenile rheumatoid, Caplan's syndrome, Felty's syndrome, rheumatoid nodule, ankylosing spondylitis, and still's disease), hyperostosis, polymyalgia rheumatics; circumscribed scleroderma, and systemic scleroderma (CREST syndrome).

Examples of skin diseases include angiolymphoid hyperplasia with eosinophilia; cicatix (including hypertophic); cutaneous fistula, cuis laxa; dermatitis, inclding acrodermatitis, atopic dermatitis, contact dermatitis (allergic contact, photoallergic, toxicodendron), irritant dermatitis (phototoxic, diaper rash), occupational dermatitits; exfoliative dermatitis, herpetiformis dermatittis, seborrheic dermatitis, drug eruptions (such as toxic epidermal necrolysis, eryuthema nodosum, serum sickness) eczema, including dyshidrotic, intertrigo, neurodermatitis, and radiodermatitis; dermatomyositis; erythema, including chronicum migrans, induratum, infectiosum, multiforme (Stevens-Johnson syndrome), and nodosum (Sweet's syndrome); exanthema, including subitum; facial dermatosis, including acneiform eruptions (keloid, rosacea, vulgaris and Favre-Racouchot syndrome); foot dermatosis, including tinea pedis; hand dermatoses; keratoacanthoma; keratosis, inlcuding callosities, cholesteatoma (including middle ear), ichthyosis (including congentical ichtyosiform erythroderms, epidermolytic hyperkeratosis, lamellar ichthyosis, ichthyosis vulgaris, X-linked ichthyosis, and Sjogren-Larsson syndrome), keratoderma blennorrhagicum, palmoplantar keratoderms, follicularis keratosis, seborrheic keratosis, parakeratosis and porokeratosis; leg dermatosis, mastocytosis (urticaria pigmentosa), necrobiotic disorders (granuloma annulare and necrobiosis lipoidica), photosensitivity disorders (photoallergic or photoxic dermatitis, hydroa vacciniforme, sundurn, and xeroderma pigmentosum); pigmentation disorders, including argyria, hyperpigmentation, melanosis, aconthosis nigricans, lentigo, Peutz-Jeghers syndrome, hypopigmentation, albinism, pibaldism, vitiglio, incontinentia pigmenti, urticaria pigmentosa, and xeroderma pigmentosum.

Further examples of skin disorders include prurigo; pruritis (including ani and vulvae); pyoderma, including ecthyma and pyoderma gangrenosum; sclap dermatoses; sclerodema adultorum; sclerma neonatorum; skin appenage diseases, including hair diseases (alopecia, folliculitis, hirsutism, hyperticlhosis, Kinky hair syndrome), nail diseases (nail-patella syndrome, ingrown or malformed nails, onychomycosis, paronychia), sebaceous gland diseases (rhinophyma, neoplasms), sweat gland diseases (hidradentitis, hyperhidrosis, hypohidrosis, miliara, Fox-Fordyce disease, neoplasms); genetic skin deseases, including alfinism, cutis iaxa, benign familial pemphigis, porphyria, acrodermatitis, ectodermal dysplasia, Ellis-Van Creveld syndrome, focal dermal hypoplasia, Ehlers-Danlos syndrome, epidermolysis bullosa, ichtysosis; infectious skin diseases, inclyding dermatomycoses, blastomycosis, candidiasis, chromoblastomycosis, maduromycosis, paracoccidioidomycosis, sporotrichosis, tinea; bacterial skin diseases, such as cervicofacial actinomycosis, bacilliary angiomatosis, ecthyma, erysipelas, erythema chronicum migrans, erythrasma, granuloma inguinale, hidradenitis suppurativa, maduromycosis, paronychia, pinta, rhinoscleroma, staphylococcal skin infections (furuncolosis, carbuncle, impetigo, scalded skin syndrome), cutaneous syphilis, cutaneous tuberculosis, yaws; parasitic skin diseases, including larva migrans, Leishmaniasis, pediculosis, and scabies; viral skin diseases, including eythema infectiosum, exanthema subitum, herpes simplex, moolusum contagiosum, and warts.

Further examples of skin diseases include metabolic skin disesases, such as adiposis dolorosa, lipodystrophy, necrobiosis lipoidica, porhphyria, juvenile xanthogranuloma, xanthomatosis (Wolman disease); papulosequamous skin diseases, inclyding lichenoid eruptions, parpasoriasis, pityriasis, and psoriasis; vascular skin diseases, such as Behcet's syndrome, mucocutaneous lymph node syndrome, polyarteritis nodosa, pyoderma gangernosum, Takayasu's arteritis; vesculobullous skin diseases, including acantholysis, blisters, herpes gestationis, hybroa vacciniforme, pemphigoid, pemphigus; skin neoplasms; skin ulcers, such as decubitus ulcer, leg ulcers, foot ulcers, diabetic foot ulcers, varicose ulcers and pyoderma gangrenosum.

Uro-genital Diseases and Disorders

KGF-2 may stimulate the proliferation of the cells of the uro-genital tract. Therefore, KGF-2 polynucleotides, polypeptides, agonists, and/or antagonists can be used to treat and/or detect male and female genital diseases and/or disorders and pregnancy complications.

Examples of urologic and male genital diseases which can be treated or detected include epididymitis, male genital neoplasms, penile neoplasms, prostatic neoplasms, testicular neoplasms, hematocele, herpes genitalis, hydrocele, male infertility, oligospermia, penile diseases including balanitis, hypospadias, penile induration, penile neoplasms, phimosis, paraphimosis, priapism, prostatic diseases such as hypertrophy, neoplasms, and prostatitis, sexual disorders such as impotensce and vasculogenic impotence, sperm atic cord torsion, spermatocele, testicular diseases including cryptorchidism, orchitis, and testicular neoplasms, male genital tuberculosis, varicocele, urogenital tuberculosis (male genital, renal), urogenital abnormalities, bladder exstrophy, cryptorchidism, epispadias, hypospadias, polycystic kidney (autosomal dominant and autosomal recessive), hereditary nephritis, sex differentiation disorders, gonadal dysgenesis, mixed gonadal dysgenesis, hermaphroditism, pseudohermaphroditism, Kallman Syndrome, Klinefelter's Syndrome, testicular feminization, WAGR Syndrome, urogenital neoplasms, male genital neoplasms (penile, prostatic, testicular), urologic neoplasms (bladder, kidney, ureteral, urethral), bladder diseases (calculi, exstrophy, fistula, vesicovaginal fistula, neck obstruction, neoplasms, neurogenic, cystitis, vesico-ureteral reflux), hematuria, hemoglobinuria, AIDS-associated nephropathy, anuria, oliguria, diabetic nephropathies, Fanconi Syndrome, hepatorenal syndrome, hydronephrosis, primary hyperoxaluria, renal hypertension, renovascular hypertension, kidney calculi, kidney cortex necrosis, cystic kidney, polycystic kidney, policistic kidney (autosomal dominant, autosomal recessive), sponge kidney, kidney failure (nephrogenic disbetes insipidus, acute kidney failure, kidney papillary necrosis), nephritis (glomerulonephritis (IGA, membronoprol iferative, membranous, focal, Goodpasture's Syndrome, Lupus Nephritis), hereditary nephritis, insterstitial nephritis, balkan nephropathy, pyelonephritis, xanthogranulomatous pyelonephritis, nephrocalcinosis, nephrosclerosis, nephrosis, lipoid nephrosis, nephrotic syndrome, perinephritis), pyelitis (pyelocystitis, pyelonephritis, xanthogranulomatous pyelonephritis), renal artery obstruction, renal osteodystrophy, inborn errors in renal tubular transport, renal tubular acidosis, renal aminoaciduria, cystinuria, Hartnup Disease, Cystinosis, Franconi Syndrome, Renal glycosuria, familial hypophosphatemia, oculocerebrorenal syndrome, psudohypoaldosteronism, renal tuberculosis, uremia, Hemolytic-Uremic Syndrome, Wegener's Granulomatosis, Zellweger Syndrome, proteinuria, albuminuria, ureteral diseases including ureteral calculi, ureteral neoplasms, ureteral obstructionm, ureterocele, urethral diseases including epispadias, urethral neoplasms, urethral obstrauction, urethral stricture, urethritis (reiter's disease), urinary calculi (bladder, kidney, ureteral), urinary fistula (bladder fistula (vesicovaginal fistula)), urinary tract infections (bacteruria, pyuria, schistosomiasis haematobia), and urination disorders (enuresis, polyuria, urinary incontinence, stress-related urinary incontinence, urinary retention).

Examples of female genital disease and pregnancy complications which can be treated or detected include adnexal diseases including adnexitis (oophoritis, parametritis, salpingitis), fallopian tube diseases such as fallopian tube neoplasms and salpingitis, ovarian diseases (anovulation, oophoritis, ovarian cysts, polycystic ovary syndrome, premature ovarian failure, ovarian hyperstimulation syndrome, ovarian neoplasms, Meigs' Syndrome), Parovarian cyst, endometriosis, female genital neoplasms ovarian neoplasms, uterine neoplasms, cervis neoplasms, endometrial neoplasms, vaginal neoplams, vulvar neoplasms, gynatresia, hematocolpos, hematometra, herpes genitalis, female infertility, menstruation disorders including amenorrhea, dysmenorrhea, menorrhagia, oligomenorrhea, and premenstrual syndrome, pseudopregnancy, sex disorders such as dypareunia and frigidity, urogenital tuberculosis, female genital tuberculosis, urogenital diseases including bladder exstrophy, epispadias, polycystic kidney (autosomal dominant and autosomal recessive), hereditary nephritis, sex differentiation disorders including gonad dysgenesis (46 XY, Mixed), Turners' Syndrome, hermaphroditism, pseudohermaphroditism, Kallmann Syndrome, WAGR Syndrome, urogenital neoplasms, urologic neoplasms (bladder, ureteral, urethral), uterine diseases including cervix diseases (cervicitis, cervix erosion, cervix hypertrophy, cervix incompetence, cervix neoplasms), endometrial hyperplasia, endometritis, uterine hemmorrhage, menorrhagia, metrorrhagia, uterine neoplasms including cervix neoplams and endometrial neoplasms, uterine prolapse, uterine rupture, uterine perforation, vaginal diseases including vulvovaginal candidiasis, dysparenunia, hematocolpos, leukorrhea, vaginal fistula, rectovaginal fistula, vesicovaginal fistula, vaginal neoplasms, vaginitis (trichomonas vaginitis, bacterial vaginosis, vulvovaginitis), pregnancy complications including habitual abortion, cervix incompetence, incomplete abortion, missed abortion, septic abortion, threatened abortion, veterinary abortion, fetal death, embryo resorption, fetal resorption, fetal diseases (chorioamnionitis, fetal erythroblastosis, hydrops fetalis, fetal alcohol syndrome, fetal anoxia, fetal distress, fetal growth retardation, fetal macrosomia, and meconium aspiration, herpes gestationis, labor complications including abruptio placentae, dystocia, uterine inertia, premature rupture of fetal membranes, chorioamnionitis, placenta accreta, placenta praevia, postpartum hemorrhage, uterine rupture, premature labor, oligohydramnios, maternal phenylketonuria, placenta diseases (abruptio placentae, chorioamnionitis, placenta accreta, placenta retained, placental insufficiency), polyhydramnios, cardiovascular pregnancy cmplications, amniotic fluid embolism, hematologic pregnancy complications, infectious pregnancy complications (septic abortion, parasitic pregnancy complications, puerperal infection), neoplastic pregnancy complications (trophoblastic neoplasms, choriocarcinoma, hydatidiform mole, invasive hydatidiform mole, placental site trophoblastic tumor), ectopic pregnancy, abdominal pregnancy, tubal pregnancy, pregnancy in diabetes, gestational diabetes, fetal macrosomia, pregnancy outcome, pregnancy toxemias (eclampsia, HELLP Syndrome, pre-eclamsia, EPH Gestsis, hyperemesis gravidarum), puerperal disorders, lactation disorders such as Chiari-Frommel Syndrome, galactorrhea, and mastitis, postpartum hemorrhage, and puerperal infection.

Infertility

As stated above, KGF-2 polynucleotides, polypeptides, variants, antibodies, agonists and/or antagonists can be used to treat male or female infertility. Thus, in one embodiment of the invention, a method is provided using KGF-2 polynucleotides, polypeptides, variants, antibodies, agonists and/or antagonists to treat and/or prevent male infertility. In another embodiment, a method is provided using KGF-2 polynucleotides, polypeptides, variants, antibodies, agonists and/or antagonists to treat and/or prevent female infertility. Preferred KGF-2 polypeptides used for treating infertility include KGF-2 Δ33, full length and mature KGF-2, KGF-2 Δ28, and polypeptides comprising amino acids 77 to 208, 80 to 208, and 93 to 208 of KGF-2; as well as any KGF-2 mutant described herein. Also preferred are polynucleotide encoding these polypeptides.

For treatment or prevention of infertility, preferred modes of administration of KGF-2 include orally, rectally, parenterally, intracisternally, intradermally, intravaginally, intraperitoneally, topically (as by powders, ointments, gels, creams, drops or transdermal patch), bucally, or as an oral or nasal spray. Other modes of administration are described herein. Preferably, the KGF-2 polynucleotide, polypeptide, variant, antibody, agonist and/or antagonist is administered with a pharmaceutical carrier as part of a pharmaceutical composition. Suitable carriers are described herein.

KGF-2 polynucleotides, polypeptides, variants, antibodies, agonists and/or antagonists can be used to treat infertility caused by any factor, including environmental causes, such as coffee, MSG, plastics, Nutrasweet, alcohol, food additives, chemicals, cigarettes, pesticides, vehicle exhaust, and pollution; age; congenital infertility; low sperm count; infectious diseases, such as mumps, tuberculosis, influenza, small pox, cytomegalovirus (CMV) infection, chlamydia, mycoplasma, gonorrhea, syphilis and other sexually transmitted diseases; endocrine diseases, such as diabetes; neurological diseases, such as paraplegia; high fevers; endometriosis; toxins, such as lead in paints, varnishes and auto manufacturing agents, ethylene oxide, substances found in chemical and material industries such as paper manufacturing; chemotherapy; low weight or excessive weight loss; obesity or extreme weight gain; stress; ovulatory disorders; hormonal imbalances, Cushings Syndrome; fallopian tube blockage; pelvic infection; surgical adhesions; intrauterine devices (IUD); cervical disorders, such as anatomical problems, cervical infections, and mucus quality; cervical stenosis; uterine disorders, such as intrauterine adhesions, trauma to and/or infection of the uterine lining, Asherman's Syndrome, uterine fibroids; ovarian scar tissue; ovarian cysts, including chocolate cyst; asthenospermia; maturation arrest; hypospermia; Sertoli Cell-syndrome; gonadotropin deficiency, including that arising from expanded pituitary tumors that compromises LH and FSH secretion, from surgical damage, or from external trauma to the cranium with damage to the portal blood supply; anabolic steroids; nicotine; illicit drugs, such as marijuana, heroine, and cocaine; alkaline agents, procarbozine, some halogenated hydrocarbons used in pesticides, and frequent exposure to large amount of ethanol; pelvic inflammatory disease (PID); epididymitis; exposure to toxic substances or hazards, such as lead, cadmium, mercury, ethylene oxide, vinyl chloride, radioactivity, and x-rays; prescription drugs for ulcers or psoriasis; DES exposure in utero; exposure of the male genitals to elevated temperatures—hot baths, whirlpools, steam rooms; hernia repair; undescended testicles; vitamin deficiency; prior abortions; and cyclophosphamide.

KGF-2 polynucleotides, polypeptides, variants, antibodies, agonists and/or antagonists can be used to treat or prevent primary or secondary infertility. KGF-2 can also be used to treat temporary or permanent infertility.

KGF-2 polynucleotides, polypeptides, variants, antibodies, agonists and/or antagonists can be administered along with other fertility promoting substances, such as clomiphenne citrate (clomid, serophene), progesterone, and/or 17β-estradiol.

KGF-2 can be used to treat infertility in females during natural conception or during assisted reproduction. Assisted reproduction techniques include in vitro fertilization (IVF), embryo transfer (ET), gamete intrafallopian transfer (GIFT), zygote intrafallopian transfer (ZIFT), IVF with donor eggs, donor sperm, and donor embryos, and micromanipulation of eggs and embryos. In IVF-ET, an oocyte is surgically removed, fertilized in vitro, and placed in the uterus or Fallopian tube of the same woman. In oocyte donation, the oocyte is recovered from a donor and after IVF it is transferred to an infertile recipient as in ET. This procedure requires synchronization between the donor and the recipient, which is generally achieved by administering steroid hormones to the recipient. In regular IVF-ET, the treatments given to induce multiple follicle growth often lead to insufficient luteal function. Therefore, implantation may not take place without supplemental treatment with molecules such as KGF-2.

One preferred method of delivery of KGF-2 for treating or preventing infertility in a female is through a sustained-release system via a vaginal ring, as disclosed in U.S. Pat. No. 5,869,081, the disclosure of which is herein incorporated by reference.

Polysiloxane carriers have been used for delivery of progesterone as a contraceptive for lactating women (Croxatto et al., 1991, in "Female Contraception and Male Fertility Regulation. Advances in Gynecological and Obstetric Research Series", Reinnebaum et al., eds.) and for delivery of estradiol in postmenopausal women (Stumpf et al. (1982), J. Clin. Endocrinol. Metab., 58:208). Simon et al. (1986), Fertility and Sterility, 46:619 disclose 17β-estradiol and/or progesterone-impregnated polysiloxane vaginal rings and cylinders for endometrial priming in functionally agonadal women. The ring and cylinder system was used to achieve serum levels of 17β-estradiol and progesterone within the normal range for an entire menstrual cycle. U.S. Pat. No. 4,816,257 discloses the use of polysiloxane rings containing 17β-estradiol or 17β-estradiol and progesterone to mimic normal steroid hormone levels in a functionally agonadal human female.

The present invention provides a method of administering KGF-2 for the establishment and maintenance of pregnancy. The method of the invention comprises inserting a carrier containing KGF-2 into the vagina of the female and maintaining the carrier intravaginally for about 1–28 days. In a preferred embodiment, the carrier is a polysiloxane ring having an in vitro release rate from about 1 μg/day to 1000 mg/day, although this amount is subject to therapeutic discretion.

Further, the method may be used to treat or prevent infertility in a female undergoing assisted reproduction. The method comprises inserting a carrier containing KGF-2 into the vagina of a female and maintaining the carrier intravaginally until about the seventh to twelfth week of pregnancy. In a preferred embodiment, the carrier is a polysiloxane ring having an in vitro release rate of from about 1 μg/day to 1000 mg/day KGF-2.

The present invention relates to methods for administering KGF-2 to women with functioning ovaries and to functionally agonadal women. Women with functioning ovaries who are infertile or cannot conceive because their partner is infertile can become pregnant through assisted reproduction techniques. However, the hormonal treatments used to induce multiple follicle growth cause insufficient production of progesterone by the corpus luteum. Thus, initiation and maintenence of implantation is impaired. Functionally agonadal women are infertile as a result of undeveloped or improperly developed ovaries, surgical removal of ovaries, or other ovarian failure or dysfunction. Assisted reproduction techniques such as OD, IVF and ET allow functionally agonadal women to become pregnant. However, hormone supplementation is necessary in assisted reproduction techniques in order to prepare the endometrium for the establishment and continuation of pregnancy.

Thus, in accordance with the present invention, KGF-2 may be used to treat or prevent infertility through, inter alia, promotion of embryo implantation. The present invention provides a method of administering KGF-2 for the establishment and maintenance of pregnancy by assisted reproduction techniques in a normogonadal and in a functionally agonadal human female. The method comprises inserting a KGF-2 containing carrier into the vagina of a normogonadal or a functionally agonadal human female and maintaining the carrier intravaginally for at least about twenty-eight days.

The present invention also provides a method of hormone replacement therapy for a human female undergoing assisted reproduction. The method comprises inserting a KGF-2 containing carrier into the vagina of a human female undergoing assisted reproduction and maintaining the carrier intravaginally until about the seventh to twelfth week of pregnancy.

The physiologically acceptable KGF-2 containing carriers useful in the method of the present invention are preferably ring-shaped solid carriers made of silicone rubber, also referred to herein as polysiloxane, or other suitable material. Delivery of steroid hormones by polysiloxane vagina rings is known in the art. The rate of passage of KGF-2 from a polysiloxane ring is dependent upon factors including the surface area of the ring. Accordingly, the amount of KGF-2 in the ring is conveniently described in terms of the in vitro release rate of KGF-2 from the ring. In vitro release rates are routinely used in the art to characterize hormone-containing polysiloxane rings. KGF-2 containing polysiloxane rings having in vitro release rates of from about 0.001 to about 1000 mg of KGF-2 per day are contemplated for use in the present method. In a preferred embodiment the polysiloxane rings have an in vitro release rate of from about 0.01 to about 100 mg of KGF-2 per day. In a most preferred embodiment the polysiloxane rings have an in vitro release rate of about 0.1 to about 10 mg of KGF-2 per day.

The KGF-2 containing polysiloxane carriers are administered by insertion into the vagina. The rings are inserted into the vagina and positioned around the cervix. The ring can be inserted and removed by the female subject in a manner similar to that of the commonly used diaphragm, thus providing yet another advantage of the present invention.

The KGF-2 containing carrier may be administered about two to seven days, and preferably three days, before embryo transfer, and may be supplemented by other hormone administration, for example oral administration of estradiol-17β or progesterone. In a preferred embodiment the carrier is a ring and is inserted three days before embryo transfer. The carrier is removed and replaced by another carrier after about twenty-eight days. If pregnancy occurs, the carrier allows sufficient KGF-2 for the maintenance of pregnancy until the luteal-placental shift, at which time administration may be discontinued. In a preferred embodiment, the ring is maintained continuously in the vagina, and administration is discontinued at about the twelfth week of pregnancy.

Injuries, Occupational Diseases

KGF-2 has been shown to stimulate the proliferation of a variety of tissues. Therefore, KGF-2 polynucleotides, polypeptides, agonists and/or antagonists can be used to treat injuries or occupational diseases.

Examples of injuries, occupational diseases and poisoning which can be treated or detected include occupational diseases such as agricultural worker's diseases which include farmer's lung and silo filler's disease, bird fancier's lung, occupational dermatitis, high pressure nervous syndrome, inert gas narcosis, laboratory infection, pneumoconiosis such as asbestosis, berylliosis, byssinosis, Caplan's Syndrome, siderosis, silicosis such as anthracosilicosis and silicotuberculosis, poisoning such as alcoholic intoxication which include alcoholism such as alcoholic cardiomyopathy, fetal alcohol syndrome, alcoholic fatty liver, alcoholic hepatitis, alcoholic liver cirrhosis, alcoholic psychoses such as alcoholic amnestic disorder, alcoholic withdrawal delirium, argyria, bites and stings such as arachnidism, insect bites and stings, snake bites, tick toxicoses such as tick paralysis, cadmium poisoning, carbon tetrachloride poisoning, drug toxicity such as drug-induced akathisia, drug eruptions such as toxic epidermal necrolysis, erythema nodosum and serum sickness, drug-induced dyskinesia and neuroleptic malignant syndrome, ergotism, fluoride poisoning, food poisoning such as botulism, favism, mushroom poisoning, salmonella food poisoning and staphylococcal food poisoning, gas poisoning such as carbon monoxide poisoning, inert gas narcosis, toxic hepatitis, lead poisoning, mercury poisoning, mycotoxicosis such as ergotism and mushroom poisoning, overdose, plant poisoning such as ergotism, favism, lathyrism, and milk sickness, substance-induced psychoses, wounds and injuries such as abdominal injuries which includes traumatic diaphragmatic hernia, splenic rupture such as splenosis, stomach rupture, traumatic amputation, arm injuries such as forearm injuries which includes radius fractures and ulna fractures, humeral fractures, shoulder dislocation, shoulder fractures, tennis elbow and wrist injuries, asphyxia, athletic injuries, barotrauma such as blast injuries and decompression sickness, birth injuries such as obstetric paralysis, bites and stings such as human bites, burns such as chemical burns, electric burns, inhalation burns such as smoke inhalation injury, eye burns and sunburn, contusions, dislocations such as hip and shoulder dislocations, drowning such as near drowning, electric burns and lightning injuries, esophageal perforation, extravasation of diagnostic and therapeutic materials, foreign bodies such as bezoars, eye foreign bodies, foreign-body migration, foreign-body reaction such as foreign-body granuloma, fractures such as femoral fractures such as hip fractures which includes femoral neck fractures, closed fractures, comminuted fractures, malunited fractures, open fractures, spontaneous fractures, stress fractures, ununited fractures such as pseudarthrosis, humeral fractures, radius fractures such as Colles' Fractures, rib fractures, shoulder fractures, skull fractures such as jaw fractures such as mandibular and maxillary fractures, orbital fractures and zygomatic fractures, spinal fractures, tibial fractures, ulna fractures such as Monteggia's Fractures, frostbite such as chilblains, hand injuries such as finger injuries, head injuries such as brain injuries which include brain concussion, cerebrospinal otorrhea, cerebrospinal rhinorrhea, closed head injuries, maxillofacial injuries such as facial injuries which include eye injuries such as eye burns, eye foreign bodies and penetrating eye injuries,jaw fractures such as mandibular and maxillary fractures, mandibular injuries such as mandibular fractures, and zygomatic fractures, maxillary fractures, pneumocephalus, skull fractures such as jaw fractures which includes mandibular and maxillary fractures, orbital fractures and zygomatic fractures, heat exhaustion such as sunstroke, leg injuries such as ankle injuries, femoral fractures such as hip fractures which include femoral neck fractures, foot injuries, hip dislocation, knee injuries and tibial fractures, motion sickness such as space motion sickness, multiple trauma, radiation injuries such as radiation-induced abnormalities, radiation-induced leukemia, radiation-induced neoplasms, osteoradionecrosis, experimental radiation injuries, radiation pneumonitis and radiodermatitis, retropneumoperitoneum, rupture such as aortic rupture, splenic rupture such as splenosis, stomach rupture and uterine rupture such as uterine perforation, self mutilation, traumatic shock such as crush syndrome, soft tissue injuries, spinal cord injuries such as spinal cord compression, spinal injuries such as spinal fractures and whiplash injuries, sprains and strains such as repetition strain injury, tendon injuries, thoracic injuries such as flail chest, heart injuries and rib fractures, tooth injuries such as tooth fractures which include cracked tooth syndrome, tooth luxation, tympanic membrane perforation, wound infection, nonpenetrating wounds such as brain concussion and closed head injuries and penetrating wounds such as penetrating eye injuries, gunshot wounds and stab wounds such as needlestick injuries.

Hemic and Lymphatic Diseases

KGF-2 polynucleotides, polypeptides, agonists, and/or antagonists can be used to treat and/or detect hemic and/or lymphatic diseases.

Examples of Hemic and Lymphatic Diseases which can be treated or detected include aplastic anemia (such as Fanconia's Anemia), hemolytic anemia (such as autoimmune hemolytic anemia and congenital hemolytic anemia including congenital dyserythropoietic anemia, congenital nonspherocytic hemolytic anemia, sickle cell anemia, such as hemoglobin SC disease and sickle cell trait; hereditary elliptocytosis and glucosephosphate dehydrogenase deficiency, such as favism, hemoglobin C disease, hereditary spherocytosis, thalassemia, such as alpha-thalassemia including hydrops fetalis, and beta-thalassemia, favism, hemoglobinuria, such as paroxysmal heboglobinuria, and hemolytic-uremic syndrome), hypochromic anemia (such as iron-deficiency anemia), macrocytic anemia (such as megaloblastic anemia, including pernicious anemia), myelophthisic anemia, neonatal anemia (such as fetofatal transfusion and fetomaternal transfusion), refractory anemia (such as refractory anemia with excess of blasts), sideroblastic anemia, pure red-cell aplasia, fetal erythroblastosis (such as hydrops fetalis and kernicterus), Rh Isimmunization, abetalipoproteinemia, agammaglobulinemia, dysgamma-globulinemia (such as IgA Deficiency and IgG Deficiency), hypergammaglobulinemia (such as benign monoclonal gammopathies), hyperproteinemia, paraproteinemias (such as amyloidosis, including amyloid neuropathies and cerebral amyloid angiopathy, cryoglobulinemia, heavy chain disease, such as immunoproliferative small intestinal disease, multiple myeloma, POEMS Syndrome, Waldenstrom's Macroglobulinemia), Protein S Deficiency.

Further examples of hemic and lymphatic diseases which can be treated or detected include bone marrow diseases such as aplastic anemia, myelodysplastic syndromes (including refractory anemia such as refractory anemia with excess of blasts, sideroblastic anemia, paroxysmal hemoglobinuria, and myeloid leukemia), myeloproliferative disorders (including myelophthisic anemia, acute erythroblastic leukemia, leukemoid reaction, myelofibrosis, myeloid metaplasia, polycythemia vera, hemorrhagic thrombocythemia, and thrombocytosis), intravascular erythrocyte aggregation, hemoglobinopathies such as sickle cell anemia (including hemoglobin SC Disease and Sickle Cell Trait), Hemoglobin SC Disease, Thalassemia (including alpha-thalassemia such as hydrops fetalis, and beta thalassemia), hemorrhagic diathesis such as abrinogenemia, Christmas Disease, disseminated intravascular coagulation, Factor VII Deficiency, Factor XI Deficiency, Factor XII Deficiency, Factor XIII Deficiency, hemophilia, hypoprothrombinemias (including Factor V Deficiency and Factor X Deficiency), Schwartzman Phenomenon, Bernard-Soulier Syndrome, hemolytic-uremic syndrome, platelet storage pool deficiency, thrombasthenia, hemorrhagic thrombocytopenia (including thrombocytopenic purpura such as idiopathic thrombocytopenic purpura, thrombotic thrombocytopenic purpura, and Wiskott-Aldrich Syndrome), hyperglobulinemic purpura, Schoenlich-Henoch Purpura, thrombocytopenic purpura (idiopathic thrombocytopenic purpura), thrombotic thrombocytopenic purpura, Wiskott-Aldrich Syndrome, hereditary hemorrhagic telangiectasia, vitamin K Deficiency (including hemorrhagic disease of newborn), and von Willebrand's Disease, leukocyte disorders such as eosinophilia (including angiolymphoid hyperplasia with eosinophilia, eosinophilia-myalgia syndrome, eosinophilic granuloma, and hypereosinophilic syndrome such as pulmonary eosinophilia), infectious mononucleosis, leukocytosis (including leukamoid reaction and lymphocytosis), leukopenia (including agranulocytosis such as neutropenia, and lymphopenia such as idiopathic CD4-Positive T-Lymphopenia), Pelger-Huet Anomaly, phagocyte bactericidal dysfunction (including Chediak-Higashi Syndrome, Chronic Granulomatous Disease, Job's Syndrome), methemoglobinemia, pancytopenia, polycythemia, hematologic, preleukemia, and sulfhemoglobinemia.

Additional examples of hemic and lymphatic diseases which can be treated or detected include lymphatic diseases such as lymphadenitis (including cat-scratch disease and mesenteric lymphadenitis), lymphangiectasis, lymphangitis, lymphedema (including elephantiasis and filarial elephantiasis), lymphocele, lymphoproliferative disorders (including agammaglobulinemia, amyloidosis such as amyloid neuropathies and cerebral amyloid angiopathy, giant lymph node hyperplasia, heavy chain disease such as immunoproliferative small intestinal disease, immunoblastic lymphadenopathy, infectious mononucleosis, hairy cell leukemia, lymphocytic leukemia, myeloid leukemia (including acute nonlymphocytic leukemia and acute myelocytic leukemia), lymphangiomyoma (including lymphangiomyomatosis), and lymphoma (including Hodgkin's Disease, Non-Hodgkin's Lymphoma such as B-Cell Lymphoma including Burkitt's Lymphoma, AIDS-Related Lymphoma, mucosa-associated lymphoid tissue lymphoma, and small-cell lymphoma, diffuse lymphoma including diffuse large-cell lymphoma, immunoblastic large-cell lymphoma, lymphoblastic lymphoma, diffuse mixed-cell lymphoma, small lymphocytic lymphoma, and small noncleaved-cell lymphoma, follicular lymphoma including follicular large-cell lymphoma, follicular mixed-cell lymphoma, and follicular small cleaved-cell lymphoma, high-grade lymphoma including immunoblastic large-cell lymphoma, lymphoblastic lymphoma, and small noncleaved-cell lymphoma such as Burkitt's Lymphoma, intermediate-grade lymphoma including diffuse large-cell lymphoma, follicular large-cell lymphoma, diffuse mixed-cell lymphoma, and diffuse small cleaved-cell lymphoma, large-cell lymphoma including diffuse large-cell lymphoma, follicular large-cell lymphoma, immunoblastic large-cell lymphoma, Ki-1 large-cell lymphoma, and immunoblastic large-cell lymphoma, low-grade lymphoma including follicular mixed-cell lymphoma, mucosa-associated lymphoid tissue, follicular small cleaved-cell lymphoma, and small lymphocytic lymphoma, mixed-cell lymphoma including diffuse mixed-cell lymphoma and follicular mixed-cell lymphoma, small-cell lymphoma including diffuse small-cleaved cell lymphoma, follicular small cleaved-cell lymphoma, small lymphocytic lymphoma, and small noncleaved-cell lymphoma, t-cell lymphoma including lymphoblastic lymphoma, cutaneous T-cell lymphoma such as Ki-1 large-cell lymphoma, fungoides mycosis, and Sezary Syndrome, and peripheral T-cell lymphoma, undifferentiated lymphoma including diffuse large-cell lymphoma, and small noncleaved-cell lymphoma such as Burkitt's Lymphoma, lymphomatoid granulomatosis), Marek's Disease, sarcoidosis (including pulmonary sarcoidosis and uveoparotid Fever), tumor lysis syndrome, mucocutaneous lymph node syndrome, reticuloendotheliosis (including Gaucher's Disease, histiocytosis such as malignant histiocytic disorders including malignant histiocytosis, acute monocytic leukemia, large-cell lymphoma such as Ki-1 Large-Cell Lymphoma, Langerhans-Cell Histiocytosis such as Eosinophilic Granuloma, Hand-Scheller-Christian Syndrome, and Letterer-Siwe Disease, Non-Langerhans-Cell Histiocytosis such as Sinus Histiocytosis, Niemann-Pick Disease, Sea-Blue Histiocyte Syndrome, and Juvenile Xanthogranuloma, Mast-Cell Sarcoma), Splenic Diseases (including Hypersplenism, Myeloid Metaplasia, Splenic Infarction, Splenic Neoplasms, Splenic Rupture such as Splenosis, Splenomegaly, and Splenic Tuberculosis), Thymus Hyperplasia, Thymus Neoplasms, Lymph Node Tuberculosis such as King's Evil.

Neonatal Diseases and Abnormalities

KGF-2 polynucleotides, polypeptides, agonists and/or antagonists can be used to treat, prevent, and/or detect neonatal diseases and/or abnormalities.

Examples of neonatal diseases and abnormalities which can be treated or detected include drug-induced abnormalities, multiple abnormalities including Alagille Syndrome, Angelman Syndrome, basal cell nevus syndrome, Beckwith-Widemann Syndrome, Bloom Syndrome, Bonnevie-Ulrich Syndrome, Cockayne Syndrome, Cri-du-Chat Syndrome, De Lange's Syndrome, Down Syndrome, Ectodermal Dysplasia such as Ellis-Van Creveld Syndrome and Focal Dermal Hypoplasia, Gardner Syndrome, holoprosencephaly, incontinentia pigmenti, Laurence-Moon Biedl Syndrome, Marfan Syndrome, Nail-Patella Syndrome, Oculocerebrorenal Syndrome, Orofaciodigital Syndromes, Prader-Willi Syndrome, Proteus Syndrome, Prune Belly Syndrome, Congenital Rubella Syndrome, Rubenstein-Taybi Syndrome, Short Rib-Polydactyly Syndrome, Waardenburg's Syndrome, Wolfram Syndrome, Zelweger Syndrome, Radiation-Induced Abnormalities, Chromosome abnormalities including Angelman Syndrome, Beckwith-Wiedemann, Cri-du-Chat Syndrome, Down Syndrome, holoprosencephaly, Prader-Willi Syndrome, sex chromosome abnormalities such as Bonnevie-Ulrich Syndrome, Ectodermal Dysplasia including Focal Dermal Hypoplasia, Fragile X Syndrome, 46,XY Gonadal Dysgenesis, Mixed Gonadal Dysgenesis, Kallman Syndrome, Klinefelter's Syndrome, Oculocerebrorenal Syndrome, Orofaciodigital Syndromes, Turner's Syndrome, and XYY Karyotype, and digestive system abnormalities.

Respiratory Diseases

KGF-2 has been shown to stimulate proliferation of cells of the respiratory tract. Thus, KGF-2 polynucleotides, polypeptides, agonists and/or antagonists can be used to treat and/or detect respiratory diseases.

Examples of respiratory tract diseases which can be treated or detected include bronchial diseases, such as asthma (including exercise-induced asthma and status asthmaticus) bronchial fistula, bronchial hyperreactivity, bronchial neoplasms, bronchial spasm, bronchiectasis, bronchitis (including bronchiolitis, bronchiolitis obliterans, organizing pneumonia, viral bronchiolitis, bronchogenic cyst, bronchopneumonia, tracheobronchomegaly), ciliary motility disorders such as Kartagener's Syndrome, laryngeal diseases (such as laryngeal granuloma, laryngeal edema, laryngeal neoplasms, laryngeal perichondritis, laryngismus, laryngitis such as croup, laryngostenosis, laryngeal tuberculosis, vocal cord paralysis, voice disorders such as aphonia and hoarseness), lung diseases, such as atelectasis which includes middle lobe syndrome, bronchopulomonary dysplasia, congenital cystic adenomatoid malformation of lung, cystic fibrosis, pulmonary plasma cell granuloma, hemoptysis, lung abscess, fungal lung diseases such as allergic bronchopulmonary aspergillosis and *Pneumocystis carinii* pneumonia, interstitial lung diseases such as extrinsic allergic alveolitis such as Bird Fancier's Lung, Farmer's Lung, Goodpasture's Syndrome, langerhans-cell histiocytosis, pneumoconiosis such as asbestosis, berylliosis, byssinosis, Caplan's Syndrome, siderosis, silicosis such as anthracosilicosis and silicotuberculosis, pulmonary fibrosis, radiation pneumonitis, pulmonary sarcoidosis, Wegener's Granulomatosis), obstructive lung diseases, viral bronchiolitis, pulmonary emphysema, parasitic lung diseases such as pulmonary echinococcosis, lung neoplasms such as bronchogenic carcinoma, pulmonary coin lesion and Pancoast's Syndrome, Meconium Aspiration, Pneumonia (such as bronchopneumonia, pleuropneumonia, aspiration pneumonia such as lipid pneumonia, bacterial pneumonia such as lobar pneumonia, Mycoplasma Pneumonia, Rickettsial Pneumonia and Staphylococcal Pneumonia, *Pneumocystis carinii* pneumonia, viral pneumonia), pulmonary alveolar proteinosis, pulmonary edema, pulmonary embolism, pulmonary eosinophilia, pulmonary veno-occlusive disease, respiratory distress syndrome such as hyaline membrane disease, adult respiratory distress syndrome, Scimitar Syndrome, Silo Filler's Disease, Pulmonary tuberculosis such as silicotuberculosis; nose diseases, such as choanal atresia, epistaxis, lethal midline granuloma, nasal obstruction, nasal polyps, acquired nose deformities, nose neoplasms such as nasal polyps, paranasal sinus neoplasms such as maxillary sinus neoplasms, paranasal sinus neoplasms such as maxillary sinus neoplasms, sinusitis such as ethmoid sinusitis, frontal sinusitis, maxillary sinusitis and sphenoid sinusitis, rhinitis such as hay fever, perennial allergic rhinitis, atrophic rhinitis and vasomotor rhinitis, rhinoscleroma).

Respiratory disease which may be treated and/or diagnosed also include pleural diseases, such as chylothorax, pleural empyema (such as tuberculous empyema), hemopneumothorax, hemothorax, hydropneumothorax, hydrothorax, pleural effusion such as malignant pleural effusion, pleural neoplasms such as malignant pleural effusion, pleurisy such as pleuropneumonia, pneumothorax, pleural tuberculosis such as tuberculous empyema, respiration disorders such as apnea such as sleep apnea syndromes which include Pickwickian Syndrome, Cheyne-Stokes Respiration, cough, dyspnea such as paroxysmal dyspnea, hoarseness, hyperventilation such as respiratory alkalosis, laryngismus, meconium aspiration, mouth breathing, respiratory distress syndrome such as hyaline membrane disease, adult respiratory distress syndrome, respiratory insufficiency such as respiratory acidosis, airway obstruction such as nasal obstruction, laryngeal granuloma, hantavirus pulmonary syndrome, hypoventilation, intrinsic positive-pressure respiration and respiratory paralysis, respiratory hypersensitivity such as extrinsic allergic alveolitis such as Bird Fancier's Lung and Farmer's Lung, allergic bronchopulomary aspergillosis, asthma such as exercise-induced asthma and status asthmaticus, hay fever, perennial allergic rhinitis, respiratory system abnormalities such as bronchogenic cyst, bronchopulmonary sequestration, choanal atresia, congenital cystic adenomatoid malformation of lung, Kartagener's Syndrome, Scimitar Syndrome, tracheobronchomegaly, respiratory tract fistula such as bronchial fistula which includes tracheoesophageal fistula), respiratory tract infections (such as bronchitis which includes bronchiolitis such as viral bronchiolitis, common cold, pleural empyema such as tuberculous empyema, influenza, laryngitis such as epiglottitis, legionellosis such as Legionnaries' Disease, Lung Abscess, Pleurisy such as Pleuropneumonia, Pneumonia such as Bronchopneumonia, Pleuropneumonia, Aspiration Pneumonia such as Lipid Pneumonia, Bacterial Pneumonia such as Lobar Pneumonia, Mycoplasma Pneumonia, Rickettsial Pneumonia and Staphylococcal Pneumonia, Pneumocystis carinii Pneumonia, Viral Pneumonia, Rhinitis, Rhinoscleroma, Sinusitis such as Ethmoid Sinusitis, Frontal Sinusitis, Maxillary Sinusitis and Sphenoid Sinusitis, Tonsillitis such as Peritonsillar Abscess, Tracheitis, Laryngeal Tuberculosis, Pleural Tuberculosis such as Tuberculous Empyema, Pulmonary Tuberculosis such as Silicotuberculosis, Whooping Cough, Respiratory Tract Neoplasms such as Bronchial Neoplasms, Laryngeal Neoplasms, Lung Neoplasms such as Bronchogenic Carcinoma, Pulmonary Coin Lesion and Pancoast's Syndrome, Nose Neoplasms such as Nasal Polyps, Paranasal Sinus Neoplasms such as Maxillary Sinus Neoplasms, Pleural Neoplasms such as Malignant Pleural Effusion, Tracheal Neoplasms, Tracheal Diseases such as Tracheal Neoplasms, Tracheal Stenosis, Tracheitis, Tracheobronchomegaly and Tracheoesophageal Fistula.

Examples of Otorhinolaryngologic Diseases which can be treated or detected include Ciliary Motility Disorders such as Kartagener's Syndrome, Ear Diseases such as Middle Ear Cholesteatoma, Acquired Ear Deformities, Ear Neoplasms, Earache, Hearing Disorders such as Deafness which include Sudden Deafness, Partial Hearing Loss such as Bilateral Hearing Loss, Conductive Hearing Loss, Functional Hearing Loss, High-Frequency Hearing Loss, Sensorineural Hearing Loss such as Central Hearing Loss, Noise-Induced Hearing Loss and Presbycusis, Loudness Recruitment, Tinnitus, Herpes Zoster Oticus, Labyrinth Diseases such as Cochlear Diseases, Endolymphatic Hydrops such as Meniere's Disease, Labyrinthitis, Vestibular Diseases such as Motion Sickness which includes Space Motion Sickness, Vertigo, Otitis such as Otitis Externa, Otitis Media such as Mastoiditis, Otitis Media with Effusion and Suppurative Ottitis Media, Otosclerosis, Retrocochlear Diseases such as Acoustic Nerve Diseases which include Acoustic Neuroma such as Neurofibromatosis 2, Central Auditory Diseases such as Auditory Perceptual Disorders and Central Hearing Loss, Tympanic Membrane Perforation), Laryngeal Diseases such as Laryngeal Granuloma, Laryngeal Edema, Laryngeal Neoplasms, Laryngeal Perichondritis, Laryngismus, Laryngitis such as Croup, Laryngostenosis, Laryngeal Tuberculosis, Vocal Cord Paralysis, Voice Disorders such as Aphonia and Hoarseness, Nose Diseases (such as Choanal Atresia, Epistaxis, Lethal Midline Granuloma, Nasal Obstruction, Nasal Polyps, Acquired Nose Deformities, Nose Neoplasms such as Nasal Polyps, Paranasal Sinus Neoplasms such as Maxillary Sinus Neoplasms, Paranasal Sinus Diseases such as Paranasal Sinus Neoplams which include Maxillary Sinus Neoplasms, Sinusitis such as Ethmoid Sinusitis, Frontal Sinusitis, Maxillary Sinusitis and Sphenoid Sinusitis, Rhinitis such as Hay Fever, Perennial Allergic Rhinitis, Atrophic Rhinitis and Vasomotor Rhinitis, Rhinoscleroma), otorhinolaryngologic neoplasms such as ear neoplasms, laryngeal neoplasms, acoustic neuroma such as Neurofibromatosis 2, nose neoplasms such as nasal polyps, paranasal sinus neoplasms such as maxillary sinus neoplasms, pharyngeal neoplasms such as hypopharyngeal neoplasms, nasopharyngeal neoplasms, oropharyngeal neoplasms such as tonsillar neoplasms, pharyngeal neoplasms such as hypopharyngeal neoplasms, nasopharyngeal neoplasms, oropharyngeal neoplasms which includes tonsillar neoplasms, pharyngitis, retropharyngeal abscess, tonsillitis, and velopharyngeal insufficiency.

Neurologic Diseases

KGF-2 polynucleotides, polypeptides, agonists and/or antagonists may be used to treat and/or detect neurologic diseases.

Examples of neurologic diseases which can be treated or detected include brain diseases (such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis, cerebrovascular disorders (such as carotid artery diseases which include carotid artery thrombosis, carotid stenosis and Moyamoya Disease, cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache, migraine, dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, Hallervorden-Spatz Syndrome, hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, cerebral malaria, meningitis such as arachnoiditis, aseptic meningtitis such as viral meningitis which includes lymphocytic choriomeningitis. Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie) cerebral toxoplasmosis, central nervous system neoplasms such as brain neoplasms that include cerebellear neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta, hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoci onus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Homer's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Homer's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, Diabetic neuropathies such as diabetic foot, nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Metabolic and Endocrine Diseases

KGF-2 polynucleotides, polypeptides, agonists and/or antagonists may be used to treat and/or diagnose metabolic or endocrine diseases.

Examples of nutritional and metabolic diseases which can be treated or detected include achlorhydria, acid-base imbalance, acidosis (including lactic, renal tubular, or respiratory), diabetic ketoacidosis, ketosis, alkalosis, respiratory alkalosis, calcium metabolism sisorders, calcinosis, calciphylaxis, CREST syndrome, nephrocalcinosis, pathologic decalcification, hypercalcemia, hypocalcemia, tetany, osteomalacia, pseudohypoparathyroidism, Rickets, diabetes insipidus, nephrogenic diabetes insipidus, Wolfram Syndrome, diabetes mellitus (including experimental and insulin-dependent, lipoatrophic, non-insulin-dependent), diabetic angiopathies, diabetic foot, gestational diabetes, fetal macrosomia, glucose intolerance, glycosuria, renal glycosuria, hyperglycemia, hyperlipidemia, hypercholesterolemia, hyperlipoproteinemia, hypertriglyceridemia, hyperprolactinemia, hypervitaminosis A, hypoglycemia, insulin coma, malabsorption syndromes (including Blind Loop Syndrome, Celiac Disease, lactose intolerance, intestinal lipodystrophy, Tropical Sprue), inborn errors in metabolism (including inborn errors in amino acid metabolism, ocular albinism, oculocutaneous albinism, piebaldism), alkaptonuria, ochronosis, renal aminoaciduria, cystinuria, Hartnup Disease, homocystinuria, Maple Syrup Urine Disease, multiple carboxylase deficiency, phenylketonuria, maternal phenylketonuria, amyloidosis, amyloid neuropathies, cerebral amyloid angiopathy, inborn errors in carbohydrate metabolism such as inborn errors in fructose metabolism (Fructose-1,6-Diphosphatase Deficiency, fructose intolerance), galactosemia, glucose intolerance, glycogen storage disease (Types I, II, III, IV, V, VI, VII, VIII), hyperoxaluria, primary hyperoxalura, mannosidosis, mucopolysaccharidoses (I, II, III, IV, VI, VII), multiple carboxylase deficiency, inborn errors in pyruvate metabolism, Leigh Disease, pyruvate carboxylase deficiency, pyruvate dehydrogenase complex deficiency, glucosephosphate dehadrogenase deficiency, hereditary hyperbilirubinemia, Crigler-Najjar Syndrome, Gilbert's Disease, chronic idiopathic jaundice, inborn errors in lipid metabolism such as hyperlipoproteinemia, familial hypercholestrolemia, familial combined hyperlipidemia, hypercholesterolemia (familial, Type III, IV, V), familial lipoprotein lipase deficiency, hypolipoproteinemia (abetalipoproteinemia, hypobetalipoproteinemia, lecithin acyltransferase deficiency, Tangier Disease), lipoidosis (cholesterol ester storage disease, lipoidproteinosis, neuronal ceroid-lipofuscinosis, Refsum's Disease, Sjogren-Larsson Syndrome, sphingolipidoses (adrenoleukodystrophy, Fabry's Disease, ganglisidoses, Sandhoff Disease, Tay-Sachs Disease, Gaucher's Disease, globoid cell leukodystrophy, metachromatic leukodystrophy, Niemann-Pick Disease, Sea-Blue Histiocyte Syndrome, Wolman Disease, mitochrondrial myopathies, mitochorondrial encephalomyopathies, MELAS Syndrome, MERRF Syndrome, external chronic progressive ophthalmoplegia, lysosomal storage diseases such as cholestrol ester storage disease, mannosidosis, mucolipidosis, fucosidosis, muchopolysaccharidosis (I, II, III, IV, VI, and VII), inborn errors in metal metabolism including hemochromatosis, hepatolenticular degeneration, hypophosphatasia, familial hypophosphatemia, kinky hair syndrome, familial periodic paralysis, and pseudohypoparathyroidism, mucolipidosis, fucosidosis, porphyria, (erythroheatic, erythropoietic, hepatic, acute intermittent, cutanea tarda), inborn errors in purine-pyrimidine metabolism such as gout, gouty arthritis, and Lesch-Nyhan Syndrome, inborn errors in renal tubular transport such as renal tubular acidosis, renal aminoaciduria, cystinuria, hartnup disease, cystinosis, Fanconi Syndrome, renal gylycosuria, familial hypophosphatemia, oculocerbrorenal syndrome, and pseudohypoaldosteronism, phosphorus metabolism disorders, hypophosphatemia, protein-losing enteropathies, intestinal lymphangiectasis, water-electrolyte imbalance (dehydration, hypercalcemia, hyperkalemia, hypernatremia, hypocalcemia, hyponatremia, inappropriate adh syndrome, water intoxication), xanthomatosis, Wolman Disease, Child nutrition disorders such as infant nutrition disorders, deficiency diseases such as avitaminosis, ascorbic acid deficiency, scurvy, vitamin A deficiency, vitamin B deficiency, choline deficiency, folic acid deficiency, pellagra, pyridoxine deficiency, riboflavin deficiency, thiamine deficiency, beriberi, Wernicke's Encephalopathy, vitamin $B_{12}$ deficiency (anemia, pernicious), vitamin D deficiency, (osteomalacia, steatitis), vitamin E deficiency (steatitis), vitamin K deficiency, magnesium deficiency, potassium deficiency, protein deficiency (protein-energy malnutrition, kwashiorkor), swayback, obesity in diabetes, morbid obesity, Pickwickian Syndrome, Prader-Willi Syndrome, and starvation.

Examples of endocrine diseases which can be treated or detected include adrenal gland diseases (cortex diseases, nortex neoplasms), adrenal gland hyperfunction (Cushing's Syndrome, hyperaldosteronism, Bartter's Disease), adrenal gland hypofunction (Addison's Disease, adrenoleukodystrophy, hypoaldosteronism), adrenal gland neoplasms, adrenal cortex neoplasms, congenital adrenal hyperplasia, Waterhouse-Friderichsen Syndrome, breast neoplasms, male breast neoplasms, fibrocystic disease of the breast, gynecomastia, lactation disorders such as Chiari-Frommel Syndrome and galactorrhea, mastitis, Bowie mastitis, diabetes mellitus (experimental, insulin-dependent, Wolfram Syndrome, lipoatrophic, and non-insulin dependent), diabetic angiopathies, diabetic foot, diabetic retinopathy, diabetic coma, hyperglycemic hyperosmolar nonketotic coma, diabetic ketoacidosis, diabetic nephropathies and that associated with diabetic foot, obesity in diabetes, gestational diabetes, fetal macrosomia, dwarfism (Cockayne Syndrome, pituitary, thanatophoric dysplasia), endocrine gland neoplasms such as adrenal cortex neoplasma, multiple endocrine neoplasia (types 1, 2a, 2b), neoplastic endocrine-like syndromes, ACTH syndrome (ectopic), Zollinger-Ellison Syndrome, Ovarian neoplasms, Meig's Syndrome, parathyroid neoplasms, pituitary neoplasms, Nelson Syndrome, Testicular Neoplasms, thymus neoplasms, thyroid neoplasms, thyroid nodule, gonadal disorders such as adrenal hyperplasia (congenital), feminization, testicular feminization, hyperandrogenism, hypogonadism, eunuchism, Kallmann Syndrome, Klinefelter's Syndrome, ovarian diseases such as anovulation, oophoritis, ovarian cysts, polycystic ovary syndrome, premature ovarian failure, ovarian hyperstimulation syndrome, ovarian neoplasms, Meigs' Syndrome, delayed puberty, and precocious puberty, sex differentiation disorders such as gonadal dysgenesis (46,XY, mixed) and Turner's Syndrome, hermaphroditism, pseudohermaphroditism, Kallmann Syndrome, Klinefelter's Syndrome, Testicular feminization, testicular diseases such as Cryptorchidism, Orchitis, testicular neoplasms, virilism, hirsutism, hyperinsulinism, neoplastic endocrine-like syndromes such as ACTH Syndrome (Ectopic) and Zollinger-Ellison Syndrome, parathyroid diseases including hyperparathyroidism (secondary), renal osteodystrophy, hypoparathyroidism, tetany, parathyroid neoplasms, pituitary diseases, Empy Sella Syndrome, hyperpituitarism, acromegaly, gigantism, hypopituitarism (diabetes insipidus, nephrogenic disbetes insipidus, Wolfram Syndrome, pituitary dwarfism), inappropriate ADH syndrome, pituitary apoplexy, pituitary neoplasms, Nelson Syndrome, autoimmune polyendocrinopathies, progeria, Werner's Syndrome, thymus hyperplasia, thyroid diseases such as euthyroid sick syndromes, goiter (endemic, nodular, substernal, Graves' Disease), hyperthyroidism and that associated with Graves' Disease, hyperthyroxinemia, hypothyroidism (cretinism and myxedema), thyroid hormone resistance syndrome, thyroid neoplasms, thyroid nodule, thyroiditis (autoimmune, subacute, suppurative), thyrotoxicosis, thyroid crisis, and endocrine tuberculosis.

Diseases at the Cellular Level

Diseases associated with increased cell survival or the inhibition of apoptosis that could be treated or detected by KGF-2 polynucleotides or polypeptides, as well as antagonists or agonists of KGF-2, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, KGF-2 polynucleotides, polypeptides, and/or antagonists of the invention are used to inhibit growth, progression, and/or metasis of cancers, in particular those listed above.

Additional diseases or conditions associated with increased cell survival that could be treated or detected by KGF-2 polynucleotides or polypeptides, or agonists or antagonists of KGF-2, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by KGF-2 polynucleotides or polypeptides, as well as agonists or antagonists of KGF-2, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion inj ury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing KGF-2 polynucleotides or polypeptides, as well as agonists or antagonists of KGF-2, for therapeutic purposes, for example, to stimulate epithelial cell proliferation and basal keratinocytes for the purpose of wound healing, and to stimulate hair follicle production and healing of dermal wounds. KGF-2 polynucleotides or polypeptides, as well as agonists or antagonists of KGF-2, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. KGF-2 polynucleotides or polypeptides, as well as agonists or antagonists of KGF-2, could be used to promote dermal reestablishment subsequent to dermal loss.

KGF-2 polynucleotides or polypeptides, as well as agonists or antagonists of KGF-2, could be used to increase the adherence of skin grafts to a wound bed and to stimulate re-epithelialization from the wound bed. The following are types of grafts that KGF-2 polynucleotides or polypeptides, agonists or antagonists of KGF-2, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, and thick split graft. KGF-2 polynucleotides or polypeptides, as well as agonists or antagonists of KGF-2, can also be used to promote skin strength and to improve the appearance of aged skin.

It is believed that KGF-2 polynucleotides or polypeptides, as well as agonists or antagonists of KGF-2, will also produce changes in hepatocyte proliferation, and epithelial cell proliferation in the lung, breast, pancreas, stomach, small intestine, and large intestine. KGF-2 polynucleotides or polypeptides, as well as agonists or antagonists of KGF-2, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. KGF-2 polynucleotides or polypeptides, agonists or antagonists of KGF-2, may promote proliferation of endothelial cells, keratinocytes, and basal keratinocytes.

KGF-2 polynucleotides or polypeptides, as well as agonists or antagonists of KGF-2, could also be used to reduce the side effects of gut toxicity that result from radiation, chemotherapy treatments or viral infections. KGF-2 polynucleotides or polypeptides, as well as agonists or antagonists of KGF-2, may have a cytoprotective effect on the small intestine mucosa. KGF-2 polynucleotides or polypeptides, as well as agonists or antagonists of KGF-2, may also stimulate healing of mucositis (mouth ulcers) that result from chemotherapy and viral infections.

KGF-2 polynucleotides or polypeptides, as well as agonists or antagonists of KGF-2, could further be used in full regeneration of skin in full and partial thickness skin defects, including bums, (i.e., repopulation of hair follicles, sweat glands, and sebaceous glands), treatment of other skin defects such as psoriasis. KGF-2 polynucleotides or polypeptides, as well as agonists or antagonists of KGF-2, could be used to treat epidermolysis bullosa, a defect in adherence of the epidermis to the underlying dermis which results in frequent, open and painful blisters by accelerating reepithelialization of these lesions. KGF-2 polynucleotides or polypeptides, as well as agonists or antagonists of KGF-2, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, KGF-2 polynucleotides or polypeptides, as well as agonists or antagonists of KGF-2, could be used to promote the resurfacing of the mucosal surface to aid more rapid healing and to prevent progression of inflammatory bowel disease. Treatment with KGF-2 polynucleotides or polypeptides, agonists or antagonists of KGF-2, is expected to have a significant effect on the production of mucus throughout the gastrointestinal tract and could be used to protect the intestinal mucosa from injurious substances that are ingested or following surgery. KGF-2 polynucleotides or polypeptides, as well as agonists or antagonists of KGF-2, could be used to treat diseases associated with the under expression of KGF-2.

Moreover, KGF-2 polynucleotides or polypeptides, as well as agonists or antagonists of KGF-2, could be used to prevent and heal damage to the lungs due to various pathological states. A growth factor such as KGF-2 polynucleotides or polypeptides, as well as agonists or antagonists of KGF-2, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and bums, that cause necrosis of the bronchiolar epithelium and alveoli could be effectively treated using KGF-2 polynucleotides or polypeptides, agonists or antagonists of KGF-2. Also, KGF-2 polynucleotides or polypeptides, as well as agonists or antagonists of KGF-2, could be used to stimulate the proliferation of and differentiation of type II pneumocytes, which may help treat or prevent disease such as hyaline membrane diseases, such as infant respiratory distress syndrome and bronchopulmonary displasia, in premature infants.

KGF-2 polynucleotides or polypeptides, as well as agonists or antagonists of KGF-2, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetrachloride and other hepatotoxins known in the art).

In addition, KGF-2 polynucleotides or polypeptides, as well as agonists or antagonists of KGF-2, could be used treat or prevent the onset of diabetes mellitus. In patients with newly diagnosed Types I and II diabetes, where some islet cell function remains, KGF-2 polynucleotides or polypeptides, as well as agonists or antagonists of KGF-2, could be used to maintain the islet function so as to alleviate, delay or prevent permanent manifestation of the disease. Also, KGF-2 polynucleotides or polypeptides, as well as agonists or antagonists of KGF-2, could be used as an auxiliary in islet cell transplantation to improve or promote islet cell function.

Infectious Disease

KGF-2 polynucleotides or polypeptides, or agonists or antagonists of KGF-2, can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, KGF-2 polynucleotides or polypeptides, or agonists or antagonists of KGF-2, may also directly inhibit the infectious agent, without necessarily eliciting an immune response.

Viruses are one example of an infectious agent that can cause disease or symptoms that can be treated or detected by KGF-2 polynucleotides or polypeptides, or agonists or antagonists of KGF-2. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. KGF-2 polynucleotides or polypeptides, or agonists or antagonists of KGF-2, can be used to treat or detect any of these symptoms or diseases.

Similarly, bacterial or fungal agents that can cause disease or symptoms and that can be treated or detected by KGF-2 polynucleotides or polypeptides, or agonists or antagonists of KGF-2, include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, and wound infections. KGF-2 polynucleotides or polypeptides, or agonists or antagonists of KGF-2, can be used to treat or detect any of these symptoms or diseases.

Moreover, parasitic agents causing disease or symptoms that can be treated or detected by KGF-2 polynucleotides or polypeptides, or agonists or antagonists of KGF-2, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. KGF-2 polynucleotides or polypeptides, or agonists or antagonists of KGF-2, can be used to treat or detect any of these symptoms or diseases.

Preferably, treatment using KGF-2 polynucleotides or polypeptides, or agonists or antagonists of KGF-2, could either be by administering an effective amount of KGF-2 polypeptide to the patient, or by removing cells from the patient, supplying the cells with KGF-2 polynucleotide, and returning the engineered cells to the patient (ex vivo therapy). Moreover, the KGF-2 polypeptide or polynucleotide can be used as an antigen in a vaccine to raise an immune response against infectious disease.

Regeneration

KGF-2 polynucleotides or polypeptides, or agonists or antagonists of KGF-2, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, KGF-2 polynucleotides or polypeptides, or agonists or antagonists of KGF-2, may increase regeneration of tissues difficult to heal. For example, increased tendon/ligament regeneration would quicken recovery time after damage. KGF-2 polynucleotides or polypeptides, or agonists or antagonists of KGF-2, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using KGF-2 polynucleotides or polypeptides, or agonists or antagonists of KGF-2, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the KGF-2 polynucleotides or polypeptides, or agonists or antagonists of KGF-2.

Chemotaxis

KGF-2 polynucleotides or polypeptides, or agonists or antagonists of KGF-2, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

KGF-2 polynucleotides or polypeptides, or agonists or antagonists of KGF-2, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, KGF-2 could also attract fibroblasts, which can be used to treat wounds.

It is also contemplated that KGF-2 polynucleotides or polypeptides, or agonists or antagonists of KGF-2, may inhibit chemotactic activity. These molecules could also be used to treat disorders. Thus, KGF-2 polynucleotides or polypeptides, or agonists or antagonists of KGF-2, could be used as an inhibitor of chemotaxis.

Binding Activity

KGF-2 polypeptides may be used to screen for molecules that bind to KGF-2 or for molecules to which KGF-2 binds. The binding of KGF-2 and the molecule may activate (agonist), increase, inhibit (antagonist), or decrease activity of the KGF-2 or the molecule bound. Examples of such molecules include antibodies, oligonucleotides, proteins (e.g., receptors), or small molecules.

Preferably, the molecule is closely related to the natural ligand of KGF-2, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which KGF-2 binds, or at least, a fragment of the receptor capable of being bound by KGF-2 (e.g., active site). In either case, the molecule can be rationally designed using known techniques.

Preferably, the screening for these molecules involves producing appropriate cells which express KGF-2, either as a secreted protein or on the cell membrane. Preferred cells include cells from mammals, yeast, Drosophila, or *E. coli*. Cells expressing KGF-2 (or cell membrane containing the expressed polypeptide) are then preferably contacted with a test compound potentially containing the molecule to observe binding, stimulation, or inhibition of activity of either KGF-2 or the molecule.

The assay may simply test binding of a candidate compound to KGF-2, wherein binding is detected by a label, or in an assay involving competition with a labeled competitor. Further, the assay may test whether the candidate compound results in a signal generated by binding to KGF-2.

Alternatively, the assay can be carried out using cell-free preparations, polypeptide/molecule affixed to a solid support, chemical libraries, or natural product mixtures. The assay may also simply comprise the steps of mixing a candidate compound with a solution containing KGF-2, measuring KGF-2/molecule activity or binding, and comparing the KGF-2/molecule activity or binding to a standard.

Preferably, an ELISA assay can measure KGF-2 level or activity in a sample (e.g., biological sample) using a monoclonal or polyclonal antibody. The antibody can measure KGF-2 level or activity by either binding, directly or indirectly, to KGF-2 or by competing with KGF-2 for a substrate.

Additionally, the receptor to which KGF-2 binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from acell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of KGF-2 thereby effectively generating agonists and antagonists of KGF-2. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Trends Biotechnol.* 16(2):76–82 (1998); Hansson, L. O., et al., *J. Mol. Biol.* 287:265–76 (1999); and Lorenzo, M. M. and Blasco, R. *Biolechniques* 24(2):308–13 (1998) (each of these patents and publications are hereby incorporated by reference). In one embodiment, alteration of KGF-2 polynucleotides and corresponding polypeptides may be achieved by DNA shuffling. DNA shuffling involves the assembly of two or more DNA segments into a desired KGF-2 molecule by homologous, or site-specific, recombination. In another embodiment, KGF-2 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of KGF-2 may be recombined with one or more components, motifs, sections, parts, domains, fragments, etc. of one or more heterologous molecules. In preferred embodiments, the heterologous molecules are fibroblast growth factor family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active KGF-2 fragments. Biologically active fragments are those exhibiting activity similar, but not necessarily identical, to an activity of the KGF-2 polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, the polypeptide of the present invention, the compound to be screened and $^3[H]$ thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3[H]$ thymidine in each case. The amount of fibroblast cell proliferation is measured by liquid scintillation chromatography which measures the incorporation of $^3[H]$ thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the KGF-2 receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the KGF-2/molecule. Moreover, the assays can discover agents which may inhibit or enhance the production of KGF-2 from suitably manipulated cells or tissues.

Therefore, the invention includes a method of identifying compounds which bind to KGF-2 comprising the steps of: (a) incubating a candidate binding compound with KGF-2; and (b) determining if binding has occurred. Moreover, the invention includes a method of identifying agonists/antagonists comprising the steps of: (a) incubating a candidate compound with KGF-2, (b) assaying a biological activity, and (c) determining if a biological activity of KGF-2 has been altered.

Also, one could identify molecules bind KGF-2 experimentally by using the beta-pleated sheet regions disclosed in FIG. 4 and Table 1. Accordingly, specific embodiments of the invention are directed to polynucleotides encoding polypeptides which comprise, or alternatively consist of, the amino acid sequence of each beta pleated sheet regions disclosed in FIG. 4/Table 1. Additional embodiments of the invention are directed to polynucleotides encoding KGF-2 polypeptides which comprise, or alternatively consist of, any combination or all of the beta pleated sheet regions disclosed in FIG. 4/Table 1. Additional preferred embodiments of the invention are directed to polypeptides which comprise, or alternatively consist of, the KGF-2 amino acid sequence of each of the beta pleated sheet regions disclosed in FIG. 4/Table 1. Additional embodiments of the invention are directed to KGF-2 polypeptides which comprise, or alternatively consist of, any combination or all of the beta pleated sheet regions disclosed in FIG. 4/Table 1.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained in the deposited clone 75977. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the KGF-2 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the KGF-2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding KGF-2, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metal lothionein gene (Brinster, et al., Nature 296:39–42 (1982)), etc.

The antisense nucleic acids of the invention comprise a sequence complementary to at least a portion of an RNA transcript of a KGF-2 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded KGF-2 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a KGF-2 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'- non-translated, non-coding regions of KGF-2 shown in FIGS. 1A–B could be used in an antisense approach to inhibit translation of endogenous KGF-2 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of KGF-2 mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the KGF-2 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy KGF-2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of KGF-2 (FIGS. 1A–B). Preferably, the ribozyme is engineered so that the cleavage recognition site is located near the 5' end of the KGF-2 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express KGF-2 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous KGF-2 messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed to stimulate neuronal growth and to treat and prevent neuronal damage which occurs in certain neuronal disorders or neuro-degenerative conditions such as Alzheimer's disease, Parkinson's disease, and AIDS-related complex. KGF-2 may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The KGF-2 polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The KGF-2 polypeptide may also be employed to maintain organs before transplantation or for supporting cell culture of primary tissues.

The polypeptide of the present invention may also be employed for inducing tissue of mesodermal origin to differentiate in early embryos.

KGF-2 polynucleotides or polypeptides, or agonists or antagonists of KGF-2, may also increase or decrease the differentiation or proliferation of embryonic stem cells, besides, as discussed above, hematopoietic lineage.

KGF-2 polynucleotides or polypeptides, or agonists or antagonists of KGF-2, may also be used to modulate mammalian characteristics, such as body height, weight, hair color, eye color, skin, percentage of adipose tissue, pigmentation, size, and shape (e.g., cosmetic surgery). Similarly, KGF-2 polynucleotides or polypeptides, or agonists or antagonists of KGF-2, may be used to modulate mammalian metabolism affecting catabolism, anabolism, processing, utilization, and storage of energy.

KGF-2 polynucleotides or polypeptides, or agonists or antagonists of KGF-2, may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

KGF-2 polynucleotides or polypeptides, or agonists or antagonists of KGF-2, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., *J. Cell. Biol.* 101:976–985 (1985); Jalkanen, et al., *J. Cell. Biol.* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston el al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96 well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Having generally described the invention, the same will be more readily understood by reference to the following examples, which are provided by way of illustration and are not intended as limiting.

EXAMPLE 1

Bacterial Expression and Purification of KGF-2

The DNA sequence encoding KGF-2, ATCC #75977, is initially amplified using PCR oligonucleotide primers corresponding to the 5' and 3' end sequences of the processed KGF-2 cDNA (including the signal peptide sequence). The 5' oligonucleotide primer has the sequence: 5° CCCCACAT-GTGGAAATGGATACTGACACATTGTCC 3' (SEQ ID No. 3) contains an Afl III restriction enzyme site including and followed by 30 nucleotides of KGF-2 coding sequence starting from the presumed initiation codon. The 3' sequence: 5° CCCAAGCTTCCACAAACGTTGCCTTC-CTCTATGAG 3' (SEQ ID No.4) contains complementary sequences to Hind III site and is followed by 26 nucleotides of KGF-2. The restriction enzyme sites are compatible with the restriction enzyme sites on the bacterial expression vector pQE-60 (Qiagen, Inc. Chatsworth, Calif.). pQE-60 encodes antibiotic resistance (Ampr), a bacterial origin of replication (ori), an IPTG-regulatable promoter operator (P/O), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform E. coli strain M15/rep 4 (Qiagen, Inc.) by the procedure described in Sambrook, J., et al., *Molecular Cloning. A Laboratory Manual*, Cold Spring Laboratory Press, (1989). M15/rep4 contains multiple copies of the plasmid pREP4, which expresses the lacI repressor and also confers kanamycin resistance (Kan). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG interacts with the lad repressor to cause it to dissociate from the operator, forcing the promoter to direct transcription. Cells are grown an extra 3 to 4 hours. Cells are then harvested by centrifugation. The cell pellet is solubilized in the chaotropic agent 6 Molar Guanidine HCl. After clarification, solubilized KGF-2 is purified from this solution by chromatography on a Heparin affinity column under conditions that allow for tight binding of the proteins (Hochuli, E., et al., *J. Chromatography* 411:177–184 (1984)). KGF-2 (75% pure) is eluted from the column by high salt buffer.

EXAMPLE 2

Bacterial Expression and Purification of a Truncated Version of KGF-2

The DNA sequence encoding KGF-2, ATCC #75977, is initially amplified using PCR oligonucleotide primers corresponding to the 5' and 3' sequences of the truncated version of the KGF-2 polypeptide. The truncated version comprises the polypeptide minus the 36 amino acid signal sequence, with a methionine and alanine residue being added just before the cysteine residue which comprises amino acid 37 of the full-length protein. The 5' oligonucleotide primer has the sequence 5° CATGCCATGGCGTGC-CAAGCCCTTGGTCAGGACATG 3' (SEQ ID NO:5) contains an NcoI restriction enzyme site including and followed by 24 nucleotides of KGF-2 coding sequence. The 3' sequence 5' CCCAAGCTTCCACAAACGTTGC CTTC-CTC TATGAG 3' (SEQ ID NO:6) contains complementary sequences to Hind III site and is followed by 26 nucleotides of the KGF-2 gene. The restriction enzyme sites are compatible with the restriction enzyme sites on the bacterial expression vector pQE-60 (Qiagen, Inc., Chatsworth, Calif.). pQE-60 encodes antibiotic resistance (Amp'), a bacterial origin of replication (ori), an IPTG-regulatable promoter operator (P/O), a ribosome binding site (RBS), a 6-His tag and restriction enzyme sites. pQE-60 is then digested with NcoI and HindIII. The amplified sequences are ligated into pQE-60 and are inserted in frame. The ligation mixture is then used to transform E. coli strain M15/rep 4 (Qiagen, Inc.) by the procedure described in Sambrook, J., et al., *Molecular Cloning: A Laboratory Manual*, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized KGF-2 is purified from this solution by chromatography on a Heparin affinity column under conditions that allow for tight binding the proteins (Hochuli, E. et al., *J. Chromatography* 411:177–184 (1984)). KGF-2 protein is eluted from the column by high salt buffer.

EXAMPLE 3

Cloning and Expression of KGF-2 Using the Baculovirus Expression System

The DNA sequence encoding the full length KGF-2 protein, ATCC #75977, is amplified using PCR oligonucleotide primers corresponding to the 5' and 3' sequences of the gene:

The 5' primer has the sequence 5' GCGGGATCCGCCAT-CATGTGGAAATGGATACTCAC 3' (SEQ ID NO:7) and contains a BamHI restriction enzyme site (in bold) followed by 6 nucleotides resembling an efficient signal for the initiation of translation in eukaryotic cells (Kozak, M., *J. Mol. Biol.*, 196:947–950 (1987)) and just behind the first 17 nucleotides of the KGF-2 gene (the initiation codon for translation "ATG" is underlined).

The 3' primer has the sequence 5' GCGCGGTACCA-CAAACGTTGCCTTCCT 3' (SEQ ID NO:8) and contains the cleavage site for the restriction endonuclease Asp718 and 19 nucleotides complementary to the 3' non-translated sequence of the KGF-2 gene. The amplified sequences are isolated from a 1% agarose gel using a commercially available kit from Qiagen, Inc., Chatsworth, Calif. The fragment is then digested with the endonucleases BamHI and Asp718 and then purified again on a 1% agarose gel. This fragment is designated F2.

The vector pA2 (modification of pVL941 vector, discussed below) is used for the expression of the KGF-2 protein using the baculovirus expression system (for review see: Summers, M. D. & Smith, G. E., *A manual of methods for baculovirus vectors and insect cell culture procedures,* Texas Agricultural Experimental Station Bulletin No. 1555 (1987)). This expression vector contains the strong polyhedrin promoter of the Autographa californica nuclear polyhidrosis virus (AcMNPV) followed by the recognition sites for the restriction endonucleases BamHI and Asp718. The polyadenylation site of the simian virus (SV) 40 is used for efficient polyadenylation. For an easy selection of recombinant viruses the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used such as pAc373, pVL941- and pAcIM1 (Luckow, V. A. & Summers, M. D., *Virology*, 170:31–39).

The plasmid is digested with the restriction enzymes BamHI and Asp718. The DNA is then isolated from a 1% agarose gel using the commercially available kit (Qiagen, Inc., Chatsworth, Calif.). This vector DNA is designated V2.

Fragment F2 and the plasmid V2 are ligated with T4 DNA ligase. *E. coli* HB101 cells are then transformed and bacteria identified that contained the plasmid (pBacKGF-2) with the KGF-2 gene using PCR with both cloning oligonucleotides. The sequence of the cloned fragment is confirmed by DNA sequencing.

5 μg of the plasmid pBacKGF-2 is co-transfected with 1.0 μg of a commercially available linearized baculovirus ("BaculoGold™ baculovirus DNA", Pharmingen, San Diego, Calif.) using the lipofection method (Felgner, et al., *Proc. Natl. Acad. Sci. USA*, 84:7413–7417 (1987)).

1 μg of BaculoGold™ virus DNA and 5 μg of the plasmid pBacKGF-2 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9-insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-KGF-2 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S methionine and 5 μCi $^{35}$S cysteine (Amersham) are added. The cells are further incubated for 16 hours before they are harvested by centrifugation and the labelled proteins are visualized by SDS-PAGE and autoradiography.

EXAMPLE 4

Most of the vectors used for the transient expression of the KGF-2 protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the immediate early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC1-3 cells, 293T cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J*. 227:277–279(1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

A. Expression of Recombinant KGF-2 in COS Cells

The expression of plasmid, KGF-2 HA was derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. The HA tag correspond to an epitope derived from the influenza hemagglutinin protein as previously described (Wilson, I., et al., *Cell* 37:767, (1984)). The infusion of HA tag to the target protein allows easy detection of the recombinant protein with an antibody that recognizes the HA epitope. A DNA fragment encoding the entire KGF-2 precursor HA tag fused in frame with the HA tag, therefore, the recombinant protein expression is directed under the CMV promoter.

The plasmid construction strategy is described as follows:
The DNA sequence encoding KGF-2, ATCC #75977, is constructed by PCR using two primers: the 5' primer 5' TAACGAGGATCCGCCATCATGTG-GAAATGGATACTGACAC 3'(SEQ ID NO:9) contains a BamHI site followed by 22 nucleotides of KGF-2 coding sequence starting from the initiation codon; the 3' sequence 5' TAAGCACTCGAGTGAGTGTACCACCAT-TGGAAGAAATG 3' (SEQ ID NO:10) contains complementary sequences to an XhoI site, HA tag and the last 26 nucleotides of the KGF-2 coding sequence (not including the stop codon). Therefore, the PCR product contains a BamHI site, KGF-2 coding sequence followed by an XhoI site, an HA tag fused in frame, and a translation termination stop codon next to the HA tag. The PCR amplified DNA fragment and the vector, pcDNA-3'HA, are digested with BamHI and XhoI restriction enzyme and ligated resulting in pcDNA-3'HA-KGF-2. The ligation mixture is transformed into E. coli strain XL1 Blue (Stratagene Cloning Systems, La Jolla, Calif.) the transformed culture is plated on ampicillin media plates and resistant colonies are selected. Plasmid DNA was isolated from transformants and examined by PCR and restriction analysis for the presence of the correct fragment. For expression of the recombinant KGF-2, COS cells were transfected with the expression vector by DEAE-DEXTRAN method (Sambrook, J., et al., *Molecular Cloning: A Laboratory Manual*, Cold Spring Laboratory Press, (1989)). The expression of the KGF-2 HA protein was detected by radiolabelling and immunoprecipitation method (Harlow, E. & Lane, D., *Antibodies: A Laboratory Manual*, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5) (Wilson, I., et al., Id. 37:767 (1984)). Both cell lysate and culture media were precipitated with a HA specific monoclonal antibody. Proteins precipitated were analyzed on 15% SDS-PAGE gels.

B: Expression and Purification of Human KGF-2 Protein Using the CHO Expression System The vector pC1 is used for the expression of KFG-2 protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology Vol.* 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding KFG-2, ATCC No. 75977, is amplified using PCR oligonucleotide primers corresponding to the 5' and 3' sequences of the gene:

The 5' primer has the sequence: 5'TAACGA GGATCCGCCATCATGTGGAA ATGGATACTGACAC 3' (SEQ ID NO:9) containing the underlined BamH1 restriction enzyme site followed by 21 bases of the sequence of KGF-2 of FIG. 1 (SEQ ID NO:1). Inserted into an expression vector, as described below, the 5' end of the amplified fragment encoding human KGF-2 provides an efficient signal peptide. An efficient signal for initiation of translation in eukaryotic cells, as described by Kozak, M., J. Mol. Biol. 196:947–950 (1987) is appropriately located in the vector portion of the construct.

The 3' primer has the sequence: 5' TAAGCA GGATCCTGAGTGTA CCACCATTGGAAGAAATG 3' (SEQ ID NO:10) containing the BamHI restriction followed by nucleotides complementary to the last 26 nucleotides of the KGF-2 coding sequence set out in FIG. 1 (SEQ ID NO:1), not including the stop codon.

The amplified fragments are isolated from a 1% agarose gel as described above and then digested with the endonuclease BamHI and then purified again on a 1% agarose gel.

The isolated fragment and the dephosphorylated vector are then ligated with T4 DNA ligase. E. coli HB101 cells are then transformed and bacteria identified that contain the plasmid pC1. The sequence and orientation of the inserted gene is confirmed by DNA sequencing.

Transfection of CHO-DHFR-Cells

Chinese hamster ovary cells lacking an active DHFR enzyme are used for transfection. 5 μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated for 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 5

Transcription and Translation of Recombinant KGF-2 in vitro

A PCR product is derived from the cloned cDNA in the pA2 vector used for insect cell expression of KGF-2. The primers used for this PCR were: 5' ATTAACCCTCAC-TAAAGGGAGGCCATGTGGAAATGGATACTGACAC ATTGTGCC 3' (SEQ ID NO:11) and 5' CCCAAGCTTC-CACAAACGTTGCCTTCCTCTATGAG 3' (SEQ ID NO:12).

The first primer contains the sequence of a T3 promoter 5' to the ATG initiation codon. The second primer is complimentary to the 3' end of the KGF-2 open reading frame, and encodes the reverse complement of a stop codon.

The resulting PCR product is purified using a commercially available kit from Qiagen. 0.5 µg of this DNA is used as a template for an in vitro transcription-translation reaction. The reaction is performed with a kit commercially available from Promega under the name of TNT. The assay is performed as described in the instructions for the kit, using radioactively labeled methionine as a substrate, with the exception that only ½ of the indicated volumes of reagents are used and that the reaction is allowed to proceed at 33° C. for 1.5 hours.

Five µl of the reaction is electrophoretically separated on a denaturing 10 to 15% polyacrylamide gel. The gel is fixed for 30 minutes in a mixture of water:Methanol:Acetic acid at 6:3:1 volumes respectively. The gel is then dried under heat and vacuum and subsequently exposed to an X-ray film for 16 hours. The film is developed showing the presence of a radioactive protein band corresponding in size to the conceptually translated KGF-2, strongly suggesting that the cloned cDNA for KGF-2 contains an open reading frame that codes for a protein of the expected size.

EXAMPLE 6

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin) is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA*, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 7

KGF-2 Stimulated Wound Healing in the Diabetic Mouse Model

To demonstrate that keratinocyte growth factor-2 (KGF-2) would accelerate the healing process, the genetically diabetic mouse model of wound healing was used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al *Proc. Natl. Acad. Sci.*

USA 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., Diabetes 29(1):60–67 (1980); Giacomelli et al., Lab Invest. 40(4):460–473 (1979); Coleman, D. L., Diabetes 31 (Suppl):1–6 (1982)). These homozygous diabetic mice develop hyperglycemia that is resistant to insulin analogous to human type II diabetes (Mandel et al., *J. Immunol.* 120:1375–1377(1978)).

The characteristics observed in these animals suggests that healing in this model may be similar to the healing observed in human diabetes (Greenhalgh, et al., *Am. J. of Pathol.* 136:1235–1246 (1990)). The results of this study demonstrated that KGF-2 has a potent stimulatory effect on the healing of full thickness wounds in diabetic and non-diabetic heterozygous littermates. Marked effects on re-epithelialization and an increase in collagen fibrils, granulation tissue within the dermis were observed in KGF-2 treated animals. The exogenous application of growth factors may accelerate granulation tissue formation by drawing inflammatory cells into the wound.

Animals

Genetically diabetic female C57BL/KsJ (db+/db+) mice and their non-diabetic (db+/+m) heterozygous littermates were used in this study (Jackson Laboratories). The animals were purchased at 6 weeks of age and were 8 weeks old at the beginning of the study. Animals were individually housed and received food and water ad libitum. All manipulations were performed using aseptic techniques. The experiments were conducted according to the rules and guidelines of Human Genome Sciences, Inc. Institutional Animal Care and Use Committee and the Guidelines for the Care and Use of Laboratory Animals.

KGF-2

The recombinant human KGF-2 used for the wound healing studies was over-expressed and purified from pQE60-Cys37, an *E. coli* expression vector system (pQE-9, Qiagen). The protein expressed from this construct is the KGF-2 from Cysteine at position 37 to Serine at position 208 with a 6×(His) tag attached to the N-terminus of the protein (SEQ ID NOS:29–30) (FIG. 15). Fractions containing greater than 95% pure recombinant materials were used for the experiment. Keratinocyte growth factor-2 was formulated in a vehicle containing 100 mM Tris, 8.0 and 600 mM NaCl. The final concentrations were 80 μg/mL and 8 μg/mL of stock solution. Dilutions were made from stock solution using the same vehicle.

Surgical Wounding

Wounding protocol was performed according to previously reported methods (Tsuboi, R. and Rifkin, D. B., J. Exp. Med. 172:245–251 (1990)). Briefly, on the day of wounding, animals were anesthetized with an intraperitoneal injection of Avertin (0.01 mg/mL), 2,2,2-tribromoethanol and 2-methyl-2-butanol dissolved in deionized water. The dorsal region of the animal was shaved and the skin washed with 70% ethanol solution and iodine. The surgical area was dried with sterile gauze prior to wounding. An 8 mm full-thickness wound was then created using a Keyes tissue punch. Immediately following wounding, the surrounding skin was gently stretched to eliminate wound expansion. The wounds were left open for the duration of the experiment. Application of the treatment was given topically for 5 consecutive days commencing on the day of wounding. Prior to treatment, wounds were gently cleansed with sterile saline and gauze sponges.

Wounds were visually examined and photographed at a fixed distance at the day of surgery and at two day intervals thereafter. Wound closure was determined by daily measurement on days 1–5 and on day 8. Wounds were measured horizontally and vertically using a calibrated Jameson caliper. Wounds were considered healed if granulation tissue was no longer visible and the wound was covered by a continuous epithelium.

KGF-2 was administered using two different doses of KGF-2, one at 4 μg per wound per day for 8 days and the second at 40 μg per wound per day for 8 days in 50 μL of vehicle. Vehicle control groups received 50 μL of vehicle solution.

Animals were euthanized on day 8 with an intraperitoneal injection of sodium pentobarbital (300 mg/kg). The wounds and surrounding skin were then harvested for histology and immunohistochemistry. Tissue specimens were placed in 10% neutral buffered formalin in tissue cassettes between biopsy sponges for further processing.

Experimental Design

Three groups of 10 animals each (5 diabetic and 5 non-diabetic controls) were evaluated: 1) Vehicle placebo control, 2) KGF-2 4 μg/day and 3) KGF-2 40 μg/day. This study was designed as follows:

| N | Group | Treatment |
| --- | --- | --- |
| N = 5 db+/db+ | vehicle | 50 μL |
| N = 5 db+/+m | vehicle | 50 μL |
| N = 5 db+/db+ | KGF-2 | 4 μg/50 μL |
| N = 5 db+/+m | KGF-2 | 4 μg/50 μL |
| N = 5 db+/db+ | KGF-2 | 40 μg/50 μL |
| N = 5 db+/+m | KGF-2 | 40 μg/50 μL |

Measurement of Wound Area and Closure

Wound closure was analyzed by measuring the area in the vertical and horizontal axis and obtaining the total square area of the wound. Contraction was then estimated by establishing the differences between the initial wound area (day 0) and that of post treatment (day 8). The wound area on day 1 was 64 mm$^2$, the corresponding size of the dermal punch. Calculations were made using the following formula:

[Open area on day 8]–[Open area on day 1]/[Open area on day 1]

Histology

Specimens were fixed in 10% buffered formalin and paraffin embedded blocks were sectioned perpendicular to the wound surface (5 μm) and cut using a Reichert-Jung microtome. Routine hematoxylin-eosin (H&E) staining was performed on cross-sections of bisected wounds. Histologic examination of the wounds were used to assess whether the healing process and the morphologic appearance of the repaired skin was altered by treatment with KGF-2. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)) (Table 1). A calibrated lens micrometer was used by a blinded observer.

Immunohistochemistry
Re-epithelialization

Tissue sections were stained immunohistochemically with a polyclonal rabbit anti-human keratin antibody using ABC Elite detection system. Human skin was used as a positive tissue control while non-immune IgG was used as a negative control. Keratinocyte growth was determined by evaluating the extent of reepithelialization of the wound using a calibrated lens micrometer.

Cell Proliferation Marker

Proliferating cell nuclear antigen/cyclin (PCNA) in skin specimens was demonstrated by using anti-PCNA antibody (1:50) with an ABC Elite detection system. Human colon cancer served as a positive tissue control and human brain tissue was used as a negative tissue control. Each specimen included a section with omission of the primary antibody and substitution with non-immune mouse IgG. Ranking of these sections was based on the extent of proliferation on a scale of 0–8, the lower side of the scale reflecting slight proliferation to the higher side reflecting intense proliferation.

Statistical Analysis

Experimental data were analyzed using an unpaired t test. A p value of <0.05 was considered significant. The data were expressed as the mean±SEM.

Results
Effect of KGF-2 on Wound Closure

Figure 4A:
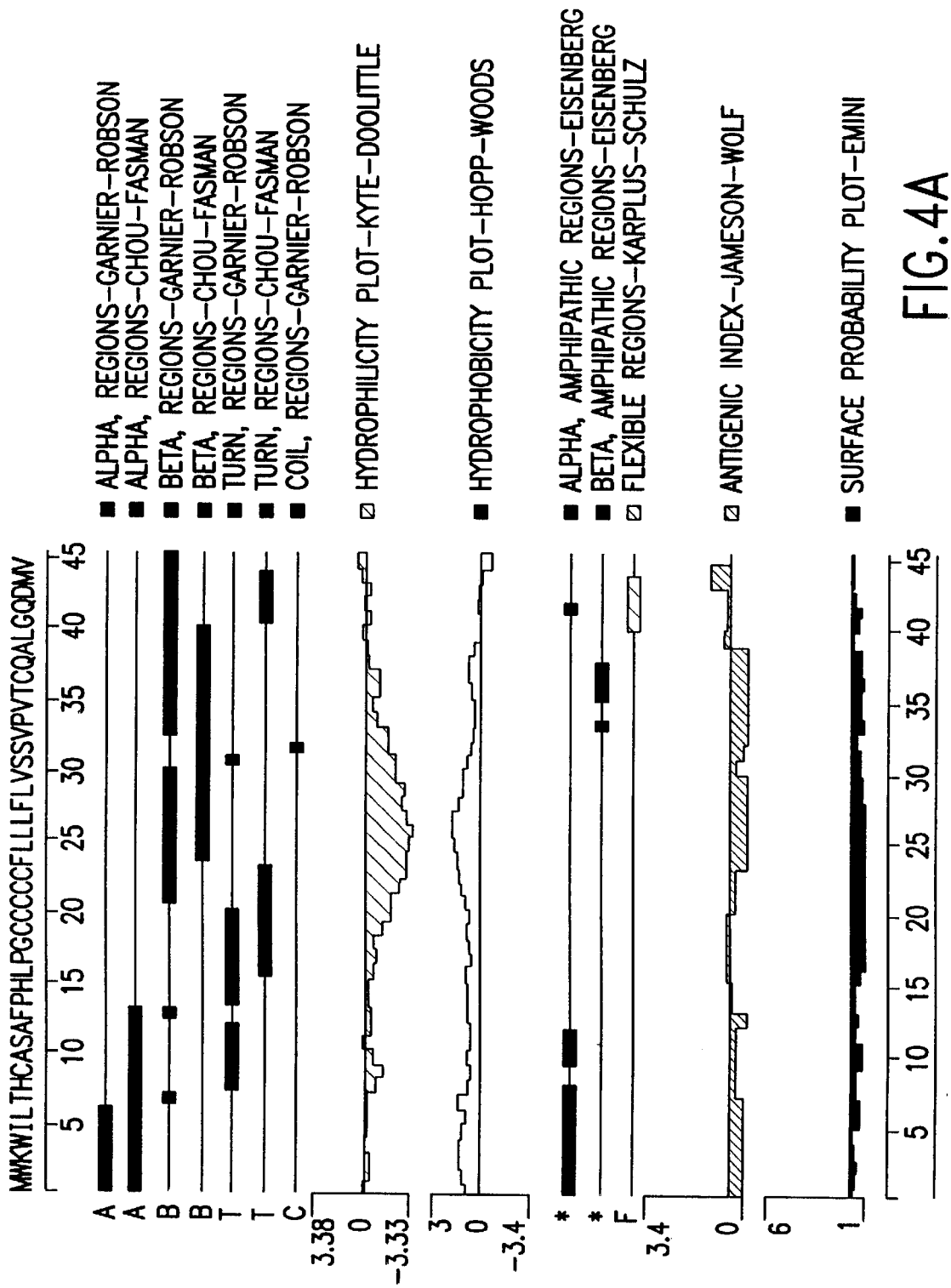
FIGS. 4A–4E show an analysis of the KGF-2 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 41–109 in FIG. 1 [SEQ ID NO:2] correspond to the shown highly antigenic regions of the KGF-2 protein. Hydrophobic regions (Hopp-Woods Plot) fall below the median line (negative values) while hydrophilic regions (Kyte-Doolittle Plot) are found above the median line (positive values, e.g. amino acid residues 41–109). The plot is over the entire 208 amino acid ORF.
Figure 4B:
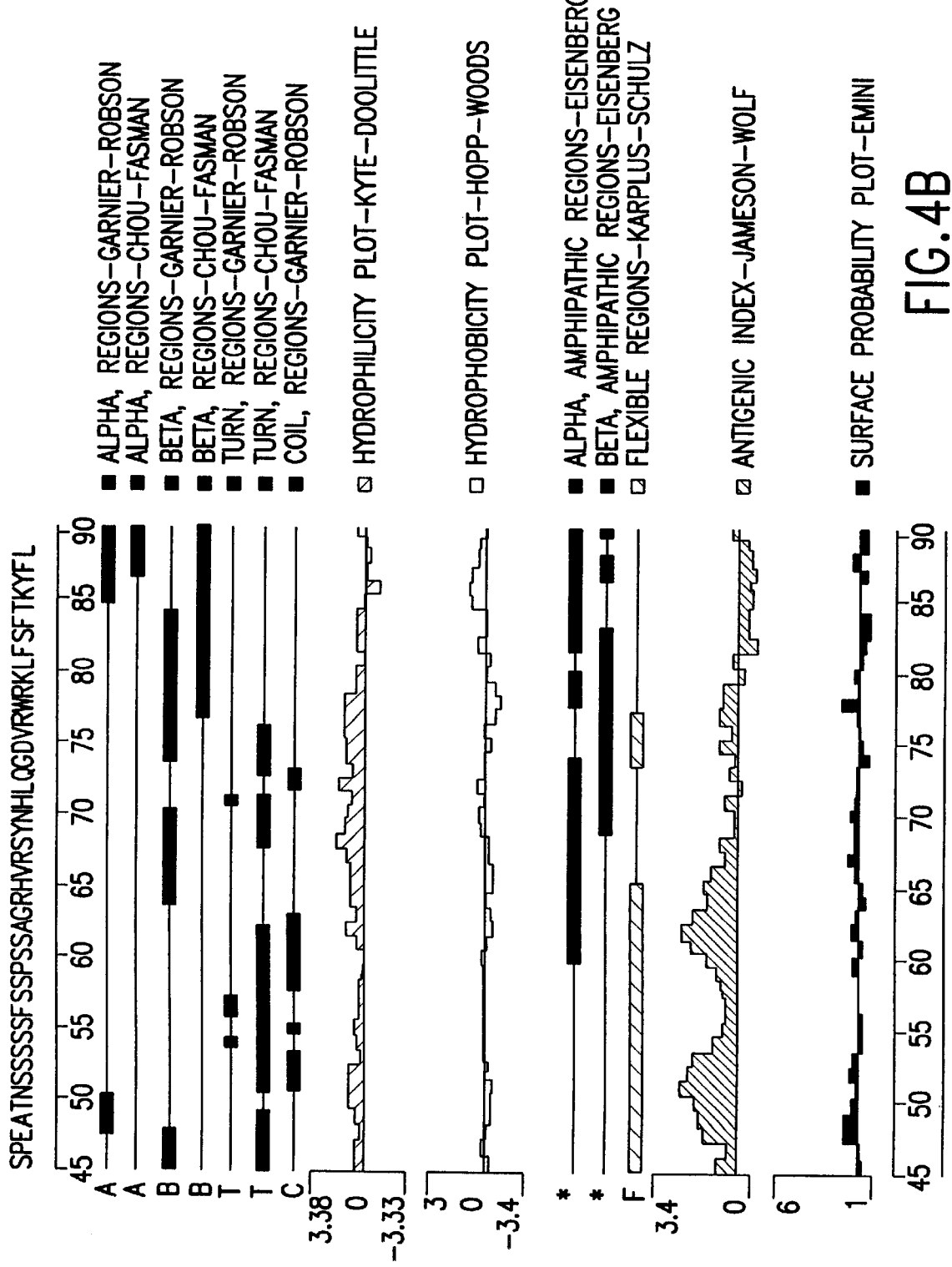
Figure 4C:
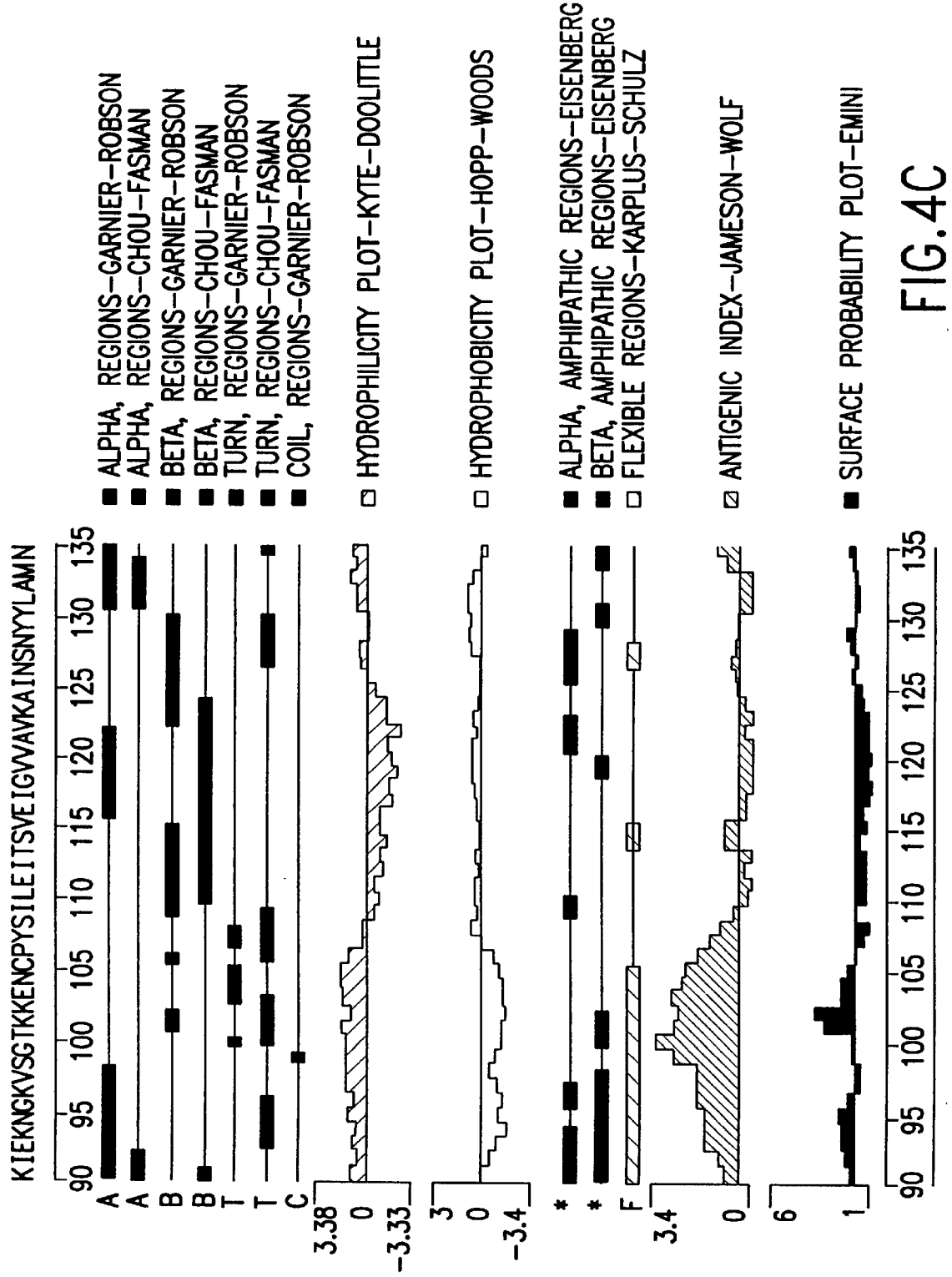
Figure 4D:
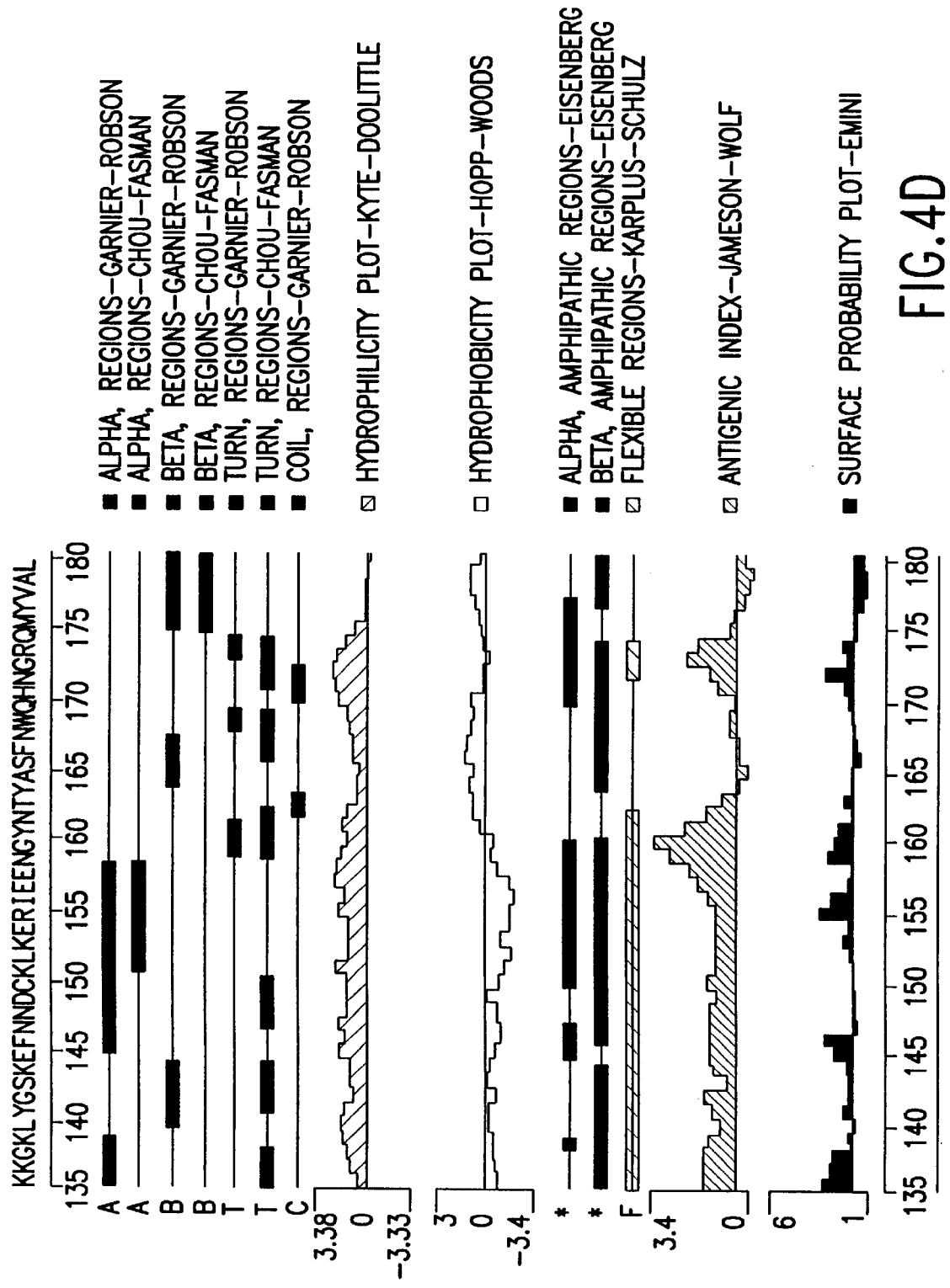
Figure 4E:
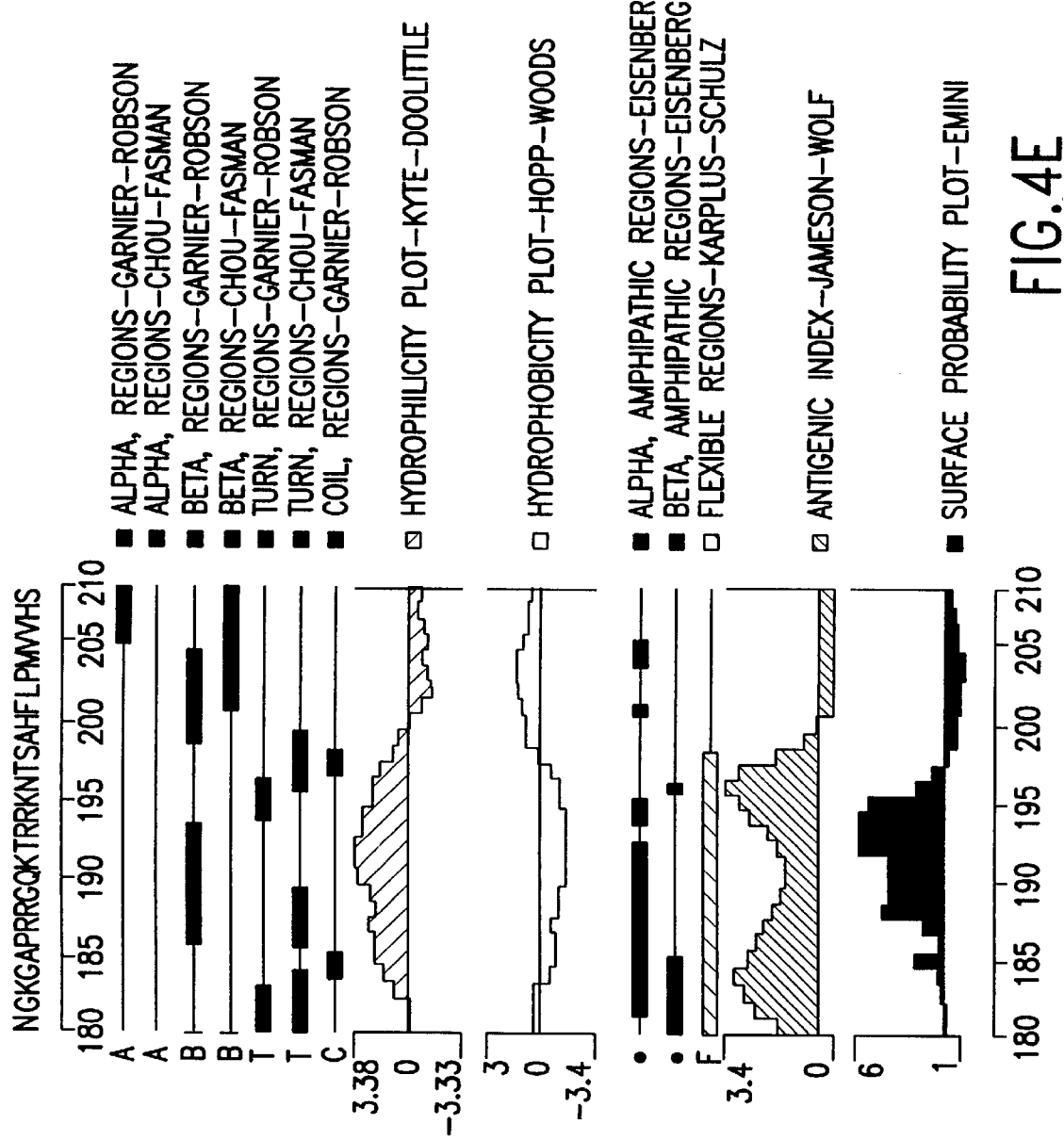
Figure 5:
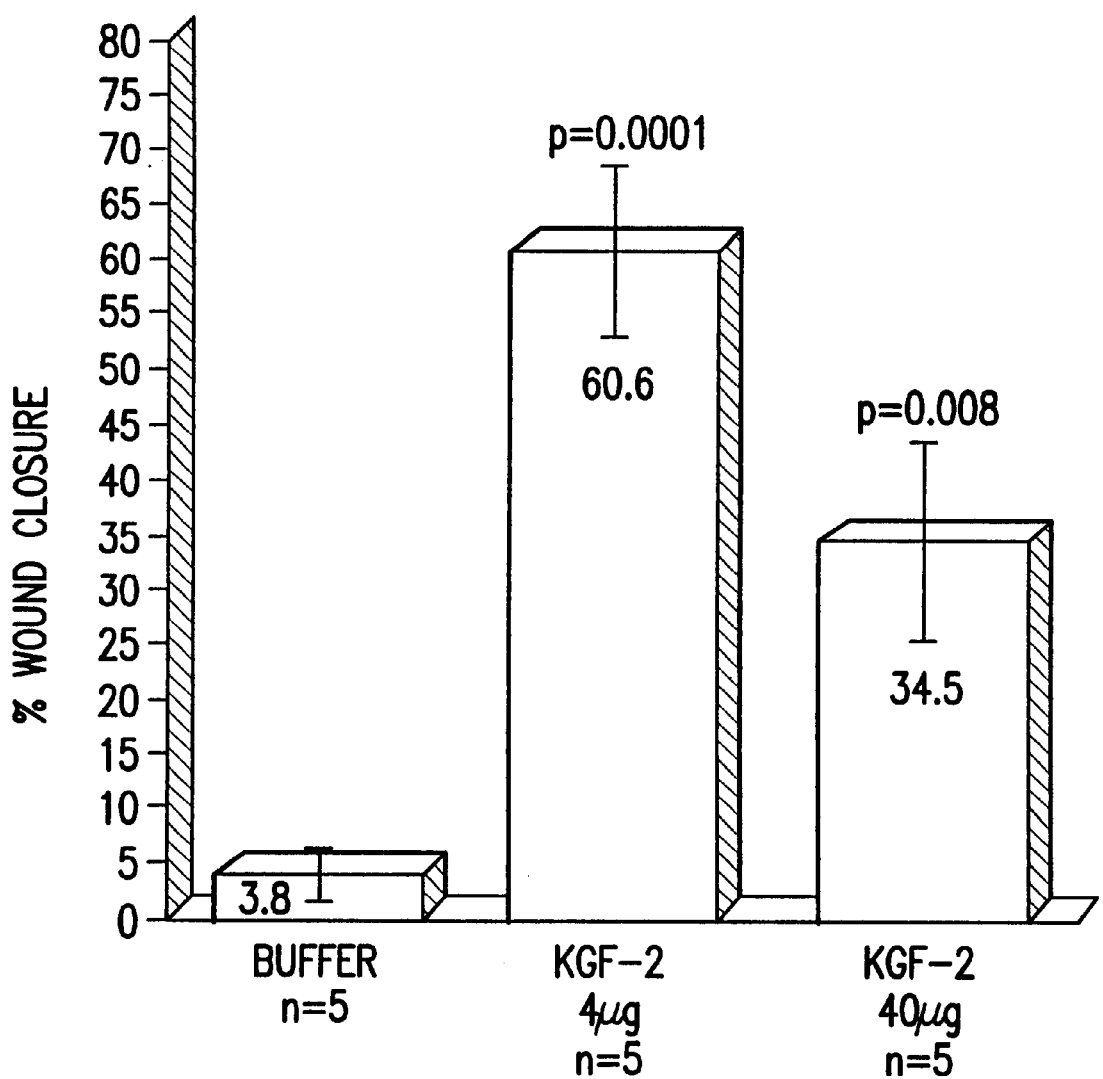
FIG. 5 shows the evaluation of KGF-2 on wound closure in the diabetic mice. Wounds were measured immediately after wounding and every day for 5 consecutive days and on day 8. Percent wound closure was calculated using the following formula: [Area on day 1]-[Area on day 8]/[Area on day 1]. Statistical analysis performed using an unpaired t test (mean +/– SEM, n=5).
Figure 6:
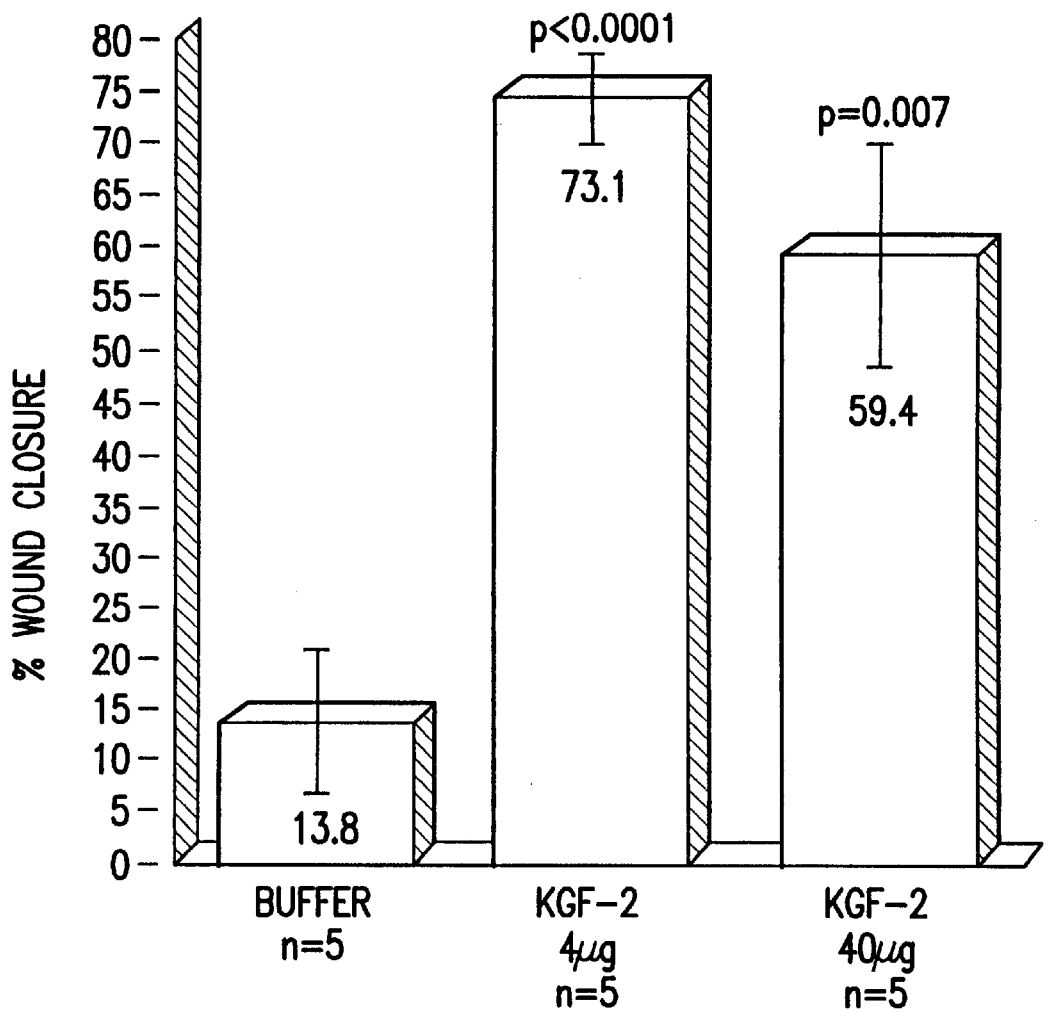
FIG. 6 shows the evaluation of KGF-2 on wound closure in the non-diabetic mice. Wounds were measured immediately after wounding and every day for 5 consecutive days and on day 8. Percent wound closure was calculated using the following formula: [Area on day 1]-[Area on day 8]/[Area on day 1]. Statistical analysis performed using an unpaired t test (mean +/– SEM, n=5).
Figure 7:
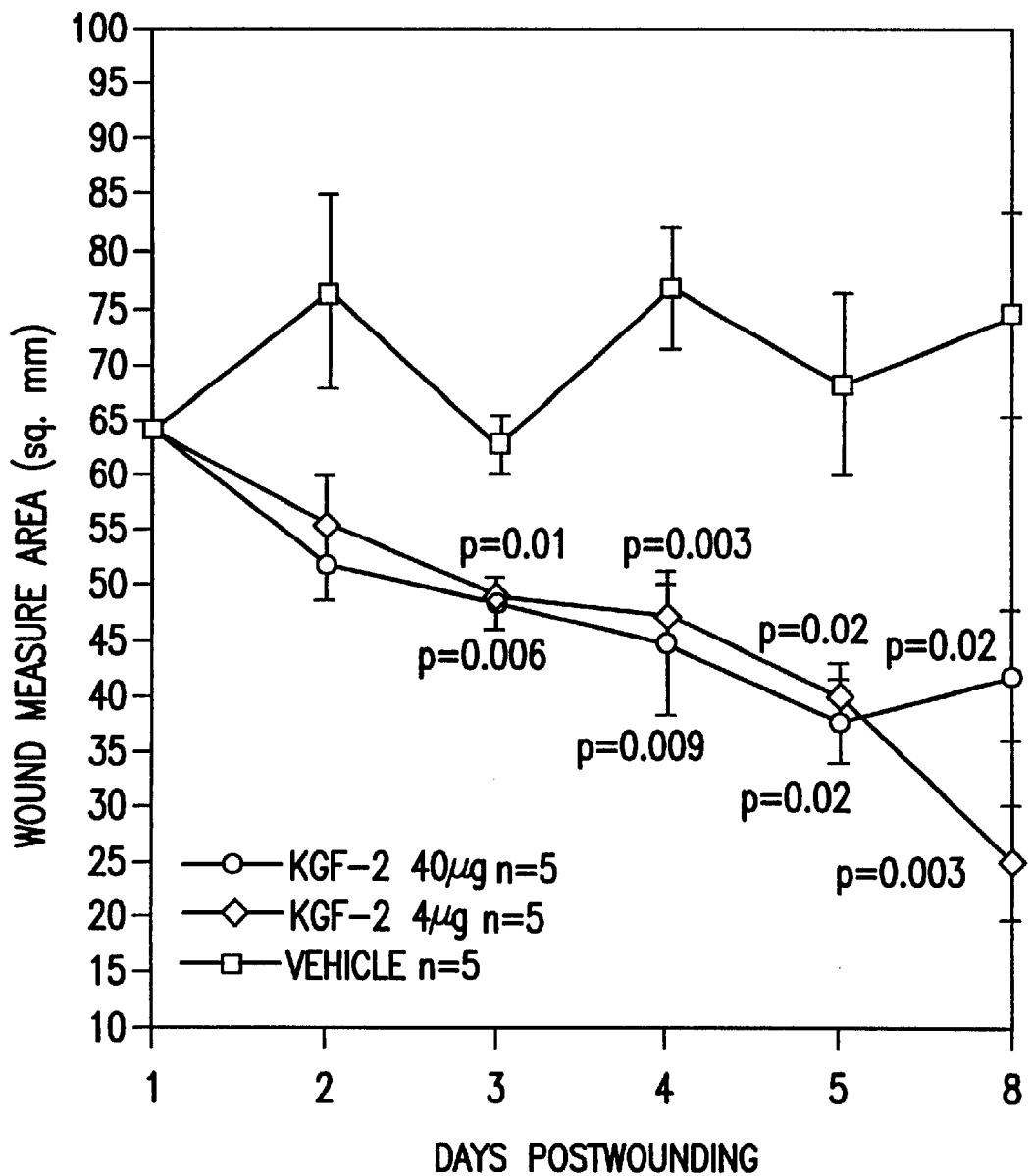
FIG. 7 shows a time course of wound closure in diabetic mice. Wound areas were measured immediately after wounding and every day for 5 consecutive days and on day 8. Values are presented as total area (sq. mm). Statistical analysis performed using an unpaired t test (mean +/– SEM, n=5).
Figure 8:
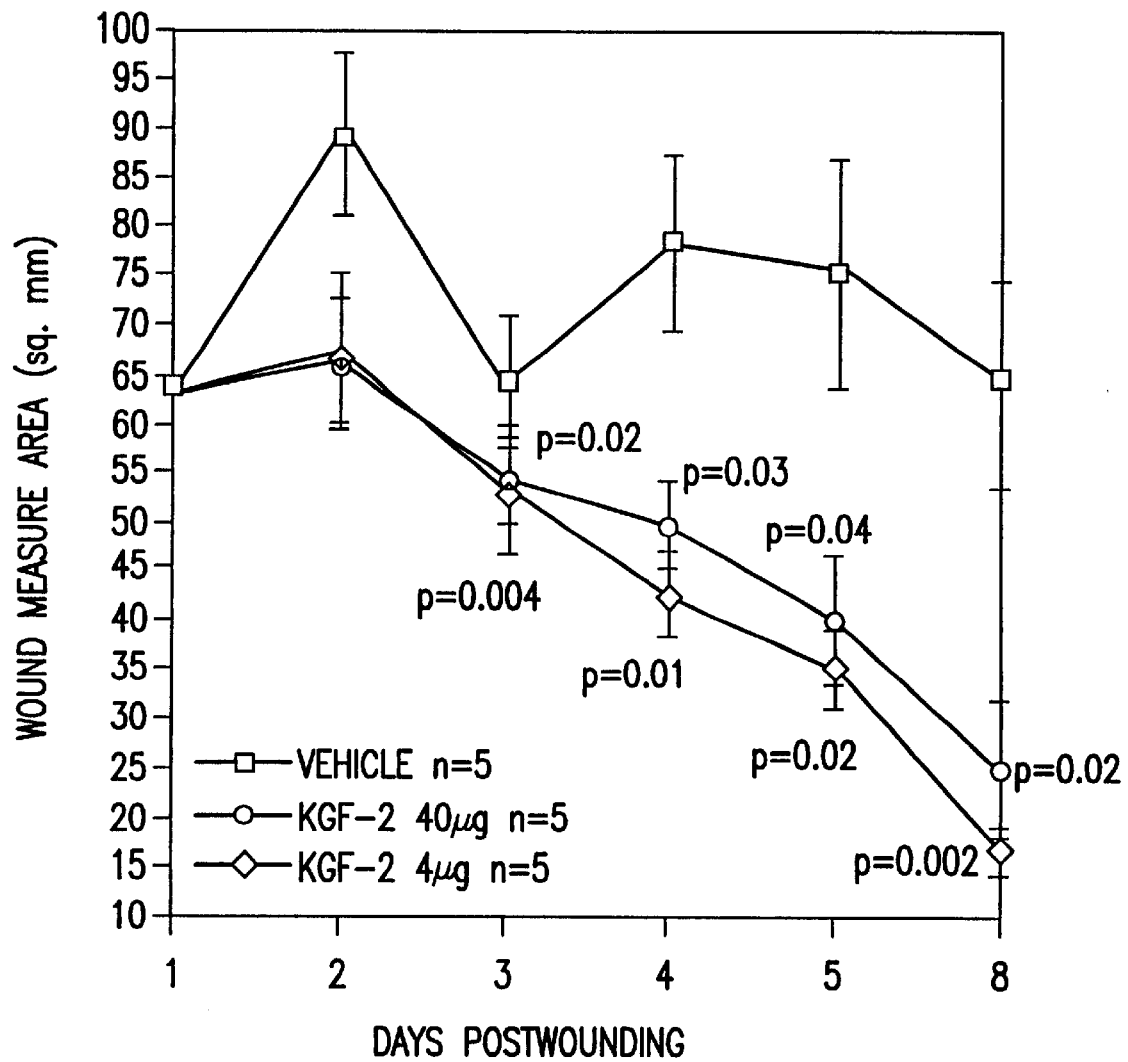
FIG. 8 shows a time course of wound closure in non-diabetic mice. Wound areas were measured immediately after wounding and every day for 5 consecutive days and on day 8. Values are presented as total area (sq. mm). Statistical analysis performed using an unpaired t test (mean +/– SEM, n=5).

Diabetic mice showed impaired healing compared to heterozygous normal mice. The dose of 4 μg of KGF-2 per site appeared to produce maximum response in diabetic and non-diabetic animals (FIGS. 5, 6). These results were statistically significant (p=0.002 and p<0.0001) when compared with the buffer control groups. Treatment with KGF-2 resulted in a final average closure of 60.6% in the group receiving 4 μg/day and 34.5% in the 40 μg/day group. Wounds in the buffer control group had only 3.8% closure by day 8. Repeated measurements of wounds on days 2–5 post-wounding and on day 8 taken from the db+/db+ mice treated with KGF-2 demonstrated a significant improvement in the total wound area (sq. mm) by day 3 post-wounding when compared to the buffer control group. This improvement continued and by the end of the experiment, statistically significant results were observed (FIG. 7). Animals in the db/+m groups receiving KGF-2 also showed a greater reduction in the wound area compared to the buffer control groups in repetitive measurements (FIG. 8). These results confirmed a greater rate of wound closure in the KGF-2 treated animals.

Effect of KGF-2 on Histologic Score

Figure 9:
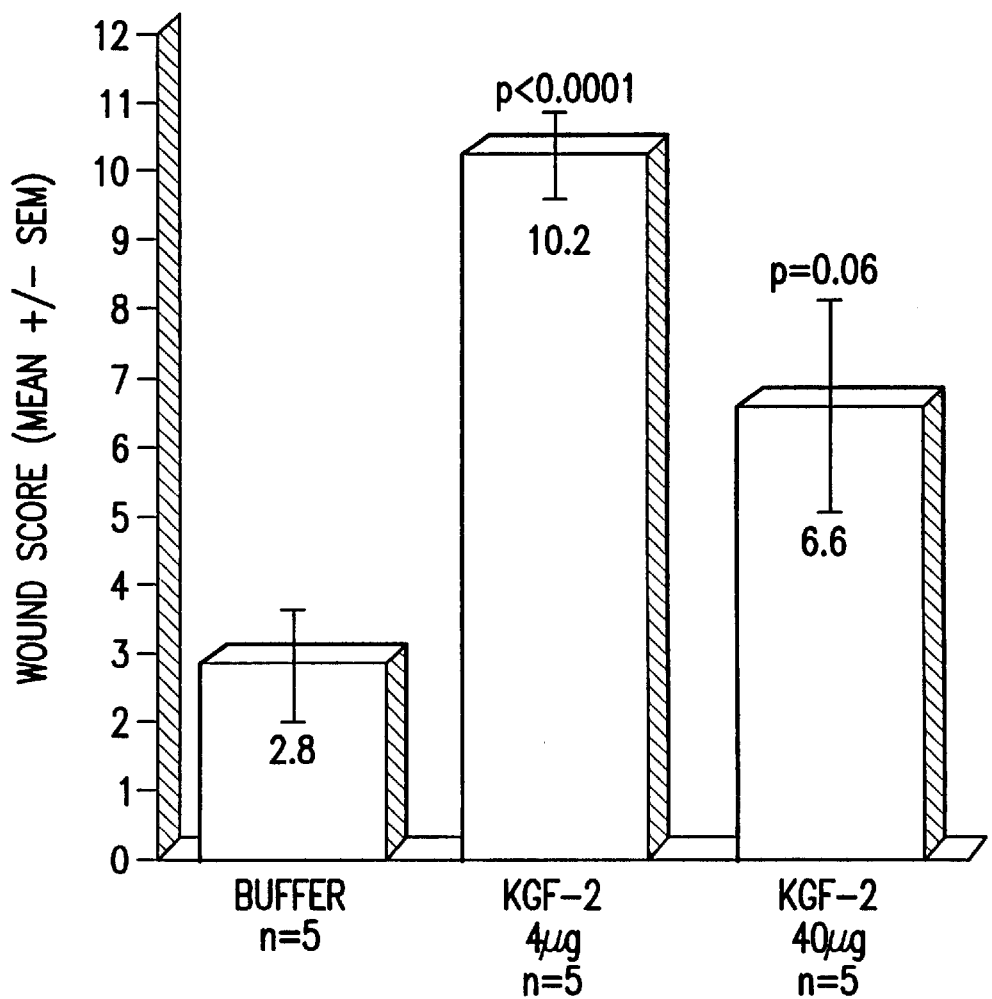
FIG. 9 shows a histopathologic evaluation on KGF-2 on the diabetic mice. Scores were given by a blind observer. Statistical analysis performed using an unpaired t test (mean +/– SEM, n=5).

Histopathologic evaluation of KGF-2 in the diabetic (db+/db+) model on day 8 demonstrated a statistically significant improvement (p<0.0001) in the wound score when compared with the buffer control. The pharmacologic effects observed with both the 4 μg and the 40 μg doses of KGF-2 were not significantly different from each other. The buffer control group showed minimal cell accumulation with no granulation tissue or epithelial travel while the 4 μg and 40 μg doses of KGF-2 (p<0.0001 & p=0.06 respectively) displayed epithelium covering the wound, neovascularization, granulation tissue formation and fibroblast and collagen deposition (FIG. 9).

Histopathologic assessment of skin wounds was performed on hematoxylin-eosin stained samples. Scoring criteria included a scale of 1–12, a score of one representing minimal cell accumulation with little to no granulation and a score of 12 representing the abundant presence of fibroblasts, collagen deposition and new epithelium covering the wound (Table 1).

TABLE 1

Scoring of Histology Sections

| Score | Criteria |
|---|---|
| 1–3 | None to minimal cell accumulation. No granulation tissue or epithelial travel. |
| 4–6 | Thin, immature granulation that is dominated by inflammatory cells but has few fibroblasts, capillaries or collagen deposition. Minimal epithelial migration. |
| 7–9 | Moderately thick granulation tissue, can range from being dominated by inflammatory cells to more fibroblasts and collagen deposition. Extensive neovascularization. Epithelium can range from minimal to moderate migration. |
| 10–12 | Thick, vascular granulation tissue dominated by fibroblasts and extensive collagen deposition. Epithelium partially to completely covering the wound. |

Figure 10:
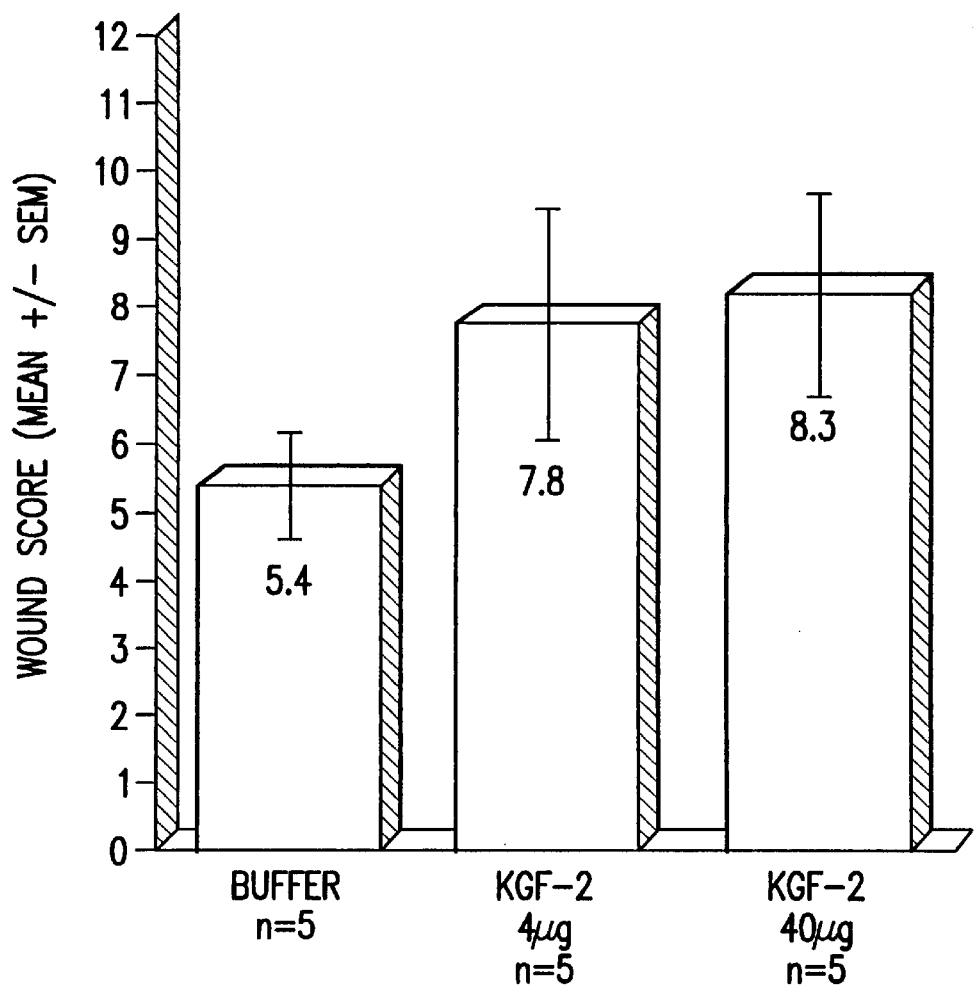
FIG. 10 shows a histopathologic evaluation on KGF-2 on the non-diabetic mice. Scores were given by a blind observer. Statistical analysis performed using an unpaired t test (mean +/– SEM, n=5).

Evaluation of the non diabetic littermates, after both doses of KGF-2, showed no significant activity in comparison with the buffer control group for all measurements evaluated (FIG. 10). The buffer control group showed immature granulation tissue, inflammatory cells, and capillaries. The mean score was higher than the diabetic group indicating impaired healing in the diabetic (db+/db+) mice.

Effect of KGF-2 on Re-epithelialization

Figure 11:
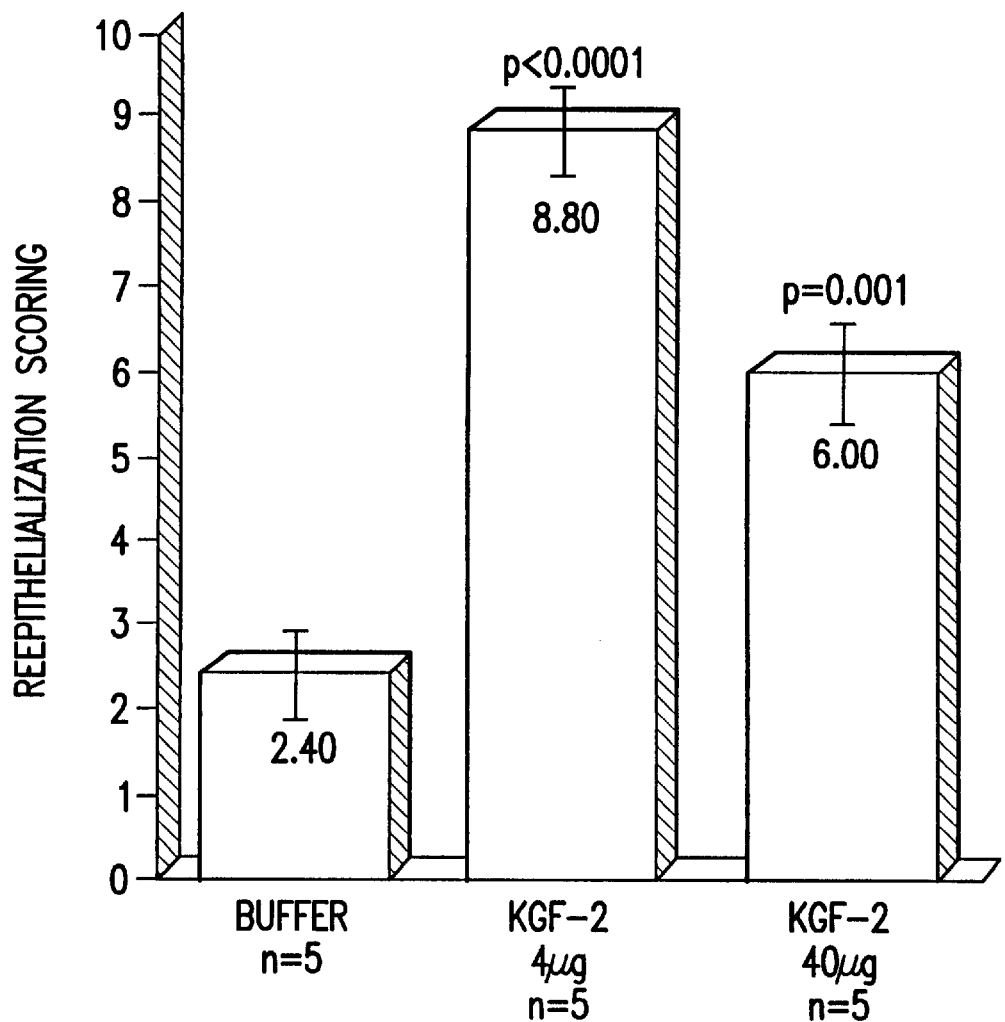
FIG. 11 shows the effect of keratinocyte growth in the diabetic mice. Scores were given by a blind observer. Statistical analysis performed using an unpaired t test (mean +/– SEM, n=5).
Figure 12:
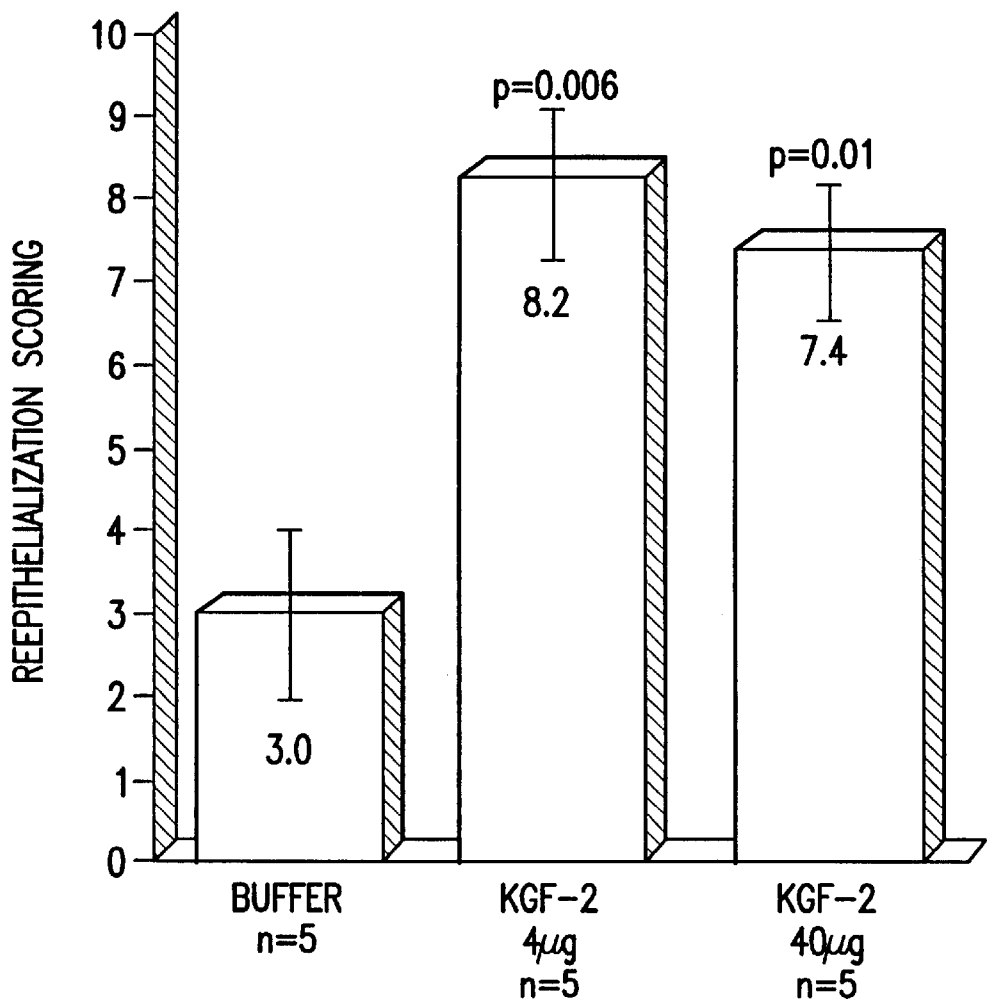
FIG. 12 shows the effect of keratinocyte growth in the non-diabetic mice. Scores were given by a blind observer based. Statistical analysis performed using an unpaired t test (mean +/– SEM, n=5).

Cytokeratine Immunostaining was used to determine the extent of re-epithelialization. Scores were given based on degree of closure on a scale of 0 (no closure) to 8 (complete closure). In the groups receiving 41 μg/day, there was a statistically significant improvement on the re-epithelialization score when compared to the buffer control group p<0.001 (FIG. 11). In this group, keratinocytes were observed localized in the newly formed epidermis covering the wound. Both doses of KGF-2 also exhibited mitotic figures in various stages. Assessment of the non-diabetic groups at both doses of KGF-2 also significantly improved reepithelialization ranking (p=0.006 and 0.01 respectively) (FIG. 12).

Effect of KGF-2 on Cell Proliferation

Figure 13:
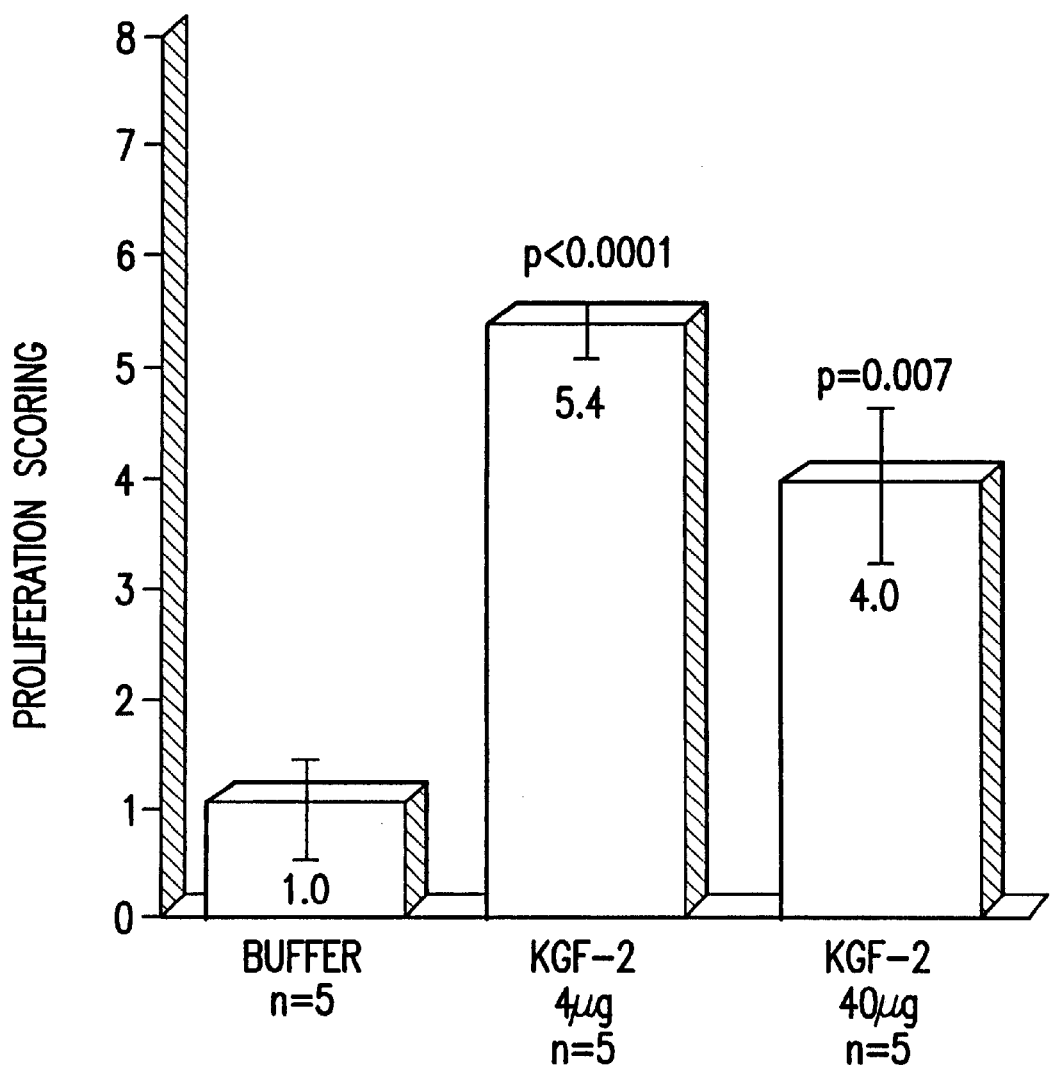
FIG. 13 shows the effect of skin proliferation in the diabetic mice. Scores were given by a blind observer. Statisical analysis performed using an unpaired t test (mean +/– SEM, n=5).
Figure 14:
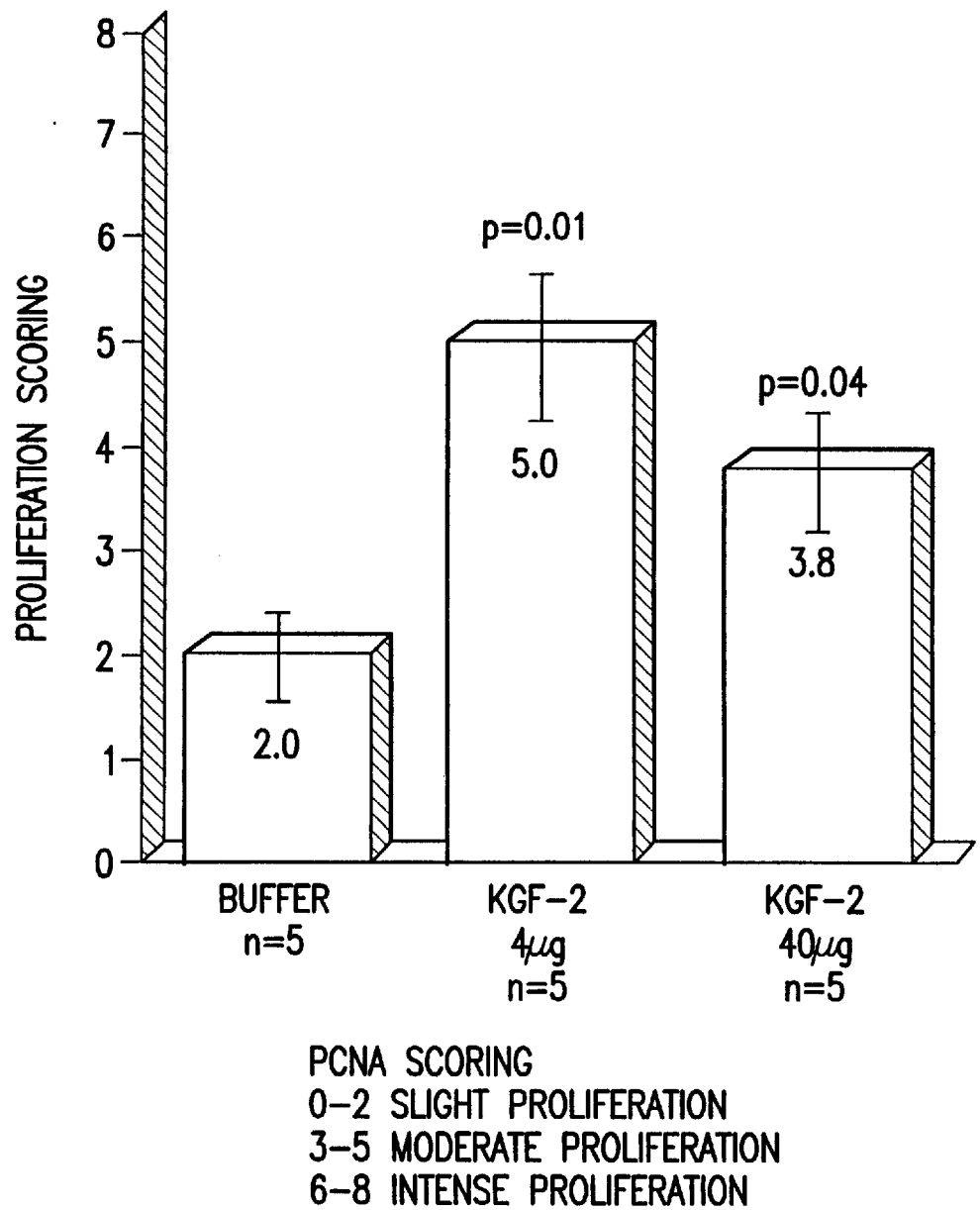
FIG. 14 shows the effect of skin proliferation in the non-diabetic mice. Scores were given by a blind observer. Statistical analysis performed using an unpaired t test (mean +/– SEM, n=5).

Proliferating cell nuclear antigen immunostaining demonstrated significant proliferation in both the 4 μg and 40 μg groups (FIG. 13). The non-diabetic group displayed similar results as both groups receiving both doses of KGF-2 showed higher significant scoring compared to the buffer control group (FIG. 14). Epidermal proliferation was observed especially on the basal layer of the epidermis. In addition, high density PCNA-labeled cells were observed in the dermis, especially in the hair follicles.

Conclusion

The results demonstrate that KGF-2 specifically stimulates growth of primary epidermal keratinocytes. In addition, these experiments demonstrate that topically applied recombinant human KGF-2 markedly accelerates the rate of healing of full-thickness excisional dermal wounds in diabetic mice. Histologic assessment shows KGF-2 to induce keratinocyte proliferation with epidermal thickening. This proliferation is localized in the basal layer of the epidermis as demonstrated by proliferating cell nuclear antigen (PCNA). At the level of the dermis, collagen deposition, fibroblast proliferation, and neo-vascularization re-established the normal architecture of the skin.

The high density of PCNA-labeled cells on KGF-2 treated animals in contrast with the buffer group, which had fewer PCNA-labeled cells, indicates the stimulation of keratinocytes at the dermal-epidermal level, fibroblasts and hair follicles. The enhancement of the healing process by KGF-2 was consistently observed in this experiment. This effect was statistically significant in the parameters evaluated (percent re-epithelialization and wound closure). Importantly, PCNA-labeled keratinocytes were mainly observed at the lower—basal layer of the epidermis. The dermis showed normalized tissue with fibroblasts, collagen, and granulation tissue.

The activity observed in the non-diabetic animals indicates that KGF-2 had significant pharmacologic response in the percentage of wound closure at day 8, as well as during the course of the experiment, based on daily measurements. Although the histopathologic evaluation was not significantly different when compared with the buffer control, keratinocyte growth and PCNA scores demonstrated significant effects.

In summary, these results demonstrated that KGF-2 shows significant activity in both impaired and normal excisional wound models using the db+/db+ mouse model and therefore may be useful in the treatment of wounds including surgical wounds, diabetic ulcers, venous stasis ulcers, bums, and other skin conditions.

EXAMPLE 8

KGF-2 Mediated Wound Healing in tile Steroid-impaired Rat Model

The inhibition of wound healing by steroids has been well documented in various in vitro and in vivo systems (Wahl, S. M. Glucocorticoids and Wound healing. In Anti-Inflammatory Steroid Action: Basic and Clinical Aspects. 280–302 (1989); Wahl, S. M. et al., *J. Immunol.* 115:476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F., et al.,*J. Clin. Invest.* 61. 703–797 (1978)) and producing a transient reduction of circulating monocytes (Haynes, B. F., et al., *J. Clin. Invest.* 61: 703–797 (1978); Wahl, S. M. Glucocorticoids and wound healing. In Antiinflammatory Steroid Action: Basic and Clinical Aspects. Academic Press. New York. pp. 280–302 (1989)). The systemic administration of steroids to impaired wound healing is a well establish phenomenon in rats (Beck, L. S. et al., *Growth Factors.* 5: 295–304 (1991); Haynes, B. F., et al.,*J. Clin. Invest.* 61: 703–797 (1978); Wahl, S. M. Glucocorticoids and wound healing. In Antiinflammatory Steroid Action: Basic and Clinical Aspects. Academic Press. New York. pp. 280–302 (1989); Pierce, G. F., et al., *Proc. Natl. Acad. Sci. USA*. 86: 2229–2233 (1989)).

To demonstrate that KGF-2 would accelerate the healing process, the effects of multiple topical applications of KGF-2 on full thickness excisional skin wounds in rats in which healing has been impaired by the systemic administration of methylprednisolone was assesed. In vitro studies have demonstrated that KGF-2 specifically stimulates growth of primary human epidermal keratinocytes. This example demonstrates that topically applied recombinant human KGF-2 accelerates the rate of healing of full-thickness excisional skin wounds in rats by measuring the wound gap with a calibrated Jameson caliper and by histomorphometry and immunohistochemistry. Histologic assessment demonstrates that KGF-2 accelerates re-epithelialization and subsequently, wound repair.

Animals

Young adult male Sprague Dawley rats weighing 250–300 g (Charles River Laboratories) were used in this example. The animals were purchased at 8 weeks of age and were 9 weeks old at the beginning of the study. The healing response of rats was impaired by the systemic administration of methylprednisolone (17 mg/kg/rat intramuscularly) at the time of wounding. Animals were individually housed and received food and water ad libitum. All manipulations were performed using aseptic techniques. This study was conducted according to the rules and guidelines of Human Genome Sciences, Inc. Institutional Animal Care and Use Committee and the Guidelines for the Care and Use of Laboratory Animals.

KGF-2

Recombinant human KGF-2 was over-expressed and purified from pQE60-Cys37, an *E. coli* expression vector system (pQE-9, Qiagen). The protein expressed from this construct is the KGF-2 from Cysteine at position 37 to Serine at position 208 with a 6×(His) tag attached to the N-terminus of the protein (FIG. 15) (SEQ ID NOS:29–30). Fractions containing greater than 95% pure recombinant materials were used for the experiment. KGF-2 was formulated in a vehicle containing 1×PBS. The final concentrations were 20 µg/mL and 80 µg/mL of stock solution. Dilutions were made from stock solution using the same vehicle.

KGF-2Δ28 was over-expressed and purified from an *E. coli* expression vector system. Fractions containing greater than 95% pure recombinant materials were used for the experiment. KGF-2 was formulated in a vehicle containing 1×PBS. The final concentrations were 20 µg/mL and 80 µg/mL of stock solution. Dilutions were made from stock solution using the same vehicle.

Surgical Wounding

The wounding protocol was followed according to Example 7, above. On the day of wounding, animals were anesthetized with an intramuscular injection of ketamine (50 mg/kg) and xylazine (5 mg/kg). The dorsal region of the animal was shaved and the skin washed with 70% ethanol and iodine solutions. The surgical area was dried with sterile gauze prior to wounding. An 8 mm full-thickness wound was created using a Keyes tissue punch. The wounds were left open for the duration of the experiment. Applications of the testing materials were given topically once a day for 7 consecutive days commencing on the day of wounding and subsequent to methylprednisolone administration. Prior to treatment, wounds were gently cleansed with sterile saline and gauze sponges.

Wounds were visually examined and photographed at a fixed distance at the day of wounding and at the end of treatment. Wound closure was determined by daily measurement on days 1–5 and on day 8 for Figure. Wounds were measured horizontally and vertically using a calibrated Jameson caliper. Wounds were considered healed if granulation tissue was no longer visible and the wound was covered by a continuous epithelium.

A dose response was performed using two different doses of KGF-2, one at 1 μg per wound per day and the second at 4 μg per wound per day for 5 days in 50 μL of vehicle. Vehicle control groups received 50 μL of 1×PBS.

Animals were euthanized on day 8 with an intraperitoneal injection of sodium pentobarbital (300 mg/kg). The wounds and surrounding skin were then harvested for histology. Tissue specimens were placed in 10% neutral buffered formalin in tissue cassettes between biopsy sponges for further processing.

Experimental Design

Four groups of 10 animals each (5 with methylprednisolone and 5 without glucocorticoid) were evaluated: 1) Untreated group 2) Vehicle placebo control 3) KGF-2 1 μg/day and 4) KGF-2 4 μg/day. This study was designed as follows:

| n | Group | Treatment |
|---|---|---|
| Glucocorticoid-Treated | | |
| N = 5 | Untreated | — |
| N = 5 | Vehicle | 50 μL |
| N = 5 | KGF-2 (1 μg) | 50 μL |
| N = 5 | KGF-2 (4 μg) | 50 μL |
| Without Glucocorticoid | | |
| N = 5 | Untreated | — |
| N = 5 | Vehicle | 50 μL |
| N = 5 | KGF-2 (1 μg) | 50 μL |
| N = 5 | KGF-2 (4 μg) | 50 μL |

Measurement of Wound Area and Closure

Wound closure was analyzed by measuring the area in the vertical and horizontal axis and obtaining the total area of the wound. Closure was then estimated by establishing the differences between the initial wound area (day 0) and that of post treatment (day 8). The wound area on day 1 was 64 mm², the corresponding size of the dermal punch. Calculations were made using the following formula:

[Open area on day 8]–[Open area on day 1]/[Open area on day 1]

Histology

Specimens were fixed in 10% buffered formalin and paraffin embedded blocks were sectioned perpendicular to the wound surface (5 μm) and cut using an Olympus microtome. Routine hematoxylin-eosin (H&E) staining was performed on cross-sections of bisected wounds. Histologic examination of the wounds allowed us to assess whether the healing process and the morphologic appearance of the repaired skin was improved by treatment with KGF-2. A calibrated lens micrometer was used by a blinded observer to determine the distance of the wound gap.

Statistical Analysis

Experimental data were analyzed using an unpaired t test. A p value of <0.05 was considered significant. The data was expressed as the mean±SEM.

Results

Figure 16:
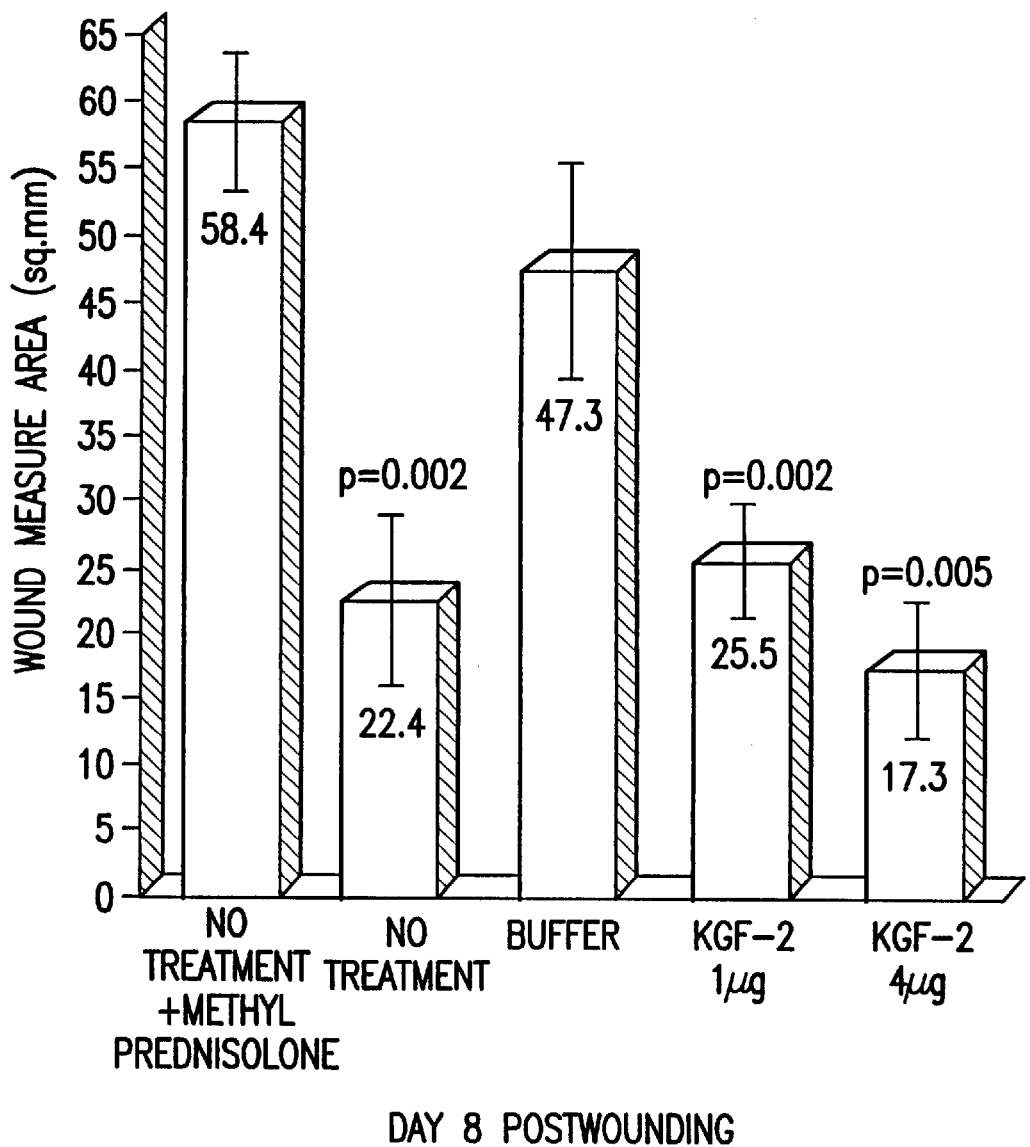
FIG. 16 shows the effect of methyl-prednisolone on wound healing in rats. Male SD adult rats (n=5) were injected on day of wounding with 5 mg of methyl prednisolone. Animals received dermal punch wounds (8 mm) and were treated daily with buffer solution or KGF-2 solution in 50 μL buffer solution for 5 consecutive days. Wounds were measured daily on days 1–5 and on day 8 with a calibrated Jameson caliper. Values represent measurements taken on day 8. (Mean +/– SEM)

A comparison of the wound closure of the untreated control groups with and without methylprednisolone demonstrates that methylprednisolone-treated rats have significant impairment of wound healing at 8 days post-wounding compared with normal rats. The total wound area measured 58.4 mm² in the methylprednisolone injected group and 22.4 mm² in the group not receiving glucocorticoid (FIG. 16).

Effect of KGF-2 on Wound Closure

Figure 17:
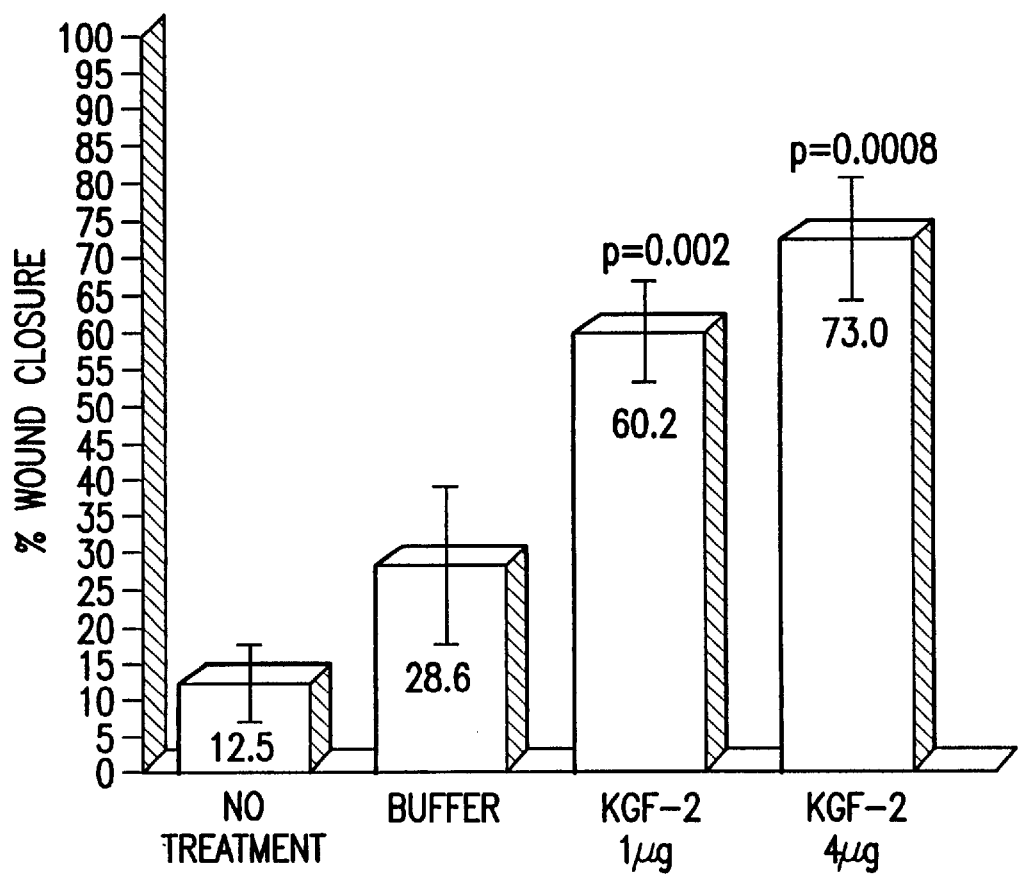
FIG. 17 shows the effect of KGF-2 on wound closure. Male SD adult rats (n=5) received dermal punch wounds (8 mm) and 5 mg of methyl-prednisolone on day of wounding. Animals were treated daily with a buffer solution or KGF-2 in 50 μL of buffer solution for 5 consecutive days commencing on the day of wounding. Measurements were made daily for 5 consecutive days and on day 8. Wound closure was calculated by the following formula: [Area on Day 8]-[Area on Day 1]/[Area on Day 1]. Area on day 1 was determined to be 64 sq. mm, the area made by the dermal punch. Statistical analysis was done using an unpaired t test. (Mean +/– SEM)

Systemic administration of methylprednisolone in rats at the time of wounding delayed wound closure (p=0.002) of normal rats. Wound closure measurements of the methlyprednisolone-impaired groups at the end of the experiment on day 8 demonstrated that wound closure with KGF-2 was significantly greater statistically (1 μg p=0.002 & 4 μg p=0.005) when compared with the untreated group (FIG. 16). Percentage wound closure was 60.2% in the group receiveing 1 μg KGF-2 (p=0.002) and 73% in the group receiving 4 μg KGF-2 (p=0.0008). In contrast, the wound closure of untreated group was 12.5% and the vehicle placebo group was 28.6% (FIG. 17).

Figure 18:
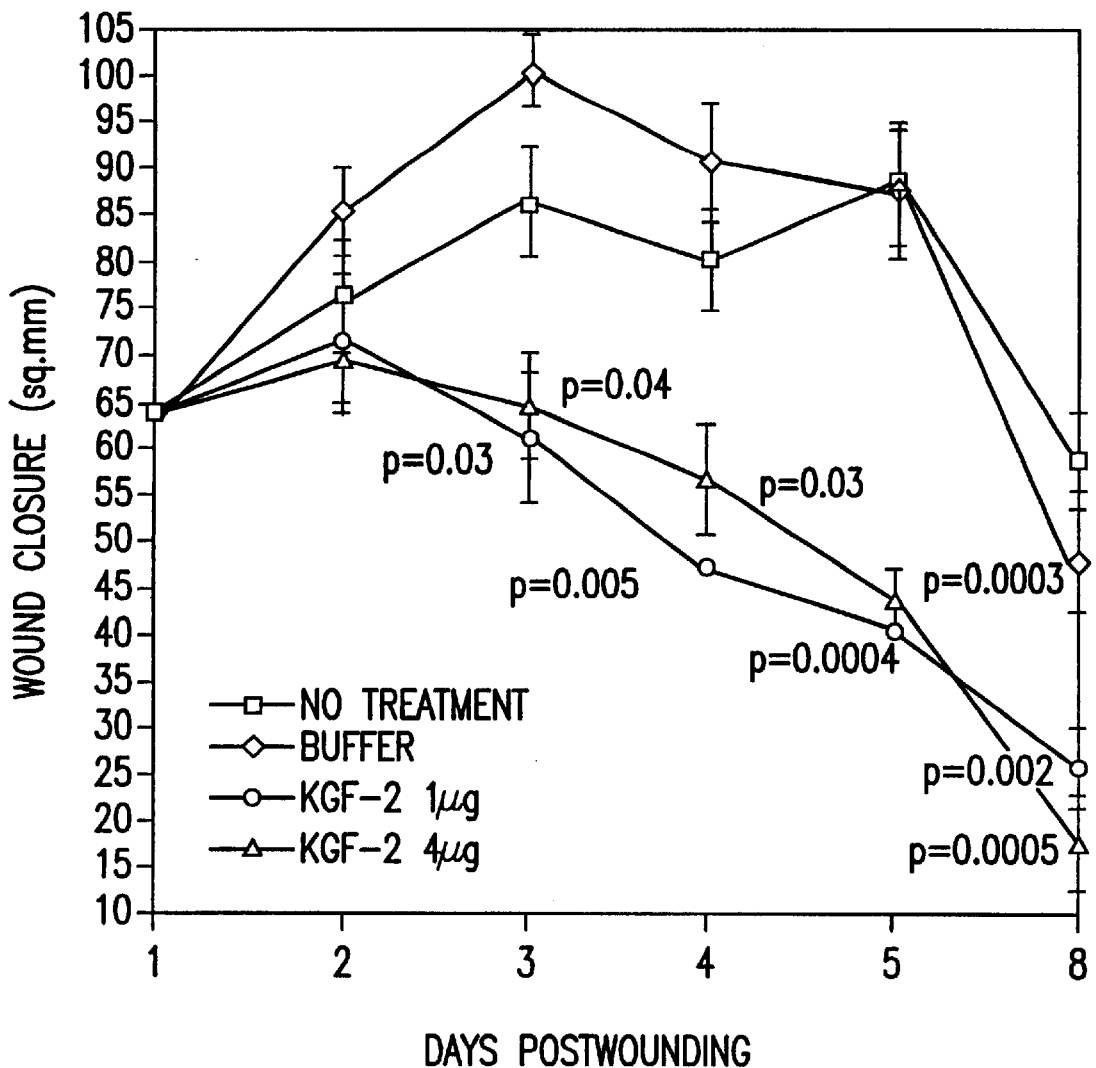
FIG. 18 shows the time course of wound healing in the glucocorticoid-impaired model of wound healing. Male SD adult rats (n=5) received dermal punch wounds (8 mm) on day 1 and were treated daily for 5 consecutive days with a buffer solution or a KGF-2 solution in 50 μL. Animals received 5 mg of methyl-prednisolone on day of wounding. Wounds were measured daily for five consecutive days commencing on day of wounding and on day 8 with a calibrated Jameson caliper. Statistical analysis was done using an unpaired t test. (Mean +/− SEM)

Longitudinal analysis of wound closure in the glucocorticoid groups from day 1 to 8 shows a significant reduction of wound size from day 3 to 8 postwounding in both doses of KGF-2 in the treated groups (FIG. 18).

Figure 19A:
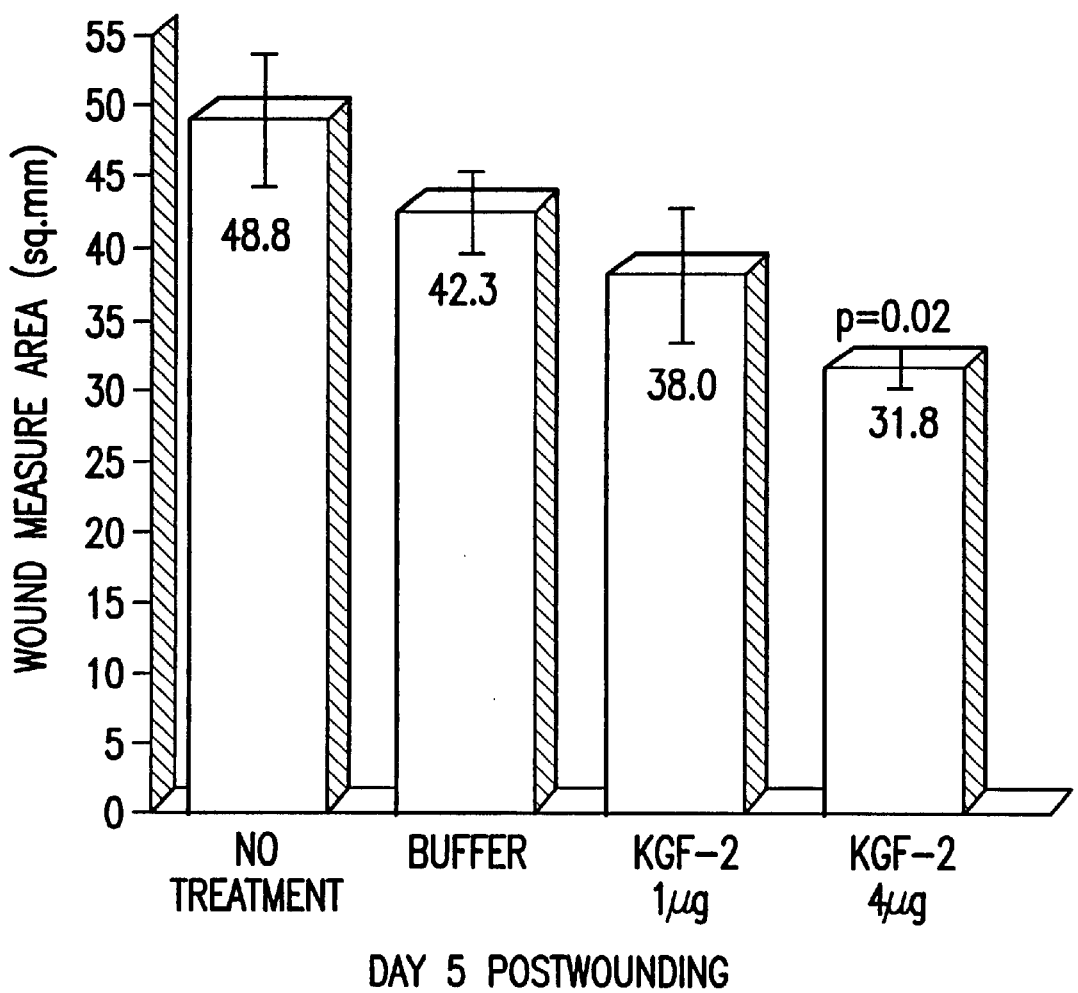
FIG. 19 (A) shows the effect of KGF-2 on wound area in rat model of wound healing without methyl-prednisolone at day 5 postwounding. Male SD rats (n=5) received dermal punch wounds (8 mm) on day 1 and were treated daily with either a buffer solution or KGF-2 in a 50 μL solution on day of wounding and thereafter for 5 consecutive days. Wounds were measured daily using a calibrated Jameson caliper. Statistical analysis was done using an unpaired t test. (Mean +/− SEM). (B) Evaluation of PDGF-BB and KGF-2 in Male SD Rats (n=6). All rats received 8 mm dorsal wounds and methylprednisolone (MP) (17 mg/kg) to impair wound healing. Wounds were treated daily with buffer or various concentrations of PDGF-BB and KGF-2. Wounds were measured on Days 2, 4, 6, 8, and 10 using a calibrated Jameson caliper. Statistical analysis was performed using an unpaired t-test. (Mean +/− SE) *Compared with buffer. **PDGF-BB 1 μg vs KGF-2/E3 1 μg.

The results demonstrate that the group treated with the 4 μg KGF-2 had statistically significant (p=0.05) accelerated wound closure compared with the untreated group (FIG. 19A). Although it is difficult to assess the ability of a protein or other compounds to accelerate wound healing in normal animal (due to rapid recovery), nonetheless, KGF-2 was shown to accelerate wound healing in this model.

Histopathologic Evaluation of KGF-2 Treated Wounds

Figure 20:
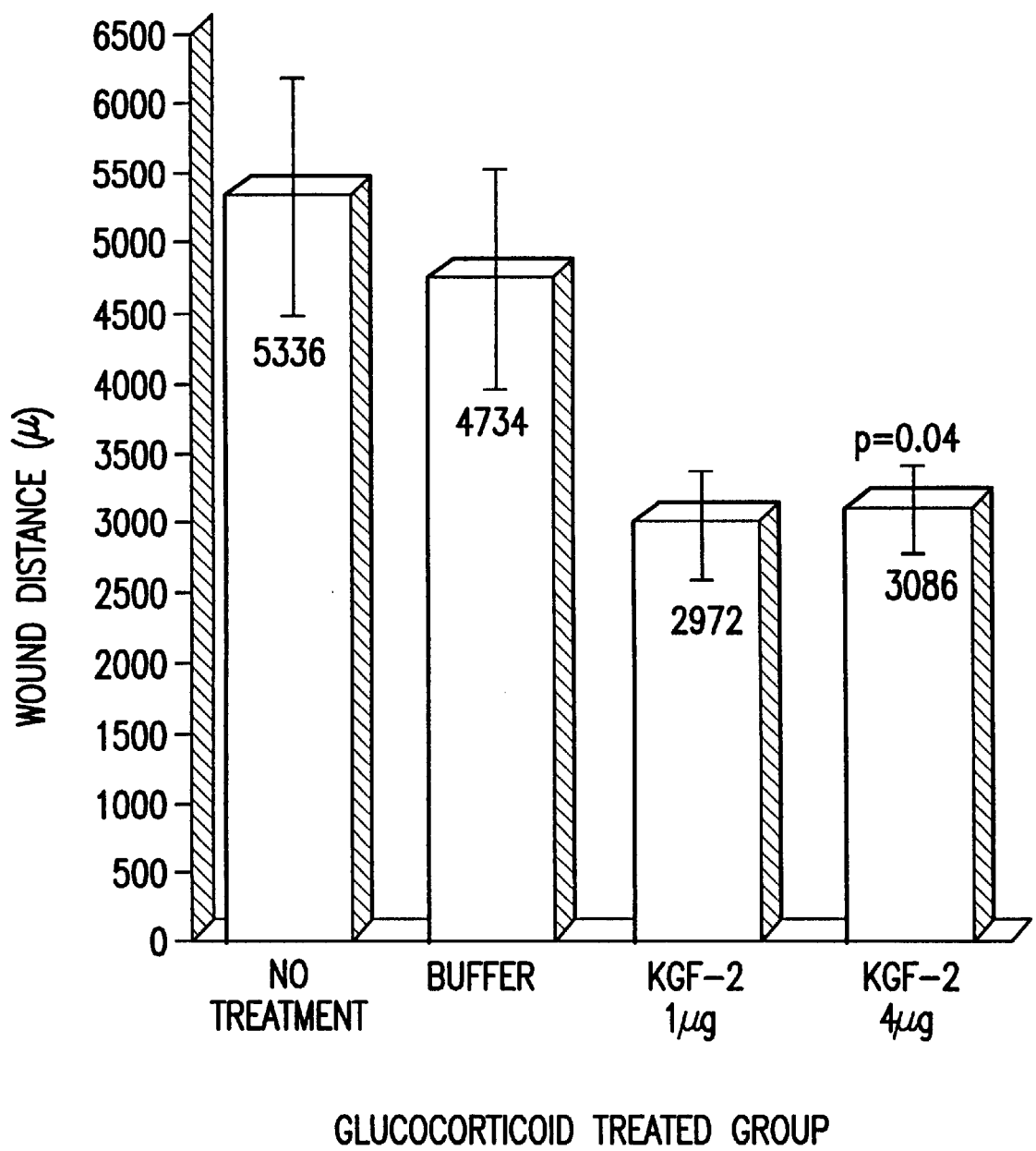
FIG. 20 shows the effect of KGF-2 on wound distance in the glucocorticoid-impaired model of wound healing. Male SD adult rats (n=5) received dermal punch wounds (8 mm) and of 17 mg/kg methyl-prednisolone on the day of wounding. Animals were treated daily with a buffer solution or KGF-2 in 50 μL of buffer solution for 5 consecutive days and on day 8. Wound distance was measured under light microscopy with a calibrated micrometer. Statistical analysis was done using an unpaired t test. (Mean +/− SEM)

Histomorphometry of the wound gap indicated a reduction in the wound distance of the KGF-2 treated group. The wound gap observed for the untreated group was 5336μ while the group treated with 1 μg KGF-2 had a wound gap reduction to 2972μ; and the group treated with 4 μg KGF-2 (p=0.04) had a wound gap reduction to 3086μ (FIG. 20).

Effects of KGF-2Δ28 in Wound Healing

Evaluation of KGF-2Δ28 and PDGF-BB in wound healing in the methylprednisolone impared rat model was also examined. The experiment was carried out the same as for the KGF-2 protein above, except that the KGF-2 Δ28 protein is not His tagged and wound healing was measured on days 2, 4, 6, 8, and 10. The buffer vehicle for the proteins was 40 mM NaOAc and 150 mM NaCl, pH6.5 for all but the "E2" preparation of the full length KGF-2. The buffer vehicle for the "E2" KGF-2 preparation was 20 mM NaOAc and 400 mM NaCl, pH6.4.

Figure 19B:
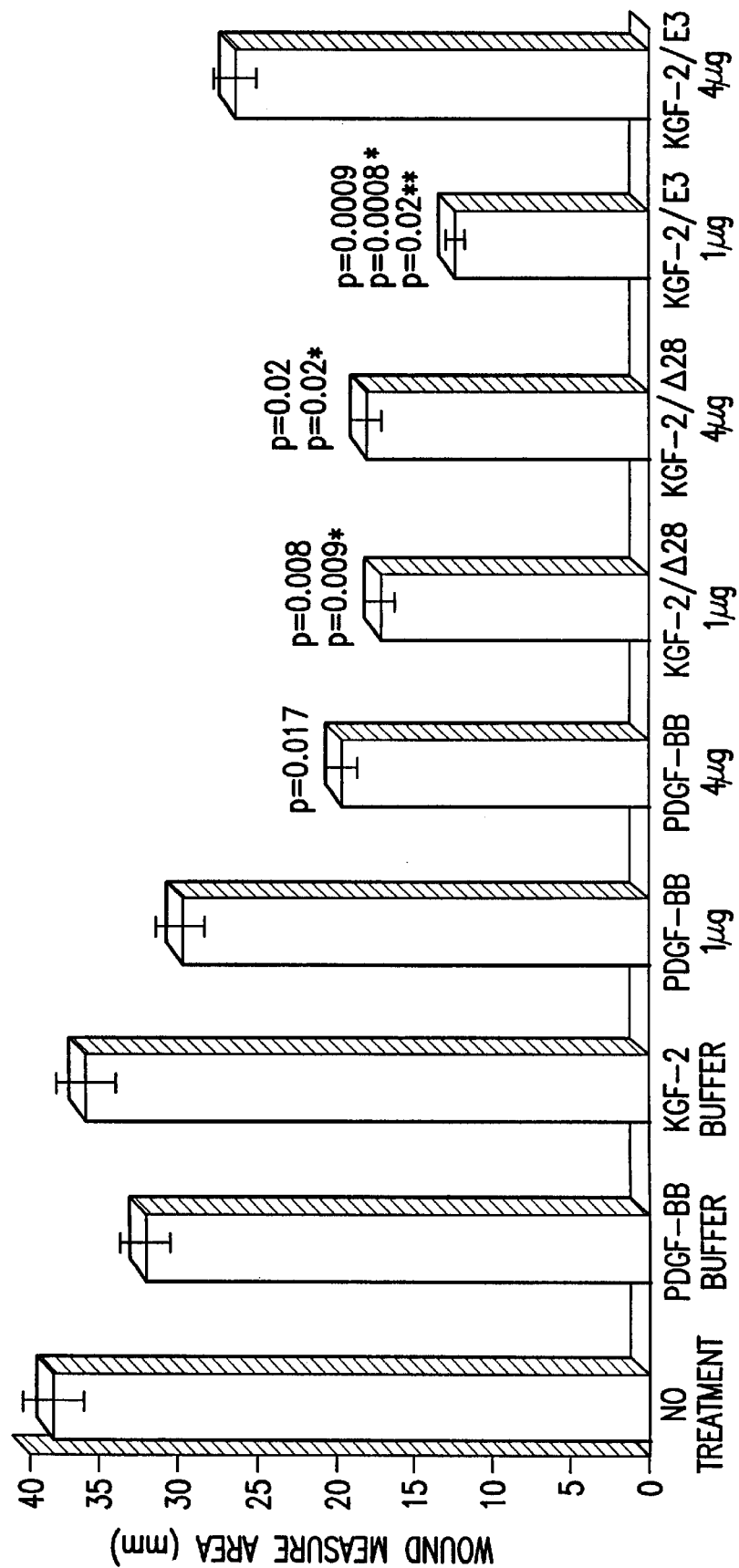

The results shown in FIG. 19B demonstrate that KGF-2Δ28 has statistically significant accelerated wound closure compared with the untreated group and has reversed the effects of methylprednisolone on wound healing.

Conclusions

This example demonstrates that KGF-2 reversed the effects of methylprednisolone on wound healing. The exogenous application of growth factors may accelerate granulation tissue formation by drawing inflammatory cells into the wound. Similar activity was also observed in animals not receiving methylprednisolone indicating that KGF-2 had significant pharmacologic response in the percentage of wound closure at day 5 based on daily measurements. The glucocorticoid-impaired wound healing model in rats was shown to be a suitable and reproducible model for measuring efficacy of KGF-2 and other compounds in the wound healing area.

In summary, the results demonstrate that KGF-2 shows significant activity in both glucocorticoid impaired and in normal excisional wound models. Therefore, KGF-2 may be clinically useful in stimulating wound healing including surgical wounds, diabetic ulcers, venous stasis ulcers, burns, and other abnormal wound healing conditions such as uremia, malnutrition, vitamin deficiencies and systemic treatment with steroids and antineoplastic drugs.

EXAMPLE 9

Tissue Distribution of KGF-2 mRNA Expression

Northern blot analysis is carried out to examine the levels of expression of the gene encoding the KGF-2 protein in human tissues, using methods described by, among others, Sambrook et al., cited above. A probe corresponding to the entire open reading frame of KGF-2 of the present invention (SEQ ID NO:1) was obtained by PCR and was labeled with $^{32}$P using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding KGF-2.

Multiple Tissue Northern (MTN) blots containing poly A RNA from various human tissues (H) or human immune system tissues (IM) were obtained from Clontech and were examined with labelled probe using ExpressHyb™ Hybridization Solution (Clontech) according to manufacturer's protocol number PT1190-1. Following hybridization and washing, the blots are mounted and exposed to film at −70° C. overnight, and films developed according to standard procedures.

A major mRNA species of approximately 4.2 kb was observed in most human tissues. The KGF-2 mRNA was relatively abundant in heart, pancreas, placenta and ovary. A minor mRNA species of about 5.2 kb was also observed ubiquitously. The identity of this 5.2 kb mRNA species was not clear. It is possible that the 5.2 kb transcript encodes an alternatively spliced form of KGF-2 or a third member of the KGF family. The KGF-2 cDNA was 4.1 kb, consistent with the size of the mRNA of 4.2 kb.

EXAMPLE 10

Keratinocyte Proliferation Assays

Dermal keratinocytes are cells in the epidermis of the skin. The growth and spreading of keratinocytes in the skin is an important process in wound healing. A proliferation assay of keratinocyte is therefore a valuable indicator of protein activities in stimulating keratinocyte growth and consequently, wound healing.

Keratinocytes are, however, difficult to grow in vitro. Few keratinocyte cell lines exist. These cell lines have different cellular and genetic defects. In order to avoid complications of this assay by cellular defects such as loss of key growth factor receptors or dependence of key growth factors for growth, primary dermal keratinocytes are chosen for this assay. These primary keratinocytes are obtained from Clonetics, Inc. (San Diego, Calif.).

Keratinocyte Proliferation Assay With AlamarBlue

AlamarBlue is a viable blue dye that is metabolized by the mitochondria when added to the culture media. The dye then turns red in tissue culture supernatants. The amounts of the red dye may be directly quantitated by reading difference in optical densities between 570 nm and 600 nm. This reading reflects cellular activities and cell number.

Normal primary dermal keratinocytes (CC-0255, NHEK-Neo pooled) are purchased from Clonetics, Inc. These cells are passage 2. Keratinocytes are grown in complete keratinocyte growth media (CC-3001, KGM; Clonetics, Inc.) until they reach 80% confluency. The cells are trypsinized according to the manufacturer's specification. Briefly, cells were washed twice with Hank's balanced salt solution. 2–3 ml of trypsin was added to cells for about 3–5 min at room temperature. Trypsin neutralization solution was added and cells were collected. Cells are spun at 600×g for 5 min at room temperature and plated into new flasks at 3,000 cells per square centi-meter using pre-warmed media.

For the proliferation assay, plate 1,000–2,000 keratinocytes per well of the Corning flat bottom 96-well plates in complete media except for the outermost rows. Fill the outer wells with 200 µl of sterile water. This helps to keep temperature and moisture fluctuations of the wells to the minimum. Grow cells overnight at 37° C. with 5% $CO_2$. Wash cells twice with keratinocyte basal media (CC-3101, KBM, Clonetics, Inc.) and add 100 µl of KBM into each well. Incubate for 24 hours. Dilute growth factors in KBM in serial dilution and add 100 µl to each well. Use KGM as a positive control and KBM as a negative control. Six wells are used for each concentration point. Incubate for two to three days. At the end of incubation, wash cells once with KBM and add 100 µl of KBM with 10% v/v alamarBlue pre-mixed in the media. Incubate for 6 to 16 hours until media color starts to turn red in the KGM positive control. Measure O.D. 570 nm minus O.D. 600 nm by directly placing plates in the plate reader.

Results

Stimulation of Keratinocyte Proliferation by KGF-2

Figure 21A:
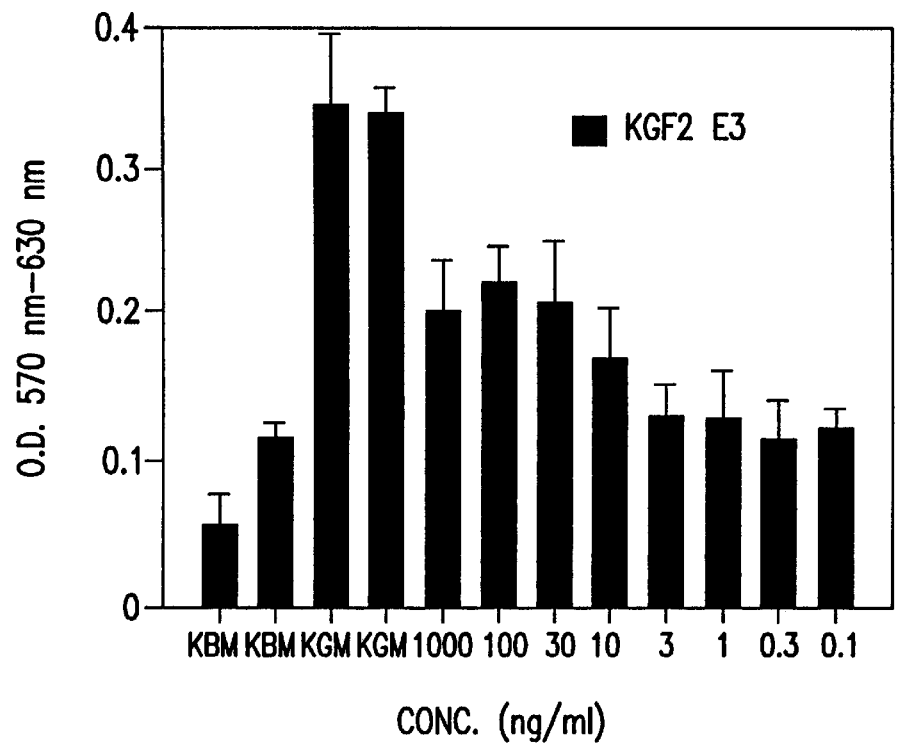
FIG. 21 (A) shows the stimulation of normal primary epidermal keratinocyte proliferation by KGF-2. (B) shows the stimulation of normal primary epidermal keratinocyte proliferation by KGF-2 Δ33. (C) shows the stimulation of normal primary epidermal keratinocyte proliferation by KGF-2 Δ28. Human normal primary epidermal keratinocytes were incubated with various concentrations of KGF-2, KGF-2 Δ33 or KGF-2 Δ28 for three days. For all three experiments alamarBlue was then added for 16 hr and the intensity of the red color converted from alamarBlue by the cells was measured by the difference between O.D. 570 nm and O.D. 600 nm. For each of the KGF-2 proteins a positive control with complete keratinocyte growth media (KGM), and a negative control with keratinocyte basal media (KBM) were included in the same assay plate.
Figure 21B:
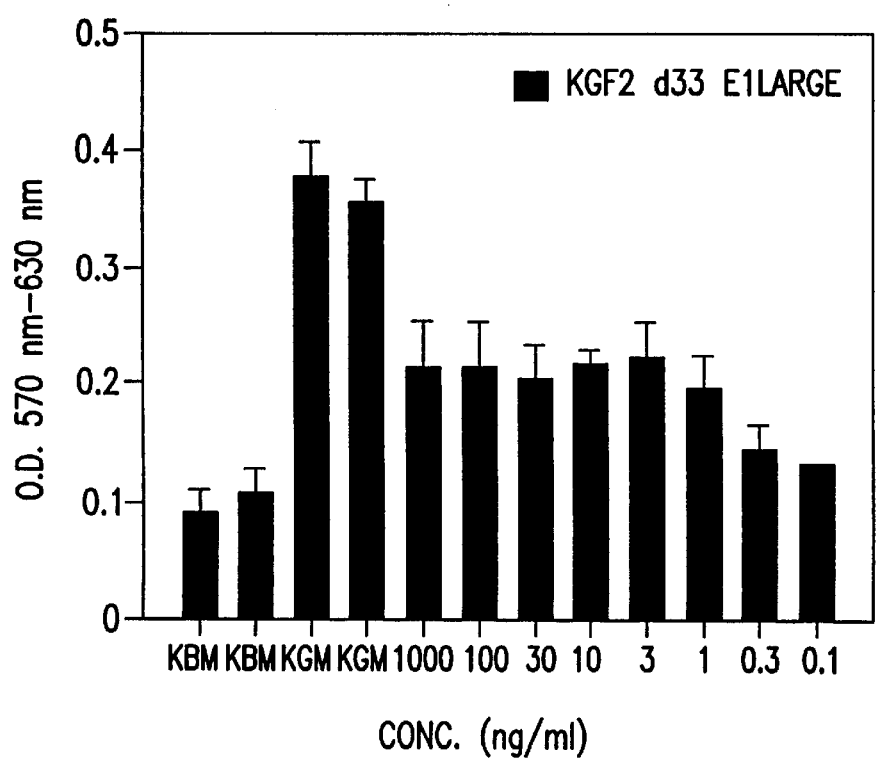
Figure 21C:
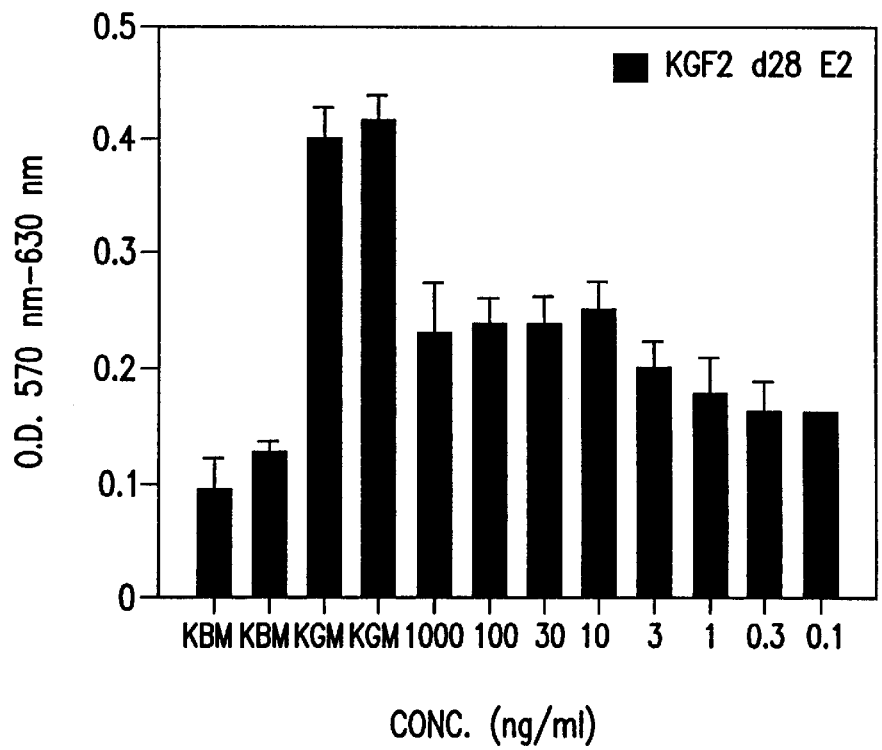

To demonstrate that KGF-2 (i.e., starting at amino acid Cys37 as described in Examples 7 and 8 above) and N-terminal deletion mutants KGF-2Δ33 and KGF-2Δ28 were active in stimulating epidermal keratinocyte growth, normal primary human epidermal keratinocytes were incubated with the E. coli-expressed and purified KGF-2 protein (batch number E3)(SEQ ID NO:2), KGF-2Δ33 (batch number E1) and KGF-2Δ28 (batch number E2). The KGF-2 protein stimulated the growth of epidermal keratinocytes with an EC50 of approximately 5 ng/ml, equivalent to that of FGF7/KGF-1 (FIG. 21A). In contrast, other FGF's such as FGF-1 and FGF-2 did not stimulate the growth of primary keratinocytes. The EC50 for KGF-2Δ33 was 0.2 ng/ml and that for KGF-2Δ28 2ng/ml (See FIGS. 21B and C). Thus, KGF-2 appeared to be as potent as FGF7/KGF in stimulating the proliferation of primary epidermal keratinocytes. However, KGF-2Δ33 is more potent in stimulating keratinocyte proliferation than the "Cys (37)" KGF-2 described in Examples 7 and 8 above and the KGF-2Δ28.

Scarring of wound tissues involves hyperproliferation of dermal fibroblasts. To determine whether the stimulatory effects of KGF-2 was specific for keratinocytes but not for fibroblasts, mouse Balb.c.3T3 fibroblsts and human lung fibroblasts were tested. Niether types of fibroblasts responded to KGF-2 in proliferation assays. Therefore, KGF-2 appeared to be a mitogen specific for epidermal keratinocytes but not mesenchymal cells such as fibroblasts. This suggested that the likelyhood of KGF-2 causing scarring of the wound tissues was low.

EXAMPLE 11

A. Mitogenic Effects of KGF-2 on Cells Transfected With Specific FGF Receptors

To determine which FGF receptor isoform(s) mediate the proliferative effects of KGF-2, the effects of KGF-2 on cells expressing specific FGF receptor isoforms were tested according to the method described by Santos-Ocampo et al. *J. Biol. Chem.* 271:1726–1731 (1996). FGF7/KGF was known to induce mitogenesis of epithelial cells by binding to and specifically activating the FGFR2iiib form (Miki et al. *Science* 251:72–75 (1991)). Therefore, the proliferative effects of KGF-2 in mitogensis assays were tested using cells expressing one of the following FGF receptor isoforms: FGFR1iiib, FGFR2iiib, FGFR3iiib, and FGFR4.

Mitopensis Assay of Cells Expressing FGF Receptors

Thymidine incorporation of BaF3 cells expressing specific FGF receptors were performed as described by Santos-Ocampo et al. *J. Biol. Chem.* 271:1726–1731(1996). Briefly, BaF3 cells expressing specific FGF receptors were washed and resuspended in Dulbecco's modified Eagle's medium, 10% neonatal bovine serum, L-glutanime. Approximately 22,500 cells were plated per well in a 96-well assay plate in media containing 2 µg/ml Heparin. Test reagents were added to each well for a total volume of 200 µl per well. The cells were incubated for 2 days at 37° C. To each well , 1 µCi of $^3$H-thymidine was then added in a volume of 50 µl. Cells were harvested after 4–5 hours by filteration through glass fiber paper. Incorporated $^3$H-thymidine was counted on a Wallac beta plate scintillaion counter.

Results

The results revealed that KGF-2 protein (Thr (36)-Ser (208) of FIG. 1 (SEQ ID NO:2) with a N-terminal Met added thereto) strongly stimulated e the proliferation of Baf3 cells expressing the KGF receptor, FGFR2iiib isoform, as indicated by $^3$H-thymidine incorporation (FIG. 22A). Interestingly, a slight stimulatory effect of KGF-2 on the proliferation of Baf3 cells expressing the FGFR1iiib isoform was observed. KGF-2 did not have any effects on cells expressing the FGFR3iiib or the FGFR4 forms of the receptor.

FGF7/KGF stimulated the proliferation of cells expressing the KGF receptor, FGFR2iiib but not FGFR1iiib isoform. The difference between KGF-2 and FGF7/KGF was intriguing. In the control experiments, aFGF stimulated its receptors, FGFR1iiib and iiic and bFGF stimulated its receptor FGFR2iiic. Thus, these results suggested that KGF-2 binds to F(3FR2iiib isoform and stimulates mitogenesis. In contrast to FGF7/KGF, KGF-2 also binds FGFR1iiib isoform and stimulates mitogenesis.

B. Mitogenic Effects of KGF-2Δ33 on Cells Transfected With Specific FGF Receptors As demonstrated above FGFs or KGF-1 and -2 both bind to and activate the FGF2iiib receptor (FGFR2iiib). The proliferative effects of KGF-2Δ33 in mitogenesis assays were tested using cells expressing one of the following FGF receptor isoforms: FGFR2iiib or FGFR2iiic (the 2iiic receptor-transfected cells are included as a negative control).

The experiments were performed as above in part A of this example.

Briefly, BaF3 cells were grown in RPMI containing 10% bovine calf serum (BCS—not fetal serum), 10% conditioned medium from cultures of WEHI3 cells (grown in RPMI containing 5%BCS), 50 nM β-mercaptoethanol, L-Glu (2% of a 100×stock) and pen/strep (1% of a 100×stock).

For the assay, BaF3 cells were rinsed twice in RPMI medium containing 10% BCS and 1 µg/ml heparin. BaF3 cells (22,000/well) were plated in a 96-well plate in 150 µl of RPMI medium containing 10% BCS and 1 µg/ml heparin. Acidic FGF, basic FGF, KGF-1 (HG15400) or KGF-2 proteins (HG03400, 03401, 03410 or 03411) were added at concentrations from approximately 0 to 10 nM. The cells were incubated in a final volume of 200 µl for 48 hours at 37° C. All assays were done in triplicate. Tritiated thymidine (0.5 µCi) was added to each well for 4 hours at 37° C. and the cells were then harvested by filtration through a glass fiber filter. The total amount of radioactivity incorporated was then determined by liquid scintillation counting. The following positive controls were used: basic FGF and acidic FGF for FGFR2iiic cells; acidic FGF and KGF-1 for FGFR2iiib cells. The following negative controls were used: Basal medium (RPMI medium containing 10% BCS and 1 µg/ml heparin).

Results

Figure 22B:
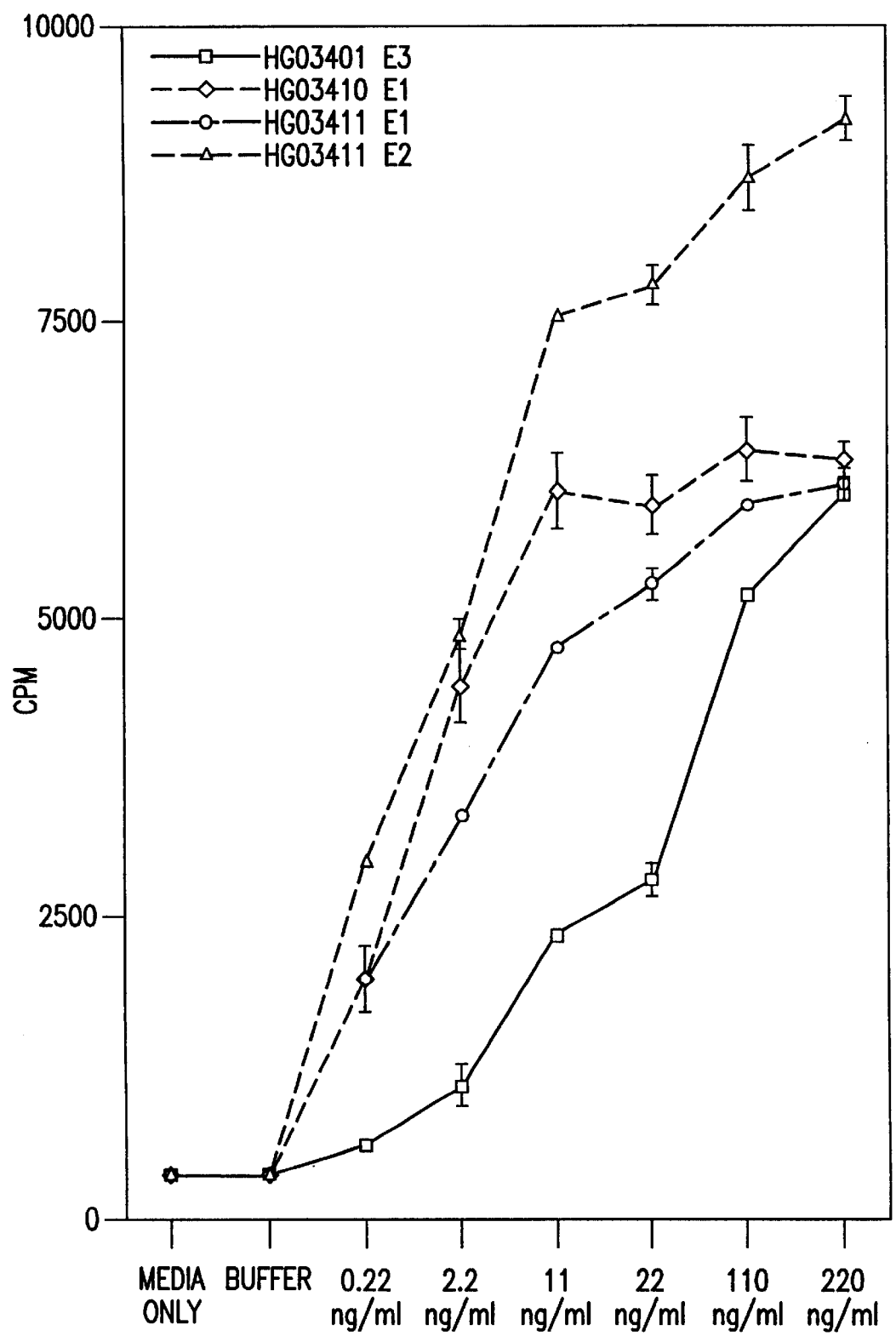
Figure 22C:
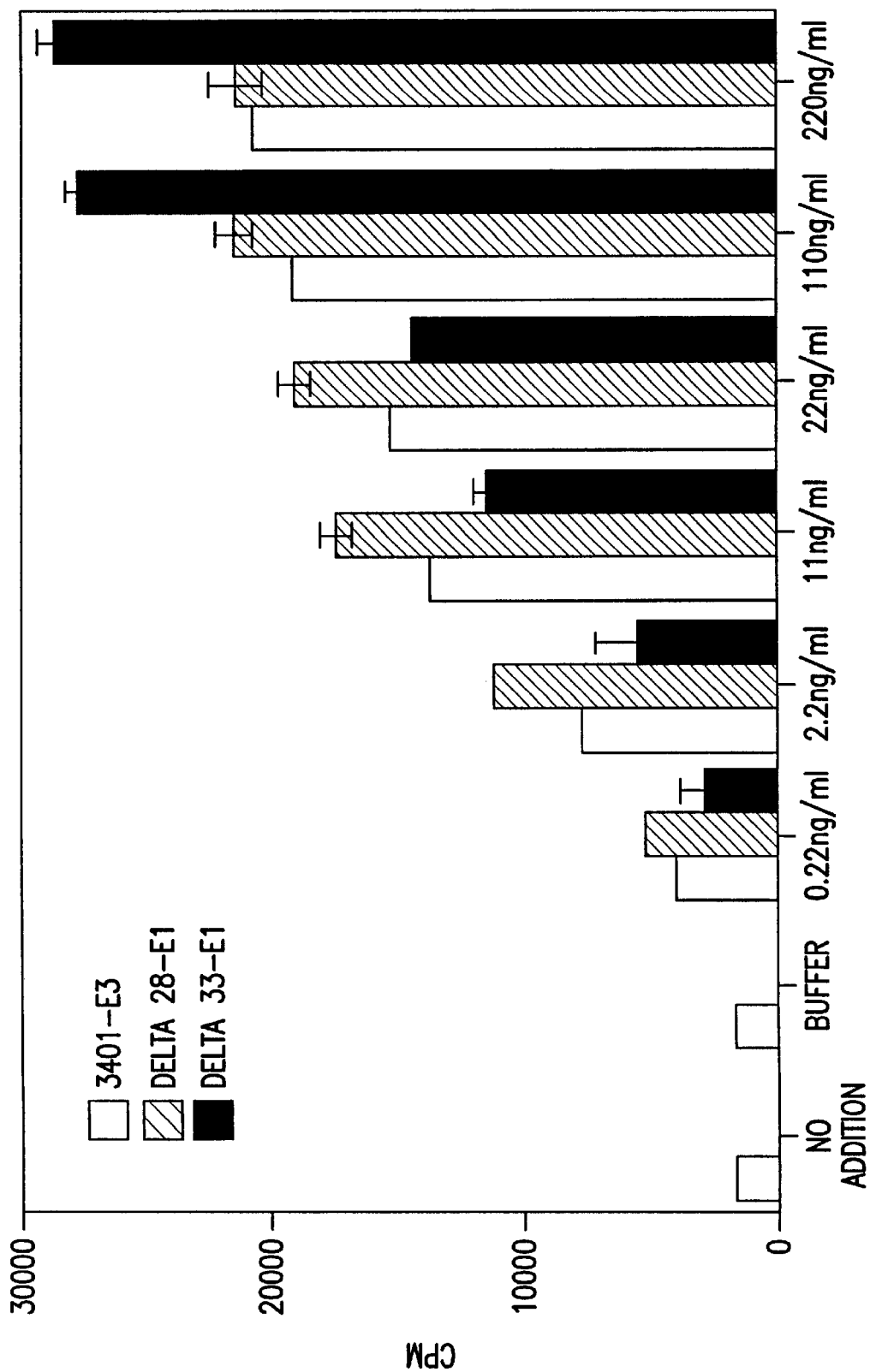

The results revealed that KGF-2 (Thr (36)-Ser (208) with N-terminal Met added), KGF-2Δ33 and KGF-2Δ28 proteins strongly stimulated the proliferation of BaF3 cells expressing the KGF receptor, FGFR2iiib isoform, as indicated by $^3$H-thymidine incorporation (FIGS. 22A–C). The KGF-2 proteins did not have any effects on cells expressing the FGFR2iiic forms of the receptor. These results suggested that KGF-2 proteins bind to FGFR2iiib isoform and stimulates mitogenesis. In addition, it appears that KGF-2Δ33 was able to stimulate the proliferation of the BaF3 cells better than the KGF-2 (Thr (36)-Ser (208)).

EXAMPLE 12

A. Construction of *E. coli* Optimized Full Length KGF-2

In order to increase expression levels of full length KGF-2 in an *E. coli* expression system, the codons of the amino terminal portion of the gene were optimized to highly used *E. coli* codons. For the synthesis of the optimized region of KGF-2, a series of six oligonucleotides were synthesized: numbers 1–6 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

A second PCR reaction was set up using 1 µl of the first PCR reaction with KFG-2 synthetic primer 6 as the 3' primer and KGF-2 synthetic 5' BamHI as the 5' primer using the same conditions as described above for 25 cycles. The product produced by this final reaction was restricted with AvaII and BamHI. The KGF-2 construct of Example 1 was restricted with AvaII and HindIII and the fragment was isolated. These two fragments were cloned into pQE-9 restricted with BamHI and HindIII in a three fragment ligation.

Primers used for constructing the optimized synthetic KGF-2 1/208:

KGF-2 Synthetic Primer 1:
A T G T G G A A A T G G A T A C T G A C C C A C T-GCGCTTCTGCTTTCCCGCACC

T G C C G G G T-TGCTGCTGCTGCTTCCTGCTGCTGTTC (SEQ ID NO: 31)

KGF-2 Synthetic Primer 2:
C C G G A G A A A C C A T G T C C T G A C C C A G A G C-CTGGCAGGTAACCGGAA

C A G A A G A A A C C A G G A A C A G C A G C A G-GAAGCAGCAGCA (SEQ ID NO: 32)

KGF-2 Synthetic Primer 3:
  GGGTCAGGACATGGTTTCTCCGGAAGC-
    TACCAACTCTTCTTCTTCTT
  CTTTCTCTTCTCCGTCTTCTGCTGGTCGTCACG
    (SEQ ID NO: 33)
KGF-2 Synthetic Primer 4:
  GGTGAAAGAGAACAGTTTACGCCAAC-
    GAACGTCACCCTGCAGGTG
  GTTGTAAGAACGAACGTGACGACCAGCA-
    GAAGACGG (SEQ ID NO:34)
KGF-2 Synthetic Primer 5:
  CGTTGGCGTAAACTGTTCTCTTTCAC-
    CAAATACTTCCTGAAAATCGA
  AAAAAACGGTAAAGTTTCTGGGACCAAA (SEQ ID NO:35)
KGF-2 Synthetic Primer 6:
  TTTGGTCCCAGAAACTTTAC-
    CGTTTTTTTCGATTTTCAG (SEQ ID NO:36)
KGF-2 Synthetic 5' BamHI
  AAAGGATCCATGTGGAAATGGATACT-
    GACCCACTGC (SEQ ID NO:37)
The Resulting Clone is Shown in FIG. 23 (SEQ ID NOS: 38 and 39).

B. Construction of *E. coli* Optimized Mature KGF-2

In order to further increase expression levels of the mature form of KGF-2 in an *E. coli* expression system, the codons of the amino terminal portion of the gene were optimized to highly used *E. coli* codons. To correspond with the mature form of KGF-1, a truncated form of KGF-2 was constructed starting at threonine 36. *E. coli* synthetic KGF-2 from Example 12A was used as a template in a PCR reaction using BspHI 5' KGF-2 as the 5' primer (sequence given below) and HindIII 3' KGF-2 as the 3' primer (sequence given below). Amplification was performed using standard conditions as given above in Example 12A for 25 cycles. The resulting product was restricted with BspHI and HindII and cloned into the *E. coli* expression vector pQE60 digested with NcoI and HindIII.

BspHI 5' KGF-2 Primer:
  TTTCATGACTTGTCAAGCTCTGGGTCAA-
    GATATGGTTC (SEQ ID NO:40)
HindIII 3' KGF-2 Primer:
  GCCCAAGCTTCCACAAACGTTGCCTTCC (SEQ ID NO:41)
The resulting clone is shown in FIG. 24A (SEQ ID NO:42 and 43).

C. Construction of an Alternate *E. coli* Optimized Mature KGF-2

In order to further increase expression levels of the mature form of KGF-2 in an *E. coli* expression system, the codons of 53 amino acids at the amino terminal portion of the *E. coli* optimized gene were changed to alternate highly used *E. coli* codons. For the synthesis of the optimized region of KGF-2, a series of six oligonucleotides were synthesized: numbers 18062, 18061, 18058, 18064, 18059, and 18063 (sequences set forth below). These overlapping oligos were used in a PCR reaction for seven rounds at the following conditions:

| Denaturation | 95 degrees | 20 seconds |
| Annealing | 58 degrees | 20 seconds |
| Extension | 72 degrees | 60 seconds |

Following the seven rounds of synthesis, a 5' primer to this region, 18169 and a 3' primer to this entire region, 18060, were added to a PCR reaction, containing 1 microliter from the initial reaction of the six oligonucleotides. This product was amplified for 30 rounds using the following conditions:

| Denaturation | 95 degrees | 20 seconds |
| Annealing | 55 degrees | 20 seconds |
| Extension | 72 degrees | 60 seconds |

A second PCR reaction was set up to amplify the 3' region of the gene using primers 18066 and 18065 under the same conditions as described above for 25 rounds. The resulting products were separated on an agarose gel. Gel slices containing the product were diluted in 10 mM Tris, 1 mM EDTA, pH 7.5 One microliter each from each of diluted gel slices were used in an additional PCR reaction using primer 18169 as the 5' primer, and primer 18065 as the 3' primer. The product was amplified for 25 cycles using the same conditions as above. The product produced by this final reaction was and restricted with Eco R1 and HindIII, and cloned into pQE60, which was also cut with Eco R1 and HindIII (pQE6 now).

Sequences of the 5' Synthetic Primers:
18169 KGF2 5' EcoRI/RBS:
  TCAGTGAATTCATTAAAGAGGAGAAAT-
    TAATCATGACTTGCCAGG [SEQ ID NO:44]
18062 KGF2 Synth new R1 Sense:
  TCATGACTTGCCAGGCACTGGGTCAAGA-
    CATGGTTTCCCCGGAAGCTA [SEQ ID NO:45]
18061 KGF2 Synth R2 Sense:
  GCTTCAGCAGCCCATCTAGCGCAG-
    GTCGTCACGTTCGCTCTTACAACC [SEQ ID NO:46]
18058 KGF2 Synth R3 Sense:
  GTTCGTTGGCGCAAACTGTTCAGCTT-
    TACCAAGTACTTCCTGAAAATC [SEQ ID NO:47]
18066 KGF 2 20 bp Ava II Sense:
  TCGAAAAAAACGGTAAAGTTTCTGGGAC [SEQ ID NO:48]
18064 KGF2 synth F1 Antisense:
  GATGGGCTGCTGAAGCTAGAGCTG-
    GAGCTGTTGGTAGCTTCCGGGG AA [SEQ ID NO:49]
18059 KGF2 Synth F2 Antisense:
  AACAGTTTGCGCCAACGAACATCACCCT-
    GTAAGTGGTTGTAAGAG [SEQ ID NO:50]
18063 KGF2 Synth F3 Antisense:
  TTCTTGGTCCCAGAAACTTTAC-
    CGTTTTTTTCGATTTTCAGGAAGTA [SEQ ID NO:51]
18060 KGF 2 Ava II Antisense:
  TTCTTGGTCCCAGAAACTTTACCG [SEQ ID NO:52]
18065 KGF2 HindIII 3' Stop:
  AGATCAGGCTTCTATTATTATGAGTG-
    TACCACCATTGGAAGAAAG [SEQ ID NO:53]

The sequence of the synthetic KGF-2 gene and it corresponding amino acid is shown in FIG. 24B (SEQ ID NO: 54 and 55)

EXAMPLE 13

Construction of KGF-2 Deletion Mutants

Deletion mutants were constructed from the 5' terminus and 3' terminus of KGF-2 gene using the optimized KGF-2 construct from Example 12A as a template. The deletions were selected based on regions of the gene that might negatively affect expression in *E. coli*. For the 5' deletion the primers listed below were used as the 5' primer. These primers contain the indicated restriction site and an ATG to code for the initiator methionine. The KGF-2 (FGF-12) 208 amino acid 3' HindIII primer was used for the 3' primer. PCR amplification for 25 rounds was performed using standard conditions as set forth in Example 12. The products for the KGF-2 36aa/208aa deletion mutant were restricted BspHI for the 5' site and HindIII for the 3' site and cloned into the pQE60 which has been digested with BspHI and HindIII. All other products were restricted with NcoI for the 5' restriction enzyme and HindIII for the 3' site, and cloned into the pQE60 which had been digested with NcoI and HindIII. For KGF-2 (FGF-12), 36aa/153aa and 128aa 3' HindIII was used as the 3' primer with FGF-12 36aa/208aa as the 5' primer. For FGF-12 62aa/153aa, 128aa 3' HindIII was used as the 3' primer with FGF-12 62aa/208aa as the 5' primer. The nomenclature of the resulting clones indicates the first and last amino acid of the polypeptide that results from the deletion. For example, KGF-2 36aa/153aa indicates that the first amino acid of the deletion mutant is amino acid 36 and the last amino acid is amino acid 153 of KGF-2. Further, as indicated in FIGS. 25–33, each mutant has N-terminal Met added thereto.

Sequences of the Deletion Primers:
FGF12 36aa/208aa:
  5' BsphI GGACCCTCATGACCTGCCAG-GCTCTGGGTCAGGAC [SEQ ID NO:56]
FGF12 63aa/208aa:
  5' NcoI GGACAGCCATGGCTGGTCGTCACGTTCG [SEQ ID NO:57]
FGF12 77aa/208aa:
  5' NcoI GGACAGCCATGGTTCGTTGGCGTAAACTG [SEQ ID NO:58]
FGF12 93aa/208aa:
  5' NcoI GGACAGCCATGGAAAAAACGG-TAAAGTTTC [SEQ ID NO:59]
FGF12 104aa/208aa:
  5' NcoI GGACCCCCATGGAGAACTGCCCGTAGAGC [SEQ ID NO:60]
FGF12 123aa/208aa:
  5' NcoI GGACCCCCATGGTCAAAGCCATTAACAG-CAAC [SEQ ID NO:61]
FGF12 138aa/208aa:
  5' NcoI GGACCCCCATGGGGAAACTCTATGGCT-CAAAAG [SEQ ID NO:62]
FGF12 3' HindIII: (Used for all Above Deletion Clones)
  CTGCCCAAGCTTATTATGAGTGTACCAC-CATTGGAAG [SEQIDNO:63]
FGF12 36aa/153aa:
  5' BsphI (as above)
  3' HindIII CTGCCCAAGCTTATTACTTCAGCTTA-CAGTCATTGT [SEQ ID NO:64]
FGF12 63aa/153aa:
  5'NcoI and 3' HindIII, as above The sequences for the resulting deletion mutations are set forth in FIGS. 25–33. [SEQ ID NOS:65–82].

When expressing KGF-2 Δ28 (amino acids 63–208) in *E. coli*, a protease inhibitor, such as Guanidine Hydrochloride (Gu-HCl), is used prevent degradation of the protein. For example, the *E. coli* paste is resuspended in 50 mM Tris-Acetate, 10 mM EDTA-NA$_2$, pH 7.7±0.2 followed by lysis. The lysed suspension is treated with an equal volume of 1.0 M Gu-HCl solution and gently stirred for 2–4 hours at 2–8° C. The suspension is then centrifuges and filtered before loading onto the first column for purification. Initial purification takes place on a SP-Sepharose FF column wherein the bound KGF-2 is eluted with a salt gradient. The resulting SP-Sepharose elution pool is diluted and 0.2 μm filtered and loaded onto a Fractogel COO⁻(S) column. Elution is carried out through a salt gradient and the elution pool is diafiltered and concentrated into a buffer.

EXAMPLE 14

Construction of Cysteine Mutants of KGF-2

Construction of C-37 mutation primers 5457 5' BsphI and 5258 173aa 3' HindIII were used to amplify the KGF-2 (FGF-12) template from Example 12A. Primer 5457 5' BsphI changes cysteine 37 to a serine. Amplification was done using the standard conditions outlined above in Example 12A for 25 cycles. The resulting product was restricted with BspHI and HindIII and cloned into *E. coli* expression vector pQE60, digested with BspHI and HindIII. (FIG. 34) [SEQ ID NO:83].

For mutation of Cysteine 106 to serine, two PCR reactions were set up for oligonucleotide site directed mutagenesis of this cysteine. In one reaction, 5453 BsphI was used as the 5' primer, and 5455 was used as the 3' primer in the reaction. In a second reaction, 5456 was used as the 5' primer, and 5258 HindIII was used as the 3' primer. The reactions were amplified for 25 rounds under standard conditions as set forth in Example 12. One microliter from each of these PCR reactions was used as template in a subsequent reaction using, as a 5' primer, 5453 BsphI, and as a 3' primer, 5258 HindIII. Amplification for 25 rounds was performed using standard conditions as set forth in Example 12. The resulting product was restricted with BspHI and HindIII and cloned into the *E. coli* expression vector pQE60, which was restricted with NcoI and HindIII.

Two PCR reactions were required to make the C-37/C-106 mutant. Primers 5457 Bsph1 and 5455 were used to create the 5' region of the mutant containing cysteine 37 to serine substitution, and primer 5456 and 5258 HindIII were used to create the 3' region of the mutant containing cysteine 106 to serine substitution. In the second reaction, the 5457 BsphI primer was used as the 5' primer and the 5258 HindIII primer was used as the 3' primer to create the C-37/C-106 mutant using 1 μl from each of the initial reactions together as the template. This PCR product was restricted with BsphI and HindIII, and cloned into pQE60 that had been restricted with NcoI and HindIII. The resulting clone is shown in FIG. 35 (SEQ ID NO:84)

Sequences of the Cysteine Mutant Primers:
  5457 BspHI: GGACCCTCATGACCTCTCAG-GCTCTGGGT (SEQ ID NO:85)
  5456: AAGGAGAACTCTCCGTACAGC (SEQ ID NO: 86)
  5455: GCTGTACGGTCTGTTCTCCTT (SEQ ID NO: 87)
  5453 BspHI: GGACCCTCATGACCTGCCAG-GCTCTGGGTCAGGAC (SEQ ID NO: 88)
  5258 HindIII: CTGCCCAAGCTTATTATGAGTGTAC-CACCATTGGAAG (SEQ ID NO: 89)

EXAMPLE 15

Production and Purification of KGF-2 (FGF-12)

The DNA sequence encoding the optimized mature protein described in Example 12B (i.e., amino acids T36 through S208 of KGF-2) was cloned into plasmid pQE-9 (Qiagen). *E. coli* (M15/rep4;Qiagen) were grown to stationary phase overnight at 37° C. in LB containing 100 μg/ml Ampicillin and 25 μg/ml Kanamycin. This culture was used to innoculate fresh LB media containing containing 100 μg/ml Ampicillin and 25 μg/ml Kanamycin at a dilution of 1:50. The cells were grown at 37° C. to an O.D.$_{595}$ of 0.7, induced by the addition of isopropyl 1-thio-b-D-galactopyranoside (IPTG) to a final concentration of 1 mM. After 3–4 hours, the cells were harvested by centrifugation, and resuspended in a buffer containing 60 mM NaPO$_4$ and 360 mM NaCl at a ratio of 5 volumes of buffer: 1 volume of cell paste. After disruption in a Mautin Gaulin, the extract was adjusted to pH to 8.0 by the addition of NaOH and clarified by centrifugation.

The clarified soluble extract was applied to a Poros HS-50 column (2.0×10.0 cm; PerSeptive Biosystems, Inc.) and bound proteins step-eluted with 50 mM NaPO$_4$ pH 8.0 containing 0.5M, 1.0M and 1.5M NaCl. The KGF-2 eluted in the 1.5M salt fraction which was then diluted five-fold with 50 mM NaPO$_4$ pH 6.5 to a final salt concentration of 300 mM. This KGF-2 containing fraction was then passed sequentially over a Poros HQ-20 column (2.0×7.0 cm; PerSeptive Biosystems, Inc.) and then bound to a Poros CM-20 column (2.0×9.0 cm; PerSeptive Biosystems, Inc.). KGF-2 (FGF-12)-containing fractions that eluted at about 500 mM to about 750 mM NaCl were pooled, diluted and re-applied to an CM-20 column to concentrate. Finally, the protein was seperated on a gel filtration column (S-75; Pharmacia) in 40 mM NaOAC pH6.5; 150 mM NaCl (Batch E-5) Alternatively, the gel filtration column was run in Phosphate Buffered Saline (PBS, Batch E-4). KGF-2 containing fractions were pooled and protein concentration determined by Bio-Rad Protein Assay. Proteins were judged to be >90% pure by SDS-PAGE. Finally, endotoxin levels determined by Limulus Amebocyte Lysate Assay (Cape Cod Associates) were found to be ≦1 Eu/mg. Proteins prepared in this way were able to bind heparin which is a hallmark of FGF family members.

EXAMPLE 16
A. Construction of N-Terminal Deletion Mutant KGF-2Δ33

To increase the level of expression of KGF2 in *E.coli*, and to enhance the solubilty and stability properties of *E.coli* expressed KGF2, a deletion variant KGF-2Δ33 (KGF-2 aa 69–208) (SEQ ID NO:96) which removes the first 68 amino acids of the pre-processed KGF-2 was generated. The rationale for creating this deletion variant was based on the following observations. Firstly, mature KGF2 (KGF-2 aa 36–208) contains an uneven number (three) of cysteine residues which can lead to aggregation due to intra-molecular disulphide bridge formation. The KGF Δ33 deletion variant contains only two cysteine residues, which reduces the potential for intra-molecular disulphide bridge formation and subsequent aggregation. A decrease in aggregation should lead to an increase in the yield of active KGF2 protein. Secondly, the KGF Δ33 deletion variant removes a poly-serine stretch which is not present in KGF-1 and does not appear to be important for activity, but may hinder expression of the protein in *E. coli*. Thus, removal of the poly-serine stretch may increase expression levels of active KGF-2 protein. Thirdly, expression of KGF Δ33 in *E.coli*, results in natural cleavage of KGF-2 between residues 68 and 69. Thus, it is anticipated that KGF2 Δ33 will be processed efficiently and will be stable in *E.coli*.

Construction of KGF2Δ33 in pQE6

To permit Polymerase Chain Reaction directed amplification and sub-cloning of KGF2 Δ33 into the *E.coli* protein expression vector, pQE6, two oligonucleotide primers (5952 and 19138) complementary to the desired region of KGF2 were synthesized with the following base sequence.

Primer 5952: 5' GCGGCACATGTCTTACAACCACCT-GCAGGGTG 3' (SEQ ID NO:91)

Primer 19138: 5' GGGCCCAAGCTTATGAGTGTAC-CACCAT 3' (SEQ ID NO:92)

In the case of the N-terminal primer (5952), an AflIII restriction site was incorporated, while in the case of the C-terminal primer (19138) a HindIII restriction site was incorporated. Primer 5952 also contains an ATG sequence adjacent and in frame with the KGF2 coding region to allow translation of the cloned fragment in *E.coli*, while primer 19138 contains two stop codons (preferentially utilized in *E.coli*) adjacent and in frame with the KGF2 coding region which ensures correct translational termination in *E.coli*.

The Polymerase Chain Reaction was performed using standard conditions well known to those skilled in the art and the nucleotide sequence for the mature KGF-2 (aa 36–208) (constructed in Example 12C) as template. The resulting amplicon was restriction digested with AflIII and HindIII and subcloned into NcoI/HindIII digested pQE6 protein expression vector.

Construction of KGF2Δ33 in pHE1

To permit Polymerase Chain Reaction directed amplification and subcloning of KGF2 Δ33 into the *E.coli* expression vector, pHE1, two oligonucleotide primers (6153 and 6150) corresponding to the desired region of KGF2 were synthesized with the following base sequence.

Primer 6153: 5' CCGGCGGATCCCATATGTCTTA-CAACCACCTGCAGG 3' (SEQ ID NO:93)

Primer 6150: 5' CCGGCGGTACCTTATTATGAGTG-TACCACCATTGG 3' (SEQ ID NO:94)

In the case of the N-terminal primer (6153), an NdeI restriction site was incorporated, while in the case of the C-terminal primer (6150) an Asp718 restriction site was incorporated. Primer 6153 also contains an ATG sequence adjacent and in frame with the KGF2 coding region to allow translation of the cloned fragment in *E.coli*, while primer 6150 contains two stop codons (preferentially utilized in *E.coli*) adjacent and in frame with the KGF2 coding region which ensures correct translational termination in *E.coli*.

The Polymerase Chain Reaction was performed using standard conditions well known to those skilled in the art and the nucleotide sequence for the mature KGF-2 (aa 36–208) (constructed in Example 12C) as template. The resulting amplicon was restriction digested with NdeI and Asp718 and subcloned into NdeI/Asp718 digested pHE1 protein expression vector.

Nucleotide Sequence of KGF2 Δ33:

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-

GTGGCATTGAATGGAAAAGGAGCTC-
CAAGGAGAGG
ACAGAAAACACGAAGGAAAAACACCTCT-
GCTCACTTTCTTCCAATG GTGGTACACTCATAA
(SEQ ID NO:95)

Amino Acid Sequence of KGF Δ33

MSYNHLQGDVRWRKLFSFTKYFLK-
IEKNGKVSGTKKENCPYSILEITS VEIGVVAV-
KAINSNYYLAMNKKGKLYGSKEFNNDCK-
LKERIEENGYN
TYASFNWQHNGRQMYVALNGK-
GAPRRGQKTRRKNTSAHFLPMVVHS (SEQ ID NO:96)

B. Construction of an Optimized KGF-2Δ33

In order to increase the expression levels of KGF2 Δ33 in E. coli, the codons of the complete gene were optimized to match those most highly used in E. coli. As the template utilised to generate the KGF2 Δ33 was codon optimized within the N-terminal region, the C-terminal amino acids (84–208) required optimization.

Firstly, amino acids 172–208 were codon optimized to generate KGF2Δ33(s172–208). This was achieved by an overlapping PCR strategy. Oligonucleotides PM07 and PM08 (corresponding to amino acids 172–208) were combined and annealed together by heating them to 70° C. and allowing them to cool to 37° C. The annealed oligonucleotides were then utilized as template for a standard PCR reaction which was directed by primers PM09 and PM10. In a separate PCR reaction following standard conditions well known to those skilled in the art and using KGF2Δ33 as template, oligonucleotides PM05 (which overlaps with the Pst1 site within coding region of KGF2) and PM11 were used to amplify the region of KGF2 corresponding to amino acids 84–172. In a third PCR reaction, the product of the first PCR reaction (corresponding to codon optimized amino acids 172–208) and the product of the second PCR reaction (corresponding to codon non-optimized amino acids 84–172) were combined and used as template for a standard PCR reaction directed by oligonucleotides PM05 and PM10. The resulting amplicon was digested with Pst1/HindIII and sub-cloned into Pst1/HindIII digested pQE6KGF2Δ33, effectively substituting the corresponding non codon optimized region, and creating pQE6KGF2Δ33(s172–208).

To complete the codon optimization of KGF2, a synthetic gene codon optimized for the region of KGF2 corresponding to amino acids 84–172 was generated utilising overlapping oligonucleotides. Firstly, four oligonucleotides (PM31, PM32, PM33 and PM 34) were combined and seven cycles of the following PCR was performed: 94° C., 30 secs; 46.5° C., 30 secs; and 72° C., 30 secs.

A second PCR reaction directed by primers PM35 and PM36 was then performed following standard procedures, utilizing 1 μl of the first PCR reaction as template. The resulting codon optimized gene fragment was then digested with Pst1/Sal1 and subcloned into Pst1/Sal1 digested pQE6KGF2Δ33(s172–208) to create a fully optimized KGF2 encoding gene, pQE6KGF2Δ33s.

To create an alternative E.coli protein expression vector, KGF2Δ33s was PCR amplified utilising primers PM102 and PM130 on pQE6KGF2Δ33s. The resulting amplicon was digested with NdeI and EcoRV and subcloned into the pHE1 expression vector which had been digested with NdeI and Asp718 (blunt ended) to create pHE1Δ33s.

Oligonucleotide Sequences used in construction of codon optimized
KGF2 Δ33s:
PM05: CAACCACCTGCAGGGTGACG (SEQ ID NO:97)
PM07: AACGGTCGACAAATGTATGTGGCACT-
GAACGGTAAAGGTGCTCCAC GTCGTGGTCA-
GAAAACCCGTCGTAAAAACACC (SEQ ID NO:98)
PM08: GGGCCCAAGCTTAAGAGTGTACCACCAT-
TGGCAGAAAGTGAGCAG AGGTGTTTTTAC-
GACGGGTTTCTGACCACG (SEQ ID NO:99)
PM09: GCCACATACATTTGTCGACCGTT (SEQ ID NO:100)
PM10: GGGCCCAAGCTTAAGAGTG (SEQ ID NO:101)
PM11:GCCACATACATTTGTCGACCGTT (SEQ ID NO:102)
PM31: CTGCAGGGTGACGTTCGTTGGCG-
TAAACTGTTCTCCTTCACCAAAT ACTTCCT-
GAAAATCGAAAAAAACGG-
TAAAGTTTCTGGTACCAAG (SEQ ID NO:103)
PM32: AGCTTTAACAGCAACAACAC-
CGATTTCAACGGAGGTGATTTCCAGG ATG-
GAGTACGGGCAGTTTTCTTTCTTGGTAC-
CAGAAACTTTACC (SEQ ID NO:104)
PM33: GGTGTTGTTGCTGTTAAAGCTAT-
CAACTCCAACTACTACCTGGCTAT GAACAA-
GAAAGGTAAACTGTACGGTTCCAAA-
GAATTTAACAAC (SEQ ID NO:105)
PM34: GTCGACCGTTGTGCTGCCAGTTGAAG-
GAAGCGTAGGTGTTGTAACC GTTTTCTTC-
GATACGTTCTTTCAGTTTACAGTCGT-
TGTTAAATTCTTT GGAACC (SEQ ID NO:106)
PM35: GCGGCGTCGACCGTTG(TGCTGCCAG (SEQ ID NO:107)
PM36: GCGGCCTGCAGGGTGACGTTCGTTGG (SEQ ID NO:108)
PM102: CCGGCGGATCCCATATGTCTTACAAC-
CACCTGCAGG (SEQ ID NO:109)
PM130: CGCGCGATATCTTATTAAGAGTGTAC-
CACCATTG (SEQ ID NO:110)

Nucleotide Sequence of KGF2 Δ33(s172–208)

ATGTCTTACAACCACCTGCAGGGT-
GACGTTCGTTGGCGTAAACTGT TCTCCTTCAC-
CAAATACTTCCTGAAAATC-
GAAAAAAACGGTAAAGT
TTCTGGTACCAAGAAAGAAAACTGCCCG-
TACTCCATCCTGGAAATC ACCTCCGT-
TGAAATCGGTGTTGTTGCTGTTAAAGC-
TATCAACTCCA
ACTACTACCTGGCTATGAACAAGAAAGG-
TAAACTGTACGGTTCCAA AGAATTTAACAAC-
GACTGTAAACTGAAAGAACGTATCGAA-
GAAA
CGGTTACAACACCTACGCTTCCT-
TCAACTGGCAGCACAACGGTCGA CAAATG-
TATGTGGCACTGAACGGTAAAGGTGCTC-
CACGTCGTGGTC
AGAAAACCCGTCGTAAAAACACCTCT-
GCTCACTTTCTGCCAATGGT GGTACACTCTTAA
(SEQ ID NO:111)

Amino Acid Sequence of KGF2 Δ33(s172–208)

MSYNHLQGDVRWRKLFSFTKYFLK-
IEKNGKVSGTKKENCPYSILEITS VEIGVVAV-

KAINSNYYLAMNKKGKLYGSKEFNNDCK-
LKERIEENGYN
TYASFNWQffNGRQMYALNGK-
GAPRRGQKTRRKNTSAHFLPMVVHS (SEQ ID
NO:112)

C. Construction of N-Terminal Deletion Mutant KGF-2Δ4

To increase the level of expression of KGF2 in E.coli and to enhance the stability and solubility properties of E.coli expressed KGF2, a deletion variant KGF2Δ4 (amino acids 39–208) which removes the first 38 amino acids of pre-processed KGF2 was constructed, including the cysteine at position 37. As the resulting KGF2 deletion molecule contains an even number of cysteines, problems due to aggregation caused by intra-molecular disulphide bridge formation should be reduced, resulting in an enhanced level of expresssion of active protein.

To permit Polymerase Chain Reaction directed amplification and sub-cloning of KGF2 Δ4 into the E.coli protein expression vector, pQE6, two oligonucleotide primers (PM61 and 19138) were synthesized with the following base sequence.

PM61: CGCGGCCATGGCTCTGGGTCAGGACATG (SEQ ID NO:113)

19138: GGGCCCAAGCTTATGAGTGTACCACCAT (SEQ ID NO:114)

In the case of the N-terminal primer (PM61), an NcoI restriction site was incorporated, while in the case of the C-terminal primer (19138) a HindIII restriction site was incorporated. PM61 also contains an ATG sequence adjacent and in frame with the KGF2 coding region to allow translation of the cloned fragment in E.coli, while 19138 contains a stop codon (preferentially utilized in E.coli) adjacent to and in frame with the KGF2 coding region which ensures correct translational termination in E.coli.

The Polymerase Chain Reaction was performed using standard conditions well known to those skilled in the art and the full length KGF2 (aa 36–208) as template (constructed in Example 12C). The resulting amplicon was restriction digested with NcoI and HindIII and subdloned into NcoI/HindIII digested pQE6 protein expression vector.

Nucleotide Sequence of KGF2 Δ4

ATGGCTCTGGGTCAAGATATGGTTTCTC-
CGGAAGCTACCAACTCTT CCTCTTC-
CTCTTTCTCTTCCCCGTCTTCCGCTG-
GTCGTCACGTTCGTT
CTTACAACCACCTGCAGGGTGACGT-
TCGTTGGCGTAAACTGTTCTC TTTCAC-
CAAATACTTCCTGAAAATC-
GAAAAAAACGGTAAAGTTTCT
GGGACCAAGAAGGAGAACTGCCCGTA-
CAGCATCCTGGAGATAACA TCAGTA-
GAAATCGGAGTTGTTGCCGTCAAAGC-
CATTAACAGCAACT
ATTACTTAGCCATGAACAAGAAGGG-
GAAACTCTATGGCTCAAAAG AATTTAACAAT-
GACTGTAAGCTGAAGGAGAGGATAGAG-
GAAAATG
GATACAATACCTATGCATCATTTAACTG-
GCAGCATAATGGGAGGCA AATGTATGTGGCAT-
TGAATGGAAAAGGAGCTCCAAGGAGAGGACA
GAAAACACGAAGGAAAAACACCTCTGCT-
CACTTTCTTCCAATGGTG GTACACTCATAA
(SEQ ID NO:115)

Amino Acid Sequence of KGF2Δ4

MALGQDMVSPEATNSSSSF-
SSPSSAGRHVRSYNHLQGDVRWRKLFSF TKY-
FLKIEKNGKVSGTKKENCPYSILEITS-
VEIGVVAVKAINSNYYLAM
NKKGKLYGSKEFNNDCKLKERIEENG-
YNTYASFNWQHNGRQMYVAL NGK-
GAPRRGQKTRRKNTSAHFLPMVVHS (SEQ ID
NO:116)

EXAMPLE 17

KGF-2Δ33 Stimulated Wound Healing in Normal Rat

To demonstrate that KGF-2Δ33 would accelerate the healing process, wound healing of excisional wounds were examined using the following model.

A dorsal 6 mm excisional wound is created on Sprague Dawley rats (n=5) with a Keyes skin punch. The wounds are left open and treated topically with various concentrations of KGF-2 Δ33 (in 40 mM NaOAc and 150 mM NaCl, pH 6.5 buffer) and buffer (40 mM NaOAc and 150 mM NaCl, pH 6.5) for 4 days commencing on the day of wounding. Wounds are measured daily using a calibrated Jameson caliper. Wound size is expressed in square millimeters. On the final day wounds were measured and harvested for further analysis. Statistical analysis was done using an unpaired t test (mean±SE). Evaluation parameters include percent wound closure, histological score (1–3 minimal cell accumulation, no granulation; 4–6 immature granulation, inflammatory cells, capillaries; 7–9 granulation tissue, cells, fibroblasts, new epithelium 10–12 mature dermis with fibroblasts, collagen, epithelium), re-epithelialization and immunohistochemistry.

Figure 36:
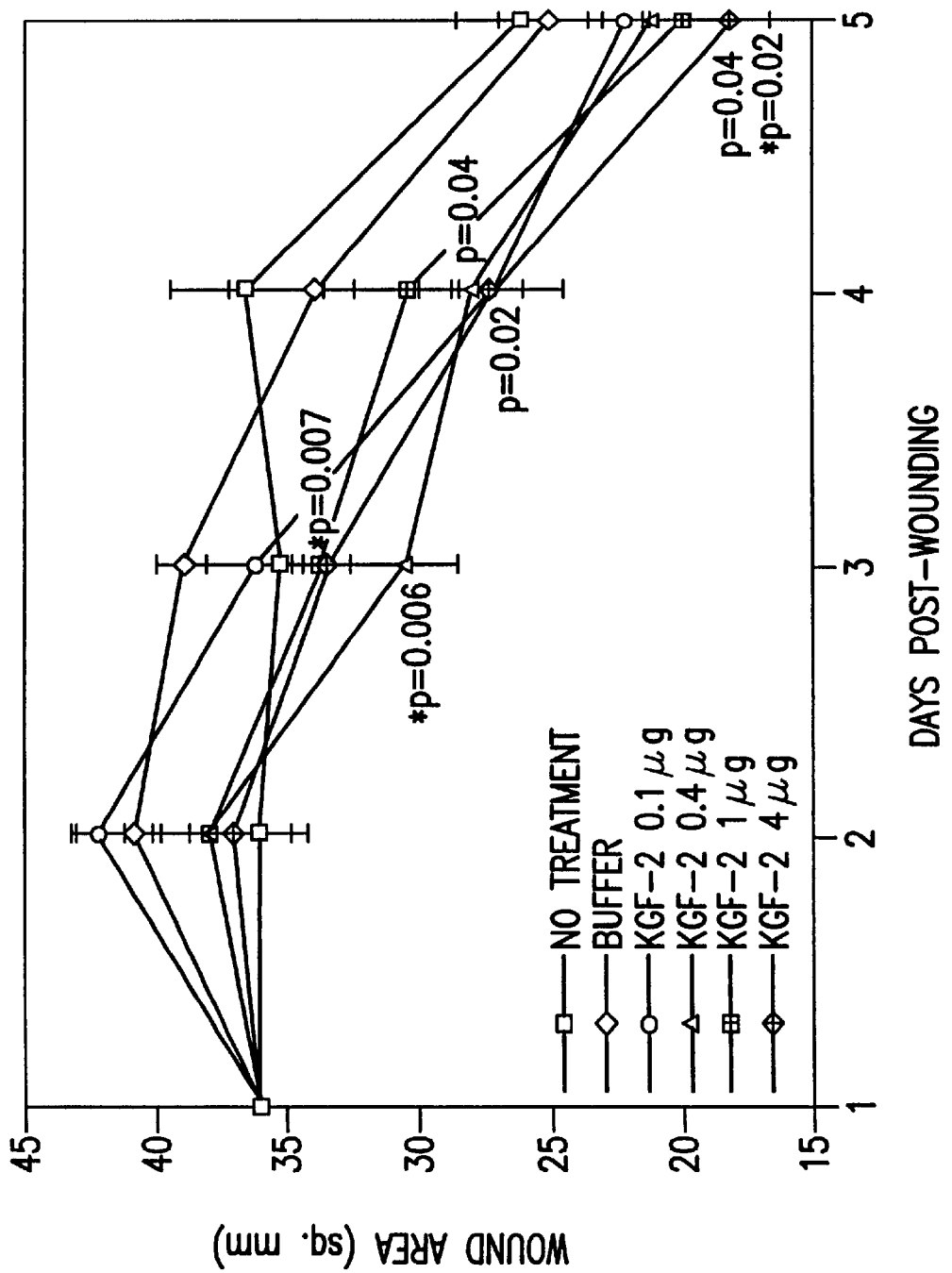
FIG. 36 shows the evaluation of KGF-2 Δ33 effects on wound healing in male SD rats (n=5). Animals received 6 mm dorsal wounds and were treated with various concentrations of buffer, or KGF-2 Δ33 for 4 consecutive days. Wounds were measured daily using a calibrated Jameson caliper. Statistical analysis was done using an unpaired t-test.(Mean +/− SE) *Compared with buffer.

At three days postwounding, treatment with KGF-2 Δ33 displayed a decrease in wound size (30.4 mm$^2$ at 4 μg, p=0.006, 33.6 mm$^2$ at 1 μg, p=0.0007) when compared to the buffer control of 38.9 mm$^2$. At day four postwounding, treatment with KGF-2 Δ33 displayed a decrease in wound size (27.2 mm$^2$ at 0.1 μg p=0.02, 27.9 mm$^2$ at 0.4 μg p=0.04) when compared to buffer control of 33.8 mm$^2$. At day five postwounding, treatment with KGF-2 Δ33 displayed a decrease in wound size (18.1) mm$^2$ at 4 μg p=0.02 when compared to buffer control of 25.1 mm$^2$. See FIG. 36.

Following wound harvest on day 5, additional parameters were evaluated. KGF-2 Δ33 displayed an increase in the percentage of wound closure at 4 μg (71.2%, p=0.02) when compared to buffer control 60.2%. Administration of KGF-2 Δ33 also results in an improvement in histological score at 1 and 4 μg (8.4 at 1 μg p=0.005, 8.5 at 4 μg p=0.04) relative to buffer control of 6.4. Re-epithelialization was also improved at 1 and 4 μg KGF-2 Δ33 (1389 μm at 1 μg p=0.007, 1220 μm at 4 μg p=0.02) relative to the buffer control of 923 μm. See FIG. 37.

This study demonstrates that daily treatment with KGF-2 Δ33 accelerates the rate of wound healing in normal animals as shown by a decrease in the gross wound area. In addition, the histological evaluation of wound samples and assessment of re-epithelialization also show that KGF-2 Δ33 improves the rate of healing in this normal rat model.

EXAMPLE 18

KGF-2Δ33 Effect on Tensile Strength and Epidermal Thickness in Normal Rat

To demonstrate that KGF-2Δ33 would increase tensile strength and epidermal thickness of wounds the following experiment was performed.

A 2.5 cm full thickness midline incisional wound is created on the back of male Sprague Dawley rats (n=8 or 9).

Skin incision is closed using 3 equidistant metal skin staples. Buffer (40 mM NaOAc and 150 mM NaCl, pH 6.5) or KGF-2 Δ33 (in 40 mM NaOAc and 150 mM NaCl, pH 6.5 buffer) were topically applied at the time of wounding. Four wound strips measuring 0.5 cm in width are excised at day 5. Specimens are used for the study of breaking strength using an Instron™ skin tensiometer, hydroxyproline determination and histopathological assessment. Breaking strength was defined as the greatest force withheld by each wound prior to rupture. Statistical analysis was done using an unpaired t test (mean±SE).

Figure 38:
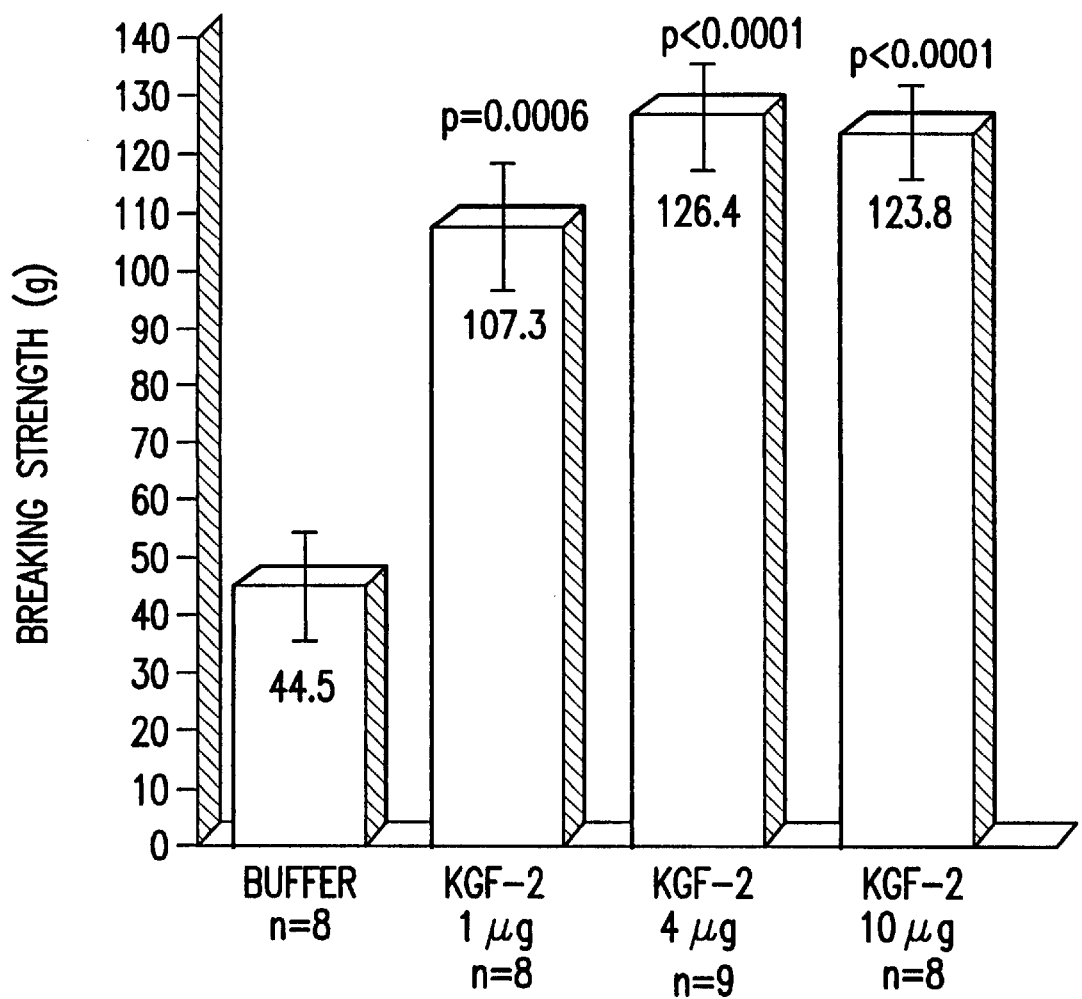
FIG. 38 shows the effect of KGF-2 Δ33 on breaking strength in incisional wounds. Male adult SD rats (n=10) received 2.5 cm full thickness incisional wounds on day 1 and were intraincisionally treated postwounding with one application of either buffer or KGF-2 (Delta 33) (1, 4, and 10 μg). Animals were sacrificed on day 5 and 0.5 cm wound specimens were excised for routine histology and breaking strength analysis. Biomechanical testing was accomplished using an Instron skin tensiometer with a force applied across the wound. Breaking strength was defined as the greatest force withheld by each wound prior to rupture. Statistical analysis was done using an unpaired t-test. (Mean +/− SE).

In an incisional skin rat model, topically applied KGF-2 Δ33 exhibited a statistically significant increase in breaking strength, tensile strength and epidermal thickness as a result of a single intraincisional application subsequent to wounding. In one study, the breaking strength of KGF-2 treated wounds at 1, 4, and 10 μg was significantly higher when compared to the buffer controls (107.3 g at 1 μg p=0.0006, 126.4 g at 4 μg p<0.0001, 123.8 g at 10 μg p<0.0001). See FIG. 38.

Figure 39:
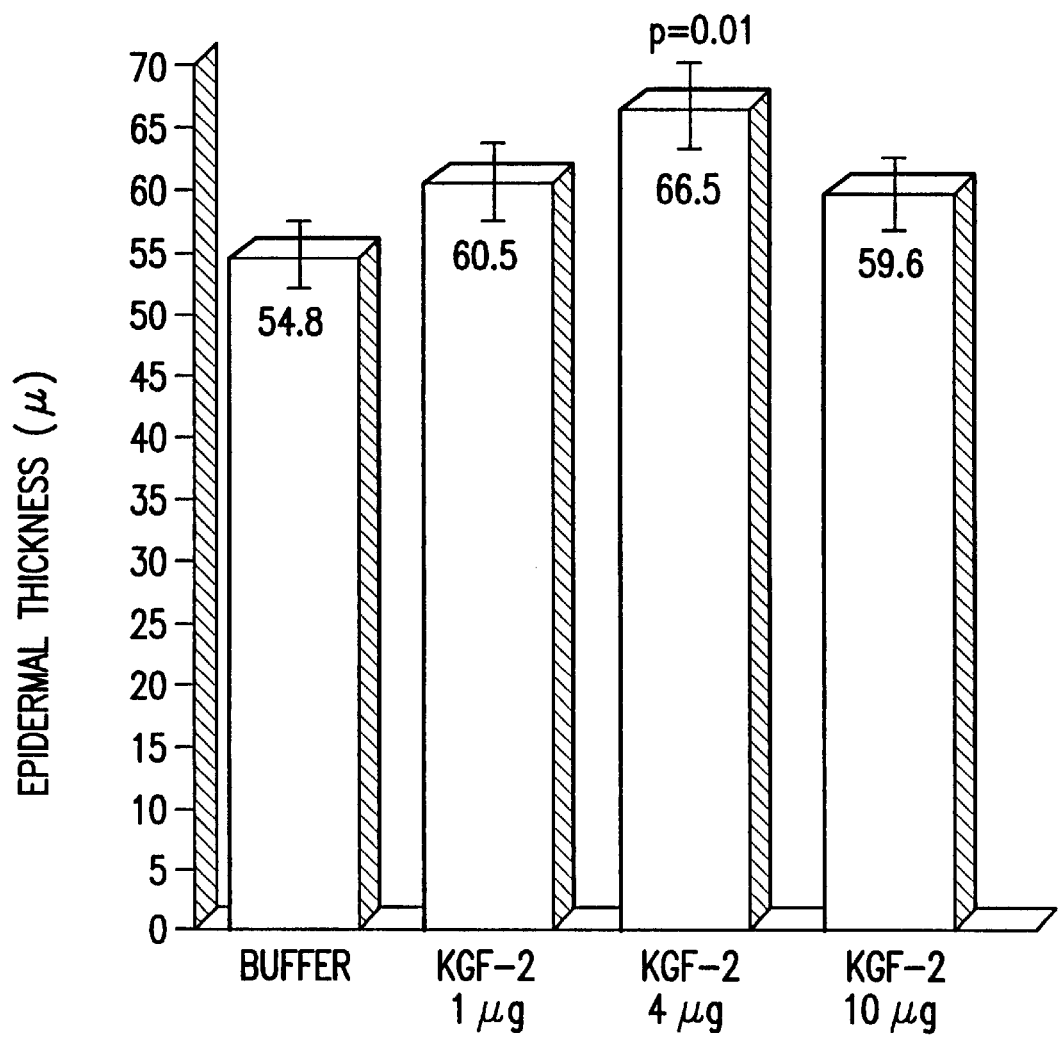
FIG. 39 shows the effect of KGF-2 (Delta 33) on epidermal thickness in incisional wounds. Male adult SD rats (n=0) received 2.5 cm full thickness incisional wounds on day 1 and were intracisionally treated postwounding with one application of either buffer or KGF-2 (Delta 33) (1, 4, and 10 μg). Animals were sacrificed on day 5 and 0.5 cm wound specimens were excised for routine histology and breaking strength analysis. Epidermal thickness was determined by taking the mean of 6 measurements taken around the wound site. Measurements were taken by a blind observer on Masson Trichrome stained sections under light microscopy using a calibrated lens micrometer. Statistical analysis was done using an unpaired t-test. (Mean +/− SE).

Epidermal thickness was assessed under light microscopy on Masson Trichrome sections. KGF-2 Δ33 treated wounds displayed increased epidermal thickening (60.5μ at 1 μg, 66.51μ at 4 μg p=0.01, 59.6μ at 10 μg) in contrast with the buffer control of 54.8μ. See FIG. 39.

These studies demonstrate that a single intraincisional application of KGF-2 augments and accelerates the wound healing process characterized by an increase in breaking strength and epidermal thickness of incisional wounds.

EXAMPLE 19

KGF-2Δ33 Effect on Normal Rat Skin

In order to determine the effect of KGF-2 Δ33 on normal rat skin following intradermal injection the following experiment was performed.

Male adult SD rats (n=3) received six intradermal injections of either placebo or KGF-2 Δ33 (in 40 mM NaOAc and 150 mM NaCl, pH 6.5 buffer) in a concentration of 1 and 4 μg in 50 μl on day 0. Animals were injected with 5-2'-bromodeoxyrudine (BrdU)(100 mg/kg i.p.) two hours prior to sacrifice at 24 and 48 hours. Epidermal thickness was measured from the granular layer to the bottom of the basal layer. Approximately, 20 measurements were made along the injection site and the mean thickness quantitated. Measurements were determined using a calibrated micrometer on Masson Trichrome stained sections under light microscopy. BrdU scoring was done by two blinded observers under light microscopy using the following scoring system: 0–3 none to minimal BrdU labeled cells; 4–6 moderate labeling; 7–10 intense labeled cells. Animals were sacrificed 24 and 48 hours post injection. Statistical analysis was done using an unpaired t test. (mean±SE).

Figure 40:
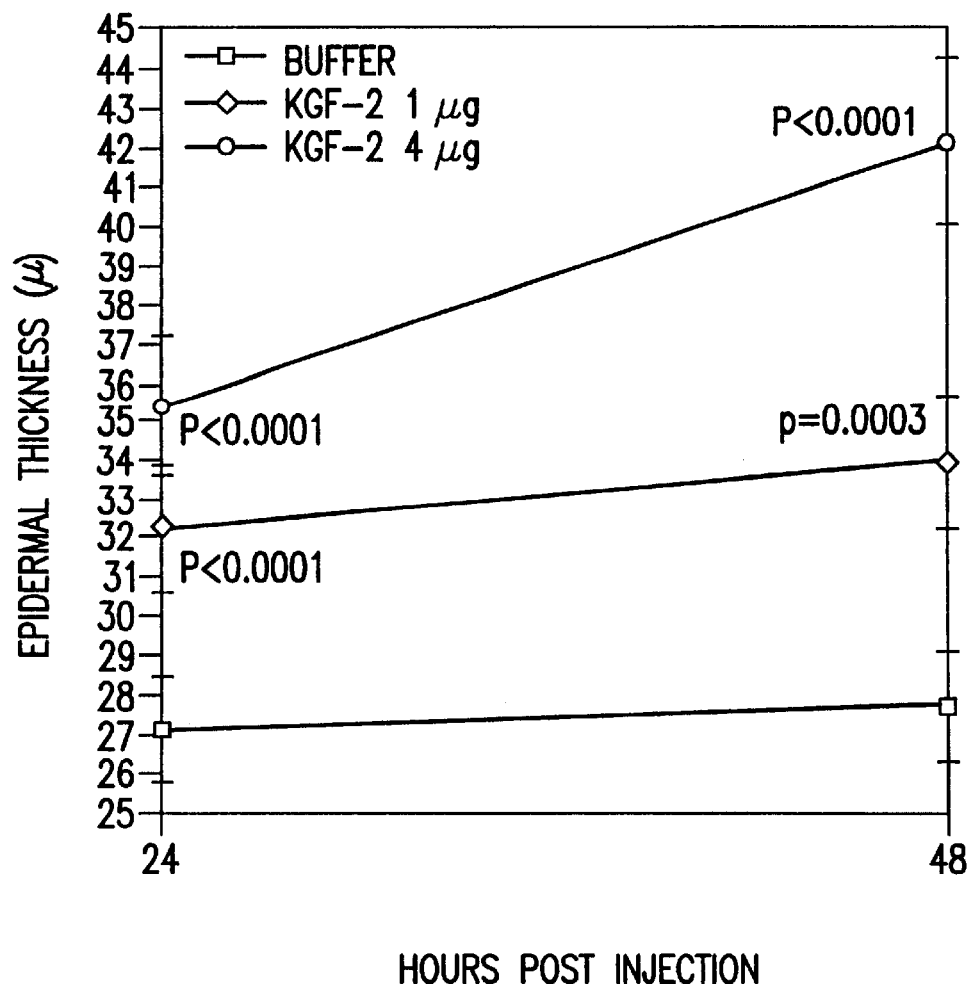
FIG. 40 shows the effect of KGF-2 (Delta 33) on epidermal thickness after a single intradermal injection. Male adult SD rats (n=18) received 6 intradermal injections of either buffer or KGF-2 in a concentration of 1 and 4 μg in 50 μL on day 0. Animals were sacrificed 24 and 48 hours post injection. Epidermal thickness was measured from the granular layer to the bottom of the basal layer. Approximately 20 measurements were made along the injection site and the mean thickness quantitated. Measurements were determined using a calibrated micrometer on Masson Trichrome stained sections under light microscopy. Statistical analysis was done using an unpaired t-test. (Mean +/− SE).
Figure 41:
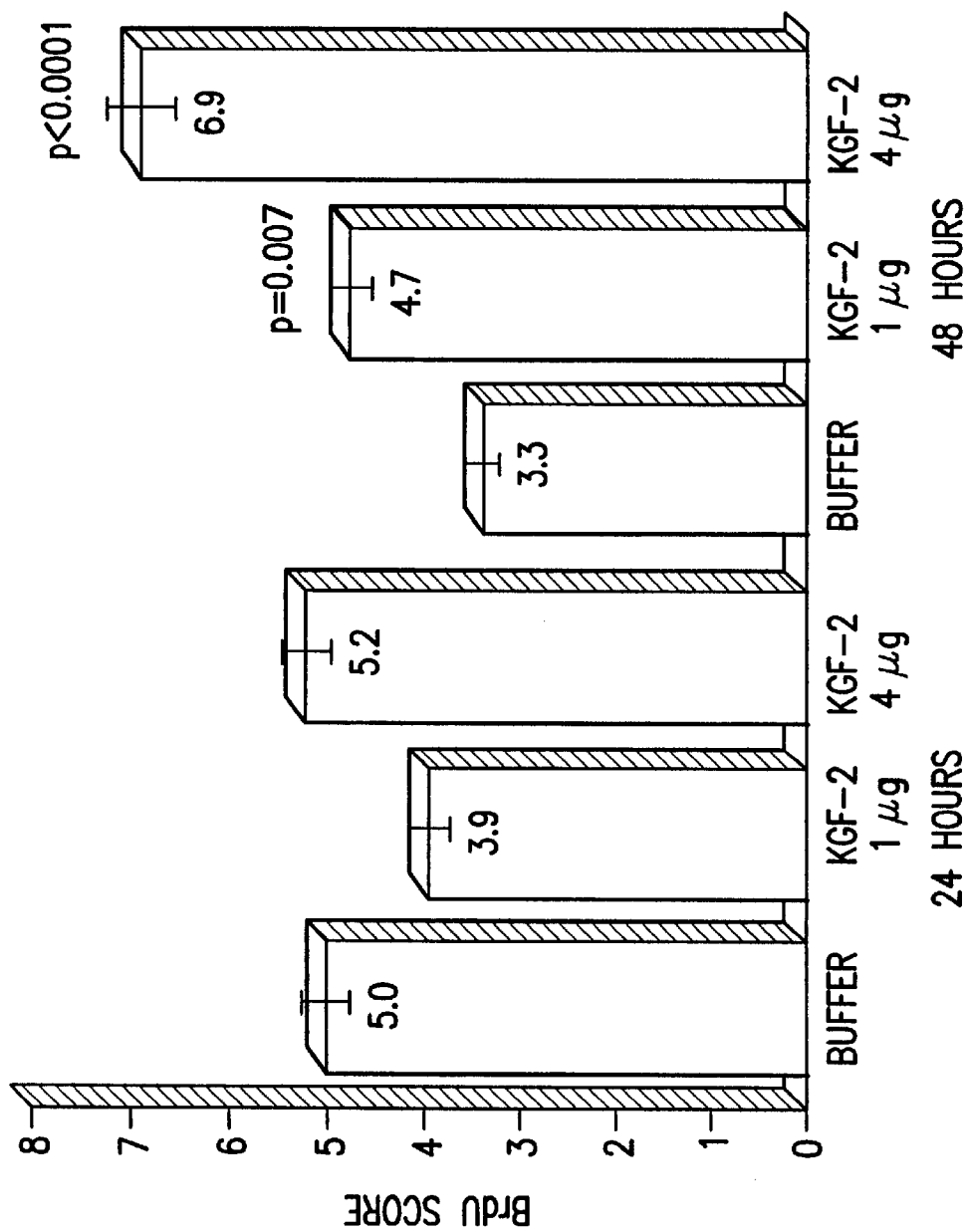
FIG. 41 shows the effect of KGF-2 (Delta 33) on BrdU scoring. Male adult SD rats (n=18) received 6 intradermal injections of either placebo or KGF-2 in a concentration of 1 and 4 μg in 50 μL on day 0. Animals were sacrificed 24 and 48 hours post injection. Animals were injected with 5-2'-Bromo-deoxyrudine (100 mg/kg ip) two hours prior to sacrifice. Scoring was done by a blinded observer under light microscopy using the following scoring system: 0–3 none to minimal BrdU labeled cells; 4–6 moderate labeling; 7–10 intense labeled cells. Statistical analysis was done using an unpaired t-test. (Mean +/− SE).

KGF-2 Δ33 treated skin displayed increased epidermal thickening at 24 hours (32.2μ at 1 μg p<0.001, 35.4μ at 4 μg p<0.0001) in contrast with the buffer control of 27.1μ. At 48 hours KGF-2 Δ33 treated skin displayed increased epidermal thickening (34.0μ at 1 μg p=0.0003, 42.4μ at 4 μg p<0.0001) compared to buffer control of 27.8μ. See FIG. 40. KGF-2 Δ33 treated skin also displayed increased BrdU immunostaining at 48 hours (4.73 at 1 μg p=0.07, 6.85 at 4 μg p<0.0001) compared to buffer control of 3.33. See FIG. 41.

These studies demonstrate that a intradermal injection of KGF-2 augments and accelerates epidermal thickening. Thus, KGF-2 would have applications to prevent or alleviate wrinkles, improve aging skin and reduce scaring or improve healing from cosmetic surgery. In addition, KGF-2 can be used prophylactically to prevent or reduce oral mucosistis (mouth ulcers), intestinal inflammation in response to chemotherapy or other agents.

EXAMPLE 20

Anti-inflammatory Effect of KGF-2 on PAF-Induced Paw Edema

To demonstrate an anti-inflammatory effect of KGF-2 the following experiment was performed using PAF-induced paw edema inflammation model.

Groups of four lewis rats (190~210 gm) were injected subcutaneously in the foot pad of the right hind paw with 120 μl solution containing 2.5 nMol of PAF, together with the following reagents: 125 μg of Ckb-10(B5), 24 ∞g of LPS, 73 μg of KGF-2 (Thr (36)-Ser (208) of FIG. 1 (SEQ ID NO:2) with a N-terminal Met) or no protein. The left hind paws were given the same amount of buffer to use as parallel control. Paw volume was quantified immediately before, or 30 and 90 minutes after PAF injection using a plethysmograph system. Percent (%) change of paw volume were calculated.

| | Testing reagents in experiment No. 1 and No. 2 | | | | |
|---|---|---|---|---|---|
| Groups (N = 4) | PAF(R.) 2.5 nMol | Ckβ-10(R.) 1.04 mg/ml | LPS(R.) 200 μg/ml | KGF-2(R.) 0.73 mg/ml | Buffer |
| 1 | 20 μl | — | — | — | 100 μl |
| 2 | 20 μl | 100 μl | — | — | — |
| 3 | 20 μl | — | 100 μl | — | — |
| 4 | 20 μl | — | — | 100 μl | — |

Figure 42A:
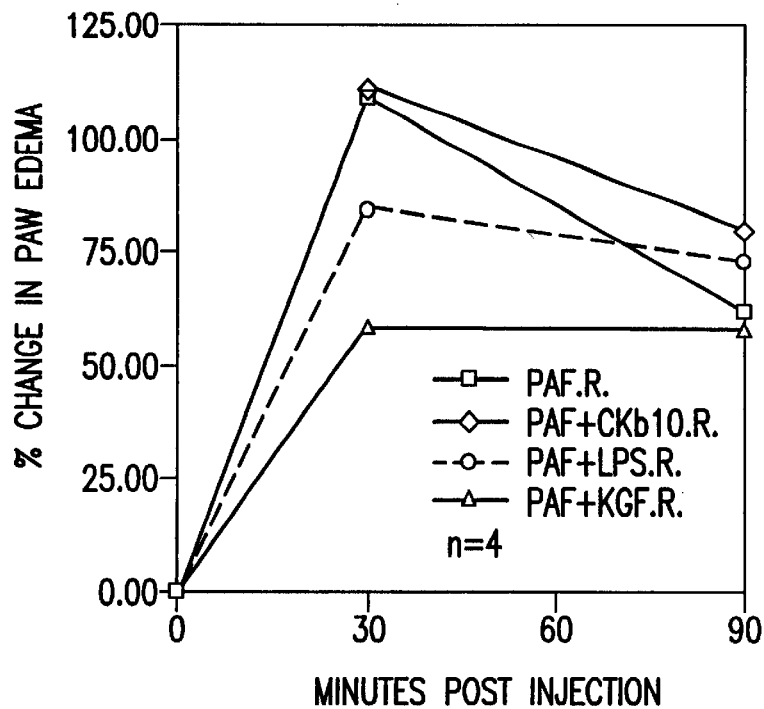
FIG. 42 shows the anti-inflammatory effect of KGF-2 on PAF-induced paw edema.
Figure 42B:
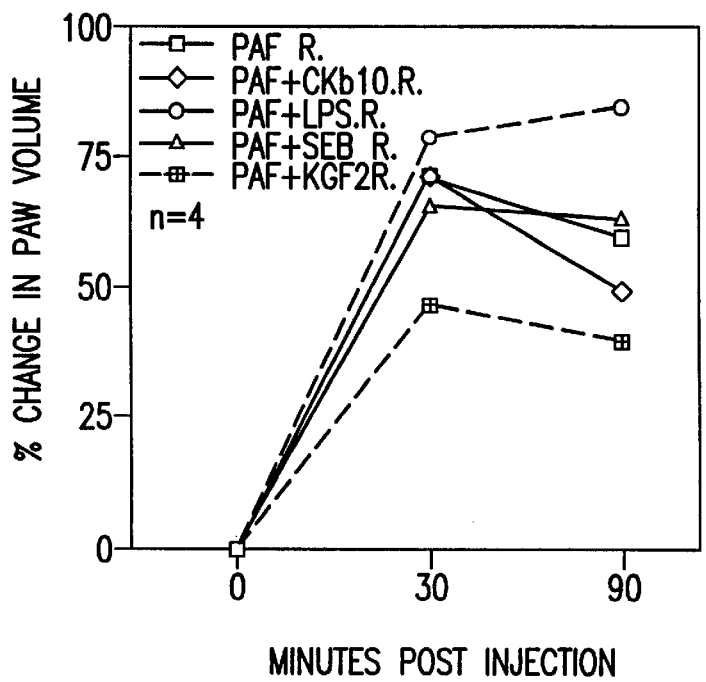

As shown in FIG. 42, right hind paws injected with PAF alone resulted in a significant increase in paw volume (75 or 100% for experiment No. 1 or No. 2, respectively) at 0.5 hour post injection as expected; while left hind paws receiving buffer or right hind paws receiving LPS or SEB alone show little sign of edema (data not shown). However, when KGF-2 was given together with PAF locally, there is a substantial reduction (25 or 50% for experiment No. 1 or No. 2, respectively) in paw volume compared with PAF alone-challenged paws. The reduction of paw edema was not observed in animal receiving PAF together with Ckb-10 (a different protein), LPS or SEB (two inflammatory mediators). These results suggest that the anti-inflammatory effect of KGF-2 is specific and not due to some non-specific nature of the protein.

Effect of KGF-2 Δ33 on PAF-Induced Paw Edema in Rats

Following the experiments described above with KGF-2 Δ33 to confirm its in vitro biological activities for stimulating keratinocyte proliferation and its in vivo effect on wound healing, KGF-2 Δ33 was further evaluated in the PAF-induced paw edema model in rats. Groups of four Lewis rats (190~210 gm) were injected subcutaneously in the foot pad of the right hind paw with 120 μl solution containing 2.5 nMol of PAF, together with 210 μg of KGF-2 Δ33 or albumin. The left hind paws were given the same amount of buffer, albumin or KGF-2 Δ33 alone to use as parallel control. Paw volume was quantified at different intervals after PAF injection using a plethysmograph system. Percent (%) change of paw volume was calculated.

Figure 43:
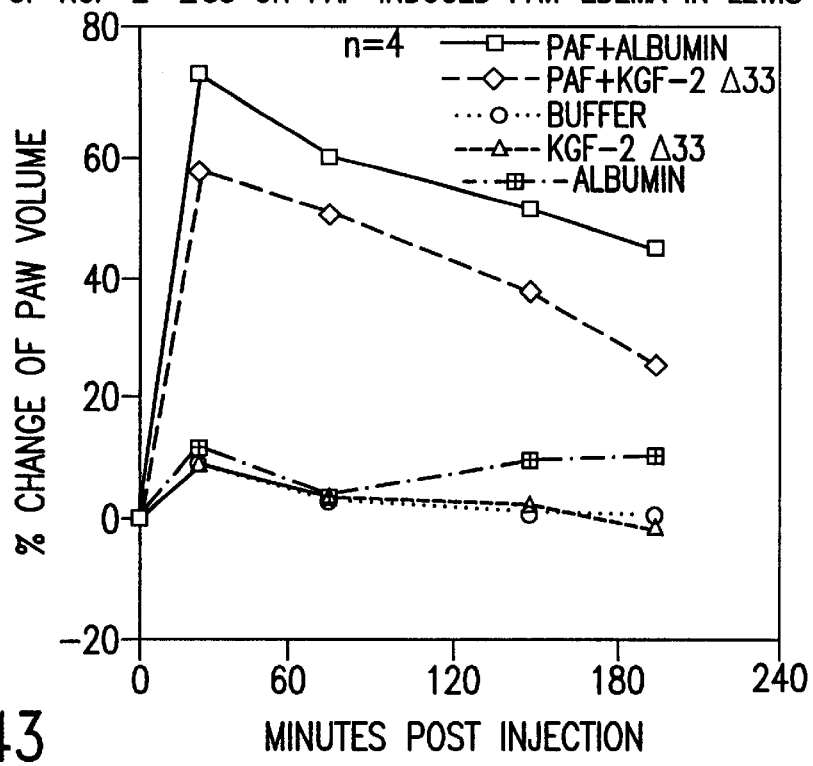
FIG. 43 shows the anti-inflammatory effect of KGF-2 Δ33 on PAF-induced paw edema in Lewis rats.

As shown in FIG. 43, right hind paws injected with PAF and albumin resulted in a significant increase (75%) in paw volume at 0.5 hour post injection as expected; while left hind paws receiving buffer, albumin or KGF-2 Δ33 alone showed little sign of edema. However, when KGF-2 Δ33 was given together with PAF locally, there was a substantial reduction (average 20%) in paw volume, when compared with PAF plus albumin-challenged paws, throughout the entire experiment which was ended in 4 hours. These results confirm the anti-inflammatory property of KGF-2 Δ33.

| Groups (N = 4) | Testing Reagents | | | |
|---|---|---|---|---|
| | PAF 2.5 nMol | Albumin 2.1 mg/ml | KGF-2 Δ33 2.1 mg/ml | Buffer |
| 1 | 20 μl | 100 μl | — | — |
| 2 | 20 μl | — | 100 μl | — |
| 3 | — | 120 μl | — | — |
| 4 | — | — | 120 μl | — |
| 5 | — | — | — | 120 μl |

Thus, KGF-2 is useful for treating acute and chronic conditions in which inflammation is a key pathogenesis of the diseases including but not limiting to psoriasis, eczema, dermatitis and/or arthritis.

EXAMPLE 21

Effect of KGF-2 Δ33 on End-to-end Colonic Anastomosis Rat Model

This example demonstrates that KGF-2 Δ33 will increase the rate of intestinal repair in a model of intestinal or colonic anastomosis in Wistar or Sprague Dawley rats. The use of the rat in experimental anastomosis is a well characterized, relevant and reproducible model of surgical wound healing. This model can also be extended to study the effects of chronic steriod treatment or the effects of various chemotherapeutic regimens on the quality and rate of surgical wound healing in the colon and small intestine (Mastboom W. J. B. et al. Br. J. Surg. 78: 54–56 (1991), Salm R. et al. J Surg. Oncol. 47: 5–11, (1991), Weiber S. et al. Eur. Surg. Res. 26: 173–178 (1994)). Healing of anastomosis is similar to that of wound healing elsewhere in the body. The early phases of healing are characterized by acute inflammation followed by fibroblast proliferation and synthesis of collagen. Collagen is gradually modeled and the wound is strengthened as new collagen is synthesized. (Koruda M. J., and Rolandelli, R. H. J. Surg. Res. 48: 504–515 (1990). Most postoperative complications such as anastomotic leakage occur during the first few days following surgery—a period during which strength of the colon is mainly secured by the ability of the wound margin to hold sutures. The suture holding capacity of the GI tract has been reported to decrease by as much as 80% during the first postoperative days (Hogstrom H and Haglund U. Acta Chir Scand 151: 533–535 (1985), Jonsson K, et al. Am J. Surg. 145: 800–803 (1983)).

Male adult SD rats (n=5) were anesthetized with a combination of ketamine (50 mg/kg) and xylazine (5 mg/kg) intramuscularly. The abdominal cavity was opened with a 4 cm long midline incision. A 1 cm wide segment of the left colon was resected 3 cm proximal to the peritoneal reflection while preserving the marginal vessels. A single layer end-to-end anastomosis was performed with 8-10 interrupted 5-0 Vicryl inverted sutures to restore intestinal continuity. The anastomosis was then topically treated via syringe with either buffer or KGF-2 Δ33 at concentrations of 1 and 4 μg. The incisional wound was closed with 3-0 running silk suture for the muscle layer and surgical staples for the skin. Treatments were then administered daily thereafter and consisted of buffer or KGF-2 Δ33 and 1 and 5 mg/kg sc. Weights were taken on the day of surgery and daily thereafter. Animals were euthanized 24 hours following the last treatment (day 5). Animals were anesthetized and received barium enemas and were x-rayed at a fixed distance. Radiologic analysis following intracolonic administration by 2 blinded observers revealed that KGF-2 Δ33 treated groups had 1) a decreased rate of barium leakage at the surgical site, 2) lesser degree of constriction at the surgical site, and 3) an increase in the presence of fecal pellets distal to the surgical site.

| Groups | Colonic Anastomosis Radiologic Analysis | | | |
|---|---|---|---|---|
| | Feces Present | Anastomotic Constriction | Proximal Distension | Peritoneal Leakage |
| No Treatment (N = 5) | 20% | 80% | 80% | 60% |
| Buffer (N = 5) | 40% | 60% | 80% | 75% |
| KGF-2 Δ33 [1 mg/kg] (N = 5) | 60% | 20% | 100% | 20% |
| KGF-2 Δ33 [5 mg/kg] (N = 4) | 100% | 0% | 75% | 25% |

EXAMPLE 22

Construction of Carboxy Terminal Mutations in KGF-2

The carboxyl terminus of KGF-2 is highly charged. The density of these charged residues may affect the stability and consequently the solubility of the protein. To produce muteins that might stabilize the protein in solution a series of mutations were created in this region of the gene.

To create point mutants 194 R/E, 194 R/Q, 191 K/E, 191 K/Q, 188R/E, 188R/Q, the 5952 KGFΔ33 5' AflIII 5' primer was used with the indicated 3' primers, which contain the appropriate point mutations for KGF-2, in PCR reactions using standard conditions well known to those skilled in the art with KGF-2Δ33 as template. The resulting products were restricted with AflIII and HindIII and cloned into the E. coli expression vector, pQE60 restricted with NcoI and HindIII.

KGF2Δ33,194 R/E Construction

The following primers were used:

5952 KGF Δ 33 5' AflIII: 5' GCGGCACATGTCTTA-CAACCACCTGCAGGGTG 3' (SEQ ID NO:117)

KGF2 3'HindIII 194aa R to E: 5'CTGCCC AAGCTTTTATGAGTGTACCACCATTGGAAGA AAGTGAGC AGAGGTGTTTTT TTCTCGTGTTTTCTGTCC 3' (SEQ ID NO:118)

KGF2Δ33,194 R/E Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAACGGTAAAGT
TTCTGGGACCAAGAAGGAGAACTGCCCG-

TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTC-
CAAGGAGAGG ACAGAAAACACGA
GAAAAAAACACCTCTGCTCACTTTCTTCCAATG
GTGGTACACTCATAG (SEQ ID NO:119)

KGF2Δ33,194 R/E Amino Acid Sequence

MSYNHLQGDVRWRKLFSFTKYFLK-
IEKNGKVSGTKKENCPYSILEITS VEIGVVAV-
KAINSNYYLAMNKKGKLYGSKEFNNDCK-
LKERIEENGYN
TYASFNWQHNGRQMYVALNGKGAPRRGQKTR
EKNTSAHFLPMVVHS (SEQ ID NO:120)

KGF2 Δ33,194 R/Q Construction

The following primers were used:
5952 KGF Δ33 5' AflIII: 5' GCGGCACATGTCTTA-
CAACCACCTGCAGGGTG 3' (SEQ ID NO:121)

KGF2 3' HindIII 194 aa R to Q: 5' CTGCCC
AAGCTTTTATGAGTGTACCACCATTGGAAGAA
AGTGAGC AGAGGTGTTTTT
CTGTCGTGTTTTCTGTCC 3' (SEQ ID NO:122)

KGF2 Δ33,194 R/Q Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTC-
CAAGGAGAGG ACAGAAAACACGA
CAGAAAAACACCTCTGCTCACT TTCTTC-
CAATGGTGGTACACTCATAG (SEQ ID NO:123)

KGF2 Δ33,194 R/Q Amino Acid Sequence

MSYNHLQGDVRWRKLFSFTKYFLK-
IEKNGKVSGTKKENCPYSILEITS VEIGVVAV-
KAINSNYYLAMNKKGKLYGSKEFNNDCK-
LKERIEENGYN
TYASFNWQHNGRQMYVALNGKGAPRRGQKTR
QKNTSAHFLPMVVHS (SEQ ID NO:124)

KGF2Δ33,191 K/E Construction

The following primers were used:
5952 KGF Δ 33 5' AflIII: 5' GCGGCACATGTCTTA-
CAACCACCTGCAGGGTG 3' (SEQ ID NO:125)

KGF2 3' HindIII 191aa K to E 5' CTGCCC
AAGCTTTTATGAGTGTACCACCATTGGAAGAA
AGTGAGC AGAGGTGTTTTTCCTTCGTGT
TTCCTGTCCTCTCCTTGG 3' (SEQ ID NO:126)

KGF2Δ33,191 K/E Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAG CATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTC-
CAAGGAGAGG ACAG
GAAACACGAAGGAAAAACACCTCTGCTCACT
TTCTTCCAATGGTGGTACACTCATAG (SEQ ID
NO:127)

KGF2Δ33,191 K/E Amino Acid Sequence

MSYNHLQGDVRWRKLFSFTKYFLK-
IEKNGKVSGTKKENCPYSILEITS VEIGVVAV-
KAINSNYYLAMNKKGKLYGSKEFNNDCK-
LKERIEENGYN
TYASFNWQHNGRQMYVALNGKGAPRRGQ
ETRRKNTSAHFLPMVVHS (SEQ ID NO:128)

KGF2 Δ33, 191 K/Q Construction

The following primers were used:
5952 KGF Δ33 5' AflIII: 5' GCGGCACATGTCTTA-
CAACCACCTGCAGGGTG 3' (SEQ ID NO:129)
KGF2 3' HindIII 191aa K to Q 5' CTGCCC
AAGCTTTTATGAGTGTACCACCATTGGAAGA
AAGTGAGC AGAGGTGTTTTTCCTTCGTGT
CTGCTGTCCTCTCCTTGG 3' (SEQ ID NO:130)

KGF2 Δ33, 191 K/Q Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTC-
CAAGGAGAGG ACAG
CAGACACGAAGGAAAAACACCTCTGCTCACT
TTCTTCCAATGGTGGTACACTCATAG (SEQ ID
NO:131)

KGF2 Δ33, 191 K/Q Amino Acid Sequence

MSYNHLQGDVRWRKLFSFTKYFLK-
IEKNGKVSGTKKENCPYSILEITS VEIGVVAV-

KAINSNYYLAMNKKGKLYGSKEFNNDCK-
LKERIEENGYN
TYASFNWQHNGRQMYVALNGKGAPRRGQ
QTRRKNTSAHFLPMVVHS (SEQ ID NO:132)

KGF2Δ33, 188R/E Construction

The following primers were used:

5952 KGF Δ33 5' AflIII: 5' GCGGCACATGTCTTA-
CAACCACCTGCAGGGTG 3' (SEQ ID NO:133)

KGF2 3' HindIII 188aa R to E: 5'CTGCCC
AAGCTTTTATGAGTGTACCACCATTGGAAGA
AAGTGAGC AGAGGTGTTTTCCTTCGT-
GTTTTCTGTCCTTCCCTTGGAGCTCCTTT 3'
(SEQ ID NO:134)

KGF2Δ33, 188R/E Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTCCAAGG
GAAGG ACAGAAAACACGAAGGAAAAACAC-
CTCTGCTCACTTTCTTCCAATG GTGGTACACT-
CATAG (SEQ ID NO:135)

KGF2Δ33, 188R/E Amino Acid Sequence

MYNHLQGDVRWRKLFSFTKYFLK-
IEKNGKVSGTKKENCPYSILEITSV EIGVVAV-
KAINSNYYLAMNKKGKLYGSKEFNNDCK-
LKERIEENGYNT
YASFNWQHNGRQMYVALNGKGAPR
EGQKTRRKNTSAHFLPMVVHS (SEQ ID NO:136)

KGF2Δ33, 188 R/Q Construction

The following primers were used:

5952 KGF Δ33 5' AflIII: 5'GCGGCACATGTCTTA-
CAACCACCTGCAGGGTG 3' (SEQ ID NO:137)

KGF2 3' HindIII 188aa R to Q: 5'CTGCCC
AAGCTTTTATGAGTGTACCACCATTGGAAGA
AAGTGAGC AGAGGTGTTTTCCTTCGT-
GTTTTCTGTCCCTGCCTTGGAGCTCCTTT 3'
(SEQ ID NO:138)

KGF2Δ33, 188 R/Q Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGAAAAGGAGCTCCAAGG
CAGGG ACAGAAAACACGAAGGAAAAACAC-
CTCTGCTCACTTTCTTCCAATG GTGGTACACT-
CATAG (SEQ ID NO:139)

KGF2Δ33, 188 R/Q Amino Acid Sequence

MSYNHLQGDVRWRKLFSFTKYFLK-
IEKNGKVSGTKKENCPYSILEITS VEIGVVAV-
KAINSNYYLAMNKKGKLYGSKEFNNDCK-
LKERIEENGYN
TYASFNWQHNGRQMYVALNGKGAPR
QGQKTRRKNTSAHFLPMVVHS (SEQ ID NO:140)

KGF2 Δ33, 183K/E Construction

For mutation 183K/E, two PCR reactions were set up for oligonucleotide site directed mutagenesis of this lysine. In one reaction, 5952 KGFΔ 33 5' AflIII was used as the 5' primer, and KGF2 183aa K to E antisense was used as the 3' primer in the reaction. In a second reaction, KGF2 5' 183aa K to E sense was used as the 5' primer, and KGF2 3' HindIII TAA stop was used as the 3' primer. KGF-2 Δ33 was used as template for these reactions. The reactions were amplified under standard conditions well known to those skilled in the art. One microliter from each of these PCR reactions was used as template in a subsequent reaction using, as a 5' primer, 5453 BsphI, and as a 3' primer, 5258 HindIII. Amplification was performed using standard conditions well known to those skilled in the art. The resulting product was restricted with AflIII and HindIII and cloned into the E. coli expression vector pQE60, which was restricted with NcoI and HindIII.

The following primers were used:

5952 KGF Δ33 5' AflIII: 5' GCGGCACATGTCTTA-
CAACCACCTGCAGGGTG 3' (SEQ ID NO:141)

KGF2 5' 183aa K to E sense: 5' TTGAATGGAGAA
GGAGCTCCA 3' (SEQ ID NO:142)

KGF2 183aa K to E antisense: 5' TGGAGCTCC
TTCTCCATTCAA 3' (SEQ ID NO:143)

KGF2 3' HindIII TAA stop: 5' CTGCCC
AAGCTTTTATGAGTGTACCACCATTGG 3' (SEQ ID NO:144)

KGF2 Δ33, 183K/E Nucleotide Sequence

ATGTCTTACAACCACCTGCAGGGT-
GACGTTCGTTGGCGTAAACTGT TCTCTTTCAC-
CAAATACTTCCTGAAAATC-
GAAAAAAACGGTAAAGT
TTCTGGGACCAAGAAGGAGAACTGCCCG-
TACAGCATCCTGGAGAT AACATCAGTA-
GAAATCGGAGTTGTTGCCGTCAAAGC-
CATTAACAGC
AACTATTACTTAGCCATGAACAA-
GAAGGGGAAACTCTATGGCTCAA AAGAATT-
TAACAATGACTGTAAGCTGAAGGAGAG-
GATAGAGGAAA
ATGGATACAATACCTATGCATCATT-
TAACTGGCAGCATAATGGGAG GCAAATGTAT-
GTGGCATTGAATGGA
GAAGGAGCTCCAAGGAGAGG ACAGAAAA-
CACGAAGGAAAAACACCTCTGCT-
CACTTTCTTCCAATG GTGGTACACTCATAG
(SEQ ID NO:145)

KGF2 Δ33, 183K/E Amino Acid Sequence

MSYNHLQGDVRWRKLFSFTKYFLK-
IEKNGKVSGTKKENCPYSILEITS VEIGVVAV-

KAINSNYYLAMNKKGKLYGSKEFNNDCK-
LKERIEENGYN TYASFNWQHNGRQMYVALNG
EGAPRRGQKTRRKNTSAHFLPMVVHS (SEQ ID
NO:146)

EXAMPLE 23

Effect of KGF-2 on Survival After Total Body
Irradiation in Balb/c Mice

Ionizing radiation is commonly used to treat many malignancies, including lung and breast cancer, lymphomas and pelvic tumors (Ward, W. F. et al., *CRC Handbook of Animal Models of Pulmonary Disease*, CRC Press, pp. 165–195 (1989)). However, radiation-induced injury (lung, intestine, etc.) limits the intensity and the success of radiation therapy (Morgan, G. W. et al., *Int. J. Radiat. Oncol. Biol. Phys.* 31:361 (1995)). The gastrointestinal mucosa has a rapid cell cycle and is particularly sensitive to cytotoxic agents (Potten, C. S., et al., In: *Cytotoxic Insult to Tissue*, Churchill Livingstone, pp. 105–152 (1983)). Some of the manifestations of intestinal radiation damage include acute proctitis, intestinal fibrosis, stricture or fistula formation (Anseline, D. F. et al. *Ann. Surg.* 194:716–724 (1981)). A treatment which protects normal structures from radiation without altering the radiosensisitivity of the tumor would be beneficial in the management of these disorders. Regardless of the irradiated area, the dose of radiation is limited by the radiosensitivity of normal tissue. Complications following total or partial body irradiation include pneumonitis, fibrosis, gastro-intestinal injury and bone marrow disorders.

Several cytokines including IL-1, TNF, IL-6, IL-12 have demonstrated radioprotective effects following TBI (Neta, R. et al., *J. Exp. Med.* 173:1177 (1991)). IL-11 has been shown to protect small intestinal mucosal cells after combined irradiation and chemotherapy (Du, X. X. et al., *Blood* 83:33 (1994)) and radiation-induced thoracic injury (Redlich, C. A. et al. *The Journal of Immunology* 157:1705–1710 (1996)).

Animals

All experiments were performed using BALB/c mice. Animals were purchased at 6 weeks of age and were 7 weeks old at the beginning of the study. All manipulations were performed using aseptic techniques. This study was conducted according to the guidelines set forth by the Human Genome Sciences, Inc., Institutional Animal Care and Use Committee which reviewed and approved the experimental protocol.

KGF-2

The protein consists of a 141 amino acid human protein termed KGF-2 Δ33. This protein is a truncated isoform of KGF-2 that lacks the first 33 amino-terminal residues of the mature protein. The gene encoding this protein has been cloned into an *E. coli* expression vector. Fractions containing greater that 95% pure recombinant materials were used for the experiment. KGF-2 was formulated in a vehicle containing 40 mM Na Acetate+150 mM NaCl, pH 6.5. Dilutions were made from the stock solution using the same vehicle.

Total Body Irradiation and Experimental Design

Mice were irradiated with 519 RADS (5.19 Gy) using a 68 Mark I Shepherd Cesium Irradiator. The KGF-2 Δ33 was administered daily subcutaneously, starting 2 days before irradiation and continuing for 7 days after irradiation. Daily weights were obtained in all mice. Groups of mice were randomized to receive one of three treatments: Total body irradiation (TBI) plus buffer, TBI plus KGF-2 Δ33 (1 mg/kg sq), TBI plus KGF-2 Δ33 (5 mg/kg sq). Two independent experiments were performed.

Results

Figure 44:
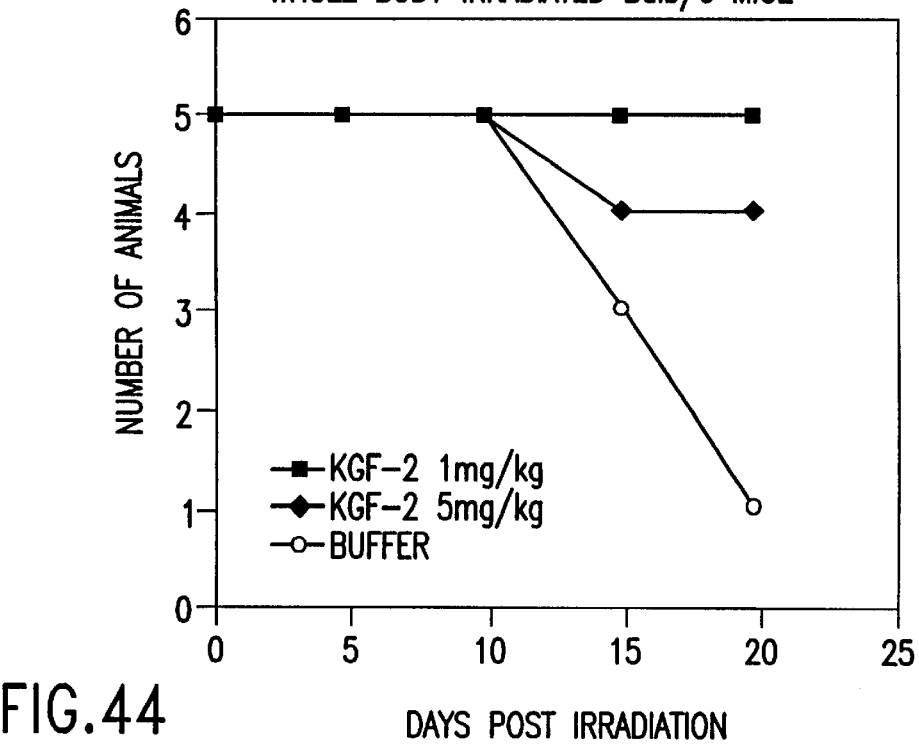
FIG. 44 shows the effect of KGF-2 Δ33 on the survival of whole body irradiated Balb/c mice. Balb/c male mice (n=5), 22.1 g were irradiated with 519 RADS. Animals were treated with buffer or KGF-2 (1 & 5 mg/kg, s.q.) 2 days prior to irradiation and daily thereafter for 7 days.

Two studies were performed using irradiated animals. In the first study, animals were irradiated with 519 RADS (5.19 Gy). Animals were treated with buffer or KGF-2 Δ33 at 1 & 5 mg/kg, s.q. two days prior to irradiation and daily thereafter for 7 days. At day 25 after total body irradiation 1/5 animals survived in the buffer group. In contrast, KGF-2 treated groups had 5/5 animals @ 1 mg/kg and 4/5 @ 5 mg/kg (FIG. 44).

Figure 45:
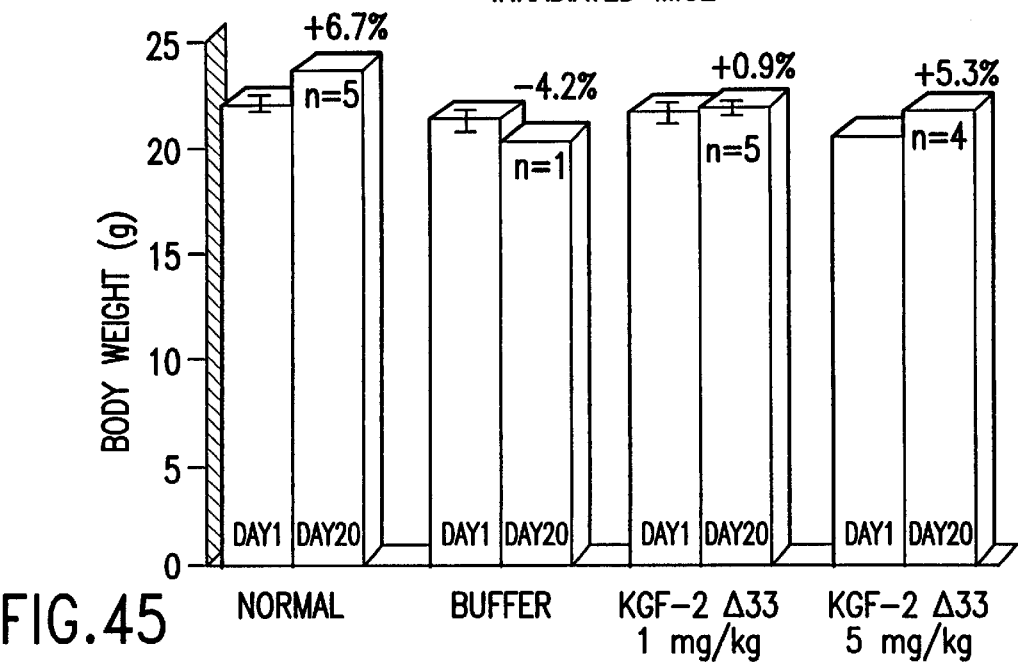
FIG. 45 shows the effect of KGF-2 Δ33 on body weight of irradiated mice. Balb/c male mice (n=5) weighing 22.1 g were injected with either Buffer or KGF-2 Δ33 (1, 5 mg/kg) for 2 days prior to irradiation with 519 Rad/min. The animals were weighed daily and injected for 7 days following irradiation.

In addition, KGF-2 treated animals displayed 0.9% and 5.3% weight gain at day 20 post-TBI. In contrast, the buffer treated group had 4.2% weight loss at day 20. Normal non-irradiated age matched control animals showed 6.7% weight gain in the same time period (FIG. 45).

Figure 46:
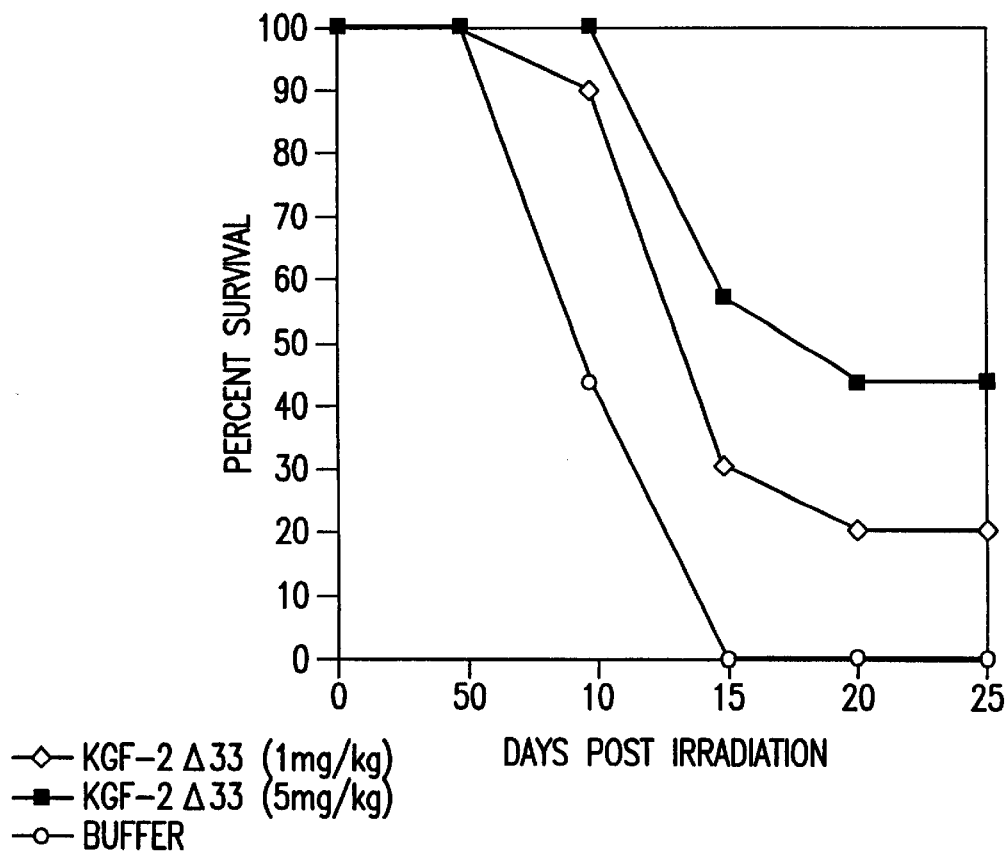
FIG. 46 shows the effect of KGF-2 Δ33 on the survival rate of whole body irradiated Balb/c mice. Balb/c male mice (n=7), 22.1 g were irradiated with 519 RADS. Animals were treated with buffer or KGF-2 (1 and 5 mg/kg, s.q.) 2 days prior to irradiation and daily thereafter for 7 days.

Animals in the second study were also irradiated with 519 RADS (5.19 Gy). These animals were treated with buffer or KGF-2 Δ33 at 1 & 5 mg/kg, s.q. two days prior to irradiation and daily thereafter for 7 days. At day 15 after total body irradiation all the animals in the buffer group were dead. KGF-2 at 1 mg/kg had 30% survival and 60% survival at 5 mg/kg. At day 25 after TBI the 1 mg/kg group showed 20% survival and the 5 mg/kg 50% survival (FIG. 46).

Conclusions

In summary, these results demonstrate that KGF-2 has a protective effect after TBI. The ability of KGF-2 to increase survival rate of animals subjected to TBI suggests that it would also be useful in radiation-induced injuries and to increase the therapeutic ratio of irradiation in the treatment of malignancies.

EXAMPLE 24

Evaluation of KGF-2 in the TPA Model of
Cutaneous Inflammation in Mice

To demonstrate that KGF-2 would attenuate the progression of contact dermatitis, a tetradecanoylphorbol acetate (TPA)-induced cutaneous inflammation model in mice is used. The use of the female BALB/c and male Swiss Webster mice in experimental cutaneous inflammation are well-characterized, relevant and reproducible models of contact dermatitis. These strains of mice have been shown to develop a long-lasting inflammatory response, following topical application of TPA, which is comprised of local hemodynamics, vascular permeability and local migration of leukocytes, and these pathological changes are similar to those of human dermatitis (Rao et al. 1993, Inflammation 17(6):723; Rao et al. 1994, J. Kipid Mediators Cell Signalling 10:213).

Groups of mice receive either vehicle or KGF-2 intraperitoneally, sub-cutaneously, or intravenously 60 min after the topical application of TPA (4 μg/ear) applied as a solution in acetone (200 μg/ml), 10 μl each to the inner and outer surface of ear. The control group receives 20 μl of acetone as a topical application. Four hours following the application of TPA, increase in ear thickness is measured and ears are excised for histology. To determine vascular permeability in response to TPA, mice are intravenously injected through tail veins with Evans blue (300 mg/kg) at selected times after topical application of TPA and mice are sacrificed 15 min thereafter. Ears are excised and removed, then extracted into dimethylformamide and centrifuged. Absorbance readings are spectrophotometrically measured at 590 nm.

EXAMPLE 25

Effect of KGF-2 Δ33 in Wound Healing

The biological effects of KGF-2 Δ33 in the skin were examined based on the initial in vitro data demonstrating KGF-2' s capacity to stimulate primary human epidermal keratinocytes as well as murine pro-B BaF3 cells transfected with the FGFR isoform 2iiib. Initial experiments were performed to determine the biological effects of KGF-2 Δ33 following intradermal administration. Following the intradermal studies, KGF-2 Δ33 was explored in a variety of wound healing models (including full thickness punch biopsy wounds and incisional wounds) to determine its potential as a wound healing agent.

Effect of KGF-2 Δ33 in a Glucocorticoid-impaired Rat Model of Wound Healing

Impaired wound healing is an important clinical problem associated with a variety of pathologic conditions such as diabetes and is a complication of the systemic administration of steroids or antimetabolites. Treatment with systemic glucocorticoids is known to impair wound healing in humans and in animal models of tissue repair. A decrease in circulating monocyte levels and an inhibition of procollagen synthesis have been observed subsequent to glucocorticoid administration. The inflammatory phase of healing and matrix synthesis are therefore important factors involved in the complex process of tissue repair. In the present study the effects of multiple topical applications of KGF-2 were assessed on full thickness excisional skin wounds in rats in which healing has been impaired by the systemic administration of methylprednisolone.

Figure 47:
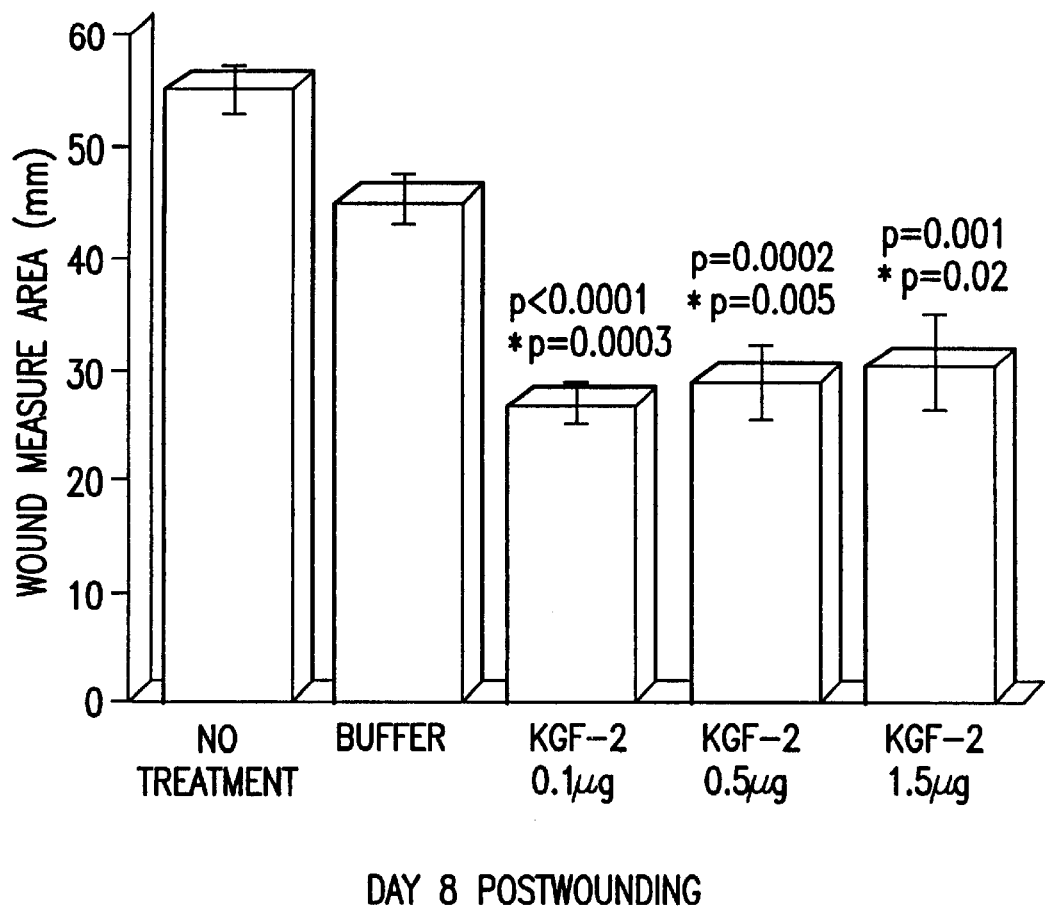
FIG. 47 shows the effect of KGF-2 Δ33 on wound healing in a glucocorticoid-impaired rat model.

Sprague Dawley rats (n=5/treatment group) received 8 mm dorsal wounds and methylprednisolone (17 mg/kg, i.m.) to impair healing. Wounds were treated topically each day with buffer or KGF-2 at doses of 0.1, 0.5 and 1.5 μg in a volume of 50 μl. Wounds were measured on days 2, 4, 6, and 8 using a calibrated Jameson caliper. On day 6 (data not shown), and day 8 (FIG. 47) KGF-2 treated groups showed a statistically significant reduction in wound closure when compared to the buffer control.

Effect of KGF-2 Δ33 on Wound Healing in a Diabetic Mouse Model

Genetically diabetic homozygous female (db+/db+) mice, 6 weeks of age (n=6), weighing 30–35 g were given a dorsal full thickness wound with a 6 mm biopsy punch. The wounds were left open and treated daily with placebo or KGF-2 at 0. 1, 0.5 and 1.5 μg. Wound closure was determined using a Jameson caliper. Animals were euthanized at day 10 and the wounds were harvested for histology.

KGF-2 displayed a significantly improvement in percent wound closure at 0.1 μg (p=0.02) when compared to placebo or with the untreated group. Administration of KGF-2 also resulted in an improvement in histological score at 0.1 μg (p=0.03) when compared to placebo or with the untreated group (p=0.01) and 1.5 μg (p=0.05) compared to the untreated group.

Conclusions

Based on the results presented above, KGF-2 shows significant activity in impaired conditions such as glucocorticoid administration and diabetes. Therefore, KGF-2 may be clinically useful in stimulating healing of wounds after surgery, chronic ulcers in patients with diabetes or poor circulation (e.g., venous insufficiency and venous ulcers), bums and other abnormal wound healing conditions such as uremia, malnutrition, vitamin deficiencies and systemic treatment with steroids and antineoplastic drugs.

EXAMPLE 26

Effects of KGF-2 Δ33 on Oral Mucosa

Cytotoxic agents used clinically have the unfortunate effect of inhibiting the proliferation of the normal epithelia in some locations, such as the oral mucosa, leading to life-threatening disturbances in the mucosal barrier. We have conducted studies to examine the efficacy of KGF-2 in this clinical area. The data supports a therapeutic effect of KGF-2 in models of mucositis.

Effects of KGF-2 Δ33 on Hamster Oral Mucosa

Figure 48:
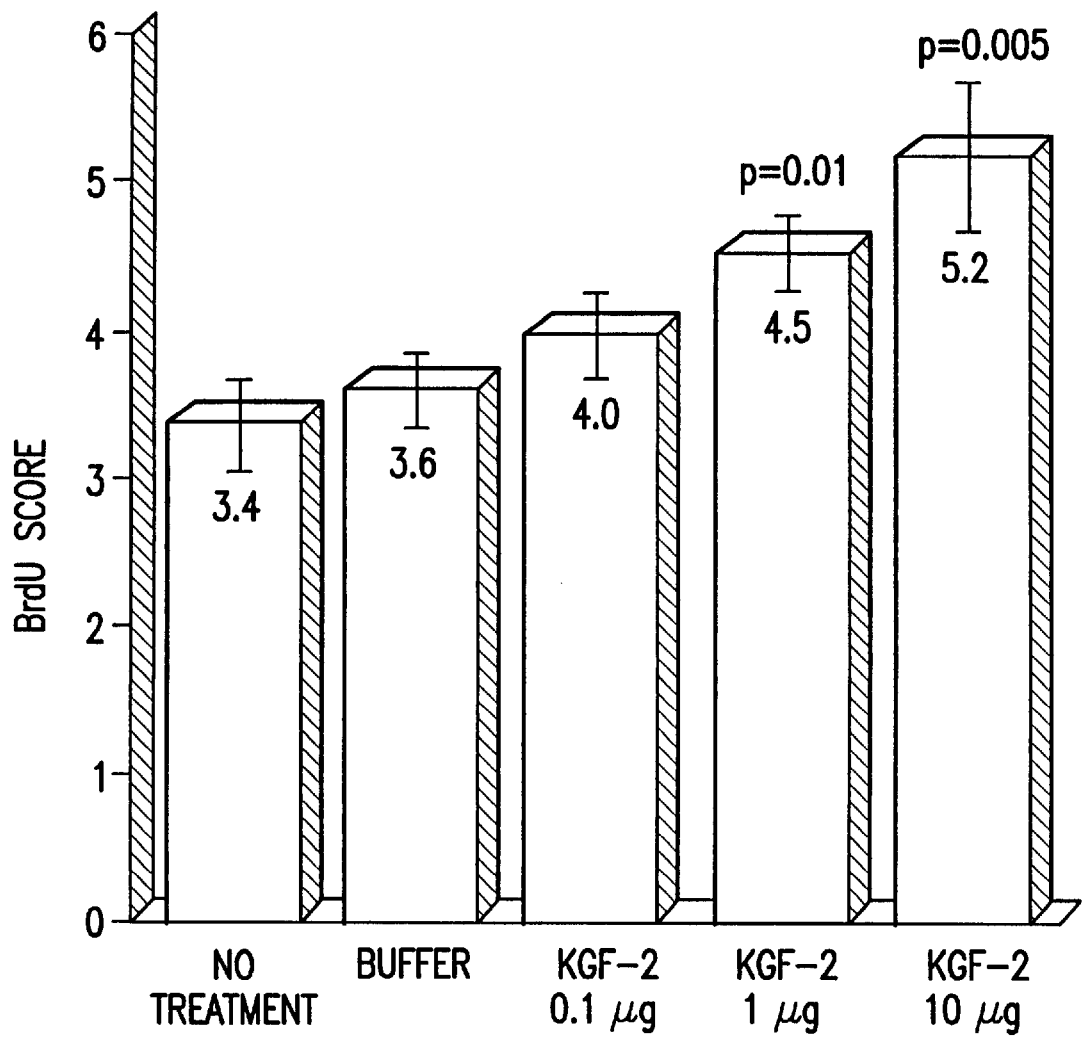
FIG. 48 shows the effect of KGF-2 Δ33 on cell proliferation as determined using BrdU labeling.

We sought to determine if KGF-2 might induce proliferation of normal oral mucosal epithelium. The effect of KGF-2 in the oral mucosa was assessed in male Golden Syrian hamsters. The cheek pouch of the hamster was treated daily with buffer or KGF-2 Δ33 (at 0.1, 1 and 10 μg/cheek) which were applied topically to anesthetized hamster cheeks in a volume of 100 μl per cheek. The compound was in contact with the cheek for a minimum of 60 seconds and subsequently swallowed. After 7 days of treatment, animals were injected with BrdU and sacrificed as described above. Proliferating cells were labeled using anti-BrdU antibody. FIG. 48 shows that there was a significant increase in BrdU labeling (cell proliferation) when animals were treated with 1 μg and 10 μg of KGF-2 Δ33 (when compared to buffer treatment).

Topical treatment with KGF-2 induced the proliferation of normal mucosal epithelial cells. Based upon these results, KGF-2 may be clinically useful in the prevention of oral mucositis caused by any chemotherapeutic agents (or other toxic drug regimens), radiation therapy, or any combined chemotherapeutic-radiation therapy regimen. In addition, KGF-2 may be useful as a therapeutic agent by decreasing the severity of damage to the oral mucosa as a result of toxic agents (chemotherapy) or radiotherapy.

EXAMPLE 27

The Effect of KGF-2 Δ33 on Ischemic Wound Healing in Rats

The aim of the experiments presented in this example was to determine the efficacy of KGF-2 in wound healing using an ischemic wound healing model.

The blood supply of local skin was partially interrupted by raising of a single pedicle full-thickness random myocutaneous flap (3×4 cm). A full-thickness wound was made into the local skin, which is composed of the myocutaneous flap. Sixty, adult Sprague-Dawley rats were used and randomly divided into treatments of KGF-2 Δ33 and placebo groups for this study (5 animals/group/time-point). The wounds were harvested respectively at day 1, 3, 5, 7, 10 and 15 post-wounding.

The wound breaking strength did not show a significant difference between KGF-2 and buffer treated groups at early time points until day 10 and 15 post-wounding.

The results indicated that KGF-2 improved significantly the wound breaking strength in ischemic wound repair after 10 days post-wounding. These results also suggest that ischemia delays the healing process in both groups compared to the data previously obtained in studies of normal wound healing.

This myocutaneous flap model supplies data and information in an ischemic situation which results from venous return. These results suggest that KGF-2 could be used in the treatment of chronic venous leg ulcers caused by an impairment of venous return and/or insufficiency.

EXAMPLE 28

Evaluation of KGF-2 in the Healing of Colonic Anastomosis in Rats

The results of the present experiment demonstrate that KGF-2 Δ33 increases the rate of intestinal repair in a model of intestinal or colonic anastomosis in Wistar or Sprague Dawley rats. In addition, this model can be used to demonstrate that KGF-2 and its isoforms increase the capability of the gastrointestinal or colon wall to bind sutures.

The use of the rat in experimental anastomosis is a well characterized, relevant and reproducible model of surgical wound healing. This model can also be extended to study the effects of chronic steroid treatment or the effects of various chemotherapeutic regimens on the quality and rate of surgical wound healing in the colon and small intestine (Mastboom, W. J. B. et al., *Br. J. Surg.* 78:54–56 (1991); Salm, R. et al., *J Surg. Oncol.* 47:5–11 (1991); Weiber, S. et al., *Eur. Surg. Res.* 26:173–178 (1994)). Healing of anastomosis is similar to that of wound healing elsewhere in the body. The early phases of healing are characterized by acute inflammation followed by fibroblast proliferation and synthesis of collagen. Collagen is gradually modeled and the wound is strengthened as new collagen is synthesized (Koruda, M. J., and Rolandelli, R. H., *J. Surg. Res.* 48:504–515 (1990)). Most postoperative complications such as anastomotic leakage occur during the first few days following surgery—a period during which strength of the colon is mainly secured by the ability of the wound margin to hold sutures. The suture holding capacity of the GI tract has been reported to decrease by as much as 80% during the first postoperative days (Hogstrom, H. and Haglund, U., *Acta Chir. Scand.* 151:533–535 (1985); Jonsson, K. et al., *Am J. Surg.* 145:800–803 (1983)).

Rats were anesthetized with a combination of ketamine (50 mg/kg) and xylazine (5 mg/kg) intramuscularly. Animals were kept on a heating pad during skin disinfection, surgery, and post-surgery. The abdominal cavity was opened with a 4 cm long midline incision. A 1 cm wide segment of the left colon was resected 3 cm proximal to the peritoneal reflection while preserving the marginal blood vessels. A single layer end-to-end anastomosis was performed with 8-10 interrupted 8-0 propylene inverted sutures which were used to restore intestinal continuity. The incisional wound was closed with 3-O running silk suture for the muscle layer and surgical staples for the skin. Daily clinical evaluations were conducted on each animal consisting of individual body weight, body temperature, and food consumption patterns.

KGF-2 Δ33 and placebo treatment were daily administered sc, topically, ip, im, intragastrically, or intracolonically immediately following surgery and were continued thereafter until the day of sacrifice, day 7. There was an untreated control, a placebo group, and KGF-2 Δ33 groups. Two hours prior to euthanasia, animals were injected with 100 mg/kg BrdU i.p. Animals were euthanized 24 hours following the last treatment (day 5). A midline incision was made on the anterior abdominal wall and a 1 cm long colon segment, including the anastomosis, was removed. A third segment at the surgical site was taken for total collagen analysis.

Figure 49:
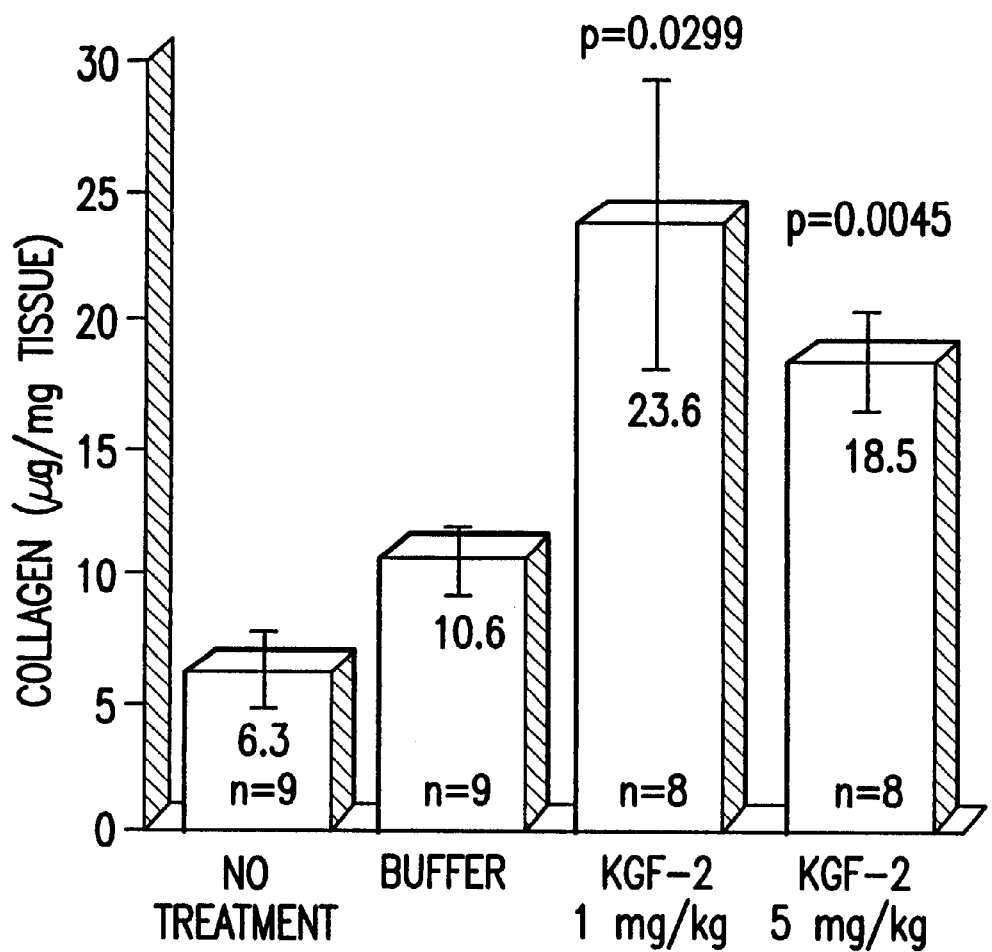
FIG. 49 shows the effect of KGF-2 Δ33 on the collagen content localized at anastomotic surgical sites in the colons of rats.

In a series of two experiments, male adult SD rats (n=5) were anaesthetized and received a single layer end-to-end anastomosis of the distal colon with 8-10 interrupted 6-0 prolene inverted sutures. The anastomotic site was then topically treated via syringe with either buffer or KGF-2 Δ33 at concentrations of 1 and 4 μg. Animals were then treated daily thereafter with either buffer or KGF-2 Δ33 at concentrations of 1 mg/kg or 5 mg/kg ip. Animals were euthanized on day 5 and the colon excised and snap frozen in liquid nitrogen, lyophilized and subjected to collagen determinations. Collagen concentration is expressed as μg collagen/mg dry weight tissue. Statistical analysis was done using an unpaired t test. Mean±SE. On day 5 rats were anesthetized and subjected to barium enemas followed by radiographic analysis. Barium enema radiologic assessment of end-to-end left colonic anastomosis from two experiments showed a consistent reduction in peritoneal leakage with KGF-2 treated animals at 1 and 5 mg/kg. This data is shown in the Table below. In addition, breaking strength at the site of surgery was also examined using a tensiometer. No significant differences were observed between the KGF-2 Δ33 and buffer groups. As shown in FIG. 49, significant increases in collagen content at the surgical site were demonstrated at both 1 mg/kg KGF-2 Δ33 (p=0.02) and 5 mg/kg (p=0.004) relative to buffer controls.

TABLE

| Groups | Colonic Anastomosis Radiologic Analysis | | |
|---|---|---|---|
| | Feces Present | Anastomotic Constriction* | Peritoneal Leakage |
| No Treatment (N = 8) | 50% | 2.0 | 75% |
| Buffer (N = 7) | 57% | 1.0 | 50% |
| KGF-2 Δ33 [1 mg/kg] (N = 8) | 50% | 1.3 | 37% |
| KGF-2 Δ33 [5 mg/kg] (N = 9) | 77% | 1.6 | 11% |

*Anastomic Constriction Scoring: 0 -no constriction: 1—5 -minimal to severe constriction Male adult SD rats (n=5) were anesthetized with a combination of ketamine (50 mg/kg) and xylazine (5 mg/kg) intramuscularly. The abdominal cavity was opened with a 4 cm long midline incision. A 1 cm wide segment of the left colon was resected 3 cm proximal to the peritoneal reflection while preserving the marginal vessels. A single layer end-to-end anastomosis was performed with 8-10 interrupted 6-0 prolene inverted sutures to restore intestinal continuity. The anastomosis was then topically treated via syringe with either buffer or KGF-2 at concentrations of 1 and 4 μg. The incisional wound was closed with 3-O running silk suture for the muscle layer and surgical staples for the skin. Treatments were then administered daily thereafter and consisted of buffer or KGF-2 Δ33 at 1 and 5 mg/kg sc. Weights were taken on the day of surgery and daily thereafter. Animals were euthanized 24 hours following the last treatment (day 5). Animals were anesthetized and received barium enemas and were x-rayed at a fixed distance. The anastomosis was then excised for histopathological and biomechanical analysis.

EXAMPLE 29

Evaluation of KGF-2 in a Model of Inflammatory Bowel Disease

KGF-2 is a protein that induces keratinocyte proliferation in vitro and is active in a variety of wound healing models in vivo. The purpose of this study was to determine whether KGF-2 was efficacious in a model of murine colitis induced by ad libitum exposure to dextran sodium sulfate in the drinking water.

Six to eight week old female Swiss Webster mice (20–25 g, Charles River, Raleigh, N.C.) were used in a model of inflammatory bowel disease induced with a 4% solution of sodium sulfate (DSS, 36,000–44,000 MW, American International Chemistry, Natick, Mass.)) administered ad libitum for one week. KGF-2 was given by daily parenteral administration (n=10). Three parameters were used to determine efficacy: 1) clinical score, based on evaluation of the stool; 2) histological score, based on evaluation of the colon; and 3) weight change. The clinical score was comprised of two parts totaling a maximum of score of four. Stool consistency was graded as: 0=firm; 1=loose; 2=diarrhea. Blood in the stool was also evaluated on a 0 to 2 scale with 0=no blood; 1=occult blood; and 2=gross rectal bleeding. A mean group score above 3 indicated probable lethality, and disease which had progressed beyond its treatable stage. Clinical scores were taken on Day 0, 4, 5, 6, and 7. To arrive at a histological score, slides of the ascending, transverse and descending colon were evaluated in a blinded fashion based on inflammation score (0–3) and crypt score (0–4). Body weight was measured daily. Data was expressed as mean+SEM. An unpaired Student's t test was used to determine significant differences compared to the disease control (*$p<0.05$; $p<0.01$; *$p<0.001$).

When DSS-treated mice were given a daily, intraperitoneal (IP) injection of KGF-2 Δ33 at a dose of 1, 5 or 10 mg/kg for 7 days, KGF-2 significantly reduced clinical score, 28, 38 and 50 percent, respectively. Histological evaluation closely paralleled the dose dependent inhibition of the clinical score, with the 1, 5 and 10 mg/kg dose reducing histological score a significant 26, 48 and 51 percent. KGF-2 also significantly reduced weight loss associated with DSS-induced colitis.

In a second study, a comparison was made of the relative efficacy of KGF-2 Δ33 (10 mg/kg) when given IP or sub-cutaneous (SC) daily. By the end of the experiment on Day 7, animals injected IP with KGF-2 had a significant, 34 percent reduction in clinical score while KGF-2 injected SC resulted in a significant 46 percent reduction. The SC dose also significantly reduced weight loss over DSS controls. Based on measurement of clinical score and body weight, SC administration of KGF-2 is at least as efficacious as IP administration.

EXAMPLE 30

Effects of KGF-2 Δ33 on Normal Urinary Bladder and Prostate and in Cyclophosphamide-induced Hemorrhagic Cystitis in Rats The purpose of this example is to show that KGF-2 Δ33 is capable of stimulating urinary bladder proliferation in normal rats and that there is a therapeutic effect of KGF-2 Δ33 in a rat model of cyclophosphamide-induced hemorrhagic cystitis.

Some cytotoxic agents used clinically have side effects resulting in the inhibition of the proliferation of the normal epithelium in the bladder, leading to potentially life-threatening ulceration and breakdown in the epithelial lining of the bladder. For example, cyclophosphamide causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment and occurs in patients who previously had hemorrhagic cystitis (CYTOXAN (cyclophosphamide) package insert). Cyclophosphamide has toxic effects on the prostate and male reproductive systems. Cyclophosphamide treatment can result in the development of sterility, and result in some degree of testicular atrophy.

Effects of KGF-2 Δ33 on Normal Bladder, Testes and Prostate

Experimental Design Male Sprague-Dawley rats (160–220 g), (n=4 to 6/treatment group) were used in these studies. KGF-2 Δ33 was administered at a dose of 5 mg/kg/day. Daily ip or sc injections of recombinant KGF-2 Δ33 or buffer (40 mM sodium acetate+150 mM NaCl at pH 6.5) were administered for a period of 1–7 days and the rats were sacrificed the following day. To examine the reversibility of effects induced with KGF-2 Δ33, additional animals were injected ip daily for 7 days with KGF-2 Δ33 or buffer and sacrificed after a 7 day treatment-free period.

On the day of sacrifice, rats were injected ip with 100 mg/kg of BrdU. Two hours later the rats were overdosed with ether and selected organs removed. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by blinded observers. The number of proliferating cells was counted in 10 random fields per animal at a 10×magnification for the prostate. To assess the effects of KGF-2 Δ33 in the bladder, cross-sections of these tissues were prepared and the number of proliferating and non-proliferating cells were counted in ten random fields at 20×magnification. The results are expressed as the percentage of labeled to unlabeled cells. Data are presented as mean+SEM. Statistical analyses (two-tailed unpaired t-test) were performed with the StatView Software Package and statistical significance is defined as $p<0.05$.

Results

Bladder.

Intraperitoneal injection of KGF-2 Δ33 induced proliferation of bladder epithelial cells over the 7 day study period (solid squares, FIG. 52) but this did not influence the weight of the organ. Subcutaneous administration elicited a small increase in proliferation but this failed to achieve statistical significance (solid circles, FIG. 52).

Prostate and Testes.

Both sc and ip administration of KGF-2 Δ33 induced significant proliferation of the prostate (FIG. 53) but this normalized after two injections. Prolonged ip treatment with KGF-2 Δ33 did not increase the weight of the prostate or testes.

Effects of KGF-2 33 on Cycloplhosphamide-induced Hemorrhagic Cystitis Experimental Design Male Sprague Dawley rats (300–400 g) (n=5/group) were injected i.v. via the tail vein with buffer placebo or KGF-2

Δ33 at concentrations of 1 or 5 mg/kg 24 hours prior to a 200 mg/kg i.p. injection of cyclophosphamide. On the final day, 48 hours after cyclophosphamide injection, rats were injected ip with 100 mg/kg of BrdU. Two hours later the rats were killed by $CO_2$ administration. Fixation of the bladder was done by direct injection of 10% formalin into the lumen of the bladder and rinsing of the exterior of the bladder with formalin. After 5 minutes, the bladder and prostate were removed. The urinary bladder and prostate gland were paraffin embedded, cross-sectioned and stained with H&E and a mouse anti-BrdU monoclonal antibody. The extent of urothelial damage was assessed using the following scoring system: Bladders were graded by two independent observers to describe the extent of the loss of urothelium. (Urothelial damage was scored as 0, 25%, 50%, 75% and 100% loss of the urothelium). In addition, the thickness of the bladder wall was measured at 10 random sites per section and expressed in $\mu$m.

Results

Macroscopic Observations

In rats treated with placebo and cyclophosphamide, bladders were thick and rigid. Upon injection of 10% formalin, very little expansion of the bladders was noted. However, in the groups pretreated with KGF-2 Δ33, a greater elasticity of the bladder was noted upon direct injection with formalin suggesting a lesser degree of fibrosis.

Microscopic Observations

Figure 54:
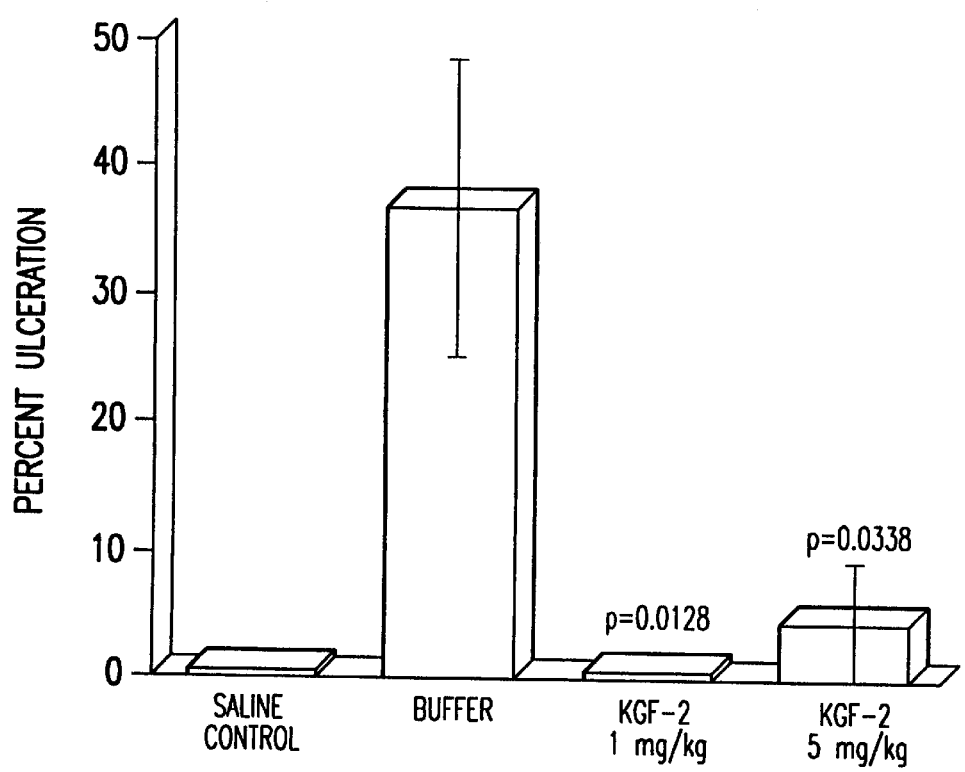
FIG. 54 shows the effect of KGF-2 Δ33 on bladder wall ulceration in a cyclophosphamide-induced hemorrhagic cystitis model in the rat.

FIG. 54 shows the results of KGF-2 Δ33 pretreatment on the extent of ulceration in the bladder. In normal rats treated with i.p. saline (saline control), the bladders appeared normal histologically and no ulceration of the urothelium was observed. Administration of 200 mg/kg i.p. of cyclophosphamide resulted in ulceration of the bladder epithelium that was between 25 and 50% of the total epithelial area (with a mean of 37%). Administration of KGF-2 Δ33 24 hours prior to cyclophosphamide resulted in a significant reduction in the extent of ulceration (1 mg/kg 0.4% p=0.0128, and 5 mg/kg 5%, p=0.0338%) when compared to placebo treated animals receiving cyclophosphamide.

Figure 55:
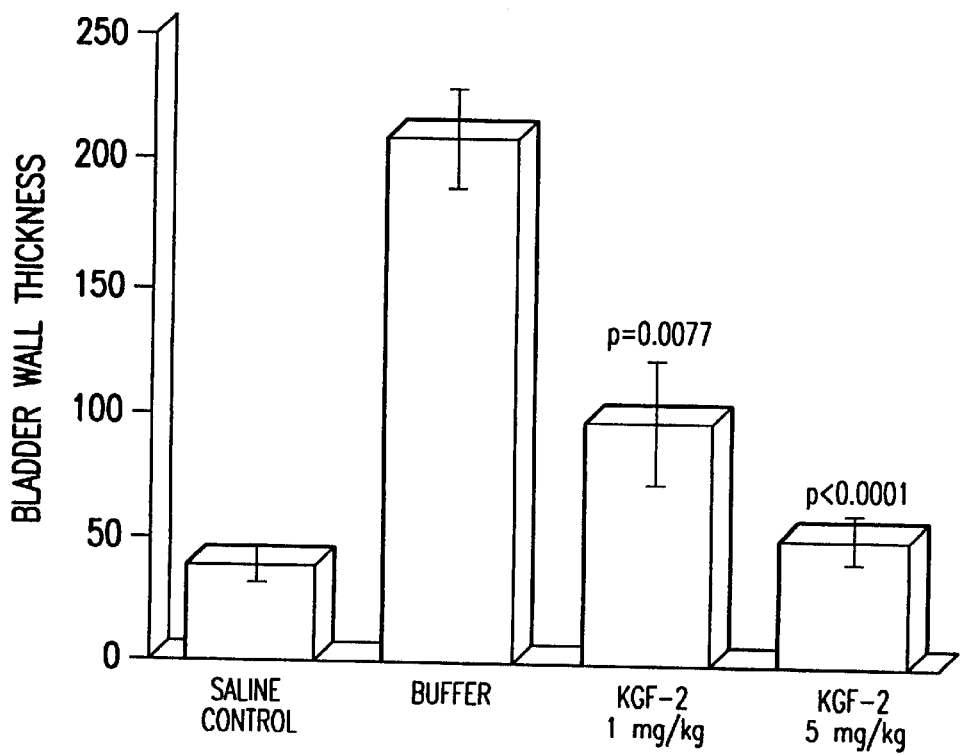
FIG. 55 shows the effect of KGF-2 Δ33 on bladder wall thickness in a cyclophosphamide-induced cystitis rat model.

FIG. 55 shows the effects of KGF-2 Δ33 on the thickness of the urinary bladder wall which includes epithelium, smooth muscle layers and the serosal surface. In groups treated with buffer alone, the thickness of the bladder wall is approximately 40 $\mu$m. Treatment with cyclophosphamide results in a 5 fold increase in bladder wall thickness to 210 $\mu$m. KGF-2 Δ33 pretreatment of cyclophosphamide treated animals resulted in a significant inhibition of cyclophosphamide enlargement of the bladder wall (1 mg/kg 98.6 $\mu$m (p=0.007) and at 5 mg/kg 52.3 $\mu$m (p<0.0001)) when compared to the cyclophosphamide treatment alone.

Microscopic Observations

Prostate Gland: In rats receiving buffer and cyclophosphamide, marked atrophy of the prostatic glands (acini) was observed accompanied by enlargement of interstitial spaces with remarkable edema when compared to normals. In addition, epithelial cells lining the prostatic glands were observed to be much shorter and less dense than in corresponding normal prostatic tissue. KGF-2 Δ33 pretreatment at both 1 mg/kg and 5 mg/kg displayed a normal histological appearance of the prostatic gland. No increase in the interstitial spaces or edema was observed, and the epithelial cells lining the prostatic glands were similar in size and density to normal prostatic tissue.

Conclusion

The results demonstrate that KGF-2 specifically induces proliferation of bladder epithelial cells and the epithelial cells lining the prostatic glands. The results also demostrate that KGF-2 specifically results in a significant reduction in the extent of ulceration in cyclophosphamide-induced hemorrhagic cystitis.

EXAMPLE 31

Effect of KGF-2 on the Proliferation of Cells in Normal Rats Introduction

KGF-2, a member of the FGF family, induces proliferation of normal human and rat keratinocytes. It has approximately 57% homology to KGF-1 (a member of the FGF family). KGF-1 has been reported to induce proliferation of epithelia of many organs (Housley et al., Keratinocyte growth factor induces proliferation of hepatocytes and epithelial cells throughout the rat gastrointestinal tract. *J Clin Invest* 94: 1764–1777 (1994); Ulich et al., Keratinocyte growth factor is a growth factor for type II pneumocytes in vivo. *J Clin Invest* 93: 1298–1306 (1994); Ulich et al., Keratinocyte growth factor is a growth factor for mammary epithelium in vivo. The mammary epithelium of lactating rats is resistant to the proliferative action of keratinocyte growth factor. *Am J Pathol* 144:862–868 (1994); Nguyen et al., Expression of keratinocyte growth factor in embryonic liver of transgenic mice causes changes in epithelial growth and differentiation resulting in polycystic kidneys and other organ malformations. *Oncogene* 12:2109–2119 (1996); Yi et al., Keratinocyte growth factor induces pancreatic ductal epithelial proliferation. *Am J Pathol* 145:80–85 (1994); and Yi et al., Keratinocyte growth factor causes proliferation of urothelium in vivo. *J Urology* 154:1566–1570 (1995)). We performed similar experiments with KGF-2 to determine if it induces proliferation of normal epithelia in rats when administered systemically using sc and ip routes.

Methods

Male Sprague-Dawley rats, weighing 160–220 g, were obtained from Harlan Sprague Dawley for these studies. KGF-2 Δ33 (HG03411-E2) was administered at a dose of 5 mg/kg/day. Daily ip or sc injections of KGF-2 Δ33 or recombinant buffer (40 mM sodium acetate+150 mM NaCl at pH 6.5) were administered for a period of 1–7 days and the rats were sacrificed the following day (see below). To examine the reversibility of effects induced with KGF-2 Δ33, additional animals were injected ip daily for 7 days with KGF-2 Δ33 or buffer and sacrificed after a 7 day treatment-free period.

On the day of sacrifice, rats were injected ip with 100 mg/kg of BrdU. Two hours later the rats were overdosed with ether and selected organs removed. Samples of tissues were fixed in 10% neutral buffered formalin for 24 hours and paraffin embedded. To detect BrdU incorporation into replicating cells, five micron sections were subjected to immunohistochemical procedures using a mouse anti-BrdU monoclonal antibody (Boehringer Mannheim) and the ABC Elite detection system (Vector Laboratories). The sections were lightly counterstained with hematoxylin.

Sections were read by blinded observers. The number of proliferating cells was counted in 10 random fields per animal at a 10×magnification for the following tissues: liver, pancreas, prostate, and heart. Ten random fields were used also for the lung analysis except the proliferation was quantitated at 20×magnification. Since the kidney has many functionally discrete areas, the proliferation was assessed in a coronal cross-section taken through the center of one kidney per animal. To assess the effects of KGF-2 Δ33 in the esophagus and bladder, cross-sections of these tissues were prepared and the number of proliferating and non-proliferating cells were counted in ten random fields at a 10× and 20×magnification, respectively. The results are expressed as the percentage of labeled to unlabeled cells.

Data are presented as mean±SEM. Statistical analyses (two-tailed unpaired t-test) were performed with the Stat-View Software Package (Abacus Concepts, Inc., Berkeley, Calif.) and statistical significance is defined as $p<0.05$.

Results

Figure 56:
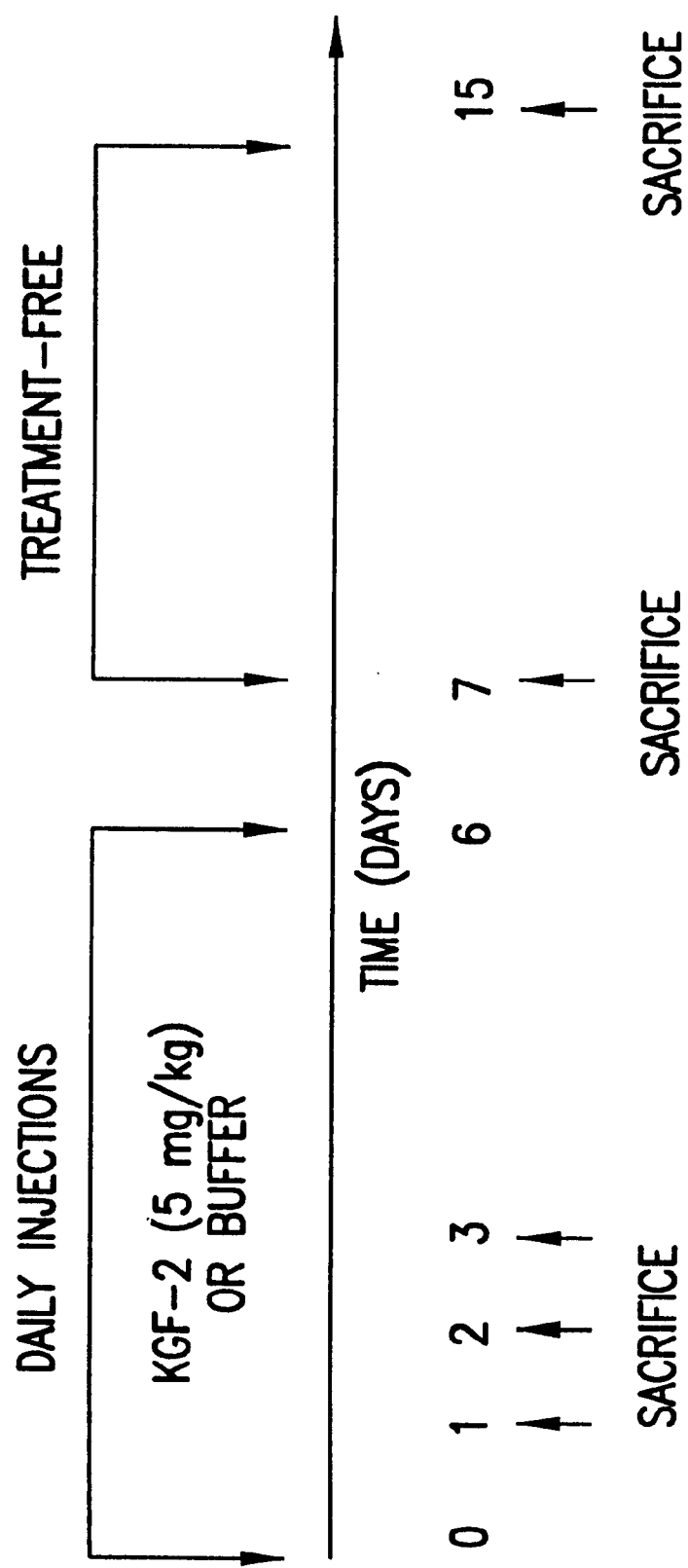
FIG. 56 provides an overview of the study design to determine whether KGF-2 Δ33 induces proliferation of normal epithelia in rats when administered systemically using SC and IP routes.

FIG. 56 shows an overview of the experimental protocol. Six animals were used per group. However, during the analysis by the blinded observers it became clear that occasionally the BrdU injection was unsuccessful. Before the results were uncoded, the data from 8 rats out of 116 rats (or 7% of the animals) were excluded from the study and the resultant group sizes are shown in the Table below.

| Group sizes used in these studies | | | |
|---|---|---|---|
| | | n = | |
| Treatment | Time | ip | sc |
| KGF-2 Δ33 | 1 day | 6 | 5 |
| buffer | 1 day | 6 | 6 |
| KGF-2 Δ33 | 2 days | 6 | 4 |
| buffer | 2 days | 6 | 6 |
| KGF-2 Δ33 | 3 days | 5 | 5 |
| buffer | 3 days | 5 | 5 |
| KGF-2 Δ33 | 7 days | 6 | 6 |
| buffer | 7 days | 6 | 5 |
| KGF-2 Δ33 | 7 days + 7 days treatment-free | 6 | ND |
| buffer | 7 days + 7 days treatment-free | 6 | ND |

Figure 57:
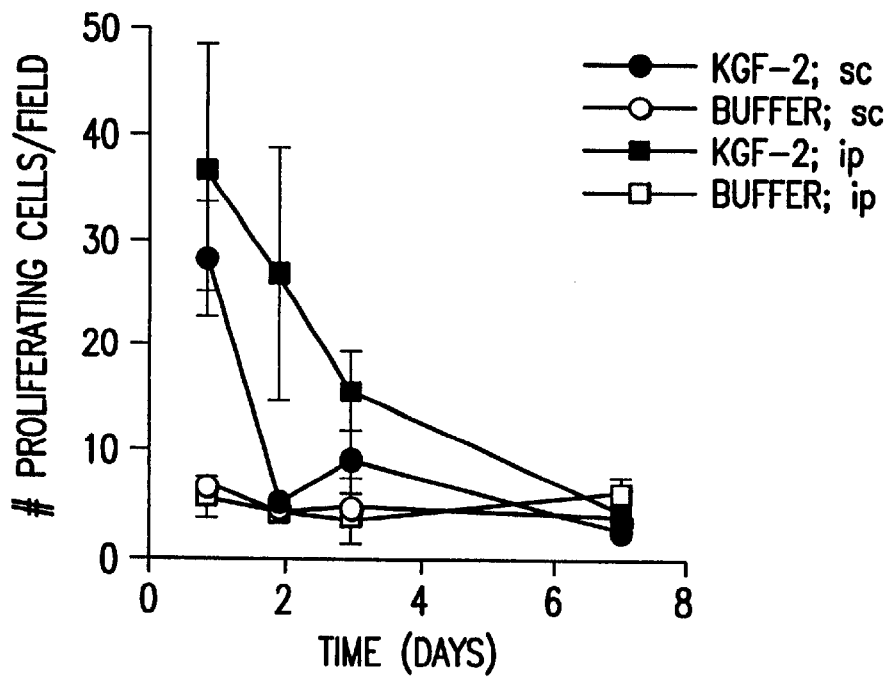
FIG. 57. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animals at a 10×magnification. SC administration of KGF-2 Δ33 elicited a significant proliferation after one day which then returned to normal by 2 days. KGF-2 Δ33 given ip stimulated proliferation from 1–3 days but only the results from days 1 and 3 were statistically significant.

Liver. When administered ip, KGF-2 Δ33 induced a rapid proliferation of hepatocytes (solid squares) (FIG. 57) after 1 injection and this augmented mitotic activity persisted for three days, returning to normal after 7 days of daily injections. In contrast to the dramatic effect ip administration of KGF-2 exerted on the liver, when given sc (solid circle, FIG. 57) this growth factor demonstrated minor effects. Proliferation was elevated after one day of treatment but returned to normal values after two daily injections.

Figure 58:
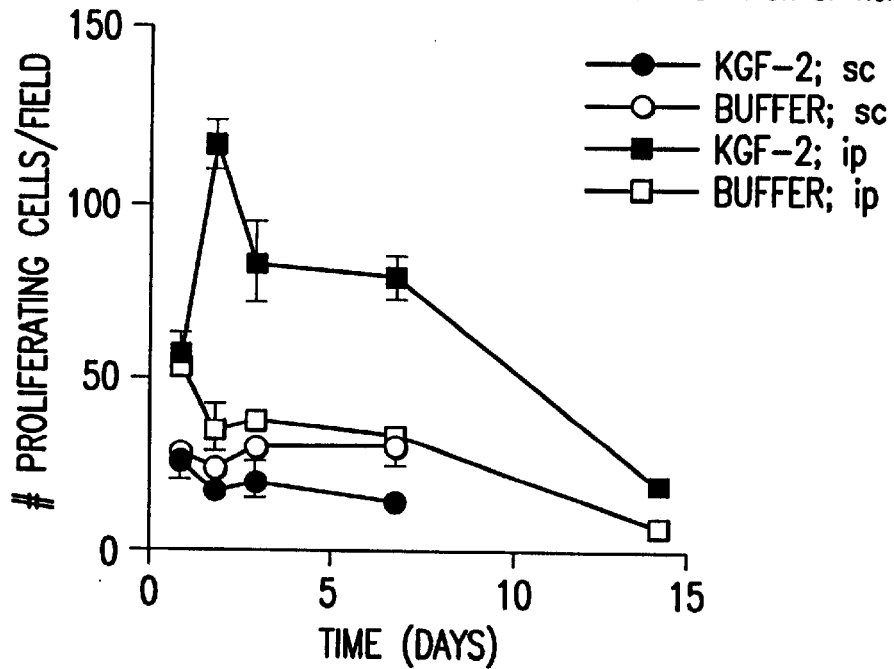
FIG. 58. Normal Sprague Dawley rats were injected daily with KGF-2 Δ33 (5 mg/kg; HG03411-E2) or buffer and sacrificed one day after the final injection. A blinded observer counted the proliferating cells in ten randomly chosen fields per animal at a 10×magnification. KGF-2 Δ33 given ip stimulated proliferation over the entire study period while sc administration of KGF-2 Δ33 did not increase the proliferation at any time point.

Pancreas. In contrast to the quickly reversible effects of ip administered KGF-2 Δ33 on the liver, such injections induced proliferation of the pancreas which continued over the 14 day study period (solid squares, FIG. 58). Surprisingly, subcutaneous administration of KGF-2 Δ33 (solid circles) failed to induce proliferation at any time point.

Figure 59:
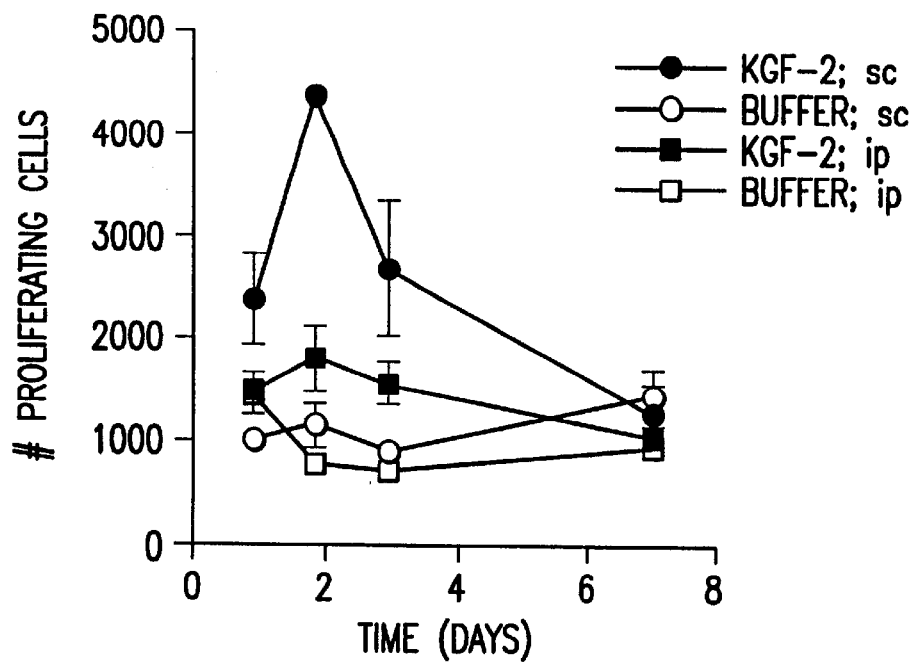
FIG. 59. Normal Sprague Dawley rats were injected daily with KGF-2 Δ33 (5 mg/kg; HG03411-E2) or buffer and sacrificed one day after the final injection. A blinded observer counted the proliferating cells in one cross-section per animal at a 10×magnification. KGF-2 Δ33 given sc elicited a significant increase in proliferation after 1, 2, and 3 days of daily administration. When KGF-2 Δ33 was given ip, proliferation was seen after 2 and 3 days only.

Kidney and Bladder. KGF-2 Δ33 induced proliferation of renal epithelia when given either by the sc or ip route but the former induced a greater effect. SC administration induced a rapid increase in proliferation (solid circles) that peaked after 2 days which then returned to normal after 7 daily treatments (FIG. 59). When KGF-2 Δ33 was given ip (solid squares), there was a modest, but significant increase in proliferation seen at days 2 and 3 only. Intraperitoneal injection of KGF-2 Δ33 also induced proliferation of bladder epithelial cells over the 7 day study period (solid squares, FIG. 52). Subcutaneous administration elicited a small increase in proliferation but this failed to achieve statistical significance (solid circles, FIG. 52).

Prostate. Both sc and ip administration of KGF-2 Δ33 induced significant proliferation of the prostate (FIG. 53) but this normalized after two injections.

Esophagus. KGF-2 Δ33 given sc or ip elicited an early, short-lived increase in the proliferation of the esophageal cells (1 and 2 days, respectively) that rapidly returned to normal (results not shown).

Other organs. Systemic administration of KGF-2 Δ33 by the ip and sc routes failed to elicit proliferation of the lung epithelia over a 7 day dosing period (results not shown).

Discussion

When administered in a sc route, we observed stimulation of normal epithelial proliferation in some organs (liver, kidney, esophagus, and prostate) but these effects, for the most part, were short-lived and all were reversible. The proliferation in these organs reversed even during daily sc administration of KGF-2.

The route of administration had dramatic effects on the observed proliferation. While daily ip administration increased the rate of liver proliferation over a 3 day period, animals given KGF-2 sc daily exhibited elevated rates after one day of treatment only. Even more surprising was the response of the pancreas. When animals were given KGF-2 ip, the pancreas exhibited a significantly elevated level of proliferation over the 14 day study period. However, sc administration of KGF-2 induced no increased mitotic activity in the pancreas. Likewise, ip, but not sc, treatment with KGF-2 elicited 1 5 proliferation of the bladder mucosa.

IP administration of KGF-2 elicited a short-lived, small burst of proliferation in the kidney that was centered in the region containing collecting ducts. Daily sc treatment induced a prolonged, exaggerated proliferation in this area.

EXAMPLE 32

Effects of KGF-2 Δ33 on Lung Cellular Proliferation Following Intratracheal Administration The purpose of this example is to show that KGF-2 Δ33 is capable of stimulating lung proliferation in normal rats following intratracheal administration (administration of KGF-2 Δ33 directly to the lung).

Methods: Male Lewis rats (220–270 g), (n=5/treatment group) were used in these studies. KGF-2 Δ33 or placebo (40 mM sodium acetate+150 mM NaCl at pH 6.5) was administered intratracheally at doses of 1 and 5 mg/kg in a volume of 0.6 mls followed by 3 mls of air. Treatments were administered on day 1 and day 2 of the experimental protocol.

On day 3, the day of sacrifice, rats were injected ip with 100 mg/kg of BrdU. Two hours later the rats were killed by $CO_2$ asphyxiation. Lungs were inflated with 10% buffered formalin via intratracheal catheter, and saggital sections of lung were paraffin embedded. To detect BrdU incorporation into replicating cells, five micron sections were subjected to immunohistochemical procedures using a mouse anti-BrdU monoclonal antibody and the ABC Elite detection system. The sections were lightly counterstained with hematoxylin.

Sections were read by two blinded observers. The number of proliferating cells was counted in 10 random fields per section at a 20×magnification. The results are expressed as the number of BrdU positive cells per field. Data are presented as mean±SEM. Statistical analyses (unpaired t-test) were performed with the Instat v2.0.1 and statistical significance is defined as $p<0.05$.

Figure 60:
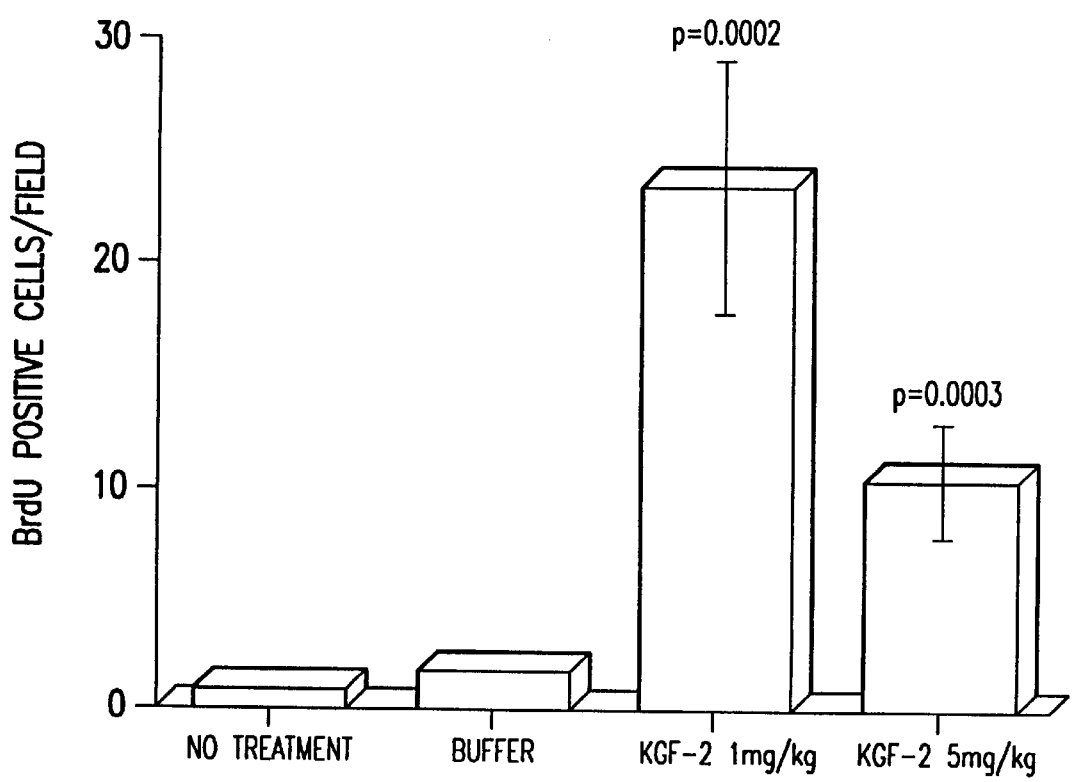
FIG. 60 demonstrates KGF-2 Δ33 induced proliferation in normal rat lung.

Results: Intratracheal injection of KGF-2 Δ33 at 1 and 5 mg/kg resulted in an increase in proliferation of lung epithelial cells as shown in FIG. 60. KGF-2 Δ33 treatment resulted in statistically significant increases in the number of BrdU positive cells/field at 1 mg/kg 23.4 cells/field (p=0.0002) and at 5 mg/kg 10.3 cells/field (p=0.0003) relative to buffer controls of 1.58 cells per field.

EXAMPLE 33

Topical KGF-2 in Infected Incisional Wounds

Bacterial infection of wounds continues to be of great clinical importance. Under normal situations, the complex process of wound healing progresses without difficulty. However, inoculation of a wound by bacteria causes an imbalance of cellular mediators in the inflammatory response resulting in delayed wound healing. Contamination of the open wound inhibits the wound healing process as characterized by decreased wound contraction, lower than normal wound collagen content and decreased tensile strength. Male adult Sprague Dawley rats (n+10/group) were anesthetized with a combination of ketamine (53 mg/kg im) and xylazine (5.3 mg/kg im) on day 1. The dorsal region was shaved and disinfected with 70% alcohol. A full thickness (through the epidermis, dermis to the subcutaneous layer) 2.5 cm surgical wound was created starting approximately 1 cm below the shoulder blades using a sterile no. 10 scalpel. Wounds were coated with 3 equidistant skin staples. The incisions were then inoculated intraincisionally with *Staphylococcus aureus* (107 cfu/50 µl) in PBS. KGF-2 Δ33 was applied topically at the time of wounding (Day 0) at doses of 0.1, 1 and 10 µg per wound in a volume of 50 µl. Wounds were then covered with a gas permeable occlusive dressing (Tegaderm). Animals were sacrificed on day 5 by anesthesia with ketamine/xylazine followed by lethal intracardiac administration of sodium pentobarbital (300 mg/kg). The middle 0.5 cm segment of the wound was excised and snap frozen for collagen determination. Two additional wound strips measuring 0.5 cm in width were excised. Excised wound strips were used for the study of breaking strength using an Instron skin tensiometer. Breaking strength was defined as the greatest force withheld by each wound prior to rupture using and 11 lb load cell at a speed of 0 mm/sec. Two values for each animal were averaged to provide a mean breaking strength value per wound. Statistical analysis was done using an unpaired t test (mean±SE).

Intraincisional application of *Staphylococcus aureus* in the wound resulted in a significant impairment in wound healing as measured by breaking strength (noninfected wound treated with bacteria vehicle 136±6 g; infected wound 87±6 g; p<0.0001 in one experiment; noninfected wound treated with bacteria vehicle 200±14 g; infected wound 154±10 g p=0.01 in another experiment). Topical administration of KGF-2 caused an increase in breaking strength which was statistically significant at the 0.1, 1 and 10 µg doses when compared with the KGF-2 buffer+*S. aureus* control (KGF-2 0.1 µg 152±16 g (p=0.002); 1 µg 135±12 g (p=0.003); 10 µg 158±10 g (p<0.0001) in one experiment; 0.1 µg 185±10 g (p=0.03); 1 µg 186±11 g (p=0.03); 10 µg 190±7 g p+0.009) in another experiment). Collagen analysis of the middle 0.5 cm wound strip revealed that there was increased collagen content in KGF-2 treated wounds. However, when compared with the buffer controls, a statistically significant increase in collagen content was not observed.

EXAMPLE 33

Proliferative effect of dosing i.v. every other day with 1 mg/kg of KGF-2Δ33

Male Sprague Dawley rats were intravenously injected with either KGF-2 Δ33 at a dose of 1 mg/kg, or buffer. The animals were injected either daily or every other day. Each treatment group was injected for one week and sacrificed at the end of the week. On the day of sacrifice, the animals were injected i.p. with 100 mg/kg of BrdU. Two hours later, the animals were sacrificed, and the serum was collected. Various tissues were collected and fixed in 10% neutral buffered formalin. The tissues were processed for histological evaluation. The tissues were stained with hematocylin and eosin, periodic-acid-Schiff, or alcian blue. Additional sections were subjected to immunohistochemical staining with an anti-BrdU antibody. Proliferation was quantitated using an image analysis spectrum, IPlab Spectrum. The serum chemistry analysis was performed using an automated chemistry analyzer. The following parameters were quantitated: thyroid gland weight; proliferation of goblet cells in the small intestine (duodenum, jejunum and ileum); proliferation of goblet cells in the colon; proliferation in the parotid and submandibular glands; and serum chemistry analytes (glucose, BUN, calcium, total protein, albumin, alkaline phosphatase, alanine aminotransferase, aspartate aminotransferase, cholesterol, and triglycerides).

In the small intestine and colon, daily treatment with KGF-2 caused a significant increase in the number of goblet cells. The every other day treatment did cause a slight increase in the number of goblet cells, however, it did not attain a statistically significant level. In the salivary gland, an increase in cells was observed in the parotid gland only. There was no difference between the treatment groups. There was an enlargement of the thyroid gland due to both dosing regimens. The magnitude of this increase was greater in the daily treatment group. Daily treatment with KGF-2 resulted in statistically significant increase in the following analytes: triglycerides, alkaline phosphatase, calcium, albumin, and total protein. The every other day treatment had no effect on these analytes. Cholesterol levels were elevated in both treatment groups. However, the magnitude of the increase was greater in the daily treatment group. Markers of cellular injury, such as ALT and AST, were similarly reduced in both treatment groups.

EXAMPLE 34

Formulating a Polypeptide

The KGF-2 composition will be formulated and dosed in a fashion consistent with good medical practice, taking into account the clinical condition of the individual patient (especially the side effects of treatment with the KGF-2 polypeptide alone), the site of delivery, the method of administration, the scheduling of administration, and other factors known to practitioners. The "effective amount" for purposes herein is thus determined by such considerations.

As a general proposition, the total pharmaceutically effective amount of KGF-2 administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, KGF-2 is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing KGF-2 are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

KGF-2 is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped KGF-2 polypeptides. Liposomes containing the KGF-2 are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, KGF-2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting KGF-2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

KGF-2 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

KGF-2 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

KGF-2 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous KGF-2 polypeptide solution, and the resulting mixture is lyophilized. The infusion solution is prepared by reconstituting the lyophilized KGF-2 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, KGF-2 may be employed in conjunction with other therapeutic compounds.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1 BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR 12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

EXAMPLE 35

Method of Treating Decreased Levels of KGF-2

The present invention also relates to a method for treating an individual in need of an increased level of KGF-2 activity in the body comprising administering to such an individual a composition comprising a therapeutically effective amount of KGF-2 or an agonist thereof.

Moreover, it will be appreciated that conditions caused by a decrease in the standard or normal expression level of KGF-2 in an individual can be treated by administering KGF-2, preferably in the secreted form. Thus, the invention also provides a method of treatment of an individual in need of an increased level of KGF-2 polypeptide comprising administering to such an individual a pharmaceutical composition comprising an amount of KGF-2 to increase the activity level of KGF-2 in such an individual.

For example, a patient with decreased levels of KGF-2 polypeptide receives a daily dose 0.1–100 μg/kg of the polypeptide for six consecutive days. Preferably, the pofypeptide is in the secreted form. The exact details of the dosing scheme, based on administration and formulation, are provided in Example 24.

EXAMPLE 36

Method of Treating Increased Levels of KGF-2

The present invention relates to a method for treating an individual in need of a decreased level of KGF-2 activity in the body comprising, administering to such an individual a composition comprising a therapeutically effective amount of KGF-2 antagonist. Preferred antagonists for use in the present invention are KGF-2-specific antibodies.

Antisense technology is used to inhibit production of KGF-2. This technology is one example of a method of decreasing levels of KGF-2 polypeptide, preferably a secreted form, due to a variety of etiologies, such as cancer.

For example, a patient diagnosed with abnormally increased levels of KGF-2 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 24.

EXAMPLE 37

Method of Treatment Using Gene Therapy—Ex Vivo

One method of gene therapy transplants fibroblasts, which are capable of expressing KGF-2 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding KGF-2 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted KGF-2.

The amphotropic pA317 or GP+am 12 packaging cells are grown in tissue culture to confluent density in Dulbecco's Modified Eagles Medium (DMEM) with 10% calf serum (CS), penicillin and streptomycin. The MSV vector containing the KGF-2 gene is then added to the media and the packaging cells transduced with the vector. The packaging cells now produce infectious viral particles containing the KGF-2 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether KGF-2 protein is produced.

The engineered fibroblasts are then transplanted onto the host, either alone or after having been grown to confluence on cytodex 3 microcarrier beads.

EXAMPLE 38

Gene Therapy Using Endogenous KGF-2 Gene

Another method of gene therapy according to the present invention involves operably associating the endogenous KGF-2 sequence with a promoter via homologous recombination as described, for example, in U.S. Pat. No. 5,641, 670, issued Jun. 24, 1997; International Publication No. WO 96/29411, published Sep. 26, 1996; International Publication No. WO 94/12650, published Aug. 4,1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous KGF-2, flanking the promoter. The targeting sequence will be sufficiently near the 5' end of KGF-2 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous KGF-2 sequence. This results in the expression of KGF-2 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the KGF-2 locus, plasmid pUC18 (MBI Fermentas, Amherst, N.Y.) is digested with HindIII. The CMV promoter is amplified by PCR with an XbaI site on the 5' end and a BamHI site on the 3' end. Two KGF-2 non-coding sequences are amplified via PCR: one KGF-2 non-coding sequence (KGF-2 fragment 1) is amplified with a HindIII site at the 5' end and an Xba site at the 3' end; the other KGF-2 non-coding sequence (KGF-2 fragment 2) is amplified with a BamHI site at the 5' end and a HindIII site at the 3' end. The CMV promoter and KGF-2 fragments are digested with the appropriate enzymes (CMV promoter—XbaI and BamHI; KGF-2 fragment 1—XbaI; KGF-2 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 39

Method of Treatment Using Gene Therapy—In Vivo

Advances in gene research have resulted in the development of techniques to deliver and express genes in human cells. The ideal goal for gene therapy is the delivery of normal genes in order to generate active proteins and compensate for the lack of endogenous production (Gorecki, D. C. et al., Arch. Immunol. Ther. Exp. 45(5–6):375–381 (1997)).

Delivery of genes encoding cytokines or growth factors involved in the different phases of wound healing and tissue repair have the potential to modify the outcome of wound healing (Taub, P. J. et al., J. Reconst. Microsur. 14(6):387–390 (1998)). The use of cDNA of growth factors or other cytokines for wound healing and tissue repair has been extensively described (Tchorzewski, M. T. et al., J. Surg. Res. 77:99–103(1998)). Genes transferred by a vector can be used to generate new cell lines, identify transplanted cells and express growth factors or enzymes. One of the advantages of gene therapy is to achieve therapeutic concentrations of gene-derived protein locally within the lesion site. Human recombinant KGF-2 protein has been shown to stimulate wound healing of the skin, gastro-intestinal tract and other organ containing cells of epithelial origin. The use of KGF-2 gene is expected to have similar pharmacological profile as the recombinant protein. KGF-2 gene may be involved in events related to tissue repair such as cell proliferation, migration and the formation of extracellular matrix.

Transcribed and translated cDNA has been used to deliver genes to sites of interest. Some examples of genes used in this fashion include aFGF, BMP-7 (Breitbart, A. S. et al., Ann. Plast. Surg. 24(5):488–495 (1999)). These cells have also been seeded into cell carriers including biodegradable matrices (ex. polyglycoloic acid), tissue substitutes or equivalents (ex. artificial skin), artificial organs, collagen-derived matrices, etc. Liposomes have been used to carry cDNA. PDGF-BB cDNA in haemagglutinating virus of Japan (HVJ)-liposome suspension was studied in the healing of patellar ligament (Nakamura et al., Gene Ther. 5(9):1165–1170 (1998)). Genes can also be delivered directly to the site of action by direct injection (ex. heart).

Thus, another aspect of the present invention is using in vivo gene therapy methods to treat disorders, diseases and conditions. The gene therapy method relates to the introduction of naked nucleic acid (DNA, RNA, and antisense DNA or RNA) KGF-2 sequences into an animal to increase or decrease the expression of the KGF-2 polypeptide. The KGF-2 polynucleotide may be operatively linked to a promoter or any other genetic elements necessary for the expression of the KGF-2 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata, H., et al., Cardiovasc. Res. 35(3):470–479 (1997), Chao, J., et al., Pharmacol. Res. 35(6):517–522 (1997), Wolff, J. A., Neuromuscul. Disord. 7(5):314–318 (1997), Schwartz B., et al., Gene Ther. 3(5):405–411 (1996), Tsurumi, Y., et al., Circulation 94(12):3281–3290 (1996) (incorporated herein by reference).

The KGF-2 polynucleotide constructs may be delivered by any method that delivers injectable materials to the cells of an animal, such as, injection into the interstitial space of tissues (heart, muscle, skin, lung, liver, intestine and the like). The KGF-2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the KGF-2 polynucleotides may also be delivered in liposome formulations (such as those taught in Felgner P. L. et al., *Ann. NY Acad. Sci.* 772:126–139 (1995) and Abdallah B. et al., *Biol. Cell* 85(1):1–7 (1995)) which can be prepared by methods well known to those skilled in the art.

The KGF-2 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The KGF-2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. in vivo muscle cells are particularly competent in their ability to take up and express polynucleotides.

For the naked KGF-2 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked KGF-2 polynucleotide constructs can be delivered to arteries during angioplasty by the catheter used in the procedure.

The dose response effects of injected KGF-2 polynucleotide in muscle in vivo is determined as follows. Suitable KGF-2 template DNA for production of mRNA coding for KGF-2 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The KGF-2 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for KGF-2 protein expression. A time course for KGF-2 protein expression may be done in a similar fashion except that quadriceps from different mice are harvested at different times. Persistence of KGF-2 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using KGF-2 naked DNA.

EXAMPLE 40

KGF-2 Therapy for Inflammatory Bowel Disease

In this example, the inhibition of pathologic changes in colons of mice caused by exposure to dextran sodium sulfate (DSS) in drinking water by systemic (intranasal) and intraperotineal administration of KGF-2 polynucleotides is determined.

Intranasal administration. A polynucleotide encoding KGF-2 $\Delta 33$ is introduced into the nasal passages of anaesthetized female Swiss Webster mice (n=10/group) through a blunted 26 gauge needle at a dosage of 1, 10 or 100 $\mu$g of polynucleotide. Control polynucleotide is administered to a separate group of mice. Five days after intranasal administration of the polynucleotide, 5% DSS is added to the drinking water. Mice are monitored for body weight, hematocrit, and stool score. After seven days of exposure to DSS in the drinking water, mice are sacrificed. Histopathologic assessment of colon and small intestine is performed. RT-PCR analysis is performed to determine expression of KGF-2 in liver, spleen and colon.

Intraperotineal administration. A polynucleotide encoding KGF-2 $\Delta 33$ is injected intraperitoneally into female Swiss Webster mice (n=10/group) through a blunted 26 gauge needle at a dosage of 1, 10 or 100 $\mu$g of polynucleotide on days 0 and 3. Control polynucleotide is administered to a separate group of mice using and identical regimen. On day 7, 5% DSS is added to the drinking water. Mice are monitored for body weight, hematocrit, and stool score. On day 14, mice are sacrificed. Histopathologic assessment of colon and small intestine is performed. RT-PCR analysis is performed to determine expression of KGF-2 in liver, diaphragm and colon.

The studies described in this example test activity in KGF-2 $\Delta 33$ polynucleotides. However, one skilled in the art could easily modify the exemplified studies to test the activity of other KGF-2 polynucleotides, including full length and mature KGF-2, KGF-2 $\Delta 28$, and polynucleotides encoding amino acids 77 to 208, 80 to 208, and 93 to 208 of KGF-2; and KGF-2 polypeptides, variants, fragments, agonists, and/or antagonists; and any KGF-2 mutant described herein.

EXAMPLE 41

KGF-2 Therapy for Ocular Surface Disease

In this example, the effect of subconjuctival administration of Δ33 KGF-2 polynucleotides on the conjunctiva, cornea or lacrimal gland of rats is determined.

A polynucleotide encoding Δ33 KGF-2 is injected into the subconjuctival space of anaesthetized Female Sprague Dawley rats (150–200 g body weight, 6/treatment group) at a dosage of 1, 10 or 100 μg. Control polynucleotide is injected in a similar fashion to a separate group of control rats. Separate groups of rats are sacrificed at 3, 7 and 14 days post injection. BrdU is administered intraperitoneally to some of the rats 30 minutes before euthanasia. The eye and surrounding tissues are removed for histologic analysis. The extent of BrdU incorporation in the epithelial cells of the cornea, conjunctiva and lacrimal glands is measured. The thickness of the epithelial layer in the cornea and conjunctiva is assessed. The number of goblet cells in the conjunctiva is measured.

The studies described in this example test activity in KGF-2 Δ33 polynucleotides. However, one skilled in the art could easily modify the exemplified studies to test the activity of other KGF-2 polynucleotides, including full length and mature KGF-2, KGF-2 Δ28, and polynucleotides encoding amino acids 77 to 208, 80 to 208, and 93 to 208 of KGF-2; and KGF-2 polypeptides, variants, fragments, agonists, and/or antagonists; as well as any KGF-2 mutant described herein.

EXAMPLE 42

KGF-2 Therapy for Salivary Gland Dysfunction

In this example, the effect of KGF-2 polynucleotide administration into the papillae of the parotid salivary gland duct of normal rats on the epithelial cells of the ducts and acini of that gland is determined.

Female Sprague Dawley Rats (150–250 grams, 6/group) are anesthetized by the intramuscular injection of ketamine and xylazine. A polynucleotide encoding Δ33 KGF-2 is introduced into the papilla of the parotid salivary gland using a 30 gauge steel gavage needle, at a dosage of 1, 10 or 100 μg. The polynucleotide is infused over a ten minute period at a rate of 1 μl per minute. Control polynucleotide is administered to a separate group of rats. Separate groups of rats are sacrificed at 3, 7 and 14 days after infusion. BrdU is administered intraperitoneally 30 minutes before euthanasia. The salivary glands are weighed, and the number of BrdU-staining cells is counted on histologic section. In a separate experiment, pilocarpine-stimulated saliva secretion is measured in rats at 7 days after infusion.

The studies described in this example test activity in KGF-2 Δ33 polynucleotides. However, one skilled in the art could easily modify the exemplified studies to test the activity of other KGF-2 polynucleotides, including full length and mature KGF-2, KGF-2 Δ28, and polynucleotides encoding amino acids 77 to 208, 80 to 208, and 93 to 208 of KGF-2; and KGF-2 polypeptides, variants, fragments, agonists, and/or antagonists; as well as any KGF-2 mutant described herein.

EXAMPLE 43

KGF-2 Therapy for Dermal Wound Healing

In this example, the ability of KGF-2 polynucleotide to stimulate wound healing in the normal rat and diabetic mice is determined.

Normal rat. Anesthetized female Sprague Dawley rats (175–250 gm 6/treatment group) are wounded with 8 mm biopsy punches. Δ33 KGF-2 polynucleotide (1, 10 or 30 μg) is delivered intradermally at 4 different sites along the wound. Control polynucleotide is administered in a similar manner to a separate group of rats. The wounds are covered with sterile ventilated fabric pads. After the pad is positioned, waterproof adhesive tape is wrapped around the midsection of the rat. Separate groups of rats are sacrificed at 2 and 5 days post wounding. The wound tissues are fixed in 10% formalin embedded in paraffin. BrdU incorporation in proliferating epithelial cells in pre-existing and new epidermis, and the length and thickness of the new epithelial tongue is measured.

Diabetic mice. Diabetic mice (db+/db+, 10/treatment group) and nondiabetic mice (db+/m+, 10/treatment group) are wounded with a 6 mm punch wound in the dorsum. Δ33 KGF-2 polynucleotide (1, 10 or 30 μg) is delivered intradermally at 4 different sites along the wound. Control polynucleotide is administered in a similar manner to a separate group of mice. The wounds are covered with Tegaderm (diabetic mice) or Tegaderm plus adhesive tape (nondiabetic mice). The wounds are photographed on days 0, 3, 7,10 and 14 post wounding. The surface area of the wounds are measured by image analysis.

The studies described in this example test activity in KGF-2 Δ33 polynucleotides. However, one skilled in the art could easily modify the exemplified studies to test the activity of other KGF-2 polynucleotides, including full length and mature KGF-2, KGF-2 Δ28, and polynucleotides encoding amino acids 77 to 208, 80 to 208, and 93 to 208 of KGF-2; and KGF-2 polypeptides, variants, fragments, agonists, and/or antagonists; as well as any KGF-2 mutant described herein.

EXAMPLE 44

Constructs for KGF-2 Delivery

An appropriate construct for KGF-2 gene therapy delivery is pVGI.0-KGF-2. This construct contains the full native open reading frame of KGF-2 cloned into the expression vector pVGI.0. pVGI.0 contains a kanamycin resistance gene, a CMV enhancer, and an RSV promoter. pVGI.0-KGF-2 was deposited at the American Type Culture Collection Patent Depository, 10801 University Boulevard, Manassas, Va. 20110–2209, on Jun. 30, 1999, and given ATCC Deposit No. PTA290. This construct was made by subcloning the KGF-2 ORF from a previously sequence verified KGF-2 construct into the expression vector pVGI-0, using methods well known in the art.

Another appropriate construct for KGF-2 delivery is pVGI-0-MPIFspKGF2Δ33. This construct contains the native sequence of KGF-2 Δ33 fused to the MPIF (CKβ8) heterologous signal peptide cloned into the expression vector pVGI-0. pVGI.0-MPIFspKGF2Δ33 was deposited at the American Type Culture Collection Patent Depository, 10801 University Boulevard, Manassas, Va. 20110–2209, on Jun. 30,1999, and given ATCC Deposit No. PTA289. This construct was made using methods well known in the art and the following primers:

5' primer: GAGCGCGGATCCGCCACCATGAAG-GTCTCCGTGGCTGCCCTCTCC TGCCTCATGCT-TGTTACTGCCCTTGGATCTCAGGCCAGC-TACAATCA CCTTCAAGGAGATG (SEQ ID NO:149)

3' primer: GAGCGC GGATCC CTATGAGTGTACCAC-CATTGGAAG (SEQ ID NO:150)

EXAMPLE 45

Angiogenesis During KGF-2 Gene Therapy

Characterization of the multiple aspects of microvascular physiology in transparent window systems in mice have provided valuable data on angiogenesis, inflammation, microvascular transport, tissue rejection and tumor physiology. In this example, the development of vasculature during a wound healing response in implanted collagen gels is assessed through direct observation of the tissue and associated microvascular bed through an implanted skin window. This model is used to determine if KGF-2 gene therapy can simultaneously induce an accelerated tissue regrowth and revascularization.

Skin biopsies from nude mice are digested in collagenase, the resulting cell suspensions washed and then cultured in DMEM with 10% FBS to obtain dermal fibroblasts. Confluent fibroblast cultures are transfected with KGF-2 or control polynucleotide then collected and washed in PBS. 106 cells are suspended in 20 µl of collagen matrix. Samples of cell suspension are removed for Western blot confirmation of KGF-2 production. A 2 mm punch biopsy is made into an existing dorsal skin window and the skin sandwiched between two glass coverslips. The cell collagen mixture is placed into the circular wound and the chamber sealed. The implanted gels are observed at regular intervals for vessel development. Tissue regrowth into the wound is monitored as changes in the optical density of the collagen gel over a three week period. Tissue from the dorsal chambers is removed following the conclusion of the study for histological evaluation. Control experiments involve the addition of KGF-2 polypeptide or buffer into collagen gels in place of fibroblasts.

Mousepreparation. The surgical procedures are performed in Swiss nude mice. For the surgical procedures, animals (20–30 g) are anesthetized with s.c. injection of a cocktail of 90 mg Ketamine and 9 mg Xylazine per kg body weight. All surgical procedures are performed under aseptic conditions in a horizontal laminar flow hood, with all equipment being steam, gas or chemically sterilized. During surgery, the body temperature of the animals is kept constant by means of a heated work surface. All mice are housed individually in miscroisolator cages and all manipulations are done in laminar flow hoods. Buprenorphine (0.1 mg/kg q 12 h) is administered as an analgesic for 3 days post implantation.

Mice are positioned such that the chamber is sandwiched between a double layer of skin that extends above the dorsal surface. One layer of skin is removed in a circular area ~15 mm in diameter. The second layer (consisting of epidermis, fascia, and striated muscle) is positioned on the frame of the chamber and covered with a sterile glass coverslip. The chamber is held in place with nylon posts which pass through the extended skin and holes along the top of the chamber. After 3 days, the coverslip is carefully removed and the gel inserted. A new, sterile coverslip is then placed on the viewing surface. Measurements are made by morphometric analysis using an Intensified CCD camera, S-VHS videocassette recorder and direct digital image acquisition. Mice with implanted changers were observed for 28 days.

Measurements. Mice are anesthetized with s.c. injection of a cocktail of 90 mg Ketamine and 9 mg Xylazine per kg body weight, then positioned on a sterile plastic stage assembly. Vascular maps of the window are made using transillumination (dorsal skin window) or following an injection of 100 µl of BSA-FITC (1 mg/ml, i.v.) and epi-illumination. Video recordings of vascular beds are made at a range of magnifications (from 1× to 40×) as well as digital frames for off-line analysis. Angiogenesis determinations of implanted gels are made from offline analysis of video tapes.

The studies described in this example test activity in KGF-2 Δ33 polynucleotides. However, one skilled in the art could easily modify the exemplified studies to test the activity of other KGF-2 polynucleotides, including full length and mature KGF-2, KGF-2 Δ28, and polynucleotides encoding amino acids 77 to 208, 80 to 208, and 93 to 208 of KGF-2; and KGF-2 polypeptides, variants, fragments, agonists, and/or antagonists; as well as any of the KGF-2 mutants described herein.

EXAMPLE 46

KGF-2 Transgenic Animals

The KGF-2 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., *Biotechnology (NY)* 11:1263–1270 (1993); Wright et al., *Biotechnology (NY)* 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol. Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of KGF-2 polypeptides, studying conditions and/or disorders associated with aberrant KGF-2 expression, and in screening for compounds effective in ameliorating such conditions and/or disorders.

EXAMPLE 47

KGF-2 Knock-out Animals

Endogenous KGF-2 gene expression can also be reduced by inactivating or "knocking out" the KGF-2 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the KGF-2 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of KGF-2 polypeptides, studying conditions and/or disorders associated with aberrant KGF-2 expression, and in screening for compounds effective in ameliorating such conditions and/or disorders.

EXAMPLE 48

Construction of KGF-2 Mutants

To create point mutants, the indicated primers were used in PCR reactions using standard conditions well known to those skilled in the art. The resulting products were restricted with either Nde and Asp718 and cloned into pHE4; or with BamHI and Xba and cloned into pcDNA3; as indicated. Any of the described KGF-2 variants can be produced in other vectors, or by themselves, using methods well known in the art.

pHE4:KGF2:R80-S208 was constructed using following primers:
   5' primer: CCGGC CATATG CGTAAACTGT-TCTCTTTCACC (SEQ ID NO:151)
   3' primer: CCGGC GGTACC TTATTATGAGTGTAC-CACCATTGG (SEQ ID NO:152)

pHE4:KGF2:A63-S208(R68G) was constructed using following primers:
   5' primer: GATCGC CATATG GCTGGTCGTCACGT-TCGTTC (SEQ ID NO:153)
   3' primer: GATCGC GGTACC TTATTATGAGTGTAC-CACCATTGGAAG (SEQ ID NO:154)

pHE4:KGF2:A63-S208(R68S) was constructed using following primers:
   5' primer: GATCGC CATATG GCTGGTCGTCACGT-TCGTTC (SEQ ID NO:155)
   3' primer: GATCGC GGTACC TTATTATGAGTGTAC-CACCATTGGAAG (SEQID NO:156)

pHE4:KGF2:A63-S208(R68A) was constructed using following primers:
   5' primer: GATCGC CATATG GCTGGTCGTCACGT-TCGTTC (SEQ ID NO:157)
   3' primer: GATCGC GGTACC TTATTATGAGTGTAC-CACCATTGGAAG (SEQ ID NO:158)

pHE4:KGF2:A63-S208(R78R80K81A) was constructed using following primers:
   5' primer: GATCGC CATATG GCTGGTCGTCACGT-TCGTTC (SEQ ID NO:159)
   3' primer: GATCGC GGTACC TTATTATGAGTGTAC-CACCATTGGAAG (SEQ ID NO:160)

pcDNA3:KGF2(K136137139144A) was constructed using following primers:
   5' primer: GATCGCGGATCCGCCACCATGTG-GAAATGGATACTGACACATTGTG C (SEQ ID NO:161)
   3' primer: GATCGCTCTAGATTATGAGTGTACCAC-CATTGGAAGAAAG (SEQ ID NO:162)

pcDNA3:KGF2(K151 153R155A) was constructed using following primers:
   5' primer: GATCGCGGATCCGCCACCATGTG-GAAATGGATACTGACACATTGTG C (SEQ ID NO:163)
   3' primer: GATCGCTCTAGATTATGAGTGTACCAC-CATTGGAAGAAAG (SEQ ID NO:164)

pcDNA3:KGF2(R174K183A) was constructed using following primers:
   5' primer: GATCGCGGATCCGCCACCATGTG-GAAATGGATACTGACACATTGTG C (SEQ ID NO:165)
   3' primer: GATCGCTCTAGATTATGAGTGTACCAC-CATTGGAAGAAAG (SEQ ID NO:166)

pcDNA3:KGF2(R187R188A) was constructed using following primers:
   5' primer: GATCGCGGATCCGCCACCATGTG-GAAATGGATACTGACACATTGTG C (SEQ ID NO:167)
   3' primer: GATCGCTCTAGATTATGAGTGTACCAC-CATTGGAAGAAAG (SEQ ID NO:168)

pHE4:KGF2.A63(K1 36137139144A) was constructed using the following primers:
   5' primer: GATCGCCATATGGCTGGTCGTCACGT-TCGTTC (SEQ ID NO:169)
   3' primer: GATCGCGGTACCTTATTATGAGTGTAC-CACCATTGGAAG (SEQ ID NO:170)

pHE4:KGF2.A63(K151153R155A) was constructed using the following primers:
   5' primer: GATCGCCATATGGCTGGTCGTCACGT-TCGTTC (SEQ ID NO:171)
   3' primer: GATCGCGGTACCTTATTATGAGTGTAC-CACCATTGGAAG (SEQ ID NO:172)

EXAMPLE 49

Use of KGF-2 for Treating and/or Preventing Infertility

Implantation is the single most critical factor in a successful pregnancy and is clinically and economically important. In humans, the greatest fraction of the 70% loss in embryonic life occurs at implantation. The mouse is the model of choice for studying mammalian implantation. Three essential cell lineages differentiate and divide in the peri-implantation mouse embryo: embryonic, placental and yolk sac precursors. Fibroblast growth factor (FGF)-4 is essential for development of all three cell lineages.

It has been found, using a 'transient transgenic' approach to deliver gain-of-function and loss-of-function (dominant negative) FGF receptor genes, that endogenous FGF signaling is necessary for cell division of all stem cells for the embryo and placenta lineages in the mouse embryo starting at the fifth cell division two days before implantation.

Interestingly, it has been found that null mutant for fgfr-2 and fgf4 die in uteri within a day after implantation and the ICM dies. Before the embryo implants into the uterus cells in the embryonic lineage and in the placental lineage require FGF to continue proliferating.

It is possible that one or several of the other 19 FGF ligand is expressed transiently in the mouse preimplantation embryo and this ligand delays the effect of the fgfr-2 and fgf4 null mutants until after implantation. We have tested for six FGF ligand using RT-PCR. To date, KGF-2 and FGF-8 are the only FGF ligands, besides FGF-4, detected in the preimplantation embryo. KGF-2 mRNA is detected in the embryo after the two cell stage and through early post-implantation.

KGF-2 null mutants suggest that KGF-2 is not essential for survival during the expression of KGF-2 in peri-implantation mouse embryos (Min et al., 1998; Sekine et al., 1999). However, other FGF family members may compensate or be redundant for KGF-2 during peri-implantation embryonic development. Many redundant genetic effects have been observed during analysis of null mutants in mice and compensation within a gene family has also been observed (Thomas et al., 1995; Stein et al., 1994). KGF-2 may be more important in early development than is suggested by the KGF-2 null mutants.

The best way to detect whether KGF-2 may have role in early development at a time when the null mutants suggest no essential function, is to do gain-of-function experiments. These experiments test whether KGF-2 has an influence on growth of perimplantation embryos (Rappolee et al., 1994), on the placental/trophoblast cells in blastocyst outgrowths (Chai et al., 1998) and in endoderm lineage cells in inner call mass (ICM) outgrowths (Rappolee et al., 1994). Loss-of-function tests can be done in a limited way by use of antisense oligonucleotides (Rappolee et al., 1992) or blocking antibodies (LaFleur et al., 1996). It is known that the embryos undergo size regulation, large positive and negative changes in cell number are homoeostatically regulated, soon after implantation (Rappolee, 1998). This suggests that small, sublethal KGF-2-dependent effects might be totally missed in the KGF-2 null mutants. Loss- and gain-of-function experiments are use to test peri-implantation mouse embryos for the effects of KGF-2.

To date, the detection of mRNA for a growth factor in the preimplantation mouse embryo has universally led to detection of the corresponding protein. (Rappolee et al., 1998, 1992, 1994; reviewed in Rappolee 1998, 1999). To determine whether KGF-2 protein is present (and where) in embryos where KGF-2 mRNA was detected, an antibody to KGF-2 suitable for immunocytochemistry is used.

EXAMPLE 50

Detection of KGF-2 in a Clinical Sample

Purified Goat PAb is diluted to 2 µg/ml in the coating buffer (0.05 M NaHCO$_3$, Ph 9.5). 100 µl diluted antibody is added per well to an Immuno 4 microplate. The microplate is stored overnight at 4° C. The antibody solution is decanted from the plate. 200 µl of blocking buffer (1% dry milk (BioRad) in coating buffer) is added to each well. The plate is allowed to incubate at room temperature for 2 hours. The blocking buffer is decanted from the plate. The plate is vacuum aspirated and allowed to dry completely in a vacuum chamber at 32° C. for 1.5 hours. The plate is removed from the vacuum chamber and sealed in a mylar pouch with 3 desiccant packs. The plate is stored at 4° C. until ready to be used.

KGF-2 is diluted to 16 ng/ml with diluent 1 (0.1% Tween 20, 1×PBS, 1% BSA, and 0.001% Thimerosal), then a subsequent 2.5×dilution is made for the next 7 dilutions. The concentration range from 16 ng/ml to 0.026 ng/ml is used as the standard. The background wells consist of diluent without protein.

The unknown samples are diluted 10×, 50×, and 250× with diluent 1. 100 µl per well of the serial diluted standard solution and the unknown samples are added to the coated ELISA plate. The plate is stored at 4° C. overnight. The solutions are decanted from the plate. The plate is washed with washing buffer (0.1% Tween 20 and 1×PBS) five times, using the Wheaton Instrument set at 1.6 ml (each well receives 200 µl per wash). 15 seconds of incubation of washing buffer is allowed between each wash.

The detector, biotinylated chicken anti-KGF-2 is diluted to 0.5 µg/ml in diluent 1. 100 µl of the diluted detector is added to each well. The plate is incubated for 2 hours at room temperature. The solution is decanted and the plate is washed with washing buffer 5 times, as before. 15 seconds of incubation time is allowed between each wash.

Peroxidase streptavidin is diluted to 1:2000 in diluent 1. 100 µl per well of the diluted peroxidase streptavidin is added to the plate and allowed to incubate at room temperature for 1 hour. The plate is decanted and washed with washing buffer five times. 15 seconds of incubation of washing buffer is allowed between each wash. The plate is not allowed to dry.

Equal amounts of room temperature TMB peroxidase substrate and the peroxidase solution B (from the TMB Peroxidase Microwell Substrate System, KPL) are mixed. 100 µl of the mixed solution is added to each well and the color is allowed to develop at room temperature for 10 minutes. The color development is stopped by adding 50 µl of 1M H$_2$SO$_4$ to each well. The plate is read at 450 nm.

EXAMPLE 51

Construction of E. coli Optimized Truncated KGF-2

In order to increase expression levels of a truncated KGF-2 in an E. coli expression system, the codons of the gene were optimized to highly used E. coli codons.

For example, the following construct, termed pHE4:KGF-2.A63-S608, was made.

5' CATATGGCTGGTCGTCACGTTCGTTCT-TACAACCACCTGCAGGGT GACGTTCGTTG-GCGTAAACTGTTCTCTTTCAC-CAAATACTTCCTGAA AATCGAAAAAAACGGTAAAGTTTCTGG-GACCAAGAAGGAGAACTG CCCGTACAGCATC-CTGGAGATAACATCAGTAGAAATCG-GAGTTGTT GCCGTCAAAGCCATTAACAGCAACTAT-TACTTAGCCATGAACAAGA AGGGGAAACTC-TATGGCTCAAAAGAATTTAACAATGACT-GTAAGCT GAAGGAGAGGATAGAGGAAAATGGATA-CAATACCTATGCATCATT TAACTGGCAGCAT-AATGGGAGGCAAATGTATGTGGCATTGAATGG AAAAGGAGCTCCAAGGAGAGGACA-GAAAACACGAAGGAAAAACA CCTCTGCT-CACTTTCTTCCAATGGTGGTACACTCAT-AATAAGGTACC 3' (SEQ ID NO:173)

A plasmid comprising a cDNA having the nucleotide sequence of SEQ ID NO:173 was deposited as ATCC Deposit No. on at the American Type Culture Collection, Patent Depository, 10801 University Boulevard, Manassas, Va. 20110–2209.

Another construct, termed pHE4:KGF-2.A63-S208 cod.opt, was constructed using the following primers:

sense 5' GACTACATATGGCTGGTCGTCACGT-TCGTTCTTACAACC ACCTGCA GG3' (SEQ ID NO:174)

antisense 5' CTAGTCTCTAGATTATTATGAGTGTA-CAACCATCG GCAGGAAGTGAG 3' (SEQ ID NO:175)

The nucleotide sequence of the pHE4:KGF-2.A63–208 cod.opt is as follows:

5' ATGGCTGGTCGTCACGTTCGTTCTTA-CAACCACCTGCAGGGTG ACGTTCGTTGGCG-TAAACTGTTCTCTTTCACCAAATACTTC-CTGAAA ATCGAAAAGAACGGTAAAGTTTCTGG-TACCAAGAAAGAAACTGC CCGTACTCTATC-CTGGAAATCACCTCCGTTGAAATCGGT-GTTGTAG CCGTTAAAGCCATCAACTCCAACTAT-TACCTGGCCATGAACAAAAA GGGTAAACTG-TACGGCTCTAAAGAATTCAACAACGACT-

GCAAACTG AAAGAACGTATCGAAGAGAACGGTTA- CAACACCTACGCATCCTTC AACTGGCAGCA- CAACGGTCGTCAGATGTACGTTGCACT- GAACGGTA AAGGCGCTCCGCGTCGCGGTCAGAAAAC- CCGTCGCAAAAACACCT CTGCTCACTTCCT- GCCGATGGTTGTACACTCATAATAA 3' (SEQ ID NO:176)

A plasmid comprising a cDNA having the nucleotide sequence of SEQ ID NO:176 was deposited as ATCC Deposit No. on at the American Type Culture Collection, Patent Depository, 10801 University Boulevard, Manassas, Va. 20110–2209.

Both constructs described in this example are useful in the production of KGF-2 polypeptides, for example, as described in Example 13. Nucleotides 4 to 444 of SEQ ID NO:173 and nucleotides 1 to 441 of SEQ ID NO:176 encode amino acids 63 to 208 of SEQ ID NO:2, plus an N-terminal methionine.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

SEQUENCE LISTING

<160> NUMBER OF SEQ ID NOS: 176

<210> SEQ ID NO 1
<211> LENGTH: 627
<212> TYPE: DNA
<213> ORGANISM: Homo sapiens
<220> FEATURE:
<221> NAME/KEY: CDS
<222> LOCATION: (1)..(624)

<400> SEQUENCE: 1

```
atg tgg aaa tgg ata ctg aca cat tgt gcc tca gcc ttt ccc cac ctg      48
Met Trp Lys Trp Ile Leu Thr His Cys Ala Ser Ala Phe Pro His Leu
 1               5                  10                  15 ccc ggc tgc tgc tgc tgc ttt ttg ttg ctg ttc ttg gtg tct tcc          96
Pro Gly Cys Cys Cys Cys Phe Leu Leu Leu Phe Leu Val Ser Ser
            20                  25                  30 gtc cct gtc acc tgc caa gcc ctt ggt cag gac atg gtg tca cca gag     144
Val Pro Val Thr Cys Gln Ala Leu Gly Gln Asp Met Val Ser Pro Glu
        35                  40                  45 gcc acc aac tct tct tcc tcc tcc ttc tct cct tcc agc gcg gga         192
Ala Thr Asn Ser Ser Ser Ser Ser Phe Ser Ser Pro Ser Ser Ala Gly
 50                  55                  60 agg cat gtg cgg agc tac aat cac ctt caa gga gat gtc cgc tgg aga     240
Arg His Val Arg Ser Tyr Asn His Leu Gln Gly Asp Val Arg Trp Arg
 65                  70                  75                  80 aag cta ttc tct ttc acc aag tac ttt ctc aag att gag aag aac ggg     288
Lys Leu Phe Ser Phe Thr Lys Tyr Phe Leu Lys Ile Glu Lys Asn Gly
                 85                  90                  95 aag gtc agc ggg acc aag aag gag aac tgc ccg tac agc atc ctg gag     336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc     384
Ile Thr Ser Val Glu Ile Gly Val Val Ala Val Lys Ala Ile Asn Ser
        115                 120                 125 aac tat tac tta gcc atg aac aag aag ggg aaa ctc tat ggc tca aaa     432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga     480
Glu Phe Asn Asn Asp Cys Lys Leu Lys Glu Arg Ile Glu Glu Asn Gly
145                 150                 155                 160 tac aat acc tat gca tca ttt aac tgg cag cat aat ggg agg caa atg     528
Tyr Asn Thr Tyr Ala Ser Phe Asn Trp Gln His Asn Gly Arg Gln Met
                165                 170                 175
```

```
tat gtg gca ttg aat gga aaa gga gct cca agg aga gga cag aaa aca    576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca    624
Arg Arg Lys Asn Thr Ser Ala His Phe Leu Pro Met Val Val His Ser
        195                 200                 205 tag                                                                 627

<210> SEQ ID NO 2
<211> LENGTH: 208
<212> TYPE: PRT
<213> ORGANISM: Homo sapiens

<400> SEQUENCE: 2

Met Trp Lys Trp Ile Leu Thr His Cys Ala Ser Ala Phe Pro His Leu
  1               5                  10                  15

Pro Gly Cys Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
         35                  40                  45

Ala Thr Asn Ser Ser Ser Ser Ser Phe Ser Ser Pro Ser Ser Ala Gly
     50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ccccacatgt ggaaatggat actgacacat tgtgcc                             36

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:
      oligonucleotide
```

<400> SEQUENCE: 4
cccaagcttc cacaaacgtt gccttcctct atgag         35

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
catgccatgg cgtgccaagc ccttggtcag gacatg        36

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
cccaagcttc cacaaacgtt gccttcctct atgag         35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gcgggatccg ccatcatgtg gaaatggata ctcac         35

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gcgcggtacc acaaacgttg ccttcct                  27

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
taacgaggat ccgccatcat gtggaaatgg atactgacac    40

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:
      oligonucleotide -continued

```
<400> SEQUENCE: 10
taagcactcg agtgagtgta ccaccattgg aagaaatg                              38

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
attaaccctc actaaaggga ggccatgtgg aaatggatac tgacacattg tgcc           54

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cccaagcttc cacaaacgtt gccttcctct atgag                                35

<210> SEQ ID NO 13
<211> LENGTH: 206
<212> TYPE: PRT
<213> ORGANISM: Homo sapiens

<400> SEQUENCE: 13

Met Ser Gly Pro Gly Thr Ala Ala Val Ala Leu Leu Pro Ala Val Leu
  1               5                  10                  15

Leu Ala Leu Leu Ala Pro Trp Ala Gly Arg Gly Gly Ala Ala Ala Pro
                 20                  25                  30

Thr Ala Pro Asn Gly Thr Leu Glu Ala Glu Leu Glu Arg Arg Trp Glu
             35                  40                  45

Ser Leu Val Ala Leu Ser Leu Ala Arg Leu Pro Val Ala Ala Gln Pro
     50                  55                  60

Lys Glu Ala Ala Val Gln Ser Gly Ala Gly Asp Tyr Leu Leu Gly Ile
 65                  70                  75                  80

Lys Arg Leu Arg Arg Leu Tyr Cys Asn Val Gly Ile Gly Phe His Leu
                 85                  90                  95

Gln Ala Leu Pro Asp Gly Arg Ile Gly Gly Ala His Ala Asp Thr Arg
                100                 105                 110

Asp Ser Leu Leu Glu Leu Ser Pro Val Glu Arg Gly Val Val Ser Ile
            115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205

<210> SEQ ID NO 14
```

<211> LENGTH: 198
<212> TYPE: PRT
<213> ORGANISM: Homo sapiens

<400> SEQUENCE: 14

Met Ser Arg Gly Ala Gly Arg Leu Gln Gly Thr Leu Trp Ala Leu Val
1               5                   10                  15

Phe Leu Gly Ile Leu Val Gly Met Val Val Pro Ser Pro Ala Gly Thr
            20                  25                  30

Arg Ala Asn Asn Thr Leu Leu Asp Ser Arg Gly Trp Gly Thr Leu Leu
        35                  40                  45

Ser Arg Ser Arg Ala Gly Leu Ala Gly Glu Ile Ala Gly Val Asn Trp
50                  55                  60

Glu Ser Gly Tyr Leu Val Gly Ile Lys Arg Gln Arg Arg Leu Tyr Cys
65                  70                  75                  80

Asn Val Gly Ile Gly Phe His Leu Gln Val Leu Pro Asp Gly Arg Ile
                85                  90                  95

Ser Gly Thr His Glu Glu Asn Pro Tyr Ser Leu Leu Glu Ile Ser Thr
            100                 105                 110

Val Glu Arg Gly Val Val Ser Leu Phe Gly Val Arg Ser Ala Leu Phe
        115                 120                 125

Val Ala Met Asn Ser Lys Gly Arg Leu Tyr Ala Thr Pro Ser Phe Gln
130                 135                 140

Glu Glu Cys Lys Phe Arg Glu Thr Leu Leu Pro Asn Asn Tyr Asn Ala
145                 150                 155                 160

Tyr Glu Ser Asp Leu Tyr Gln Gly Thr Tyr Ile Ala Leu Ser Lys Tyr
                165                 170                 175

Gly Arg Val Lys Arg Gly Ser Lys Val Ser Pro Ile Met Thr Val Thr
            180                 185                 190

His Phe Leu Pro Arg Ile
        195

<210> SEQ ID NO 15
<211> LENGTH: 268
<212> TYPE: PRT
<213> ORGANISM: Homo sapiens

<400> SEQUENCE: 15

Met Ser Leu Ser Phe Leu Leu Leu Phe Phe Ser His Leu Ile Leu
1               5                   10                  15

Ser Ala Trp Ala His Gly Glu Lys Arg Leu Ala Pro Lys Gly Gln Pro
            20                  25                  30

Gly Pro Ala Ala Thr Asp Arg Asn Pro Arg Gly Ser Ser Ser Arg Gln
        35                  40                  45

Ser Ser Ser Ser Ala Met Ser Ser Ser Ala Ser Ser Pro Ala
50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
        115                 120                 125

Gly Ile Val Gly Ile Arg Gly Val Phe Ser Asn Lys Phe Leu Ala Met
130                 135                 140

```
Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

<210> SEQ ID NO 16
<211> LENGTH: 155
<212> TYPE: PRT
<213> ORGANISM: Homo sapiens

<400> SEQUENCE: 16

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 17
<211> LENGTH: 155
<212> TYPE: PRT
<213> ORGANISM: Homo sapiens

<400> SEQUENCE: 17

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45
```

```
Val Asp Gly Val Arg Glu Lys Ser Asp Pro His Ile Lys Leu Gln Leu
         50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 18
<211> LENGTH: 208
<212> TYPE: PRT
<213> ORGANISM: Homo sapiens

<400> SEQUENCE: 18

Met Ala Pro Leu Gly Glu Val Gly Asn Tyr Phe Gly Val Gln Asp Ala
  1               5                  10                  15

Val Pro Phe Gly Asn Val Pro Val Leu Pro Val Asp Ser Pro Val Leu
                 20                  25                  30

Leu Ser Asp His Leu Gly Gln Ser Glu Ala Gly Gly Leu Pro Arg Gly
             35                  40                  45

Pro Ala Val Thr Asp Leu Asp His Leu Lys Gly Ile Leu Arg Arg Arg
     50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 19
<211> LENGTH: 194
<212> TYPE: PRT
<213> ORGANISM: Homo sapiens

<400> SEQUENCE: 19

Met His Lys Trp Ile Leu Thr Trp Ile Leu Pro Thr Leu Leu Tyr Arg
  1               5                  10                  15
```

-continued

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 20
<211> LENGTH: 208
<212> TYPE: PRT
<213> ORGANISM: Homo sapiens

<400> SEQUENCE: 20

Met Trp Lys Trp Ile Leu Thr His Cys Ala Ser Ala Phe Pro His Leu
1               5                   10                  15

Pro Gly Cys Cys Cys Cys Cys Phe Leu Leu Leu Phe Leu Val Ser Ser
            20                  25                  30

Val Pro Val Thr Cys Gln Ala Leu Gly Gln Asp Met Val Ser Pro Glu
        35                  40                  45

Ala Thr Asn Ser Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

```
Arg Arg Lys Asn Thr Ser Ala His Phe Leu Pro Met Val Val His Ser
        195                 200                 205
```

<210> SEQ ID NO 21
<211> LENGTH: 239
<212> TYPE: PRT
<213> ORGANISM: Homo sapiens

<400> SEQUENCE: 21

```
Met Gly Leu Ile Trp Leu Leu Leu Ser Leu Leu Glu Pro Gly Trp
 1               5                  10                  15

Pro Ala Ala Gly Pro Gly Ala Arg Leu Arg Arg Asp Ala Gly Gly Arg
                20                  25                  30

Gly Gly Val Tyr Glu His Leu Gly Ala Pro Arg Arg Lys Leu
            35                  40                  45

Tyr Cys Ala Thr Lys Tyr His Leu Gln Leu His Pro Ser Gly Arg Val
        50                  55                  60

Asn Gly Ser Leu Glu Asn Ser Ala Tyr Ser Ile Leu Glu Ile Thr Ala
 65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Val Ser Ser Thr Pro Gly Ala Arg
        130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
                180                 185                 190

Gln Leu Gln Ser Gly Leu Pro Arg Pro Pro Gly Lys Gly Val Gln Pro
            195                 200                 205

Arg Arg Arg Arg Gln Lys Gln Ser Pro Asp Asn Leu Glu Pro Ser His
        210                 215                 220

Val Gln Ala Ser Arg Leu Gly Ser Gln Leu Glu Ala Ser Ala His
225                 230                 235
```

<210> SEQ ID NO 22
<211> LENGTH: 268
<212> TYPE: PRT
<213> ORGANISM: Homo sapiens

<400> SEQUENCE: 22

```
Met Gly Ser Pro Arg Ser Ala Leu Ser Cys Leu Leu His Leu Leu
 1               5                  10                  15

Val Leu Cys Leu Gln Ala Gln Val Arg Ser Ala Ala Gln Lys Arg Gly
                20                  25                  30

Pro Gly Ala Gly Asn Pro Ala Asp Thr Leu Gly Gln Gly His Glu Asp
            35                  40                  45

Arg Pro Phe Gly Gln Arg Ser Arg Ala Gly Lys Asn Phe Thr Asn Pro
        50                  55                  60

Ala Pro Asn Tyr Pro Glu Gly Ser Lys Glu Gln Arg Asp Ser Val
 65                  70                  75                  80
```

-continued

```
Leu Pro Lys Val Thr Gln Arg His Val Arg Glu Gln Ser Leu Val Thr
                 85                  90                  95

Asp Gln Leu Ser Arg Arg Leu Ile Arg Thr Tyr Gln Leu Tyr Ser Arg
            100                 105                 110

Thr Ser Gly Lys His Val Gln Val Leu Ala Asn Lys Arg Ile Asn Ala
        115                 120                 125

Met Ala Glu Asp Gly Asp Pro Phe Ala Lys Leu Ile Val Glu Thr Asp
    130                 135                 140

Thr Phe Gly Ser Arg Val Arg Val Arg Gly Ala Glu Thr Gly Leu Tyr
145                 150                 155                 160

Ile Cys Met Asn Lys Lys Gly Lys Leu Ile Ala Lys Ser Asn Gly Lys
                165                 170                 175

Gly Lys Asp Cys Val Phe Thr Glu Ile Val Leu Glu Asn Asn Tyr Thr
            180                 185                 190

Ala Leu Gln Asn Ala Lys Tyr Glu Gly Trp Tyr Met Ala Phe Thr Arg
        195                 200                 205

Lys Gly Arg Pro Arg Lys Gly Ser Lys Thr Arg Gln His Gln Arg Glu
    210                 215                 220

Val His Phe Met Lys Arg Leu Pro Arg Gly His His Thr Thr Glu Gln
225                 230                 235                 240

Ser Leu Arg Phe Glu Phe Leu Asn Tyr Pro Pro Phe Thr Arg Ser Leu
                245                 250                 255

Arg Gly Ser Gln Arg Thr Trp Ala Pro Glu Pro Arg
            260                 265

<210> SEQ ID NO 23
<211> LENGTH: 4177
<212> TYPE: DNA
<213> ORGANISM: Homo sapiens
<220> FEATURE:
<221> NAME/KEY: CDS
<222> LOCATION: (593)..(1216)

<400> SEQUENCE: 23
ggaattccgg gaagagaggg aagaaaacaa cggcgactgg gcagctgcct ccacttctga    60
caactccaaa gggatatact tgtagaagtg gctcgcaggc tggggctccg cagagagaga   120
ccagaaggtg ccaaccgcag aggggtgcag atatctcccc ctattcccca ccccacctcc   180
cttgggtttt gttcaccgtg ctgtcatctg tttttcagac cttttttggca tctaacatgg   240 tgaagaaagg agtaaagaag agaacaaagt aactcctggg ggagcgaaga gcgctggtga   300
ccaacaccac caacgccacc accagctcct gctgctgcgg ccacccacgt ccaccattta   360
ccgggaggct ccagaggcgt aggcagcgga tccgagaaag gagcgagggg agtcagccgg   420
cttttccgag gagttatgga tgttggtgca ttcacttctg gccagatccg cgcccagagg   480
gagctaacca gcagccacca cctcgagctc tctccttgcc ttgcatcggg tcttacccct   540
ccagtatgtt ccttctgatg agacaatttc cagtgccgag agtttcagta ca atg tgg   598
                                                          Met Trp
                                                            1 aaa tgg ata ctg aca cat tgt gcc tca gcc ttt ccc cac ctg ccc ggc   646
Lys Trp Ile Leu Thr His Cys Ala Ser Ala Phe Pro His Leu Pro Gly
        5                  10                  15 tgc tgc tgc tgc tgc ttt ttg ttg ctg ttc ttg gtg tct tcc gtc cct   694
Cys Cys Cys Cys Cys Phe Leu Leu Leu Phe Leu Val Ser Ser Val Pro
 20                  25                  30 gtc acc tgc caa gcc ctt ggt cag gac atg gtg tca cca gag gcc acc   742
```

```
Val Thr Cys Gln Ala Leu Gly Gln Asp Met Val Ser Pro Glu Ala Thr
 35                  40                  45                  50 aac tct tct tcc tcc tcc ttc tcc tct cct tcc agc gcg gga agg cat      790
Asn Ser Ser Ser Ser Ser Phe Ser Ser Pro Ser Ser Ala Gly Arg His
                 55                  60                  65 gtg cgg agc tac aat cac ctt caa gga gat gtc cgc tgg aga aag cta      838
Val Arg Ser Tyr Asn His Leu Gln Gly Asp Val Arg Trp Arg Lys Leu
             70                  75                  80 ttc tct ttc acc aag tac ttt ctc aag att gag aag aac ggg aag gtc      886
Phe Ser Phe Thr Lys Tyr Phe Leu Lys Ile Glu Lys Asn Gly Lys Val
         85                  90                  95 agc ggg acc aag aag gag aac tgc ccg tac agc atc ctg gag ata aca      934
Ser Gly Thr Lys Lys Glu Asn Cys Pro Tyr Ser Ile Leu Glu Ile Thr
     100                 105                 110 tca gta gaa atc gga gtt gtt gcc gtc aaa gcc att aac agc aac tat      982
Ser Val Glu Ile Gly Val Val Ala Val Lys Ala Ile Asn Ser Asn Tyr
115                 120                 125                 130 tac tta gcc atg aac aag aag ggg aaa ctc tat ggc tca aaa gaa ttt     1030
Tyr Leu Ala Met Asn Lys Lys Gly Lys Leu Tyr Gly Ser Lys Glu Phe
                 135                 140                 145 aac aat gac tgt aag ctg aag gag agg ata gag gaa aat gga tac aat     1078
Asn Asn Asp Cys Lys Leu Lys Glu Arg Ile Glu Glu Asn Gly Tyr Asn
             150                 155                 160 acc tat gca tca ttt aac tgg cag cat aat ggg agg caa atg tat gtg     1126
Thr Tyr Ala Ser Phe Asn Trp Gln His Asn Gly Arg Gln Met Tyr Val
         165                 170                 175 gca ttg aat gga aaa gga gct cca agg aga gga cag aaa aca cga agg     1174
Ala Leu Asn Gly Lys Gly Ala Pro Arg Arg Gly Gln Lys Thr Arg Arg
     180                 185                 190 aaa aac acc tct gct cac ttt ctt cca atg gtg gta cac tca               1216
Lys Asn Thr Ser Ala His Phe Leu Pro Met Val Val His Ser
195                 200                 205 tagaggaagg caacgtttgt ggatgcagta aaaccaatgg ctcttttgcc aagaatagtg   1276
gatattcttc atgaagacag tagattgaaa ggcaaagaca cgttgcagat gtctgcttgc   1336
ttaaaagaaa gccagccttt gaaggttttt gtattcactg ctgacatatg atgttctttt   1396
aattagttct gtgtcatgtc ttataatcaa gatataggca gatcgaatgg gatagaagtt   1456
attcccaagt gaaaaacatt gtggctgggt ttttttgttgt tgttgtcaag tttttgtttt   1516
taaacctctg agatagaact taaggacat agaacaatct gttgaaagaa cgatcttcgg   1576
gaaagttatt tatggaatac gaactcatat caaagacttc attgctcatt caagcctaat   1636
gaatcaatga acagtaatac gtgcaagcat ttactggaaa gcacttgggt catatcatat   1696
gcacaaccaa aggagttctg gatgtggtct catggaataa ttgaatagaa tttaaaaata   1756
taaacatgtt agtgtgaaac tgttctaaca atacaaatag tatggtatgc ttgtgcattc   1816
tgccttcatc cctttctatt tctttctaag ttatttattt aataggatgt taaatatctt   1876
ttggggtttt aaagagtatc tcagcagctg tcttctgatt tatcttttct tttattcag   1936 cacaccacat gcatgttcac gacaaagtgt ttttaaaact tggcgaacac ttcaaaaata   1996
ggagttggga ttagggaagc agtatgagtg cccgtgtgct atcagttgac ttaatttgca   2056
cttctgcagt aataaccatc aacaataaat atggcaatgc tgtgccatgg cttgagtgag   2116
agatgtctgc tatcatttga aaacatatat tactctcgag gcttcctgtc tcaagaaata   2176
gaccagaagg ccaaattctt ctctttcaat acatcagttt gcctccaaga atatactaaa   2236
aaaaggaaaa ttaattgcta aatacatttta aatagcctag cctcattatt tactcatgat   2296
```

-continued

```
ttcttgccaa atgtcatggc ggtaaagagg ctgtccacat ctctaaaaac cctctgtaaa    2356
ttccacataa tgcatctttc ccaaaggaac tataaagaat ttggtatgaa gcgcaactct    2416
cccaggggct taaactgagc aaatcaaata tatactggta tatgtgtaac catatacaaa    2476
aacctgttct agctgtatga tctagtcttt acaaaaccaa ataaaacttg ttttctgtaa    2536
atttaaagag ctttacaagg ttccataatg taaccatatc aaaattcatt ttgttagagc    2596
acgtatagaa aagagtacat aagagtttac caatcatcat cacattgtat tccactaaat    2656
aaatacataa gccttatttg cagtgtctgt agtgatttta aaaatgtaga aaaatactat    2716
ttgttctaaa tacttttaag caataactat aatagtatat tgatgctgca gttttatctt    2776
catatttctt gttttgaaaa agcattttat tgtttggaca cagtattttg gtacaaaaaa    2836
aaagactcac taaatgtgtc ttactaaagt ttaacctttg gaaatgctgg cgttctgtga    2896
ttctccaaca aacttatttg tgtcaatact taaccagcac ttccagttaa tctgttattt    2956
ttaaaaattg ctttattaag aaattttttg tataatccca taaaaggtca tattttcccc    3016
attcttcaaa aaaactgtat ttcagaagaa acacatttga ggcactgtct tttggcttat    3076
agtttaaatt gcatttcatc atactttgct tccaacttgc tttttggcaa atgagattat    3136
aaaaatgttt aattttgtg gttggaatct ggatgttaaa atttaattgg taactcagtc    3196
tgtgagctat aatgtaatgc attcctatcc aaactaggta tctttttttc ctttatgttg    3256
aaataataat ggcacctgac acatagacat agaccaccca caacctaaat taaatgtttg    3316
gtaagacaaa tacacattgg atgaccacag taacagcaaa cagggcacaa actggattct    3376
tatttcacat agacatttag attactaaag agggctatgt gtaaacagtc atcattatag    3436
tactcaagac actaaaacag cttctagcca aatatattaa agcttgcaga ggccaaaaat    3496
agaaaacatc tcccctgtct ctcccacatt tccctcacag aaagacaaaa aacctgcctg    3556
gtgcagtagc tcacacctgt aatcccagca gtttgggaga ctgtgggaag atggcttgag    3616
tccaggagtt ctagacaggc ctgagaaacc tagtgagaca tccttctctt aaacaaaaca    3676
aaacaaaaca aatgtagcca tgcgtggtgg catatacctg tggtcccaac tactcaggag    3736
gctgaaacgg aaggatctct tgggccccag gagtttgagg ctgcagtgag ctataatctt    3796
gccattgcac tccagcctgg gtgaaaaaga gccagaaaga aaggaaagag agaaaagaga    3856
aaagaaagag agaaaagaca gaaagacagg aaggaaggaa ggaaggaagg aaggaaggaa    3916
ggaagcaagg aaagaaggaa ggaaggaaag aaggagggga aggaaggaga gagaaagaaa    3976
gattgtttgg taaggagtaa tgacattctc ttgcatttaa aagtggcata tttgcttgaa    4036
atggaaatag aattctggtc ccttttgcaa ctactgaaga aaaaaaaaag cagtttcagc    4096
cctgaatgtt gtagatttga aaaaaaaaaa aaaaaactc gagggggggc ccgtacccaa    4156
ttcgccctat agtgagtcgt a                                             4177
```

<210> SEQ ID NO 24
<211> LENGTH: 208
<212> TYPE: PRT
<213> ORGANISM: Homo sapiens

<400> SEQUENCE: 24

```
Met Trp Lys Trp Ile Leu Thr His Cys Ala Ser Ala Phe Pro His Leu
  1               5                  10                  15

Pro Gly Cys Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
```

```
             35                  40                  45
Ala Thr Asn Ser Ser Ser Ser Phe Ser Ser Pro Ser Ser Ala Gly
         50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Ala Val Lys Ala Ile Asn Ser
            115                 120                 125

Asn Tyr Tyr Leu Ala Met Asn Lys Lys Gly Lys Leu Tyr Gly Ser Lys
        130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 25
<211> LENGTH: 31
<212> TYPE: PRT
<213> ORGANISM: Homo sapiens

<400> SEQUENCE: 25

```
Gly Gln Asp Met Val Ser Pro Glu Ala Thr Asn Ser Ser Ser Ser
 1               5                  10                  15

Phe Ser Ser Pro Ser Ser Ala Gly Arg His Val Arg Ser Tyr Asn
                20                  25                  30
```

<210> SEQ ID NO 26
<211> LENGTH: 19
<212> TYPE: PRT
<213> ORGANISM: Homo sapiens

<400> SEQUENCE: 26

```
Lys Ile Glu Lys Asn Gly Lys Val Ser Gly Thr Lys Lys Glu Asn Cys
 1               5                  10                  15

Pro Tyr Ser
```

<210> SEQ ID NO 27
<211> LENGTH: 30
<212> TYPE: PRT
<213> ORGANISM: Homo sapiens

<400> SEQUENCE: 27

```
Asn Lys Lys Gly Lys Leu Tyr Gly Ser Lys Glu Phe Asn Asn Asp Cys
 1               5                  10                  15

Lys Leu Lys Glu Arg Ile Glu Glu Asn Gly Tyr Asn Thr Tyr
                20                  25                  30
```

<210> SEQ ID NO 28
<211> LENGTH: 19
<212> TYPE: PRT
<213> ORGANISM: Homo sapiens

```
<400> SEQUENCE: 28

Asn Gly Lys Gly Ala Pro Arg Arg Gly Gln Lys Thr Arg Arg Lys Asn
  1               5                  10                  15

Thr Ser Ala

<210> SEQ ID NO 29
<211> LENGTH: 555
<212> TYPE: DNA
<213> ORGANISM: Artificial Sequence
<220> FEATURE:
<221> NAME/KEY: CDS
<222> LOCATION: (1)..(552)
<223> OTHER INFORMATION: Description of Artificial Sequence: pQE60-Cys37
      construct

<400> SEQUENCE: 29 atg aga gga tcg cat cac cat cac cat cac gga tcc tgc cag gct ctg         48
Met Arg Gly Ser His His His His His His Gly Ser Cys Gln Ala Leu
  1               5                  10                  15 ggt cag gac atg gtt tct ccg gaa gct acc aac tct tcc tct tcc tct         96
Gly Gln Asp Met Val Ser Pro Glu Ala Thr Asn Ser Ser Ser Ser Ser
                 20                  25                  30 ttc tct tcc ccg tct tcc gct ggt cgt cac gtt cgt tct tac aac cac        144
Phe Ser Ser Pro Ser Ser Ala Gly Arg His Val Arg Ser Tyr Asn His
             35                  40                  45 ctg cag ggt gac gtt cgt tgg cgt aaa ctg ttc tct ttc acc aaa tac        192
Leu Gln Gly Asp Val Arg Trp Arg Lys Leu Phe Ser Phe Thr Lys Tyr
 50                  55                  60 ttc ctg aaa atc gaa aaa aac ggt aaa gtt tct ggg acc aag aag gag        240
Phe Leu Lys Ile Glu Lys Asn Gly Lys Val Ser Gly Thr Lys Lys Glu
 65                  70                  75                  80 aac tgc ccg tac agc atc ctg gag ata aca tca gta gaa atc gga gtt        288
Asn Cys Pro Tyr Ser Ile Leu Glu Ile Thr Ser Val Glu Ile Gly Val
                 85                  90                  95 gtt gcc gtc aaa gcc att aac agc aac tat tac tta gcc atg aac aag        336
Val Ala Val Lys Ala Ile Asn Ser Asn Tyr Tyr Leu Ala Met Asn Lys
            100                 105                 110 aag ggg aaa ctc tat ggc tca aaa gaa ttt aac aat gac tgt aag ctg        384
Lys Gly Lys Leu Tyr Gly Ser Lys Glu Phe Asn Asn Asp Cys Lys Leu
        115                 120                 125 aag gag agg ata gag gaa aat gga tac aat acc tat gca tca ttt aac        432
Lys Glu Arg Ile Glu Glu Asn Gly Tyr Asn Thr Tyr Ala Ser Phe Asn
    130                 135                 140 tgg cag cat aat ggg agg caa atg tat gtg gca ttg aat gga aaa gga        480
Trp Gln His Asn Gly Arg Gln Met Tyr Val Ala Leu Asn Gly Lys Gly
145                 150                 155                 160 gct cca agg aga gga cag aaa aca cga agg aaa aac acc tct gct cac        528
Ala Pro Arg Arg Gly Gln Lys Thr Arg Arg Lys Asn Thr Ser Ala His
                165                 170                 175 ttt ctt cca atg gtg gta cac tca tag                                    555
Phe Leu Pro Met Val Val His Ser
            180

<210> SEQ ID NO 30
<211> LENGTH: 184
<212> TYPE: PRT
<213> ORGANISM: Artificial Sequence
<220> FEATURE:
<223> OTHER INFORMATION: Description of Artificial Sequence: pQE60-Cys37

<400> SEQUENCE: 30

Met Arg Gly Ser His His His His His His Gly Ser Cys Gln Ala Leu
```

```
                1               5               10              15
              Gly Gln Asp Met Val Ser Pro Glu Ala Thr Asn Ser Ser Ser Ser
                              20                  25                  30

Phe Ser Ser Pro Ser Ser Ala Gly Arg His Val Arg Ser Tyr Asn His
                          35                  40                  45

Leu Gln Gly Asp Val Arg Trp Arg Lys Leu Phe Ser Phe Thr Lys Tyr
                      50                  55                  60

Phe Leu Lys Ile Glu Lys Asn Gly Lys Val Ser Gly Thr Lys Lys Glu
              65                  70                  75                  80

Asn Cys Pro Tyr Ser Ile Leu Glu Ile Thr Ser Val Glu Ile Gly Val
                              85                  90                  95

Val Ala Val Lys Ala Ile Asn Ser Asn Tyr Tyr Leu Ala Met Asn Lys
                              100                 105                 110

Lys Gly Lys Leu Tyr Gly Ser Lys Glu Phe Asn Asn Asp Cys Lys Leu
                              115                 120                 125

Lys Glu Arg Ile Glu Glu Asn Gly Tyr Asn Thr Tyr Ala Ser Phe Asn
                          130                 135                 140

Trp Gln His Asn Gly Arg Gln Met Tyr Val Ala Leu Asn Gly Lys Gly
              145                 150                 155                 160

Ala Pro Arg Arg Gly Gln Lys Thr Arg Arg Lys Asn Thr Ser Ala His
                              165                 170                 175

Phe Leu Pro Met Val Val His Ser
                              180

<210> SEQ ID NO 31
<211> LENGTH: 84
<212> TYPE: DNA
<213> ORGANISM: Artificial Sequence
<220> FEATURE:
<223> OTHER INFORMATION: Description of Artificial Sequence: synthetic
      primer

<400> SEQUENCE: 31
atgtggaaat ggatactgac ccactgcgct tctgctttcc cgcacctgcc gggttgctgc    60
tgctgctgct tcctgctgct gttc                                          84

<210> SEQ ID NO 32
<211> LENGTH: 82
<212> TYPE: DNA
<213> ORGANISM: Artificial Sequence
<220> FEATURE:
<223> OTHER INFORMATION: Description of Artificial Sequence: synthetic
      primer

<400> SEQUENCE: 32
ccggagaaac catgtcctga cccagagcct ggcaggtaac cggaacagaa gaaaccagga    60
acagcagcag gaagcagcag ca                                            82

<210> SEQ ID NO 33
<211> LENGTH: 80
<212> TYPE: DNA
<213> ORGANISM: Artificial Sequence
<220> FEATURE:
<223> OTHER INFORMATION: Description of Artificial Sequence: synthetic
      primer

<400> SEQUENCE: 33
gggtcaggac atggtttctc cggaagctac caactcttct tcttcttctt tctcttctcc    60
gtcttctgct ggtcgtcacg                                               80
```

<210> SEQ ID NO 34
<211> LENGTH: 81
<212> TYPE: DNA
<213> ORGANISM: Artificial Sequence
<220> FEATURE:
<223> OTHER INFORMATION: Description of Artificial Sequence: synthetic primer

<400> SEQUENCE: 34
ggtgaaagag aacagtttac gccaacgaac gtcaccctgc aggtggttgt aagaacgaac  60
gtgacgacca gcagaagacg g  81

<210> SEQ ID NO 35
<211> LENGTH: 75
<212> TYPE: DNA
<213> ORGANISM: Artificial Sequence
<220> FEATURE:
<223> OTHER INFORMATION: Description of Artificial Sequence: synthetic primer

<400> SEQUENCE: 35
cgttggcgta aactgttctc tttcaccaaa tacttcctga aaatcgaaaa aaacggtaaa  60
gtttctggga ccaaa  75

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence: synthetic primer

<400> SEQUENCE: 36
tttggtccca gaaactttac cgttttttc gattttcag  39

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: synthetic primer

<400> SEQUENCE: 37
aaaggatcca tgtggaaatg gatactgacc cactgc  36

<210> SEQ ID NO 38
<211> LENGTH: 627
<212> TYPE: DNA
<213> ORGANISM: Escherichia coli
<220> FEATURE:
<221> NAME/KEY: CDS
<222> LOCATION: (1)..(627)

<400> SEQUENCE: 38

```
atg tgg aaa tgg ata ctg acc cac tgc gct tct gct ttc ccg cac ctg      48
Met Trp Lys Trp Ile Leu Thr His Cys Ala Ser Ala Phe Pro His Leu
 1               5                  10                  15 ccg ggt tgc tgc tgc tgc tgc ttc ctg ctg ctg ttc ctg gtt tct tct      96
Pro Gly Cys Cys Cys Cys Cys Phe Leu Leu Leu Phe Leu Val Ser Ser
            20                  25                  30 gtt ccg gtt acc tgc cag gct ctg ggt cag gac atg gtt tct ccg gaa     144
Val Pro Val Thr Cys Gln Ala Leu Gly Gln Asp Met Val Ser Pro Glu
        35                  40                  45
```

```
gct acc aac tct tcc tct tcc tct ttc tct tcc ccg act tcc gct ggt      192
Ala Thr Asn Ser Ser Ser Ser Ser Phe Ser Ser Pro Thr Ser Ala Gly
     50                  55                  60 cgt cac gtt cgt tct tac aac cac ctg cag ggt gac gtt cgt tgg cgt      240
Arg His Val Arg Ser Tyr Asn His Leu Gln Gly Asp Val Arg Trp Arg
 65                  70                  75                  80 aaa ctg ttc tct ttc acc aaa tac ttc ctg aaa atc gaa aaa aac ggt      288
Lys Leu Phe Ser Phe Thr Lys Tyr Phe Leu Lys Ile Glu Lys Asn Gly
                 85                  90                  95 aaa gtt tct ggg acc aag aag gag aac tgc ccg tac agc atc ctg gag      336
Lys Val Ser Gly Thr Lys Lys Glu Asn Cys Pro Tyr Ser Ile Leu Glu
            100                 105                 110 ata aca tca gta gaa atc gga gtt gtt gcc gtc aaa gcc att aac agc      384
Ile Thr Ser Val Glu Ile Gly Val Val Ala Val Lys Ala Ile Asn Ser
        115                 120                 125 aac tat tac tta gcc atg aac aag aag ggg aaa ctc tat ggc tca aaa      432
Asn Tyr Tyr Leu Ala Met Asn Lys Lys Gly Lys Leu Tyr Gly Ser Lys
    130                 135                 140 gaa ttt aac aat gac tgt aag ctg aag gag agg ata gag gaa aat gga      480
Glu Phe Asn Asn Asp Cys Lys Leu Lys Glu Arg Ile Glu Glu Asn Gly
145                 150                 155                 160 tac aat acc tat gca tca ttt aac tgg cag cat aat ggg agg caa atg      528
Tyr Asn Thr Tyr Ala Ser Phe Asn Trp Gln His Asn Gly Arg Gln Met
                165                 170                 175 tat gtg gca ttg aat gga aaa gga gct cca agg aga gga cag aaa aca      576
Tyr Val Ala Leu Asn Gly Lys Gly Ala Pro Arg Arg Gly Gln Lys Thr
            180                 185                 190 cga agg aaa aac acc tct gct cac ttt ctt cca atg gtg gta cac tca      624
Arg Arg Lys Asn Thr Ser Ala His Phe Leu Pro Met Val Val His Ser
        195                 200                 205 tag                                                                  627
```

<210> SEQ ID NO 39
<211> LENGTH: 208
<212> TYPE: PRT
<213> ORGANISM: Escherichia coli

<400> SEQUENCE: 39

```
Met Trp Lys Trp Ile Leu Thr His Cys Ala Ser Ala Phe Pro His Leu
 1               5                  10                  15

Pro Gly Cys Cys Cys Cys Cys Phe Leu Leu Leu Phe Leu Val Ser Ser
             20                  25                  30

Val Pro Val Thr Cys Gln Ala Leu Gly Gln Asp Met Val Ser Pro Glu
         35                  40                  45

Ala Thr Asn Ser Ser Ser Ser Ser Phe Ser Ser Pro Thr Ser Ala Gly
     50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
                 85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
    130                 135                 140

Glu Phe Asn Asn Asp Cys Lys Leu Lys Glu Arg Ile Glu Glu Asn Gly
```

```
                145                 150                 155                 160
Tyr Asn Thr Tyr Ala Ser Phe Asn Trp Gln His Asn Gly Arg Gln Met
                    165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205
```

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 40
tttcatgact tgtcaagctc tgggtcaaga tatggttc                                38

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 41
gcccaagctt ccacaaacgt tgccttcc                                           28

<210> SEQ ID NO 42
<211> LENGTH: 525
<212> TYPE: DNA
<213> ORGANISM: Escherichia coli
<220> FEATURE:
<221> NAME/KEY: CDS
<222> LOCATION: (1)..(522)

<400> SEQUENCE: 42

```
atg acc tgc cag gct ctg ggt cag gac atg gtt tct ccg gaa gct acc        48
Met Thr Cys Gln Ala Leu Gly Gln Asp Met Val Ser Pro Glu Ala Thr
 1               5                  10                  15 aac tct tcc tct tcc tct ttc tct tcc ccg tct tcc gct ggt cgt cac        96
Asn Ser Ser Ser Ser Ser Phe Ser Ser Pro Ser Ser Ala Gly Arg His
             20                  25                  30 gtt cgt tct tac aac cac ctg cag ggt gac gtt cgt tgg cgt aaa ctg       144
Val Arg Ser Tyr Asn His Leu Gln Gly Asp Val Arg Trp Arg Lys Leu
         35                  40                  45 ttc tct ttc acc aaa tac ttc ctg aaa atc gaa aaa aac ggt aaa gtt       192
Phe Ser Phe Thr Lys Tyr Phe Leu Lys Ile Glu Lys Asn Gly Lys Val
 50                  55                  60 tct ggg acc aag aag gag aac tgc ccg tac agc atc ctg gag ata aca       240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat       288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt       336
Tyr Leu Ala Met Asn Lys Lys Gly Lys Leu Tyr Gly Ser Lys Glu Phe
            100                 105                 110 aac aat gac tgt aag ctg aag gag agg ata gag gaa aat gga tac aat       384
Asn Asn Asp Cys Lys Leu Lys Glu Arg Ile Glu Glu Asn Gly Tyr Asn
        115                 120                 125 acc tat gca tca ttt aac tgg cag cat aat ggg agg caa atg tat gtg       432
```

```
Thr Tyr Ala Ser Phe Asn Trp Gln His Asn Gly Arg Gln Met Tyr Val
        130                 135                 140 gca ttg aat gga aaa gga gct cca agg aga gga cag aaa aca cga agg        480
Ala Leu Asn Gly Lys Gly Ala Pro Arg Arg Gly Gln Lys Thr Arg Arg
145                 150                 155                 160 aaa aac acc tct gct cac ttt ctt cca atg gtg gta cac tca tag            525
Lys Asn Thr Ser Ala His Phe Leu Pro Met Val Val His Ser
                165                 170

<210> SEQ ID NO 43
<211> LENGTH: 174
<212> TYPE: PRT
<213> ORGANISM: Escherichia coli

<400> SEQUENCE: 43

Met Thr Cys Gln Ala Leu Gly Gln Asp Met Val Ser Pro Glu Ala Thr
1               5                   10                  15

Asn Ser Ser Ser Ser Phe Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
65                  70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
            100                 105                 110

Asn Asn Asp Cys Lys Leu Lys Glu Arg Ile Glu Glu Asn Gly Tyr Asn
        115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: synthetic
      primer

<400> SEQUENCE: 44
tcagtgaatt cattaaagag gagaaattaa tcatgacttg ccagg                       45

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: synthetic
      primer

<400> SEQUENCE: 45
tcatgacttg ccaggcactg ggtcaagaca tggtttcccc ggaagcta                    48
```

```
<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: synthetic
      primer

<400> SEQUENCE: 46
gcttcagcag cccatctagc gcaggtcgtc acgttcgctc ttacaacc                    48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: synthetic
      primer

<400> SEQUENCE: 47
gttcgttggc gcaaactgtt cagctttacc aagtacttcc tgaaaatc                    48

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 48
tcgaaaaaaa cggtaaagtt tctgggac                                          28

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence: synthetic
      primer

<400> SEQUENCE: 49
gatgggctgc tgaagctaga gctggagctg ttggtagctt ccgggaa                     48

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: synthetic
      primer

<400> SEQUENCE: 50
aacagtttgc gccaacgaac atcaccctgt aagtggttgt aagag                       45

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: synthetic
      primer

<400> SEQUENCE: 51
ttcttggtcc cagaaacttt accgtttttt tcgattttca ggaagta                     47

<210> SEQ ID NO 52
```

```
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 52
ttcttggtcc cagaaacttt accg                                              24

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: synthetic
      primer

<400> SEQUENCE: 53
agatcaggct tctattatta tgagtgtacc accattggaa gaaag                       45

<210> SEQ ID NO 54
<211> LENGTH: 525
<212> TYPE: DNA
<213> ORGANISM: Escherichia coli
<220> FEATURE:
<221> NAME/KEY: CDS
<222> LOCATION: (1)..(522)

<400> SEQUENCE: 54 atg act tgc cag gca ctg ggt caa gac atg gtt tcc ccg gaa gct acc         48
Met Thr Cys Gln Ala Leu Gly Gln Asp Met Val Ser Pro Glu Ala Thr
  1               5                  10                  15 aac agc tcc agc tct agc ttc agc agc cca tct agc gca ggt cgt cac         96
Asn Ser Ser Ser Ser Ser Phe Ser Ser Pro Ser Ser Ala Gly Arg His
             20                  25                  30 gtt cgc tct tac aac cac tta cag ggt gat gtt cgt tgg cgc aaa ctg        144
Val Arg Ser Tyr Asn His Leu Gln Gly Asp Val Arg Trp Arg Lys Leu
         35                  40                  45 ttc agc ttt acc aag tac ttc ctg aaa atc gaa aaa aac ggt aaa gtt        192
Phe Ser Phe Thr Lys Tyr Phe Leu Lys Ile Glu Lys Asn Gly Lys Val
     50                  55                  60 tct ggg acc aag aag gag aac tgc ccg tac agc atc ctg gag ata aca        240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat        288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt        336
Tyr Leu Ala Met Asn Lys Lys Gly Lys Leu Tyr Gly Ser Lys Glu Phe
            100                 105                 110 aac aat gac tgt aag ctg aag gag agg ata gag gaa aat gga tac aat        384
Asn Asn Asp Cys Lys Leu Lys Glu Arg Ile Glu Glu Asn Gly Tyr Asn
        115                 120                 125 acc tat gca tca ttt aac tgg cag cat aat ggg agg caa atg tat gtg        432
Thr Tyr Ala Ser Phe Asn Trp Gln His Asn Gly Arg Gln Met Tyr Val
    130                 135                 140 gca ttg aat gga aaa gga gct cca agg aga gga cag aaa aca cga agg        480
Ala Leu Asn Gly Lys Gly Ala Pro Arg Arg Gly Gln Lys Thr Arg Arg
145                 150                 155                 160 aaa aac acc tct gct cac ttt ctt cca atg gtg gta cac tca tag            525
Lys Asn Thr Ser Ala His Phe Leu Pro Met Val Val His Ser
                165                 170
```

<210> SEQ ID NO 55
<211> LENGTH: 174
<212> TYPE: PRT
<213> ORGANISM: Escherichia coli

<400> SEQUENCE: 55

Met Thr Cys Gln Ala Leu Gly Gln Asp Met Val Ser Pro Glu Ala Thr
 1               5                  10                  15

Asn Ser Ser Ser Ser Phe Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
65                  70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
            100                 105                 110

Asn Asn Asp Cys Lys Leu Lys Glu Arg Ile Glu Glu Asn Gly Tyr Asn
        115                 120                 125

Thr Tyr Ala Ser Phe Asn Trp Gln His Asn Gly Arg Gln Met Tyr Val
    130                 135                 140

Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 56
ggaccctcat gacctgccag gctctgggtc aggac                              35

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 57
ggacagccat ggctggtcgt cacgttcg                                      28

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 58
ggacagccat ggttcgttgg cgtaaactg                                     29

<210> SEQ ID NO 59

<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 59
ggacagccat ggaaaaaaac ggtaaagttt c                            31

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 60 ggaccccat ggagaactgc ccgtagagc                                29

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 61 ggaccccat ggtcaaagcc attaacagca ac                            32

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 62 ggaccccat ggggaaactc tatggctcaa aag                           33

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 63
ctgcccaagc ttattatgag tgtaccacca ttggaag                      37

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 64
ctgcccaagc ttattacttc agcttacagt cattgt                       36

<210> SEQ ID NO 65
<211> LENGTH: 525
<212> TYPE: DNA
<213> ORGANISM: Homo sapiens
<220> FEATURE:
<221> NAME/KEY: CDS
<222> LOCATION: (1)..(522)

```
<400> SEQUENCE: 65 atg acc tgc cag gct ctg ggt cag gac atg gtt tct ccg gaa gct acc      48
Met Thr Cys Gln Ala Leu Gly Gln Asp Met Val Ser Pro Glu Ala Thr
 1               5                  10                  15 aac tct tcc tct tcc tct ttc tct tcc ccg tct tcc gct ggt cgt cac      96
Asn Ser Ser Ser Ser Ser Phe Ser Ser Pro Ser Ser Ala Gly Arg His
                20                  25                  30 gtt cgt tct tac aac cac ctg cag ggt gac gtt cgt tgg cgt aaa ctg     144
Val Arg Ser Tyr Asn His Leu Gln Gly Asp Val Arg Trp Arg Lys Leu
             35                  40                  45 ttc tct ttc acc aaa tac ttc ctg aaa atc gaa aaa aac ggt aaa gtt     192
Phe Ser Phe Thr Lys Tyr Phe Leu Lys Ile Glu Lys Asn Gly Lys Val
         50                  55                  60 tct ggg acc aag aag gag aac tgc ccg tac agc atc ctg gag ata aca     240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat     288
Ser Val Glu Ile Gly Val Val Ala Val Lys Ala Ile Asn Ser Asn Tyr
                 85                  90                  95 tac tta gcc atg aac aag aag ggg aaa ctc tat ggc tca aaa gaa ttt     336
Tyr Leu Ala Met Asn Lys Lys Gly Lys Leu Tyr Gly Ser Lys Glu Phe
                100                 105                 110 aac aat gac tgt aag ctg aag gag agg ata gag gaa aat gga tac aat     384
Asn Asn Asp Cys Lys Leu Lys Glu Arg Ile Glu Glu Asn Gly Tyr Asn
            115                 120                 125 acc tat gca tca ttt aac tgg cag cat aat ggg agg caa atg tat gtg     432
Thr Tyr Ala Ser Phe Asn Trp Gln His Asn Gly Arg Gln Met Tyr Val
        130                 135                 140 gca ttg aat gga aaa gga gct cca agg aga gga cag aaa aca cga agg     480
Ala Leu Asn Gly Lys Gly Ala Pro Arg Arg Gly Gln Lys Thr Arg Arg
145                 150                 155                 160 aaa aac acc tct gct cac ttt ctt cca atg gtg gta cac tca tag         525
Lys Asn Thr Ser Ala His Phe Leu Pro Met Val Val His Ser
                165                 170

<210> SEQ ID NO 66
<211> LENGTH: 174
<212> TYPE: PRT
<213> ORGANISM: Homo sapiens

<400> SEQUENCE: 66

Met Thr Cys Gln Ala Leu Gly Gln Asp Met Val Ser Pro Glu Ala Thr
 1               5                  10                  15

Asn Ser Ser Ser Ser Ser Phe Ser Ser Pro Ser Ser Ala Gly Arg His
                20                  25                  30

Val Arg Ser Tyr Asn His Leu Gln Gly Asp Val Arg Trp Arg Lys Leu
             35                  40                  45

Phe Ser Phe Thr Lys Tyr Phe Leu Lys Ile Glu Lys Asn Gly Lys Val
         50                  55                  60

Ser Gly Thr Lys Lys Glu Asn Cys Pro Tyr Ser Ile Leu Glu Ile Thr
 65                  70                  75                  80

Ser Val Glu Ile Gly Val Val Ala Val Lys Ala Ile Asn Ser Asn Tyr
                 85                  90                  95

Tyr Leu Ala Met Asn Lys Lys Gly Lys Leu Tyr Gly Ser Lys Glu Phe
                100                 105                 110

Asn Asn Asp Cys Lys Leu Lys Glu Arg Ile Glu Glu Asn Gly Tyr Asn
            115                 120                 125

Thr Tyr Ala Ser Phe Asn Trp Gln His Asn Gly Arg Gln Met Tyr Val
```

```
                130              135              140
Ala Leu Asn Gly Lys Gly Ala Pro Arg Arg Gly Gln Lys Thr Arg Arg
145                 150                 155                 160

Lys Asn Thr Ser Ala His Phe Leu Pro Met Val Val His Ser
                165                 170
```

<210> SEQ ID NO 67
<211> LENGTH: 444
<212> TYPE: DNA
<213> ORGANISM: Homo sapiens
<220> FEATURE:
<221> NAME/KEY: CDS
<222> LOCATION: (1)..(444)

<400> SEQUENCE: 67

```
atg gct ggt cgt cac gtt cgt tct tac aac cac ctg cag ggt gac gtt      48
Met Ala Gly Arg His Val Arg Ser Tyr Asn His Leu Gln Gly Asp Val
 1               5                  10                  15 cgt tgg cgt aaa ctg ttc tct ttc acc aaa tac ttc ctg aaa atc gaa      96
Arg Trp Arg Lys Leu Phe Ser Phe Thr Lys Tyr Phe Leu Lys Ile Glu
                20                  25                  30 aaa aac ggt aaa gtt tct ggg acc aag aag gag aac tgc ccg tac agc     144
Lys Asn Gly Lys Val Ser Gly Thr Lys Lys Glu Asn Cys Pro Tyr Ser
            35                  40                  45 atc ctg gag ata aca tca gta gaa atc gga gtt gtt gcc gtc aaa gcc     192
Ile Leu Glu Ile Thr Ser Val Glu Ile Gly Val Val Ala Val Lys Ala
        50                  55                  60 att aac agc aac tat tac tta gcc atg aac aag aag ggg aaa ctc tat     240
Ile Asn Ser Asn Tyr Tyr Leu Ala Met Asn Lys Lys Gly Lys Leu Tyr
 65                  70                  75                  80 ggc tca aaa gaa ttt aac aat gac tgt aag ctg aag gag agg ata gag     288
Gly Ser Lys Glu Phe Asn Asn Asp Cys Lys Leu Lys Glu Arg Ile Glu
                85                  90                  95 gaa aat gga tac aat acc tat gca tca ttt aac tgg cag cat aat ggg     336
Glu Asn Gly Tyr Asn Thr Tyr Ala Ser Phe Asn Trp Gln His Asn Gly
            100                 105                 110 agg caa atg tat gtg gca ttg aat gga aaa gga gct cca agg aga gga     384
Arg Gln Met Tyr Val Ala Leu Asn Gly Lys Gly Ala Pro Arg Arg Gly
        115                 120                 125 cag aaa aca cga agg aaa aac acc tct gct cac ttt ctt cca atg gtg     432
Gln Lys Thr Arg Arg Lys Asn Thr Ser Ala His Phe Leu Pro Met Val
    130                 135                 140 gta cac tca tag                                                     444
Val His Ser
145
```

<210> SEQ ID NO 68
<211> LENGTH: 147
<212> TYPE: PRT
<213> ORGANISM: Homo sapiens

<400> SEQUENCE: 68

```
Met Ala Gly Arg His Val Arg Ser Tyr Asn His Leu Gln Gly Asp Val
 1               5                  10                  15

Arg Trp Arg Lys Leu Phe Ser Phe Thr Lys Tyr Phe Leu Lys Ile Glu
                20                  25                  30

Lys Asn Gly Lys Val Ser Gly Thr Lys Lys Glu Asn Cys Pro Tyr Ser
            35                  40                  45

Ile Leu Glu Ile Thr Ser Val Glu Ile Gly Val Val Ala Val Lys Ala
        50                  55                  60
```

```
Ile Asn Ser Asn Tyr Tyr Leu Ala Met Asn Lys Lys Gly Lys Leu Tyr
 65                  70                  75                  80

Gly Ser Lys Glu Phe Asn Asn Asp Cys Lys Leu Lys Glu Arg Ile Glu
                 85                  90                  95

Glu Asn Gly Tyr Asn Thr Tyr Ala Ser Phe Asn Trp Gln His Asn Gly
            100                 105                 110

Arg Gln Met Tyr Val Ala Leu Asn Gly Lys Gly Ala Pro Arg Arg Gly
        115                 120                 125

Gln Lys Thr Arg Arg Lys Asn Thr Ser Ala His Phe Leu Pro Met Val
    130                 135                 140

Val His Ser
145

<210> SEQ ID NO 69
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 69 atg gtt cgt tgg cgt aaa ctg ttc tct ttc acc aaa tac ttc ctg aaa      48
Met Val Arg Trp Arg Lys Leu Phe Ser Phe Thr Lys Tyr Phe Leu Lys
  1               5                  10                  15 atc gaa aaa aac ggt aaa gtt tct ggg acc aag aag gag aac tgc ccg      96
Ile Glu Lys Asn Gly Lys Val Ser Gly Thr Lys Lys Glu Asn Cys Pro
             20                  25                  30 tac agc atc ctg gag ata aca tca gta gaa atc gga gtt gtt gcc gtc     144
Tyr Ser Ile Leu Glu Ile Thr Ser Val Glu Ile Gly Val Val Ala Val
         35                  40                  45 aaa gcc att aac agc aac tat tac tta gcc atg aac aag aag ggg aaa     192
Lys Ala Ile Asn Ser Asn Tyr Tyr Leu Ala Met Asn Lys Lys Gly Lys
     50                  55                  60 ctc tat ggc tca aaa gaa ttt aac aat gac tgt aag ctg aag gag agg     240
Leu Tyr Gly Ser Lys Glu Phe Asn Asn Asp Cys Lys Leu Lys Glu Arg
 65                  70                  75                  80 ata gag gaa aat gga tac aat acc tat gca tca ttt aac tgg cag cat     288
Ile Glu Glu Asn Gly Tyr Asn Thr Tyr Ala Ser Phe Asn Trp Gln His
                 85                  90                  95 aat ggg agg caa atg tat gtg gca ttg aat gga aaa gga gct cca agg     336
Asn Gly Arg Gln Met Tyr Val Ala Leu Asn Gly Lys Gly Ala Pro Arg
            100                 105                 110 aga gga cag aaa aca cga agg aaa aac acc tct gct cac ttt ctt cca     384
Arg Gly Gln Lys Thr Arg Arg Lys Asn Thr Ser Ala His Phe Leu Pro
        115                 120                 125 atg gtg gta cac tca tag                                              402
Met Val Val His Ser
    130

<210> SEQ ID NO 70
<211> LENGTH: 133
<212> TYPE: PRT
<213> ORGANISM: Homo sapiens

<400> SEQUENCE: 70

Met Val Arg Trp Arg Lys Leu Phe Ser Phe Thr Lys Tyr Phe Leu Lys
  1               5                  10                  15

Ile Glu Lys Asn Gly Lys Val Ser Gly Thr Lys Lys Glu Asn Cys Pro
             20                  25                  30
```

```
Tyr Ser Ile Leu Glu Ile Thr Ser Val Glu Ile Gly Val Val Ala Val
         35                  40                  45

Lys Ala Ile Asn Ser Asn Tyr Tyr Leu Ala Met Asn Lys Lys Gly Lys
 50                  55                  60

Leu Tyr Gly Ser Lys Glu Phe Asn Asn Asp Cys Lys Leu Lys Glu Arg
 65                  70                  75                  80

Ile Glu Glu Asn Gly Tyr Asn Thr Tyr Ala Ser Phe Asn Trp Gln His
                 85                  90                  95

Asn Gly Arg Gln Met Tyr Val Ala Leu Asn Gly Lys Gly Ala Pro Arg
                100                 105                 110

Arg Gly Gln Lys Thr Arg Arg Lys Asn Thr Ser Ala His Phe Leu Pro
            115                 120                 125

Met Val Val His Ser
        130
```

<210> SEQ ID NO 71
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 71

```
atg gaa aaa aac ggt aaa gtt tct ggg acc aag aag gag aac tgc ccg      48
Met Glu Lys Asn Gly Lys Val Ser Gly Thr Lys Lys Glu Asn Cys Pro
 1               5                  10                  15 tac agc atc ctg gag ata aca tca gta gaa atc gga gtt gtt gcc gtc      96
Tyr Ser Ile Leu Glu Ile Thr Ser Val Glu Ile Gly Val Val Ala Val
             20                  25                  30 aaa gcc att aac agc aac tat tac tta gcc atg aac aag aag ggg aaa     144
Lys Ala Ile Asn Ser Asn Tyr Tyr Leu Ala Met Asn Lys Lys Gly Lys
         35                  40                  45 ctc tat ggc tca aaa gaa ttt aac aat gac tgt aag ctg aag gag agg     192
Leu Tyr Gly Ser Lys Glu Phe Asn Asn Asp Cys Lys Leu Lys Glu Arg
 50                  55                  60 ata gag gaa aat gga tac aat acc tat gca tca ttt aac tgg cag cat     240
Ile Glu Glu Asn Gly Tyr Asn Thr Tyr Ala Ser Phe Asn Trp Gln His
 65                  70                  75                  80 aat ggg agg caa atg tat gtg gca ttg aat gga aaa gga gct cca agg     288
Asn Gly Arg Gln Met Tyr Val Ala Leu Asn Gly Lys Gly Ala Pro Arg
                 85                  90                  95 aga gga cag aaa aca cga agg aaa aac acc tct gct cac ttt ctt cca     336
Arg Gly Gln Lys Thr Arg Arg Lys Asn Thr Ser Ala His Phe Leu Pro
            100                 105                 110 atg gtg gta cac tca tag                                              354
Met Val Val His Ser
        115
```

<210> SEQ ID NO 72
<211> LENGTH: 117
<212> TYPE: PRT
<213> ORGANISM: Homo sapiens

<400> SEQUENCE: 72

```
Met Glu Lys Asn Gly Lys Val Ser Gly Thr Lys Lys Glu Asn Cys Pro
 1               5                  10                  15

Tyr Ser Ile Leu Glu Ile Thr Ser Val Glu Ile Gly Val Val Ala Val
             20                  25                  30

Lys Ala Ile Asn Ser Asn Tyr Tyr Leu Ala Met Asn Lys Lys Gly Lys
```

```
                   35                  40                  45
Leu Tyr Gly Ser Lys Glu Phe Asn Asn Asp Cys Lys Leu Lys Glu Arg
     50                  55                  60

Ile Glu Glu Asn Gly Tyr Asn Thr Tyr Ala Ser Phe Asn Trp Gln His
 65                  70                  75                  80

Asn Gly Arg Gln Met Tyr Val Ala Leu Asn Gly Lys Gly Ala Pro Arg
                 85                  90                  95

Arg Gly Gln Lys Thr Arg Arg Lys Asn Thr Ser Ala His Phe Leu Pro
                100                 105                 110

Met Val Val His Ser
            115

<210> SEQ ID NO 73
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 73 atg gag aac tgc ccg tac agc atc ctg gag ata aca tca gta gaa atc      48
Met Glu Asn Cys Pro Tyr Ser Ile Leu Glu Ile Thr Ser Val Glu Ile
 1               5                  10                  15 gga gtt gtt gcc gtc aaa gcc att aac agc aat tat tac tta gcc atg      96
Gly Val Val Ala Val Lys Ala Ile Asn Ser Asn Tyr Tyr Leu Ala Met
             20                  25                  30 aac aag aag ggg aaa ctc tat ggc tca aaa gaa ttt aac aat gac tgt     144
Asn Lys Lys Gly Lys Leu Tyr Gly Ser Lys Glu Phe Asn Asn Asp Cys
         35                  40                  45 aag ctg aag gag agg ata gag gaa aat gga tac aat acc tat gca tca     192
Lys Leu Lys Glu Arg Ile Glu Glu Asn Gly Tyr Asn Thr Tyr Ala Ser
     50                  55                  60 ttt aac tgg cag cat aat ggg agg caa atg tat gtg gca ttg aat gga     240
Phe Asn Trp Gln His Asn Gly Arg Gln Met Tyr Val Ala Leu Asn Gly
 65                  70                  75                  80 aaa gga gct cca agg aga gga cag aaa aca cga agg aaa aac acc tct     288
Lys Gly Ala Pro Arg Arg Gly Gln Lys Thr Arg Arg Lys Asn Thr Ser
                 85                  90                  95 gct cac ttt ctt cca atg gtg gta cac tca tag                         321
Ala His Phe Leu Pro Met Val Val His Ser
                100                 105

<210> SEQ ID NO 74
<211> LENGTH: 106
<212> TYPE: PRT
<213> ORGANISM: Homo sapiens

<400> SEQUENCE: 74

Met Glu Asn Cys Pro Tyr Ser Ile Leu Glu Ile Thr Ser Val Glu Ile
 1               5                  10                  15

Gly Val Val Ala Val Lys Ala Ile Asn Ser Asn Tyr Tyr Leu Ala Met
             20                  25                  30

Asn Lys Lys Gly Lys Leu Tyr Gly Ser Lys Glu Phe Asn Asn Asp Cys
         35                  40                  45

Lys Leu Lys Glu Arg Ile Glu Glu Asn Gly Tyr Asn Thr Tyr Ala Ser
     50                  55                  60

Phe Asn Trp Gln His Asn Gly Arg Gln Met Tyr Val Ala Leu Asn Gly
 65                  70                  75                  80
```

```
Lys Gly Ala Pro Arg Arg Gly Gln Lys Thr Arg Arg Lys Asn Thr Ser
                85                  90                  95

Ala His Phe Leu Pro Met Val Val His Ser
            100                 105

<210> SEQ ID NO 75
<211> LENGTH: 264
<212> TYPE: DNA
<213> ORGANISM: Homo sapiens
<220> FEATURE:
<221> NAME/KEY: CDS
<222> LOCATION: (1)..(261)

<400> SEQUENCE: 75 atg gtc aaa gcc att aac agc aac tat tac tta gcc atg aac aag aag        48
Met Val Lys Ala Ile Asn Ser Asn Tyr Tyr Leu Ala Met Asn Lys Lys
 1               5                  10                  15 ggg aaa ctc tat ggc tca aaa gaa ttt aac aat gac tgt aag ctg aag        96
Gly Lys Leu Tyr Gly Ser Lys Glu Phe Asn Asn Asp Cys Lys Leu Lys
            20                  25                  30 gag agg ata gag gaa aat gga tac aat acc tat gca tca ttt aac tgg      144
Glu Arg Ile Glu Glu Asn Gly Tyr Asn Thr Tyr Ala Ser Phe Asn Trp
        35                  40                  45 cag cat aat ggg agg caa atg tat gtg gca ttg aat gga aaa gga gct      192
Gln His Asn Gly Arg Gln Met Tyr Val Ala Leu Asn Gly Lys Gly Ala
    50                  55                  60 cca agg aga gga cag aaa aca cga agg aaa aac acc tct gct cac ttt      240
Pro Arg Arg Gly Gln Lys Thr Arg Arg Lys Asn Thr Ser Ala His Phe
 65                  70                  75                  80 ctt cca atg gtg gta cac tca tag                                      264
Leu Pro Met Val Val His Ser
                85

<210> SEQ ID NO 76
<211> LENGTH: 87
<212> TYPE: PRT
<213> ORGANISM: Homo sapiens

<400> SEQUENCE: 76

Met Val Lys Ala Ile Asn Ser Asn Tyr Tyr Leu Ala Met Asn Lys Lys
 1               5                  10                  15

Gly Lys Leu Tyr Gly Ser Lys Glu Phe Asn Asn Asp Cys Lys Leu Lys
            20                  25                  30

Glu Arg Ile Glu Glu Asn Gly Tyr Asn Thr Tyr Ala Ser Phe Asn Trp
        35                  40                  45

Gln His Asn Gly Arg Gln Met Tyr Val Ala Leu Asn Gly Lys Gly Ala
    50                  55                  60

Pro Arg Arg Gly Gln Lys Thr Arg Arg Lys Asn Thr Ser Ala His Phe
 65                  70                  75                  80

Leu Pro Met Val Val His Ser
                85

<210> SEQ ID NO 77
<211> LENGTH: 219
<212> TYPE: DNA
<213> ORGANISM: Homo sapiens
<220> FEATURE:
<221> NAME/KEY: CDS
<222> LOCATION: (1)..(219)

<400> SEQUENCE: 77 atg ggg aaa ctc tat ggc tca aaa gaa ttt aac aat gac tgt aag ctg        48
```

```
Met Gly Lys Leu Tyr Gly Ser Lys Glu Phe Asn Asn Asp Cys Lys Leu
 1               5                  10                  15 aag gag agg ata gag gaa aat gga tac aat acc tat gca tca ttt aac        96
Lys Glu Arg Ile Glu Glu Asn Gly Tyr Asn Thr Tyr Ala Ser Phe Asn
                20                  25                  30 tgg cag cat aat ggg agg caa atg tat gtg gca ttg aat gga aaa gga       144
Trp Gln His Asn Gly Arg Gln Met Tyr Val Ala Leu Asn Gly Lys Gly
            35                  40                  45 gct cca agg aga gga cag aaa aca cga agg aaa aac acc tct gct cac       192
Ala Pro Arg Arg Gly Gln Lys Thr Arg Arg Lys Asn Thr Ser Ala His
     50                  55                  60 ttt ctt cca atg gtg gta cac tca tag                                   219
Phe Leu Pro Met Val Val His Ser
 65                  70
```

<210> SEQ ID NO 78
<211> LENGTH: 72
<212> TYPE: PRT
<213> ORGANISM: Homo sapiens

<400> SEQUENCE: 78

```
Met Gly Lys Leu Tyr Gly Ser Lys Glu Phe Asn Asn Asp Cys Lys Leu
 1               5                  10                  15

Lys Glu Arg Ile Glu Glu Asn Gly Tyr Asn Thr Tyr Ala Ser Phe Asn
                20                  25                  30

Trp Gln His Asn Gly Arg Gln Met Tyr Val Ala Leu Asn Gly Lys Gly
            35                  40                  45

Ala Pro Arg Arg Gly Gln Lys Thr Arg Arg Lys Asn Thr Ser Ala His
     50                  55                  60

Phe Leu Pro Met Val Val His Ser
 65                  70
```

<210> SEQ ID NO 79
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 79

```
atg acc tgc cag gct ctg ggt cag gac atg gtt tct ccg gaa gct acc        48
Met Thr Cys Gln Ala Leu Gly Gln Asp Met Val Ser Pro Glu Ala Thr
 1               5                  10                  15 aac tct tcc tct tcc tct ttc tct tcc ccg tct tcc gct ggt cgt cac        96
Asn Ser Ser Ser Ser Ser Phe Ser Ser Pro Ser Ser Ala Gly Arg His
                20                  25                  30 gtt cgt tct tac aac cac ctg cag ggt gac gtt cgt tgg cgt aaa ctg       144
Val Arg Ser Tyr Asn His Leu Gln Gly Asp Val Arg Trp Arg Lys Leu
            35                  40                  45 ttc tct ttc acc aaa tac ttc ctg aaa atc gaa aaa aac ggt aaa gtt       192
Phe Ser Phe Thr Lys Tyr Phe Leu Lys Ile Glu Lys Asn Gly Lys Val
     50                  55                  60 tct ggg acc aag aag gag aac tgc ccg tac agc atc ctg gag ata aca       240
Ser Gly Thr Lys Lys Glu Asn Cys Pro Tyr Ser Ile Leu Glu Ile Thr
 65                  70                  75                  80 tca gta gaa atc gga gtt gtt gcc gtc aaa gcc att aac agc aac tat       288
Ser Val Glu Ile Gly Val Val Ala Val Lys Ala Ile Asn Ser Asn Tyr
                85                  90                  95 tac tta gcc atg aac aag aag ggg aaa ctc tat ggc tca aaa gaa ttt       336
Tyr Leu Ala Met Asn Lys Lys Gly Lys Leu Tyr Gly Ser Lys Glu Phe
```

```
                    100                 105                 110
aac aat gac tgt aag ctg aag                                                 357
Asn Asn Asp Cys Lys Leu Lys
        115

<210> SEQ ID NO 80
<211> LENGTH: 119
<212> TYPE: PRT
<213> ORGANISM: Homo sapiens

<400> SEQUENCE: 80

Met Thr Cys Gln Ala Leu Gly Gln Asp Met Val Ser Pro Glu Ala Thr
 1               5                  10                  15

Asn Ser Ser Ser Ser Ser Phe Ser Ser Pro Ser Ser Ala Gly Arg His
            20                  25                  30

Val Arg Ser Tyr Asn His Leu Gln Gly Asp Val Arg Trp Arg Lys Leu
        35                  40                  45

Phe Ser Phe Thr Lys Tyr Phe Leu Lys Ile Glu Lys Asn Gly Lys Val
    50                  55                  60

Ser Gly Thr Lys Lys Glu Asn Cys Pro Tyr Ser Ile Leu Glu Ile Thr
65                  70                  75                  80

Ser Val Glu Ile Gly Val Val Ala Val Lys Ala Ile Asn Ser Asn Tyr
                85                  90                  95

Tyr Leu Ala Met Asn Lys Lys Gly Lys Leu Tyr Gly Ser Lys Glu Phe
            100                 105                 110

Asn Asn Asp Cys Lys Leu Lys
        115

<210> SEQ ID NO 81
<211> LENGTH: 276
<212> TYPE: DNA
<213> ORGANISM: Homo sapiens
<220> FEATURE:
<221> NAME/KEY: CDS
<222> LOCATION: (1)..(276)

<400> SEQUENCE: 81 atg gct ggt cgt cac gtt cgt tct tac aac cac ctg cag ggt gac gtt   48
Met Ala Gly Arg His Val Arg Ser Tyr Asn His Leu Gln Gly Asp Val
 1               5                  10                  15 cgt tgg cgt aaa ctg ttc tct ttc acc aaa tac ttc ctg aaa atc gaa   96
Arg Trp Arg Lys Leu Phe Ser Phe Thr Lys Tyr Phe Leu Lys Ile Glu
            20                  25                  30 aaa aac ggt aaa gtt tct ggg acc aag aag gag aac tgc ccg tac agc  144
Lys Asn Gly Lys Val Ser Gly Thr Lys Lys Glu Asn Cys Pro Tyr Ser
        35                  40                  45 atc ctg gag ata aca tca gta gaa atc gga gtt gtt gcc gtc aaa gcc  192
Ile Leu Glu Ile Thr Ser Val Glu Ile Gly Val Val Ala Val Lys Ala
    50                  55                  60 att aac agc aac tat tac tta gcc atg aac aag aag ggg aaa ctc tat  240
Ile Asn Ser Asn Tyr Tyr Leu Ala Met Asn Lys Lys Gly Lys Leu Tyr
65                  70                  75                  80 ggc tca aaa gaa ttt aac aat gac tgt aag ctg aag                  276
Gly Ser Lys Glu Phe Asn Asn Asp Cys Lys Leu Lys
                85                  90

<210> SEQ ID NO 82
<211> LENGTH: 92
<212> TYPE: PRT
<213> ORGANISM: Homo sapiens
```

```
<400> SEQUENCE: 82

Met Ala Gly Arg His Val Arg Ser Tyr Asn His Leu Gln Gly Asp Val
 1               5                  10                  15

Arg Trp Arg Lys Leu Phe Ser Phe Thr Lys Tyr Phe Leu Lys Ile Glu
             20                  25                  30

Lys Asn Gly Lys Val Ser Gly Thr Lys Lys Glu Asn Cys Pro Tyr Ser
         35                  40                  45

Ile Leu Glu Ile Thr Ser Val Glu Ile Gly Val Val Ala Val Lys Ala
     50                  55                  60

Ile Asn Ser Asn Tyr Tyr Leu Ala Met Asn Lys Lys Gly Lys Leu Tyr
 65                  70                  75                  80

Gly Ser Lys Glu Phe Asn Asn Asp Cys Lys Leu Lys
                 85                  90

<210> SEQ ID NO 83
<211> LENGTH: 525
<212> TYPE: DNA
<213> ORGANISM: Homo sapiens

<400> SEQUENCE: 83
atgacctctc aggctctggg tcaggacatg gtttctccgg aagctaccaa ctcttcctct      60
tcctctttct cttccccgtc ttccgctggt cgtcacgttc gttcttacaa ccacctgcag     120
ggtgacgttc gttggcgtaa actgttctct ttcaccaaat acttcctgaa aatcgaaaaa     180
aacggtaaag tttctgggac caagaaggag aactctccgt acagcatcct ggagataaca     240
tcagtagaaa tcggagttgt tgccgtcaaa gccattaaca gcaactatta cttagccatg     300
aacaagaagg ggaaactcta tggctcaaaa gaatttaaca atgactgtaa gctgaaggag     360
aggatagagg aaaatggata caatacctat gcatcattta actggcagca taatgggagg     420
caaatgtatg tggcattgaa tggaaaagga gctccaagga gaggacagaa aacacgaagg     480
aaaaacacct gctgctcactt tcttccaatg gtggtacact catag                    525

<210> SEQ ID NO 84
<211> LENGTH: 525
<212> TYPE: DNA
<213> ORGANISM: Homo sapiens

<400> SEQUENCE: 84
atgacctgcc aggctctggg tcaggacatg gtttctccgg aagctaccaa ctcttcctct      60
tcctctttct cttccccgtc ttccgctggt cgtcacgttc gttcttacaa ccacctgcag     120
ggtgacgttc gttggcgtaa actgttctct ttcaccaaat acttcctgaa aatcgaaaaa     180
aacggtaaag tttctgggac caagaaggag aactctccgt acagcatcct ggagataaca     240
tcagtagaaa tcggagttgt tgccgtcaaa gccattaaca gcaactatta cttagccatg     300
aacaagaagg ggaaactcta tggctcaaaa gaatttaaca atgactgtaa gctgaaggag     360
aggatagagg aaaatggata caatacctat gcatcattta actggcagca taatgggagg     420
caaatgtatg tggcattgaa tggaaaagga gctccaagga gaggacagaa aacacgaagg     480
aaaaacacct gctgctcactt tcttccaatg gtggtacact catag                    525

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: primer
```

```
<400> SEQUENCE: 85
ggaccctcat gacctctcag gctctgggt                                      29

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 86
aaggagaact ctccgtacag c                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 87
gctgtacggt ctgttctcct t                                              21

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 88
ggaccctcat gacctgccag gctctgggtc aggac                               35

<210> SEQ ID NO 89
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 89
ctgcccaagc ttattatgag tgtaccacca ttggaag                             37

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 90
aaaggatcct gccaggctct gggtcaggac atg                                 33

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 91
gcggcacatg tcttacaacc acctgcaggg tg                                  32

<210> SEQ ID NO 92
```

```
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 92
gggcccaagc ttatgagtgt accaccat                                           28

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 93
ccggcggatc ccatatgtct tacaaccacc tgcagg                                  36

<210> SEQ ID NO 94
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 94
ccggcggtac cttattatga gtgtaccacc attgg                                   35

<210> SEQ ID NO 95
<211> LENGTH: 426
<212> TYPE: DNA
<213> ORGANISM: Homo sapiens

<400> SEQUENCE: 95
atgtcttaca accacctgca gggtgacgtt cgttggcgta aactgttctc tttcaccaaa         60
tacttcctga aaatcgaaaa aaacggtaaa gtttctggga ccaagaagga gaactgcccg        120
tacagcatcc tggagataac atcagtagaa atcggagttg ttgccgtcaa agccattaac        180
agcaactatt acttagccat gaacaagaag gggaaactct atggctcaaa agaatttaac        240
aatgactgta agctgaagga gaggatagag gaaaatggat acaataccta tgcatcattt        300
aactggcagc ataatgggag gcaaatgtat gtggcattga atggaaaagg agctccaagg        360
agaggacaga aaacacgaag gaaaaacacc tctgctcact tcttccaat ggtggtacac         420 tcataa                                                                  426

<210> SEQ ID NO 96
<211> LENGTH: 141
<212> TYPE: PRT
<213> ORGANISM: Homo sapiens

<400> SEQUENCE: 96

Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
```

```
                65                  70                  75                  80
Asn Asp Cys Lys Leu Lys Glu Arg Ile Glu Glu Asn Gly Tyr Asn Thr
                            85                  90                  95
Tyr Ala Ser Phe Asn Trp Gln His Asn Gly Arg Gln Met Tyr Val Ala
                100                 105                 110
Leu Asn Gly Lys Gly Ala Pro Arg Arg Gly Gln Lys Thr Arg Arg Lys
            115                 120                 125
Asn Thr Ser Ala His Phe Leu Pro Met Val Val His Ser
        130                 135                 140
```

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 97
caaccacctg cagggtgacg                                                    20

<210> SEQ ID NO 98
<211> LENGTH: 78
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 98
aacggtcgac aaatgtatgt ggcactgaac ggtaaaggtg ctccacgtcg tggtcagaaa        60
acccgtcgta aaacacc                                                       78

<210> SEQ ID NO 99
<211> LENGTH: 76
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 99
gggcccaagc ttaagagtgt accaccattg gcagaaagtg agcagaggtg tttttacgac        60
gggttttctg accacg                                                        76

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 100
gccacataca tttgtcgacc gtt                                                23

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 101
gggcccaagc ttaagagtg                                                       19

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 102
gccacataca tttgtcgacc gtt                                                  23

<210> SEQ ID NO 103
<211> LENGTH: 90
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 103
ctgcagggtg acgttcgttg gcgtaaactg ttctccttca ccaaatactt cctgaaaatc          60 gaaaaaacg gtaaagtttc tggtaccaag                                            90

<210> SEQ ID NO 104
<211> LENGTH: 90
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 104
agctttaaca gcaacaacac cgatttcaac ggaggtgatt tccaggatgg agtacgggca          60
gttttctttc ttggtaccag aaactttacc                                           90

<210> SEQ ID NO 105
<211> LENGTH: 90
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 105
ggtgttgttg ctgttaaagc tatcaactcc aactactacc tggctatgaa caagaaaggt          60
aaactgtacg gttccaaaga atttaacaac                                           90

<210> SEQ ID NO 106
<211> LENGTH: 100
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 106
gtcgaccgtt gtgctgccag ttgaaggaag cgtaggtgtt gtaaccgttt tcttcgatac          60
gttctttcag tttacagtcg ttgttaaatt ctttggaacc                               100

<210> SEQ ID NO 107

```
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 107
gcggcgtcga ccgttgtgct gccag                                            25

<210> SEQ ID NO 108
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 108
gcggcctgca gggtgacgtt cgttgg                                           26

<210> SEQ ID NO 109
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 109
ccggcggatc ccatatgtct tacaaccacc tgcagg                                36

<210> SEQ ID NO 110
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 110
cgcgcgatat cttattaaga gtgtaccacc attg                                  34

<210> SEQ ID NO 111
<211> LENGTH: 426
<212> TYPE: DNA
<213> ORGANISM: Homo sapiens

<400> SEQUENCE: 111
atgtcttaca accacctgca gggtgacgtt cgttggcgta aactgttctc cttcaccaaa       60
tacttcctga aaatcgaaaa aaacggtaaa gtttctggta ccaagaaaga aaactgcccg      120
tactccatcc tggaaatcac ctccgttgaa atcggtgttg ttgctgttaa agctatcaac      180
tccaactact acctggctat gaacaagaaa ggtaaactgt acggttccaa agaatttaac      240
aacgactgta aactgaaaga acgtatcgaa gaaaacggtt acaacaccta cgcttccttc      300
aactggcagc acaacggtcg acaaatgtat gtggcactga acggtaaagg tgctccacgt      360
cgtggtcaga aacccgtcg taaaacacc tctgctcact ttctgccaat ggtggtacac        420
tcttaa                                                                426

<210> SEQ ID NO 112
<211> LENGTH: 141
<212> TYPE: PRT
<213> ORGANISM: Homo sapiens
```

-continued

<400> SEQUENCE: 112

Met Ser Tyr Asn His Leu Gln Gly Asp Val Arg Trp Arg Lys Leu Phe
1               5                   10                  15

Ser Phe Thr Lys Tyr Phe Leu Lys Ile Glu Lys Asn Gly Lys Val Ser
            20                  25                  30

Gly Thr Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Arg Lys
        115                 120                 125

Asn Thr Ser Ala His Phe Leu Pro Met Val Val His Ser
130                 135                 140

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 113
cgcggccatg gctctgggtc aggacatg                                        28

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 114
gggcccaagc ttatgagtgt accaccat                                        28

<210> SEQ ID NO 115
<211> LENGTH: 516
<212> TYPE: DNA
<213> ORGANISM: Homo sapiens

<400> SEQUENCE: 115
atggctctgg gtcaagatat ggtttctccg gaagctacca actcttcctc ttcctctttc     60
tcttccccgt cttccgctgg tcgtcacgtt cgttcttaca accacctgca gggtgacgtt    120
cgttggcgta aactgttctc tttcaccaaa tacttcctga aaatcgaaaa aaacggtaaa    180
gtttctggga ccaagaagga gaactgcccg tacagcatcc tggagataac atcagtagaa    240
atcggagttg ttgccgtcaa agccattaac agcaactatt acttagccat gaacaagaag    300
gggaaactct atggctcaaa agaatttaac aatgactgta agctgaagga gaggatagag    360
gaaaatggat acaataccta tgcatcattt aactggcagc ataatgggag gcaaatgtat    420
gtggcattga atggaaaagg agctccaagg agaggacaga aaacacgaag gaaaaacacc    480

```
tctgctcact ttcttccaat ggtggtacac tcataa                              516
```

<210> SEQ ID NO 116
<211> LENGTH: 171
<212> TYPE: PRT
<213> ORGANISM: Homo sapiens

<400> SEQUENCE: 116

```
Met Ala Leu Gly Gln Asp Met Val Ser Pro Glu Ala Thr Asn Ser Ser
 1               5                  10                  15
Ser Ser Ser Phe Ser Ser Pro Ser Ser Ala Gly Arg His Val Arg Ser
                20                  25                  30
Tyr Asn His Leu Gln Gly Asp Val Arg Trp Arg Lys Leu Phe Ser Phe
            35                  40                  45
Thr Lys Tyr Phe Leu Lys Ile Glu Lys Asn Gly Lys Val Ser Gly Thr
     50                  55                  60
Lys Lys Glu Asn Cys Pro Tyr Ser Ile Leu Glu Ile Thr Ser Val Glu
 65                  70                  75                  80
Ile Gly Val Val Ala Val Lys Ala Ile Asn Ser Asn Tyr Tyr Leu Ala
                 85                  90                  95
Met Asn Lys Lys Gly Lys Leu Tyr Gly Ser Lys Glu Phe Asn Asn Asp
                100                 105                 110
Cys Lys Leu Lys Glu Arg Ile Glu Glu Asn Gly Tyr Asn Thr Tyr Ala
            115                 120                 125
Ser Phe Asn Trp Gln His Asn Gly Arg Gln Met Tyr Val Ala Leu Asn
    130                 135                 140
Gly Lys Gly Ala Pro Arg Arg Gly Gln Lys Thr Arg Arg Lys Asn Thr
145                 150                 155                 160
Ser Ala His Phe Leu Pro Met Val Val His Ser
                165                 170
```

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 117

```
gcggcacatg tcttacaacc acctgcaggg tg                                  32
```

<210> SEQ ID NO 118
<211> LENGTH: 75
<212> TYPE: DNA
<213> ORGANISM: Artificial Sequence
<220> FEATURE:
<223> OTHER INFORMATION: Description of Artificial Sequence: primer

<400> SEQUENCE: 118

```
ctgcccaagc ttttatgagt gtaccaccat tggaagaaag tgagcagagg tgttttttc     60 tcgtgttttc tgtcc                                                     75
```

<210> SEQ ID NO 119
<211> LENGTH: 426
<212> TYPE: DNA
<213> ORGANISM: Homo sapiens

<400> SEQUENCE: 119

```
atgtcttaca accacctgca gggtgacgtt cgttggcgta aactgttctc tttcaccaaa    60
```

```
tacttcctga aaatcgaaaa aaacggtaaa gtttctggga ccaagaagga gaactgcccg      120
tacagcatcc tggagataac atcagtagaa atcggagttg ttgccgtcaa agccattaac      180
agcaactatt acttagccat gaacaagaag gggaaactct atggctcaaa agaatttaac      240
aatgactgta agctgaagga gaggatagag gaaaatggat acaataccta tgcatcattt      300
aactggcagc ataatgggag gcaaatgtat gtggcattga atgaaaaagg agctccaagg      360
agaggacaga aaacacgaga aaaaaacacc tctgctcact ttcttccaat ggtggtacac      420
tcatag                                                                426
```

<210> SEQ ID NO 120
<211> LENGTH: 141
<212> TYPE: PRT
<213> ORGANISM: Homo sapiens

<400> SEQUENCE: 120

```
Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Glu Lys
        115                 120                 125

Asn Thr Ser Ala His Phe Leu Pro Met Val Val His Ser
    130                 135                 140
```

<210> SEQ ID NO 121
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 121

```
gcggcacatg tcttacaacc acctgcaggg tg                                     32
```

<210> SEQ ID NO 122
<211> LENGTH: 75
<212> TYPE: DNA
<213> ORGANISM: Artificial Sequence
<220> FEATURE:
<223> OTHER INFORMATION: Description of Artificial Sequence: primer

<400> SEQUENCE: 122

```
ctgcccaagc ttttatgagt gtaccaccat tggaagaaag tgagcagagg tgttttctg       60 tcgtgttttc tgtcc                                                        75
```

<210> SEQ ID NO 123
<211> LENGTH: 426

```
<212> TYPE: DNA
<213> ORGANISM: Homo sapiens

<400> SEQUENCE: 123
atgtcttaca accacctgca gggtgacgtt cgttggcgta aactgttctc tttcaccaaa      60
tacttcctga aaatcgaaaa aaacggtaaa gtttctggga ccaagaagga gaactgcccg     120
tacagcatcc tggagataac atcagtagaa atcggagttg ttgccgtcaa agccattaac     180
agcaactatt acttagccat gaacaagaag gggaaactct atggctcaaa agaatttaac     240
aatgactgta agctgaagga gaggatagag gaaaatggat acaataccta tgcatcattt     300
aactggcagc ataatgggag gcaaatgtat gtggcattga atggaaaagg agctccaagg     360
agaggacaga aaacacgaca gaaaaacacc tctgctcact tcttccaat ggtggtacac      420 tcatag                                                                426

<210> SEQ ID NO 124
<211> LENGTH: 141
<212> TYPE: PRT
<213> ORGANISM: Homo sapiens

<400> SEQUENCE: 124

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Lys Thr Arg Gln Lys
        115                 120                 125

Asn Thr Ser Ala His Phe Leu Pro Met Val Val His Ser
    130                 135                 140

<210> SEQ ID NO 125
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 125
gcggcacatg tcttacaacc acctgcaggg tg                                    32

<210> SEQ ID NO 126
<211> LENGTH: 84
<212> TYPE: DNA
<213> ORGANISM: Artificial Sequence
<220> FEATURE:
<223> OTHER INFORMATION: Description of Artificial Sequence: primer

<400> SEQUENCE: 126
ctgcccaagc ttttatgagt gtaccaccat tggaagaaag tgagcagagg tgttttcct      60
```

```
tcgtgtttcc tgtcctctcc ttgg                                                84
```

<210> SEQ ID NO 127
<211> LENGTH: 426
<212> TYPE: DNA
<213> ORGANISM: Homo sapiens

<400> SEQUENCE: 127

```
atgtcttaca accacctgca gggtgacgtt cgttggcgta aactgttctc tttcaccaaa          60
tacttcctga aatcgaaaa aaacggtaaa gtttctggga ccaagaagga gaactgcccg         120
tacagcatcc tggagataac atcagtagaa atcggagttg ttgccgtcaa agccattaac        180
agcaactatt acttagccat gaacaagaag gggaaactct atggctcaaa agaatttaac        240
aatgactgta agctgaagga gaggatagag gaaatggat acaataccta tgcatcattt         300
aactggcagc ataatgggag gcaaatgtat gtggcattga atggaaaagg agctccaagg        360
agaggacagg aaacacgaag gaaaaacacc tctgctcact tcttccaat ggtggtacac         420
tcatag                                                                   426
```

<210> SEQ ID NO 128
<211> LENGTH: 141
<212> TYPE: PRT
<213> ORGANISM: Homo sapiens

<400> SEQUENCE: 128

```
Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
                20                  25                  30

Gly Thr Lys Lys Glu Asn Cys Pro Tyr Ser Ile Leu Glu Ile Thr Ser
            35                  40                  45

Val Glu Ile Gly Val Val Ala Val Lys Ala Ile Asn Ser Asn Tyr Tyr
        50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
                100                 105                 110

Leu Asn Gly Lys Gly Ala Pro Arg Arg Gly Gln Glu Thr Arg Arg Lys
            115                 120                 125

Asn Thr Ser Ala His Phe Leu Pro Met Val Val His Ser
        130                 135                 140
```

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 129

```
gcggcacatg tcttacaacc acctgcaggg tg                                       32
```

<210> SEQ ID NO 130
<211> LENGTH: 84
<212> TYPE: DNA
<213> ORGANISM: Artificial Sequence

```
<220> FEATURE:
<223> OTHER INFORMATION: Description of Artificial Sequence: primer

<400> SEQUENCE: 130
ctgcccaagc ttttatgagt gtaccaccat tggaagaaag tgagcagagg tgttttcct      60 tcgtgtctgc tgtcctctcc ttgg                                            84

<210> SEQ ID NO 131
<211> LENGTH: 426
<212> TYPE: DNA
<213> ORGANISM: Homo sapiens

<400> SEQUENCE: 131
atgtcttaca accacctgca gggtgacgtt cgttggcgta aactgttctc tttcaccaaa     60
tacttcctga aatcgaaaa aaacggtaaa gtttctggga ccaagaagga gaactgcccg     120
tacagcatcc tggagataac atcagtagaa atcggagttg ttgccgtcaa agccattaac    180
agcaactatt acttagccat gaacaagaag gggaaactct atggctcaaa agaatttaac    240
aatgactgta agctgaagga gaggatagag gaaaatggat acaataccta tgcatcattt    300
aactggcagc ataatgggag gcaaatgtat gtggcattga atggaaaagg agctccaagg    360
agaggacagc agacacgaag gaaaaacacc tctgctcact tcttccaat ggtggtacac     420 tcatag                                                                426

<210> SEQ ID NO 132
<211> LENGTH: 141
<212> TYPE: PRT
<213> ORGANISM: Homo sapiens

<400> SEQUENCE: 132

Met Ser Tyr Asn His Leu Gln Gly Asp Val Arg Trp Arg Lys Leu Phe
 1               5                  10                  15

Ser Phe Thr Lys Tyr Phe Leu Lys Ile Glu Lys Asn Gly Lys Val Ser
            20                  25                  30

Gly Thr Lys Lys Glu Asn Cys Pro Tyr Ser Ile Leu Glu Ile Thr Ser
        35                  40                  45

Val Glu Ile Gly Val Val Ala Val Lys Ala Ile Asn Ser Asn Tyr Tyr
    50                  55                  60

Leu Ala Met Asn Lys Lys Gly Lys Leu Tyr Gly Ser Lys Glu Phe Asn
65                  70                  75                  80

Asn Asp Cys Lys Leu Lys Glu Arg Ile Glu Glu Asn Gly Tyr Asn Thr
                85                  90                  95

Tyr Ala Ser Phe Asn Trp Gln His Asn Gly Arg Gln Met Tyr Val Ala
            100                 105                 110

Leu Asn Gly Lys Gly Ala Pro Arg Arg Gly Gln Gln Thr Arg Arg Lys
        115                 120                 125

Asn Thr Ser Ala His Phe Leu Pro Met Val Val His Ser
    130                 135                 140

<210> SEQ ID NO 133
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 133
gcggcacatg tcttacaacc acctgcaggg tg                                   32
```

<210> SEQ ID NO 134
<211> LENGTH: 93
<212> TYPE: DNA
<213> ORGANISM: Artificial Sequence
<220> FEATURE:
<223> OTHER INFORMATION: Description of Artificial Sequence: primer

<400> SEQUENCE: 134
ctgcccaagc ttttatgagt gtaccaccat tggaagaaag tgagcagagg tgtttttcct      60
tcgtgttttc tgtccttccc ttggagctcc ttt                                  93

<210> SEQ ID NO 135
<211> LENGTH: 426
<212> TYPE: DNA
<213> ORGANISM: Homo sapiens

<400> SEQUENCE: 135
atgtcttaca accacctgca gggtgacgtt cgttggcgta aactgttctc tttcaccaaa      60
tacttcctga aaatcgaaaa aaacggtaaa gtttctggga ccaagaagga gaactgcccg     120
tacagcatcc tggagataac atcagtagaa atcggagttg ttgccgtcaa agccattaac     180
agcaactatt acttagccat gaacaagaag gggaaactct atggctcaaa agaatttaac     240
aatgactgta agctgaagga gaggatagag gaaaatggat acaataccta tgcatcattt     300
aactggcagc ataatgggag gcaaatgtat gtggcattga atggaaaagg agctccaagg     360
gaaggacaga aaacacgaag gaaaaacacc tctgctcact ttcttccaat ggtggtacac     420
tcatag                                                                426

<210> SEQ ID NO 136
<211> LENGTH: 140
<212> TYPE: PRT
<213> ORGANISM: Homo sapiens

<400> SEQUENCE: 136

Met Tyr Asn His Leu Gln Gly Asp Val Arg Trp Arg Lys Leu Phe Ser
 1               5                  10                  15

Phe Thr Lys Tyr Phe Leu Lys Ile Glu Lys Asn Gly Lys Val Ser Gly
                20                  25                  30

Thr Lys Lys Glu Asn Cys Pro Tyr Ser Ile Leu Glu Ile Thr Ser Val
            35                  40                  45

Glu Ile Gly Val Val Ala Val Lys Ala Ile Asn Ser Asn Tyr Tyr Leu
        50                  55                  60

Ala Met Asn Lys Lys Gly Lys Leu Tyr Gly Ser Lys Glu Phe Asn Asn
 65                  70                  75                  80

Asp Cys Lys Leu Lys Glu Arg Ile Glu Glu Asn Gly Tyr Asn Thr Tyr
                85                  90                  95

Ala Ser Phe Asn Trp Gln His Asn Gly Arg Gln Met Tyr Val Ala Leu
            100                 105                 110

Asn Gly Lys Gly Ala Pro Arg Glu Gly Gln Lys Thr Arg Arg Lys Asn
        115                 120                 125

Thr Ser Ala His Phe Leu Pro Met Val Val His Ser
    130                 135                 140

<210> SEQ ID NO 137
<211> LENGTH: 32
<212> TYPE: DNA
<213> ORGANISM: Artificial Sequence

```
<220> FEATURE:
<223> OTHER INFORMATION: Description of Artificial Sequence: primer

<400> SEQUENCE: 137
gcggcacatg tcttacaacc acctgcaggg tg                                    32

<210> SEQ ID NO 138
<211> LENGTH: 93
<212> TYPE: DNA
<213> ORGANISM: Artificial Sequence
<220> FEATURE:
<223> OTHER INFORMATION: Description of Artificial Sequence: primer

<400> SEQUENCE: 138
ctgcccaagc ttttatgagt gtaccaccat tggaagaaag tgagcagagg tgttttcct     60 tcgtgttttc tgtccctgcc ttggagctcc ttt                                   93

<210> SEQ ID NO 139
<211> LENGTH: 426
<212> TYPE: DNA
<213> ORGANISM: Homo sapiens

<400> SEQUENCE: 139
atgtcttaca accacctgca gggtgacgtt cgttggcgta aactgttctc tttcaccaaa     60
tacttcctga aaatcgaaaa aaacggtaaa gtttctggga ccaagaagga gaactgcccg    120
tacagcatcc tggagataac atcagtagaa atcggagttg ttgccgtcaa agccattaac    180
agcaactatt acttagccat gaacaagaag gggaaactct atggctcaaa agaatttaac    240
aatgactgta gctgaagga gaggatagag gaaaatggat acaataccta tgcatcattt    300
aactggcagc ataatgggag gcaaatgtat gtggcattga atggaaaagg agctccaagg    360
cagggacaga aaacacgaag gaaaaacacc tctgctcact ttcttccaat ggtggtacac    420
tcatag                                                               426

<210> SEQ ID NO 140
<211> LENGTH: 141
<212> TYPE: PRT
<213> ORGANISM: Homo sapiens

<400> SEQUENCE: 140

Met Ser Tyr Asn His Leu Gln Gly Asp Val Arg Trp Arg Lys Leu Phe
  1               5                  10                  15

Ser Phe Thr Lys Tyr Phe Leu Lys Ile Glu Lys Asn Gly Lys Val Ser
             20                  25                  30

Gly Thr Lys Lys Glu Asn Cys Pro Tyr Ser Ile Leu Glu Ile Thr Ser
         35                  40                  45

Val Glu Ile Gly Val Val Ala Val Lys Ala Ile Asn Ser Asn Tyr Tyr
     50                  55                  60

Leu Ala Met Asn Lys Lys Gly Lys Leu Tyr Gly Ser Lys Glu Phe Asn
 65                  70                  75                  80

Asn Asp Cys Lys Leu Lys Glu Arg Ile Glu Glu Asn Gly Tyr Asn Thr
                 85                  90                  95

Tyr Ala Ser Phe Asn Trp Gln His Asn Gly Arg Gln Met Tyr Val Ala
            100                 105                 110

Leu Asn Gly Lys Gly Ala Pro Arg Gln Gly Gln Lys Thr Arg Arg Lys
        115                 120                 125

Asn Thr Ser Ala His Phe Leu Pro Met Val Val His Ser
    130                 135                 140
```

```
<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 141
gcggcacatg tcttacaacc acctgcaggg tg                                    32

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 142
ttgaatggag aaggagctcc a                                                21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 143
tggagctcct tctccattca a                                                21

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 144
ctgcccaagc ttttatgagt gtaccaccat tgg                                   33

<210> SEQ ID NO 145
<211> LENGTH: 426
<212> TYPE: DNA
<213> ORGANISM: Homo sapiens

<400> SEQUENCE: 145
atgtcttaca accacctgca gggtgacgtt cgttggcgta aactgttctc tttcaccaaa       60
tacttcctga aaatcgaaaa aaacggtaaa gtttctggga ccaagaagga gaactgcccg      120
tacagcatcc tggagataac atcagtagaa atcggagttg ttgccgtcaa agccattaac      180
agcaactatt acttagccat gaacaagaag gggaaactct atggctcaaa agaatttaac      240
aatgactgta agctgaagga gaggatagag gaaaatggat acaataccta tgcatcattt      300
aactggcagc ataatgggag gcaaatgtat gtggcattga atgagaagg agctccaagg       360 agaggacaga aaacacgaag gaaaaacacc tctgctcact ttcttccaat ggtggtacac      420
tcatag                                                                426

<210> SEQ ID NO 146
<211> LENGTH: 141
<212> TYPE: PRT
<213> ORGANISM: Homo sapiens
```

-continued

<400> SEQUENCE: 146

| Met | Ser | Tyr | Asn | His | Leu | Gln | Gly | Asp | Val | Trp | Arg | Lys | Leu | Phe |
| 1 | | | | 5 | | | | | 10 | | | | | 15 |

| Ser | Phe | Thr | Lys | Tyr | Phe | Leu | Lys | Ile | Glu | Lys | Asn | Gly | Lys | Val | Ser |
| | | | 20 | | | | | 25 | | | | | 30 | | |

| Gly | Thr | Lys | Lys | Glu | Asn | Cys | Pro | Tyr | Ser | Ile | Leu | Glu | Ile | Thr | Ser |
| | | 35 | | | | | 40 | | | | | 45 | | | |

| Val | Glu | Ile | Gly | Val | Val | Ala | Val | Lys | Ala | Ile | Asn | Ser | Asn | Tyr | Tyr |
| | 50 | | | | | 55 | | | | | 60 | | | | |

| Leu | Ala | Met | Asn | Lys | Lys | Gly | Lys | Leu | Tyr | Gly | Ser | Lys | Glu | Phe | Asn |
| 65 | | | | | 70 | | | | | 75 | | | | | 80 |

| Asn | Asp | Cys | Lys | Leu | Lys | Glu | Arg | Ile | Glu | Glu | Asn | Gly | Tyr | Asn | Thr |
| | | | | 85 | | | | | 90 | | | | | 95 | |

| Tyr | Ala | Ser | Phe | Asn | Trp | Gln | His | Asn | Gly | Arg | Gln | Met | Tyr | Val | Ala |
| | | | | 100 | | | | | 105 | | | | | 110 | |

| Leu | Asn | Gly | Glu | Gly | Ala | Pro | Arg | Arg | Gly | Gln | Lys | Thr | Arg | Arg | Lys |
| | | | | 115 | | | | | 120 | | | | | 125 | |

| Asn | Thr | Ser | Ala | His | Phe | Leu | Pro | Met | Val | Val | His | Ser |
| | | | 130 | | | | | 135 | | | | 140 |

<210> SEQ ID NO 147
<211> LENGTH: 3974
<212> TYPE: DNA
<213> ORGANISM: Artificial Sequence
<220> FEATURE:
<223> OTHER INFORMATION: Description of Artificial Sequence: pHE4-5
    vector

<400> SEQUENCE: 147

| ggtacctaag tgagtagggc gtccgatcga cggacgcctt tttttttgaat tcgtaatcat | 60 |
| ggtcatagct gtttcctgtg tgaaattgtt atccgctcac aattccacac aacatacgag | 120 |
| ccggaagcat aaagtgtaaa gcctggggtg cctaatgagt gagctaactc acattaattg | 180 |
| cgttgcgctc actgcccgct ttccagtcgg gaaacctgtc gtgccagctg cattaatgaa | 240 |
| tcggccaacg cgcggggaga ggcggtttgc gtattgggcg ctcttccgct tcctcgctca | 300 |
| ctgactcgct gcgctcggtc gttcggctgc ggcgagcggt atcagctcac tcaaaggcgg | 360 |
| taatacggtt atccacagaa tcaggggata acgcaggaaa gaacatgtga gcaaaaggcc | 420 |
| agcaaaaggc caggaaccgt aaaaaggccg cgttgctggc gtttttccat aggctccgcc | 480 |
| cccctgacga gcatcacaaa aatcgacgct caagtcagag gtggcgaaac ccgacaggac | 540 |
| tataaagata ccaggcgttt ccccctggaa gctccctcgt gcgctctcct gttccgaccc | 600 |
| tgccgcttac cggatacctg tccgcctttc tcccttcggg aagcgtggcg ctttctcata | 660 |
| gctcacgctg taggtatctc agttcggtgt aggtcgttcg ctccaagctg ggctgtgtgc | 720 |
| acgaaccccc cgttcagccc gaccgctgcg ccttatccgg taactatcgt cttgagtcca | 780 |
| acccggtaag acacgactta tcgccactgg cagcagccac tggtaacagg attagcagag | 840 |
| cgaggtatgt aggcggtgct acagagttct tgaagtggtg cctaactac ggctacacta | 900 |
| gaagaacagt atttggtatc tgcgctctgc tgaagccagt taccttcgga aaaagagttg | 960 |
| gtagctcttg atccggcaaa caaaccaccg ctggtagcgg tggttttttt gtttgcaagc | 1020 |
| agcagattac gcgcagaaaa aaggatctc aagaagatcc tttgatcttt tctacggggt | 1080 |
| ctgacgctca gtggaacgaa aactcacgtt aagggatttt ggtcatgaga ttatcgtcga | 1140 |
| caattcgcgc gcgaaggcga agcggcatgc atttacgttg acaccatcga atggtgcaaa | 1200 |

```
acctttcgcg gtatggcatg atagcgcccg aagagagtc aattcagggt ggtgaatgtg    1260
aaaccagtaa cgttatacga tgtcgcagag tatgccggtg tctcttatca gaccgttttcc   1320 cgcgtggtga accaggccag ccacgtttct gcgaaaacgc gggaaaaagt ggaagcggcg    1380
atggcggagc tgaattacat tcccaaccgc gtggcacaac aactggcggg caaacagtcg    1440
ttgctgattg gcgttgccac ctccagtctg gccctgcacg cgccgtcgca aattgtcgcg    1500
gcgattaaat ctcgcgccga tcaactgggt gccagcgtgg tggtgtcgat ggtagaacga    1560
agcggcgtcg aagcctgtaa agcggcggtg cacaatcttc tcgcgcaacg cgtcagtggg    1620
ctgatcatta actatccgct ggatgaccag gatgccattg ctgtggaagc tgcctgcact    1680
aatgttccgg cgttatttct tgatgtctct gaccagacac ccatcaacag tattattttc    1740
tcccatgaag acggtacgcg actgggcgtg gagcatctgg tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg gcgcaatgc gcgccattac cgagtccggg    2040
ctgcgcgttg tgcggatat ctcggtagtg ggatacgacg ataccgaaga cagctcatgt    2100
tatatcccgc cgttaaccac catcaaacag gattttcgcc tgctggggca accagcgtg    2160 gaccgcttgc tgcaactctc tcagggccag gcggtgaagg gcaatcagct gttgcccgtc    2220
tcactggtga aaagaaaaac caccctggcg cccaatacgc aaaccgcctc tccccgcgcg    2280
ttggccgatt cattaatgca gctggcacga caggtttccc gactgaaaag cgggcagtga    2340
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccgc gaggtcgtcc agcctcaggc agcagctgaa    2520
ccaactcgcg aggggatcga gcccggggtg gcgaagaac tccagcatga gatccccgcg    2580
ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagaa gtcccgctca aagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccatttttcca ccatgatatt cggcaagcag    2940
gcatcgccat gggtcacgac gagatcctcg ccgtcggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg gcgcccctgc gctgacagcc ggaacacggc ggcatcagag    3420
cagccgattg tctgttgtgc ccagtcatag ccgaatagcc tctccaccca gcggccgga    3480 gaacctgcgt gcaatccatc ttgttcaatc atgcgaaacg atcctcatcc tgtctcttga    3540
```

-continued

```
tcagatcttg atccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
cctgagtgct tgcggcagcg tgaagcttaa aaactgcaa aaaatagttt gacttgtgag     3900
cggataacaa ttaagatgta cccaattgtg agcggataac aatttcacac attaaagagg    3960
agaaattaca tatg                                                      3974

<210> SEQ ID NO 148
<211> LENGTH: 112
<212> TYPE: DNA
<213> ORGANISM: Artificial Sequence
<220> FEATURE:
<223> OTHER INFORMATION: Description of Artificial Sequence: pHE4-5
      promoter sequence

<400> SEQUENCE: 148
aagcttaaaa aactgcaaaa aatagtttga cttgtgagcg gataacaatt aagatgtacc    60
caattgtgag cggataacaa tttcacacat taaagaggag aaattacata tg            112

<210> SEQ ID NO 149
<211> LENGTH: 106
<212> TYPE: DNA
<213> ORGANISM: Artificial Sequence
<220> FEATURE:
<223> OTHER INFORMATION: Description of Artificial Sequence: primer

<400> SEQUENCE: 149
gagcgcggat ccgccaccat gaaggtctcc gtggctgccc tctcctgcct catgcttgtt    60
actgcccttg gatctcaggc cagctacaat caccttcaag gagatg                   106

<210> SEQ ID NO 150
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 150
gagcgcggat ccctatgagt gtaccaccat tggaag                              36

<210> SEQ ID NO 151
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 151
ccggccatat gcgtaaactg ttctctttca cc                                  32

<210> SEQ ID NO 152
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 152
```

```
ccggcggtac cttattatga gtgtaccacc attgg                          35

<210> SEQ ID NO 153
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 153
gatcgccata tggctggtcg tcacgttcgt tc                             32

<210> SEQ ID NO 154
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 154
gatcgcggta ccttattatg agtgtaccac cattggaag                      39

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 155
gatcgccata tggctggtcg tcacgttcgt tc                             32

<210> SEQ ID NO 156
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 156
gatcgcggta ccttattatg agtgtaccac cattggaag                      39

<210> SEQ ID NO 157
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 157
gatcgccata tggctggtcg tcacgttcgt tc                             32

<210> SEQ ID NO 158
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 158
gatcgcggta ccttattatg agtgtaccac cattggaag                      39

<210> SEQ ID NO 159
<211> LENGTH: 32
<212> TYPE: DNA
<213> ORGANISM: Artificial Sequence
```

```
<220> FEATURE:
<223> OTHER INFORMATION: Description of Artificial Sequence: primer

<400> SEQUENCE: 159
gatcgccata tggctggtcg tcacgttcgt tc                              32

<210> SEQ ID NO 160
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 160
gatcgcggta ccttattatg agtgtaccac cattggaag                       39

<210> SEQ ID NO 161
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 161
gatcgcggat ccgccaccat gtggaaatgg atactgacac attgtgc              47

<210> SEQ ID NO 162
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 162
gatcgctcta gattatgagt gtaccaccat tggaagaaag                      40

<210> SEQ ID NO 163
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 163
gatcgcggat ccgccaccat gtggaaatgg atactgacac attgtgc              47

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 164
gatcgctcta gattatgagt gtaccaccat tggaagaaag                      40

<210> SEQ ID NO 165
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 165
gatcgcggat ccgccaccat gtggaaatgg atactgacac attgtgc              47
```

```
<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 166
gatcgctcta gattatgagt gtaccaccat tggaagaaag                            40

<210> SEQ ID NO 167
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 167
gatcgcggat ccgccaccat gtggaaatgg atactgacac attgtgc                    47

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 168
gatcgctcta gattatgagt gtaccaccat tggaagaaag                            40

<210> SEQ ID NO 169
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 169
gatcgccata tggctggtcg tcacgttcgt tc                                    32

<210> SEQ ID NO 170
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 170
gatcgcggta ccttattatg agtgtaccac cattggaag                             39

<210> SEQ ID NO 171
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 171
gatcgccata tggctggtcg tcacgttcgt tc                                    32

<210> SEQ ID NO 172
<211> LENGTH: 39
<212> TYPE: DNA
<213> ORGANISM: Artificial Sequence
<220> FEATURE:
<223> OTHER INFORMATION: Description of Artificial Sequence: primer
```

<400> SEQUENCE: 172
gatcgcggta ccttattatg agtgtaccac cattggaag                              39

<210> SEQ ID NO 173
<211> LENGTH: 456
<212> TYPE: DNA
<213> ORGANISM: Escherichia coli

<400> SEQUENCE: 173
catatggctg gtcgtcacgt tcgttcttac aaccacctgc agggtgacgt tcgttggcgt       60
aaactgttct ctttcaccaa atacttcctg aaaatcgaaa aaacggtaa agtttctggg       120
accaagaagg agaactgccc gtacagcatc ctggagataa catcagtaga aatcggagtt      180
gttgccgtca agccattaa cagcaactat tacttagcca tgaacaagaa ggggaaactc       240
tatggctcaa agaatttaa caatgactgt aagctgaagg agaggataga ggaaaatgga       300
tacaatacct atgcatcatt taactggcag cataatggga ggcaaatgta tgtggcattg      360
aatggaaaag gagctccaag gagaggacag aaaacacgaa ggaaaaacac ctctgctcac      420
tttcttccaa tggtggtaca ctcataataa ggtacc                                456

<210> SEQ ID NO 174
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 174
gactacatat ggctggtcgt cacgttcgtt cttacaacca cctgcagg                   48

<210> SEQ ID NO 175
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 175
ctagtctcta gattattatg agtgtacaac catcggcagg aagtgag                    47

<210> SEQ ID NO 176
<211> LENGTH: 447
<212> TYPE: DNA
<213> ORGANISM: Escherichia coli

<400> SEQUENCE: 176
atggctggtc gtcacgttcg ttcttacaac cacctgcagg gtgacgttcg ttggcgtaaa      60
ctgttctctt tcaccaaata cttcctgaaa atcgaaaaga acgtaaagt ttctggtacc      120
aagaaagaaa actgcccgta ctctatcctg gaaatcacct ccgttgaaat cggtgttgta     180
gccgttaaag ccatcaactc caactattac ctggccatga caaaaaggg taaactgtac     240
ggctctaaag aattcaacaa cgactgcaaa ctgaaagaac gtatcgaaga gaacggttac    300
aacacctacg catccttcaa ctggcagcac aacggtcgtc agatgtacgt tgcactgaac     360
ggtaaaggcg ctccgcgtcg cggtcagaaa acccgtcgca aaaacacctc tgctcacttc     420
ctgccgatgg ttgtacactc ataataa                                          447

What is claimed is:

1. A method of stimulating epithelial cell proliferation in a patient comprising administering an effective amount of a polypeptide comprising amino acids 69 to 208 of SEQ ID NO:2 to said patient, wherein said patient has a wound selected from the group consisting of:
   (a) an internal wound;
   (b) a donor site wound;
   (c) an internal surgical wound;
   (d) a wound made during cosmetic surgery;
   (e) a dermal wound;
   (f) a surgical wound;
   (g) an excisional wound;
   (h) a deep wound involving damage of the dermis and epidermis;
   (i) an eye tissue wound;
   (j) a dental tissue wound;
   (k) an oral cavity wound;
   (l) anastomosis;
   (m) a burn;
   (n) a wound from ischemia; and
   (o) tissue trauma caused by a sharp object.

2. The method of claim 1, wherein said wound is aninternal wound.

3. The method of claim 1, wherein said wound is a donor site wound.

4. The method of claim 1, wherein said wound is an internal surgical wound.

5. The method of claim 1, wherein said wound is a wound made during cosmetic surgery.

6. The method of claim 5, wherein said wound is an incisional wound.

7. The method of claim 1, wherein said wound is a dermal wound.

8. The method of claim 1, wherein said wound is a surgical wound.

9. The method of claim 1, wherein said wound is an exicisional wound.

10. The method of claim 1, wherein said wound is a deep wound involving damage of the dermis and epidermis.

11. The method of claim 1, wherein said wound is an eye tissue wound.

12. The method of claim 1, wherein said wound is a dental tissue wound.

13. The method of claim 1, wherein said wound is an oral cavity wound.

14. The method of claim 1, wherein said wound is anastomosis.

15. The method of claim 1, wherein said wound is a burn.

16. The method of claim 15, wherein said burn is from heat exposure.

17. The method of claim 15, wherein said burn is from a chemical.

18. The method of claim 1, wherein said wound is a wound from ischemia.

19. The method of claim 1, wherein said wound is tissue trauma caused by a sharp object.

20. The method of claim 1, wherein said patient is healing impaired.

21. The method of claim 20, wherein said healing impairment is due to a condition selected from the group consisting of diabetes, ischemic blockage, uremia, malnutrition, vitamin deficiency, obesity, infection, immunosuppression, and radiation therapy.

22. A method of stimulating epithelial cell proliferation in a patient comprising administering an effective amount of a polypeptide comprising amino acids 63 to 208 of SEQ ID NO:2 to said patient, wherein said patient has a wound selected from the group consisting of:
   (a) an internal wound;
   (b) a donor site wound;
   (c) an internal surgical wound;
   (d) a wound made during cosmetic surgery;
   (e) a dermal wound;
   (f) a surgical wound;
   (g) an excisional wound;
   (h) a deep wound involving damage of the dermis and epidermis;
   (i) an eye tissue wound;
   (j) a dental tissue wound;
   (k) an oral cavity wound;
   (l) anastomosis;
   (m) a burn;
   (n) a wound from ischemia; and
   (o) tissue trauma caused by a sharp object.

23. The method of claim 22, wherein said wound is an internal wound.

24. The method of claim 22, wherein said wound is a donor site wound.

25. The method of claim 22, wherein said wound is an internal surgical wound.

26. The method of claim 22, wherein said wound is a wound made during cosmetic surgery.

27. The method of claim 26, wherein said wound is an incisional wound.

28. The method of claim 22, wherein said wound is a dermal wound.

29. The method of claim 22, wherein said wound is a surgical wound.

30. The method of claim 22, wherein said wound is an excisional wound.

31. The method of claim 22, wherein said wound is a deep wound involving damage of the dermis and epidermis.

32. The method of claim 22, wherein said wound is an eye tissue wound.

33. The method of claim 22, wherein said wound is a dental tissue wound.

34. The method of claim 22, wherein said wound is an oral cavity wound.

35. The method of claim 22, wherein said wound is anastomosis.

36. The method of claim 22, wherein said wound is a burn.

37. The method of claim 36, wherein said burn is from heat exposure.

38. The method of claim 36, wherein said burn is from a chemical.

39. The method of claim 22, wherein said wound is a wound from ischemia.

40. The method of claim 22, wherein said wound is tissue trauma caused by a sharp object.

41. The method of claim 22, wherein said patient is healing impaired.

42. The method of claim 41, wherein said healing impairment is due to a condition selected from the group consisting of diabetes, ischemic blockage, uremia, malnutrition, vitamin deficiency, obesity, infection, immunosuppression, and radiation therapy.

43. The method of claim 20, wherein said healing impairment is due to a treatment selected from the group consisting of treatment with steroids, treatment with non-steroids, treatment with antineoplastic drugs, and treatment with antimetabolites.

44. The method of claim 43, wherein said polypeptide is administered prior to the administration of said treatment.

45. The method of claim 43, wherein said polypeptide is administered after the administration of said treatment.

46. The method of claim 41, wherein said healing impairment is due to a treatment selected from the group consisting of treatment with steroids, treatment with non-steroids, treatment with antineoplastic drugs, and treatment with antimetabolites.

47. The method of claim 46, wherein said polypeptide is administered prior to the administration of said treatment.

48. The method of claim 46, wherein said polypeptide is administered after the administration of said treatment.

* * * * *